United States Patent
Boehm et al.

(10) Patent No.: US 9,700,543 B2
(45) Date of Patent: *Jul. 11, 2017

(54) GLP-1 RECEPTOR STABILIZERS AND MODULATORS

(71) Applicant: Celgene International II SÀRL, Couvet (CH)

(72) Inventors: Marcus F. Boehm, San Diego, CA (US); Esther Martinborough, San Diego, CA (US); Manisha Moorjani, San Diego, CA (US); Junko Tamiya, Carlsbad, CA (US); Liming Huang, San Diego, CA (US); Thomas Fowler, Melton Mowbray (GB); Andrew Novak, Long Eaton (GB); Premji Meghani, Loughborough (GB); Enugurthi Brahmachary, San Diego, CA (US); Adam Richard Yeager, La Mesa, CA (US)

(73) Assignee: Celgene International II SÀRL, Couvet (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/997,364

(22) Filed: Jan. 15, 2016

(65) Prior Publication Data

US 2016/0310471 A1 Oct. 27, 2016

Related U.S. Application Data

(63) Continuation of application No. 14/122,176, filed as application No. PCT/US2012/040250 on May 31, 2012, now Pat. No. 9,278,910.

(Continued)

(51) Int. Cl.
*A61K 31/4245* (2006.01)
*A61K 9/00* (2006.01)
(Continued)

(52) U.S. Cl.
CPC ........ *A61K 31/4245* (2013.01); *A61K 9/0019* (2013.01); *A61K 9/0095* (2013.01); *A61K 31/155* (2013.01); *A61K 31/235* (2013.01); *A61K 31/341* (2013.01); *A61K 31/4406* (2013.01); *A61K 31/4439* (2013.01); *A61K 31/4465* (2013.01); *A61K 31/4725* (2013.01); *A61K 31/495* (2013.01); *A61K 31/505* (2013.01); *A61K 31/5375* (2013.01); *A61K 31/54* (2013.01); *A61K 38/26* (2013.01); *A61K 45/06* (2013.01); *A61K 47/20* (2013.01); *A61K 47/26* (2013.01); *A61K 47/40* (2013.01); *A61K 47/48969* (2013.01); *B82Y 5/00* (2013.01); *C07C 229/14* (2013.01); *C07C 233/47* (2013.01); *C07C 233/51* (2013.01); *C07C 233/81* (2013.01); *C07C 233/83* (2013.01); *C07C 235/12* (2013.01); *C07C 235/38* (2013.01); *C07C 235/48* (2013.01); *C07C 237/22* (2013.01); *C07C 237/36* (2013.01); *C07C 237/42* (2013.01); *C07C 255/57* (2013.01); *C07C 271/28* (2013.01); *C07C 275/42* (2013.01); *C07C 311/08* (2013.01); *C07C 311/13* (2013.01); *C07C 311/21* (2013.01); *C07C 311/29* (2013.01); *C07C 311/48* (2013.01); *C07C 317/28* (2013.01); *C07C 317/44* (2013.01); *C07C 323/62* (2013.01); *C07D 207/267* (2013.01); *C07D 209/08* (2013.01); *C07D 211/14* (2013.01); *C07D 211/34* (2013.01); *C07D 211/62* (2013.01); *C07D 213/55* (2013.01); *C07D 213/65* (2013.01); *C07D 213/79* (2013.01); *C07D 213/80* (2013.01); *C07D 213/81* (2013.01); *C07D 213/82* (2013.01); *C07D 215/48* (2013.01); *C07D 217/02* (2013.01); *C07D 231/12* (2013.01); *C07D 233/60* (2013.01); *C07D 235/06* (2013.01);
(Continued)

(58) Field of Classification Search
CPC .................................................. A61K 31/4245
See application file for complete search history.

(56) References Cited

U.S. PATENT DOCUMENTS 4,004,008 A 1/1977 Makovec et al.
4,067,726 A 1/1978 Sasse et al.
(Continued)

FOREIGN PATENT DOCUMENTS

EP  1 477 482 A1  11/2004
EP  1 700 850 A1   9/2006
(Continued)

OTHER PUBLICATIONS

Banker et al., "Modern Pharmaceutics," Third Edition, Marcel Dekker, Inc., pp. 451 and 596, 1996. (3 pages).
(Continued)

*Primary Examiner* — Bruck Kifle
(74) *Attorney, Agent, or Firm* — Seed IP Law Group LLP

(57) ABSTRACT

Compounds that bind the glucagon-like peptide 1 (GLP-1) receptor, methods of their synthesis, methods of their therapeutic and/or prophylactic use, and methods of their use in stabilizing GLP-1 receptor in vitro for crystallization of the GLP-1 receptor are provided. Certain compounds may have activity as modulators or potentiators with respect to glucagon receptor, GIP receptor, GLP-1 and GLP-2 receptors, and PTH receptor on their own or in the presence of receptor ligands such as GIP(1-42), PTH(1-34), Glucagon(1-29), GLP-2(1-33), GLP-1(7-36), GLP-1(9-36), oxyntomodulin and exendin variants.

8 Claims, No Drawings

Related U.S. Application Data

(60) Provisional application No. 61/491,446, filed on May 31, 2011, provisional application No. 61/535,750, filed on Sep. 16, 2011, provisional application No. 61/569,759, filed on Dec. 12, 2011.

(51) Int. Cl.

| | |
|---|---|
| A61K 47/20 | (2006.01) |
| A61K 47/26 | (2006.01) |
| A61K 47/40 | (2006.01) |
| A61K 47/48 | (2006.01) |
| A61K 45/06 | (2006.01) |
| A61K 31/155 | (2006.01) |
| A61K 38/26 | (2006.01) |
| C07C 255/57 | (2006.01) |
| C07D 213/79 | (2006.01) |
| C07D 213/80 | (2006.01) |
| C07D 213/81 | (2006.01) |
| C07D 213/82 | (2006.01) |
| C07D 309/06 | (2006.01) |
| C07D 309/08 | (2006.01) |
| C07D 311/16 | (2006.01) |
| C07C 271/28 | (2006.01) |
| C07D 215/48 | (2006.01) |
| C07D 217/02 | (2006.01) |
| C07C 275/42 | (2006.01) |
| C07D 317/68 | (2006.01) |
| C07D 231/12 | (2006.01) |
| C07D 333/38 | (2006.01) |
| C07D 233/60 | (2006.01) |
| C07C 311/08 | (2006.01) |
| C07C 311/13 | (2006.01) |
| C07C 311/21 | (2006.01) |
| C07D 235/06 | (2006.01) |
| C07C 311/29 | (2006.01) |
| C07D 235/12 | (2006.01) |
| C07D 235/18 | (2006.01) |
| C07C 311/48 | (2006.01) |
| C07D 239/26 | (2006.01) |
| C07D 239/28 | (2006.01) |
| C07C 317/28 | (2006.01) |
| C07C 317/44 | (2006.01) |
| C07D 239/74 | (2006.01) |
| C07D 413/04 | (2006.01) |
| C07D 239/91 | (2006.01) |
| C07D 413/12 | (2006.01) |
| C07D 241/42 | (2006.01) |
| C07D 241/44 | (2006.01) |
| C07D 417/12 | (2006.01) |
| C07C 323/62 | (2006.01) |
| C07C 229/14 | (2006.01) |
| C07D 249/08 | (2006.01) |
| C07D 257/04 | (2006.01) |
| C07C 233/47 | (2006.01) |
| C07C 233/51 | (2006.01) |
| C07D 261/18 | (2006.01) |
| C07C 233/81 | (2006.01) |
| C07C 233/83 | (2006.01) |
| C07C 235/12 | (2006.01) |
| C07D 263/32 | (2006.01) |
| C07C 235/38 | (2006.01) |
| C07D 263/34 | (2006.01) |
| C07C 235/48 | (2006.01) |
| C07D 263/48 | (2006.01) |
| C07D 263/57 | (2006.01) |
| C07C 237/22 | (2006.01) |
| C07C 237/36 | (2006.01) |
| C07C 237/42 | (2006.01) |
| C07D 271/06 | (2006.01) |
| C07D 271/07 | (2006.01) |
| C07D 271/107 | (2006.01) |
| C07D 207/267 | (2006.01) |
| C07D 277/30 | (2006.01) |
| C07D 209/08 | (2006.01) |
| C07D 277/56 | (2006.01) |
| C07D 277/66 | (2006.01) |
| C07D 279/12 | (2006.01) |
| C07D 211/14 | (2006.01) |
| C07D 211/34 | (2006.01) |
| C07D 211/62 | (2006.01) |
| C07D 295/15 | (2006.01) |
| C07D 295/155 | (2006.01) |
| C07D 295/205 | (2006.01) |
| C07D 213/55 | (2006.01) |
| C07D 213/65 | (2006.01) |
| C07D 307/24 | (2006.01) |
| C07D 307/54 | (2006.01) |
| C07D 307/68 | (2006.01) |
| C07D 307/79 | (2006.01) |
| C08B 37/16 | (2006.01) |
| C08L 5/16 | (2006.01) |
| B82Y 5/00 | (2011.01) |
| A61K 31/235 | (2006.01) |
| A61K 31/341 | (2006.01) |
| A61K 31/4406 | (2006.01) |
| A61K 31/4465 | (2006.01) |
| A61K 31/495 | (2006.01) |
| A61K 31/505 | (2006.01) |
| A61K 31/5375 | (2006.01) |
| A61K 31/54 | (2006.01) |
| C07D 295/24 | (2006.01) |
| A61K 31/4439 | (2006.01) |
| A61K 31/4725 | (2006.01) |

(52) U.S. Cl.
CPC ......... *C07D 235/12* (2013.01); *C07D 235/18* (2013.01); *C07D 239/26* (2013.01); *C07D 239/28* (2013.01); *C07D 239/74* (2013.01); *C07D 239/91* (2013.01); *C07D 241/42* (2013.01); *C07D 241/44* (2013.01); *C07D 249/08* (2013.01); *C07D 257/04* (2013.01); *C07D 261/18* (2013.01); *C07D 263/32* (2013.01); *C07D 263/34* (2013.01); *C07D 263/48* (2013.01); *C07D 263/57* (2013.01); *C07D 271/06* (2013.01); *C07D 271/07* (2013.01); *C07D 271/107* (2013.01); *C07D 277/30* (2013.01); *C07D 277/56* (2013.01); *C07D 277/66* (2013.01); *C07D 279/12* (2013.01); *C07D 295/15* (2013.01); *C07D 295/155* (2013.01); *C07D 295/205* (2013.01); *C07D 295/24* (2013.01); *C07D 307/24* (2013.01); *C07D 307/54* (2013.01); *C07D 307/68* (2013.01); *C07D 307/79* (2013.01); *C07D 309/06* (2013.01); *C07D 309/08* (2013.01); *C07D 311/16* (2013.01); *C07D 317/68* (2013.01); *C07D 333/38* (2013.01); *C07D 413/04* (2013.01); *C07D 413/12* (2013.01); *C07D 417/12* (2013.01); *C08B 37/0015* (2013.01); *C08L 5/16* (2013.01); *C07C 2101/04* (2013.01); *C07C 2101/08* (2013.01); *C07C 2101/14* (2013.01)

(56) References Cited

U.S. PATENT DOCUMENTS

| | | |
|---|---|---|
| 5,424,286 A | 6/1995 | Eng |
| 6,174,905 B1 | 1/2001 | Suzuki et al. |
| 6,191,171 B1 | 2/2001 | DeLaszlo et al. |
| 6,583,139 B1 | 6/2003 | Thorsett et al. |
| 6,902,744 B1 | 6/2005 | Kolterman et al. |
| 7,297,761 B2 | 11/2007 | Beeley et al. |
| 7,368,427 B1 | 5/2008 | Dong et al. |
| 7,825,139 B2 | 11/2010 | Campbell et al. |
| 8,501,982 B2 | 8/2013 | Boehm et al. |
| 8,778,923 B2 | 7/2014 | Boehm et al. |
| 8,816,121 B2 | 8/2014 | Boehm et al. |
| 9,260,427 B2 | 2/2016 | Boehm et al. |
| 9,278,910 B2 | 3/2016 | Boehm et al. |
| 2001/0031772 A1 | 10/2001 | Schoenafinger et al. |
| 2004/0152750 A1 | 8/2004 | Kodra et al. |
| 2005/0222141 A1 | 10/2005 | Sagi et al. |
| 2007/0276034 A1 | 11/2007 | Esposito et al. |
| 2008/0300193 A1 | 12/2008 | Ahn et al. |
| 2010/0292143 A1 | 11/2010 | Bhuniya et al. |
| 2011/0306542 A1 | 12/2011 | Boehm et al. |
| 2013/0178420 A1 | 7/2013 | Boehm et al. |
| 2014/0031290 A1 | 1/2014 | Boehm et al. |
| 2014/0336185 A1 | 11/2014 | Boehm et al. |
| 2015/0011527 A1 | 1/2015 | Boehm et al. |
| 2015/0038416 A1 | 2/2015 | Boehm et al. |
| 2016/0038487 A1 | 2/2016 | Boehm et al. |

FOREIGN PATENT DOCUMENTS

| | | |
|---|---|---|
| JP | 2003/525931 A | 9/2003 |
| JP | 2006-527233 A | 11/2006 |
| JP | 2009-102360 A | 5/2009 |
| JP | 2009-542752 A | 12/2009 |
| JP | 2010-180234 A | 8/2010 |
| WO | 99/06437 A1 | 2/1999 |
| WO | 99/10312 A1 | 3/1999 |
| WO | 01/21602 A1 | 3/2001 |
| WO | 01/66531 A1 | 9/2001 |
| WO | 03/048158 A1 | 6/2003 |
| WO | 2004/022561 A1 | 3/2004 |
| WO | 2004/110983 A2 | 12/2004 |
| WO | 2005/077915 A1 | 8/2005 |
| WO | 2006/117743 A1 | 11/2006 |
| WO | 2006/127595 A1 | 11/2006 |
| WO | 2008/006561 A1 | 1/2008 |
| WO | 2011/094890 A1 | 8/2011 |
| WO | 2011/097300 A1 | 8/2011 |
| WO | 2011/156655 A2 | 12/2011 |
| WO | 2012/166951 A1 | 12/2012 |
| WO | 2013/090454 A2 | 6/2013 |
| WO | 2014/201172 A1 | 12/2014 |

OTHER PUBLICATIONS

Bundgaard, "Design of Prodrugs," Elsevier, pp. 1, 1985. (3 pages).

Devasthale et al., "Discovery of tertiary aminoacids as dual PPARα/γ agonists-I," *Bioorganic & Medicinal Chemistry Letters* *17*: 2312-2316, 2007.

International Search Report and Written Opinion of the International Searching Authority, mailed Dec. 1, 2011, for International Application No. PCT/US11/39873, 9 pages.

Knudsen et al., "Small-molecule agonists for the glucagon-like peptide 1 receptor," *PNAS* *104*(3):937-942, 2007.

Luo et al., "A new strategy for solid phase synthesis of a secondary amide library using sulfonamide linker via radical traceless cleavage," *Molecular Diversity* 6:33-41, 2003.

Notice of Reasons for Rejection, mailed Nov. 26, 2015, for Japanese Application No. 2014-513706, 14 pages. (with English Translation).

Pubchem Compound, "N-benzyl-4-[(2-phenylacetyl)amino]benzamide," CID 2980472, Jul. 30, 2005, 6 pages.

Pubchem Compound, "SMR000154147," CID 4884981, Sep. 17, 2005, 6 pages.

Reid, "Practical Use of Glucagon-Like Peptide-1 Receptor Agonist Therapy in Primary Care," *Clinical Diabetes* *31*(4):148-157, 2013.

Silverman, "The Organic Chemistry of Drug Design and Drug Action," Academic Press, Inc., pp. 352-400, 1992. (51 pages).

Thorsett et al., "Preparation of N-sulfonylproline dipeptide derivatives and analogs as inhibitors of leukocyte adhesion mediated by VLA-4," Accession No. 1999:113712, 1999, 3 pages.

Thorsett et al., "Preparation of N-sulfonylated dipeptide derivatives as inhibitors of leukocyte adhesion mediated by VLA-4," Accession No. 2003:485719, 2003, 3 pages.

Underwood et al., "Crystal Structure of Glucagon-like Peptide-1 in Complex with the Extracellular Domain of the Glucagon-like Peptide-1 Receptor," *The Journal of Biological Chemistry* *285*(1):723-730, 2010.

West, "Solid State Chemistry and Its Applications," John Wiley & Sons, 1988, pp. 358 and 365. (3 pages).

Wolff, "Burger's Medicinal Chemistry—Part 1—The Basis of Medicinal Chemistry," Fourth Edition, John Wiley & Sons, pp. 336-337, 1980. (4 pages).

Wolff, "Burger's Medicinal Chemistry and Drug Discovery—vol. I: Principles and Practice," Fifth Edition, John Wiley & Sons, pp. 975-977, 1995. (4 pages).

SEQUENCE LISTING

<160> NUMBER OF SEQ ID NOS: 4

<210> SEQ ID NO 1
<211> LENGTH: 30
<212> TYPE: PRT
<213> ORGANISM: Artificial Sequence
<220> FEATURE:
<223> OTHER INFORMATION: Synthetic Peptide sequence GLP-1 (7-36)
     purchased from GenScript

<400> SEQUENCE: 1

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg
            20                  25                  30

<210> SEQ ID NO 2
<211> LENGTH: 28
<212> TYPE: PRT
<213> ORGANISM: Artificial Sequence
<220> FEATURE:
<223> OTHER INFORMATION: Synthetic peptide sequence GLP-1 (9-36)
     purchased from Biopeptide Co. Inc.

<400> SEQUENCE: 2

Glu Gly Thr Phe Thr Ser Asp Val Ser Ser Tyr Leu Glu Gly Gln Ala
 1               5                  10                  15

Ala Lys Glu Phe Ile Ala Trp Leu Val Lys Gly Arg
            20                  25

<210> SEQ ID NO 3
<211> LENGTH: 29
<212> TYPE: PRT
<213> ORGANISM: Artificial Sequence
<220> FEATURE:
<223> OTHER INFORMATION: Synthetic peptide sequence RP-101868 purchased
     from Biopeptide Co. Inc.
<220> FEATURE:
<221> NAME/KEY: VARIANT
<222> LOCATION: (8)...(8)
<223> OTHER INFORMATION: Xaa = Nle

<400> SEQUENCE: 3

Gly Glu Gly Thr Phe Thr Ser Xaa Leu Ser Lys Gln Met Glu Glu Glu
 1               5                  10                  15

Ala Val Arg Leu Phe Ile Glu Trp Leu Lys Asn Gly Arg
            20                  25

<210> SEQ ID NO 4
<211> LENGTH: 31
<212> TYPE: PRT
<213> ORGANISM: Artificial Sequence
<220> FEATURE:
<223> OTHER INFORMATION: GLP-1 agonist liraglutide from VICTOZA

<400> SEQUENCE: 4

His Ala Glu Gly Thr Phe Thr Ser Asp Val Ser Ser Tyr Leu Glu Gly
 1               5                  10                  15

Gln Ala Ala Lys Glu Phe Ile Ala Trp Lys Val Arg Gly Arg Gly
            20                  25                  30

GLP-1 RECEPTOR STABILIZERS AND MODULATORS

CROSS-REFERENCE TO RELATED APPLICATIONS

This application claims the benefit of priority application Ser. No. 61/491,446 filed on May 31, 2011, Application Ser. No. 61/535,750 filed on Sep. 16, 2011, Application Ser. No. 61/569,759 filed on Dec. 12, 2011, PCT Application Serial No. US2012/040250 filed on May 31, 2012, and application Ser. No. 14/122,176 filed Feb. 28, 2014 all of which are expressly incorporated herein by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 800059_406D1_SEQUENCE_LISTING.txt. The text file is 2.3 KB, was created on May 31, 2016, and is being submitted electronically via EFS-Web.

FIELD OF THE INVENTION

The invention relates to compounds that bind the glucagon-like peptide 1 (GLP-1) receptor, methods of their synthesis, methods of their therapeutic and/or prophylactic use, and methods of their use in stabilizing GLP-1 receptor in vitro for crystallization of the GLP-1 receptor. Particularly, the invention relates to compounds that are modulators of the GLP-1 receptors and also compounds capable of inducing a stabilizing effect on the receptor for use in structural analyses of the GLP-1 receptor. The present invention is directed to compounds adapted to act as stabilizers, modulators or potentiators of certain Class B GPCRs. These compounds may have activity with respect to glucagon receptor, GIP receptor, GLP-1 and GLP-2 receptors, and PTH receptor on their own or in the presence of receptor ligands, which include but are not limited to GIP(1-42), PTH(1-34), Glucagon(1-29), GLP-2(1-33), GLP-1(7-36), GLP-1(9-36), oxyntomodulin and exendin variants.

BACKGROUND

Glucagon-like peptide 1 receptor (GLP-1R) belongs to Family B1 of the seven-transmembrane G protein-coupled receptors, and its natural agonist ligand is the peptide hormone glucagon-like peptide-1 (GLP-1). GLP-1 is a peptide hormone arising by its alternative enzymatic cleavage from proglucagon, the prohormone precursor for GLP-1, which is highly expressed in enteroendocrine cells of the intestine, the alpha cells of the endocrine pancreas (islets of Langerhans), and the brain (Kieffer T. J. and Habener, J. F. Endocrin. Rev. 20:876-913 (1999); Drucker, D. J., Endocrinology 142:521-7 (2001); Holst, J. J., Diabetes Metab. Res. Rev. 18:430-41 (2002)). The initial actions of GLP-1 observed were on the insulin-producing cells of the islets, where it stimulates glucose-dependent insulin secretion. Subsequently, multiple additional antidiabetogenic actions of GLP-1 were discovered including the stimulation of the growth and inhibition of the apoptosis of pancreatic beta cells (Drucker, D. J., Endocrinology 144:5145-8 (2003); Holz, G. G. and Chepurny O. G., Curr. Med. Chem. 10:2471-83 (2003); List, J. F. and Habener, J. F., Am. J. Physiol. Endocrinol. Metab. 286:E875-81 (2004)).

On activation, GLP-1 receptors couple to the a subunit of G protein, with subsequent activation of adenylate cyclase and increase of cAMP levels, thereby potentiating glucose-stimulated insulin secretion. Therefore, GLP-1 is an attractive therapeutic to lower blood glucose and preserve the β-cells of the pancreas of diabetic patients. Glucagon has been used for decades in medical practice within diabetes and several glucagon-like peptides are being developed for various therapeutic indications. GLP-1 analogs and derivatives are being developed for the treatment for patients suffering from diabetes.

As it has been well established in the field of protein crystallography that the monodispersity of protein samples is a major determinant of success in crystallization, development of compounds that are capable of maintaining the GLP-1 receptor in a monodisperse, functional state throughout purification, concentration and crystallization trials is a crucial preliminary step in the structural determination effort of the GLP-1 receptor. Disclosed herein are compounds that are capable of inducing such stabilizing effects on the GLP-1 receptor. The compounds of the disclosure are screened for their ability to support structural determination of the GLP-1 receptor to high resolution, thus allowing an additional dimension of diversity in crystallization. The compounds of the disclosure enable drug development through the structural solution of clinically relevant GPCR targets. Structural coordinates can be leveraged as a discovery platform for generating novel chemical leads through virtual ligand screening followed by in vitro screening and chemical optimization of hits for standard drug-like properties and efficacy. In addition, it is well known in the field of structural biology that the initial structural solution of a given target enables subsequent structures with less favorable ligands due to the growth in knowledge and restriction of crystallization space that must be screened.

SUMMARY OF THE INVENTION

The present invention is directed to compounds adapted to act as stabilizers, potentiators or modulators of GLP-1 receptor; methods of their preparation and methods of their use, such as in treatment of a malcondition mediated by GLP-1 receptor activation, or when modulation or potentiation of GLP-1 receptor is medically indicated.

Certain embodiments of the present invention comprise a compound having the structure of Formula III

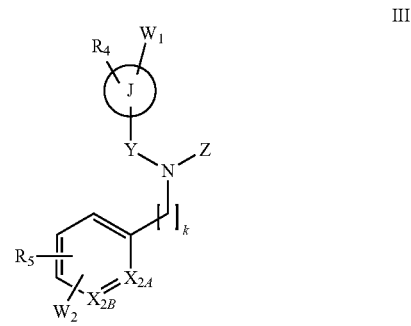

or a pharmaceutically acceptable isomer, isotope, enantiomer, salt, ester, prodrug, hydrate or solvate thereof, wherein J has a structure of

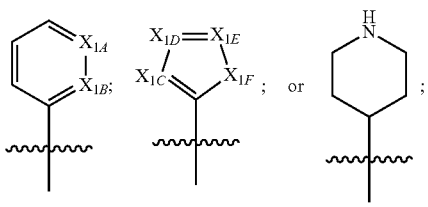

each of $X_{1A}$, $X_{1B}$, $X_{2A}$, $X_{2B}$ is C, CH or N, provided that no more than one of $X_{1A}$ and $X_{1B}$ is N and no more than one of $X_{2A}$ and $X_{2B}$ is N;
each of $X_{1C}$, $X_{1D}$, and $X_{1E}$ is CH or N;
$X_{1F}$ is O or S;
each $R_4$ is independently H, alkyl, alkoxy, or alkyl substituted with one or more $R_{43}$, halogen, perhaloalkyl, perhaloalkoxy, —CN, —$OR_{40}$, or —$NR_{41}R_{42}$;
$W_1$ is —$(CR_aR_b)_{i1}$-$L_1$-$(CR_aR_b)_{j1}$—$R_1$ or $R_4$; or $W_1$ and $R_4$ taken together comprise a 5- or 6-membered heterocyclic ring fused with the ring to which $W_1$ and $R_4$ are attached and having one, two or three heteroatoms where each such heteroatom is independently selected from O, N, and S, and where any ring atom of such heterocyclic ring may be optionally substituted with one or more-$L_1$-$R_{13}$ or $R_{13}$; or $W_1$ comprises a 5- or 6-membered heterocyclic ring fused with a phenyl ring and having one, two or three heteroatoms where each such heteroatom is independently selected from O, N, and S, and where any ring atom of such fused heterocyclic ring and phenyl ring moiety may be optionally substituted with one or more $R_{14}$; $L_1$ is —O—, —C(O)—, —OC(O)—, —C(O)O—, —$NR_{10}$—, —C(O)$NR_{10}$—, —N($R_{10}$)—C(O)—, —N($R_{10}$)—$(CH_2)_n$—C(O)—, —N($R_{10}$)—C(O)—N($R_{10}$)—, —N($R_{10}$)—S($O_2$)—, —S($O_2$)—$NR_{10}$—, or —N(S($O_2$)—$(CH_2)_n$—$R_1$)$_2$; $R_1$ is $R_{13}$, —O—$(CH_2)_n$—$R_{13}$, or $R_{10}$;
each $R_{10}$, $R_{11}$ and $R_{12}$ is independently H or alkyl;
$R_{13}$ is cycloalkyl, heterocycloalkyl, aryl, or heteroaryl, or a fused bicycle of any two of such ring moieties, or $R_{13}$ and $R_{10}$ taken together with the N atom to which they are attached form a heterocyclic ring, where any ring atom of $R_{13}$ may be optionally substituted with one or more $R_{14}$ or $R_{15}$;
each $R_{14}$ is independently H, alkyl, halo, hydroxy, cyano, alkoxy, perhaloalkyl, and perhaloalkoxy, —$OR_{10}$, —$(CH_2)_n$—$COOR_{10}$, —$SR_{10}$, —$SO_2R_{10}$, —$(CH_2)_n$—$NR_{11}R_{12}$, —NHCO$(CH_2)_n$—$R_{12}$, —N($R_{11}$)CO$(CH_2)_n$—$R_{12}$, or —NH$(CH_2)_n$—$R_{12}$; $R_{15}$ is cycloalkyl, heterocycloalkyl, aryl, or heteroaryl, or a fused bicycle of any two of such ring moieties, where any ring atom of $R_{15}$ may be optionally substituted with one or more $R_{14}$;
each $R_5$ is independently H, alkyl, alkoxy, alkyl substituted with one or more $R_{53}$, halogen, perhaloalkyl, perhaloalkoxy, —CN, —$OR_{50}$, or —$NR_{51}R_{52}$;
$W_2$ is —$(CR_aR_b)_{i2}L_2$-$(CR_aR_b)_{j2}$—$R_2$ or $R_5$; or $W_2$ and $R_5$ taken together comprise a 5- or 6-membered heterocyclic ring fused with the ring to which $W_2$ and $R_5$ are attached and having one, two or three heteroatoms where each such heteroatom is independently selected from O, N, and S, and where any ring atom of such heterocyclic ring may be optionally substituted with one or more —$(CR_aR_b)_{i2}$-$L_2$-$(CR_aR_b)_{j2}$—$R_2$ or $R_2$; or $W_2$ comprises a 5- or 6-membered heterocyclic ring fused with a phenyl ring and having one, two or three heteroatoms where each such heteroatom is independently selected from O, N, and S, and where any ring atom of such heterocyclic ring or phenyl ring may be optionally substituted with one or more of $R_{24}$ and wherein one ring atom of such fused ring moiety is optionally substituted with $L_3$-$R_{25}$;
$L_2$ is —O—, —C(O)—, —OC(O)—, —C(O)O—, —$NR_{20}$—, —C(O)$NR_{20}$—, —N($R_{20}$)—C(O)—, —N($R_{20}$)—S($O_2$)—, —S($O_2$)—$NR_{20}$—, —$SO_2$—, —O$(CH_2)_q$CO—, —CO$(CH_2)_q$O—, null, oxazolyl, oxadiazolyl, triazolyl, pyrazolyl, or pyrimidinyl;
Each $R_a$ and $R_b$ is independently H, hydroxy, methyl, or both $R_a$ and $R_b$ attached to the same carbon are, taken together, oxo, or cycloalkyl;
$R_2$ is $R_{26}$, —O—$(CH_2)_n$—$R_{26}$, $R_{23}$ or $L_4$-$R_{23}$;
$L_4$ is —O—$(CH_2)_n$—, —C≡C—, —C(O)$NR_{20}$—$(CH_2)_n$—, —N($R_{20}$)—C(O)—$(CH_2)_n$—, —N($R_{20}$)—S($O_2$)—, —S($O_2$)—$NR_{20}$—, or cyclopropylene;
each $R_{20}$ is independently H or alkyl;
$R_{23}$ is cycloalkyl, heterocycloalkyl, aryl, or heteroaryl, or a fused bicycle of any two of such ring moieties, or $R_{23}$ and $R_{20}$ taken together with the N atom to which they are attached form a heterocyclic ring optionally fused with aryl or heteroaryl, where any ring atom of $R_{23}$ may be optionally substituted with one or more of $R_{24}$ and wherein one ring atom of $R_{23}$ is optionally substituted with $L_3$-$R_{25}$;
each $R_{24}$ is independently selected from H, halo, alkyl, hydroxy, oxo, cyano, alkoxy, perhaloalkyl, perhaloalkoxy, nitro or amino, —O—$(CH_2)_n$—$R_{21}$, —$(CH_2)_n$—O—$R_{21}$, —O—$(CH_2)_n$—O—$R_{21}$, —$(CH_2)_n$—$NR_{21}R_{22}$, —$(CH_2)_n$—N($R_{21}$)CO$(CH_2)_n$—$R_{21}$, —$(CH_2)_n$—N($R_{21}$)$SO_2$$(CH_2)_n$—$R_{21}$, —$(CH_2)_n$—$SO_2$—N($R_{21}$)—$(CH_2)_n$—$R_{21}$, —$(CH_2)_n$—CO$(CH_2)_n$—$R_{21}$, —$(CH_2)_m$—COO—$R_{21}$, —O—$(CH_2)_n$—COO—$R_{21}$ or —$(CH_2)_m$—OCO—$R_{21}$;
each $R_{21}$ and $R_{22}$ is independently H or alkyl, —$(CH_2)_n$—COOH, or two taken together with the nitrogen atom to which they are attached can form a 3- to 7-membered heterocyclic ring;
$L_3$ is null, —O—, —$(CH_2)_n$—O—$(CH_2)_n$—, —$(CH_2)_n$—$NR_{20}$—$(CH_2)_n$—;
each $R_{25}$ is independently cycloalkyl, heterocycloalkyl, aryl, or heteroaryl, or a fused bicycle of any two of such ring moieties 1, where any ring atom of $R_{25}$ may be optionally substituted with one or more of $R_{24}$;
each $R_{26}$ is independently selected from H, alkyl, alkoxy, oxo, hydroxy, and hydroxy substituted alkyl;
Y is —C(O)—, —$CH_2$—, —C(O)—$CH_2$—, or —$CH_2$—C(O)—;
Z is —$(CR_aR_b)_n$—C(O)—$R_3$, —$(CR_aR_b)_n$—$R_3$, —$R_{34}$—C(O)—$R_3$ or H;
$R_3$ is —$OR_{30}$, —$NR_{31}R_{32}$ or —(CO)$NHSO_2R_{30}$; each $R_{30}$ is independently H or alkyl; each $R_{31}$ and $R_{32}$ is independently H or $C_1$-$C_6$ alkyl optionally substituted with one or more $R_{33}$, or two taken together with the N atom to which they are attached can form a 3- to 7-membered heterocyclic ring; each $R_{33}$ is independently halo, hydroxyl, alkoxy, perhaloalkyl, perhaloalkoxy, carboxyl, —COO—$R_{30}$, or —$OR_{30}$; $R_{34}$ is cycloalkyl, heterocycloalkyl, aryl, or heteroaryl; where any ring atom of $R_{34}$ may be optionally substituted with one or more $R_{35}$; each $R_{35}$ is independently H, alkyl, halo, hydroxy, cyano, alkoxy or perhaloalkyl;

each $R_{40}$ and $R_{50}$ is independently H or alkyl; each $R_{41}$ and $R_{42}$ is independently H or alkyl, —$(CH_2)_n$—COO—$R_{40}$, —C(O)—$R_{40}$, aryl, heteroaryl, or two taken together with the N atom to which they are attached can form a 3- to 7-membered heterocyclic ring; each $R_{51}$ and $R_{52}$ is independently H or alkyl, —$(CH_2)_n$—COO—$R_{50}$, —C(O)—$R_{50}$, aryl, heteroaryl, or two taken together with the N atom to which they are attached can form a 3- to 7-membered heterocyclic ring; each $R_{43}$ is independently H, halo, hydroxyl, —$NR_{41}R_{42}$, or alkoxy; each $R_{53}$ is independently H, halo, hydroxyl, —$NR_{51}R_{52}$, or alkoxy;

k is 0, 1, 2, 3 or 4;
each m is independently 0 or 1;
each n is independently 0, 1, 2, 3 or 4;
each q is independently 1 or 2; and
each i1, i2, j1 and j2 is independently 0, 1, 2, 3 or 4.

In certain embodiments, a pharmaceutical composition comprising a compound of the invention together with at least one pharmaceutically acceptable carrier, diluent or excipient is provided.

In certain embodiments, a method of use of a compound of the invention comprising preparation of a medicament is provided.

In certain embodiments, the invention provides a pharmaceutical combination comprising a compound of the invention and a second medicament. In various such embodiments, the second medicament is an agonist or modulator for glucagon receptor, GIP receptor, GLP-2 receptor, or PTH receptor, or glucagon-like peptide 1 (GLP-1) receptor. In various such embodiments, the second medicament is exenatide, liraglutide, taspoglutide, albiglutide, or lixisenatide or other insulin regulating peptide. In various such embodiments, the second medicament is a DPPIV inhibitor. In various such embodiments, the second medicament is medically indicated for the treatment of type II diabetes. In various such embodiments, the second embodiment is an insulin secretagogue such as a sulfonylurea (e.g., Carbutamide, Acetohexamide, Chlorpropamide, Tolbutamide, Tolazamide, Glipizide, Gliclazide, Glibenclamide (glyburide), Gliquidone, Glyclopyramide, and Glimepiride) or a meglitinide; a hepatic glucose reducer (e.g., metformin); a peroxisome proliferator-activated receptor (PPAR) agonist (e.g., a thiazolidinedione or glitazone) or other insulin sensitizer; a glucose absorption blocker (e.g., alpha-glucosidase inhibitors); incretin mimetics (e.g., GLP1R agonists) or an incretin enhancer or GPR119 agonist.

In certain embodiments, a method of activation, potentiation or agonism of a GLP-1 receptor is provided comprising contacting the receptor with a compound, pharmaceutical composition or pharmaceutical combination of the invention.

In certain embodiments, a method is provided for treatment of a malcondition in a subject for which activation, potentiation or agonism of a GLP-1 receptor is medically indicated where such method comprises administering to such subject a compound, pharmaceutical composition or pharmaceutical combination of the invention. In various such embodiments, selective activation, potentiation or agonism of a GLP-1 receptor, is medically indicated. In various such embodiments, the malcondition comprises type I diabetes, type II diabetes, gestational diabetes, obesity, excessive appetite, insufficient satiety, or metabolic disorder.

In certain embodiments, the invention provides methods for synthesis of certain compounds including compounds of the invention. In certain other embodiments, the invention provides certain intermediate compounds associated with such methods of synthesis.

In certain embodiments, compounds for enhancing the stabilization of a GLP-1 receptor are provided. In certain embodiments, methods for enhancing the stabilizing of a GLP-1 receptor in structural biology studies are provided through the use of compounds of the invention.

DETAILED DESCRIPTION OF THE INVENTION

Certain embodiments of the present invention comprise a compound having the structure of Formula I, II, III, IV, or V:

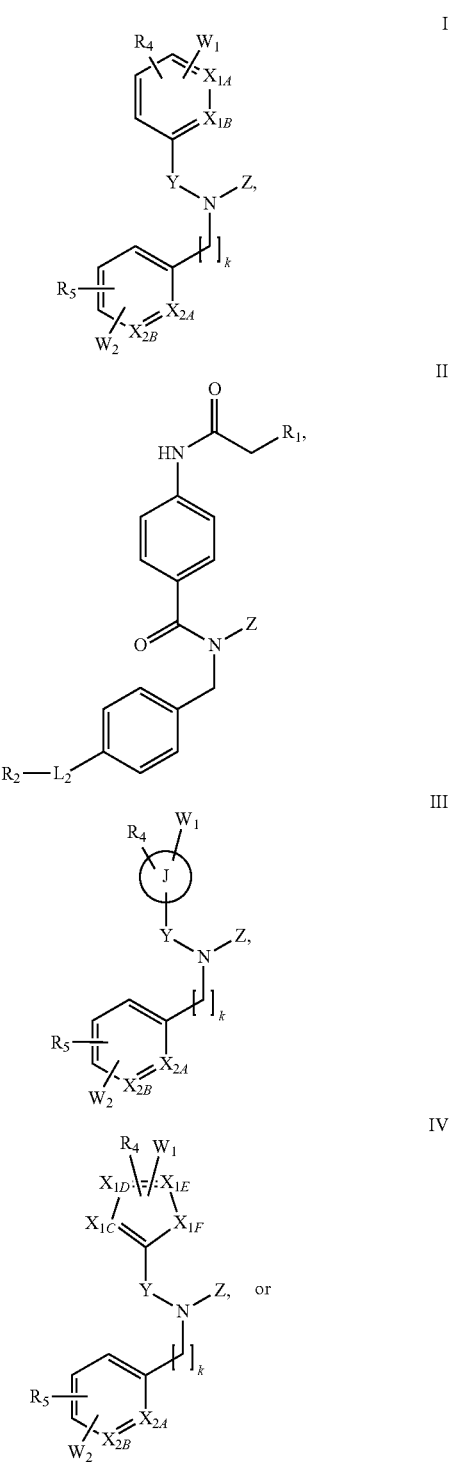

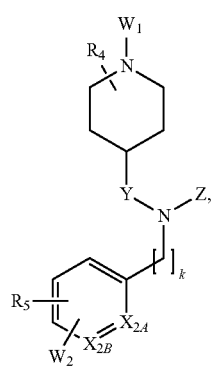

or a pharmaceutically acceptable isomer, isotope, enantiomer, salt, ester, prodrug, hydrate or solvate thereof, wherein J has a structure of

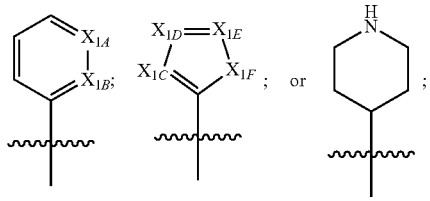

each of $X_{1A}$, $X_{1B}$, $X_{2A}$, $X_{2B}$ is C, CH or N, provided that no more than one of $X_{1A}$ and $X_{1B}$ is N and no more than one of $X_{2A}$ and $X_{2B}$ is N;

each of $X_{1C}$, $X_{1D}$, and $X_{1E}$ is C, CH or N;

$X_{1F}$ is O or S;

each $R_4$ is independently H, alkyl, alkoxy, or alkyl substituted with one or more $R_{43}$, halogen, perhaloalkyl, perhaloalkoxy, —CN, —$OR_{40}$, or —$NR_{41}R_{42}$;

$W_1$ is —$(CR_aR_b)_{i1}$-$L_1$-$(CR_aR_b)_{j1}$—$R_1$ or $R_4$; or $W_1$ and $R_4$ taken together comprise a 5- or 6-membered heterocyclic ring fused with the ring to which $W_1$ and $R_4$ are attached and having one, two or three heteroatoms where each such heteroatom is independently selected from O, N, and S, and where any ring atom of such heterocyclic ring may be optionally substituted with one or more -$L_1$-$R_{13}$ or $R_{13}$; or $W_1$ comprises a 5- or 6-membered heterocyclic ring fused with a phenyl ring and having one, two or three heteroatoms where each such heteroatom is independently selected from O, N, and S, and where any ring atom of such fused heterocyclic ring and phenyl ring moiety may be optionally substituted with one or more $R_{14}$; $L_1$ is —O—, —C(O)—, —OC(O)—, —C(O)O—, —$NR_{10}$—, —C(O)$NR_{10}$—, —$N(R_{10})$—C(O)—, —$N(R_{10})$—$(CH_2)_n$—C(O)—, —$N(R_{10})$—C(O)—$N(R_{10})$—, —$N(R_{10})$—$S(O_2)$—, —$S(O_2)$—$NR_{10}$—, or —$N(S(O_2)$—$(CH_2)_n$—$R_1)_2$; $R_1$ is $R_{13}$, —O—$(CH_2)_n$—$R_{13}$, or $R_{10}$;

each $R_{10}$, $R_{11}$ and $R_{12}$ is independently H or alkyl;

$R_{13}$ is cycloalkyl, heterocycloalkyl, aryl, or heteroaryl, or a fused bicycle of any two of such ring moieties, or $R_{13}$ and $R_{10}$ taken together with the N atom to which they are attached form a heterocyclic ring, where any ring atom of $R_{13}$ may be optionally substituted with one or more $R_{14}$ or $R_{15}$;

each $R_{14}$ is independently H, alkyl, halo, hydroxy, cyano, alkoxy, perhaloalkyl, and perhaloalkoxy, —$OR_{10}$, —$(CH_2)_n$—$COOR_{10}$, —$SR_{10}$, —SO—$R_{10}$, —$SO_2R_{10}$, —$(CH_2)_n$—$NR_{11}R_{12}$, —NHCO$(CH_2)_n$—$R_{12}$, —$N(R_{11})CO(CH_2)_n$—$R_{12}$, or —NH$(CH_2)_n$—$R_{12}$; $R_{15}$ is cycloalkyl, heterocycloalkyl, aryl, or heteroaryl, or a fused bicycle of any two of such ring moieties, where any ring atom of $R_{15}$ may be optionally substituted with one or more $R_{14}$;

each $R_5$ is independently H, alkyl, alkoxy, alkyl substituted with one or more $R_{53}$, halogen, perhaloalkyl, perhaloalkoxy, —CN, —$OR_{50}$, or —$NR_{51}R_{52}$;

$W_2$ is —$(CR_aR_b)_{i2}$-$L_2$-$(CR_aR_b)_{j2}$—$R_2$ or $R_5$; or $W_2$ and $R_5$ taken together comprise a 5- or 6-membered heterocyclic ring fused with the ring to which $W_2$ and $R_5$ are attached and having one, two or three heteroatoms where each such heteroatom is independently selected from O, N, and S, and where any ring atom of such heterocyclic ring may be optionally substituted with one or more —$(CR_aR_b)_{i2}$-$L_2$-$(CR_aR_b)_{j2}$—$R_2$ or $R_2$; or $W_2$ comprises a 5- or 6-membered heterocyclic ring fused with a phenyl ring and having one, two or three heteroatoms where each such heteroatom is independently selected from O, N, and S, and where any ring atom of such heterocyclic ring or phenyl ring may be optionally substituted with one or more of $R_{24}$ and wherein one ring atom of such fused ring moiety is optionally substituted with $L_3$-$R_{25}$;

$L_2$ is —O—, —C(O)—, —OC(O)—, —C(O)O—, —$NR_{20}$—, —C(O)$NR_{20}$—, —$N(R_{20})$—C(O)—, —$N(R_{20})$—$S(O_2)$—, —$S(O_2)$—$NR_{20}$—, —$SO_2$—, —O$(CH_2)_q$CO—, —CO$(CH_2)_q$O—, null, oxazolyl, oxadiazolyl, triazolyl, pyrazolyl, or pyrimidinyl;

Each $R_a$ and $R_b$ is independently H, hydroxy, methyl, or both $R_a$ and $R_b$ attached to the same carbon are, taken together, oxo, or cycloalkyl;

$R_2$ is $R_{26}$, —O—$(CH_2)_n$—$R_{26}$, $R_{23}$ or $L_4$-$R_{23}$;

$L_4$ is —O—$(CH_2)_n$—, —C≡C—, —C(O)$NR_{20}$—$(CH_2)_n$—, —$N(R_{20})$—C(O)—$(CH_2)_n$—$N(R_{20})$—S$(O_2)$—, —$S(O_2)$—$NR_{20}$—, or cyclopropylene;

each $R_{20}$ is independently H or alkyl;

$R_{23}$ is cycloalkyl, heterocycloalkyl, aryl, or heteroaryl, or a fused bicycle of any two of such ring moieties, or $R_{23}$ and $R_{20}$ taken together with the N atom to which they are attached form a heterocyclic ring optionally fused with aryl or heteroaryl, where any ring atom of $R_{23}$ may be optionally substituted with one or more of $R_{24}$ and wherein one ring atom of $R_{23}$ is optionally substituted with $L_3$-$R_{25}$;

each $R_{24}$ is independently selected from H, halo, alkyl, hydoxy, oxo, cyano, alkoxy, perhaloalkyl, perhaloalkoxy, nitro or amino, —O—$(CH_2)_n$—$R_{21}$, —$(CH_2)_n$—O—$R_{21}$, —O—$(CH_2)_n$—O—$R_{21}$, —$(CH_2)R_{21}R_{22}$, —$(CH_2)_n$—$N(R_{21})CO(CH_2)_n$—$R_{21}$, —$(CH_2)_n$—$N(R_{21})SO_2(CH_2)_n$—$R_{21}$, —$(CH_2)_n$—$SO_2$—$N(R_{21})$—$(CH_2)_n$—$R_{21}$, —$(CH_2)_n$—CO$(CH_2)_n$$R_{21}$, —$(CH_2)_m$—COO—$R_{21}$, —O—$(CH_2)_n$—COO—$R_{21}$ or —$(CH_2)_m$—OCO—$R_{21}$; each $R_{21}$ and $R_{22}$ is independently H or alkyl, —$(CH_2)_n$—COOH, or two taken together with the nitrogen atom to which they are attached can form a 3- to 7-membered heterocyclic ring;

$L_3$ is null, —O—, —$(CH_2)_n$—O—$(CH_2)_n$—, —$(CH_2)_n$—$NR_{20}$—$(CH_2)_n$—;

each $R_{25}$ is independently cycloalkyl, heterocycloalkyl, aryl, or heteroaryl, or a fused bicycle of any two of such ring moieties 1, where any ring atom of $R_{25}$ may be optionally substituted with one or more of $R_{24}$;

each $R_{26}$ is independently selected from H, alkyl, alkoxy, oxo, hydroxy, and hydroxy substituted alkyl;

Y is —C(O)—, —CH$_2$—, —C(O)—CH$_2$—, or —CH$_2$—C(O)—;

Z is —(CR$_a$R$_b$)$_n$—C(O)—R$_3$, —(CR$_a$R$_b$)$_n$—R$_3$, —R$_{34}$—C(O)—R$_3$ or H;

$R_3$ is —OR$_{30}$, —NR$_{31}$R$_{32}$ or —(CO)NHSO$_2$R$_{30}$; each $R_{30}$ is independently H or alkyl; each $R_{31}$ and $R_{32}$ is independently H or C$_1$-C$_6$ alkyl optionally substituted with one or more $R_{33}$, or two taken together with the N atom to which they are attached can form a 3- to 7-membered heterocyclic ring; each $R_{33}$ is independently halo, hydroxyl, alkoxy, perhaloalkyl, perhaloalkoxy, carboxyl, —COO—R$_{30}$, or —OR$_{30}$; $R_{34}$ is cycloalkyl, heterocycloalkyl, aryl, or heteroaryl; where any ring atom of $R_{34}$ may be optionally substituted with one or more $R_{35}$; each $R_{35}$ is independently H, alkyl, halo, hydroxy, cyano, alkoxy or perhaloalkyl;

each $R_{40}$ and $R_{50}$ is independently H or alkyl; each $R_{41}$ and $R_{42}$ is independently H or alkyl, —(CH$_2$)$_n$—COO—R$_{40}$, —C(O)—R$_{40}$, aryl, heteroaryl, or two taken together with the N atom to which they are attached can form a 3- to 7-membered heterocyclic ring; each $R_{51}$ and $R_{52}$ is independently H or alkyl, —(CH$_2$)$_n$—COO—R$_{50}$, —C(O)—R$_{50}$, aryl, heteroaryl, or two taken together with the N atom to which they are attached can form a 3- to 7-membered heterocyclic ring; each $R_{43}$ is independently H, halo, hydroxyl, —NR$_{41}$R$_{42}$, or alkoxy; each $R_{53}$ is independently H, halo, hydroxyl, —NR$_{51}$R$_{52}$, or alkoxy;

k is 0, 1, 2, 3 or 4;

each m is independently 0 or 1;

each n is independently 0, 1, 2, 3 or 4;

each q is independently 1 or 2; and each i1, i2, j1 and j2 is independently 0, 1, 2, 3 or 4.

Certain embodiments of the present invention comprise a compound having the structure of Formula I or a pharmaceutically acceptable isomer, isotope, enantiomer, salt, ester, prodrug, hydrate or solvate thereof. Certain embodiments of the present invention comprise a compound having the structure of Formula II or a pharmaceutically acceptable isomer, isotope, enantiomer, salt, ester, prodrug, hydrate or solvate thereof. Certain embodiments of the present invention comprise a compound having the structure of Formula III or a pharmaceutically acceptable isomer, isotope, enantiomer, salt, ester, prodrug, hydrate or solvate thereof. Certain embodiments of the present invention comprise a compound having the structure of Formula IV or a pharmaceutically acceptable isomer, isotope, enantiomer, salt, ester, prodrug, hydrate or solvate thereof. Certain embodiments of the present invention comprise a compound having the structure of Formula V or a pharmaceutically acceptable isomer, isotope, enantiomer, salt, ester, prodrug, hydrate or solvate thereof.

$W_1$ can be attached to one of $X_{1A}$, $X_{1B}$, $X_{1C}$, $X_{1D}$ and $X_{1E}$. In certain of such embodiments the ring atom of $X_{1A}$, $X_{1B}$, $X_{1C}$, $X_{1D}$ and $X_{1E}$ to which $W_1$ is attached is C. In certain embodiments, $W_1$ is attached to a carbon atom of the 5-membered heteroaryl ring in Formula IV. In certain such embodiments, $W_1$ is attached to $X_{1E}$; and $X_{1E}$ is C.

Certain embodiments of the present invention comprise a compound having the structure of Formula I

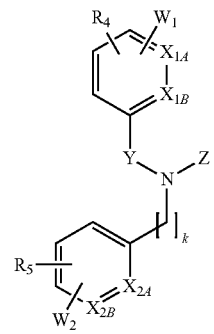

or a pharmaceutically acceptable isomer, isotope, enantiomer, salt, ester, prodrug, hydrate or solvate thereof, wherein each of $X_{1A}$, $X_{1B}$, $X_{2A}$, $X_{2B}$ is C, CH or N, provided that no more than one of $X_{1A}$ and $X_{1B}$ is N and no more than one of $X_{2A}$ and $X_{2B}$ is N;

each $R_4$ is independently H, alkyl, alkoxy, or alkyl substituted with one or more $R_{43}$, halogen, perhaloalkyl, perhaloalkoxy, —CN, —OR$_{40}$, or —NR$_{41}$R$_{42}$;

$W_1$ is —(CR$_a$R$_b$)$_{i1}$-L$_1$-(CR$_a$R$_b$)$_{j1}$—R$_1$ or $R_4$; or $W_1$ and $R_4$ taken together comprise a 5- or 6-membered heterocyclic ring fused with the ring to which $W_1$ and $R_4$ are attached and having one, two or three heteroatoms where each such heteroatom is independently selected from O, N, and S, and where any ring atom of such heterocyclic ring may be optionally substituted with one or more -L$_1$-R$_{13}$ or $R_{13}$; or $W_1$ comprises a 5- or 6-membered heterocyclic ring fused with a phenyl ring and having one, two or three heteroatoms where each such heteroatom is independently selected from O, N, and S, and where any ring atom of such fused heterocyclic ring and phenyl ring moiety may be optionally substituted with one or more $R_{14}$;

$L_1$ is —O—, —C(O)—, —OC(O)—, —C(O)O—, —C(O)NR$_{10}$—, —N(R$_{10}$)—C(O)—, —N(R$_{10}$)—(CH$_2$)$_n$—C(O)—, —N(R$_{10}$)—C(O)—N(R$_{10}$)—, —N(R$_{10}$)—S(O$_2$)—, —S(O$_2$)—NR$_{10}$—, or —N(S(O$_2$)—(CH$_2$)$_n$—R$_1$)$_2$;

$R_1$ is $R_{13}$, —O—(CH$_2$)$_n$—R$_{13}$, or $R_{10}$;

each $R_{10}$, $R_{11}$ and $R_{12}$ is independently H or alkyl;

$R_{13}$ is cycloalkyl, heterocycloalkyl, aryl, or heteroaryl, or a fused bicycle of any two of such ring moieties, or $R_{13}$ and $R_{10}$ taken together with the N atom to which they are attached form a heterocyclic ring, where any ring atom of $R_{13}$ may be optionally substituted with one or more $R_{14}$ or $R_{15}$;

each $R_{14}$ is independently H, alkyl, halo, hydroxy, cyano, alkoxy, perhaloalkyl, and perhaloalkoxy, —OR$_{10}$, —(CH$_2$)$_n$—COOR$_{10}$, —SO—R$_{10}$, —SO$_2$R$_{10}$, —NR$_{11}$R$_{12}$, —NHCO(CH$_2$)$_n$—R$_{12}$, —N(R$_{11}$)CO(CH$_2$)$_n$—R$_{12}$, or —NH(CH$_2$)$_n$—R$_{12}$;

$R_{15}$ is cycloalkyl, heterocycloalkyl, aryl, or heteroaryl, or a fused bicycle of any two of such ring moieties, where any ring atom of $R_{15}$ may be optionally substituted with one or more $R_{14}$, each $R_5$ is independently H, alkyl, alkoxy, alkyl substituted with one or more $R_{53}$, halogen, perhaloalkyl, perhaloalkoxy, —CN, —OR$_{50}$, or —NR$_{51}$R$_{52}$;

$W_2$ is —(CR$_a$R$_b$)$_{i2}$-L$_2$-(CR$_a$R$_b$)$_{j2}$—R$_2$ or $R_5$; or $W_2$ and $R_5$ taken together comprise a 5- or 6-membered heterocyclic ring fused with the ring to which $W_2$ and $R_5$ are attached and having one, two or three heteroatoms where each such heteroatom is independently selected from O, N, and S, and where any ring atom of such heterocyclic ring may be optionally substituted with one or more —$(CR_aR_b)_{i2}$-$L_2$-$(CR_aR_b)_{j2}$—$R_2$ or $R_2$; or $W_2$ comprises a 5- or 6-membered heterocyclic ring fused with a phenyl ring and having one, two or three heteroatoms where each such heteroatom is independently selected from O, N, and S, and where any ring atom of such heterocyclic ring or phenyl ring may be optionally substituted with one or more of $R_{24}$ and wherein one ring atom of such fused ring moiety is optionally substituted with $L_3$-$R_{25}$;

$L_2$ is —O—, —C(O)—, —OC(O)—, —C(O)O—, —$NR_{20}$—, —C(O)$NR_{20}$—, —$N(R_{20})$—C(O)—, —$N(R_{20})$—$S(O_2)$—, —$S(O_2)$—$NR_{20}$—, —$SO_2$—, —O$(CH_2)_qCO$—, —CO$(CH_2)_qO$—, null, oxazolyl, oxadiazolyl, triazolyl, pyrazolyl, or pyrimidinyl;

Each $R_a$ and $R_b$ is independently H, hydroxy, methyl, or both $R_a$ and $R_b$ attached to the same carbon are, taken together, oxo or cycloalkyl;

$R_2$ is $R_{26}$, —O—$(CH_2)_n$—$R_{26}$, $R_{23}$ or —O—$(CH_2)_n$—$R_{23}$;

each $R_{20}$ is independently H or alkyl;

$R_{23}$ is cycloalkyl, heterocycloalkyl, aryl, or heteroaryl, or a fused bicycle of any two of such ring moieties, or $R_{23}$ and $R_{20}$ taken together with the N atom to which they are attached form a heterocyclic ring optionally fused with aryl or heteroaryl, where any ring atom of $R_{23}$ may be optionally substituted with one or more of $R_{24}$ and wherein one ring atom of $R_{23}$ is optionally substituted with $L_3$-$R_{25}$;

each $R_{24}$ is independently selected from H, halo, alkyl, hydoxy, oxo, cyano, alkoxy, perhaloalkyl, perhaloalkoxy, nitro or amino, —O—$(CH_2)_n$—$R_{21}$, —$(CH_2)_n$—O—$R_{21}$, —O—$(CH_2)_n$—O—$R_{21}$, —$(CH_2)_n$—$NR_{21}R_{22}$, —$(CH_2)_n$—$N(R_{21})CO(CH_2)_n$—$R_{21}$, —$(CH_2)_n$—$N(R_{21})SO_2(CH_2)_n$—$R_{21}$, —$(CH_2)_n$—$SO_2$—$N(R_{21})$—$(CH_2)_n$—$R_{21}$, —$(CH_2)_n$—$CO(CH_2)_n$—$R_{21}$, —$(CH_2)_m$—COO—$R_{21}$, —O—$(CH_2)_n$—COO—$R_{21}$ or —$(CH_2)_m$—OCO—$R_{21}$;

each $R_{21}$ and $R_{22}$ is independently H or alkyl, —$(CH_2)_n$—COOH, or two taken together with the nitrogen atom to which they are attached can form a 3- to 7-membered heterocyclic ring;

$L_3$ is null, —O—, —$(CH_2)_n$—O—$(CH_2)_n$—, —$(CH_2)_n$—$NR_{20}$—$(CH_2)_n$—, each $R_{25}$ is independently cycloalkyl, heterocycloalkyl, aryl, or heteroaryl, or a fused bicycle of any two of such ring moieties 1, where any ring atom of $R_{25}$ may be optionally substituted with one or more of $R_{24}$;

each $R_{26}$ is independently selected from H, alkyl, alkoxy, oxo, hydroxy, and hydroxy substituted alkyl;

Y is —C(O)—, —$CH_2$—, —C(O)—$CH_2$—, or —$CH_2$—C(O)—;

Z is —$(CH_2)_n$—C(O)—$R_3$, —$(CH_2)_n$—$R_3$, —$R_{34}$—C(O)—$R_3$ or H;

$R_{34}$ is cycloalkyl, heterocycloalkyl, aryl, or heteroaryl; where any ring atom of $R_{34}$ may be optionally substituted with one or more $R_{35}$;

each $R_{35}$ is independently H, alkyl, halo, hydroxy, cyano, alkoxy or perhaloalkyl;

$R_3$ is —$OR_{30}$, or —$NR_{31}R_{32}$;

each $R_{30}$ is independently H or alkyl;

each $R_{31}$ and $R_{32}$ is independently H or $C_1$-$C_6$ alkyl optionally substituted with one or more $R_{33}$, or two taken together with the N atom to which they are attached can form a 3- to 7-membered heterocyclic ring;

each $R_{33}$ is independently halo, hydroxyl, alkoxy, perhaloalkyl, perhaloalkoxy, carboxyl, —COO—$R_{30}$, or —$OR_{30}$;

each $R_{40}$ and $R_{50}$ is independently H or alkyl;

each $R_{41}$ and $R_{42}$ is independently H or alkyl, —$(CH_2)_n$—COO—$R_{40}$, —C(O)—$R_{40}$, aryl, heteroaryl, or two taken together with the N atom to which they are attached can form a 3- to 7-membered heterocyclic ring;

each $R_{51}$ and $R_{52}$ is independently H or alkyl, —$(CH_2)_n$—COO—$R_{50}$, —C(O)—$R_{50}$, aryl, heteroaryl, or two taken together with the N atom to which they are attached can form a 3- to 7-membered heterocyclic ring;

each $R_{43}$ is independently H, halo, hydroxyl, —$NR_{41}R_{42}$, or alkoxy;

each $R_{53}$ is independently H, halo, hydroxyl, —$NR_{51}R_{52}$, or alkoxy;

k is 0, 1, 2, 3 or 4;
each m is independently 0 or 1;
each n is independently 0, 1, 2, 3 or 4;
each q is independently 1 or 2; and
each i1, i2, j1 and j2 is independently 0, 1, 2, 3 or 4.

Certain embodiments of the present invention comprise a compound having the structure of Formula II

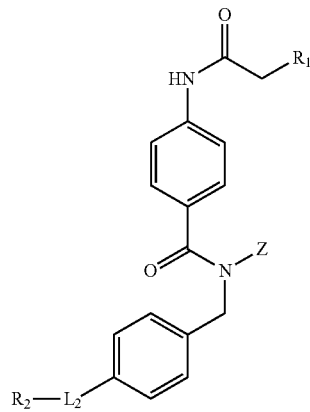

II or a pharmaceutically acceptable isomer, isotope, enantiomer, salt, ester, prodrug, hydrate or solvate thereof, wherein $R_1$ is $R_{13}$ or —O—$(CH_2)_n$—$R_{13}$ or $R_{10}$; each $R_{10}$, $R_{11}$ and $R_{12}$ is independently H or alkyl; $R_{13}$ is cycloalkyl, heterocycloalkyl, aryl, or heteroaryl, or a fused bicycle of any two of such ring moieties, or $R_{13}$ and $R_{10}$ taken together with the N atom to which they are attached form a heterocyclic ring, where any ring atom of $R_{13}$ may be optionally substituted with one or more $R_{14}$ or $R_{15}$; each $R_{14}$ is independently H, alkyl, halo, hydroxy, cyano, alkoxy, perhaloalkyl, and perhaloalkoxy, —$(CH_2)_n$—$COOR_{10}$, —SO—$R_{10}$, —$SO_2R_{10}$, —NHCO$(CH_2)_n$—$R_{12}$, —$N(R_{11})CO(CH_2)_n$—$R_{12}$, or —NH$(CH_2)_n$—$R_{12}$; $R_{15}$ is cycloalkyl, heterocycloalkyl, aryl, or heteroaryl, or a fused bicycle of any two of such ring moieties, where any ring atom of $R_{15}$ may be optionally substituted with one or more $R_{14}$;

$L_2$ is —O—, —C(O)—, —OC(O)—, —C(O)O—, —$NR_{20}$—, —C(O)$NR_{20}$—, —$N(R_{20})$—C(O)—, —$N(R_{20})$—$S(O_2)$—, —$S(O_2)$—$NR_{20}$—, —$SO_2$—, —O$(CH_2)_qCO$—, —CO$(CH_2)_qO$—, null, oxazolyl, oxadiazolyl, triazolyl, pyrazolyl, or pyrimidinyl; each $R_{20}$ is independently H or alkyl;

$R_2$ is $R_{26}$, —O—$(CH_2)_n$—$R_{26}$, $R_{23}$ or —O—$(CH_2)_n$—$R_{23}$; $R_{23}$ is cycloalkyl, heterocycloalkyl, aryl, or heteroaryl, or a fused bicycle of any two of such ring moieties, or $R_{23}$ and $R_{20}$ taken together with the N atom to which they are attached form a heterocyclic ring optionally fused with aryl or heteroaryl, where any ring atom of $R_{23}$ may be optionally substituted with one or more of $R_{24}$ and wherein one ring atom of $R_{23}$ is optionally substituted with $L_3$-$R_{25}$; each $R_{24}$ is independently selected from H, halo, alkyl, hydroxy, oxo, cyano, alkoxy, perhaloalkyl, perhaloalkoxy, nitro or amino, —O—$(CH_2)_n$—$R_{21}$, —$(CH_2)_n$—O—$R_{21}$, —O—$(CH_2)_n$—O—$R_{21}$, —$(CH_2)_n$—$NR_{21}R_{22}$, —$(CH_2)_n$—$N(R_{21})$CO$(CH_2)_n$—$R_{21}$, —$(CH_2)_n$—$N(R_{21})SO_2(CH_2)_n$—$R_{21}$, —$(CH_2)_n$—$SO_2$—$N(R_{21})$—$(CH_2)_n$—$R_{21}$, —$(CH_2)_n$—CO$(CH_2)_n$—$R_{21}$, —$(CH_2)_m$—COO—$R_{21}$, —O—$(CH_2)_n$—COO—$R_{21}$ or —$(CH_2)_m$—OCO—$R_{21}$; each $R_{21}$ and $R_{22}$ is independently H or alkyl, —$(CH_2)_n$—COOH, or two taken together with the nitrogen atom to which they are attached can form a 3- to 7-membered heterocyclic ring; $L_3$ is null, —O—, —$(CH_2)_n$—O—$(CH_2)_n$—, —$(CH_2)_n$—$NR_{20}$—$(CH_2)_n$—; each $R_{25}$ is independently cycloalkyl, heterocycloalkyl, aryl, or heteroaryl, or a fused bicycle of any two of such ring moieties 1, where any ring atom of $R_{25}$ may be optionally substituted with one or more of $R_{24}$; each $R_{26}$ is independently selected from H, alkyl, alkoxy, oxo, hydroxy, and hydroxy substituted alkyl;

Z is —$(CH_2)_n$—C(O)—$R_3$, —$(CH_2)_n$—$R_3$, —$R_{34}$—C(O)—$R_3$ or H; $R_{34}$ is cycloalkyl, heterocycloalkyl, aryl, or heteroaryl; where any ring atom of $R_{34}$ may be optionally substituted with one or more $R_{35}$; each $R_{35}$ is independently H, alkyl, halo, hydroxy, cyano, alkoxy or perhaloalkyl; $R_3$ is —$OR_{30}$, or —$NR_{31}R_{32}$; each $R_{30}$ is independently H or alkyl; each $R_{31}$ and $R_{32}$ is independently H or $C_1$-$C_6$ alkyl optionally substituted with one or more $R_{33}$, or two taken together with the N atom to which they are attached can form a 3- to 7-membered heterocyclic ring; each $R_{33}$ is independently halo, hydroxyl, alkoxy, perhaloalkyl, perhaloalkoxy, carboxyl, —COO—$R_{30}$, or —$OR_{30}$;

each m is independently 0 or 1; each n is independently 0, 1, 2, 3 or 4; and each q is independently 1 or 2. In certain of such embodiments $R_1$ may be phenyl substituted with one or more of methyl, ethyl, isopropyl, t-butyl, —$CF_3$, methoxy, ethoxy, hydroxyl, —$OCF_3$, or halogen, methylthio, and —$SO_2CH_3$; in certain of such embodiments $R_1$ may be phenyl substituted with one or more of methyl, methoxy, and —$CF_3$; in certain of such embodiments $R_1$ is

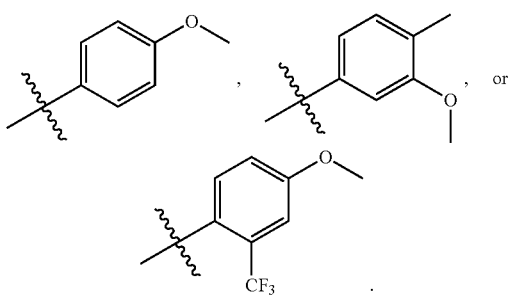

In certain of such embodiments Z is —$CH_2C(O)OH$. In certain of such embodiments $L_2$ is —OC(O)—, —O—, oxazolyl, oxadiazolyl, triazolyl, pyrazolyl, or pyrimidinyl; and in certain such embodiments $L_2$ is —OC(O)—; and in other such embodiments $L_2$ is oxazolyl, oxadiazolyl, triazolyl, pyrazolyl, or pyrimidinyl. In certain of such embodiments $R_2$ may be phenyl substituted with butyloxy, pentyloxy, hexyloxy, heptyloxy, or octyloxy; in other such embodiments $R_2$ is phenyl substituted with methyl, pentyl, hexyl, heptyl, octyl, or nonyl. In certain of such embodiments $R_2$ is biphenyl; and in certain of such embodiments, the distal ring of such biphenyl is substituted with methyl; and in certain of such embodiments the methyl substituent of the biphenyl is at the ortho position of the distal phenyl ring of the biphenyl.

In certain embodiments, the invention provides compounds where each of $X_{1A}$, $X_{1B}$, $X_{2A}$, and $X_{2B}$ is CH. In certain embodiments, the invention provides compounds where one of $X_{1A}$ and $X_{1B}$ is N. In certain of such embodiments, $X_{2A}$, and $X_{2B}$ is CH. In certain of such embodiments, one of $X_{2A}$ and $X_{2B}$ is N. In certain embodiments, the invention provides compounds where both one of $X_{1A}$ and $X_{1B}$ is N and one of $X_{2A}$ and $X_{2B}$ is N.

In certain embodiments, the invention provides compounds where one of $X_{1C}$, $X_{1D}$ and $X_{1E}$ is N. In certain embodiments, the invention provides compounds where $X_{1D}$ is N. In certain embodiments, the invention provides compounds where $X_{1F}$ is O.

In certain embodiments, the invention provides compounds where Y is —C(O)—; in certain other embodiments, Y is —$CH_2$—; in certain other embodiments, Y is —C(O)—$CH_2$—; in certain other embodiments, Y is —$CH_2$—C(O)—.

In certain embodiments, the invention provides compounds where Z is —$(CH_2)_n$—C(O)—$R_3$, and in certain of such embodiments such n is 0, 1, or 2; in certain of such embodiments $R_3$ is —OH. In certain embodiments, $R_3$ is —$NH(CR_aR_b)_n$—C(O)—$R_3$; in certain of such embodiments, both $R_a$ and $R_b$ are methyl; in certain of such embodiments, $R_3$ is —OH. In certain embodiments, the $R_3$ is —(CO)$NHSO_2R_3$; in certain of such embodiments, $R_3$ is —OH. In certain embodiments, the invention provides compounds where Z is —$(CH_2)_n$—$R_3$, and in certain of such embodiments such n is 0, 1, or 2. In certain embodiments, the invention provides compounds where Z is —$R_{34}$—C(O)—$R_3$, and in certain of such embodiments, $R_3$ is —OH. In certain embodiments, the invention provides compounds where Z can be —$R_{34}$—C(O)OH. In certain of such embodiments, —C(O)OH is attached in the ortho position of $R_{34}$, in others —C(O)OH is attached in the meta position of $R_{34}$, and in yet others —C(O)OH is attached in the para position of $R_{34}$. In certain embodiments, $R_{34}$ is aryl and in certain of such embodiments $R_{34}$ is phenyl.

In certain embodiments, the invention provides compounds where k is 1; in other embodiments k is zero and in yet other embodiments k is 2.

In certain embodiments, the invention provides compounds where $W_1$ is attached in the para position; in certain embodiments, the invention provides compounds where $W_2$ is attached in the para position; and in certain such embodiments, the invention provides compounds where $W_1$ is attached in the para position and $W_2$ is attached in the para position.

In certain embodiments, the invention provides compounds where $W_1$ can be —$(CR_aR_b)_{i1}$-$L_1$-$(CR_aR_b)_{j1}$—$R_1$ and in certain of such embodiments i1 is 0, in others i1 is 1, and in yet others i1 is 2. In certain of such embodiments j1 is 0, in others j1 is 1, and in yet others j1 is 2. In certain embodiments, the invention provides compounds where $L_1$ is —$NR_{10}C(O)$— or where $L_1$ is —$NR_{10}$— or where $L_1$ is —$N(R_{10})SO_2$—. In certain of such embodiments $R_{10}$ is —H. In certain embodiments, the invention provides compounds where $W_1$ can be —NH—C(O)—$(CH_2)_n$—$R_1$. In certain of such embodiments, the invention provides compounds where $W_1$ can be —NH—C(O)—$CH_2$—$R_1$. In certain embodiments, $R_1$ is $R_{13}$. In certain embodiments, $R_1$ can be —O—$(CH_2)_n$—$R_{13}$ and in certain of such embodiments —O—$R_{13}$ and in certain other such embodiments —O—CH$_2$—R$_{13}$. In certain of such embodiments, R$_{13}$ can be aryl optionally substituted with one or more R$_{14}$ and in certain of such embodiments R$_{13}$ is phenyl. In certain of such embodiments, R$_{14}$ can be independently halo, alkoxy, perhaloalkyl, or perhaloalkoxy. In certain of such embodiments, R$_{14}$ can be alkoxy and or perhaloalkyl. In certain embodiments, the invention provides compounds where R$_{13}$ is cycloalkyl or heterocycloalkyl and in certain of such embodiments R$_{13}$ is cyclopentyl, cyclohexyl, thiazolyl, tetrahydrofuranyl, oxazolyl, thiophenyl, 1,2,4-oxadiazolyl, furanyl, tetrahydro-2H-pyranyl, or piperidinyl.

In certain embodiments, the invention provides compounds where R$_{13}$ is unsubstituted or substituted at one or more ring position with substituents selected from the group consisting of methyl, ethyl, isopropyl, t-butyl, —CF$_3$, methoxy, ethoxy, hydroxyl, —OCF$_3$, halogen (e.g., F, Cl, Br or I), methylthio, and —SO$_2$CH$_3$. In certain embodiments, the invention provides compounds where R$_{13}$ is substituted with one or more of methyl, methoxy, F or —CF$_3$. In certain of such embodiments, wherein each R$_{31}$ and R$_{32}$ can be independently H, alkyl or alkyl substituted with carboxyl. In certain of such embodiments, at least one of R$_{31}$ and R$_{32}$ is can be H. In certain of such embodiments, the invention provides compounds where R$_1$ may be

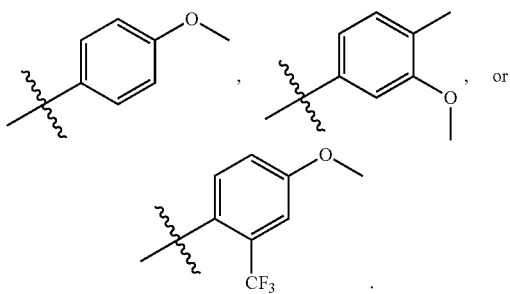

In certain embodiments each of R$_a$ and R$_b$ is H, in other embodiments, at least one of R$_a$ and R$_b$ is methyl; and in yet other embodiments at least one pair of R$_a$ and R$_b$ is, taken together, oxo or cycloalkyl.

In certain embodiments, the invention provides compounds where W$_2$ can be —(CR$_a$R$_b$)$_{i2}$-L$_2$-(CR$_a$R$_b$)$_{j2}$—R$_2$ and in certain of such embodiments i$_2$ is 0, in others i$_2$ is 1, and in yet others i$_2$ is 2. In certain of such embodiments j$_2$ is 0, in others j$_2$ is 1, and in yet others j$_2$ is 2.

In certain embodiments, the invention provides compounds where L$_2$ is —O—, —OC(O)—, —C(O)O—, —NR$_{20}$—, —C(O)NR$_{20}$—, —N(R$_{20}$)—C(O)—, —N(R$_{20}$)—S(O$_2$)— or —S(O$_2$)—NR$_{20}$—, —CO—, —SO$_2$—, —O(CH$_2$)$_q$CO—, —CO(CH$_2$)$_q$O—, null, oxazolyl, oxadiazolyl, triaxolyl, pyrazolyl, or pyrimidinyl. In certain of such embodiments L$_2$ is —OC(O)—, —O—, oxazolyl, oxadiazolyl, triazolyl, pyrazolyl, or pyrimidinyl. In certain of such embodiments L$_2$ is oxadiazolyl.

In certain embodiments, the invention provides compounds where W$_2$ can be attached in the para position. In certain embodiments, the invention provides compounds where W$_2$ can be —OC(O)—(CH$_2$)$_n$—R$_2$. In certain embodiments, the invention provides compounds where W$_2$ can be —OC(O)—CH$_2$—R$_2$. In certain embodiments, the invention provides compounds where R$_2$ is phenyl substituted with alkyl, alkoxy, —O—(CH$_2$)$_n$—R$_{21}$, cycloalkyl, hetercycloalkyl, or aryl; in certain such embodiments R$_2$ is phenyl substituted with —(CH$_2$)$_t$CH$_3$ where t is 0, 5, 6, 7, 8 or 9; in certain such embodiments R$_2$ is phenyl substituted with —O(CH$_2$)$_t$CH$_3$ where t is 4, 5, 6, 7, or 8; in certain such embodiments R$_2$ is phenyl substituted with —O—(CH$_2$)$_n$—R$_{21}$ where n is 1, 2 or 3 and R$_{21}$ is isopropyl; in certain such embodiments R$_2$ is phenyl substituted with R$_{25}$, where R$_{25}$ is phenyl, cyclohexyl, or piperidyl; in certain such embodiments R$_{25}$ is substituted with methyl, and in certain of such embodiments the methyl is attached at the ortho position of R$_{25}$.

In certain embodiments, the invention provides compounds where W$_2$ can be —C(O)NH—(CH$_2$)$_n$—R$_2$. In certain of such embodiments, W$_2$ can be —C(O)NH—R$_2$. In certain embodiments, the invention provides compounds where W$_2$ can be —NHC(O)—(CH$_2$)$_n$—R$_2$. In certain of such embodiments, W$_2$ can be —NHC(O)—R$_2$. In certain embodiments, the invention provides compounds where W$_2$ can be —C(O)—(CH$_2$)$_n$—R$_2$. In certain of such embodiments, W$_2$ can be —C(O)—(CH$_2$)—R$_2$. In certain embodiments, the invention provides compounds where W$_2$ can be —(CH$_2$)$_n$—R$_2$. In certain of such embodiments, W$_2$ can be —(CH$_2$)$_2$—R$_2$. In certain embodiments, the invention provides compounds where W$_2$ can be —(CH$_2$)$_n$O—R$_2$. In certain of such embodiments, W$_2$ can be —(CH$_2$)O—R$_2$. In certain embodiments, the invention provides compounds where W$_2$ can be —NHSO$_2$—R$_2$. In certain embodiments, the invention provides compounds where W$_2$ can be —SO$_2$NH—R$_2$. In certain embodiments, the invention provides compounds where W$_2$ can be —(CH$_2$)$_n$—SO$_2$R$_2$. In certain of such embodiments, the invention provides compounds where W$_2$ can be —(CH$_2$)$_2$—SO$_2$R$_2$. In certain embodiments, the invention provides compounds where W$_2$ can be —(CH$_2$)$_n$—NHR$_2$. In certain of such embodiments, the invention provides compounds where W$_2$ can be —(CH$_2$)$_2$—NHR$_2$. In certain embodiments, the invention provides compounds where W$_2$ can be —NH(CH$_2$)$_n$—R$_2$. In certain of such embodiments, the invention provides compounds where W$_2$ can be —NH(CH$_2$)$_2$—R$_2$. In certain embodiments, the invention provides compounds where W$_2$ can be —C(O)R$_2$. In certain embodiments, the invention provides compounds where W$_2$ can be —OR$_2$. In certain embodiments, the invention provides compounds where W$_2$ can be —NHR$_2$. In certain embodiments, the invention provides compounds where W$_2$ can be —C(O)(CH$_2$)$_n$O—R$_2$. In certain of such embodiments, the invention provides compounds where W$_2$ can be —C(O)(CH$_2$)O—R$_2$. In certain embodiments, the invention provides compounds where W$_2$ can be —O(CH$_2$)$_n$C(O)—R$_2$. In certain of such embodiments, the invention provides compounds where W$_2$ can be —O(CH$_2$)C(O)—R$_2$.

In certain embodiments, the invention provides compounds where R$_2$ can be alkyl or cycloalkyl. In certain embodiments, the invention provides compounds where R$_2$ can be heterocycloalkyl optionally substituted with one or more R$_{24}$. In certain embodiments, the invention provides compounds where R$_2$ can be aryl optionally substituted with one or more R$_{24}$. In certain embodiments, the invention provides compounds where R$_2$ is biphenyl optionally substituted with one or more alkyl. In certain of such embodiments, the invention provides compounds where R$_2$ is biphenyl substituted with methyl. In certain embodiments, the invention provides compounds where each R$_{24}$ can be independently halo or alkoxy. In certain embodiments, the invention provides compounds where R$_2$ can be phenyl substituted with at least one R$_{24}$ and R$_{24}$ can be alkoxy. In certain embodiments, the invention provides compounds where R$_2$ can be 4-heptyloxy phenyl.

In certain embodiments, the invention provides compounds where $W_1$ can be —$OR_{10}$, —$NHCO(CH_2)_n$—$R_1$, —$N(CH_3)CO(CH_2)_n$—$R_1$ or —$NH(CH_2)_n$—$R_1$; $R_{13}$ can be cycloalkyl, aryl, or heteroaryl, where any ring atom of $R_{13}$ may be optionally substituted with $R_{14}$; each $R_{14}$ can be independently H, alkyl, halo, alkoxy, perhaloalkyl or perhaloalkoxy; $W_2$ can be —$OCO$—$(CH_2)_n$—$R_2$; $R_2$ can be $R_{21}$, cycloalkyl, —O—$R_{21}$, —O—$(CH_2)_n$—O—$R_{21}$, heteroaryl or aryl, where aryl may be optionally substituted with one or more $R_{24}$; and each $R_{24}$ can be independently halo, alkyl, alkoxy, perhaloalkyl, perhaloalkoxy, —$(CH_2)_n$-aryl, —$(CH_2)_n$-cycloalkyl, —O—$R_{21}$, —O—$(CH_2)_n$—O—$R_{21}$, —$(CH_2)_n$—$NR_{21}R_{22}$, —$(CH_2)_n$—$N(R_{21})CO(CH_2)_n$—$R_{21}$, —$(CH_2)_n$—$N(R_{21})SO_2(CH_2)_n$—$R_{21}$, —$(CH_2)_n$—CO $(CH_2)_n$—$R_{21}$ or —$(CH_2)_m$—OCO—$R_{21}$.

In certain embodiments, the invention provides compounds where $W_2$ and $R_5$ taken together comprise a 5- or 6-membered heterocyclic ring fused with the ring to which $W_2$ and $R_5$ are attached to form a heterobicyclic ring, and in certain such embodiments the heterobicyclic ring moiety has one of the following structures:

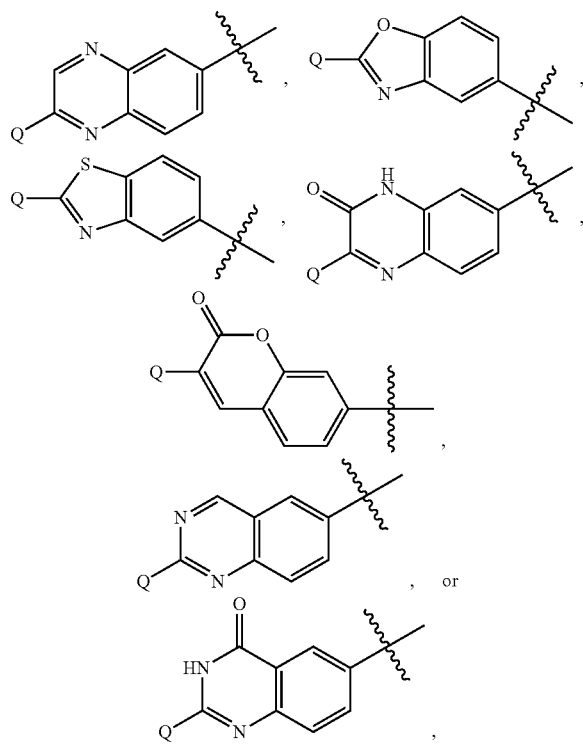

and wherein the substituent Q is —$(CR_aR_b)_{i2}$-$L_2$-$(CR_aR_b)_{j2}$—$R_2$. In certain such embodiments, Q is —$C(O)$—$R_{23}$ or $R_{23}$; and in certain such embodiments, $R_{23}$ is phenyl substituted with one or more $R_{24}$; in certain of such embodiments $R_{24}$ is attached in the para position.

In certain embodiments, the invention provides compounds where $W_2$ is benzoxazolyl, benzothiazolyl, benzimidazolyl, benzo[d]isoxazolyl, or benzo[c]isoxazolyl, where any phenyl ring atom of such fused ring moiety may be substituted with one or more of $R_{24}$ and additionally or alternatively where one phenyl ring atom of such fused ring moiety may be substituted with $L_3$-$R_{25}$.

In certain embodiments, the invention provides one or more of the following compounds 1-515 or any pharmaceutically acceptable salt, ester, prodrug, homolog, tautomer, stereoisomer, isotope, or hydrate, or solvate thereof. In certain of such embodiments, the invention provides a compound selected from compounds 1, 3, 4, 16, 17, 18, 32, 39, 40, 46, 192, 314, 347, 354, 355, 360, 361, 362, 363, 364, 405, 411, 441, 457, 458, and 496, or any pharmaceutically acceptable salt, ester, prodrug, homolog, tautomer, stereoisomer, isotope, or hydrate, or solvate thereof.

In other embodiments, a pharmaceutical composition comprising an invention compound of Formula I, II, III, IV or V, or any pharmaceutically acceptable salt, ester, prodrug, homolog, tautomer, stereoisomer, isotope, or hydrate, or solvate thereof, together with at least one pharmaceutically acceptable carrier, diluent or excipient is provided.

In other embodiments, a pharmaceutical composition comprising an invention compound of Formula I, II, III, IV or V, or any pharmaceutically acceptable salt, ester, prodrug, homolog, tautomer, stereoisomer, isotope, or hydrate, or solvate thereof, and a second medicament is provided.

In certain embodiments, the disclosure provides a method of use of compounds of the invention for preparation of a medicament.

In certain embodiments, the invention provides a pharmaceutical combination comprising a compound of the invention and a second medicament. In various such embodiments, the second medicament is an agonist or modulator for glucagon receptor, GIP receptor, GLP-2 receptor, or PTH receptor, or glucagon-like peptide 1 (GLP-1) receptor. In various such embodiments, the second medicament is exenatide, liraglutide, taspoglutide, albiglutide, or lixisenatide or other insulin regulating peptide. In various such embodiments, the second medicament is a DPPIV inhibitor. In various such embodiments, the second medicament is medically indicated for the treatment of type II diabetes. In various such embodiments, the second embodiment is a sulfonylurea (e.g., Carbutamide, Acetohexamide, Chlorpropamide, Tolbutamide, Tolazamide, Glipizide, Gliclazide, Glibenclamide (glyburide), Gliquidone, Glyclopyramide, and Glimepiride), metformin or a peroxisome proliferator-activated receptor (PPAR) agonist (e.g., a thiazolidinedione or glitazone).

In certain embodiments, a method is provided for activation, potentiation or agonism of a glucagon-like peptide 1 comprising contacting the receptor with an effective amount of a compound, pharmaceutical composition or pharmaceutical combination of the invention.

In further embodiments, a method is provided for activation, potentiation or agonism of a GLP-1 receptor by contacting the receptor with an effective amount of an invention compound, pharmaceutical composition or pharmaceutical combination, wherein the GLP-1 receptor is disposed within a living mammal; in certain embodiments wherein such mammal is a human.

In certain embodiments, a method is provided for treatment of a malcondition in a subject for which activation, potentiation or agonism of a GLP-1 receptor is medically indicated, by administering an effective amount of an invention compound to the subject at a frequency and for a duration of time sufficient to provide a beneficial effect to the patient. In yet further embodiments, a method is provided for treatment of a malcondition in a patient for which activation, potentiation or agonism of a GLP-1 receptor is medically indicated, by administering an effective amount of an invention compound to the patient at a frequency and for a duration of time sufficient to provide a beneficial effect to the patient, wherein the malcondition comprises type I diabetes, type II diabetes, gestational diabetes, obesity, excessive appetite, insufficient satiety, or metabolic disorder. In certain embodiments, the subject is a patient or a human being. In certain embodiments, the human being is afflicted with, or at risk of developing, a disease or condition selected from the group consisting of type I diabetes, type II diabetes, gestational diabetes, obesity, excessive appetite, insufficient satiety, and metabolic disorder. In certain of such embodiments, said disease is type I diabetes or type II diabetes.

In certain embodiments, the invention provides methods for synthesis of certain compounds including compounds of the invention as more fully illustrated herein. In certain other embodiments, the invention provides certain intermediate compounds associated with such methods of synthesis as illustrated herein.

In certain embodiments, compounds for enhancing the stabilization of a GLP-1 receptor are provided. In certain embodiments, methods for enhancing the stabilizing of a GLP-1 receptor in structural biology studies are provided through the use of compounds of the invention. In certain such embodiments a compound of the invention may be combined with a GLP-1 receptor in order to increase its thermal stability and additionally enhance its amenability to forming crystals suitable for use in x-ray crystallographic analysis of the structure of such GLP-1 receptor.

As used in the specification and the appended claims, the singular forms "a," "an" and "the" include plural referents unless the context clearly dictates otherwise.

As used herein, "individual" (as in the subject of the treatment) means both mammals and non-mammals. Mammals include, for example, humans; non-human primates, e.g. apes and monkeys; cattle; horses; sheep; and goats. Non-mammals include, for example, fish and birds.

A "receptor", as is well known in the art, is a biomolecular entity usually comprising a protein that specifically binds a structural class of ligands or a single native ligand in a living organism, the binding of which causes the receptor to transduce the binding signal into another kind of biological action, such as signaling a cell that a binding event has occurred, which causes the cell to alter its function in some manner. An example of transduction is receptor binding of a ligand causing alteration of the activity of a "G-protein" in the cytoplasm of a living cell. Any molecule, naturally occurring or not, that binds to a receptor and activates it for signal transduction, is referred to as an "agonist" or "activator." Any molecule, naturally occurring or not, that binds to a receptor, but does not cause signal transduction to occur, and which can block the binding of an agonist and its consequent signal transduction, is referred to as an "antagonist." Certain molecules bind to receptors at locations other than the binding sites of their natural ligands and such allosteric binding molecules may potentiate, activate or agonize the receptor and may enhance the effect of a natural ligand or a co-administered ligand.

An "GLP-1 compound" or "GLP-1 agonist" or "GLP-1 activator" or "GLP-1 inhibitor" or "GLP-1 antagonist" as the terms are used herein refer to compounds that interact in some way with the GLP-1 receptor. They can be agonist or activators, or they can be antagonists or inhibitors. An "GLP-1 compound" of the invention can be selective for action of the GLP-1 receptor family.

"Substantially" as the term is used herein means completely or almost completely; for example, a composition that is "substantially free" of a component either has none of the component or contains such a trace amount that any relevant functional property of the composition is unaffected by the presence of the trace amount, or a compound is "substantially pure" is there are only negligible traces of impurities present.

Substantially enantiomerically pure means a level of enantiomeric enrichment of one enantiomer with respect to the other enantiomer of at least 90%, 95%, 98%, 99%, 99.5% or 99.9%.

"Treating" or "treatment" within the meaning herein refers to an alleviation of symptoms associated with a disorder or disease, or inhibition of further progression or worsening of those symptoms, or prevention or prophylaxis of the disease or disorder.

The expression "effective amount", when used to describe use of a compound of the invention in providing therapy to a patient suffering from a disorder or malcondition mediated by GLP-1 refers to the amount of a compound of the invention that is effective to bind to as an agonist, potentiator or as an antagonist a GLP-1 receptor in the individual's tissues, wherein the GLP-1 is implicated in the disorder, wherein such binding occurs to an extent sufficient to produce a beneficial therapeutic effect on the patient. Similarly, as used herein, an "effective amount" or a "therapeutically effective amount" of a compound of the invention refers to an amount of the compound that alleviates, in whole or in part, symptoms associated with the disorder or condition, or halts or slows further progression or worsening of those symptoms, or prevents or provides prophylaxis for the disorder or condition. In particular, a "therapeutically effective amount" refers to an amount effective, at dosages and for periods of time necessary, to achieve the desired therapeutic result by acting as an agonist of GLP-1 activity. A therapeutically effective amount is also one in which any toxic or detrimental effects of compounds of the invention are outweighed by the therapeutically beneficial effects. For example, in the context of treating a malcondition mediated by activation of GLP-1 receptor, a therapeutically effective amount of an GLP-1 receptor agonist of the invention is an amount sufficient to control the malcondition, to mitigate the progress of the malcondition, or to relieve the symptoms of the malcondition. Examples of malconditions that can be so treated include, but not limited to, type II diabetes.

Rotational Isomerism

It is understood that due to chemical properties (i.e., resonance lending some double bond character to the C—N bond) of restricted rotation about the amide bond linkage (as illustrated below) it is possible to observe separate rotamer species and even, under some circumstances, to isolate such species, example shown below. It is further understood that certain structural elements, including steric bulk or substituents on the amide nitrogen, may enhance the stability of a rotamer to the extent that a compound may be isolated as, and exist indefinitely, as a single stable rotamer. The present invention therefore includes any possible stable rotamers of compounds of the invention which are biologically active in the treatment of type I diabetes, type II diabetes, gestational diabetes, obesity, excessive appetite, insufficient satiety, and metabolic disorder.

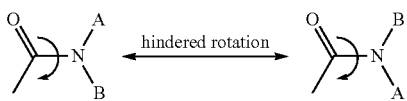

Regioisomerism

The preferred compounds of the present invention have a particular spatial arrangement of substituents on the aromatic rings, which is related to the structure activity relationship demonstrated by the compound class. Often such substitution arrangement is denoted by a numbering system; however, numbering systems are often not consistent between different ring systems. In six-membered aromatic systems, the spatial arrangements are specified by the common nomenclature "para" for 1,4-substitution, "meta" for 1,3-substitution and "ortho" for 1,2-substitution as shown below.

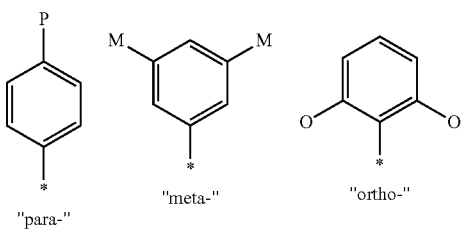

All structures encompassed within a claim are "chemically feasible", by which is meant that the structure depicted by any combination or subcombination of optional substituents meant to be recited by the claim is physically capable of existence with at least some stability as can be determined by the laws of structural chemistry and by experimentation. Structures that are not chemically feasible are not within a claimed set of compounds.

In general, "substituted" refers to an organic group as defined herein in which one or more bonds to a hydrogen atom contained therein are replaced by one or more bonds to a non-hydrogen atom such as, but not limited to, a halogen (i.e., F, Cl, Br, and I); an oxygen atom in groups such as hydroxyl groups, alkoxy groups, aryloxy groups, aralkyloxy groups, oxo(carbonyl) groups, carboxyl groups including carboxylic acids, carboxylates, and carboyxlate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR', OC(O)N(R')$_2$, CN, CF$_3$, OCF$_3$, R', O, S, C(O), S(O), methylenedioxy, ethylenedioxy, N(R')$_2$, SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R')$_2$, OC(O)N(R')$_2$, C(S)N(R)$_2$, (CH$_2$)$_{0-2}$NHC(O)R', (CH$_2$)$_{0-2}$N(R')N(R')$_2$, N(R')N(R')C(O)R', N(R')N(R')C(O)OR', N(R)N(R)CON(R')$_2$, N(R')SO$_2$R', N(R)SO$_2$N(R')$_2$, N(R')C(O)OR', N(R')C(O)R', N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R' wherein R' can be hydrogen or a carbon-based moiety, and wherein the carbon-based moiety can itself be further substituted.

Substituted alkyl, alkenyl, alkynyl, cycloalkyl, and cycloalkenyl groups as well as other substituted groups also include groups in which one or more bonds to a hydrogen atom are replaced by one or more bonds, including double or triple bonds, to a carbon atom, or to a heteroatom such as, but not limited to, oxygen in carbonyl (oxo), carboxyl, ester, amide, imide, urethane, and urea groups; and nitrogen in imines, hydroxyimines, oximes, hydrazones, amidines, guanidines, and nitriles.

Substituted ring groups such as substituted aryl, heterocyclyl and heteroaryl groups also include rings and fused ring systems in which a bond to a hydrogen atom is replaced with a bond to a carbon atom. Therefore, substituted aryl, heterocyclyl and heteroaryl groups can also be substituted with alkyl, alkenyl, cycloalkyl, aryl, heteroaryl, and alkynyl groups as defined herein, which can themselves be further substituted.

The term "heteroatoms" as used herein refers to non-carbon and non-hydrogen atoms, capable of forming covalent bonds with carbon, and is not otherwise limited. Typical heteroatoms are N, O, and S. When sulfur (S) is referred to, it is understood that the sulfur can be in any of the oxidation states in which it is found, thus including sulfoxides (R—S(O)—R') and sulfones (R—S(O)$_2$—R'), unless the oxidation state is specified; thus, the term "sulfone" encompasses only the sulfone form of sulfur; the term "sulfide" encompasses only the sulfide (R—S—R') form of sulfur. When the phrases such as "heteroatoms selected from the group consisting of O, NH, NR' and S," or "[variable] is O, S . . . " are used, they are understood to encompass all of the sulfide, sulfoxide and sulfone oxidation states of sulfur.

Alkyl groups include straight chain and branched alkyl groups and cycloalkyl groups having from 1 to about 20 carbon atoms, and typically from 1 to 12 carbons (C$_1$-C$_{12}$ alkyl), or, in some embodiments, from 1 to 8 carbon atoms (C$_1$-C$_8$ alkyl), or, in some embodiments, from 1 to 4 carbon atoms (C$_1$-C$_4$ alkyl). Examples of straight chain alkyl groups include, but are not limited to, methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. Alkyl groups as used herein may optionally include one or more further substituent groups. Representative substituted alkyl groups can be substituted one or more times with any of the groups listed above, for example, amino, hydroxy, cyano, carboxy, nitro, thio, alkoxy, and halogen groups.

Cycloalkyl groups are alkyl groups forming a ring structure, which can be substituted or unsubstituted, wherein the ring is either completely saturated, partially unsaturated, or fully unsaturated, wherein if there is unsaturation, the conjugation of the pi-electrons in the ring do not give rise to aromaticity. Examples of cycloalkyl include, but are not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups can be mono-substituted or substituted one or more times with any of the groups listed above, for example, but not limited to, amino, hydroxy, cyano, carboxy, nitro, thio, alkoxy, and halogen groups.

The terms "carbocyclic" and "carbocycle" denote a ring structure wherein the atoms of the ring are carbon. In some embodiments, the carbocycle has 3 to 8 ring members, whereas in other embodiments the number of ring carbon atoms is 4, 5, 6, or 7. Unless specifically indicated to the contrary, the carbocyclic ring can be substituted with as many as N substituents wherein N is the size of the carbocyclic ring with for example, amino, hydroxy, cyano, carboxy, nitro, thio, alkoxy, and halogen groups.

(Cycloalkyl)alkyl groups, also denoted cycloalkylalkyl, are alkyl groups as defined above in which a hydrogen or carbon bond of the alkyl group is replaced with a bond to a cycloalkyl group as defined above.

The term "cycloalkylene" refers to a divalent radical formed by the removal of two hydrogen atoms from one or more rings of a cycloalkyl group (a nonaromatic hydrocarbon that includes at least one ring). An example of cycloalkylene groups is cyclopropylene having the structure

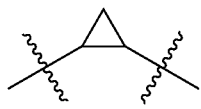

Alkenyl groups include straight and branched chain and cyclic alkyl groups as defined above, except that at least one double bond exists between two carbon atoms. Thus, alkenyl groups have from 2 to about 20 carbon atoms, and typically from 2 to 12 carbons or, in some embodiments, from 2 to 8 carbon atoms. Examples include, but are not limited to —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, vinyl, cyclohexenyl, cyclopentenyl, cyclohexadienyl, butadienyl, pentadienyl, and hexadienyl among others.

The term "cycloalkenyl" alone or in combination denotes a cyclic alkenyl group wherein at least one double bond is present in the ring structure. Cycloalkenyl groups include cycloalkyl groups having at least one double bond between two adjacent carbon atoms. Thus for example, cycloalkenyl groups include but are not limited to cyclohexenyl, cyclopentenyl, and cyclohexadienyl groups.

(Cycloalkenyl)alkyl groups are alkyl groups as defined above in which a hydrogen or carbon bond of the alkyl group is replaced with a bond to a cycloalkenyl group as defined above.

Alkynyl groups include straight and branched chain alkyl groups, except that at least one triple bond exists between two carbon atoms. Thus, alkynyl groups have from 2 to about 20 carbon atoms, and typically from 2 to 12 carbons or, in some embodiments, from 2 to 8 carbon atoms. Examples include, but are not limited to —C≡CH, —C≡C(CH$_3$), —C≡C(CH$_2$CH$_3$), —CH$_2$C≡CH, —CH$_2$C≡C(CH$_3$), and —CH$_2$C≡C(CH$_2$CH$_3$), among others.

Aryl groups are cyclic aromatic hydrocarbons that do not contain heteroatoms. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain 6-14 carbons in the ring portions of the groups. The phrase "aryl groups" includes groups containing fused rings, such as fused aromatic-aliphatic ring systems (e.g., indanyl, tetrahydronaphthyl, and the like), and also includes substituted aryl groups that have other groups, including but not limited to alkyl, halo, amino, hydroxy, cyano, carboxy, nitro, thio, or alkoxy groups, bonded to one of the ring atoms. Representative substituted aryl groups can be mono-substituted or substituted more than once, such as but not limited to, 2-, 3-, 4-, 5-, or 6-substituted phenyl or naphthyl groups, which can be substituted with groups including but not limited to those listed above.

Aralkyl groups are alkyl groups as defined above in which a hydrogen or carbon bond of an alkyl group is replaced with a bond to an aryl group as defined above. Representative aralkyl groups include benzyl and phenylethyl groups and fused (cycloalkylaryl)alkyl groups such as 4-ethyl-indanyl. The aryl moiety or the alkyl moiety or both are optionally substituted with other groups, including but not limited to alkyl, halo, amino, hydroxy, cyano, carboxy, nitro, thio, or alkoxy groups. Aralkenyl group are alkenyl groups as defined above in which a hydrogen or carbon bond of an alkyl group is replaced with a bond to an aryl group as defined above.

Heterocyclyl or heterocyclic groups include aromatic and non-aromatic ring moieties containing 3 or more ring members, of which one or more is a heteroatom such as, but not limited to, N, O, S, or P. In some embodiments, heterocyclyl include 3 to 20 ring members, whereas other such groups have 3 to 15 ring members. At least one ring contains a heteroatom, but every ring in a polycyclic system need not contain a heteroatom. For example, a dioxolanyl ring and a benzdioxolanyl ring system (methylenedioxyphenyl ring system) are both heterocyclyl groups within the meaning herein. A heterocyclyl group designated as a C$_2$-heterocyclyl can be a 5-ring with two carbon atoms and three heteroatoms, a 6-ring with two carbon atoms and four heteroatoms and so forth. Likewise a C$_4$-heterocyclyl can be a 5-ring with one heteroatom, a 6-ring with two heteroatoms, and so forth. The number of carbon atoms plus the number of heteroatoms sums up to equal the total number of ring atoms.

Heterocyclyl groups also include fused ring species including those having fused aromatic and non-aromatic groups. A heterocyclyl group also includes polycyclic ring systems containing a heteroatom such as, but not limited to, quinuclidyl and also includes heterocyclyl groups that have substituents, including but not limited to alkyl, halo, amino, hydroxy, cyano, carboxy, nitro, thio, or alkoxy groups, bonded to one of the ring members. A heterocyclyl group as defined herein can be a heteroaryl group or a partially or completely saturated cyclic group including at least one ring heteroatom. Heterocyclyl groups include, but are not limited to, pyrrolidinyl, furanyl, tetrahydrofuranyl, dioxolanyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Heterocyclyl groups can be substituted. Representative substituted heterocyclyl groups can be mono-substituted or substituted more than once, including but not limited to, rings containing at least one heteroatom which are mono, di, tri, tetra, penta, hexa, or higher-substituted with substituents such as those listed above, including but not limited to alkyl, halo, amino, hydroxy, cyano, carboxy, nitro, thio, and alkoxy groups.

Heteroaryl groups are aromatic ring moieties containing 5 or more ring members, of which, one or more is a heteroatom such as, but not limited to, N, O, and S. A heteroaryl group designated as a C$_2$-heteroaryl can be a 5-ring with two carbon atoms and three heteroatoms, a 6-ring with two carbon atoms and four heteroatoms and so forth. Likewise a C$_4$-heteroaryl can be a 5-ring with one heteroatom, a 6-ring with two heteroatoms, and so forth. The number of carbon atoms plus the number of heteroatoms sums up to equal the total number of ring atoms. Heteroaryl groups include, but are not limited to, groups such as pyrrolyl, pyrazolyl, pyridinyl, pyridazinyl, pyrimidyl, pyrazyl, pyrazinyl, pyrimidinyl, thienyl, triazolyl, tetrazolyl, triazinyl, thiazolyl, thiophenyl, oxazolyl, isoxazolyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, tetrahydroisoquinolinyl, quinoxalinyl, and quinazolinyl groups. The terms "heteroaryl" and "heteroaryl groups" include fused ring compounds such as wherein at least one ring, but not necessarily all rings, are aromatic, including tetrahydroquinolinyl, tetrahydroisoquinolinyl, indolyl and 2,3-dihydro indolyl. The term also includes heteroaryl groups that have other groups bonded to one of the ring members, including but not limited to alkyl, halo, amino, hydroxy, cyano, carboxy, nitro, thio, or alkoxy groups. Representative substituted heteroaryl groups can be substituted one or more times with groups such as those listed above.

Additional examples of aryl and heteroaryl groups include but are not limited to phenyl, biphenyl, indenyl, naphthyl (1-naphthyl, 2-naphthyl), N-hydroxytetrazolyl, N-hydroxytriazolyl, N-hydroxyimidazolyl, anthracenyl (1-anthracenyl, 2-anthracenyl, 3-anthracenyl), thiophenyl (2-thienyl, 3-thienyl), furyl (2-furyl, 3-furyl), indolyl, oxadiazolyl, isoxazolyl, quinazolinyl, fluorenyl, xanthenyl, isoindanyl, benzhydryl, acridinyl, thiazolyl, pyrrolyl (2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl 1,2,3-triazol-4-yl, 1,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]thiophenyl, (2-(2,3-dihydro-benzo[b]thiophenyl), 3-(2,3-dihydro-benzo[b]thiophenyl), 4-(2,3-dihydro-benzo[b]thiophenyl), 5-(2,3-dihydro-benzo[b]thiophenyl), 6-(2,3-dihydro-benzo[b]thiophenyl), 7-(2,3-dihydro-benzo[b]thiophenyl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f]azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f]azepine-4-yl, 10,11-dihydro-5H-dibenz[b,f]azepine-5-yl), and the like.

Heterocyclylalkyl groups are alkyl groups as defined above in which a hydrogen or carbon bond of an alkyl group is replaced with a bond to a heterocyclyl group as defined above. Representative heterocyclyl alkyl groups include, but are not limited to, furan-2-yl methyl, furan-3-yl methyl, pyridine-2-yl methyl (α-picolyl), pyridine-3-yl methyl (β-picolyl), pyridine-4-yl methyl (γ-picolyl), tetrahydrofuran-2-yl ethyl, and indol-2-yl propyl. Heterocyclylalkyl groups can be substituted on the heterocyclyl moiety, the alkyl moiety, or both.

Heteroarylalkyl groups are alkyl groups as defined above in which a hydrogen or carbon bond of an alkyl group is replaced with a bond to a heteroaryl group as defined above. Heteroarylalkyl groups can be substituted on the heteroaryl moiety, the alkyl moiety, or both.

By a "ring system" as the term is used herein is meant a moiety comprising one, two, three or more rings, which can be substituted with non-ring groups or with other ring systems, or both, which can be fully saturated, partially unsaturated, fully unsaturated, or aromatic, and when the ring system includes more than a single ring, the rings can be fused, bridging, or spirocyclic. By "spirocyclic" is meant the class of structures wherein two rings are fused at a single tetrahedral carbon atom, as is well known in the art.

A "monocyclic, bicyclic or polycyclic, aromatic or partially aromatic ring" as the term is used herein refers to a ring system including an unsaturated ring possessing 4n+2 pi electrons, or a partially reduced (hydrogenated) form thereof. The aromatic or partially aromatic ring can include additional fused, bridged, or spiro rings that are not themselves aromatic or partially aromatic. For example, naphthalene and tetrahydronaphthalene are both a "monocyclic, bicyclic or polycyclic, aromatic or partially aromatic ring" within the meaning herein. Also, for example, a benzo-[2.2.2]-bicyclooctane is also a "monocyclic, bicyclic or polycyclic, aromatic or partially aromatic ring" within the meaning herein, containing a phenyl ring fused to a bridged bicyclic system. A fully saturated ring has no double bonds therein, and is carbocyclic or heterocyclic depending on the presence of heteroatoms within the meaning herein.

When two "R" groups are said to be joined together or taken together to form a ring, it is meant that together with the carbon atom or a non-carbon atom (e.g. nitrogen atom), to which they are bonded, they may form a ring system. In general, they are bonded to one another to form a 3- to 7-membered ring, or a 5- to 7-membered ring. Non-limiting specific examples are the cyclopentyl, cyclohexyl, cycloheptyl, piperidinyl, piperazinyl, pyrolidinyl, pyrrolyl, pyridinyl. One specific example includes the formation of a heterocyclic ring between $R_1$, the N atom to which it is attached, and an $R_{10}$ in Formula I, e.g., when $L_1$ is —$NR_{10}$—, and $i_1$ and $j_1$ is zero, $W_1$ becomes —$NR_{10}R_1$.

The term "alkoxy" refers to an oxygen atom connected to an alkyl group, including a cycloalkyl group, as are defined above. Examples of linear alkoxy groups include but are not limited to methoxy, ethoxy, n-propoxy, n-butoxy, n-pentyloxy, n-hexyloxy, n-heptyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like.

The terms "aryloxy" and "arylalkoxy" refer to, respectively, an aryl group bonded to an oxygen atom and an aralkyl group bonded to the oxygen atom at the alkyl moiety. Examples include but are not limited to phenoxy, naphthyloxy, and benzyloxy.

An "acyl" group as the term is used herein refers to a group containing a carbonyl moiety wherein the group is bonded via the carbonyl carbon atom. The carbonyl carbon atom is also bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-20 additional carbon atoms bonded to the carbonyl group. An acyl group can include double or triple bonds within the meaning herein. An acryloyl group is an example of an acyl group. An acyl group can also include heteroatoms within the meaning here. A nicotinoyl group (pyridyl-3-carbonyl) group is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "amine" includes primary, secondary, and tertiary amines having, e.g., the formula N(group)$_3$ wherein each group can independently be H or non-H, such as alkyl, aryl, and the like. Amines include but are not limited to R—NH$_2$, for example, alkylamines, arylamines, alkylarylamines; R$_2$NH wherein each R is independently selected, such as dialkylamines, diarylamines, aralkylamines, heterocyclylamines and the like; and R$_3$N wherein each R is independently selected, such as trialkylamines, dialkylarylamines, alkyldiarylamines, triarylamines, and the like. The term "amine" also includes ammonium ions as used herein.

An "amino" group is a substituent of the form —NH$_2$, —NHR, —NR$_2$, —NR$_3^+$, wherein each R is independently selected, and protonated forms of each. Accordingly, any compound substituted with an amino group can be viewed as an amine.

An "ammonium" ion includes the unsubstituted ammonium ion NH$_4^+$, but unless otherwise specified, it also includes any protonated or quaternarized forms of amines. Thus, trimethylammonium hydrochloride and tetramethylammonium chloride are both ammonium ions, and amines, within the meaning herein.

The term "amide" (or "amido") includes C- and N-amide groups, i.e., —C(O)NR$_2$, and —NRC(O)R groups, respectively. Amide groups therefore include but are not limited to carbamoyl groups (—C(O)NH$_2$) and formamide groups (—NHC(O)H). A "carboxamido" group is a group of the formula C(O)NR$_2$, wherein R can be H, alkyl, aryl, etc.

The term "carbonyl," refers to a —C(O)— group.

"Halo," "halogen," and "halide" include fluorine, chlorine, bromine and iodine.

The term "perhaloalkyl" refers to an alkyl group where all of the hydrogen atoms are replaced by halogen atoms. Perhaloalkyl groups include, but are not limited to, —CF$_3$.

The term "perhaloalkoxy" refers to an alkoxy group where all of the hydrogen atoms are replaced by halogen atoms. Perhaloalkoxy groups include, but are not limited to, —OCF$_3$.

The terms "comprising," "including," "having," "composed of," are open-ended terms as used herein, and do not preclude the existence of additional elements or components. In a claim element, use of the forms "comprising," "including," "having," or "composed of" means that whatever element is comprised, had, included, or composes is not necessarily the only element encompassed by the subject of the clause that contains that word.

A "salt" as is well known in the art includes an organic compound such as a carboxylic acid, a sulfonic acid, or an amine, in ionic form, in combination with a counterion. For example, acids in their anionic form can form salts with cations such as metal cations, for example sodium, potassium, and the like; with ammonium salts such as NH$_4^+$ or the cations of various amines, including tetraalkyl ammonium salts such as tetramethylammonium, or other cations such as trimethylsulfonium, and the like. A "pharmaceutically acceptable" or "pharmacologically acceptable" salt is a salt formed from an ion that has been approved for human consumption and is generally non-toxic, such as a chloride salt or a sodium salt. A "zwitterion" is an internal salt such as can be formed in a molecule that has at least two ionizable groups, one forming an anion and the other a cation, which serve to balance each other. For example, amino acids such as glycine can exist in a zwitterionic form. A "zwitterion" is a salt within the meaning herein. The compounds of the present invention may take the form of salts. The term "salts" embraces addition salts of free acids or free bases which are compounds of the invention. Salts can be "pharmaceutically-acceptable salts." The term "pharmaceutically-acceptable salt" refers to salts which possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds of the invention.

Suitable pharmaceutically-acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, O-hydroxybutyric, salicylic, galactaric and galacturonic acid. Examples of pharmaceutically unacceptable acid addition salts include, for example, perchlorates and tetrafluoroborates.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N-dibenzylethylenediamine, chloroprocaine, choline, diethanolamine, ethylenediamine, meglumine (N-methylglucamine) and procaine. Examples of pharmaceutically unacceptable base addition salts include lithium salts and cyanate salts. Although pharmaceutically unacceptable salts are not generally useful as medicaments, such salts may be useful, for example as intermediates in the synthesis of Formula I or II compounds, for example in their purification by recrystallization. All of these salts may be prepared by conventional means from the corresponding compound according to Formula I or II by reacting, for example, the appropriate acid or base with the compound according to Formula I or II. The term "pharmaceutically acceptable salts" refers to nontoxic inorganic or organic acid and/or base addition salts, see, for example, Lit et al., Salt Selection for Basic Drugs (1986), *Int J. Pharm.*, 33, 201-217, incorporated by reference herein.

A "hydrate" is a compound that exists in a composition with water molecules. The composition can include water in stoichiometric quantities, such as a monohydrate or a dihydrate, or can include water in random amounts. As the term is used herein a "hydrate" refers to a solid form, i.e., a compound in water solution, while it may be hydrated, is not a hydrate as the term is used herein.

A "solvate" is a similar composition except that a solvent other that water replaces the water. For example, methanol or ethanol can form an "alcoholate", which can again be stoichiometric or non-stoichiometric. As the term is used herein a "solvate" refers to a solid form, i.e., a compound in solution in a solvent, while it may be solvated, is not a solvate as the term is used herein.

A "prodrug" as is well known in the art is a substance that can be administered to a patient where the substance is converted in vivo by the action of biochemicals within the patients body, such as enzymes, to the active pharmaceutical ingredient. Examples of prodrugs include esters of carboxylic acid groups, which can be hydrolyzed by endogenous esterases as are found in the bloodstream of humans and other mammals.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described. Moreover, where features or aspects of the invention are described in terms of Markush groups, those skilled in the art will recognize that the invention is also thereby described in terms of any combination of individual members or subgroups of members of Markush groups. Thus, for example, if X is described as selected from the group consisting of bromine, chlorine, and iodine, and Y is described as selected from the group consisting of methyl, ethyl, and propyl, claims for X being bromine and Y being methyl are fully described.

Compositions and Combination Treatments

The GLP-1 compounds, their pharmaceutically acceptable salts or hydrolyzable esters of the present invention may be combined with a pharmaceutically acceptable carrier to provide pharmaceutical compositions useful for treating the biological conditions or disorders noted herein in mammalian species, and more preferably, in humans. The particular carrier employed in these pharmaceutical compositions may vary depending upon the type of administration desired (e.g. intravenous, oral, topical, suppository, or parenteral).

In preparing the compositions in oral liquid dosage forms (e.g. suspensions, elixirs and solutions), typical pharmaceutical media, such as water, glycols, oils, alcohols, flavoring agents, preservatives, coloring agents and the like can be employed. Similarly, when preparing oral solid dosage forms (e.g. powders, tablets and capsules), carriers such as starches, sugars, diluents, granulating agents, lubricants, binders, disintegrating agents and the like can be employed.

Another aspect of an embodiment of the invention provides compositions of the compounds of the invention, alone or in combination with another GLP-1 agonist or another type of therapeutic agent, or both. Non-limiting examples of the GLP-1 receptor agonists include exenatide, liraglutide, taspoglutide, albiglutide, lixisenatide, and mixtures thereof.

In one embodiment, the GLP-1 agonist is exenatide (Byetta®) or Byetta LAR®. Exenatide is described, for example, in U.S. Pat. Nos. 5,424,286; 6,902,744; 7,297,761, and others, the contents of each of which is herein incorporated by reference in its entirety.

In one embodiment, the GLP-1 agonist is liraglutide (VICTOZA®) (also called NN-2211 and [Arg34, Lys26]-(N-epsilon-(gamma-Glu(N-alpha-hexadecanoyl))-GLP-1 (7-37)), includes the sequence HAEGTFTSDVS-SYLEGQAAKEFIAWKVRGRG (SEQ ID NO. 4) and is available from Novo Nordisk (Denmark) or Scios (Fremont, Calif. USA). See, e.g., Elbrond et al., 2002, Diabetes Care. August; 25(8):1398404; Agerso et al., 2002, Diabetologia. February; 45(2):195-202).

In one embodiment, the GLP-1 agonist is taspoglutide (CAS Registry No. 275371-94-3) and is available from Hoffman La-Roche. See, for example, U.S. Pat. No. 7,368,427, the contents of which is herein incorporated by reference in its entirety.

In one embodiment, the GLP-1 agonist is albiglutide (SYNCRIA® from GlaxoSmithKline).

In another embodiment, the GLP-1 agonist is lixisenatide (Lyxumia® from Sanofi-Aventis/Zealand Pharma).

As set forth herein, compounds of the invention include stereoisomers, tautomers, solvates, hydrates, isotopes, esters, salts including pharmaceutically acceptable salts, and mixtures thereof. Compositions containing a compound of the invention can be prepared by conventional techniques, e.g. as described in Remington: *The Science and Practice of Pharmacy*, 19th Ed., 1995, incorporated by reference herein. The compositions can appear in conventional forms, for example capsules, tablets, aerosols, solutions, suspensions or topical applications.

Typical compositions include a compound of the invention and a pharmaceutically acceptable excipient which can be a carrier or a diluent. For example, the active compound will usually be mixed with a carrier, or diluted by a carrier, or enclosed within a carrier which can be in the form of an ampoule, capsule, sachet, paper, or other container. When the active compound is mixed with a carrier, or when the carrier serves as a diluent, it can be solid, semi-solid, or liquid material that acts as a vehicle, excipient, or medium for the active compound. The active compound can be adsorbed on a granular solid carrier, for example contained in a sachet. Some examples of suitable carriers are water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent can include any sustained release material known in the art, such as glyceryl monostearate or glyceryl distearate, alone or mixed with a wax.

The formulations can be mixed with auxiliary agents which do not deleteriously react with the active compounds. Such additives can include wetting agents, emulsifying and suspending agents, salt for influencing osmotic pressure, buffers and/or coloring substances preserving agents, sweetening agents or flavoring agents. The compositions can also be sterilized if desired.

The route of administration can be any route which effectively transports the active compound of the invention to the appropriate or desired site of action, such as oral, nasal, pulmonary, buccal, subdermal, intradermal, transdermal or parenteral, e.g., rectal, depot, subcutaneous, intravenous, intraurethral, intramuscular, intranasal, ophthalmic solution or an ointment, the oral route being preferred.

For parenteral administration, the carrier will typically comprise sterile water, although other ingredients that aid solubility or serve as preservatives can also be included. Furthermore, injectable suspensions can also be prepared, in which case appropriate liquid carriers, suspending agents and the like can be employed.

For topical administration, the compounds of the present invention can be formulated using bland, moisturizing bases such as ointments or creams.

If a solid carrier is used for oral administration, the preparation can be tabletted, placed in a hard gelatin capsule in powder or pellet form or it can be in the form of a troche or lozenge. If a liquid carrier is used, the preparation can be in the form of a syrup, emulsion, soft gelatin capsule or sterile injectable liquid such as an aqueous or non-aqueous liquid suspension or solution.

Injectable dosage forms generally include aqueous suspensions or oil suspensions which can be prepared using a suitable dispersant or wetting agent and a suspending agent Injectable forms can be in solution phase or in the form of a suspension, which is prepared with a solvent or diluent. Acceptable solvents or vehicles include sterilized water, Ringer's solution, or an isotonic aqueous saline solution. Alternatively, sterile oils can be employed as solvents or suspending agents. Preferably, the oil or fatty acid is non-volatile, including natural or synthetic oils, fatty acids, mono-, di- or tri-glycerides.

For injection, the formulation can also be a powder suitable for reconstitution with an appropriate solution as described above. Examples of these include, but are not limited to, freeze dried, rotary dried or spray dried powders, amorphous powders, granules, precipitates, or particulates. For injection, the formulations can optionally contain stabilizers, pH modifiers, surfactants, bioavailability modifiers and combinations of these. The compounds can be formulated for parenteral administration by injection such as by bolus injection or continuous infusion. A unit dosage form for injection can be in ampoules or in multi-dose containers.

The formulations of the invention can be designed to provide quick, sustained, or delayed release of the active ingredient after administration to the patient by employing procedures well known in the art. Thus, the formulations can also be formulated for controlled release or for slow release.

Compositions contemplated by the present invention can include, for example, micelles or liposomes, or some other encapsulated form, or can be administered in an extended release form to provide a prolonged storage and/or delivery effect. Therefore, the formulations can be compressed into pellets or cylinders and implanted intramuscularly or subcutaneously as depot injections. Such implants can employ known inert materials such as silicones and biodegradable polymers, e.g., polylactide-polyglycolide. Examples of other biodegradable polymers include poly(orthoesters) and poly(anhydrides).

For nasal administration, the preparation can contain a compound of the invention, dissolved or suspended in a liquid carrier, preferably an aqueous carrier, for aerosol application. The carrier can contain additives such as solubilizing agents, e.g., propylene glycol, surfactants, absorption enhancers such as lecithin (phosphatidylcholine) or cyclodextrin, or preservatives such as parabens.

For parenteral application, particularly suitable are injectable solutions or suspensions, preferably aqueous solutions with the active compound dissolved in polyhydroxylated castor oil.

Dosage forms can be administered daily, or more than once a day, such as twice or thrice daily. Alternatively dosage forms can be administered less frequently than daily, such as every other day, or weekly, if found to be advisable by a prescribing physician.

An embodiment of the invention also encompasses prodrugs of a compound of the invention which on administration undergo chemical conversion by metabolic or other physiological processes before becoming active pharmacological substances. Conversion by metabolic or other physiological processes includes without limitation enzymatic (e.g, specific enzymatically catalyzed) and non-enzymatic (e.g., general or specific acid or base induced) chemical transformation of the prodrug into the active pharmacological substance. In general, such prodrugs will be functional derivatives of a compound of the invention which are readily convertible in vivo into a compound of the invention. Conventional procedures for the selection and preparation of suitable prodrug derivatives are described, for example, in *Design of Prodrugs*, ed. H. Bundgaard, Elsevier, 1985.

In another embodiment, there are provided methods of making a composition of a compound described herein including formulating a compound of the invention with a pharmaceutically acceptable carrier or diluent. In some embodiments, the pharmaceutically acceptable carrier or diluent is suitable for oral administration. In some such embodiments, the methods can further include the step of formulating the composition into a tablet or capsule. In other embodiments, the pharmaceutically acceptable carrier or diluent is suitable for parenteral administration. In some such embodiments, the methods further include the step of lyophilizing the composition to form a lyophilized preparation.

The compounds of the invention can be used therapeutically in combination with i) one or more other GLP-1 modulators and/or ii) one or more other types of therapeutic agents which can be administered orally in the same dosage form, in a separate oral dosage form (e.g., sequentially or non-sequentially) or by injection together or separately (e.g., sequentially or non-sequentially). Examples of combination therapeutic agents include Sitagliptin (MK-0431, Januvia) an oral antihyperglycemic (antidiabetic drug) of the dipeptidyl peptidase-4 (DPP-4) inhibitor class and Exenatide (Byetta) an incretin mimetic.

Combinations of the invention include mixtures of compounds from (a) and (b) in a single formulation and compounds from (a) and (b) as separate formulations. Some combinations of the invention can be packaged as separate formulations in a kit. In some embodiments, two or more compounds from (b) are formulated together while a compound of the invention is formulated separately.

The dosages and formulations for the other agents to be employed, where applicable, will be as set out in the latest edition of the *Physicians' Desk Reference*, incorporated herein by reference.

Methods of Treatment

In certain embodiments, the present invention encompasses compounds that bind with high affinity and specificity to the GLP-1 receptor in an agonist manner or as an activator or a potentiator. In certain embodiments a compound of the invention acts as a positive allosteric modulator of GLP-1 receptor.

In certain embodiments, the present invention provides a method for activating or agonizing (i.e., to have an agonic effect, to act as an agonist) a GLP-1 receptor, with a compound of the invention. The method involves contacting the receptor with a suitable concentration of an inventive compound to bring about activation of the receptor. The contacting can take place in vitro, for example in carrying out an assay to determine the GLP-1 receptor activation activity of an inventive compound undergoing experimentation related to a submission for regulatory approval.

In certain embodiments, the method for activating an GLP-1 receptor, can also be carried out in vivo, that is, within the living body of a mammal, such as a human patient or a test animal. The inventive compound can be supplied to the living organism via one of the routes as described above, e.g., orally, or can be provided locally within the body tissues. In the presence of the inventive compound, activation of the receptor takes place, and the effect thereof can be studied.

An embodiment of the present invention provides a method of treatment of a malcondition in a patient for which activation of an GLP-1 receptor is medically indicated, wherein the patient is administered the inventive compound in a dosage, at a frequency, and for a duration to produce a beneficial effect on the patient. The inventive compound can be administered by any suitable means, examples of which are described above.

In certain embodiments, the present invention is directed to compounds adapted to act as stabilizers, modulators or potentiators of Class B GPCRs. These compounds may have activity on their own or in the presence of receptor ligands. Receptors include but are not limited to the glucagon receptor, GIP receptor, GLP-1 and GLP-2 receptors, and PTH receptor. Ligands with which compounds of the invention may have activity include, but are not limited to, GIP(1-42), PTH(1-34), Glucagon(1-29), GLP-2(1-33), GLP-1(7-36), GLP-1(9-36), oxyntomodulin, exendin variants, and other insulin regulating peptides.

Methods of treatments provided by the invention include administration of a compound of the invention, alone or in combination with another pharmacologically active agent to a subject or patient having a malcondition for which activation, potentiation or agonism of a glucagon-like peptide 1 receptor is medically indicated such as type I diabetes, type II diabetes, gestational diabetes, obesity, excessive appetite, insufficient satiety, or metabolic disorder.

Preparation of Certain Embodiments

General Synthetic Methods for Preparing Compounds

Molecular embodiments of the present invention can be synthesized using standard synthetic techniques known to those of skill in the art. Compounds of the present invention can be synthesized using the general synthetic procedures set forth in Schemes 1-22.

Scheme 1:

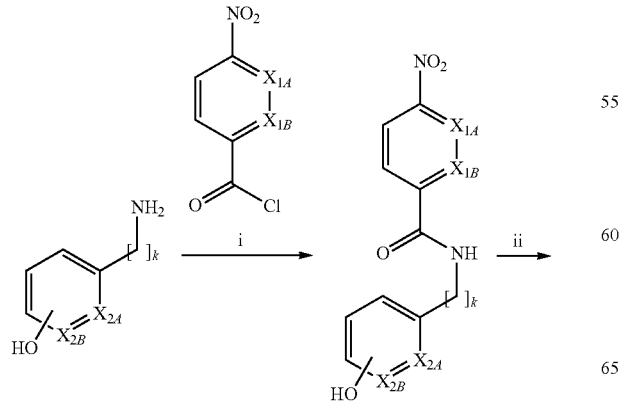

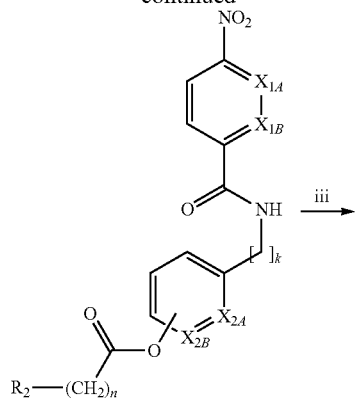

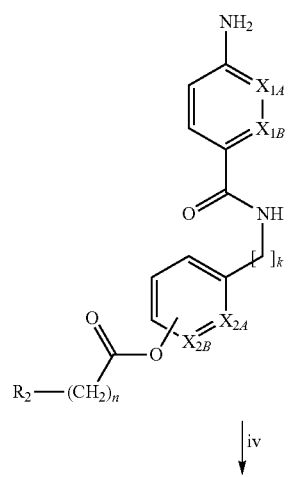

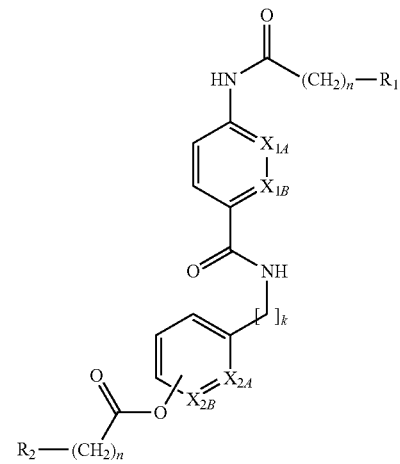

Reagents: (i) TEA, DCM; (ii) ClCO—(CH$_2$)$_n$—R$_2$, TEA, DCM; (iii) H$_2$, Pd/C, THF; (iv) ClCO—(CH$_2$)$_n$—R$_1$, TEA, DCM or HOOC—(CH$_2$)$_n$—R$_1$, HOBt, EDC, TEA, DMF.

Scheme 2:
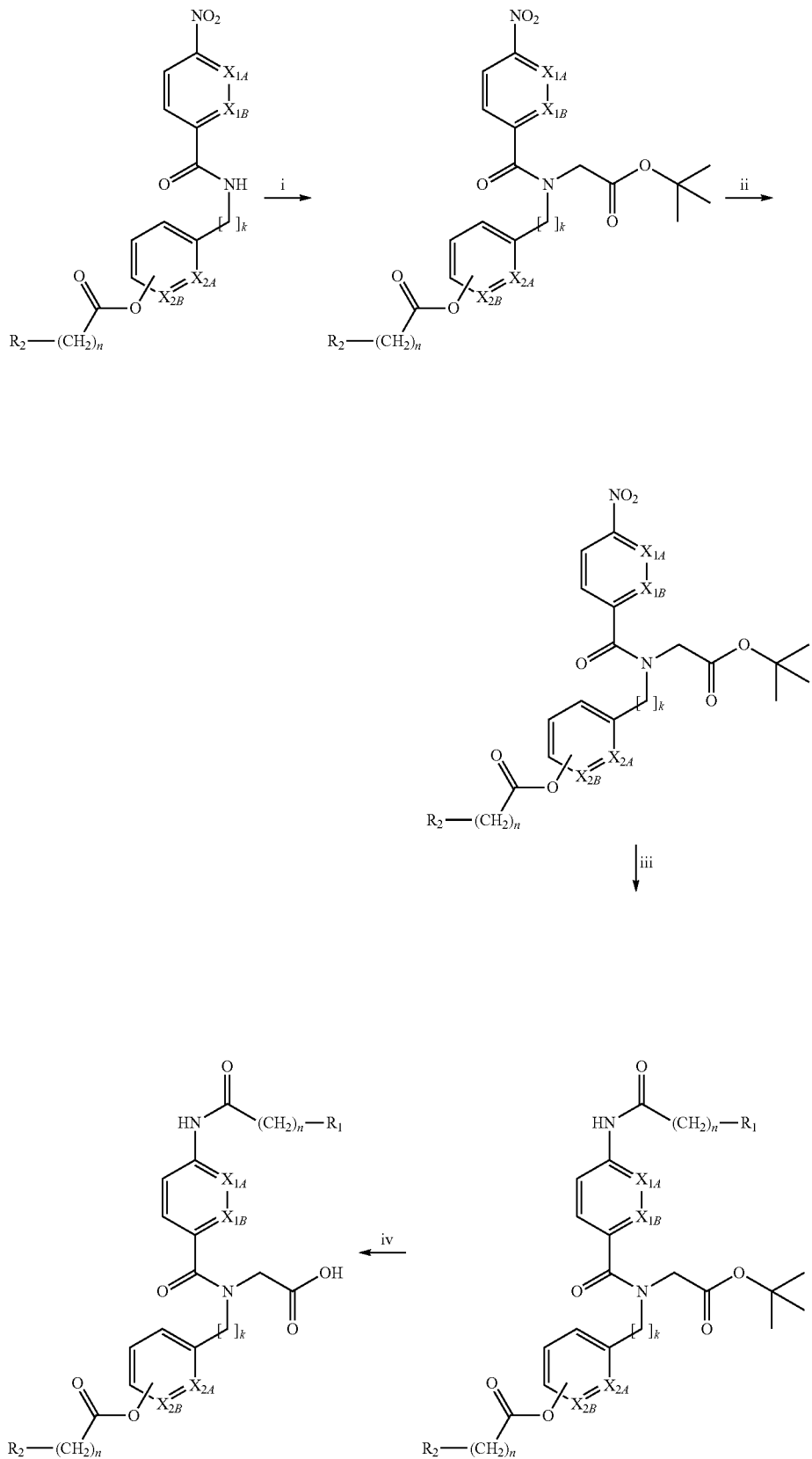

Reagents: (i) tert-Butyl 2-bromoacetate, NaH, DMF; (ii) H₂, Pd/C, THF; (iii) ClCO—(CH₂)$_n$—R₂, TEA, DCM or HOOC—(CH₂)$_n$—R₂, HATU, TEA, DMF; (iv) TFA, DCM.
Scheme 3:
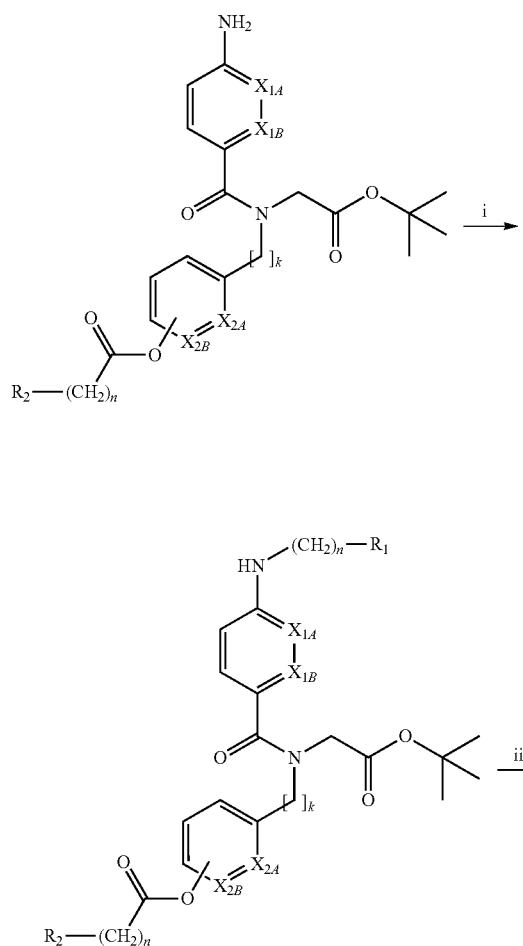
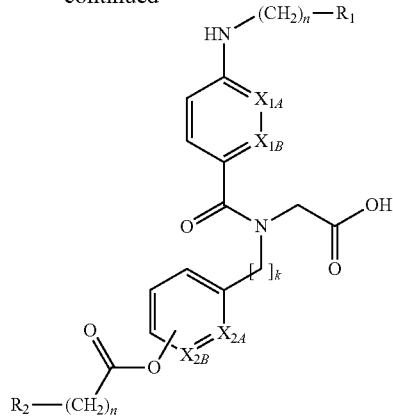
Reagents: (i) HCO(CH₂)$_n$—R₁, Na(OAc)₃BH, DCM; (ii) TFA, DCM.
Scheme 4:
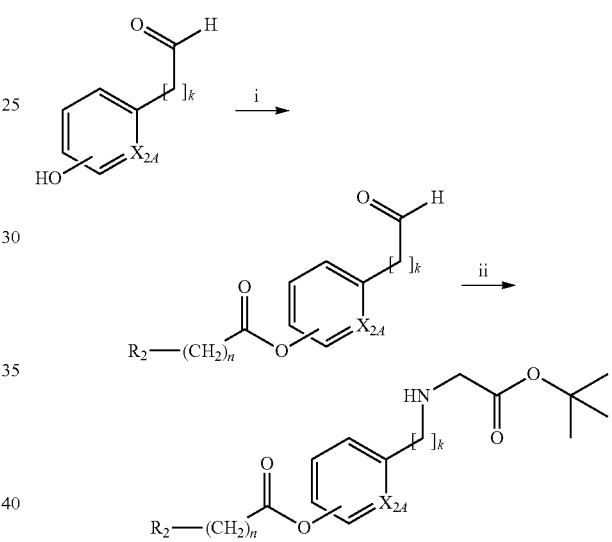
Reagents: (i) ClCO—(CH₂)$_n$—R₂, TEA, DCM; (ii) tert-Butyl 2-aminoacetate, Na(OAc)₃BH, DCM.
Scheme 5:
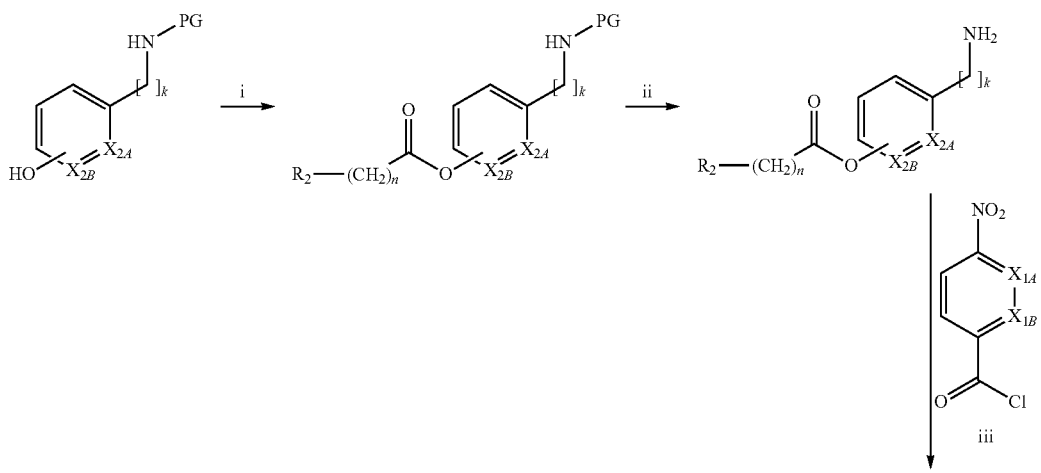

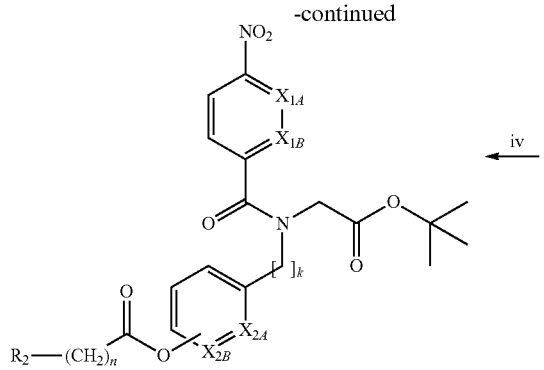
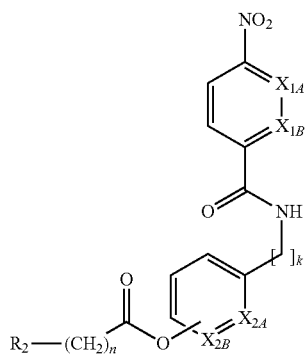
Reagents: (i) PG=Protecting Group, ClCO—(CH$_2$)$_n$—R$_2$, TEA, DCM; (ii) Deprotection e.g. if PG=Boc, then TFA, DCM; (iii) TEA, DCM; (iv) tert-Butyl 2-bromoacetate, NaH, DMF.
Scheme 6:
Scheme 7:
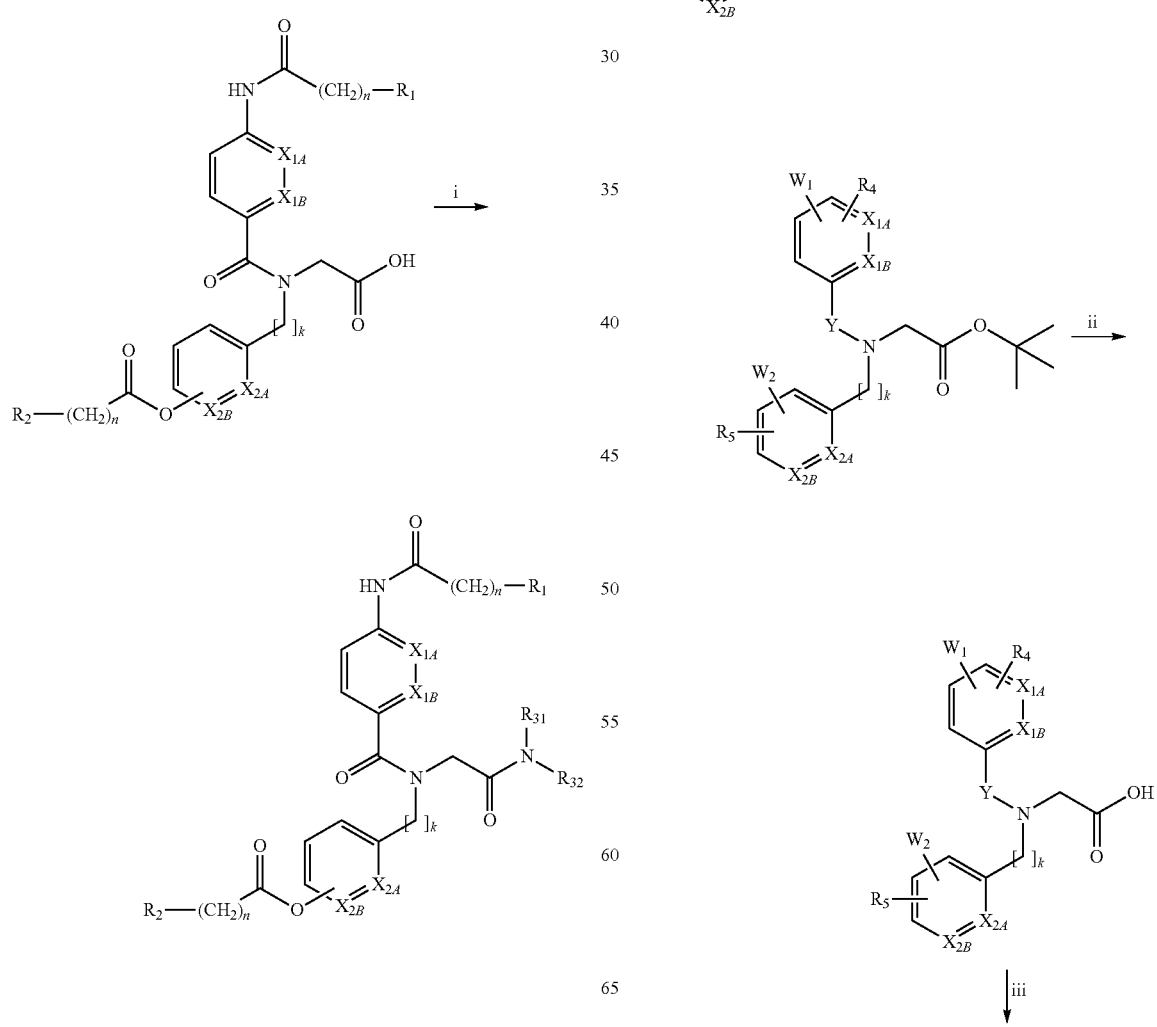
Reagents: (i) HNR$_{31}$R$_{32}$, HATU, TEA, DMF.

41
-continued
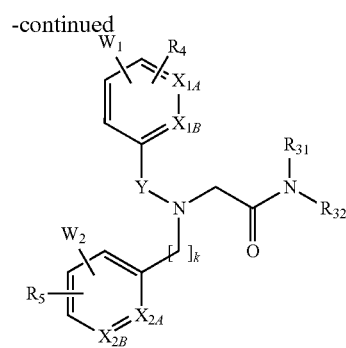
Reagents: (i) $R_4$-Ph/Pyridyl-$W_1$-COCl, TEA, DCM or $R_4$-Ph/Pyridyl-$W_1$—$CO_2H$, HOBt, EDC, TEA, DMF or $R_4$-Ph/Pyridyl-$W_1$-COH, Na(OAc)$_3$BH, DCM; (ii) TFA, DCM; (iii) $HNR_{31}R_{32}$, HATU, TEA, DMF.
Scheme 8:
42
-continued
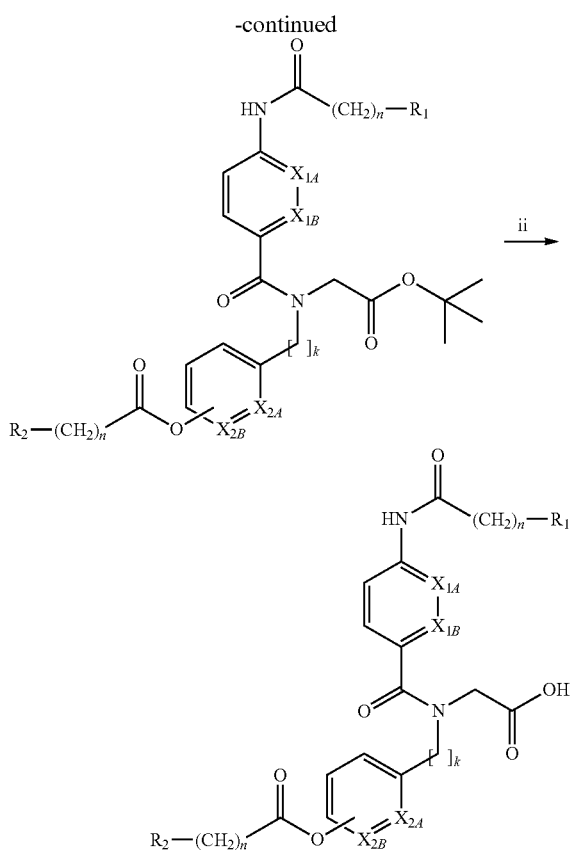
Reagents: (i) ClCO—$(CH_2)_n$—$R_2$, TEA, DCM; (ii) TFA, DCM.
Scheme 9:
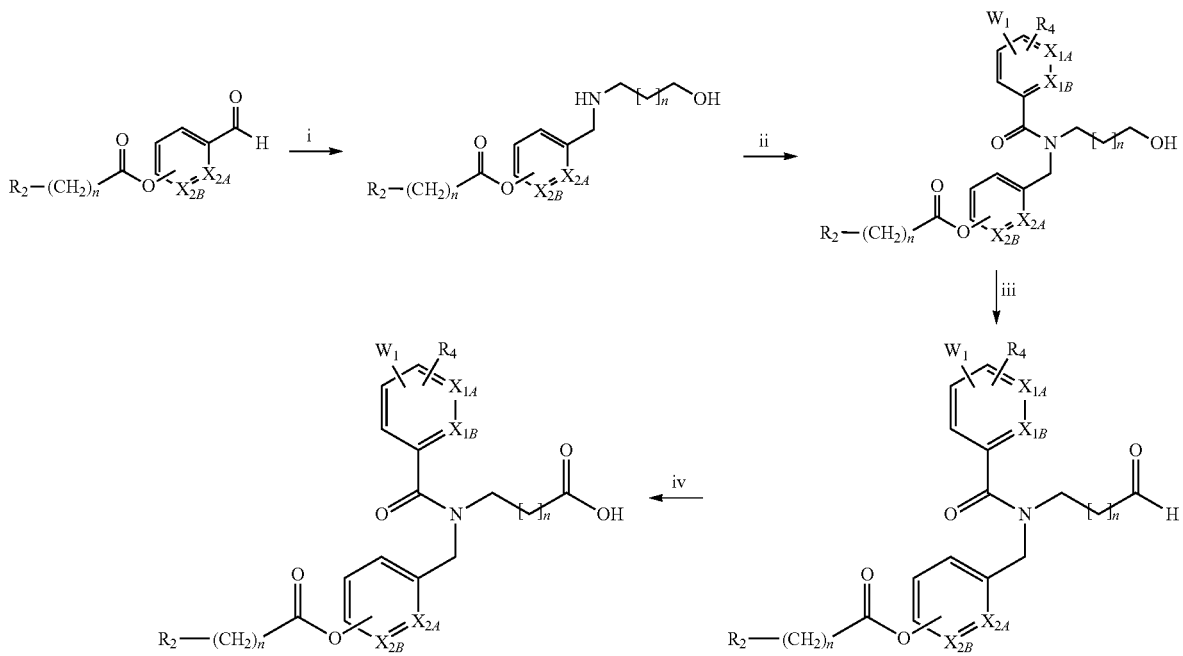

Reagents: (i) NH₂CH₂(CH₂)$_n$CH₂OH, Na(OAc)₃BH, DCM; (ii) R₄-Ph/Pyridyl-W₁-COCl, TEA, DCM or R₄-Ph/Pyridyl-W₁—CO₂H, HATU, TEA, DMF; (iii) Dess-Martin periodinane, NaHCO₃, DCM; (iv) 2-Methylbut-2-ene, sodium dihydrogen phosphate, sodium chlorite, t-BuOH.

Scheme 10:

Reagents: (i) TEA, HATU, DMF; (ii) NaOH, MeOH, THF.

Scheme 11:

Reagents: (i) TEA, HATU, DMF; (ii) Lithium formate, DIEA, acetic anhydride, PdCl₂(dppf), DMF.

Scheme 12:

-continued
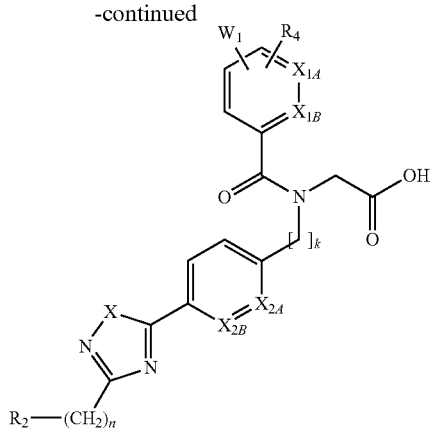
Reagents: For X=O or NH, then (i) N-Methylmorpholine, isobutyl chloroformate, dioxane; (ii) TFA, DCM.
Scheme 13:
Scheme 14:
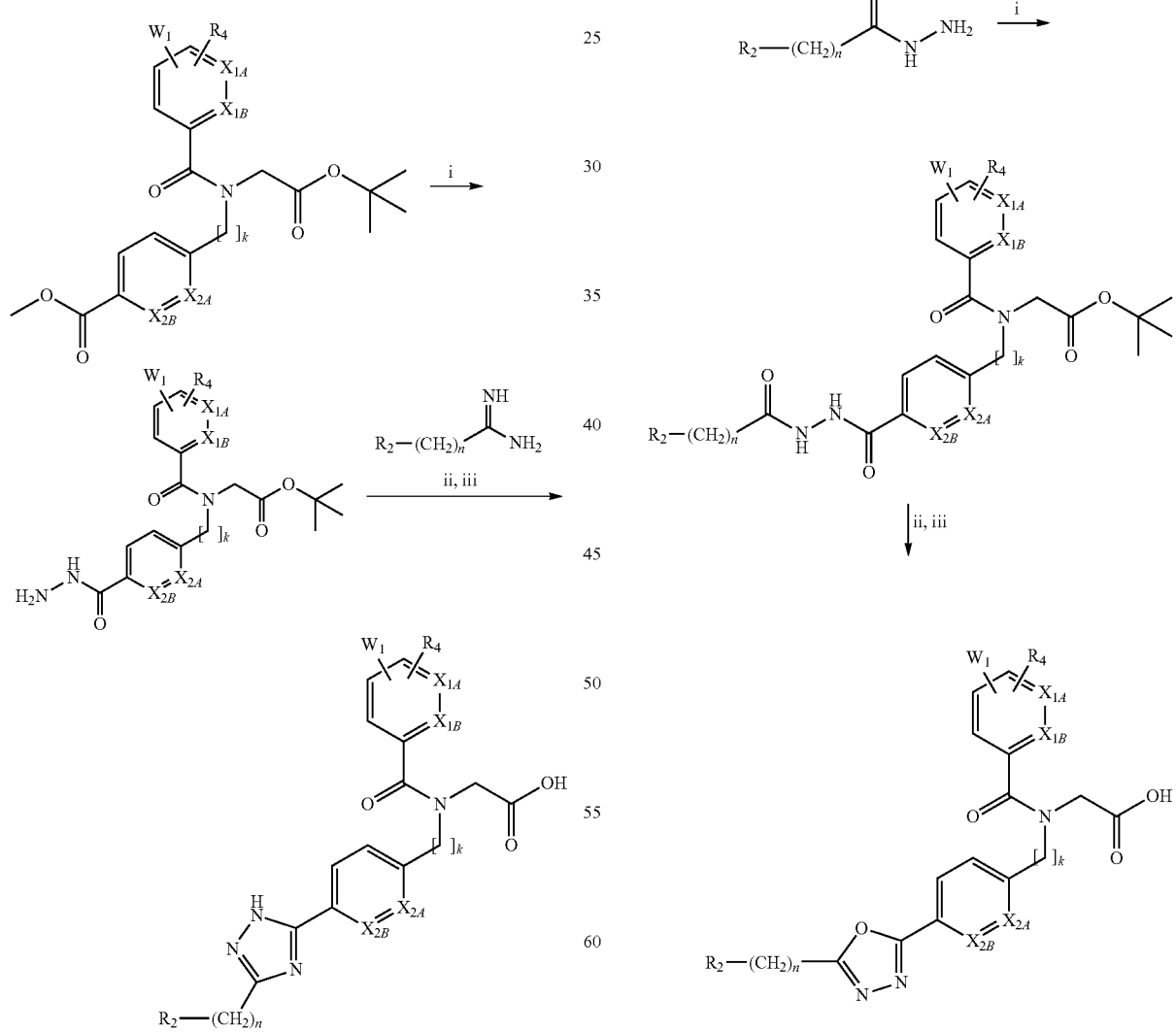
Reagents: (i) Hydrazine hydrate, EtOH; (ii) NaOEt, EtOH; (iii) TFA, DCM.
Reagents: (i) N-Methylmorpholine, isobutyl chloroformate, THF, DMF; (ii) 2-Chloro-1,3-dimethylimidazolinium chloride, TEA, DCM; (iii) TFA, DCM.

Scheme 15:
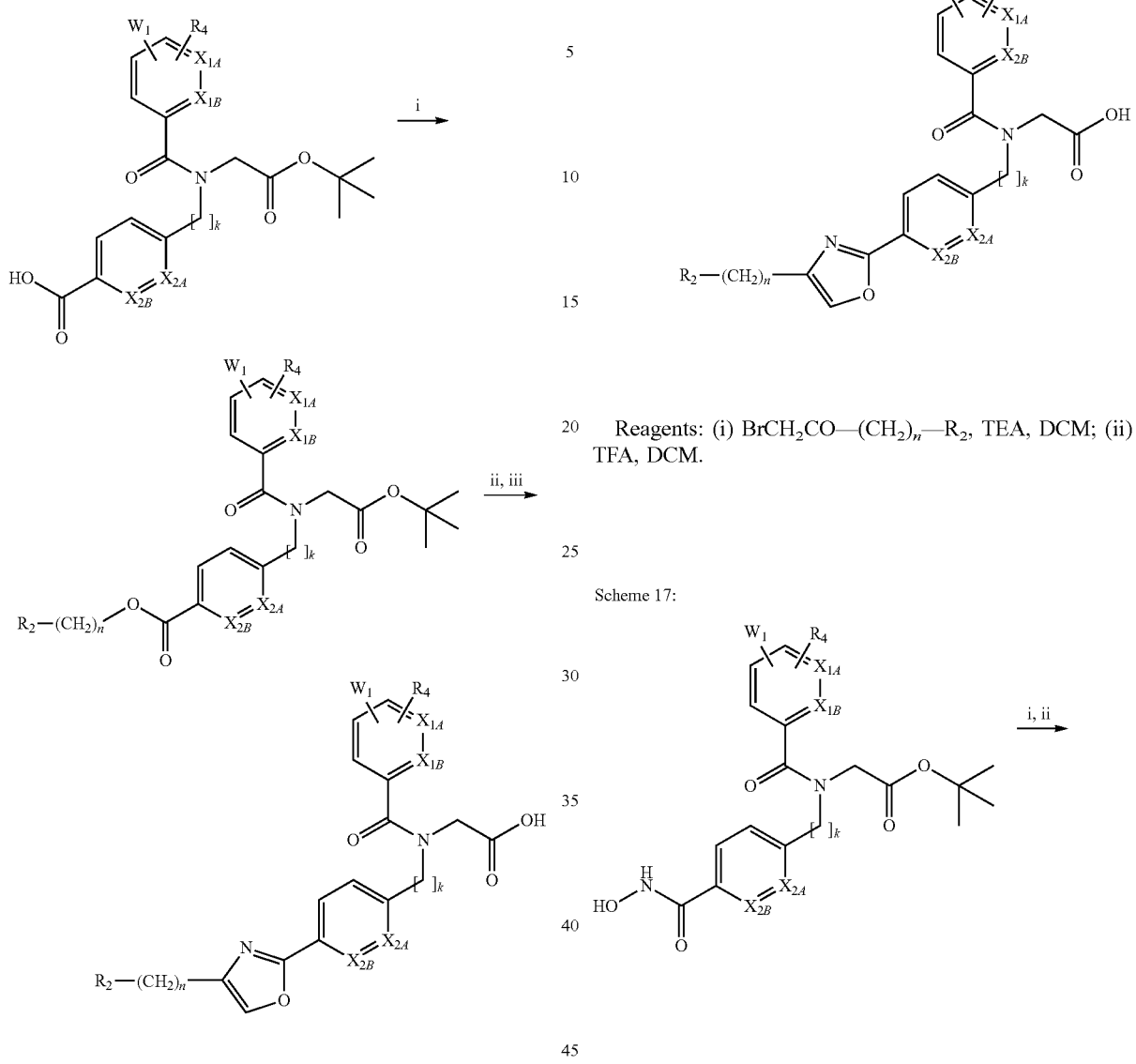
Reagents: (i) BrCH$_2$CO—(CH$_2$)$_n$—R$_2$, DIEA, acetonitrile; Acetamide, Boron trifluoride etherate, DCM; (iii) TFA, DCM.
Scheme 16:
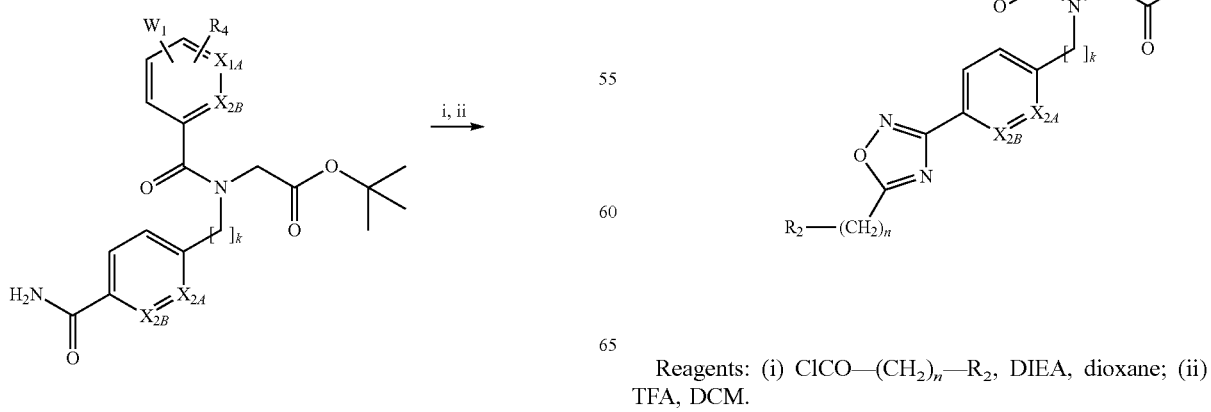
Reagents: (i) BrCH$_2$CO—(CH$_2$)$_n$—R$_2$, TEA, DCM; (ii) TFA, DCM.
Scheme 17:
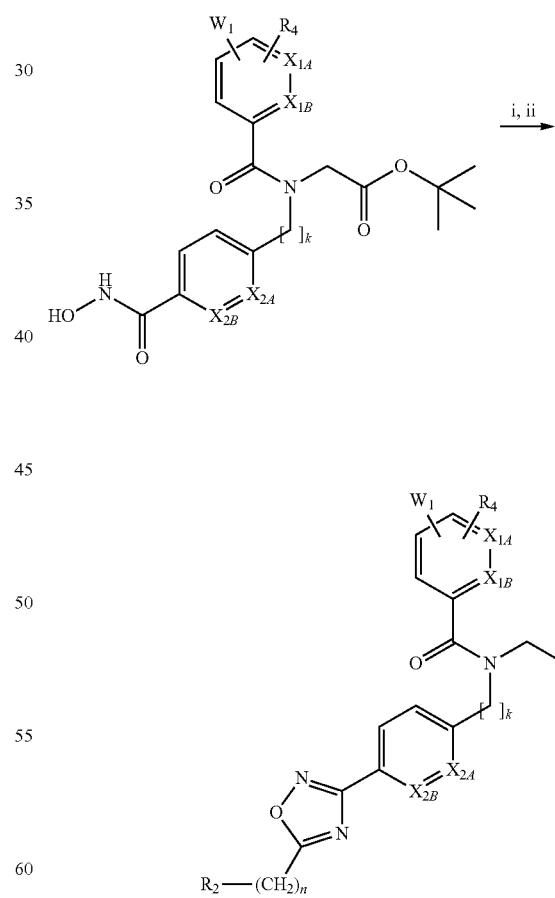
Reagents: (i) ClCO—(CH$_2$)$_n$—R$_2$, DIEA, dioxane; (ii) TFA, DCM.

Scheme 18:
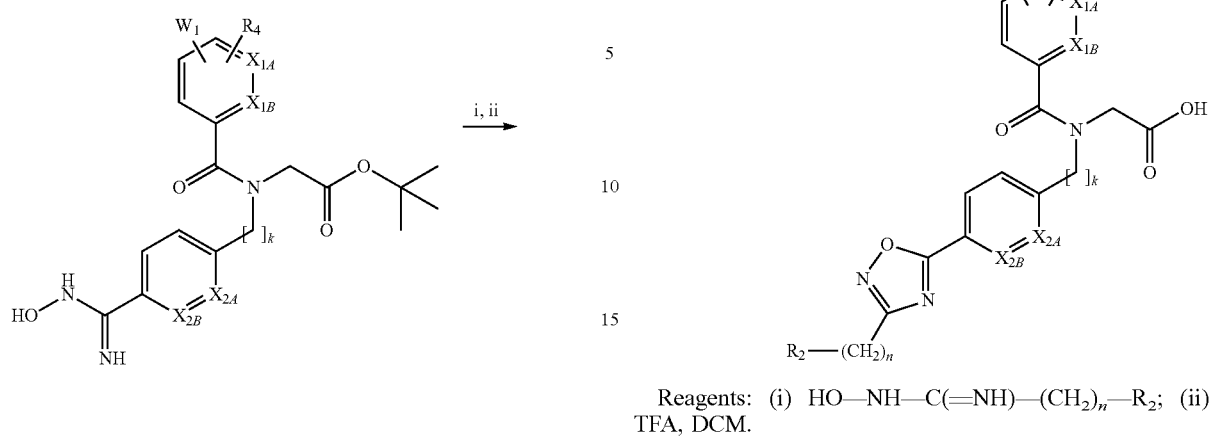
Reagents: (i) HO—NH—C(=NH)—(CH$_2$)$_n$—R$_2$; (ii) TFA, DCM.
Scheme 19:
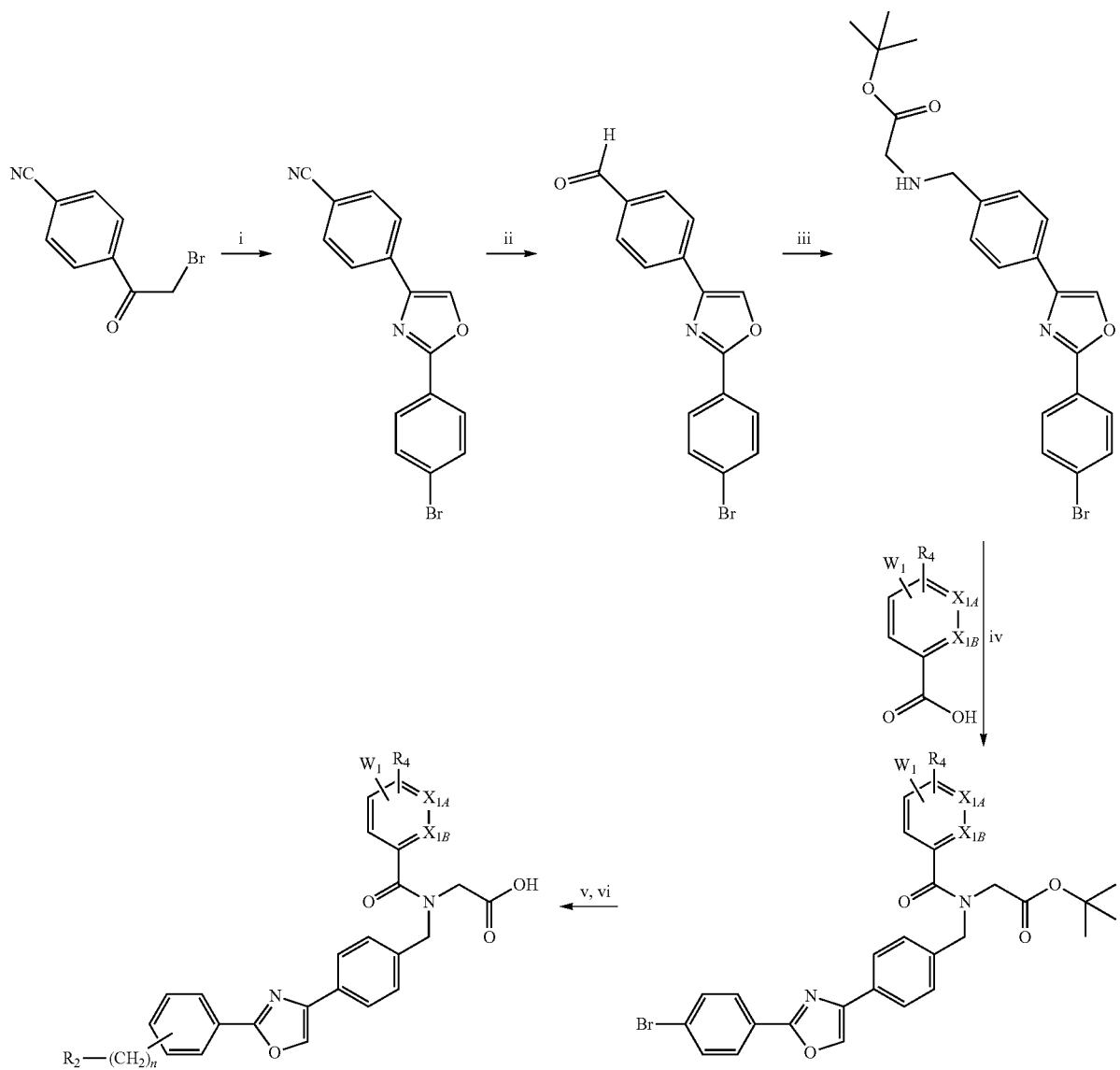

Reagents: (i) 4-Bromobenzamide, NMP; (ii) Diisobutylaluminum hydride, DCM; (iii) tert-butyl glycine hydrochloride, tetramethylammonium triacetoxyhydroborate, DCM; (iv) HATU, DIEA, DMF; (v) $Na_2CO_3$, $B(OH)_2$—$(CH_2)_n$—$R_2$, $PdCl_2(dppf)$, THF, acetonitrile; (vi) TFA, DCM.

Scheme 20:

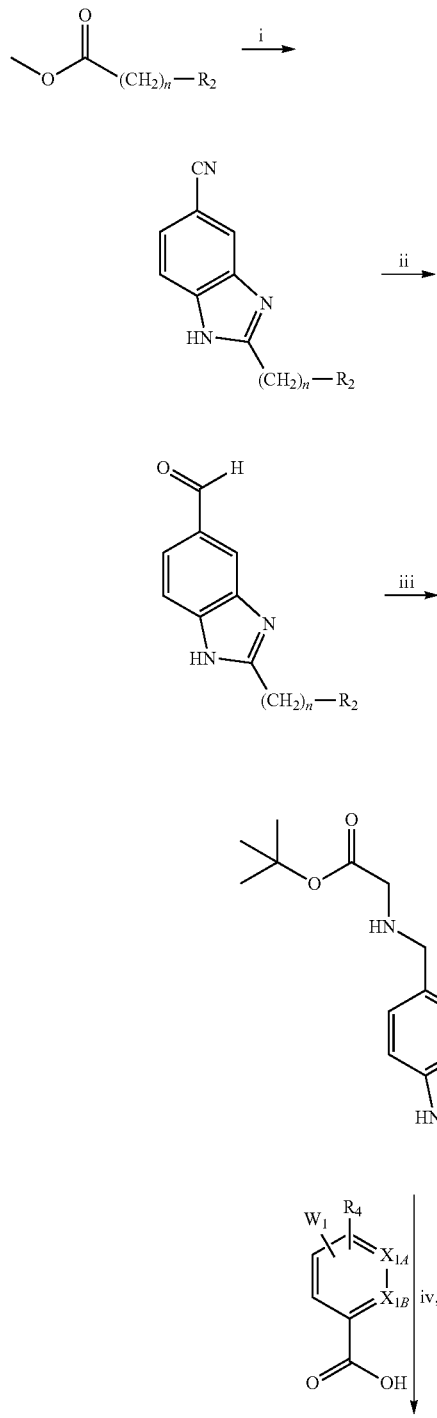

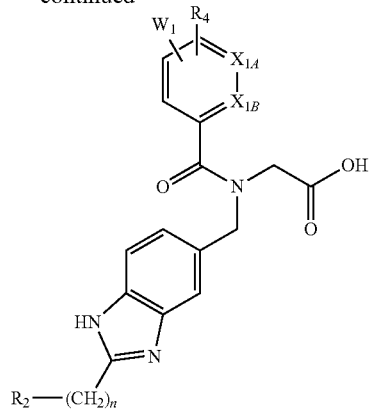

Reagents: (i) 3,4-Diaminobenzonitrile, trimethylaluminum, THF; (ii) Diisobutylaluminum hydride, THF; (iii) tert-Butyl 2-aminoacetate, $Na(OAc)_3BH$, DCM; (iv) HATU, TEA, DMF; (v) TFA, DCM. Other bicyclic compounds can be made in a similar fashion as outlined in Scheme 20.

Scheme 21:

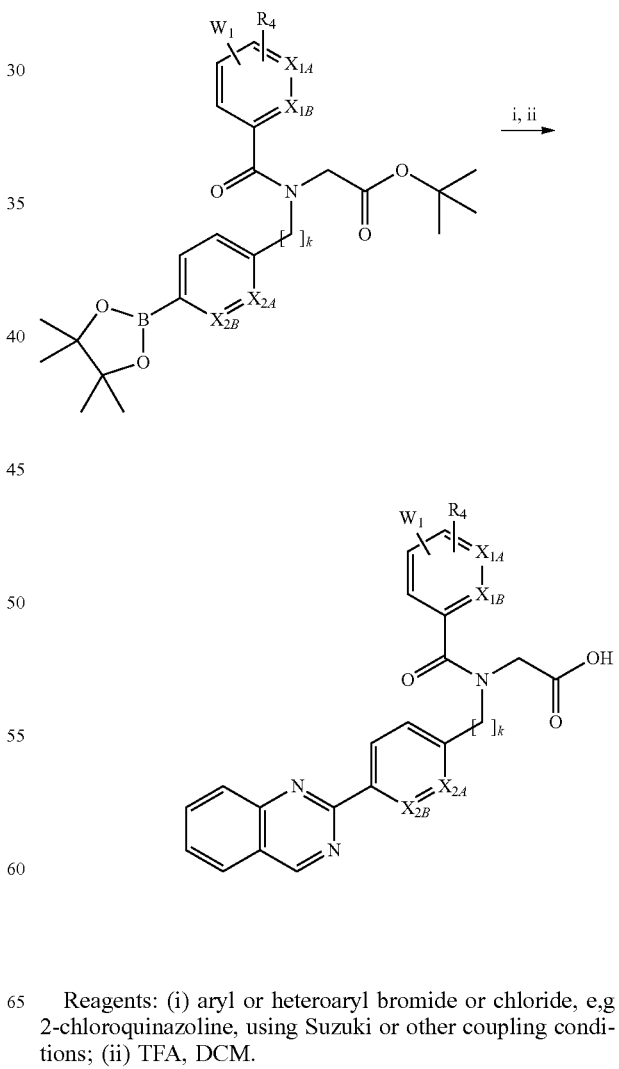

Reagents: (i) aryl or heteroaryl bromide or chloride, e.g 2-chloroquinazoline, using Suzuki or other coupling conditions; (ii) TFA, DCM.

Scheme 22:

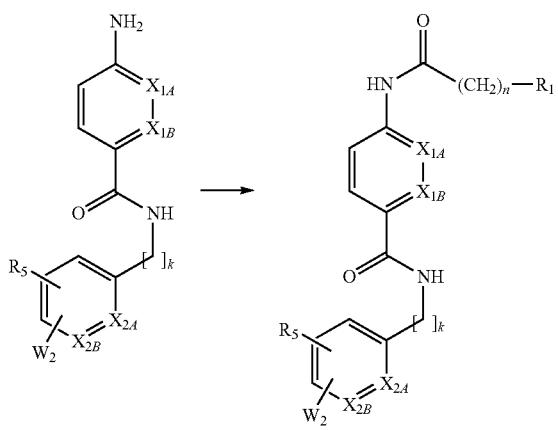

Reagents: (i) ClCO—(CH$_2$)$_n$—R$_1$, TEA, DCM or HOOC—(CH$_2$)$_n$—R$_1$, HOBt, EDC, TEA, DMF.

EXAMPLES

General Methods $^1$H NMR (400 MHz) and $^{13}$C NMR (100 MHz) were obtained in solution of deuteriochloroform (CDCl$_3$) or dimethyl sulfoxide—D$_6$ (DMSO). NMR spectra were processed using Mestrec 5.3.0, MestReNova 6.0.3-5604 or MestreNovaLITE 5.2.5-5780. Mass spectra (LCMS) were obtained using one of 3 systems. System 1: Agilent 1100/6110 HPLC system equipped with a Thompson ODS-A, 100 A, 5µ (50×4.6 mm) column using water with 0.1% formic acid as the mobile phase A, and acetonitrile with 0.1% formic acid as the mobile phase B. Method 1: The gradient was 20-100% with mobile phase B over 2.5 min then held at 100% for 2.5 min with a flow rate of 1 mL/min. Method 2: 5% for 1 min, 5-95% over 9 min, then held at 95% for 5 min, with a flow rate of 1 mL/min. System 2: Agilent 1200 LCMS equipped with an Agilent Zorbax Extend RRHT 1.8 µm (4.6×30 mm) column using water with 0.1% formic acid as mobile phase A and acetonitrile with 0.1% formic acid as mobile phase B. Method 3: The gradient was 5-95% mobile phase B over 3.0 min with a flow rate of 2.5 ml/min, then held at 95% for 0.5 min with an flow rate of 4.5 mL/min. Method 4: 5-95% over 14 min with a flow rate of 2.5 mL/min, then held at 95% for 0.5 min with a flow rate of 4.5 mL/min. System 3: Waters Fractionlynx LCMS system equipped with an Agilent Zorbax Extend RRHT 1.8 µm, (4.6×30 mm) column using water with 0.1% formic acid as mobile phase A and acetonitrile with 0.1% formic acid as mobile phase B. System 4: Agilent 1260 LCMS equipped with an Agilent Zorbax Extend RRHT 1.8 µm (4.6×30 mm) column using water with 0.1% formic acid as mobile phase A and acetonitrile with 0.1% formic acid as mobile phase B. Method 5: The gradient was 5-95% mobile phase B over 3.0 min with a flow rate of 2.5 ml/min, then held at 95% for 0.5 min with an flow rate of 4.5 mL/min. Method 6: 5-95% over 14 min with a flow rate of 2.5 ml/min, then held at 95% for 0.5 min with an flow rate of 4.5 mL/min. Method 7 (using System 1): 40-95% over 0.5 min, then held at 95% for 6 min, then 95-40% for 0.5 min with a flow rate of 1 mL/min. Method 8 (using System 1): The gradient was 20-100% with mobile phase B over 2.5 min then held at 100% for 4.5 min with a flow rate of 1 mL/min. Method 9 (using System 4): 5-95% over 14 min with a flow rate of 2.5 mL/min, then held at 95% for 0.5 min with a flow rate of 4.5 mL/min. Method 10 (using System 4): The gradient was 5-95% mobile phase B over 3.0 min with a flow rate of 2.5 ml/min, then held at 95% for 0.5 min with an flow rate of 4.5 mL/min. Pyridine, dichloromethane (DCM), tetrahydrofuran (THF), and toluene used in the procedures were from Aldrich Sure-Seal bottles or Acros AcroSeal dry solvent and kept under nitrogen (N$_2$). All reactions were stirred magnetically and temperatures are external reaction temperatures. Chromatographies were carried out using either a Combiflash Rf or Combiflash Companion flash purification system (Teledyne Isco) equipped with either Redisep (Teledyne Isco), Telos (Kinesis) or GraceResolv (Grace Davison Discovery Sciences) silica gel (SiO$_2$) columns. Preparative HPLC purifications were performed using one of two systems. System 1: Varian ProStar/PrepStar system equipped with a Waters SunFire Prep C18 OBD, 5 µm (19×150 mm) column using water containing 0.05% trifluoroacetic acid as mobile phase A, and acetonitrile with 0.05% trifluoroacetic acid as mobile phase B. The gradient was 40-95% mobile phase B over 10 min, held at 95% for 5-10 min, and then return to 40% over 2 min with flow rate of 18 mL/min. Fractions were collected using a Varian Prostar fraction collector by UV detection at 254 nm and were evaporated using a Savant SpeedVac Plus vacuum pump or a Genevac EZ-2. System 2: Waters Fractionlynx system equipped with an Agilent Prep-C18, 5 µm (21.2×50 mm) column using water containing 0.1% formic acid as mobile phase A, and acetonitrile with 0.1% formic acid as mobile phase B. The gradient was 45-95% mobile phase B over 7.5 min, held at 95% for 1 min, and then returned to 45% over 1.5 min with a flow rate of 28 mL/min. Fractions were collected by UV detection at 254 nm or by mass and evaporated using a Genevac EZ-2. Compounds with saltable centers were presumed to be either the trifluoroacetic acid (TFA) or formic acid salt. Hydrogenation reactions were performed using a Thales Nanotechnology H-Cube reactor equipped with the specified CatCart or using standard laboratory techniques. The following abbreviations are used: ethyl acetate (EA), triethylamine (TEA), N-hydroxybenzotriazole (HOBt), 1-ethyl-3-(3-dimethylaminopropyl) carbodiimide hydrochloride (EDC), N,N-dimethylformamide (DMF), dimethyl acetamide (DMA), Di-tert-butyl dicarbonate (Boc$_2$O), N,N-Diisopropylethylamine (DIEA), acetic acid (AcOH), hydrochloric acid (HCl), O-(7-azabenzotriazol-1-yl)-N,N,N',N'-tetramethyluronium hexafluorophosphate (HATU), 4-dimethylaminopyridine (DMAP), tert-butanol (t-BuOH), sodium hydride (NaH), sodium triacetoxyborohydride [Na(OAc)$_3$BH].

Experimental Procedures

N-(4-hydroxybenzyl)-4-nitrobenzamide (INT-1)

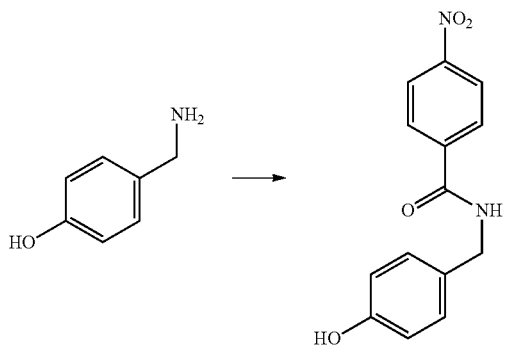 [SMILES: NCc1ccc(O)cc1 ; O=C(NCc1ccc(O)cc1)c1ccc([N+](=O)[O-])cc1]

To a stirring solution of 4-hydroxybenzylamine (0.5 g, 4.06 mmol) and TEA (2.26 mL, 16.24 mmol) in DCM (20 mL) at 0° C. was added 4-nitrobenzoyl chloride (1.66 g, 8.93 mmol) and left at room temperature for 1 h. The reaction mixture was diluted with DCM (100 mL), washed with NaHCO$_3$ (50 mL), and the organic layer reduced to dryness. The resulting residue was diluted with MeOH (25 mL) and DCM (5 mL), to which NaOH (18.0 mL, 1.0 M) was added. After stirring at room temperature for 10 min, analysis showed the bis-acylated material was cleaved to give the desired mono-acylated product. The reaction mixture was acidified with acetic acid until neutral and the MeOH removed under vacuum. The product was extracted into DCM (50 mL) and washed with brine (50 mL). The organic residue was purified by chromatography (EA/hexanes), to afford 647 mg (58%) of N-(4-hydroxybenzyl)-4-nitrobenzamide INT-1. LCMS-ESI (m/z) calculated for C$_{14}$H$_{12}$N$_2$O$_4$: 272. found 273 [M+H]$^+$, t$_R$=1.84 min (Method 5).

General Procedure 1: Preparation of Aryl Esters Via Peptide Coupling

To a stirring solution of the appropriate acid (1-1.2 eq) and DMAP (0.1 eq) in DCM was added DCC (1.3-1.5 eq). After 10 min, the phenol (1 eq) was added and the reaction mixture was stirred for up to 4 h at room temperature. The crude reaction mixture was diluted with DCM and washed with NaHCO$_3$. The organic layer was dried over MgSO$_4$ and concentrated. The final products were purified by chromatography or preparative HPLC. Alternatively, the final products can be purified directly from the crude reaction mixture.

General Procedure 2: Preparation of Aryl Esters Via Acid Chlorides

To a stirring solution of phenol (1.0-1.1 eq) in DCM at 0° C. or room temperature, was added TEA (1.5-4.0 eq) followed by an acid chloride (1.0-2.4 eq). The reaction mixture can be stirred at 0° C. for 30 min, DMAP optionally added (0.25 eq), then stirred at room temperature for up to 18 h. Alternatively, the reaction mixture can be stirred or sonicated at room temperature for up to 18 h. The reaction was quenched with NaHCO$_3$ and the aqueous layer extracted with DCM. The organic layer was dried over MgSO$_4$ and concentrated. The final products were purified by chromatography or preparative HPLC. Alternatively, the final products can be purified directly from the crude reaction mixture. Or, the crude reaction mixture can be used in the next step without purification.

4-((4-nitrobenzamido)methyl)phenyl 4-(heptyloxy) benzoate (INT-2)

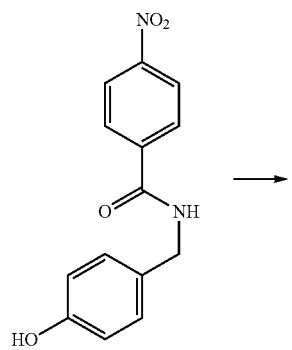

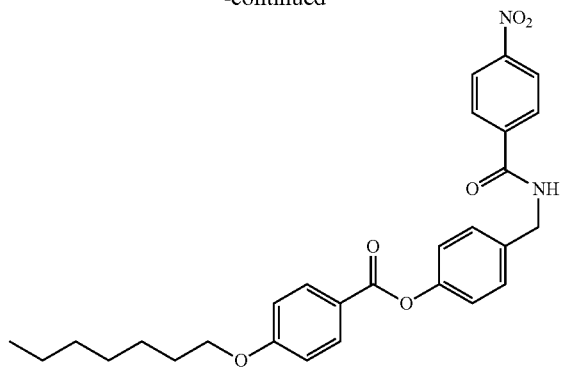

Prepared using General Procedure 2: To a stirring solution of N-(4-hydroxybenzyl)-4-nitrobenzamide INT-1 (647 mg, 2.38 mmol) in DCM (10 mL) at 0° C. was added TEA (1.03 mL, 7.13 mmol) followed by 4-(heptyloxy)benzoyl chloride (12.4 mL, 2.85 mmol). The suspension was sonicated until clear then diluted with DCM (50 mL) and washed with NaHCO$_3$ (20 mL). The organic layer was concentrated and purified by chromatography (EA/hexanes) to provide 857 mg (73%) of 4-((4-nitrobenzamido)methyl)phenyl 4-(heptyloxy)benzoate INT-2. LCMS-ESI (m/z) calculated for C$_{28}$H$_{30}$N$_2$O$_6$: 490. found 491 [M+H]$^+$, t$_R$=3.41 min (Method 5).

General Procedure 3: Introduction of Acid Via Reductive Amination

To a stirring solution of aldehyde (1 eq) in DCM was added aminoacetate (1.0-1.1 eq). After stirring at room temperature for 1 h, sodium triacetoxyborohydride (2 eq) was added and the reaction stirred overnight. The crude reaction mixture was quenched with NaHCO$_3$ and stirred for 5 min. The aqueous layer was extracted with DCM and the organic layer was dried over MgSO$_4$ and concentrated. The product was isolated by chromatography.

General Procedure 4: Introduction of Acid Via Alkylation

To a stirring solution of the appropriate amine or amide (1 eq) in DMF was added sodium hydride (1.1-2.2 eq) or TEA (2 eq) or DIEA (2 eq). After stirring at room temperature for 5 min, the bromoacetate (1.0-2.3 eq) was added and the mixture was stirred for up to 18 h. The crude reaction mixture was diluted with EA and washed with brine. The organic layer was dried over MgSO$_4$, concentrated, and the final product isolated by chromatography.

4-((N-(2-(tert-butoxy)-2-oxoethyl)-4-nitrobenzamido)methyl)phenyl 4-(heptyloxy)benzoate (INT-3)

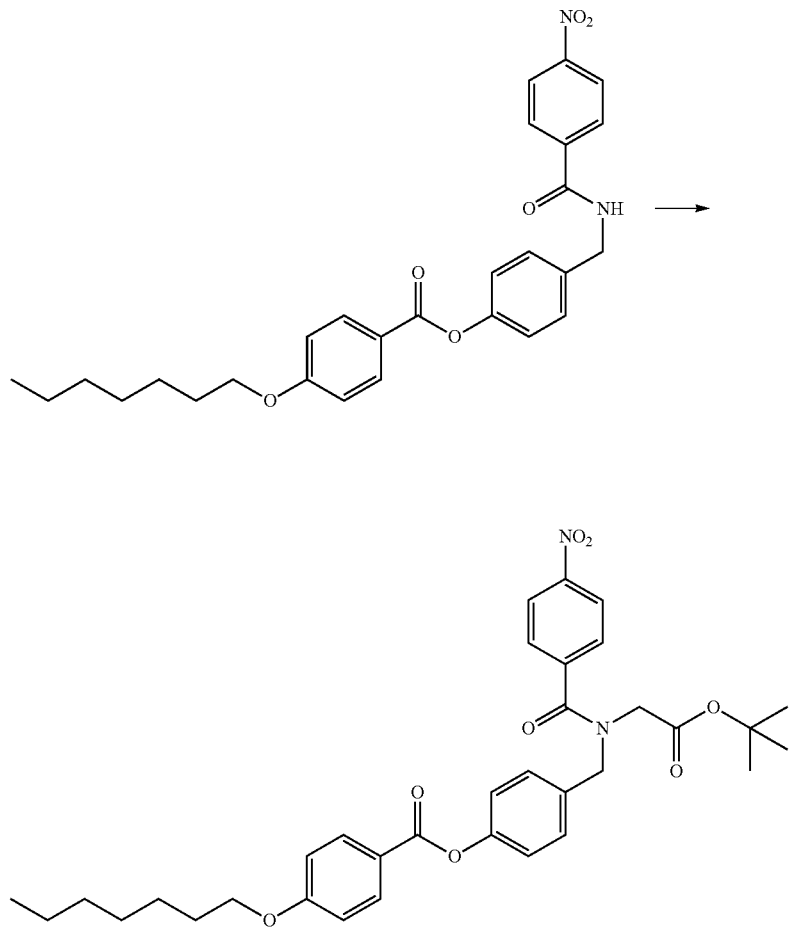

Prepared using General Procedure 4: To a stirring solution of 4-((4-nitrobenzamido)methyl)phenyl 4-(heptyloxy)benzoate INT-2 (857 mg, 1.75 mmol) in DMF (7 mL) was added sodium hydride (77.0 mg, 1.92 mmol). After 5 min, tert-butyl 2-bromoacetate (0.30 mL, 2.01 mmol) was added. After stirring at room temperature for 1 h, additional tert-butyl 2-bromoacetate (0.297 mL, 2.01 mmol) and sodium hydride (77.0 mg, 1.92 mmol) were added and the reaction stirred for another 1 h. The reaction mixture was diluted with EA (100 mL) and washed with brine (200 mL). The organic layer was concentrated and purified by chromatography (EA/hexanes) to provide 888 mg (84%) of 4-((N-(2-(tert-butoxy)-2-oxoethyl)-4-nitrobenzamido)methyl)phenyl 4-(heptyloxy)benzoate INT-3. LCMS-ESI (m/z) calculated for $C_{34}H_{40}N_2O_8$: 604; no m/z observed, $t_R$=3.62 min (Method 5).

General Procedure 5: Reduction of Aryl Nitro to an Aryl Amine

To a stirring solution of aryl nitro (1 eq) in THF purged with $N_2$ was added palladium on carbon. The reaction mixture was subjected to an $H_2$ atmosphere at room temperature or at 40° C. for up to 4 h. The reaction mixture can be filtered over a pad of celite and solvent concentrated. The crude material can be carried forward without further purification, or purified by chromatography or preparative HPLC. Alternatively, to a stirring solution of aryl nitro (1 eq) in THF and water (3:1) was added sodium dithionite (3 eq). The reaction mixture was heated to 65° C. for up to 3 h. The crude reaction mixture was diluted with EA and washed with brine. The organic layer was dried over $MgSO_4$, concentrated, and the final product isolated by chromatography.

4-((4-amino-N-(2-(tert-butoxy)-2-oxoethyl)benzamido)methyl)phenyl 4-(heptyloxy)benzoate (INT-4)

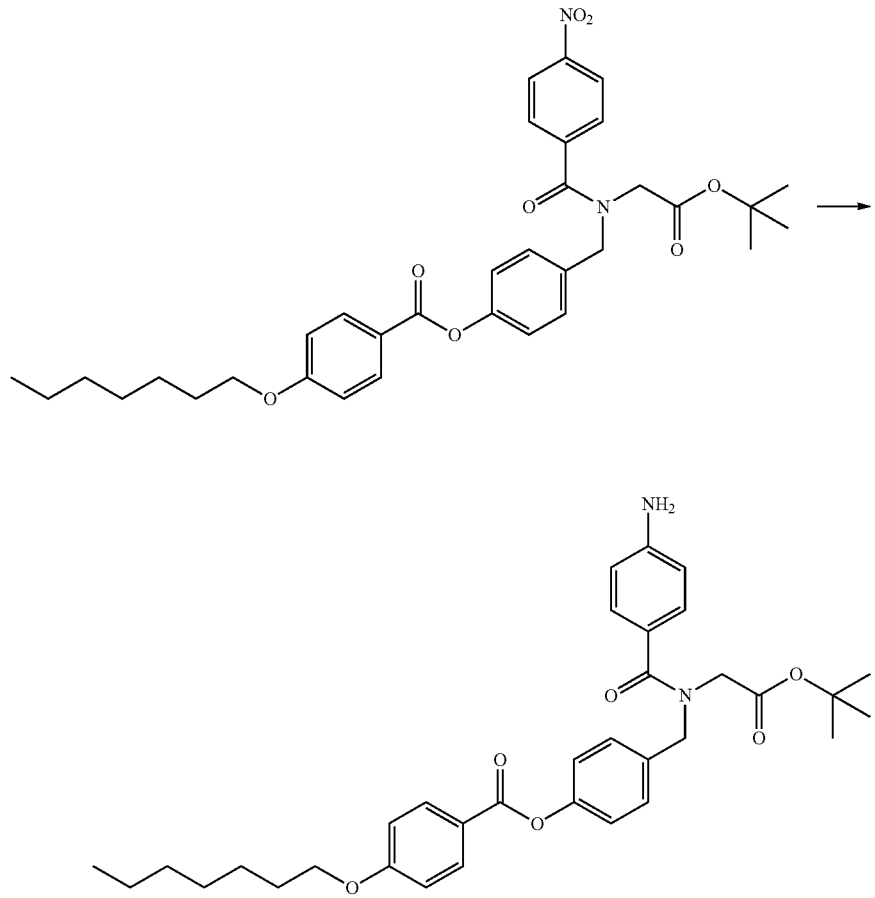

Prepared using General Procedure 5: A solution of 4-((N-(2-(tert-butoxy)-2-oxoethyl)-4-nitrobenzamido)methyl)phenyl 4-(heptyloxy)benzoate INT-3 (888 mg, 1.47 mmol) in THF (15 mL) was hydrogenated in an H-Cube (55 mmol Pd/C cartridge, 1 mL/min, 15 mL volume). The reaction mixture was concentrated to provide 896 mg of crude 4-((4-amino-N-(2-(tert-butoxy)-2-oxoethyl)benzamido)methyl)phenyl 4-(heptyloxy)benzoate INT-4. The crude material was carried forward without further purification. LCMS-ESI (m/z) calculated for $C_{34}H_{42}N_2O_6$: 574. found 475 [M+H-Boc]$^+$, $t_R$=3.48 min (Method 5). $^1$H NMR (400 MHz, CDCl$_3$) δ 8.20-8.04 (m, 2H), 7.44-7.26 (m, 4H), 7.19 (d, J=8.1 Hz, 2H), 7.01-6.90 (m, 2H), 6.63 (d, J=8.3 Hz, 2H), 4.73 (s, 2H), 4.04 (t, J=6.6 Hz, 2H), 3.80-3.67 (m, 2H), 1.89-1.76 (m, 2H), 1.45 (s, 9H), 1.42-1.23 (m, 8H), 0.90 (t, J=6.9 Hz, 3H).

General Procedure 6: Preparation of Amides Via Peptide Coupling

To a stirring solution of the appropriate acid (1-1.5 eq), amine (1 eq) and TEA (1-3 eq) in DMF was added HATU (1-1.2 eq). The reaction mixture was stirred for up to 18 h. Or, to a stirring solution of the appropriate acid (1-1.5 eq) in DMF were added HOBT (1.5 eq) and EDC (1.5 eq). After stirring for up to 2 h, the amine (1 eq) in DMF, and TEA or DIEA (0-2 eq) were added and the reaction mixture was stirred for 18 h at room temperature.

The crude reaction mixture was diluted with EA or DCM, and washed with NaHCO$_3$ or 1N HCl and brine. The organic layer was dried over MgSO$_4$ and concentrated. The final products were either purified by chromatography or preparative HPLC, or used in the next step without further purification. Alternatively, the final products can be purified directly from the crude reaction mixture.

General Procedure 7: Preparation of Amides Via Acid Chlorides

To a stirring solution of amine (1 eq) in DCM at 0° C. or room temperature were added an acid chloride (1.0-2.8 eq) and TEA or DIPEA (1.5-5.0 eq). The reaction mixture was stirred room temperature for up to 18 h. The reaction mixture was diluted with NaHCO$_3$. The aqueous layer was extracted with DCM and the organic layer was dried over MgSO$_4$. The solvent was concentrated and the final products were purified by chromatography or preparative HPLC. Alternatively, the final products can be purified directly from the crude reaction mixture, or the crude reaction mixture can be used in the next step without purification.

General Procedure 8: Deprotection of t-Butyl Acids or Boc Protected Amines

To a stirring solution of tert-butoxy amine (1 eq) in DCM was added excess TFA (50-110 eq) or excess hydrochloric acid (4M, 5-10 eq). The reaction mixture was stirred at room temperature or at 30° C. for up to 18 h. The final products were purified by chromatography or preparative HPLC. Alternatively, the reaction mixture can be concentrated and carried forward without further purification.

Compounds 1-2 were prepared from INT-4 using General Procedures 7 then 8. Compounds 3-15, 89 and 90 were prepared using General Procedures 2, 3, 7, 5, 6, and 8 sequentially. Compounds 91-127 were prepared from INT-4 using General Procedures 6 then 8. Compounds 133-165 were prepared from INT-4 using General Procedures 7 then 8. Compound 176 was prepared from INT-4 using General Procedure 8.

4-((N-(2-(tert-butoxy)-2-oxoethyl)-4-(2-(4-methoxy-phenyl)acetamido) benzamido)-methyl) phenyl 4-(heptyloxy)benzoate (INT-5)

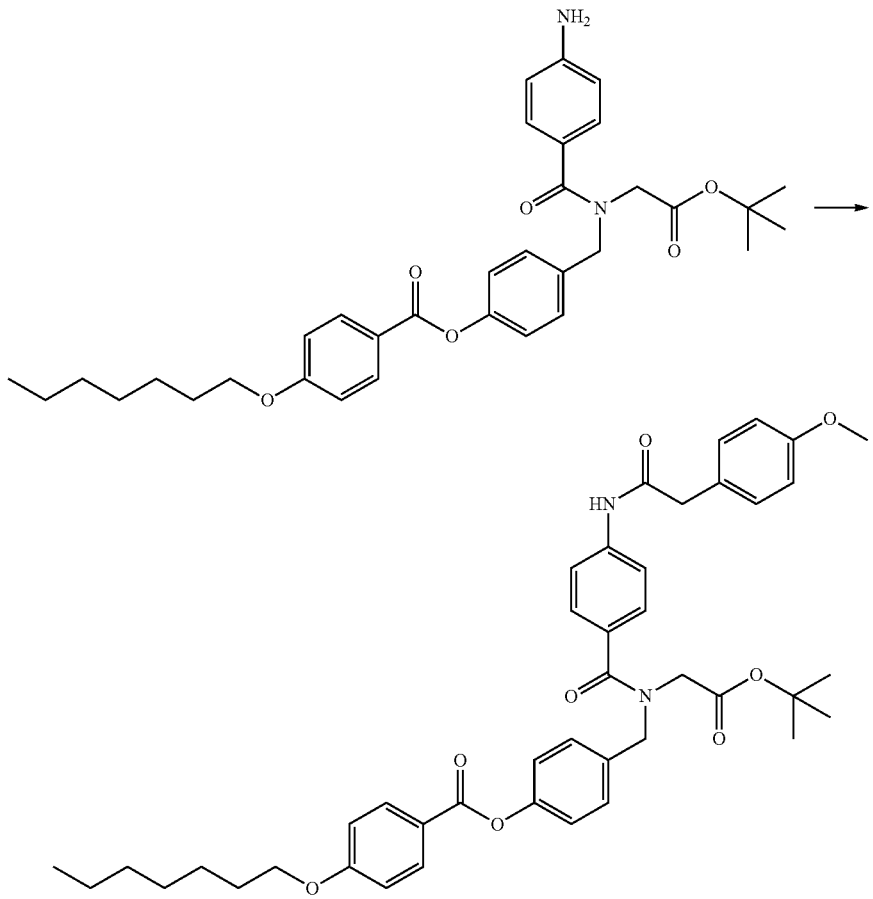

Prepared using General Procedure 7: To a stirring solution of 4-((4-amino-N-(2-(tert-butoxy)-2-oxoethyl)benzamido) methyl)phenyl 4-(heptyloxy)benzoate INT-4 (70 mg, 0.12 mmol) in DCM (2 mL) was added TEA (0.042 mL, 0.31 mmol) and 2-(4-methoxyphenyl)acetyl chloride (0.85 mL, 0.171 mmol). Additional TEA (0.042 mL, 0.31 mmol) and 2-(4-methoxyphenyl)acetyl chloride (0.85 mL, 0.171 mmol) were added and the reaction stirred for 30 min to yield 4-((N-(2-(tert-butoxy)-2-oxoethyl)-4-(2-(4-methoxyphenyl)acetamido) benzamido)methyl)phenyl 4-(heptyloxy)benzoate INT-5. The crude reaction mixture was concentrated to 1.0 mL volume and carried onto the next step without further purification. LCMS-ESI (m/z) calculated for $C_{43}H_{50}N_2O_8$: 722; no m/z observed, $t_R$=3.24 min (Method 3).

2-(N-(4-((4-(heptyloxy)benzoyl)oxy)benzyl)-4-(2-(4-methoxyphenyl)acetamido)benzamido)-acetic acid (Compound 1)

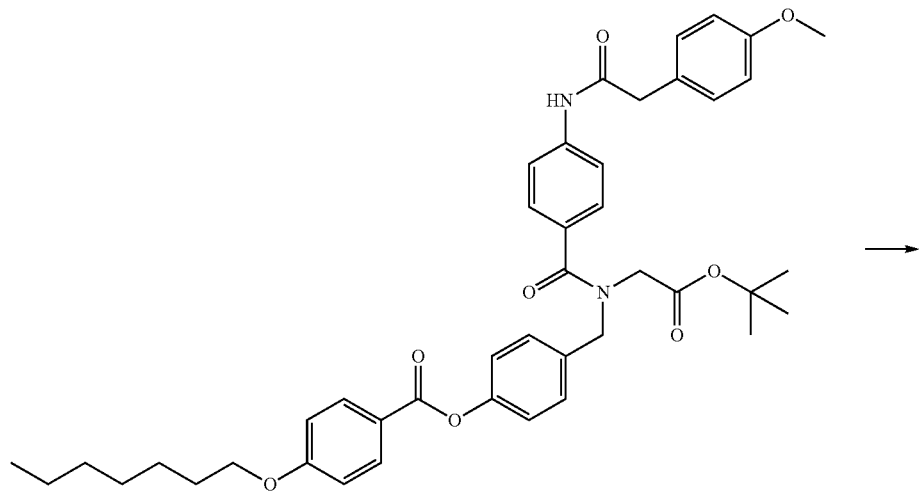

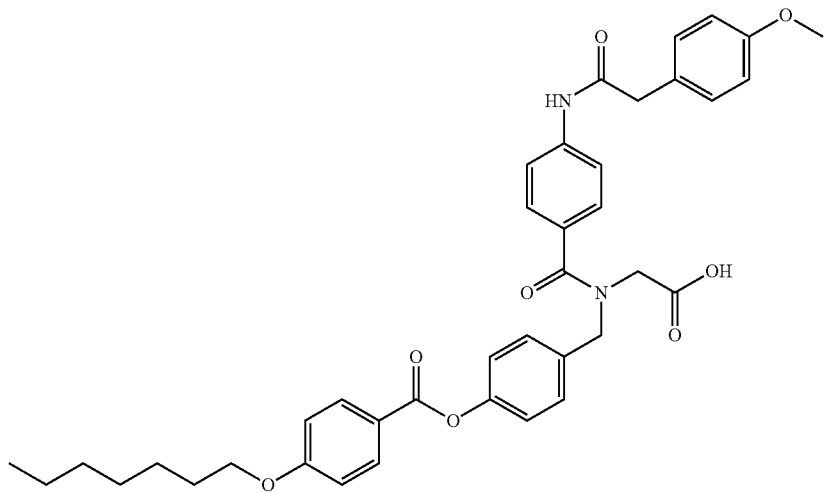

Prepared using General Procedure 8: To crude 4-((N-(2-(tert-butoxy)-2-oxoethyl)-4-(2-(4-methoxyphenyl)acetamido)benzamido)methyl)phenyl 4-(heptyloxy)benzoate INT-5 (70 mg) was added TFA (1 mL). After stirring for 1 h, the solvent was concentrated and the product was purified by preparative HPLC to provide 19 mg (23%) of 2-(N-(4-((4-(heptyloxy)benzoyl) oxy) benzyl)-4-(2-(4-methoxyphenyl) acetamido) benzamido)acetic acid 1. LCMS-ESI (m/z) calculated for $C_{39}H_{42}N_2O_8$: 667. found 666 [M–H]$^-$, $t_R$=9.51 min (Method 4). $^1$H NMR (400 MHz, DMSO) δ 12.80 (s, 1H), 10.31 (s, 1H), 8.16-7.97 (m, 2H), 7.69-7.58 (d, J=8.5 Hz, 2H), 7.48-7.27 (m, 4H), 7.28-7.19 (d, J=8.1 Hz, 4H), 7.15-7.05 (m, 2H), 6.93-6.82 (d, J=8.1 Hz, 2H), 4.74-4.51 (d, J=35.4 Hz, 2H), 4.15-3.80 (m, 4H), 3.71 (s, 3H), 3.66 (s, 2H), 1.84-1.66 (m, 2H), 1.48-1.19 (m, 8H), 0.93-0.80 (t, J=6.6 Hz, 3H).

4-((N-(2-(tert-butoxy)-2-oxoethyl)-4-(2-(4-methoxy-2-(trifluoromethyl)phenyl)acetamido) benzamido) methyl)phenyl 4-(heptyloxy)benzoate (INT-6)

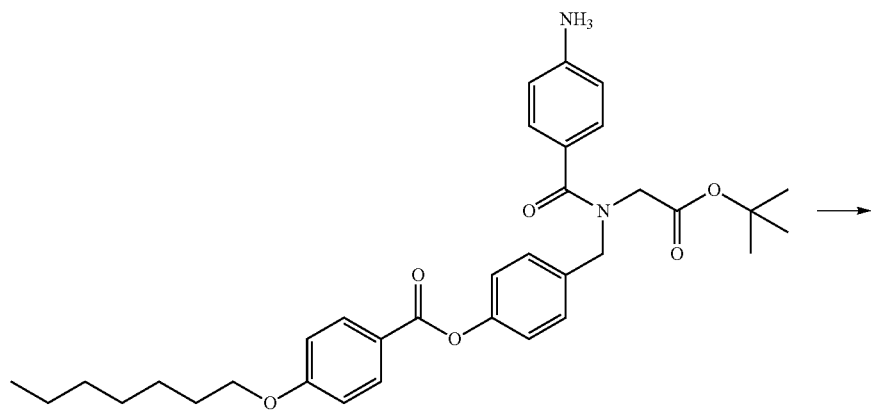

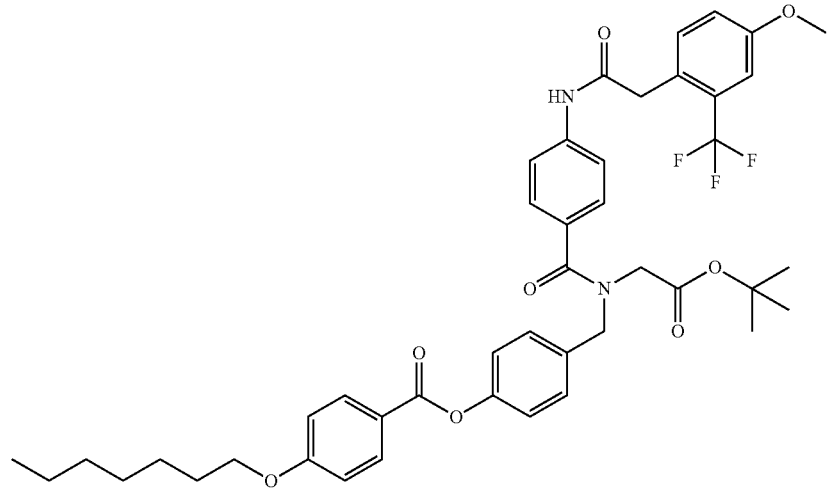

Prepared using General Procedure 7: To 2-(4-methoxy-2-(trifluoromethyl)phenyl)acetic acid (299 mg, 1.28 mmol) in DCM (5 mL) and DMF (20 µL) was added oxalyl chloride (0.117 mL, 1.34 mmol). After stirring at room temperature for 30 min, 4-((4-amino-N-(2-(tert-butoxy)-2-oxoethyl)benzamido)methyl)phenyl 4-(heptyloxy)benzoate INT-4 (700 mg, 1.22 mmol) and TEA (0.424 mL, 3.05 mmol) in DCM (10 mL) were added. The reaction was stirred for 1 h then diluted with DCM (100 mL) and washed with $NaHCO_3$ (100 mL). The crude product was purified by chromatography to provide 555 mg (58%) of 4-((N-(2-(tert-butoxy)-2-oxoethyl)-4-(2-(4-methoxy-2-(trifluoromethyl)phenyl)acetamido)benzamido) methyl) phenyl 4-(heptyloxy) benzoate INT-6. LCMS-ESI (m/z) calculated for $C_{44}H_{49}F_3N_2O_8$: 791; no m/z observed, $t_R$=3.28 min (Method 4).

2-(N-(4-((4-(heptyloxy)benzoyl)oxy)benzyl)-4-(2-(4-methoxy-2-(trifluoromethyl) phenyl)-acetamido) benzamido)acetic acid (Compound 3)

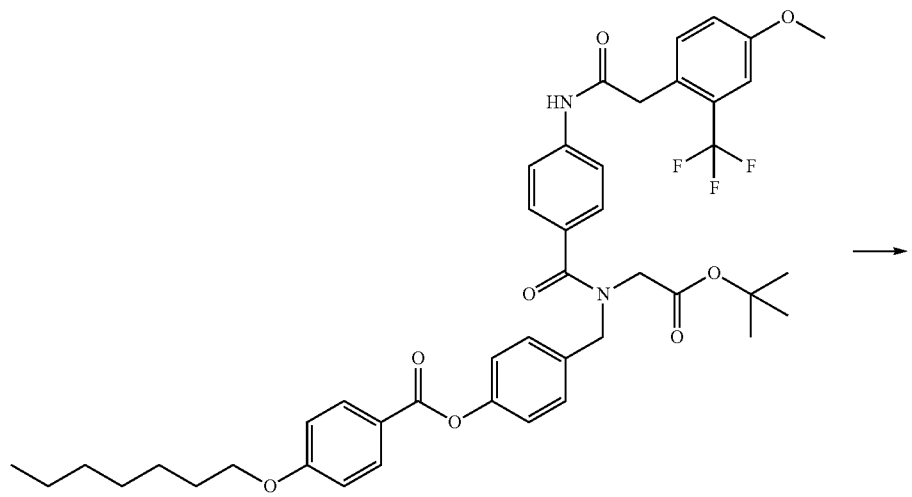

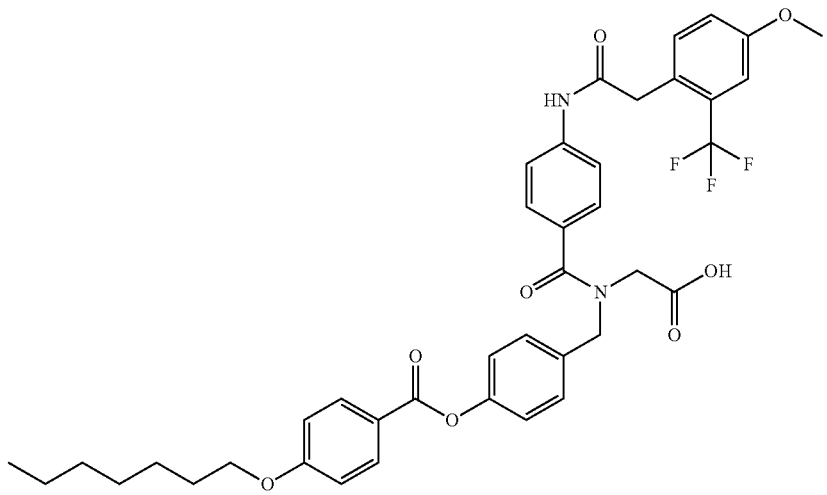

Prepared using General Procedures 8: To 4-((N-(2-(tert-butoxy)-2-oxoethyl)-4-(2-(4-methoxy-2-(trifluoromethyl)phenyl)acetamido)benzamido)methyl) phenyl 4-(heptyloxy) benzoate INT-6 (555 mg, 0.702 mmol) in DCM (3 mL) was added TFA (3 mL). The reaction was stirred at room temperature for 2 h then purified by chromatography (EA/hexanes+1% acetic acid) to provide 385 mg (74%) of 2-(N-(4-((4-(heptyloxy)benzoyl)oxy)benzyl)-4-(2-(4-methoxy-2-(trifluoromethyl)phenyl) acetamido) benzamido) acetic acid 3. LCMS-ESI (m/z) calculated for $C_{40}R_{41}F_3N_2O_8$: 734; no m/z observed, $t_R$=11.42 min (Method 2). $^1$H NMR (400 MHz, DMSO) δ 12.83 (s, 1H), 10.35 (s, 1H), 8.14-8.01 (m, 2H), 7.65 (d, J=8.3 Hz, 2H), 7.54-7.29 (m, 5H), 7.29-7.16 (m, 4H), 7.14-7.01 (m, 2H), 4.69 (s, 1H), 4.61 (s, 1H), 4.08 (t, J=6.5 Hz, 2H), 4.00 (s, 1H), 3.94 (s, 1H), 3.86 (s, 2H), 3.83 (s, 3H), 1.81-1.68 (m, 2H), 1.48-1.22 (m, 8H), 0.92-0.81 (t, J=6.8 Hz, 3H).

2-(N-(4-((4-(heptyloxy)benzoyl)oxy)benzyl)-4-(2-(3-methoxy-4-methylphenyl)-acetamido) benzamido)acetic acid (Compound 4)

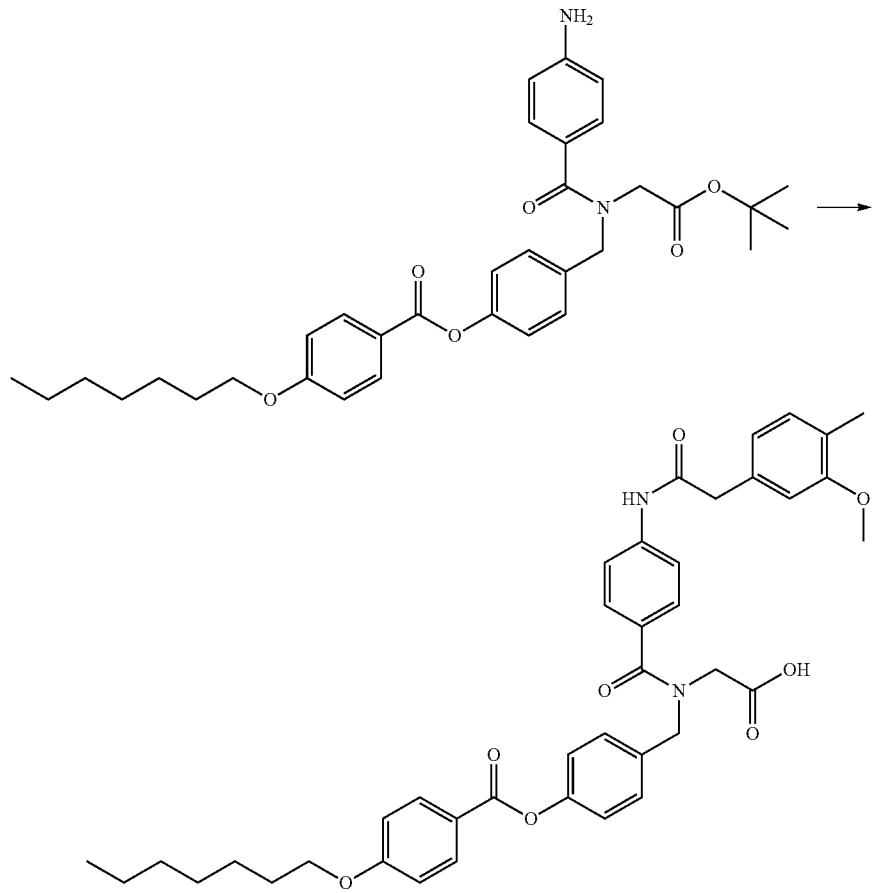

Prepared using General Procedures 6 and 8: To 2-(3-methoxy-4-methylphenyl)acetic acid (14.1 mg, 0.08 mmol) were added HOBT (12.0 mg, 0.08 mmol) in DMF (0.1 mL) and EDC (15.0 mg, 0.08 mmol) in DMF (0.1 mL). After stirring at room temperature for 30 min, 4-((4-amino-N-(2-(tert-butoxy)-2-oxoethyl)benzamido)methyl)phenyl 4-(heptyloxy)benzoate INT-4 (30 mg, 0.05 mmol) and TEA (0.019 mL, 0.10 mmol) in DMF (0.3 mL) were added. The reaction was stirred for 18 h then purified by preparative HPLC to provide 4-((N-(2-(tert-butoxy)-2-oxoethyl)-4-(2-(3-methoxy-4-methylphenyl) acetamido) benzamido) methyl) phenyl 4-(heptyloxy)benzoate. To 4-((N-(2-(tert-butoxy)-2-oxoethyl)-4-(2-(3-methoxy-4-methylphenyl)acetamido) benzamido)methyl)phenyl 4-(heptyloxy)benzoate in DCM (1.0 mL) was added TFA (0.2 mL). The reaction was stirred at 30° C. for 6 h. The reaction was concentrated to afford 22.3 mg (65%) of 2-(N-(4-((4-(heptyloxy) benzoyl)oxy) benzyl)-4-(2-(3-methoxy-4-methylphenyl)acetamido)benzamido)acetic acid 4. LCMS-ESI (m/z) calculated for $C_{40}H_{44}N_2O_8$: 680; no m/z observed, $t_R$=11.45 min (Method 2). $^1$H NMR (400 MHz, DMSO) δ 10.32 (s, 1H), 8.06 (d, J=8.8 Hz, 2H), 7.64 (d, J=8.4 Hz, 2H), 7.43 (d, J=7.2 Hz, 1H), 7.40-7.28 (m, 3H), 7.24 (d, J=8.5 Hz, 2H), 7.17-7.02 (m, 3H), 6.91 (s, 1H), 6.79 (d, J=7.5 Hz, 1H), 4.62 (d, J=36.2 Hz, 2H), 4.08 (t, J=6.5 Hz, 2H), 3.95 (d, J=28.6 Hz, 2H), 3.77 (s, 3H), 3.60 (s, 2H), 2.10 (s, 3H), 1.74 (dd, J=9.8, 4.8 Hz, 2H), 1.48-1.24 (m, 8H), 0.86 (d, J=7.0 Hz, 3H).

General Procedure 9: Hydrolysis of Esters to Acids or Phenols

To a stirring solution of ester (1 eq) in THF or dioxane and MeOH, was added NaOH or LiOH (1.0-2.0 eq). The reaction mixture was stirred at room temperature or 60° C. for up to 18 h. The reaction mixture was neutralized with AcOH or HCl and either diluted with water or concentrated. If the reaction mixture was diluted with water, HCl was added to acidify the reaction mixture to ~pH of 2. The resulting precipitate was isolated by filtration to yield product which can be purified by chromatography, preparative HPLC or carried forward without purification. If the reaction mixture was concentrated, the crude material was diluted with DCM or EA and washed with brine. The organic layer was concentrated and purified by chromatography or preparative HPLC to give final product. Alternatively, the crude material can be carried forward without purification.

tert-butyl 2-(N-(4-hydroxybenzyl)-4-(2-(4-methoxyphenyl)acetamido)benzamido)acetate (INT-7)

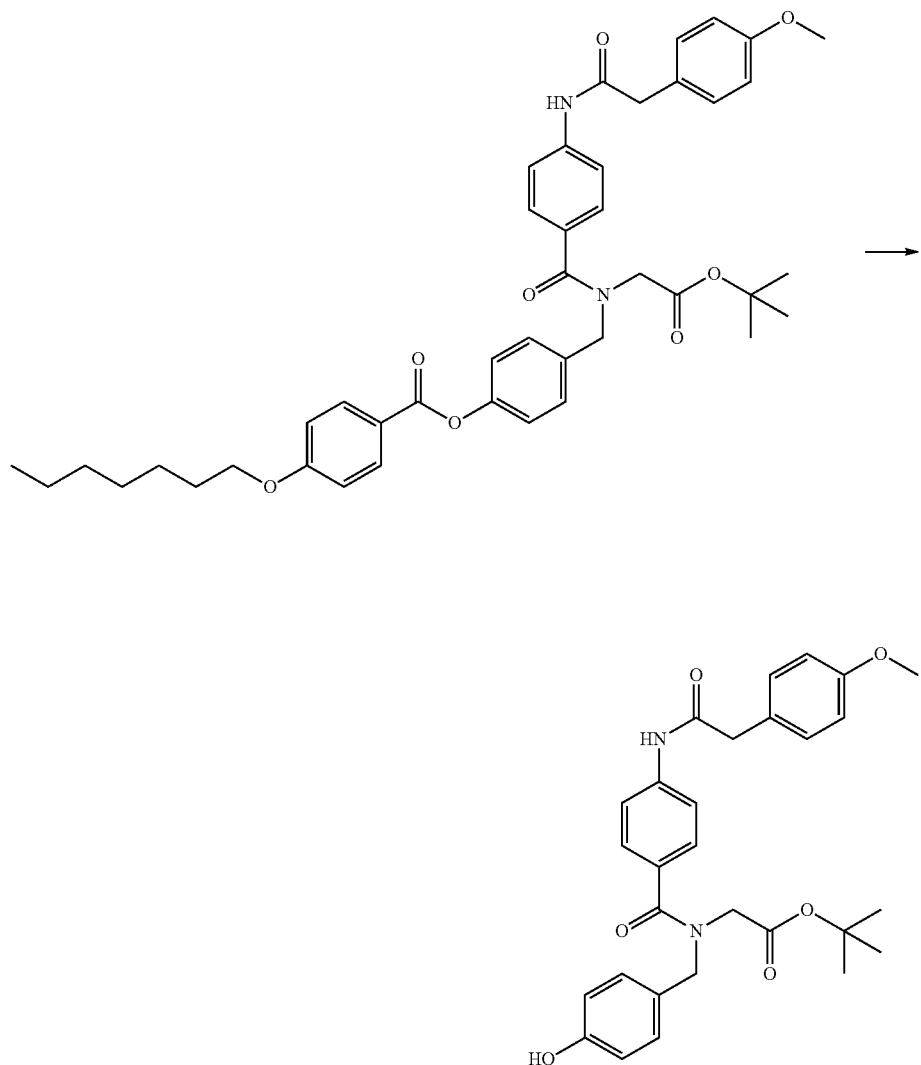

Prepared using General Procedure 9: To a stirring solution of 4-((N-(2-(tert-butoxy)-2-oxoethyl)-4-(2-(4-methoxyphenyl) acetamido) benzamido)methyl)phenyl 4-(heptyloxy) benzoate INT-5 (6.38 g, 8.83 mmol) in THF (50 mL) was added 1N NaOH (16 mL). The reaction was stirred for 1 h. MeOH (10 mL) was added causing the turbid reaction mixture to clarify. The reaction was stirred for 3 h then neutralized with AcOH. The crude mixture was concentrated then diluted with DCM (60 mL) and washed with brine (30 mL). The organic layer was concentrated and purified by chromatography (EA/hexanes) to afford 2.5 g (56%) of tert-butyl 2-(N-(4-hydroxybenzyl)-4-(2-(4-methoxyphenyl) acetamido)benzamido)acetate INT-7. LCMS-ESI (m/z) calculated for $C_{29}H_{32}N_2O_6$: 504. found 503 [M–H]$^-$, $t_R$=2.09 min. (Method 3). $^1$H NMR (400 MHz, DMSO) δ 10.22 (s, 1H), 9.41-9.29 (m, 1H), 7.69-7.59 (d, J=8.1 Hz, 2H), 7.42-7.20 (m, 4H), 7.19-6.96 (m, 2H), 6.91-6.84 (m, 2H), 6.76-6.68 (m, 2H), 4.58-4.35 (m, 2H), 3.90-3.76 (m, 2H), 3.71 (s, 3H), 3.57 (s, 2H), 1.49-1.21 (m, 9H).

Compounds 16-62 were prepared using General Procedures 2, 3, 7, 5, 7, 9, 2, and 8 sequentially. Compounds 63 and 64 were prepared using General Procedures 2, 3, 7, 5, 7, 9, 2, 5, 7, and 8 sequentially. Compounds 185-187 were prepared from INT-7 using General Procedures 2 then 8.

2-(4-(2-(4-methoxyphenyl)acetamido)-N-(4-((4-(nonyloxy)benzoyl)oxy)benzyl)benzamido) acetic acid (Compound 16)

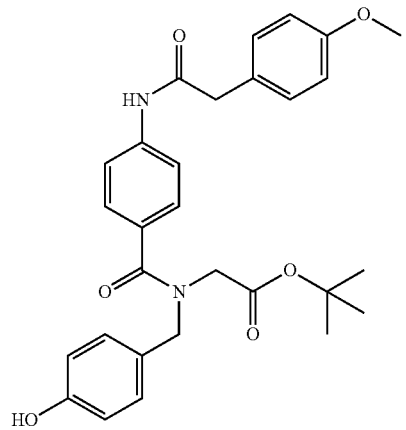

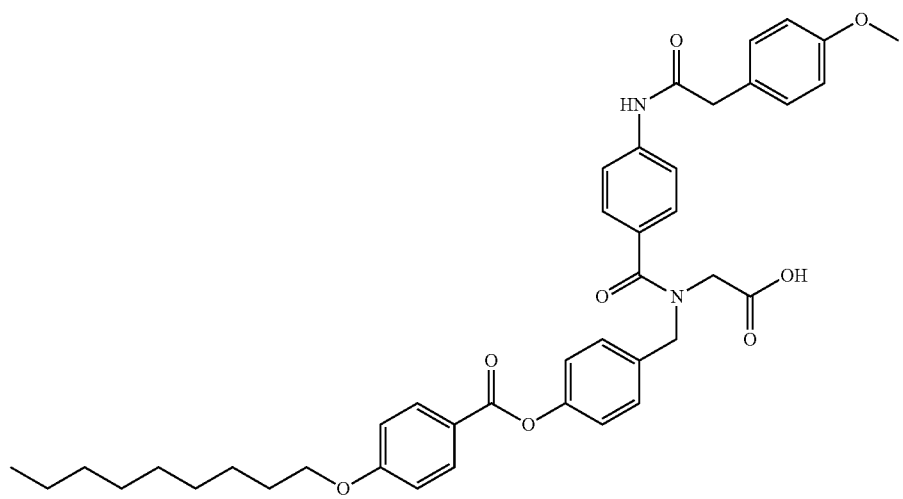

Prepared using General Procedures 2 and 8: To a stirring solution of 4-(nonyloxy)benzoic acid (31 mg, 0.119 mmol) in DCM (0.5 mL) were added DMF (1 drop) and oxalyl chloride (0.011 mL, 0.127 mmol). The reaction mixture was stirred at room temperature for 30 min. To this mixture was added a solution of tert-butyl 2-(N-(4-hydroxybenzyl)-4-(2-(4-methoxyphenyl)acetamido)benzamido)acetate INT-7 (40 mg, 0.079 mmol) and TEA (0.022 mL, 0.159 mmol) in DCM (1 mL). The reaction was stirred at room temperature for 2 h then TFA (1 mL) was added. After stirring for 2 h, the solvent was concentrated and the product was purified by preparative HPLC to afford 6.6 mg (12%) of 2-(4-(2-(4-methoxyphenyl)acetamido)-N-(4-((4-(nonyloxy)benzoyl)oxy)benzyl) benzamido) acetic acid 16. LCMS-ESI (m/z) calculated for $C_{41}H_{46}N_2O_8$: 695. found 694 [M–H]$^-$, $t_R$=10.43 min (Method 4). $^1$H NMR (400 MHz, DMSO) δ 10.30 (s, 1H), 8.05 (d, J=8.8 Hz, 2H), 7.64 (d, J=8.5 Hz, 2H), 7.47-7.27 (m, 4H), 7.23 (d, J=8.0 Hz, 4H), 7.10 (d, J=8.9 Hz, 2H), 6.87 (d, J=8.4 Hz, 2H), 4.62 (d, J=35.9 Hz, 2H), 4.07 (t, J=6.5 Hz, 2H), 3.92 (d, J=40.2 Hz, 2H), 3.71 (s, 3H), 3.56 (s, 2H), 1.85-1.66 (m, 2H), 1.53-1.10 (m, 12H), 0.85 (t, J=6.7 Hz, 3H).

2-(4-(2-(4-methoxyphenyl)acetamido)-N-(4-((4-(octyloxy)benzoyl) oxy)benzyl) benzamido) acetic acid (Compound 17)

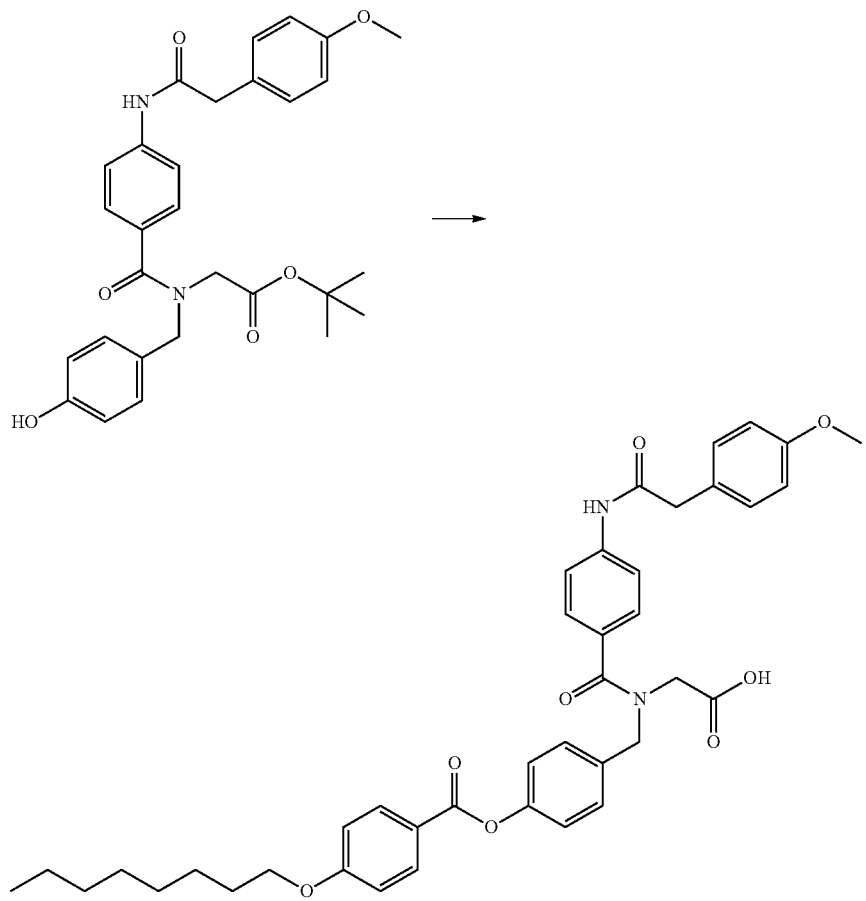

Prepared using General Procedures 2 and 8: To a stirring solution of 4-(octyloxy)benzoic acid (30 mg, 0.119 mmol) in DCM (0.5 mL) were added DMF (1 drop) and oxalyl chloride (0.011 mL, 0.127 mmol). The reaction mixture was stirred at room temperature for 30 min. To this mixture was added a solution of tert-butyl 2-(N-(4-hydroxybenzyl)-4-(2-(4-methoxyphenyl)acetamido)benzamido)acetate INT-7 (40 mg, 0.079 mmol) and TEA (0.022 mL, 0.159 mmol) in DCM (1 mL). The reaction was stirred at room temperature for 2 h then TFA (1 mL) was added. After stirring for 2 h, the solvent was concentrated and the product was purified by preparative HPLC to afford 7.6 mg (14%) of 2-(4-(2-(4-methoxyphenyl)acetamido)-N-(4-((4-(octyloxy)benzoyl) oxy)benzyl)benzamido)acetic acid 17. LCMS-ESI (m/z) calculated for $C_{40}H_{44}N_2O_8$: 680. found 679 [M–H]$^-$, $t_R$=9.96 min (Method 4).

2-(N-(4-((4-(hexyloxy)benzoyl)oxy)benzyl)-4-(2-(4-methoxyphenyl) acetamido) benzamido) acetic acid (Compound 18)

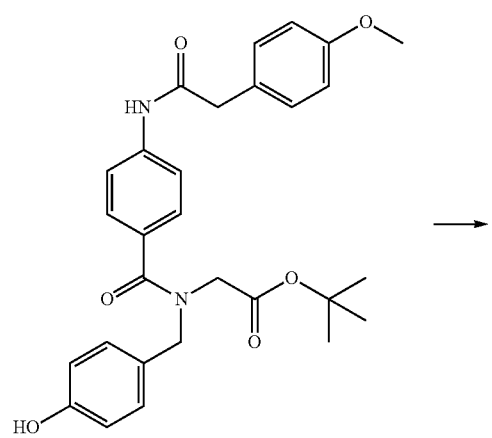

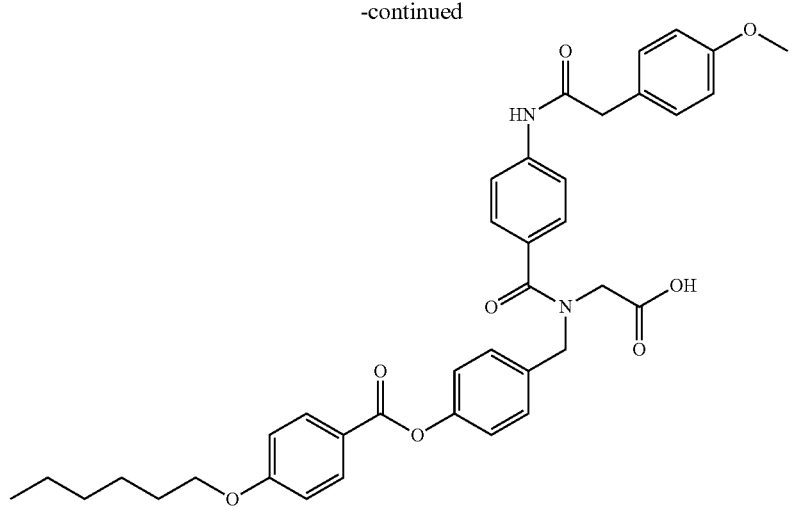

Prepared using General Procedures 2 and 8: To a stirring solution of 4-(hexyloxy)benzoic acid (26 mg, 0.119 mmol) in DCM (0.5 mL) were added DMF (1 drop) and oxalyl chloride (0.011 mL, 0.127 mmol). The reaction mixture was stirred at room temperature for 30 min. To this mixture was added a solution of tert-butyl 2-(N-(4-hydroxybenzyl)-4-(2-(4-methoxyphenyl)acetamido)benzamido)acetate INT-7 (40 mg, 0.079 mmol) and TEA (0.022 mL, 0.159 mmol) in DCM (1 mL). The reaction was stirred at room temperature for 2 h then TFA (1 mL) was added. After stirring for 2 h, the solvent was concentrated and the product was purified by preparative HPLC to yield 18.2 mg (35%) of 2-(N-(4-((4-(hexyloxy)benzoyl)oxy)benzyl)-4-(2-(4-methoxyphenyl) acetamido) benzamido) acetic acid 18. LCMS-ESI (m/z) calculated for $C_{38}H_{40}N_2O_8$: 652. found 651 [M–H]$^-$, $t_R$=9.01 min (Method 4). $^1$H NMR (400 MHz, DMSO) δ 12.80 (s, 1H), 10.25 (s, 1H), 8.10-7.99 (m, 2H), 7.68-7.62 (m, 2H), 7.50-7.19 (m, 8H), 7.17-7.07 (m, 2H), 6.91-6.84 (m, 2H), 4.70-4.54 (d, J=35.9 Hz, 2H), 4.12-4.04 (t, J=6.5 Hz, 2H), 4.00-3.86 (d, J=34.1 Hz, 2H), 3.72 (s, 3H), 3.56 (s, 2H), 1.79-1.69 (m, 2H), 1.47-1.38 (m, 2H), 1.37-1.28 (ddd, J=7.6, 3.9, 2.1 Hz, 4H), 0.91-0.84 (m, 3H).

2-(N-(4-(([1,1'-biphenyl]-4-carbonyl)oxy)benzyl)-4-(2-(4-methoxyphenyl) acetamido)-benzamido)acetic acid (Compound 32)

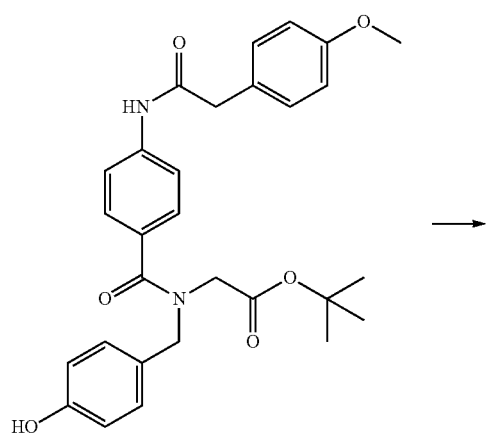

→

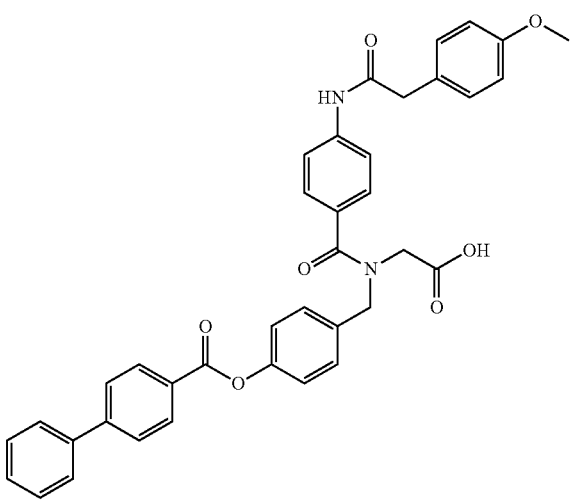

Prepared using General Procedures 2 and 8: To a stirring solution of tert-butyl 2-(N-(4-hydroxybenzyl)-4-(2-(4-methoxyphenyl)acetamido)benzamido)acetate INT-7 (40 mg, 0.079 mmol) and TEA (0.022 mL, 0.159 mmol) in DCM (1 mL) were added [1,1'-biphenyl]-4-carbonyl chloride (26 mg, 0.119 mmol). The reaction was stirred for 18 h then TFA (1 mL) was added. After stirring for 2 h, the solvent was concentrated and the product was purified by preparative HPLC to afford 12.5 mg (25%) of 2-(N-(4-(([1,1'-biphenyl]-4-carbonyl)oxy)benzyl)-4-(2-(4-methoxyphenyl)acetamido) benzamido)acetic acid 32. LCMS-ESI (m/z) calculated for $C_{38}H_{32}N_2O_7$: 629. found 628 [M–H]$^-$, $t_R$=7.83 min (Method 4). NMR (400 MHz, DMSO) δ 10.31 (s, 1H), 8.21 (d, J=8.1 Hz, 2H), 7.92 (d, J=8.4 Hz, 3H), 7.79 (d, J=7.7 Hz, 2H), 7.65 (d, J=8.2 Hz, 2H), 7.58-7.41 (m, 4H), 7.41-7.17 (m, 6H), 6.88 (d, J=8.2 Hz, 2H), 4.64 (d, J=36.7 Hz, 2H), 3.95 (d, J=33.6 Hz, 2H), 3.72 (s, 3H), 3.57 (s, 2H).

2-(N-(4-((4-cyclohexylbenzoyl)oxy)benzyl)-4-(2-(4-methoxyphenyl) acetamido) benzamido) acetic acid (Compound 39)

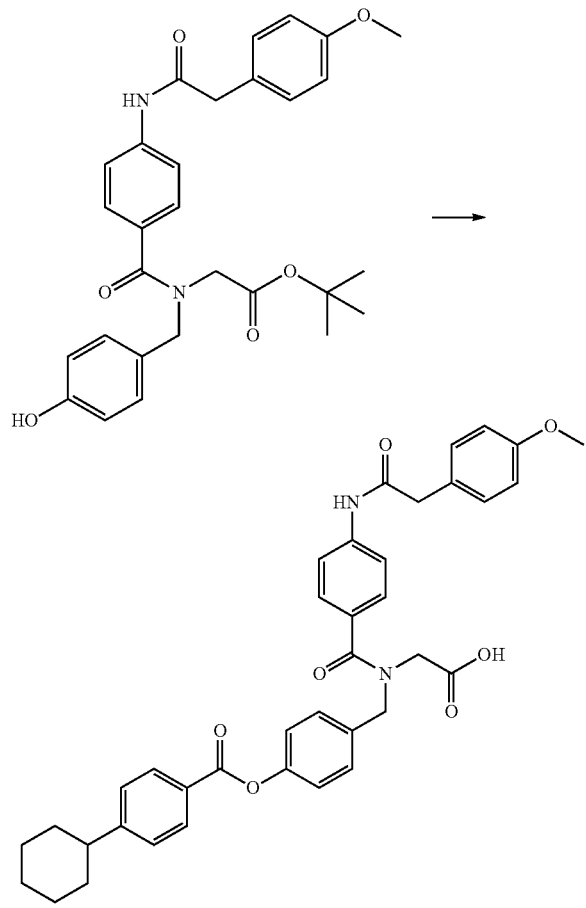

Prepared using General Procedures 2 and 8: To a stirring solution of 4-cyclohexylbenzoic acid (24 mg, 0.119 mmol) in DCM (0.5 mL) were added DMF (1 drop) and oxalyl chloride (0.011 mL, 0.127 mmol). The reaction mixture was stirred at room temperature for 2 h. To this mixture was added a solution of tert-butyl 2-(N-(4-hydroxybenzyl)-4-(2-(4-methoxyphenyl)acetamido)benzamido)acetate INT-7 (40 mg, 0.079 mmol) and TEA (0.022 mL, 0.159 mmol) in DCM (1 mL). The reaction was stirred at room temperature for 18 h then TFA (1 mL) was added. After stirring for 2 h, the solvent was concentrated and the product was purified by preparative HPLC to provide to afford 22.2 mg (44%) of 2-(N-(4-((4-cyclohexylbenzoyl)oxy)benzyl)-4-(2-(4-methoxyphenyl) acetamido) benzamido) acetic acid 39. LCMS-ESI (m/z) calculated for $C_{38}H_{38}N_2O_7$: 634. found 633 [M−H]$^-$, $t_R$=8.92 min (Method 4). $^1$H NMR (400 MHz, DMSO) δ 10.30 (s, 1H), 8.04 (d, J=7.7 Hz, 2H), 7.64 (d, J=8.2 Hz, 2H), 7.45 (t, J=7.0 Hz, 3H), 7.39-7.26 (m, 3H), 7.24 (d, J=8.4 Hz, 4H), 6.88 (d, J=8.1 Hz, 2H), 4.62 (d, J=36.7 Hz, 2H), 3.94 (d, J=31.7 Hz, 2H), 3.72 (s, 2H), 3.57 (s, 3H), 2.63 (t, J=10.7 Hz, 1H), 1.76 (dd, J=36.3, 11.5 Hz, 5H), 1.53-1.16 (m, 5H).

2-(4-(2-(4-methoxyphenyl)acetamido)-N-(4-((4-octylbenzoyl)oxy)benzyl)benzamido)acetic acid (Compound 40)

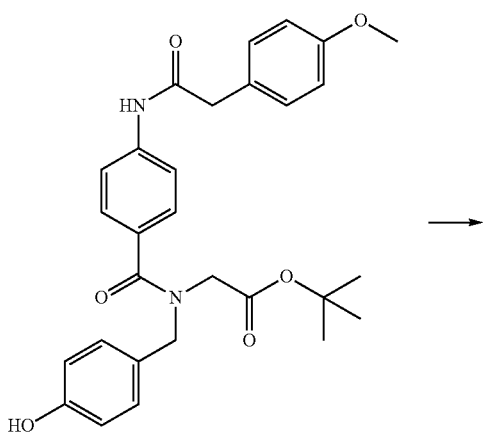

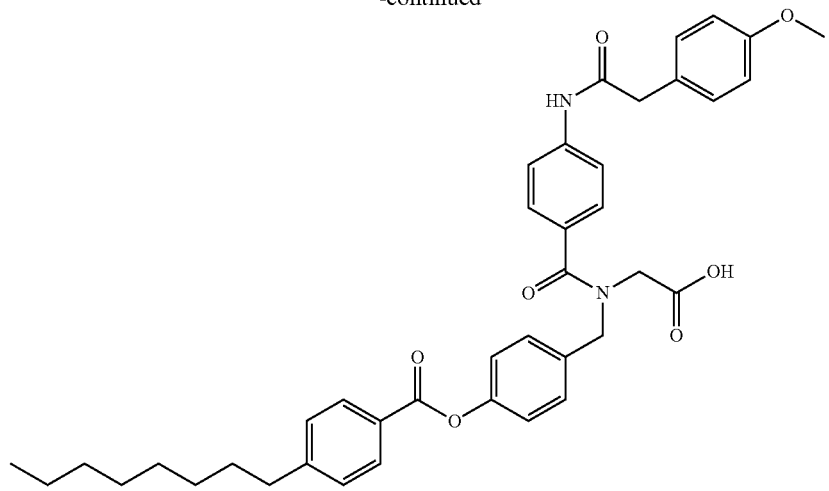

Prepared using General Procedures 2 and 8: To a stirring solution of 4-octylbenzoic acid (42 mg, 0.178 mmol) in DCM (0.5 mL) were added DMF (1 drop) and oxalyl chloride (0.016 mL, 0.190 mmol). The reaction mixture was stirred at room temperature for 2 h. To this mixture was added a solution of tert-butyl 2-(N-(4-hydroxybenzyl)-4-(2-(4-methoxyphenyl)acetamido)benzamido)acetate INT-7 (60 mg, 0.119 mmol) and TEA (0.050 mL, 0.357 mmol) in DCM (1 mL). The reaction was stirred at room temperature for 18 h then TFA (1 mL) was added. After stirring for 2 h, the solvent was concentrated and the product was purified by preparative HPLC to provide to afford 15.3 mg (19%) of 2-(4-(2-(4-methoxyphenyl)acetamido)-N-(4-((4-octylbenzoyl)oxy)benzyl)benzamido)acetic acid 40. LCMS-ESI (m/z) calculated for $C_{40}H_{44}N_2O_7$: 664. found 665 [M+H]$^+$, $t_R$=10.33 min (Method 4). $^1$H NMR (400 MHz, DMSO) δ 10.31 (s, 1H), 8.04 (d, J=8.2 Hz, 2H), 7.65 (d, J=8.5 Hz, 2H), 7.50-7.21 (m, 10H), 6.89 (d, J=8.4 Hz, 2H), 4.63 (d, J=36.7 Hz, 2H), 3.95 (d, J=33.1 Hz, 2H), 3.73 (s, 3H), 3.58 (s, 2H), 2.76-2.64 (m, 2H), 1.61 (s, 2H), 1.36-1.10 (m, 10H), 0.86 (t, J=6.8 Hz, 3H).

2-(N-(4-((4-(isopentyloxy)benzoyl)oxy)benzyl)-4-(2-(4-methoxyphenyl) acetamido) benzamido) acetic acid (Compound 46)

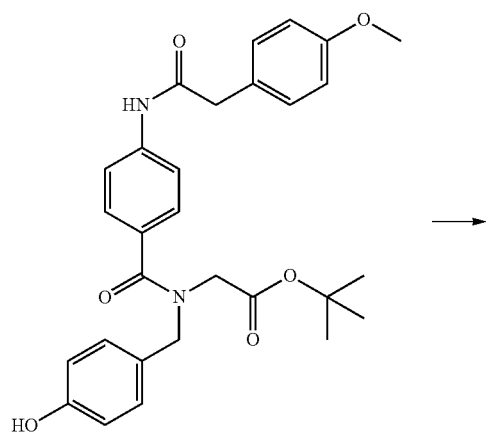

→

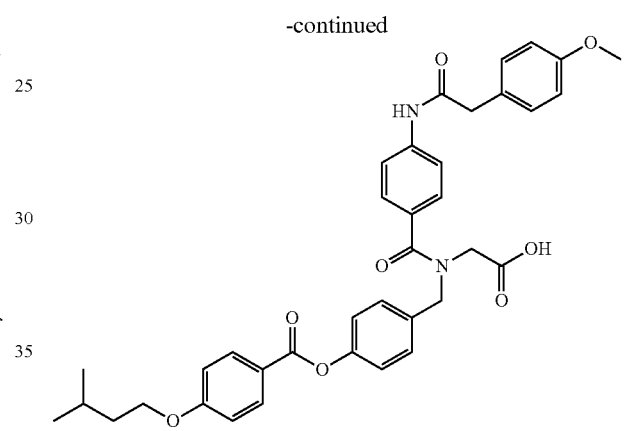

Prepared using General Procedures 2 and 8: To a stirring solution of 4-(isopentyloxy)benzoic acid (37 mg, 0.178 mmol) in DCM (0.5 mL) was added DMF (1 drop) and oxalyl chloride (0.016 mL, 0.190 mmol). The reaction mixture was stirred at room temperature for 2 h. To this mixture was added a solution of tert-butyl 2-(N-(4-hydroxybenzyl)-4-(2-(4-methoxyphenyl)acetamido)benzamido)acetate INT-7 (60 mg, 0.119 mmol) and TEA (0.050 mL, 0.357 mmol) in DCM (1 mL). The reaction was stirred at room temperature for 18 h then TFA (1 mL) was added. After stirring for 2 h, the solvent was concentrated and the product was purified by preparative HPLC to afford 41.2 mg (54%) of 2-(N-(4-((4-(isopentyloxy)benzoyl)oxy)benzyl)-4-(2-(4-methoxyphenyl) acetamido) benzamido)acetic acid 46. LCMS-ESI (m/z) calculated for $C_{37}H_{38}N_2O_8$: 638. found 637 [M−H]$^−$, $t_R$=8.44 min (Method 4). $^1$H NMR (400 MHz, DMSO) δ 12.75 (s, 1H), 10.24 (s, 1H), 8.13-8.02 (m, 2H), 7.69-7.62 (d, J=8.4 Hz, 2H), 7.48-7.28 (m, 4H), 7.26-7.19 (dt, J=6.7, 1.9 Hz, 4H), 7.16-7.08 (m, 2H), 6.93-6.83 (m, 2H), 4.72-4.54 (d, J=31.5 Hz, 2H), 4.16-4.08 (t, J=6.6 Hz, 2H), 4.05-3.86 (d, J=27.0 Hz, 2H), 3.71 (s, 3H), 3.57 (s, 2H), 1.88-1.75 (dp, J=13.3, 6.7 Hz, 1H), 1.72-1.62 (q, J=6.7 Hz, 2H), 0.97-0.86 (d, J=6.6 Hz, 6H).

General Procedure 10: Preparation of Sulfonamides Via Sulfonyl Chlorides

To a stirring solution of amine (1 eq) in DCM or THF were added TEA or potassium tert-butoxide (1.5-3 eq) and the appropriate sulfonyl chloride (1.2-2.5 eq). The reaction mixture was stirred room temperature or at 50° C. for up to 18 h then concentrated. The final products were purified by chromatography or preparative HPLC. Alternatively, the crude reaction mixture can be carried forward without further purification.

Compound 65 was prepared using General Procedures 2, 3, 7, 5, 7, 9, 2, 5, 10, and 8 sequentially. Compounds 179-184 were prepared from INT-4 using General Procedures 10 then 8.

General Procedure 11: Hydrolysis of Carbamates to Amines

To a stirring solution of carbamate (1 eq) in DCM was added excess TFA (6-50 eq). The reaction mixture was stirred at room temperature for up to 2 h. The reaction mixture was concentrated and the crude product used without further purification.

Compound 66 was prepared using General Procedures 7, 11, 4, 7, and 8 sequentially. Compound 67 was prepared using General Procedures 2, 3, 7, and 8 sequentially. Compound 68 was prepared using General Procedures 7, 9, 6, and 8 sequentially. Compounds 69-72 were prepared using General Procedures 2, 3, 7, 8, and 6 sequentially. Compounds 73-74 were prepared using General Procedures 2, 11, 7, 5, 7, and 8 sequentially. Compound 75 was prepared using General Procedures 2, 11, and 7 sequentially. Compounds 76-78 were prepared from INT-5 using General Procedures 8 then 6. Compound 79 was prepared using General Procedures 7, 9, 4, 6, 1, and 8 sequentially. Compounds 80-81 were prepared using General Procedures 2, 11, 7, 4, 5, 7, and 8 sequentially. Compounds 82-83 were prepared using General Procedures 4, 6, 2, and 8 sequentially.

General Procedure 12: Preparation of a Secondary or Tertiary Amine Via Reductive Amination To a stirring solution of aldehyde or ketone (0.9-1 eq) in DCM or MTBE or THF was added an amine (0.9-1.1 eq). After stirring at room temperature for up to 18 h, one drop of acetic acid (optional) was added followed by sodium triacetoxyborohydride or sodium borohydride or tetramethylammonium triacetoxyhydroborate (1-2 eq). The reaction mixture was stirred up to 18 h. In some cases it is necessary to filter the reaction mixture, redissolve in an appropriate solvent such as DCM or 1:1 THF/MeOH and add sodium triacetoxyborohydride or sodium borohydride or tetramethylammonium triacetoxyhydroborate (1-2 eq) then stir up to 18 h. The crude reaction mixture was quenched with NaHCO$_3$ and stirred for 5 min. The aqueous layer was extracted with DCM or EA and the organic layer was dried over MgSO$_4$ and concentrated. The final product was isolated by chromatography or preparative HPLC.

Compound 84 was prepared using General Procedures 2, 3, 12, and 8 sequentially. Compound 85 was prepared using General Procedures 2, 3, 6, and 8 sequentially. Compound 86 was prepared using General Procedures 2, 3, 7, 5, 12, and 8 sequentially. Compound 87 was prepared using General Procedures 2, 12, and 6 sequentially. Compound 175 was prepared from INT-4 using General Procedures 12 then 8.

Compounds 188 and 189 were prepared from INT-7 using General Procedures 2, 5, 12 then 8.

Compound 191 was prepared using General Procedures 2, 12, 12, 5, 6 and 8 sequentially.

4-((4-methoxy-N-(4-oxobutyl)benzamido)methyl) phenyl 4-(heptyloxy)benzoate (INT-8)

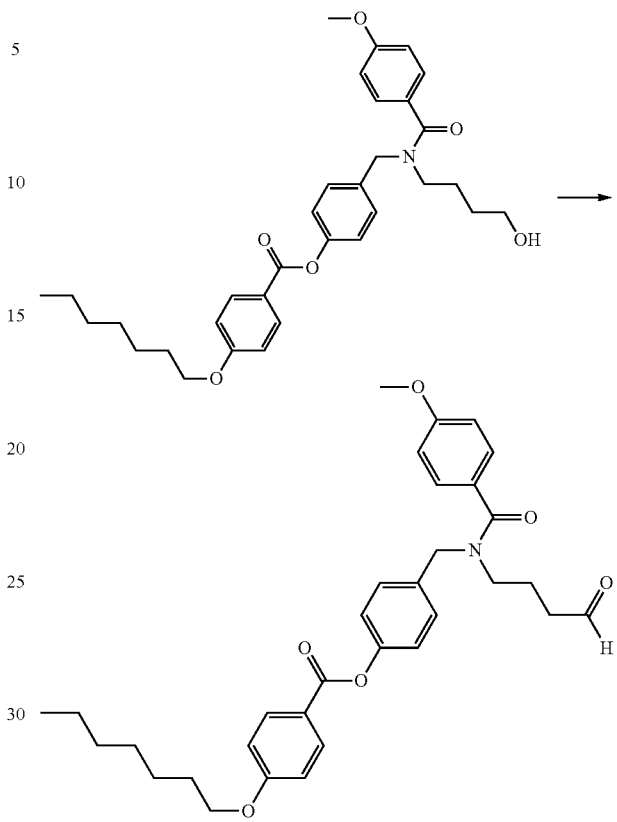

Prepared from compound 87: To a stirring solution of 4-((N-(4-hydroxybutyl)-4-methoxybenzamido)methyl)phenyl 4-(heptyloxy)benzoate 87 (258 mg, 0.484 mmol) in DCM was added sodium bicarbonate (81 mg, 0.968 mmol) and Dess-Martin periodinane (308 mg, 0.726 mmol). The reaction mixture was stirred at room temperature for 2 h. The crude reaction was diluted with EA followed by NaHCO$_3$ and aq. NaS$_2$O$_3$. The biphasic mixture was stirred overnight at room temperature. The organic phase was separated, washed with NaHCO$_3$, dried over MgSO$_4$, and concentrated to yield 264 mg of crude 4-((4-methoxy-N-(4-oxobutyl) benzamido)methyl)phenyl 4-(heptyloxy)benzoate LCMS-ESI (m/z) calculated for C$_{33}$H$_{39}$NO$_6$: 545. found 546 [M–H]$^+$, t$_R$=3.14 min (Method 3).

4-(N-(4-((4-(heptyloxy)benzoyl)oxy)benzyl)-4-methoxybenzamido)butanoic acid (Compound 88)

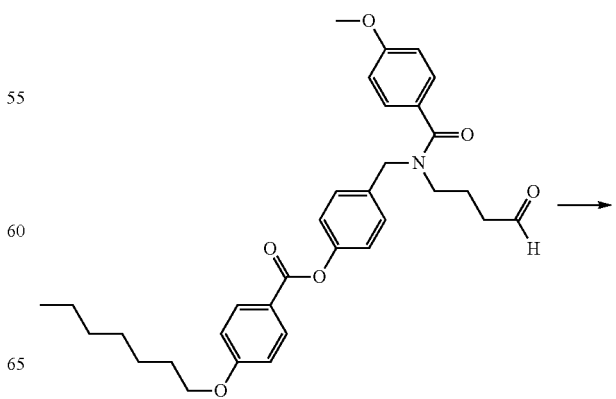

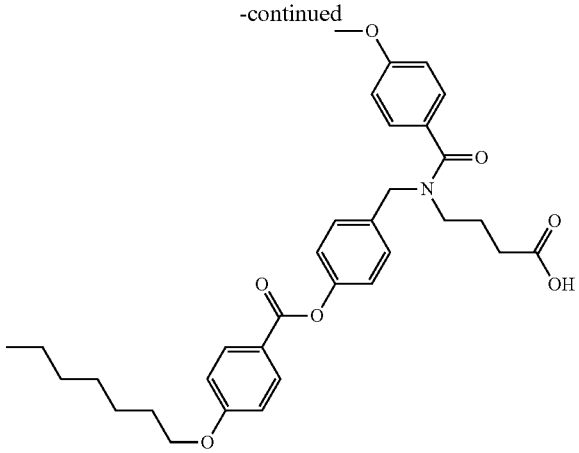

To a stirring solution of 4-((4-methoxy-N-(4-oxobutyl)benzamido)methyl)phenyl 4-(heptyloxy)benzoate INT-8 (264 mg, 0.484 mmol) in tert-butanol (12 mL) was added 2-methylbut-2-ene (4.7 ml, 44.4 mmol). A solution of sodium chlorite (400 mg, 4.42 mmol) and sodium dihydrogen phosphate (400 mg, 3.33 mmol) in H$_2$O (2.5 mL) were added and the reaction stirred for 1 h at room temperature. The reaction was quenched with aq. Na$_2$S$_2$O$_5$ (10 mL) and brine (10 mL). The aqueous phase was extracted with DCM and the combined organic phases were dried over MgSO$_4$ and concentrated. The crude product was purified by chromatography (EA/hexanes) to provide 150 mg (55%) of 4-(N-(4-((4-(heptyloxy)benzoyl)oxy)benzyl)-4-methoxybenzamido)butanoic acid 88. LCMS-ESI (m/z) calculated for C$_{33}$H$_{39}$NO$_7$: 561. found 560 [M−H]$^-$, t$_R$=9.53 min (Method 4).

tert-butyl 2-(N-(4-hydroxybenzyl)-4-(2-(4-methoxy-2-(trifluoromethyl)phenyl)acetamido) benzamido) acetate (INT-9)

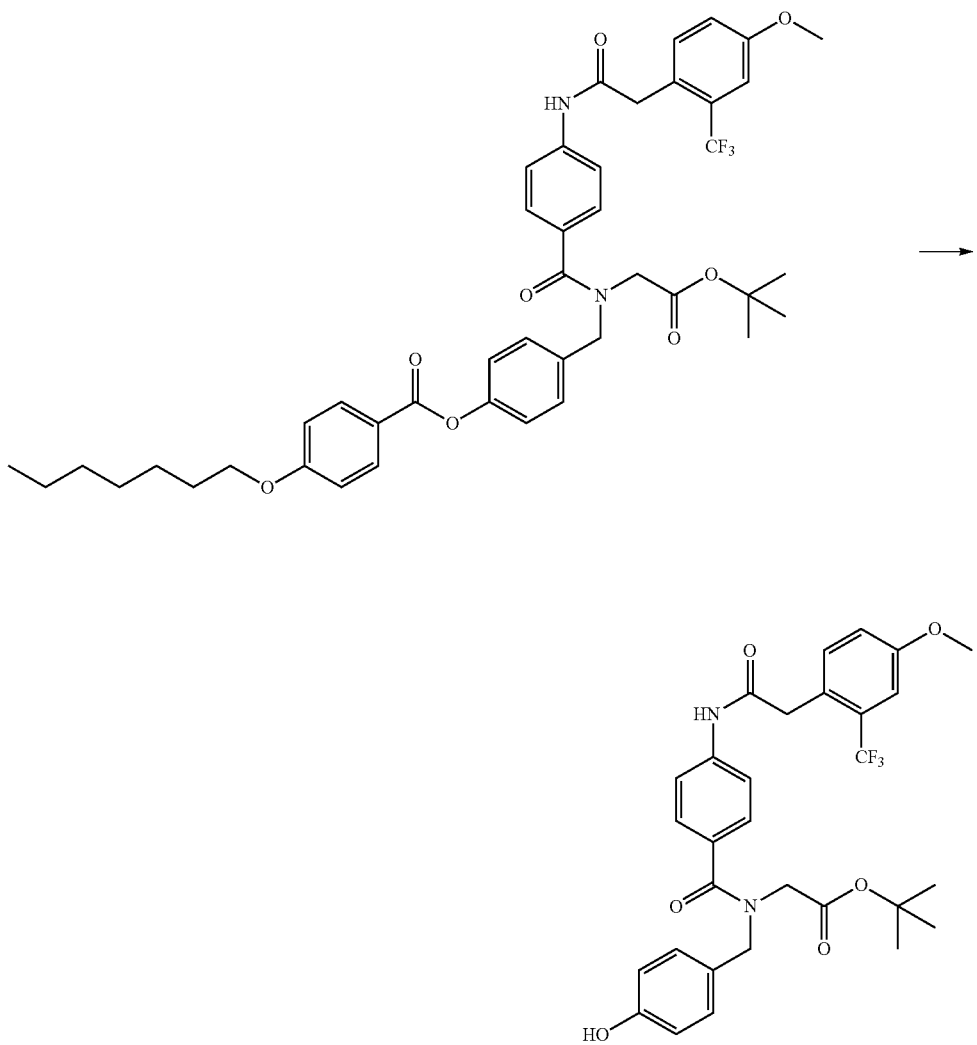

Prepared using General Procedure 9: To a stirring solution of 4-((N-(2-(tert-butoxy)-2-oxoethyl)-4-(2-(4-methoxy-2-(trifluoromethyl)phenyl)acetamido)benzamido)methyl)phenyl 4-(heptyloxy)benzoate INT-6 (2.53 g, 3.20 mmol) in THF (10 mL) and MeOH (50 mL) was added 2N NaOH (3.2 mL). The reaction mixture was stirred at room temperature for 10 min. The reaction mixture was acidified with AcOH. The crude mixture was concentrated then diluted with DCM (150 mL) and washed with brine (200 mL). The organic layer was concentrated and purified by chromatography (EA/hexanes) to afford 1.64 g (88%) of tert-butyl 2-(N-(4-hydroxybenzyl)-4-(2-(4-methoxy-2-(trifluoromethyl)phenyl)acetamido) benzamido)acetate INT-9. LCMS-ESI (m/z) calculated for $C_{30}H_{31}F_3N_2O_6$: 572. found 571 [M−H]⁻, $t_R$=2.30 min. (Method 3).

Compounds 192, 207-271, 273-276 and 371-390 were prepared from INT-9 using General Procedures 2 then 8. Compounds 277 and 278 were prepared from INT-9 using General Procedures 2, 8 then 5.

2-(4-(2-(4-methoxy-2-(trifluoromethyl)phenyl)acetamido)-N-(4-((4'-methyl-[1,1'-biphenyl]-4-carbonyl)oxy)benzyl)benzamido)acetic acid (Compound 192)

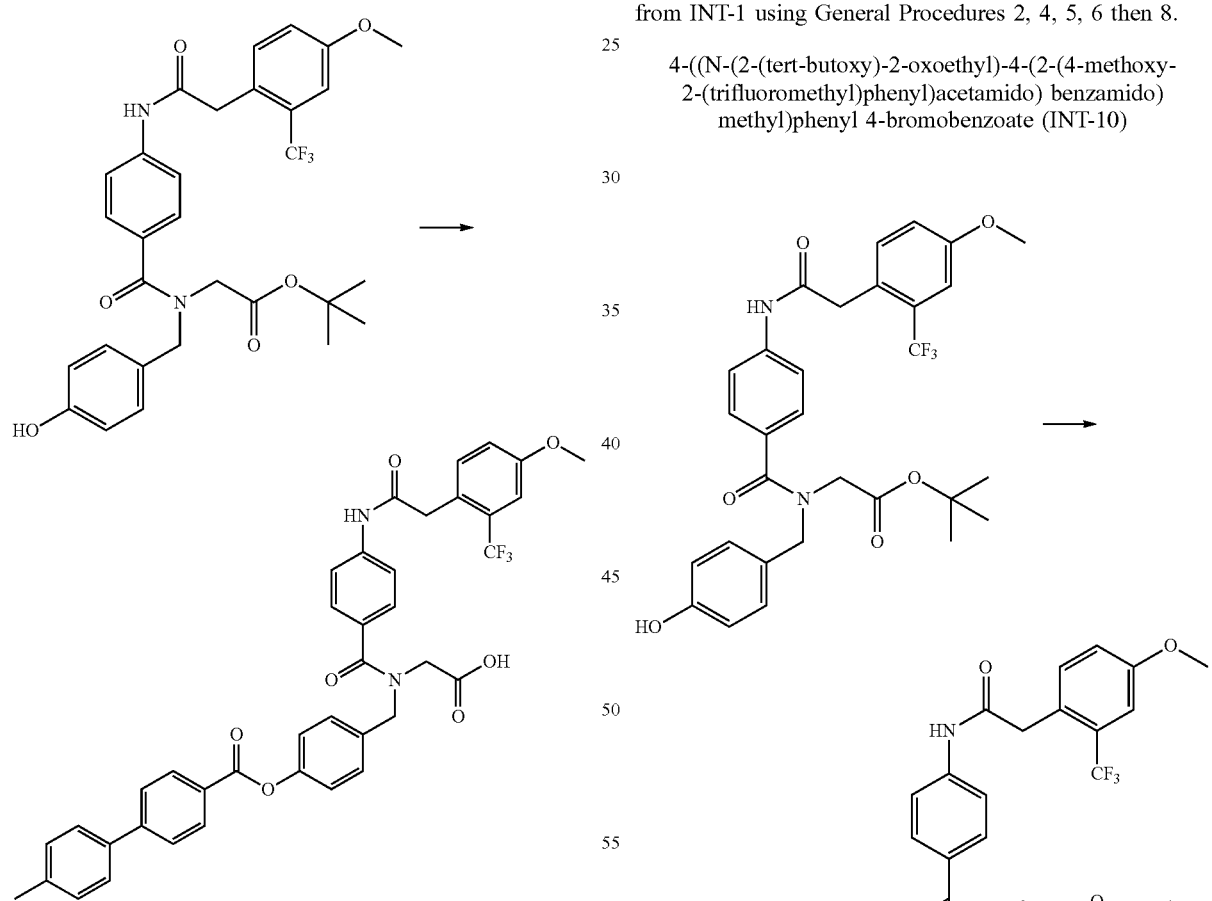

Prepared using General Procedures 2 then 8: To a stirring solution of 4'-methyl-[1,1'-biphenyl]-4-carboxylic acid (334 mg, 1.57 mmol) in DCM (10 mL) were added DMF (5 drops) and oxalyl chloride (0.14 mL, 1.68 mmol). The reaction mixture was stirred at room temperature for 1 h. To this mixture was added a solution of tert-butyl 2-(N-(4-hydroxybenzyl)-4-(2-(4-methoxyphenyl)acetamido)benzamido)acetate INT-9 (750 mg, 1.31 mmol) and TEA (0.37 mL, 2.62 mmol) in DCM (10 mL). The reaction mixture was stirred at room temperature for 1 h then DMAP (30 mg, 0.33 mmol) was added. After a further 2 h at room temperature, the reaction was diluted with DCM (50 mL) and washed with NaHCO₃ (50 mL). The organics were pre-absorbed onto silica gel and purified by chromatography (EA/isohexanes). The isolated material was taken up into DCM (10 mL) and TFA (5 mL) was added. After 2 h the solvent was removed under vacuum and solid was evaporated from diethyl ether (5 mL) and isohexanes (20 mL) to give a fine powdery solid. Trituration from DCM/isohexanes and isolation by filtration gave a fine powder that was slurried in water (20 mL) and isolated by filtration. The solid was washed with DCM and isohexanes (9:1, 50 mL) followed by isohexanes (50 mL) to afford 15.3 mg (19%) of 2-(4-(2-(4-methoxyphenyl)acetamido)-N-(4-((4-octylbenzoyl)oxy)benzyl)benzamido)acetic acid 192. LCMS-ESI (m/z) calculated for $C_{40}H_{33}F_3N_2O_7$: 710. found 711 [M+H]⁺, $t_R$=8.81 min (Method 9). ¹H NMR (400 MHz, DMSO) δ 12.96-12.60 (br s, 1H), 10.36 (s, 1H), 8.25-8.16 (m, 2H), 7.94-7.84 (m, 2H), 7.75-7.62 (m, 4H), 7.55-7.27 (m, 9H), 7.25-7.15 (m, 2H), 4.70 (s, 1H), 4.61 (s, 1H), 4.03 (s, 1H), 3.95 (s, 1H), 3.8-3.78 (m, 5H), 2.37 (s, 3H).

Compound 193 was prepared from INT-1 using General Procedures 2, 4 then 5. Compounds 194-206 were prepared from INT-1 using General Procedures 2, 4, 5, 6 then 8.

4-((N-(2-(tert-butoxy)-2-oxoethyl)-4-(2-(4-methoxy-2-(trifluoromethyl)phenyl)acetamido) benzamido)methyl)phenyl 4-bromobenzoate (INT-10)

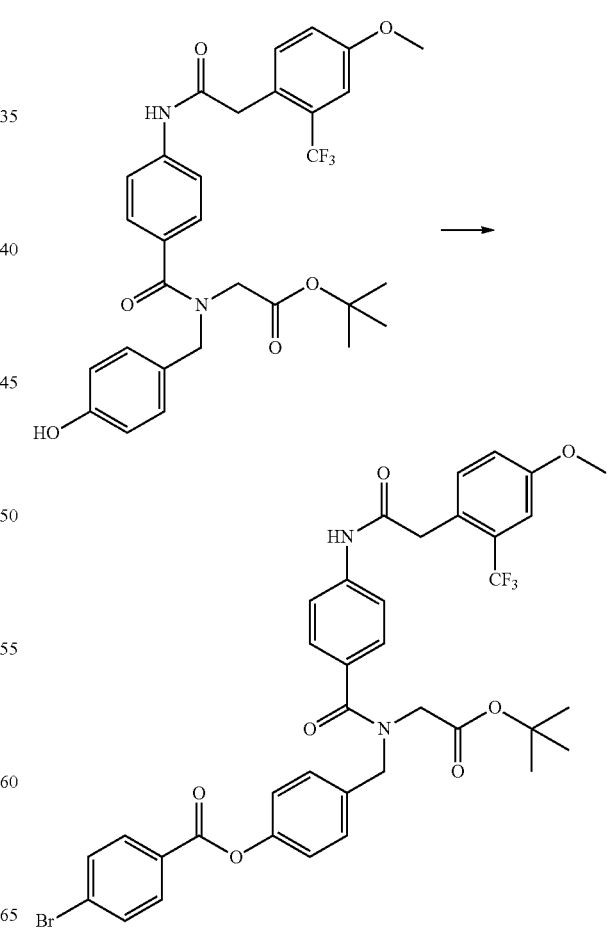

Prepared using General Procedure 2: To a stirring solution of tert-butyl 2-(N-(4-hydroxybenzyl)-4-(2-(4-methoxy-2-(trifluoromethyl)phenyl)acetamido)benzamido)acetate INT-9 (500 mg, 0.87 mmol) in DCM (10 mL) was added TEA (304 μL, 2.18 mmol) followed by 4-bromobenzoyl chloride (201 mg, 0.92 mmol). After 1 h, the reaction mixture was diluted with DCM (50 mL) and washed with NaHCO$_3$ (50 mL). The organics were pre-absorbed onto silica gel and purified by chromatography (EA/isohexanes) to afford 440 mg (63%) of 4-((N-(2-(tert-butoxy)-2-oxo-ethyl)-4-(2-(4-methoxy-2-(trifluoromethyl)phenyl)acetamido)benzamido)methyl)phenyl 4-bromobenzoate INT-10 as a white powder. LCMS-ESI (m/z) calculated for C$_{37}$H$_{34}$BrF$_3$N$_2$O$_7$: 755. found 754 [M–H]$^-$, t$_R$=2.99 min (Method 10).

6-(heptyloxy)nicotinic acid (INT-11)

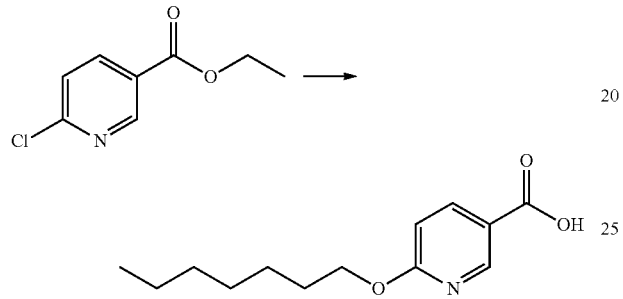

To a stirring solution of heptan-1-ol (0.84 ml, 5.93 mmol) in THF (10 mL) at 0° C. was added sodium hydride (0.25 g, 6.20 mmol, 60 wt % suspension in mineral oil). The reaction mixture was allowed to warm to room temperature. After 1 h, a solution of ethyl 6-chloronicotinate (1.00 g, 5.39 mmol) in THF (5 mL) was added and the reaction mixture was stirred at room temperature for 18 h. The reaction mixture was diluted with EA (50 mL) and washed with brine (100 mL). The organics were dried over MgSO$_4$ and evaporated to dryness. The residue was diluted with THF (5 mL) and MeOH (2 mL) then 1 N lithium hydroxide (1.08 mL, 1.08 mmol) was added. The reaction mixture was stirred for 18 h. The reaction mixture was acidified by the addition of acetic acid (to pH 5) and the solvents were removed under vacuum. The product was extracted into EA (30 mL) and washed with water (100 mL). The organics were pre-absorbed onto silica gel and purified by chromatography (EA/isohexanes) to afford 131 mg (10%) of 6-(heptyloxy)nicotinic acid INT-11 as a white powder. LCMS-ESI (m/z) calculated for C$_{13}$H$_{19}$NO$_3$: 237. found 238 [M+H]$^+$, t$_R$=2.52 min (Method 10).

2-(N-(4-((6-(heptyloxy)nicotinoyl)oxy)benzyl)-4-(2-(4-methoxy-2-(trifluoromethyl)phenyl) acetamido) benzamido)acetic acid (Compound 293)

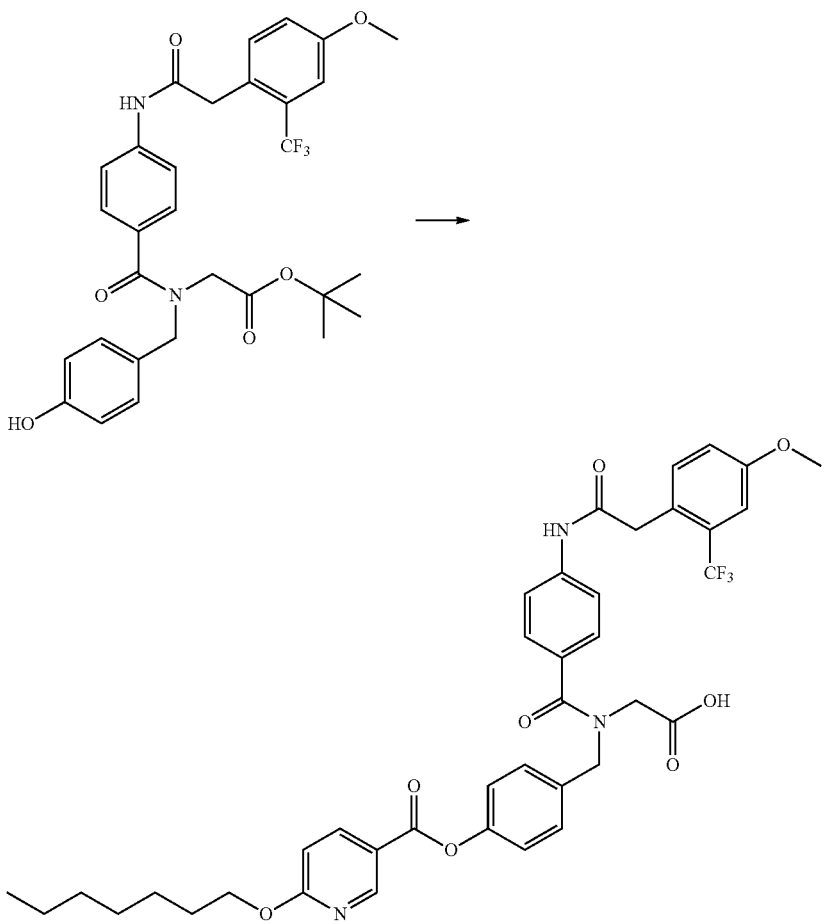 [SMILES: COc1ccc(CC(=O)Nc2ccc(C(=O)N(CC(=O)OC(C)(C)C)Cc3ccc(O)cc3)cc2)c(C(F)(F)F)c1 ; CCCCCCCOc1ccc(C(=O)Oc2ccc(CN(CC(=O)O)C(=O)c3ccc(NC(=O)Cc4ccc(OC)cc4C(F)(F)F)cc3)cc2)cn1]

Prepared using General Procedures 7 then 8: To a stirring solution of 6-(heptyloxy)nicotinic acid 4-octylbenzoic acid INT-11 (25 mg, 0.105 mmol) in DCM (1 mL) were added DMF (1 drop) and oxalyl chloride (0.09 mL, 0.105 mmol). The reaction mixture was stirred at room temperature for 1 h. To this mixture was added a solution of tert-butyl-2-(N-(4-hydroxybenzyl)-4-(2-(4-methoxy-2-trifluoromethyl)phenyl)acetamido)benzamido) acetate INT-9 (40 mg, 0.070 mmol) and TEA (0.024 mL, 0.175 mmol) in DCM (1 mL). The reaction mixture was stirred at room temperature for 18 h then TFA (1 mL) was added. After stirring for 2 h, the solvent was concentrated and the product was purified by preparative HPLC to afford 2.7 mg (5%) of 2-(4-(2-(4-methoxyphenyl)acetamido)-N-(4-((4-octylbenzoyl)oxy)benzyl)benzamido)acetic acid 293. LCMS-ESI (m/z) calculated for $C_{39}H_{40}F_3N_3O_8$: 735. found 736 $[M+H]^+$, $t_R$=9.75 min (Method 9).

General Procedure 13: Preparation of Secondary or Tertiary Amines, Secondary Alcohols, or Esters Via Alkylation To a stirring solution of halide or mesylate (1.0-1.5 eq) in DMF or THF or acetonitrile at 0° C. or room temperature, was added an amine or alcohol or acid (1 eq) and $K_2CO_3$ or TEA or DIEA (1-5 eq). The reaction mixture was stirred at room temperature or 60° C. for up to 18 h. The reaction mixture was quenched with $NaHCO_3$ or brine, the aqueous layer was extracted with EA or DCM, and the organic layer was dried over $MgSO_4$. Alternatively, the reaction mixture was diluted with EA or DCM and washed with water and the organic layer was dried over $MgSO_4$. The solvent was concentrated and the final products were purified by chromatography or preparative HPLC. Alternatively, the final products can be purified directly from the crude reaction mixture, or the crude reaction mixture can be used in the next step without purification.

Compound 128 was prepared using General Procedures 13, 6, 2 then 8. Compounds 129-131 were prepared using General Procedures 13, 6, 2 then 8. Compounds 166-174 were prepared from INT-4 using General Procedures 13 then 8.

General Procedure 14: Preparation of Carbamates

To a stirring solution of nitrophenyl chloroformate (1.1 eq) in DCM or acetonitrile at 0° C. was added the appropriate alcohol or phenol (1 eq) in DCM or acetonitrile, followed by pyridine or $K_2CO_3$ (2 eq). After 90 min, the reaction mixture was concentrated and purified by chromatography to provide the activated nitrophenyl carbamate of the alcohol or phenol. Alternatively, the reaction mixture can be filtered and the filtrate concentrated to provide the activated nitrophenyl carbamate of the alcohol or phenol. The resulting nitrophenyl carbamate (1 eq) was dissolved in DCM and pyridine (2.0 eq), then added drop wise to a solution of amine (1 eq) in DCM. A catalytic amount of DMAP was added. The reaction mixture was stirred at room temperature or at 50° C. for up to 18 h. The crude reaction mixture was diluted with DCM and washed with $NaHCO_3$ and the organic layer dried was over $MgSO_4$. The solvent was concentrated and the final product was purified by chromatography or preparative HPLC. Alternatively, the crude reaction mixture can be concentrated and used in the next step without purification.

Compound 281 was prepared from INT-9 using General Procedures 14, 8 then 12. Compounds 294 and 295 were prepared using INT-4 and General Procedures 14 then 8. Compound 296 was prepared using INT-9 and General Procedures 14 then 8.

General Procedure 15: Preparation of Ureas

To a stirring solution of nitrophenyl chloroformate (1.1 eq) in DCM at 0° C. was added (drop wise) a solution of the appropriate amine (1 eq) and DIEA (2 eq) in THF. After 90 min, a solution of another appropriate amine (1 eq) and DIEA (2 eq) in DCM was added to the reaction mixture. A catalytic amount of DMAP was added. After 40 h, the mixture was concentrated and purified by preparative HPLC.

Compound 297 was prepared using General Procedures 15 then 8.

4-formylphenyl 4-(heptyloxy)benzoate (INT-12)

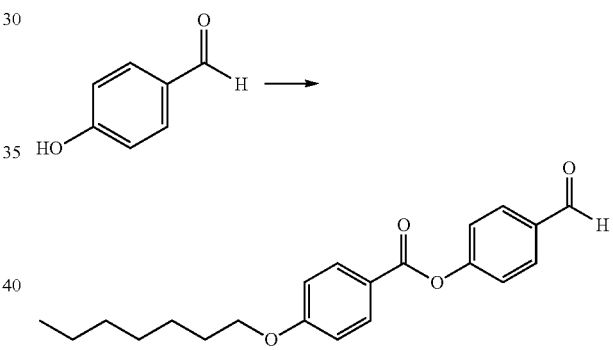

Prepared using General Procedure 2: To a stirring solution of 4-(heptyloxy)benzoic acid (1.0 g, 4.23 mmol) in DCM (10 mL) were added DMF (1 drop) and oxalyl chloride (0.47 mL, 5.5 mmol). The reaction mixture was stirred at room temperature for 1 h. Solvent was evaporated under high vacuum. DCM (10 mL) was added and the reaction mixture evaporated again to dryness. The residue was dissolved in DCM (10 mL) then added to a stirring mixture of 4-hydroxybenzaldehyde (0.56 g, 4.6 mmol) and TEA (0.706 mL, 5.07 mmol) in DCM (5 mL) at 0° C. The reaction mixture was allowed to stir at room temperature for 2 h. The reaction mixture was quenched with $NaHCO_3$ (10 mL). The aqueous phase was extracted with DCM and the combined organic phases were dried over $MgSO_4$ and concentrated to give 977 mg (62%) of 4-formylphenyl 4-(heptyloxy)benzoate INT-12 which was used in the next step without purification. LCMS-ESI (m/z) calculated for $C_{21}H_{24}O_4$: 340. found 341 $[M+H]^+$, $t_R$=11.91 min (Method 2). $^1H$ NMR (400 MHz, DMSO) δ 10.03 (s, 1H), 8.19-7.91 (m, 4H), 7.63-7.41 (m, 2H), 7.24-7.01 (m, 2H), 4.09 (t, J=6.5 Hz, 2H), 1.86-1.62 (m, 2H), 1.50-1.07 (m, 8H), 0.87 (t, J=6.9 Hz, 3H).

4-(((2-(tert-butoxy)-2-oxoethyl)amino)methyl)phenyl 4-(heptyloxy)benzoate (INT-13)

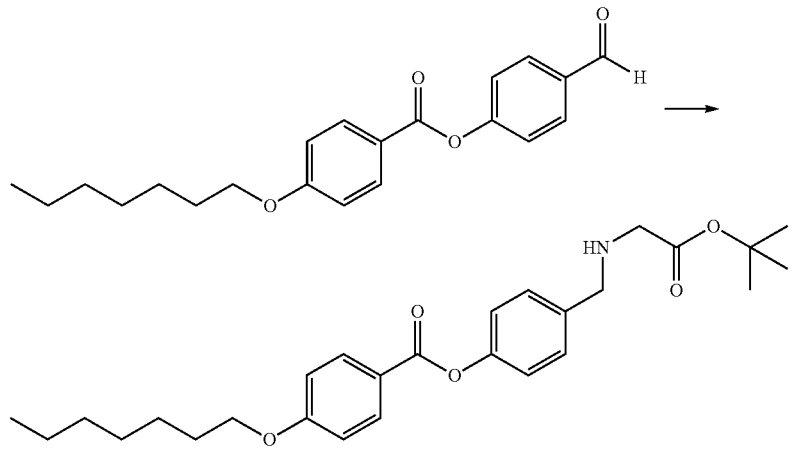

Prepared using General Procedure 12: To a stirring solution of 4-formylphenyl 4-(heptyloxy)benzoate INT-12 (6.0 g, 17.6 mmol) in THF (30 mL) was added tert-butyl 2-aminoacetate hydrochloride (3.3 g, 19.7 mmol). After stirring for 2 h, sodium triacetoxyborohydride (7.5 g, 32.3 mmol) was added. After stirring for 12 h, the reaction mixture was diluted with NaHCO$_3$ and the organic layer was separated. The remaining aqueous layer was extracted with DCM. The organic layers were combined, dried over Na$_2$SO$_4$, concentrated and purified by chromatography (EA/hexanes) to afford 155 mg (19%) of 4-(((2-(tert-butoxy)-2-oxoethyl)amino)methyl)phenyl 4-(heptyloxy)benzoate INT-13. LCMS-ESI (m/z) calculated for C$_{27}$H$_{37}$NO$_5$: 455. found 456 [M+H]+, t$_R$=3.27 min (Method 1). 1H NMR (400 MHz, CDCl$_3$) δ 8.18-8.09 (m, 2H), 7.41 (d, J=8.5 Hz, 2H), 7.18-7.08 (m, 2H), 7.01-6.88 (m, 2H), 4.08-3.98 (m, 2H), 3.78 (s, 2H), 3.23 (s, 2H), 1.89-1.75 (m, 2H), 1.55-1.41 (s, 9H), 1.45-1.21 (m, 6H), 1.15-1.06 (m, 2H), 0.88 (dd, J=8.5, 5.0 Hz, 3H).

Compound 132 was prepared using INT-13 and General Procedures 13 then 8. Compound 177 was prepared from INT-13 using General Procedures 7 then 5. Compound 178 was prepared from INT-13 and 4-((4-methoxy-2-(trifluoromethyl)benzamido)methyl)benzoic acid using General Procedures 6 then 8.

Methyl 5-(2-(4-methoxy-2-(trifluoromethyl)phenyl)acetamido)picolinate (INT-14)

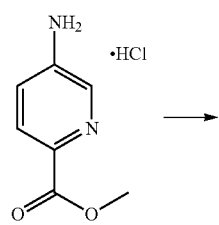

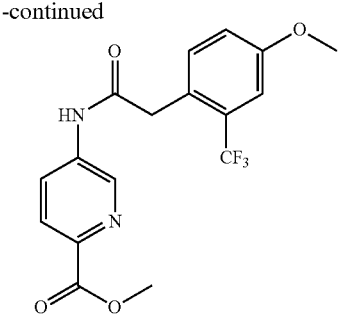

Prepared using General Procedure 6: To a stirred solution of 2-(4-methoxy-2-(trifluoromethyl)phenyl)acetic acid (200 mg, 0.85 mmol), HATU (210 mg, 0.89 mmol) in DMF (5 mL) was added methyl 5-aminopicolinate hydrochloride (156 mg, 1.02 mmol) followed by triethylamine (226 mg, 2.24 mmol). The reaction mixture was stirred at room temperature for 12 h. The reaction mixture was diluted with EA (10 mL) and washed with NaHCO$_3$ (10 mL), NH$_4$Cl (10 mL) and brine (10 mL) then dried over MgSO$_4$ and concentrated to give 78 mg (25%) of methyl 5-(2-(4-methoxy-2-(trifluoromethyl)phenyl)acetamido)picolinate INT-14 which was used in the next step without purification. LCMS-ESI (m/z) calculated C$_{17}$H$_{15}$F$_3$N$_2$O$_4$: 368. found 369 [M+H]$^+$, t$_R$=3.06 min (Method 1).

5-(2-(4-methoxy-2-(trifluoromethyl)phenyl)acetamido)picolinic acid (INT-15)

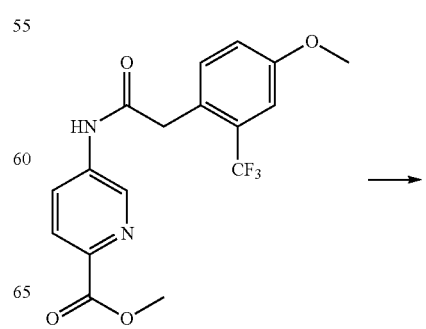

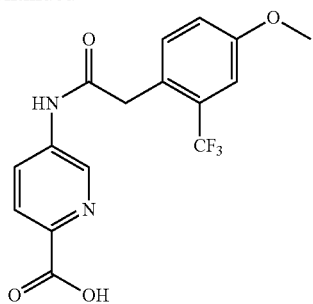

Prepared using General Procedure 9: To a stirred solution of methyl 5-(2-(4-methoxy-2-(trifluoromethyl)phenyl)acetamido)picolinate INT-14 (74 mg, 0.2 mmol) in MeOH (1 mL) and THF (4 mL) was added 2 N NaOH (1 mL). The reaction mixture was stirred at room temperature overnight then concentrated. The residue was diluted with water (1 mL) and acidified with 1 N HCl to a pH of 2. The resulting precipitate was isolated by filtration and the filter cake was washed with water. Crude product was dried under vacuum to afford 48 mg (67%) of 5-(2-(4-methoxy-2-(trifluoromethyl)phenyl)acetamido)picolinic acid INT-15 which was used in the next step without purification. LCMS-ESI (m/z) calculated $C_{16}H_{13}F_3N_2O_4$: 354. found 355, $t_R$=2.66 min (Method 1). $^1$H NMR (400 MHz, DMSO) δ 10.71 (s, 1H), 8.83 (d, J=2.2 Hz, 1H), 8.18 (dd, J=8.6, 2.5 Hz, 1H), 8.02 (d, J=8.6 Hz, 1H), 7.46 (d, J=8.5 Hz, 1H), 7.29-7.10 (m, 2H), 3.92 (s, 2H), 3.82 (d, J=5.3 Hz, 3H), 3.35 (s, 1H).

4-((N-(2-(tert-butoxy)-2-oxoethyl)-5-(2-(4-methoxy-2-(trifluoromethyl)phenyl)acetamido) picolinamido) methyl)phenyl 4-(heptyloxy)benzoate (INT-16)

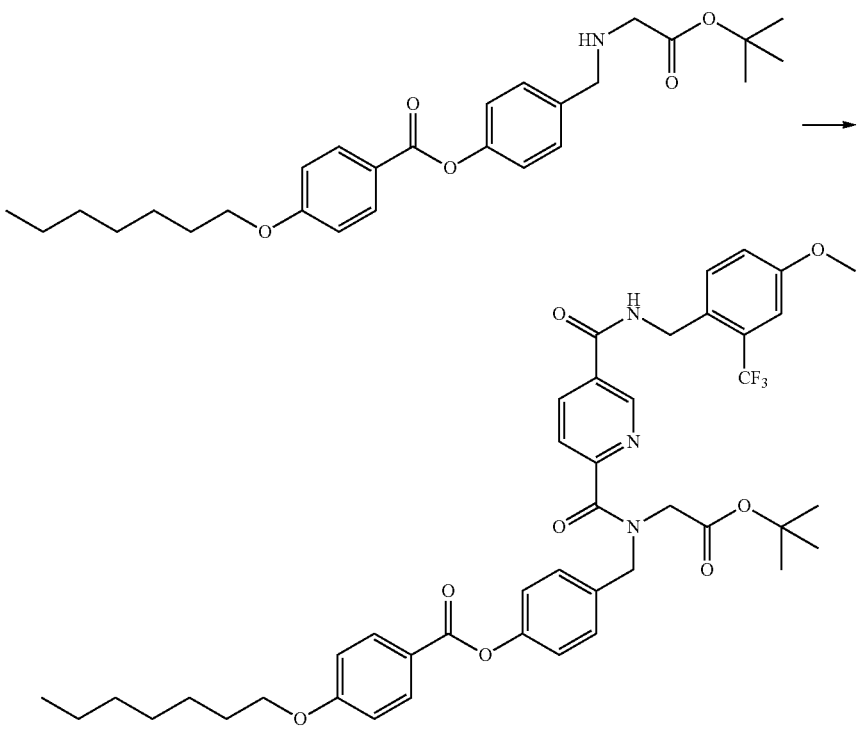

Prepared using General Procedure 6: To a stirred solution of 5-(2-(4-methoxy-2-(trifluoromethyl)phenyl)acetamido) picolinic acid INT-15 (20 mg, 0.05 mmol) in DMF (1 mL) was added HATU (22.5 mg, 0.06 mmol). After stirring for 1 h at room temperature, 4-(((2-(tert-butoxy)-2-oxoethyl)amino)methyl)phenyl 4-(heptyloxy)benzoate INT-13 (30.8 mg, 0.06 mmol) was added followed by triethylamine (11.4 mg, 0.11 mmol). The reaction mixture was allowed to stir at room temperature overnight. The final product was isolated by HPLC purification to give 4-((N-(2-(tert-butoxy)-2-oxoethyl)-5-(2-(4-methoxy-2 (trifluoromethyl)phenyl)acetamido)picolinamido)methyl)phenyl 4-(heptyloxy)benzoate INT-16. LCMS-ESI (m/z) calculated for $C_{43}H_{48}F_3N_3O_8$: 792; no m/z observed, $t_R$=4.11 min (Method 7).

2-(N-(4-((4-(heptyloxy)benzoyl)oxy)benzyl)-5-(2-(4-methoxy-2-(trifluoromethyl) phenyl) acetamido) picolinamido)acetic acid (Compound 298)

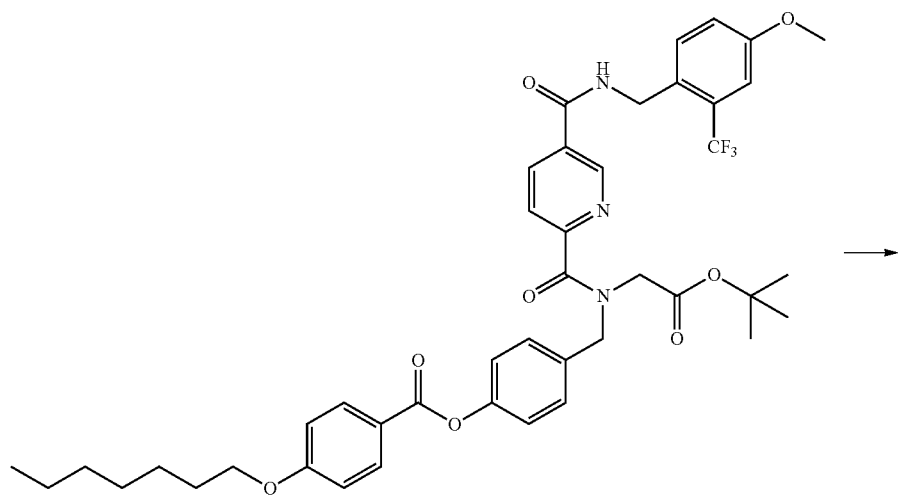

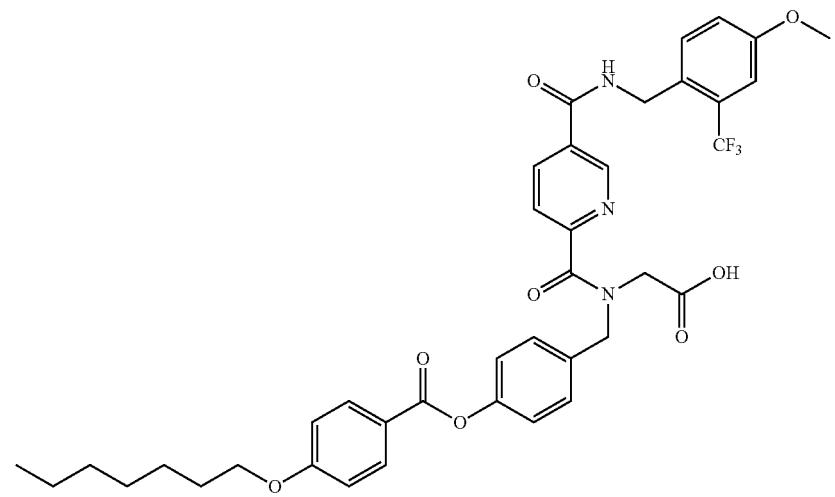

Prepared using General Procedure 8: To a stirred solution of 4-((N-(2-(tert-butoxy)-2-oxoethyl)-5-(2-(4-methoxy-2-(trifluoromethyl)phenyl)acetamido)picolinamido)methyl) phenyl 4-(heptyloxy)benzoate INT-16 (18 mg, 0.02 mmol) in DCM (1 mL) was added a solution of TFA (0.1 mL) and DCM (0.2 mL). The reaction mixture was stirred at room temperature for 12 h. The solvent was evaporated under high vacuum to give 12 mg (75%) of 2-(N-(4-((4-(heptyloxy)benzoyl)oxy)benzyl)-5-(2-(4-methoxy-2-(trifluoromethyl) phenyl) acetamido)picolinamido)acetic acid 298 as a white solid. LCMS-ESI (m/z) calculated for $C_{39}H_{40}F_3N_3O_8$: 736; no m/z observed, $t_R$=11.36 min (Method 2). $^1$H NMR (400 MHz, DMSO) δ 12.65 (s, 1H), 10.60 (s, 1H), 8.72 (dd, J=11.1, 2.1 Hz, 1H), 8.19-8.09 (m, 1H), 8.09-7.97 (m, 2H), 7.71 (dd, J=28.2, 8.7 Hz, 1H), 7.43 (dd, J=16.8, 8.3 Hz, 3H), 7.27-7.15 (m, 4H), 7.10 (d, J=8.9 Hz, 2H), 4.75 (d, J=23.0 Hz, 2H), 4.30 (s, 1H), 4.08 (t, J=6.5 Hz, 2H), 3.97 (s, 1H), 3.89 (s, 2H), 3.82 (d, J=2.0 Hz, 3H), 1.73 (dd, J=14.5, 6.6 Hz, 2H), 1.50-1.15 (m, 8H), 0.87 (t, J=6.9 Hz, 3H).

Compound 299 was prepared analogous to compound 298 by employing INT-13 and methyl 6-aminonicotinate using General Procedures 6, 10, 6 then 8. Compound 300 was prepared analogous to compound 298 by employing INT-13 and methyl 2-fluoro-4-aminobenzoate using General Procedures 6, 9, 6 then 8. Compound 301 was prepared analogous to compound 298 by employing INT-13 and methyl 2-hydroxy-4-aminobenzoate using General Procedures 6, 9, 6 then 8. Compound 302 was prepared analogous to compound 298 by employing INT-13 and methyl 3-methyl-4-aminobenzoate using General Procedures 7, 9, 6 then 8. Compound 303 was prepared analogous to compound 298 by employing INT-13 and methyl 3-fluoro-4-aminobenzoate using General Procedures 7, 9, 6 then 8. Compound 304 was prepared analogous to compound 298 by employing INT-13 and methyl 3-hydroxy-4-aminobenzoate using General Procedures 7, 9, 6 then 8. Compound 305 was prepared analogous to compound 298 by employing INT-13 and methyl 4-amino-2-methylbenzoate using General Procedures 7, 9, 6 then 8. Compound 306 was prepared analogous to compound 298 by employing INT-13 and methyl 4-amino-3-isopropoxybenzoate using General Procedures 7, 9, 6 then 8. Compound 307 was prepared analogous to compound 298 by employing INT-13 and methyl 4-amino-3-chlorobenzoate using General Procedures 7, 9, 6 then 8.

Methyl 5-(2-(4-methoxy-2-(trifluoromethyl)phenyl)acetamido)picolinate (INT-17)

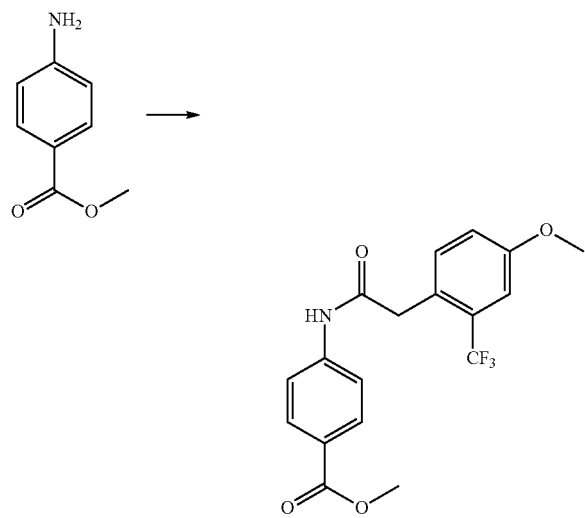

Prepared using General Procedure 6: INT-17 was prepared in a similar fashion to INT-14 using methyl 5-aminopicolinate hydrochloride in place of methyl 4-aminobenzoate to yield 2.1 g (67%) of methyl 4-(2-(4-methoxy-2-(trifluoromethyl)phenyl)acetamido)benzoate INT-17 which was used in the next step without purification. LCMS-ESI (m/z) calculated for $C_{18}H_{16}F_3NO_4$: 367. found 368, $t_R$=3.45 min (Method 1).

4-(2-(4-methoxy-2-(trifluoromethyl)phenyl)acetamido)benzoic acid (INT-18)

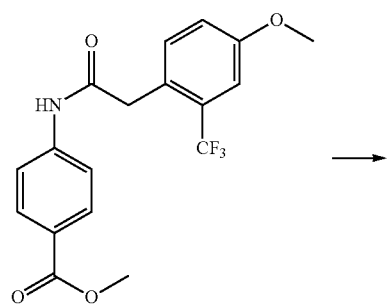

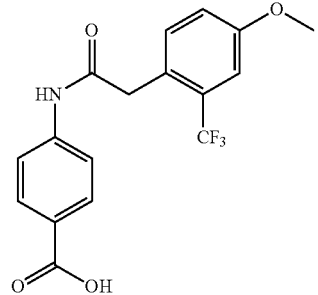

Prepared using General Procedure 9: INT-18 was prepared from INT-17, in a similar fashion to INT-15 to yield 1.78 g (88%) of 4-(2-(4-methoxy-2-(trifluoromethyl)phenyl)acetamido)benzoic acid INT-18 which was used in the next step without purification. LCMS-ESI (m/z) calculated for $C_{17}H_{14}F_3NO_4$: 353. found 354, $t_R$=2.93 min (Method 1). $^1$H NMR (400 MHz, DMSO) δ 12.69 (s, 1H), 10.46 (s, 1H), 7.99-7.77 (m, 2H), 7.75-7.55 (m, 2H), 7.44 (d, J=8.5 Hz, 1H), 7.30-7.10 (m, 2H), 3.88 (s, 2H), 3.83 (s, 3H).

Compounds 308 and 309 were prepared using INT-12 and INT-18 employing General Procedures 12, 7 then 8.

6-formylpyridin-3-yl 4-(heptyloxy)benzoate (INT-19)

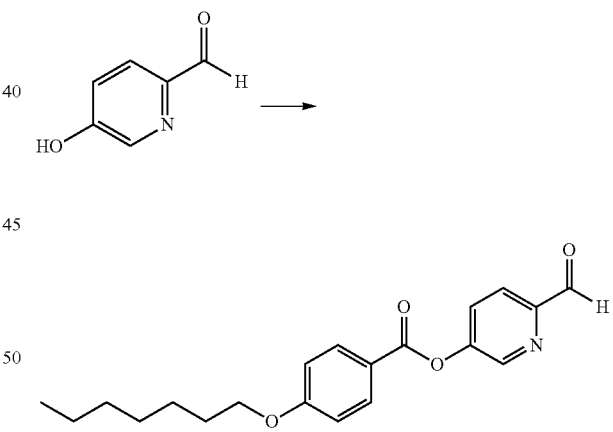

Prepared using General Procedure 2: INT-19 was prepared in a similar fashion to INT-12, using 5-hydroxypicolinaldehyde in place of 4-hydroxy benzaldehyde to yield 50 mg (35%) of 6-formylpyridin-3-yl 4-(heptyloxy)benzoate INT-19. LCMS-ESI (m/z) calculated for $C_{20}H_{23}NO_4$: 341; no m/z observed, $t_R$=4.61 min (Method 1). $^1$H NMR (400 MHz, CDCl$_3$) δ 10.09 (d, J=0.6 Hz, 1H), 8.71 (d, J=2.5 Hz, 1H), 8.18-8.11 (m, 2H), 8.07 (d, J=8.5 Hz, 1H), 7.80 (ddd, J=8.5, 2.5, 0.7 Hz, 1H), 7.05-6.88 (m, 2H), 4.06 (t, J=6.6 Hz, 2H), 1.82 (dd, J=14.8, 6.8 Hz, 2H), 1.53-1.20 (m, 7H), 0.90 (t, J=6.9 Hz, 3H).

6-(((2-(tert-butoxy)-2-oxoethyl)amino)methyl)pyridin-3-yl 4-(heptyloxy)benzoate (INT-20)

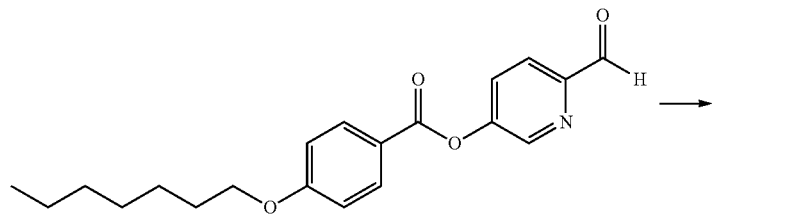

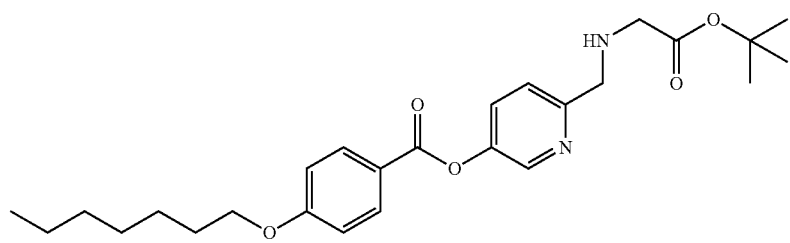

Prepared using General Procedure 12: INT-20 was prepared from INT-19 in a similar fashion to INT-13 to yield 40 mg (60%) of 6-(((2-(tert-butoxy)-2-oxoethyl)amino)methyl)pyridin-3-yl 4-(heptyloxy)benzoate INT-20 as an off-white solid. LCMS-ESI (m/z) calculated for $C_{26}H_{36}N_2O_5$: 456. found 457 $[M+H]^+$, $t_R$=3.12 min (Method 1).

6-((N-(2-(tert-butoxy)-2-oxoethyl)-4-(2-(4-methoxy-2-(trifluoromethyl)phenyl)acetamido) benzamido) methyl)pyridin-3-yl 4-(heptyloxy)benzoate (INT-21)

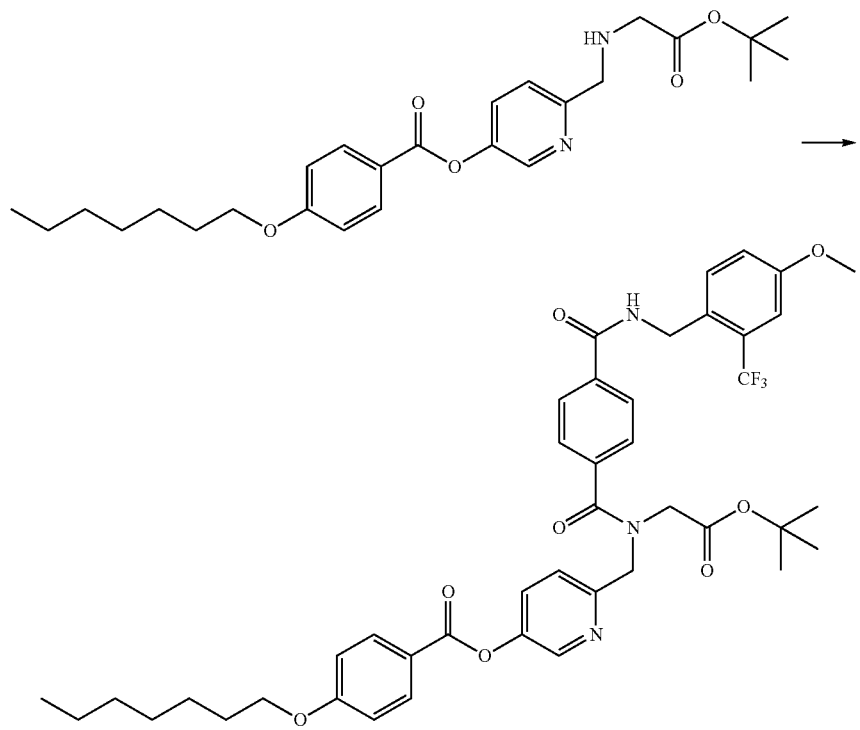

Prepared using General Procedure 6: To a stirred solution of 4-(2-(4-methoxy-2-(trifluoromethyl)phenyl)acetamido)benzoic acid INT-18 (40 mg, 0.11 mmol) in DMF (1 mL) was added HATU (45 mg, 0.11 mmol). After stirring for 1 h at room temperature, 6-(((2-(tert-butoxy)-2-oxoethyl)amino)methyl)pyridin-3-yl 4-(heptyloxy)benzoate INT-20 (61.7 mg, 0.13 mmol) was added followed by triethylamine (22.8 mg, 0.22 mmol). The reaction mixture was allowed to stir at room temperature for overnight. The final product was isolated by HPLC purification to give 6-((N-(2-(tert-butoxy)-2-oxoethyl)-4-(2-(4-methoxy-2-(trifluoromethyl)phenyl)acetamido)benzamido)methyl)pyridin-3-yl 4-(heptyloxy)benzoate INT-21. LCMS-ESI (m/z) calculated for $C_{43}H_{48}F_3N_3O_8$: 792; no m/z observed, $t_R$=4.83 min (Method 1).

2-(N-((5-((4-(heptyloxy)benzoyl)oxy)pyridin-2-yl)methyl)-4-(2-(4-methoxy-2 (trifluoromethyl)phenyl)acetamido)benzamido)acetic acid (Compound 310)

under high vacuum to give 23 mg (75%) of 2-(N-(4-((4-(heptyloxy)benzoyl)oxy)benzyl)-5-(2-(4-methoxy-2-(trifluoromethyl)phenyl)acetamido)picolinamido)acetic acid 310 as a white solid. LCMS-ESI (m/z) calculated for $C_{39}H_{40}F_3N_3O_8$: 735. found 736 [M+H]$^+$, $t_R$=11.02 min (Method 2). $^1$H NMR (400 MHz, DMSO) δ 13.06-12.79 (m, 1H), 10.35 (d, J=9.7 Hz, 1H), 8.52 (d, J=17.1 Hz, 1H), 8.09 (d, J=8.8 Hz, 2H), 7.82 (dd, J=35.0, 8.6 Hz, 1H), 7.68-7.51 (m, 2H), 7.41 (dt, J=27.9, 8.5 Hz, 3H), 7.27-7.07 (m, 5H), 4.71 (d, J=35.0 Hz, 2H), 4.09 (t, J=6.5 Hz, 3H), 3.83 (d, J=8.5 Hz, 3H), 3.62 (s, 3H), 1.74 (dd, J=14.6, 6.7 Hz, 2H), 1.36 (ddd, J=23.7, 15.1, 5.1 Hz, 8H), 0.87 (t, J=6.9 Hz, 3H).

Compound 311 was prepared using INT-18 and General Procedures 13, 6, 2 then 8. Compound 312 was prepared using INT-18 and General Procedures 2, 12, 6 then 8.

General Procedure 16: Preparation of Biaryls Via Suzuki Coupling

To a stirring solution of aryl bromide or aryl chloride or aryl iodide (1 eq) in acetonitrile and water (10:1) or THF,

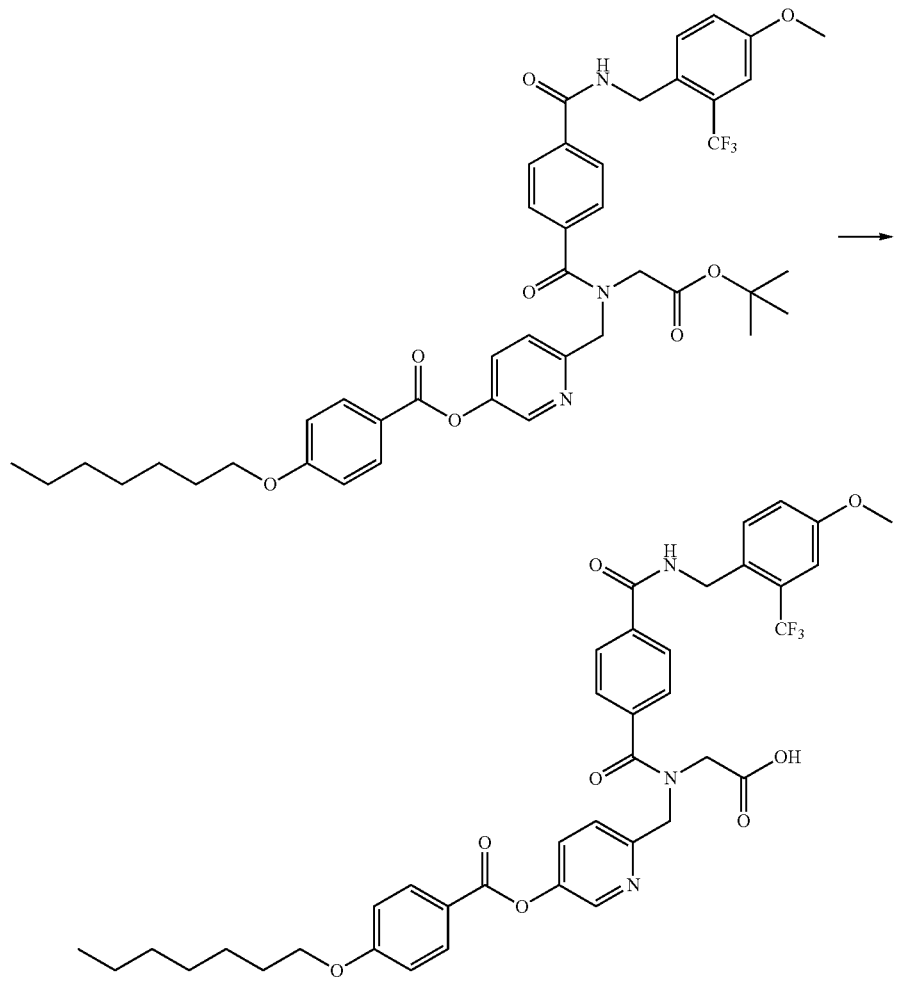

Prepared using General Procedure 8: To a stirred solution of 6-((N-(2-(tert butoxy)-2-oxoethyl)-4-(2-(4-methoxy-2-(trifluoromethyl)phenyl)acetamido) benzamido) methyl)pyridin-3-yl 4-(heptyloxy)benzoate INT-21 (40 mg, 0.02 mmol) in DCM (1 mL) was added a solution of TFA (0.1 mL) in DCM (0.2 mL) and the reaction mixture was stirred at room temperature for 12 h. The solvent was evaporated acetonitrile and water (2:2:1) was added Na$_2$CO$_3$ (1-2 eq) and the appropriate boronic acid (1.2-1.5 eq). The reaction mixture was degassed with N$_2$ for 10 min then a suitable palladium catalyst was added such as PdCl$_2$(dppf) or Pd(Ph$_3$)$_4$ (0.05 eq.). The reaction mixture was degassed with N$_2$ for 5 min then heated in a microwave reactor at 100-110° C. for up to 1 h. The crude reaction mixture was quenched with NaHCO$_3$. The aqueous layer was extracted with DCM and the organic layer was dried over MgSO$_4$. The solvent was concentrated and the final product was purified by chromatography or preparative HPLC. Alternatively, the crude reaction mixture can be diluted with DCM, passed through a phase separation cartridge, then concentrated and used in the next step without further purification.

Compound 190 was prepared from INT-7 using General Procedures 2, 16 then 8. Compounds 279-280 were prepared from INT-9 using General Procedures 2, 16 then 8. Compounds 282-292 were prepared from INT-10 using General Procedures 16 then 8.

2-(N-(4-((4'-chloro-[1,1'-biphenyl]-4-carbonyl)oxy)benzyl)-4-(2-(4-methoxy-2 (trifluoromethyl)phenyl)acetamido)benzamido)acetic acid (Compound 282)

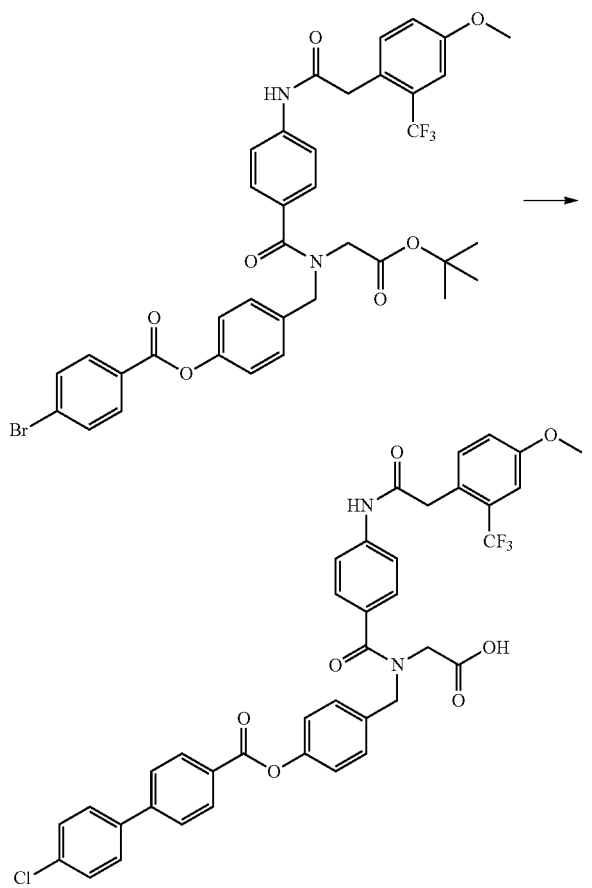

Prepared using General Procedures 16 then 8: To 4-((N-(2-(tert-butoxy)-2-oxoethyl)-4-(2-(4-methoxy-2-(trifluoromethyl)phenyl)acetamido)benzamido)methyl)phenyl 4-bromobenzoate INT-10 (50 mg, 0.07 mmol) in a microwave vessel were added Na$_2$CO$_3$ (15 mg, 0.15 mmol), 4-chlorobenzene boronic acid (17 mg, 0.07 mmol), acetonitrile (1 mL) and water (0.1 mL). The suspension was degassed with N$_2$ then treated with PdCl$_2$(dppf) (2.6 mg, 3.64 µmol) and degassed further. The reaction mixture was heated in the microwave at 100° C. for 30 min with stirring. The reaction mixture was diluted with DCM (10 mL) and passed through a phase separator cartridge. The organic layer was isolated and concentrated to 3 mL then TFA (2 mL) was added. After stirring for 2 h at room temperature, the solvent was concentrated and the product was purified by preparative HPLC to provide 17 mg (31%) of 2-(N-(4-((4'-chloro-[1,1'-biphenyl]-4-carbonyl)oxy)benzyl)-4-(2-(4-methoxy-2-(trifluoromethyl)phenyl)acetamido)benzamido)acetic acid 282. LCMS-ESI (m/z) calculated for C$_{39}$H$_{30}$ClF$_3$N$_2$O$_7$: 731. found 732 [M+H]$^+$, t$_R$=8.89 min (Method 9).

tert-butyl 2-((4-hydroxybenzyl)amino)acetate (INT-22)

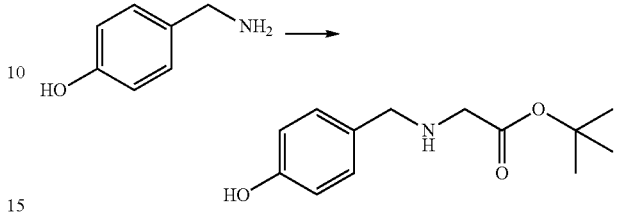

Prepared using General Procedure 13: To a stirred solution of 4-(aminomethyl)phenol (2.0 g, 16.2 mmol) in DMF (10 mL) was added TEA (4.53 mL, 32.5 mmol) followed by tert-butyl 2-bromoacetate (2.40 mL, 16.2 mmol) added drop-wise over 30 minutes. After stirring a further 1 h at room temperature, the reaction mixture was diluted with EA (100 mL) and washed with water (2×100 mL). The organics were isolated and pre-absorbed onto silica gel then purified by silica gel chromatography (EA/isohexanes) to afford 1.86 g (48%) tert-butyl 2-((4-hydroxybenzyl)amino)acetate INT-22 as a white powder. LCMS-ESI (m/z) calculated for C$_{13}$H$_{19}$NO$_3$: 237 found 236 [M−H]$^-$, t$_R$=1.20 min (Method 10). $^1$H NMR (400 MHz, DMSO) δ 9.24 (s, 1H), 7.12-7.05 (m, 2H), 6.73-6.66 (m, 2H), 3.55 (s, 2H), 3.12 (s, 2H), 2.15 (s, 1H) 1.41 (s, 9H).

2-methoxy-4-(2-(4-methoxy-2-(trifluoromethyl)phenyl)acetamido)benzoic acid (INT-23)

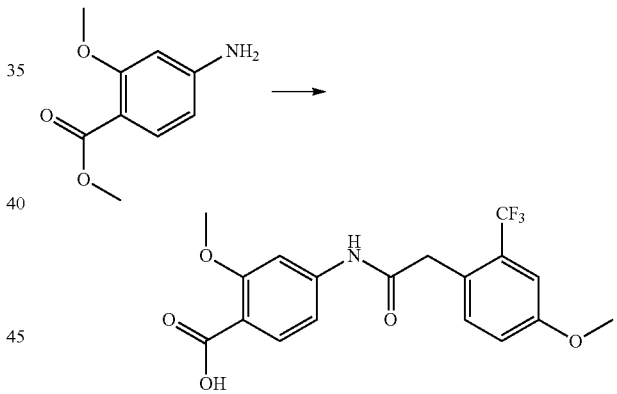

Prepared using General Procedures 6 and 9: To a stirred solution of 2-(4-methoxy-2-(trifluoromethyl)phenyl)acetic acid (500 mg, 2.14 mmol), methyl 4-amino-2-methoxybenzoate (387 mg, 2.14 mmol) and TEA (744 µL, 5.34 mmol) in DMF (5 mL) was added HATU (852 mg, 2.24 mmol). After 1 h the reaction mixture was diluted with EA (100 mL) and washed with brine (2×100 mL). The organic layer was pre-absorbed onto silica gel and then purified by chromatography (EA/isohexanes) to afford a white solid. The solid was diluted with THF (15 mL) and MeOH (10 mL) and then 1 N LiOH (427 µl, 4.27 mmol) was added and the solution stirred at room temperature. After 18 h the reaction mixture was acidified by the addition of 1 N HCl (50 mL) and the organics removed under vacuum. The residue was extracted with EA (100 mL) and the organics were washed with brine (200 mL) and dried over magnesium sulfate. The solvent was concentrated to afford 404 mg (49%) 2-methoxy-4-(2-(4-methoxy-2-(trifluoromethyl)phenyl)acetamido)benzoic acid INT-23 as a white powder. LCMS-ESI (m/z) calculated for C$_{18}$H$_{16}$F$_3$NO$_5$: 237 found 236 [M−H]$^-$, t$_R$=1.90 min (Method 10).

107 tert-butyl 2-(N-(4-hydroxybenzyl)-2-methoxy-4-(2-(4-methoxy-2-(trifluoromethyl)phenyl)acetamido)benzamido)acetate (INT-24)

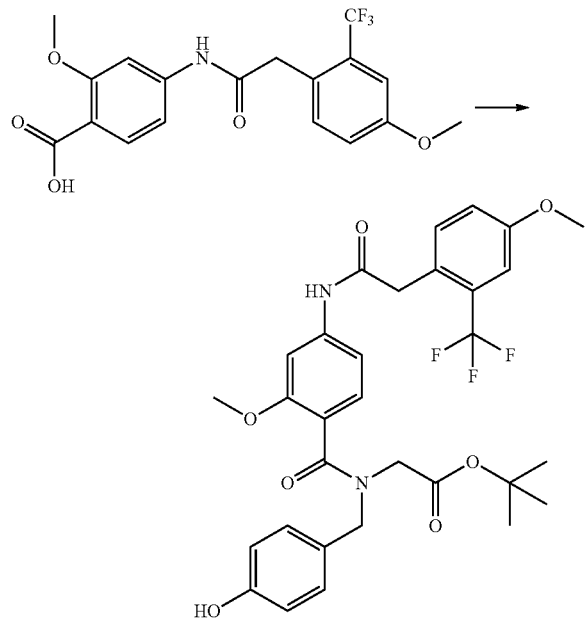

108

Prepared using General Procedure 6: To a stirred solution of 2-methoxy-4-(2-(4-methoxy-2-(trifluoromethyl)phenyl)acetamido)benzoic acid INT-23 (404 mg, 1.05 mmol), tert-butyl 2-((4-hydroxybenzyl)amino)acetate INT-22 (250 mg, 1.05 mmol) and TEA (367 μL, 2.63 mmol) in DMF (5 mL) was added HATU (421 mg, 1.11 mmol). After 2 h the reaction mixture was diluted with EA (100 mL) and washed with brine (2×150 mL). The organics were pre-absorbed onto silica gel and then purified by chromatography (EA/isohexanes) to afford 633 mg (99%) of tert-butyl 2-(N-(4-hydroxybenzyl)-2-methoxy-4-(2-(4-methoxy-2-(trifluoromethyl)phenyl)acetamido)benzamido)acetate INT-24 as a waxy solid. LCMS-ESI (m/z) calculated for $C_{31}H_{33}F_3N_2O_7$: 602 found 601 [M−H]$^-$, $t_R$=2.29 min (Method 10). $^1$H NMR (400 MHz, DMSO 100° C.) δ 10.25 (s, 1H), 9.28 (s, 1H), 7.52-7.41 (m, 2H), 7.27-7.04 (m, 5H), 6.95 (d, J=8.0 Hz, 1H), 6.72 (dd, J=20.5, 7.9 Hz, 2H), 4.52 (br s, 1H), 4.22 (s, 1H), 3.81 (m, 9H), 3.62 (s, 1H), 1.40 (d, J=2.1 Hz, 4.5H), 1.30 (d, J=2.1 Hz, 4.5H).

Compounds 313-314 were prepared using INT-24 and General Procedures 2 then 8.

2-(N-(4-((4-(heptyloxy)benzoyl)oxy)benzyl)-2-methoxy-4-(2-(4-methoxy-2-(trifluoromethyl) phenyl)acetamido)benzamido)acetic acid (Compound 313)

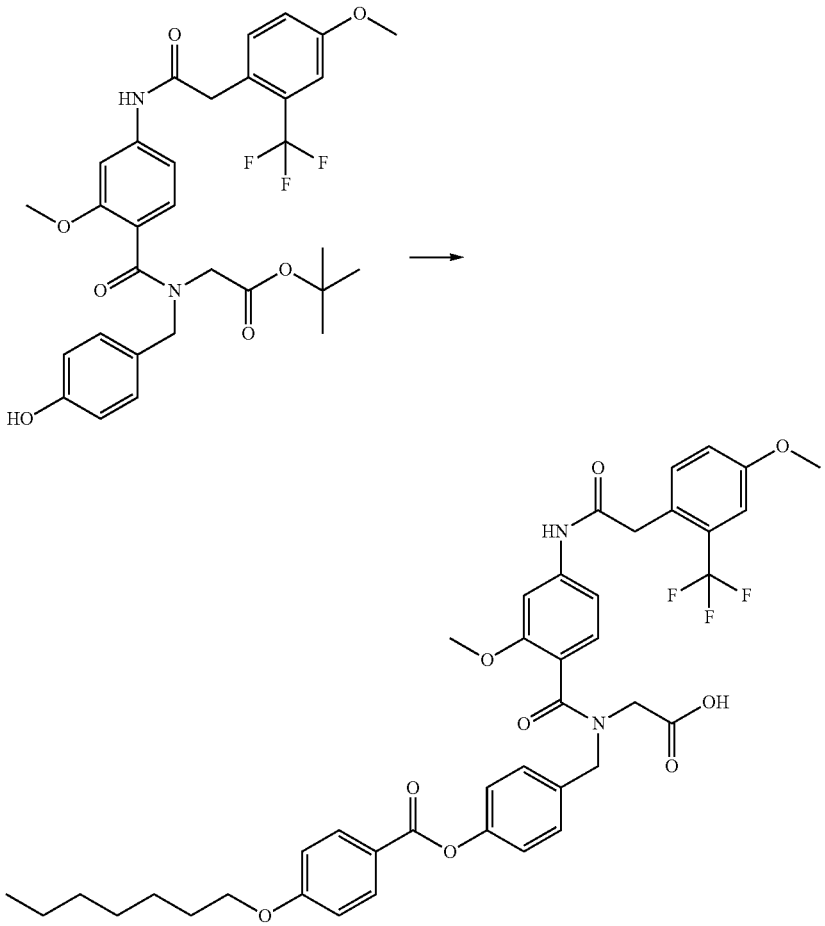

Prepared using General Procedures 2 then 8: To a stirring solution of 4-(heptyloxy)benzoic acid (43 mg, 0.183 mmol) in DCM (2 mL) were added DMF (1 drop) and oxalyl chloride (0.016 mL, 0.183 mmol). The reaction mixture was stirred at room temperature for 2 h. To this mixture was added a solution of tert-butyl 2-(N-(4-hydroxybenzyl)-2-methoxy-4-(2-(4-methoxy-2-(trifluoromethyl)phenyl)acetamido) benzamido) acetate INT-24 (92.0 mg, 0.153 mmol) and TEA (0.043 mL, 0.305 mmol) in DCM (1 mL). The reaction mixture was stirred at room temperature for 18 h then TFA (1 mL) was added. After stirring for 2 h, the solvent was concentrated and the product was purified by chromatography (EA/isohexanes+1% acetic acid) to afford 18.0 mg (15%) of 2-(N-(4-((4-(heptyloxy)benzoyl)oxy)benzyl)-2-methoxy-4-(2-(4-methoxy-2-(trifluoromethyl) phenyl)acetamido)benzamido)acetic acid 313 as a white powder. LCMS-ESI (m/z) calculated for $C_{41}H_{43}F_3N_2O_9$: 764. found 765 [M+H]$^+$, $t_R$=9.39 min (Method 9). $^1$H NMR (400 MHz, DMSO at 50° C.) δ 12.88-12.19 (br s, 1H), 10.25-10.12 (s, 1H), 8.11-8.02 (m, 2H), 7.52-7.39 (m, 3H), 7.29-7.07 (m, 9H), 4.92-4.54 (br s, 1H), 4.41 (s, 1H), 4.16-4.06 (td, J=6.5, 1.8 Hz, 2H), 4.06-3.92 (br s, 1H), 3.90-3.80 (m, 5H), 3.80-3.73 (m, 3H), 1.81-1.70 (m, 2H), 1.49-1.25 (m, 9H), 0.93-0.84 (m, 3H).

2-(2-methoxy-4-(2-(4-methoxy-2-(trifluoromethyl)phenyl)acetamido)-N-(4-((4'-methyl-[1,1'-biphenyl]-4-carbonyl)oxy)benzyl)benzamido)acetic acid (Compound 314)

Prepared using General Procedures 2 then 8: To a stirring suspension of 4'-methyl-[1,1'-biphenyl]-4-carboxylic acid (57 mg, 0.27 mmol) in DCM (5 mL) were added DMF (2 drops) and oxalyl chloride (25 µL, 0.29 mmol). The reaction mixture was stirred at room temperature for 2 h. To this mixture was added a solution of tert-butyl 2-(N-(4-hydroxybenzyl)-2-methoxy-4-(2-(4-methoxy-2-(trifluoromethyl) phenyl) acetamido) benzamido)acetate INT-24 (108 mg, 0.18 mmol) and TEA (62 µL, 0.45 mmol) in DCM (5 mL). The reaction mixture was stirred at room temperature for 2 h then TFA (3 mL) was added. After stirring for 2 h, the solvent was concentrated and the product was purified by preparative HPLC to provide to afford 23.1 mg (17%) of 2-(2-methoxy-4-(2-(4-methoxy-2-(trifluoromethyl)phenyl)acetamido)-N-(4-((4'-methyl-[1,1'-biphenyl]-4-carbonyl)oxy)benzyl) benzamido)acetic acid 314 as a white powder. LCMS-ESI (m/z) calculated for $C_{41}H_{35}F_3N_2O_8$: 740. found 741 [M+H]$^+$, $t_R$=10.33 min (Method 9). $^1$H NMR (400 MHz, DMSO) δ 12.77 (s, 1H), 10.34 (s, 0.5H), 10.32 (s, 0.5H), 8.25-8.15 (m, 2H), 7.93-7.85 (m, 2H), 7.74-7.64 (dt, J=6.3, 2.3 Hz, 2H), 7.53-7.39 (m, 3H), 7.39-7.07 (m, 9H), 5.01 (br s, 1H), 4.42 (s, 1H), 3.90-3.65 (m, 10H), 2.38 (s, 3H).

Compound 315 was prepared analogously to compound 314 by employing INT-22 and 3-methoxy-4-(2-(4-methoxy-2-(trifluoromethyl)phenyl)acetamido)benzoic acid using General Procedures 6, 2 then 8.

4-formyl-3-methoxyphenyl 4-(heptyloxy)benzoate (INT-25)

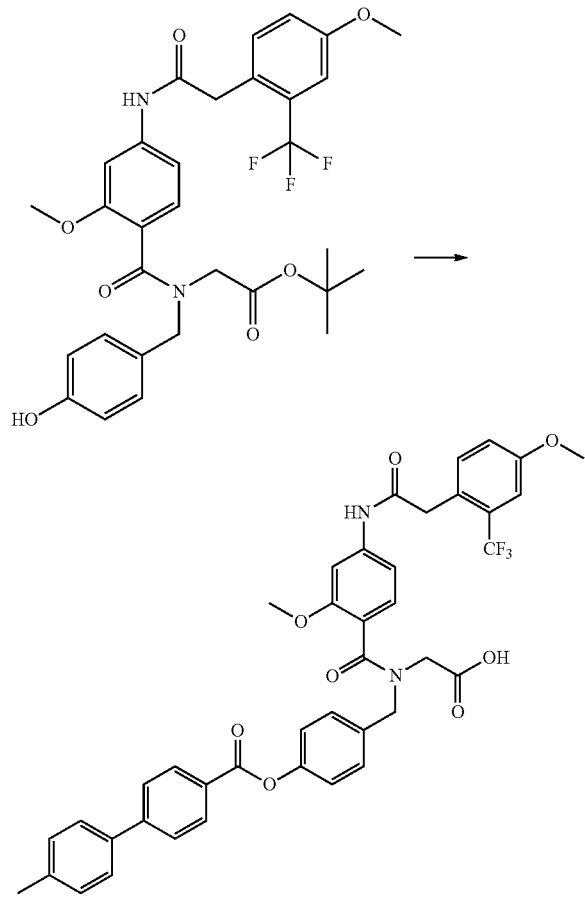
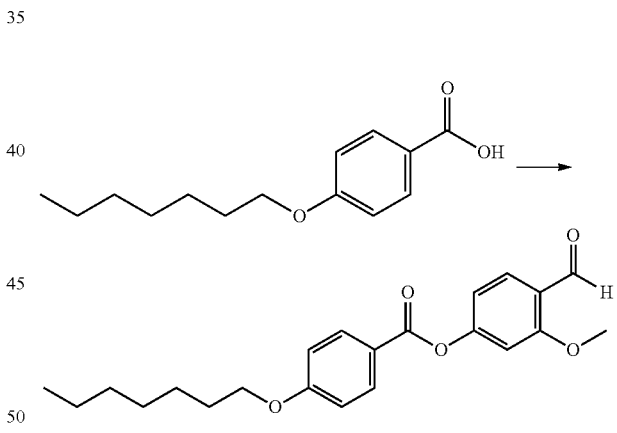

Prepared using General Procedure 2: To a stirred solution of 4-(heptyloxy)benzoic acid (1.41 g, 5.98 mmol) in DCM (10 mL) was added DMF (3 drops) and oxalyl chloride (0.589 mL, 6.87 mmol). After stirring for 2 h, the reaction mixture was added to a solution of 4-hydroxy-2-methoxybenzaldehyde (1 g, 6.57 mmol) and TEA (1.25 mL, 8.96 mmol) in DCM (10 mL) and stirred for 18 h. The reaction mixture was diluted with DCM (100 mL) and was washed with NaHCO$_3$ (100 mL). The organic layer was pre-absorbed onto silica gel and purified by chromatography (EA/isohexanes) to afford 340 mg (15%) 4-formyl-3-methoxyphenyl 4-(heptyloxy)benzoate INT-25 as a white solid. LCMS-ESI (m/z) calculated for $C_{22}H_{26}O_5$: 370. found 371 [M+H]$^+$, $t_R$=3.17 min (Method 10).

4-(((2-(tert-butoxy)-2-oxoethyl)amino)methyl)-3-methoxyphenyl 4-(heptyloxy)benzoate (INT-26)

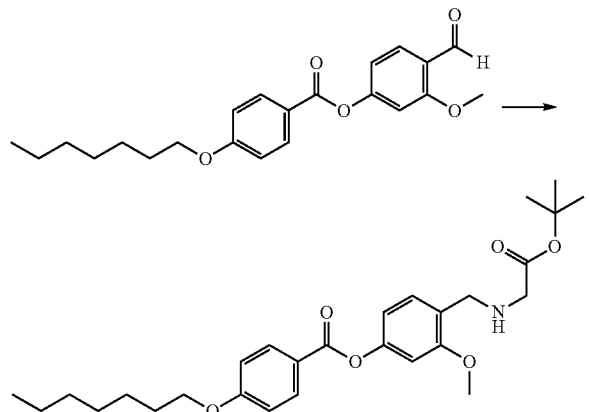

solvent removed under vacuum. Crude material was taken up into THF/MeOH (10 mL, 10 mL) and sodium borohydride (34.7 mg, 0.918 mmol) added with cooling to 0° C. After stirring for 1 h at room temperature the reaction was quenched with NaHCO$_3$ (10 mL) and the solvent removed under vacuum. The residue was diluted with NaHCO$_3$ (50 mL) and the product extracted with EA (100 mL). The organic extracts were combined and washed with brine (100 mL) and pre-absorbed onto silica gel then purified by chromatography (EA/isohexanes) to afford 270 mg (58%) of 4-(((2-(tert-butoxy)-2-oxoethyl)amino)methyl)-3-methoxyphenyl 4-(heptyloxy)benzoate INT-26 as a white solid. LCMS-ESI (m/z) calculated for C$_{28}$H$_{39}$NO$_6$: 485. found 486 [M+H]$^+$, t$_R$=2.23 min (Method 10).

2-(N-(4-((4-(heptyloxy)benzoyl)oxy)-2-methoxybenzyl)-2-methoxy-4-(2-(4-methoxy-2-(trifluoromethyl)phenyl)acetamido)benzamido)acetic acid (Compound 316)

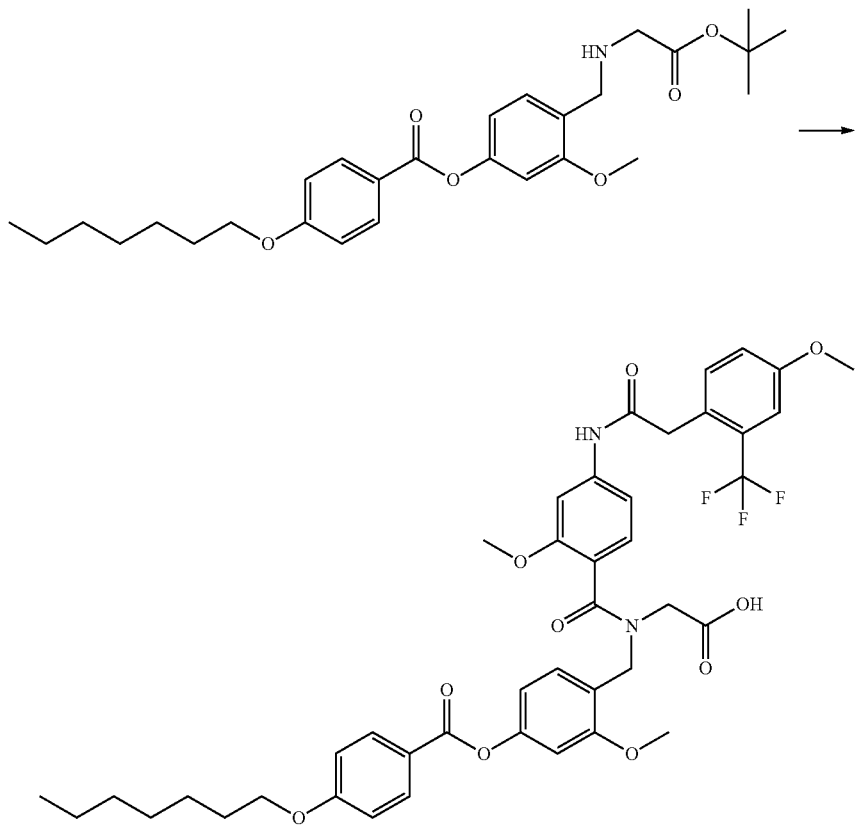

Prepared using General Procedure 12: A suspension of 4-formyl-3-methoxyphenyl 4-(heptyloxy)benzoate (340 mg, 0.918 mmol) INT-25, tert-butyl 2-aminoacetate HCl (154 mg, 0.918 mmol), TEA (128 μL, 0.918 mmol) and magnesium sulfate (500 mg) in diethyl ether (20 mL) was stirred vigorously for 18 h. The reaction mixture was filtered and Prepared using General Procedures 6 then 8: To a stirred solution of 2-methoxy-4-(2-(4-methoxy-2-(trifluoromethyl)phenyl)acetamido)benzoic acid INT-23 (107 mg, 0.278 mmol), TEA (77 μl, 0.556 mmol) and 4-(((2-(tert-butoxy)-2-oxoethyl)amino)methyl)-3-methoxyphenyl 4-(heptyloxy)benzoate INT-26 (135 mg, 0.278 mmol) in DMF (3 mL) was added HATU (111 mg, 0.292 mmol) and left at room temperature for 2 h. The reaction mixture was diluted with EA (50 mL). The organic phase was washed with brine (2×100 mL) then pre-absorbed onto silica gel and purified by chromatography (EA/isohexanes. The isolated material was taken up into DCM (3 mL) and TFA (2 mL) and stirred at room temperature for 2 h. After stirring for 2 h, the solvent was concentrated and the product was purified by preparative HPLC to afford 21 mg (9.4%) of 2-(N-(4-((4-(heptyloxy)benzoyl)oxy)-2-methoxybenzyl)-2-methoxy-4-(2-(4-methoxy-2-(trifluoromethyl) phenyl)acetamido)benzamido) acetic acid 316 as a white powder. LCMS-ESI (m/z) calculated for $C_{42}H_{45}F_3N_2O_{10}$: 794. found 795 $[M+H]^+$, $t_R$=10.02 min (Method 9). $^1$H NMR (400 MHz, DMSO) δ 12.75-12.57 (br s, 1H), 10.33 (s, 0.5H), 10.30 (s, 0.5H), 8.12-8.00 (m, 2H), 7.52-7.41 (m, 2H), 7.32 (d, J=8.3 Hz, 0.5H), 7.26-7.03 (m, 6.5H), 6.97 (d, J=2.2 Hz, 0.5H), 6.92-6.85 (m, 1H), 6.81 (dd, J=8.2, 2.1 Hz, 0.5H), 5.00-4.70 (br s, 1H), 4.35 (s, 1H), 4.09 (td, J=6.6, 2.5 Hz, 2H), 3.88-3.83 (m, 5H), 3.82 (s, 2H), 3.77 (s, 3H), 3.70 (s, 1.5H), 3.64 (s, 1.5H), 1.80-1.70 (m, 2H), 1.48-1.24 (m, 8H), 0.93-0.84 (m, 3H).

Compound 272 was prepared analogous to compound 316 by employing INT-18 and INT-26 using General Procedures 6 then 8.

Compounds 317-319 were prepared from INT-12 using General Procedures 12, 7 then 8.

Compound 320 was prepared from INT-12 and INT-18 using General Procedures 12, 7 then 8. Compound 321 was prepared from INT-12 using General Procedures 12, 7, 8, 6 then 8. Compounds 322 and 323 were prepared using General Procedures 13, 6, 2 then 8.

4-formylphenyl 4'-methyl-[1,1'-biphenyl]-4-carboxylate (INT-27)

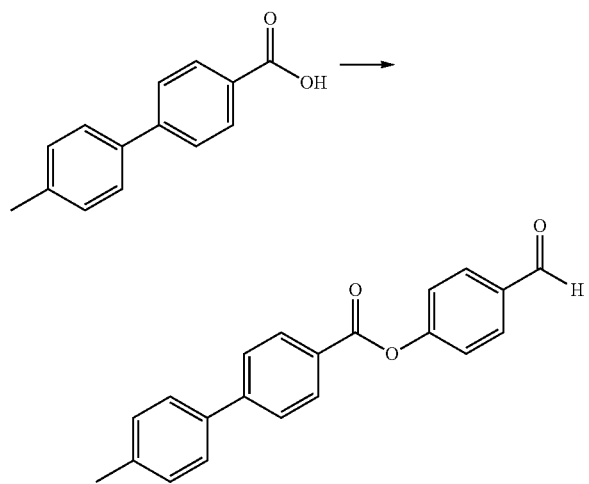

Prepared using General Procedure 2: To a stirred solution of 4'-methyl-[1,1'-biphenyl]-4-carboxylic acid (0.5 g, 2.35 mmol) in DCM (10 mL) was added DMF (3 drops) then oxalyl chloride (0.262 mL, 3.1 mmol) and left for 2 h. The reaction mixture was added to a solution of 4-hydroxybenzaldehyde (0.31 g, 2.6 mmol) and TEA (0.4 mL, 2.82 mmol) in DCM (10 mL) and stirred for 18 h. The reaction mixture was diluted with DCM (100 mL) and washed with NaHCO$_3$ (100 mL). The organic layer was pre-absorbed onto silica gel and then purified by chromatography (EA/isohexanes) to afford 300 mg (40%) 4-formylphenyl 4'-methyl-[1,1'-biphenyl]-4-carboxylate INT-27 as a white solid. LCMS-ESI (m/z) calculated for $C_{21}H_{16}O_3$: 316; no m/z observed, $t_R$=4.25 min (Method 1).

4-(((2-(tert-butoxy)-2-oxoethyl)amino)methyl)phenyl 4'-methyl-[1,1'-biphenyl]-4-carboxylate (INT-28)

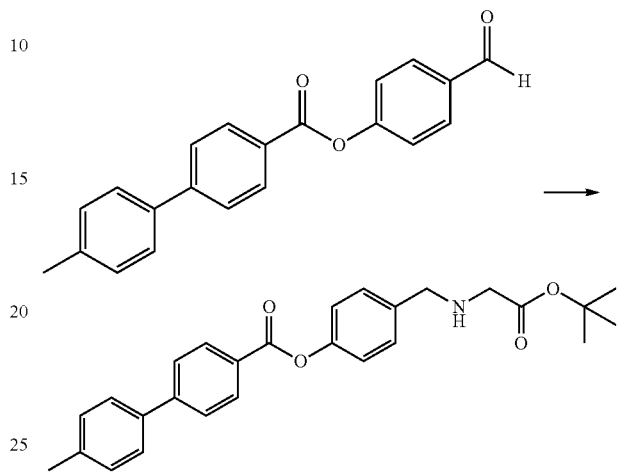

Prepared using General Procedure 12: INT-28 was prepared from INT-27 in a similar fashion as INT-13 to give 50% yield. LCMS-ESI (m/z) calculated for $C_{27}H_{29}NO_4$: 431. found 432 $[M+H]^+$, $t_R$=2.99 min (Method 1).

Isopropyl 2-isopropoxy-4-(2-(4-methoxy-2-(trifluoromethyl)phenyl)acetamido)benzoate (INT-29)

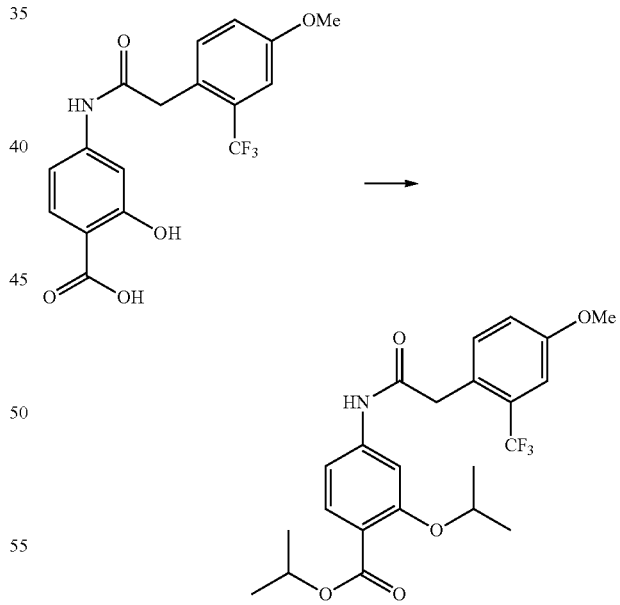

To a stirred solution of 2-hydroxy-4-(2-(4-methoxy-2-(trifluoromethyl) phenyl)acetamido)benzoic acid (40 mg, 0.1 mmol), K$_2$CO$_3$ (23.6 mg, 0.17 mmol) in DMF (1 mL) was added 2-bromopropane (56 mg, 0.4 mmol). The reaction mixture was heated at 80° C. for 24 h. The reaction mixture was cooled to room temperature, diluted with water (10 mL) and extracted with EA (3×10 mL). The combined organic extract was washed with water (30 mL), brine and dried over MgSO$_4$. Purification of the crude product by a silica gel column (EA/hexanes) gave 35 mg (73%) of isopropyl 2-isopropoxy-4-(2-(4-methoxy-2-(trifluoromethyl)phenyl)acetamido)benzoate INT-29 as white solid. LCMS-ESI (m/z) calculated for $C_{23}H_{26}F_3NO_5$: 453. found 454 [M+H]+, $t_R$=3.83 min (Method 1).

2-isopropoxy-4-(2-(4-methoxy-2-(trifluoromethyl)phenyl)acetamido)benzoic acid (INT-30)

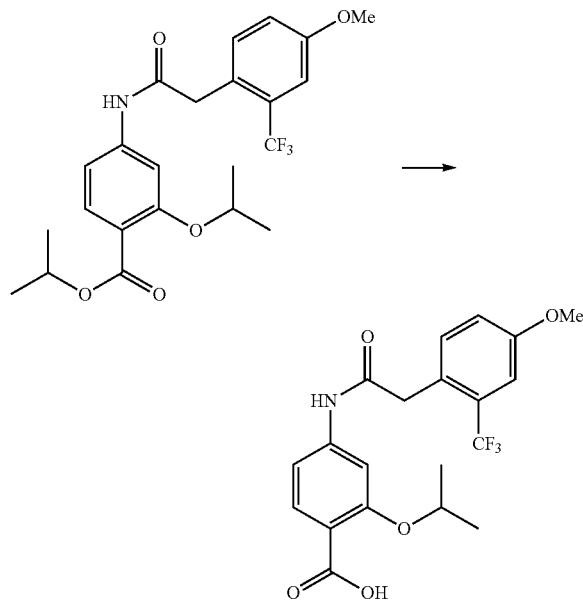

Prepared using General Procedure 9: INT-30 was prepared analogous to INT-18 from INT-29 to give 65% yield. LCMS-ESI (m/z) calculated for $C_{20}H_{20}F_3NO_5$: 411. found 412 [M+H]+, $t_R$=3.17 min (Method 1). $^1$H NMR (400 MHz, DMSO) δ 12.16 (s, 1H), 10.38 (s, 1H), 7.63 (d, J=8.5 Hz, 1H), 7.53 (d, J=1.8 Hz, 1H), 7.44 (d, J=8.5 Hz, 1H), 7.27-7.15 (m, 2H), 7.10 (dd, J=8.5, 1.9 Hz, 1H), 4.49 (dt, J=12.1, 6.0 Hz, 1H), 3.84 (d, J=11.8 Hz, 5H), 1.28 (d, J=6.0 Hz, 6H).

Compound 324 was prepared analogous to compound 298 by employing INT-28 and INT-30 using General Procedures 6 then 8. Compound 325 was prepared analogous to compound 298 by employing INT-28 and methyl 4-amino-2-chlorobenzoate using General Procedures 6, 10, 6 then 8. Compound 326 was prepared analogous to compound 298 by employing INT-28 and methyl 4-amino-2-methylbenzoate using General Procedures 6, 10, 6 then 8.

Compound 327 was prepared using INT-18 and 4-nitrobenzaldehyde employing General Procedures 12, 6, 5, 10 then 8. Compound 328 was prepared using INT-18 and 4-nitrobenzaldehyde employing General Procedures 12, 6, 5, 7 then 8. Compound 329 was prepared using INT-18 and 4-nitrobenzaldehyde employing General Procedures 12, 6, 5, 12 then 8. Compound 330 was prepared using INT-18 and 4-nitrobenzaldehyde employing General Procedures 12, 6, 5, 6 then 8. Compound 331 was prepared using INT-18 and 4-nitrobenzaldehyde employing General Procedures 12, 6, 5, 13, 10 then 8. Compound 332 was prepared using INT-18 and 4-nitrobenzaldehyde employing General Procedures 12, 6, 5, 13, 7 then 8. Compound 333 was prepared using INT-18 and methyl 4-formylbenzoate employing General Procedures 12, 6, 9, 6 then 8. Compound 334 was prepared using INT-18 and 4-(((4'-methyl-[1,1'-biphenyl]-4-yl)sulfonyl)methyl)benzaldehyde using General Procedures 12, 6 then 8. Compound 335 was prepared using INT-18 and 4-(((4'-methyl-[1,1'-biphenyl]-4-yl)oxy)methyl)benzaldehyde using General Procedures 12, 6 then 9. Compound 336 was prepared using INT-18 and 4-(((4'-methyl-[1,1'-biphenyl]-4-yl)amino)methyl)benzaldehyde using General Procedures 12, 6 then 9.

General Procedure 17: Preparation of Aryl Amines or Ethers Via Chan-Lam Coupling To a stirring solution of aniline or phenol (1 eq) and copper acetate (1 eq) in DCM was added an appropriate boronic acid (1.3-2 eq) followed by pyridine (3-5 eq) and molecular sieves. The reaction vial was sealed under dry air and stirred at room temperature for up to 16 h. The crude reaction mixture was diluted with DCM then filtered through a pad a celite. The filtrate was washed with NaHCO$_3$. The organic layer was dried over MgSO$_4$ then concentrated to yield crude product which was used in the next step without further purification.

Compound 337 was prepared using INT-18 and tert-butyl 2-((4-nitrobenzyl)amino)acetate using General Procedures 5, 17 then 9.

Compound 338 was prepared using INT-18 and General Procedures 12, 6, 16 then 8. Compound 339 was prepared using INT-18 and General Procedures 12, 6 then 8.

Compound 340 was prepared using INT-9 and (4'-methyl-[1,1'-biphenyl]-4-yl)methyl methanesulfonate using General Procedures 13 then 9. Compounds 341-348 were prepared using INT-9 and General Procedures 17 then 8. Compound 349 was prepared using INT-9 and General Procedures 1 then 8. Compound 350 was prepared using INT-9 and 2-bromo-1-(4'-methyl-[1,1'-biphenyl]-4-yl)ethanone employing General Procedures 13 then 8. Compound 351 was prepared using INT-18 and 4-(2-(4-bromophenoxy)-1-hydroxyethyl)benzaldehyde using General Procedures 12, 6, 16 then 8.

General Procedure 18: Oxidation of an Alcohol to a Ketone

To an alcohol (1 eq) in DCM and optionally water was added Dess-Martin periodinane (1 eq). The reaction mixture was stirred at room temperature for up to 18 h. The crude reaction mixture was quenched with NaHCO$_3$. The aqueous layer was extracted with DCM and the combined organic layers were dried over MgSO$_4$. The solvent was concentrated and the final product was used in the next step without further purification. Alternatively, to alcohol (1 eq) in chloroform or DCM was added manganese (IV) oxide (10 eq). The reaction mixture was allowed to stir at room temperature for up to 5 h then filtered through celite, concentrated and purified by chromatography.

Compound 352 was prepared using INT-18 and 4-(2-(4-bromophenoxy)-1-hydroxyethyl)benzaldehyde using General Procedures 12, 6, 16, 18 then 8. Compound 353 was prepared using tert-butyl 2-(N-(4-(hydroxy(4'-methyl-[1,1'-biphenyl]-4-yl)methyl)benzyl)-4-(2-(4-methoxy-2-(trifluoromethyl)phenyl)acetamido)benzamido)acetate and General Procedures 18 then 8.

tert-butyl 2-((4-cyanobenzyl)amino)acetate (INT-31)

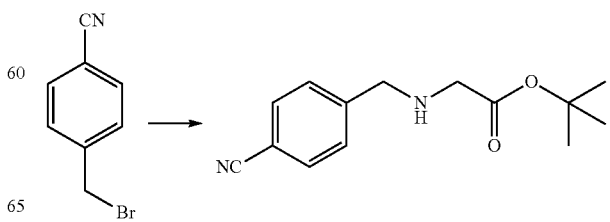

A solution of 2-(tert-butoxy)-2-oxoethanaminium chloride (3.00 g, 17.9 mmol) and potassium carbonate (4.95 g, 35.8 mmol) in DMF (20 mL) was stirred at room temperature for 2 min. To the reaction mixture was added 4-(bromomethyl)benzonitrile (3.19 g, 16.3 mmol) and stirring continued for 12 h. The reaction mixture was diluted with water (50 mL) and extracted with EA (3×20 mL). The combined organic extract was dried over MgSO$_4$ then concentrated. Purification of the crude product by a silica gel column (DCM/MeOH) gave 2.77 g (68%) of tert-butyl 2-((4-cyanobenzyl)amino)acetate INT-31 as a yellow oil. LCMS-ESI (m/z) calculated for $C_{14}H_{18}N_2O_2$: 246. found 247 [M+H]$^+$, $t_R$=0.92 min (Method 3).

tert-butyl 2-(N-(4-cyanobenzyl)-4-(2-(4-methoxy-2-(trifluoromethyl)phenyl)acetamido) benzamido)acetate (INT-32)

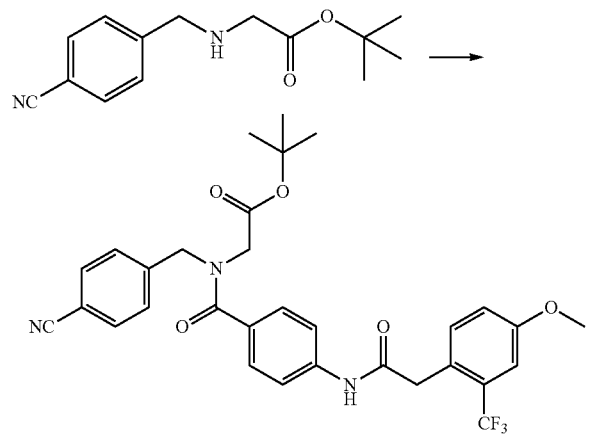

To a stirring solution of tert-butyl 2-((4-cyanobenzyl)amino)acetate INT-31 (0.97 g, 3.94 mmol) in DMF (3 mL) and DIEA (0.87 mL, 4.73 mmol) were added 4-(2-(4-methoxy-2-(trifluoromethyl)phenyl)acetamido)benzoic acid INT-18 (1.39 g, 3.94 mmol) and HATU (1.50 g, 3.94 mmol). After 2 h, the reaction mixture was poured onto HCl (50 mL of a 1 N aqueous solution) and extracted with EA (3×20 mL). The combined organic extracts were washed with NaHCO$_3$ (30 mL), dried over MgSO$_4$ and concentrated. The crude product was purified by column chromatography (EA/isohexanes) to yield 1.95 g (85%) of tert-butyl 2-(N-(4-cyanobenzyl)-4-(2-(4-methoxy-2-(trifluoromethyl)phenyl)acetamido)benzamido) acetate INT-32. LCMS-ESI (m/z) calculated for $C_{31}H_{30}F_3N_3O_5$: 581. found 604 [M+Na]$^+$, $t_R$=2.59 min (Method 10).

General Procedure 19: Preparation of Amidoximes

To a stirring solution of nitrile (1 eq) in EtOH was added hydroxylamine (50% solution in H$_2$O, 5 eq) and TEA (1.1 eq). The mixture was heated overnight at 80° C. then concentrated. The resulting solid was dissolved in EA, washed with water, then dried (Na$_2$SO$_4$), concentrated and used without further purification. Alternatively, to a stirring solution of nitrile (1 eq) and TEA (2-3 eq) in DMF or EtOH was added hydroxylamine hydrochloride (2-3 eq). The mixture was stirred at room temperature up to 80° C. for up to 24 h then concentrated. The resulting solid was dissolved in EA, washed with water or brine, then dried (Na$_2$SO$_4$), concentrated and used without further purification.

General Procedure 20: Preparation of Oxadiazoles Via Acids or Acid Chlorides

To a solution of acid (1 eq) in DMF was added HOBt (2 eq) and EDC (2 eq). After stirring for 2 h, amidoxime (2 eq) was added and the mixture was stirred at room temperature for up to 12 h. The reaction mixture was then heated to 100° C. for up to 12 h. Alternatively, after stirring at room temperature the reaction mixture was diluted with DCM, washed with NaHCO$_3$, then dried (Na$_2$SO$_4$) and concentrated. The resulting residue was dissolved in EtOH and heated in a microwave for 35 min at 110° C. The solvent was removed and the final product was purified by preparative HPLC. To synthesize oxadiazoles via acid chlorides, dioxanes and DIEA (1.5 eq) were added to a stirred solution of amidoxime (1 eq) followed by an acid chloride (1.1 eq). The reaction mixture was stirred at room temperature for 30 mins then at 120° C. for up to 6 h. The reaction mixture was allowed to cool to room temperature, diluted with EA and washed with brine. The organics were concentrated and the residue purified by chromatography.

tert-butyl 2-(N-(4-(N-hydroxycarbamimidoyl)benzyl)-4-(2-(4-methoxy-2-(trifluoromethyl)phenyl)acetamido)benzamido)acetate (INT-33)

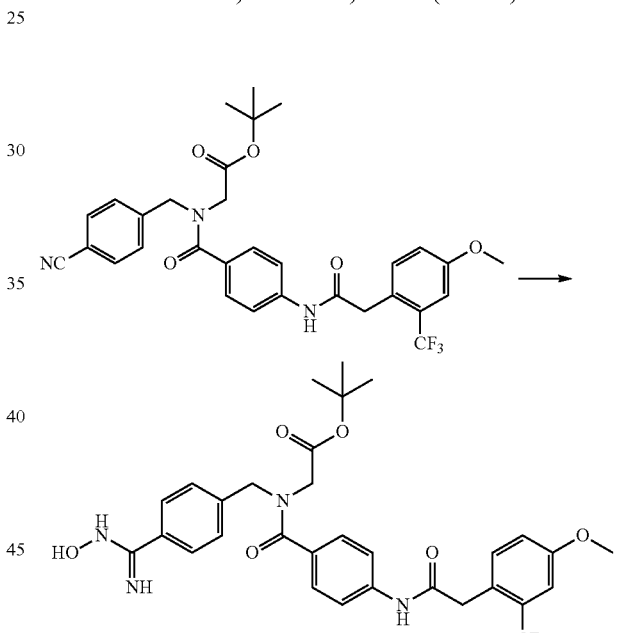

Prepared using General Procedure 19: To a stirring solution of tert-butyl 2-(N-(4-cyanobenzyl)-4-(2-(4-methoxy-2-(trifluoromethyl)phenyl)acetamido)benzamido)acetate INT-32 (229 mg, 0.394 mmol) in DMF (3 mL) were added triethylamine (142 µl, 0.984 mmol) and hydroxylamine hydrochloride (68.4 mg, 0.984 mmol). After stirring at room temperature for 72 h, the reaction mixture was diluted with water (50 mL) and extracted with DCM (3×20 mL). The organics were dried over MgSO$_4$ and evaporated. The crude product was purified by column chromatography (MeOH/DCM) to yield 107 mg (44%) of tert-butyl 2-(N-(4-(N-hydroxycarbamimidoyl)benzyl)-4-(2-(4-methoxy-2-(trifluoromethyl)phenyl)acetamido) benzamido)acetate INT-33. LCMS-ESI (m/z) calculated for $C_{31}H_{33}F_3N_4O_6$: 614. found 615 [M+H]$^+$, $t_R$=1.70 min (Method 10).

Compounds 354 and 355 are both derived from INT-33.

tert-butyl 2-(4-(2-(4-methoxy-2-(trifluoromethyl)phenyl)acetamido)-N-(4-(5-(4'-methyl-[1,1'-biphenyl]-4-yl)-1,2,4-oxadiazol-3-yl)benzyl)benzamido)acetate (INT-34)

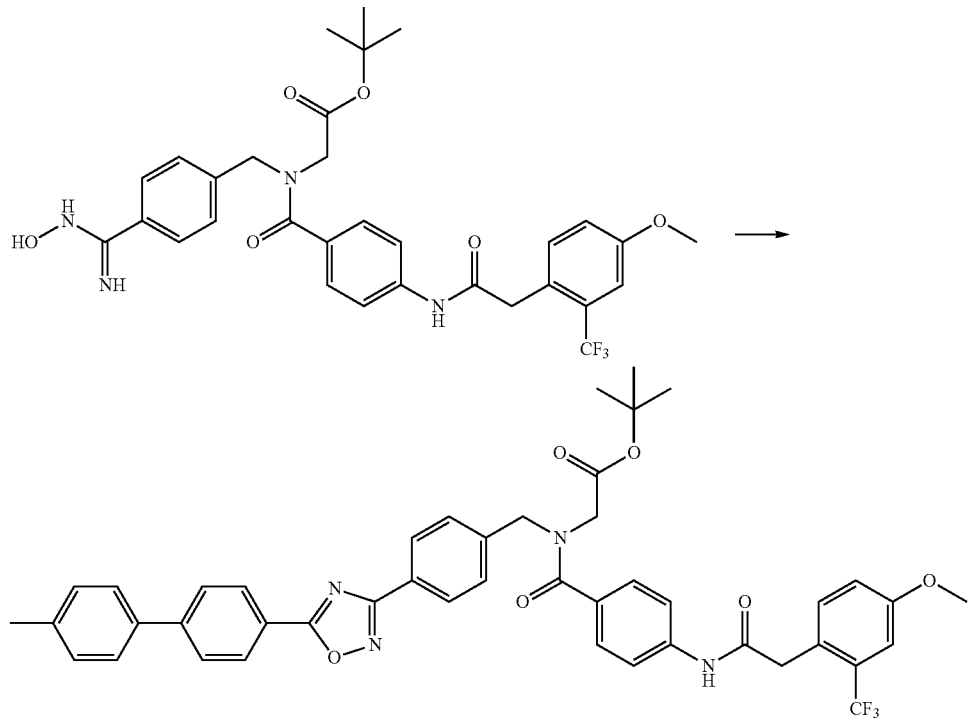

Prepared using General Procedure 20: To a stirring solution of tert-butyl 2-(N-(4-(N-hydroxycarbamimidoyl)benzyl)-4-(2-(4-methoxy-2-(trifluoromethyl)phenyl)acetamido)benzamido)acetate INT-33 (104 mg, 0.169 mmol) and DIEA (47.0 µL, 0.254 mmol) in dioxane (4 mL) was added 4'-methyl-[1,1'-biphenyl]-4-carbonyl chloride (39.0 mg, 0.169 mmol) in dioxane (1 mL). After stirring at room temperature for 30 min, the reaction mixture was heated to 120° C. for 2 h. The reaction mixture was allowed to cool to room temperature then diluted with NaHCO$_3$ (20 mL) and extracted with DCM (3×20 mL). The combined organic extracts were dried over MgSO$_4$ and concentrated. The crude product was purified by column chromatography (EA/isohexanes) to yield 54 mg (40%) of tert-butyl 2-(4-(2-(4-methoxy-2-(trifluoromethyl)phenyl)acetamido)-N-(4-(5-(4'-methyl-[1,1'-biphenyl]-4-yl)-1,2,4-oxadiazol-3-yl)benzyl)benzamido)acetate INT-34. LCMS-ESI (m/z) calculated for C$_{45}$H$_{41}$F$_3$N$_4$O$_6$: 791; no m/z observed, t$_R$=1.70 min (Method 10).

2-(4-(2-(4-methoxy-2-(trifluoromethyl)phenyl)acetamido)-N-(4-(5-(4'-methyl-[1,1'-biphenyl]-4-yl)-1,2,4-oxadiazol-3-yl)benzyl)benzamido)acetic acid (Compound 354)

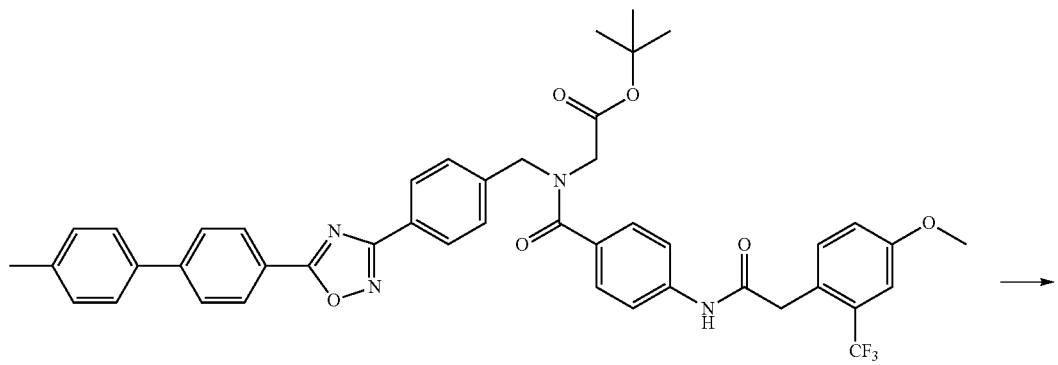

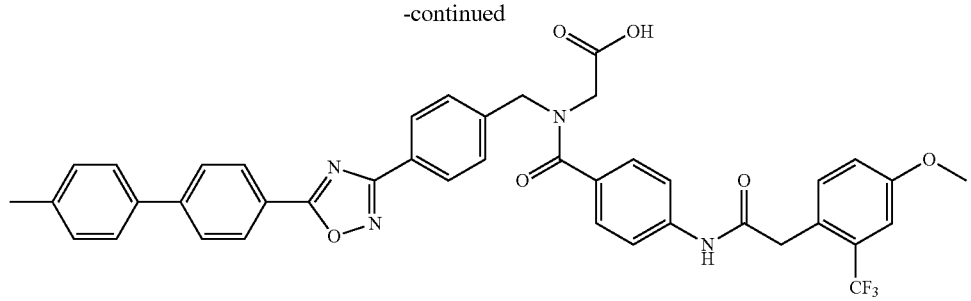

Prepared using General Procedure 8: To a stirring solution of tert-butyl 2-(4-(2-(4-methoxy-2-(trifluoromethyl)phenyl)acetamido)-N-(4-(5-(4'-methyl-[1,1'-biphenyl]-4-yl)-1,2,4-oxadiazol-3-yl)benzyl)benzamido)acetate INT-34 (54.0 mg, 0.068 mmol) in DCM (2 mL) was added TFA (2 mL). After stirring at room temperature for 2 h, the solvent was concentrated and the reaction mixture was further concentrated from acetonitrile (2×3 mL). The solid was re-slurried from DCM (4 mL), washed with DCM (2 mL) and acetonitrile (2 mL) to afford 44 mg (87%) of 2-(4-(2-(4-methoxy-2-(trifluoromethyl)phenyl)acetamido)-N-(4-(5-(4'-methyl-[1,1'-biphenyl]-4-yl)-1,2,4-oxadiazol-3-yl)benzyl)benzamido) acetic acid 354. LCMS-ESI (m/z) calculated for $C_{41}H_{33}F_3N_4O_6$: 734. found 735 $[M+H]^+$, $t_R$=9.40 min (Method 9). $^1$H NMR (400 MHz, DMSO) δ 12.80 (s, 1H), 10.34 (s, 1H), 8.33-8.22 (m, 2H), 8.15-8.06 (m, 2H), 8.02-7.91 (m, 2H), 7.76-7.69 (m, 2H), 7.69-7.56 (m, 3H), 7.53-7.33 (m, 6H), 7.26-7.14 (m, 2H), 4.77 (s, 1H), 4.69 (s, 1H), 4.04 (s, 1H), 3.98 (s, 1H), 3.90-3.77 (m, 5H), 2.39 (s, 3H).

2-(4-(2-(4-methoxy-2-(trifluoromethyl)phenyl)acetamido)-N-(4-(5-(p-tolyl)-1,2,4-oxadiazol-3-yl)benzyl)benzamido)acetic acid (Compound 355)

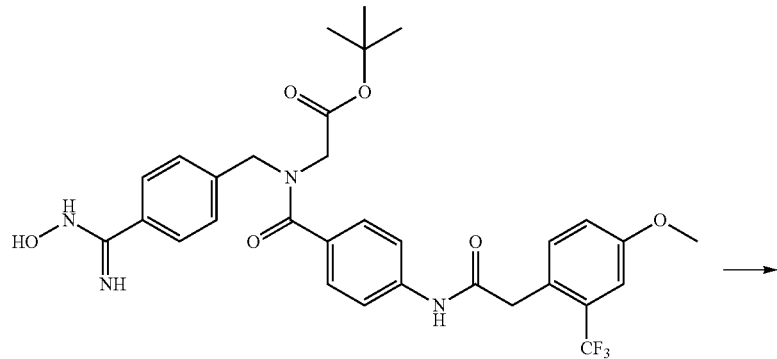

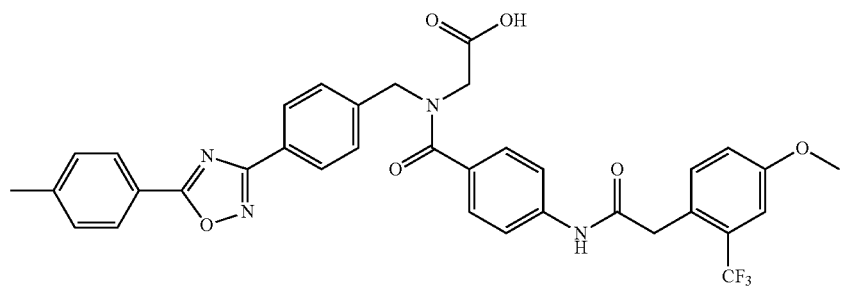

Prepared using General Procedures 20 and 8: To a stirring solution of tert-butyl 2-(N-(4-(N-hydroxycarbamimidoyl)benzyl)-4-(2-(4-methoxy-2-(trifluoromethyl)phenyl)acetamido)benzamido)acetate INT-33 (128 mg, 0.21 mmol) and DIEA (0.058 mL, 0.31 mmol) in dioxane (4 mL) was added a solution of 4-methylbenzoyl chloride (0.028 mL, 0.21 mmol) in dioxane (1 mL). After stirring at room temperature for 1 h, the reaction mixture was heated to 120° C. for 2 h. The reaction mixture was allowed to cool to room temperature, diluted with DCM (4 mL), shaken with NaHCO$_3$ (10 mL), split through a hydrophobic frit and evaporated. The crude material was purified by column chromatography (EA/isohexanes). The isolated material was dissolved in DCM (2 mL) and TFA (2 mL) was added. The reaction mixture was stirred at room temperature for 2 h then evaporated and re-slurried from acetonitrile (6 mL) to afford 77 mg (56%) of 2-(4-(2-(4-methoxy-2-(trifluoromethyl)phenyl)acetamido)-N-(4-(5-(p-tolyl)-1,2,4-oxadiazol-3-yl)benzyl)benzamido)acetic acid 355 as a white solid. LCMS-ESI (m/z) calculated for $C_{35}H_{29}F_3N_4O_6$: 658. found 659 [M+H]$^+$, $t_R$=7.97 min (Method 9). $^1$H NMR (400 MHz, DMSO) δ 12.81 (s, 1H), 10.34 (s, 1H), 8.10 (d, J=6.1 Hz, 2H), 8.09-8.05 (m, 2H), 7.70-7.56 (m, 3H), 7.53-7.41 (m, 4H), 7.38 (d, J=8.0 Hz, 2H), 7.26-7.14 (m, 2H), 4.76 (s, 1H), 4.68 (s, 1H), 4.04 (s, 1H), 3.97 (s, 1H), 3.91-3.79 (m, 5H), 2.45 (s, 3H).

tert-butyl 2-((4-iodobenzyl)amino)acetate (INT-35)

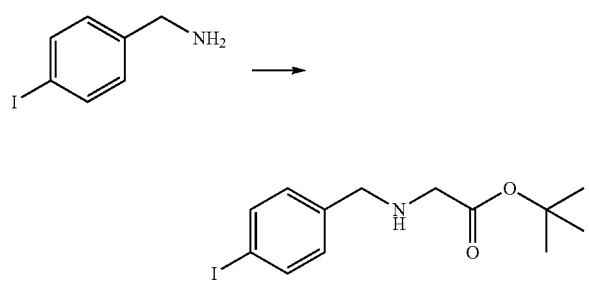

Prepared using General Procedure 13: To a stirring suspension of (4-iodophenyl)methanamine, HCl (2.27 g, 8.42 mmol) in DMF (15 mL) was added TEA (3.52 mL, 25.3 mmol) followed by tert-butyl 2-bromoacetate (1.24 ml, 8.42 mmol) drop wise, over 20 min. After stirring at room temperature for 1 h, the reaction mixture was diluted with EA (100 mL) and washed successively with NaHCO$_3$ (100 mL) and brine (2×100 mL). The organic layer was pre-absorbed onto silica gel and purified by chromatography (MeOH/DCM) to afford 2.00 g (68%) of tert-butyl 2-((4-iodobenzyl)amino)acetate INT-35 as a clear oil. LCMS-ESI (m/z) calculated for $C_{13}H_{18}INO_2$: 347. found 348 [M+H]$^+$, $t_R$=1.40 min (Method 10). $^1$H NMR (400 MHz, DMSO) δ 7.70-7.61 (m, 2H), 7.17-7.09 (m, 2H), 3.65 (m, 2H), 3.17 (s, 2H), 2.46 (s, 1H), 1.41 (s, 9H).

tert-butyl 2-(N-(4-iodobenzyl)-4-(2-(4-methoxy-2-(trifluoromethyl)phenyl)acetamido)benzamido)acetate (INT-36)

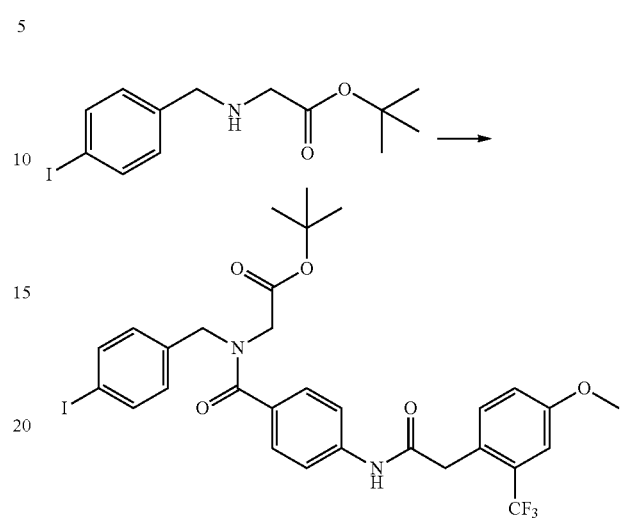

Prepared using General Procedure 8: To a stirring solution of 4-(2-(4-methoxy-2-(trifluoromethyl)phenyl)acetamido)benzoic acid INT-18 (1.38 g, 3.92 mmol), tert-butyl 2-((4-iodobenzyl)amino)acetate INT-35 (1.36 g, 3.92 mmol) and TEA (0.82 ml, 5.88 mmol) in DMF (8 mL) was added HATU (1.56 g, 4.11 mmol). After stirring at room temperature for 2 h, the reaction mixture was diluted with EA (150 mL) and washed successively with NaHCO$_3$ (100 mL) and brine (100 mL). The organics were pre-absorbed onto silica gel and then purified by chromatography (EA/isohexanes) to afford 2.05 g (75%) of tert-butyl 2-(N-(4-iodobenzyl)-4-(2-(4-methoxy-2-(trifluoromethyl)phenyl)acetamido)benzamido)acetate INT-36. LCMS-ESI (m/z) calculated for $C_{30}H_{30}F_3IN_2O_5$: 682. found 627 [M-$^t$Bu+H]$^+$, $t_R$=2.90 min (Method 10). $^1$H NMR (400 MHz, DMSO) δ 10.33 (s, 1H), 7.76-7.68 (m, 2H), 7.62 (dd, J=7.0, 1.8 Hz, 2H), 7.44 (d, J=8.3 Hz, 1H), 7.37-7.30 (m, 2H), 7.27-7.13 (m, 3H), 7.12-6.97 (s, 1H), 4.59 (s, 1H), 4.50 (s, 1H), 3.92 (m, 2H), 3.85 (s, 2H), 3.83 (s, 3H), 1.41 (s, 4.5H), 1.31 (s, 4.5H).

4-((N-(2-(tert-butoxy)-2-oxoethyl)-4-(2-(4-methoxy-2-(trifluoromethyl)phenyl)acetamido) benzamido)methyl)benzoic acid (INT-37)

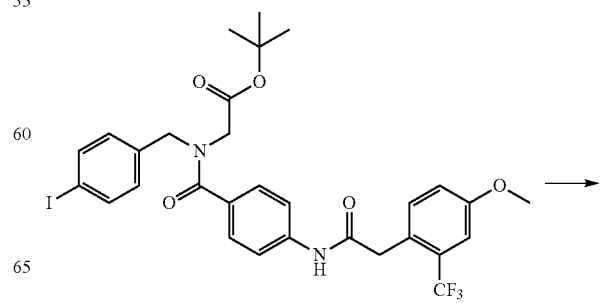

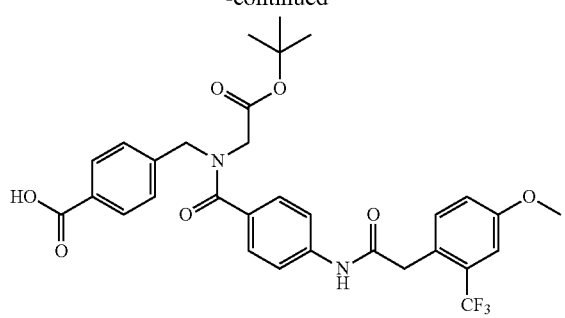

To a stirring mixture of lithium formate (0.30 g, 5.85 mmol) and DIPEA (0.68 mL, 3.90 mmol) in DMF (3 mL) was added acetic anhydride (0.37 mL, 3.90 mmol). After 30 min, a $N_2$ purged solution of tert-butyl 2-(N-(4-iodobenzyl)- 4-(2-(4-methoxy-2-(trifluoromethyl)phenyl)acetamido)benzamido)acetate INT-36 (1.33 g, 1.95 mmol) and $PdCl_2(dppf)$ (143 mg, 0.20 mmol) in DMF (2 mL) was added and the mixture heated to 110° C. for 1 h. The reaction mixture was allowed to cool to room temperature, diluted with EA (150 mL) and washed successively with 1N HCl (200 mL) and brine (200 mL). The organics were pre-absorbed onto silica gel then purified by chromatography (EA/isohexanes+1% AcOH) to afford a crude material that was further concentrated from toluene (20 mL). The crude solid was triturated from diethyl ether/isohexanes (10 mL:100 mL) and isolated by filtration to afford 721 mg (60%) of 4-((N-(2-(tert-butoxy)-2-oxoethyl)-4-(2-(4-methoxy-2-(trifluoromethyl) phenyl) acetamido)benzamido)methyl)benzoic acid INT-37. LCMS-ESI (m/z) calculated for $C_{31}H_{31}F_3N_2O_7$: 600. found 599 [M–H]$^-$, $t_R$=2.27 min (Method 10). $^1$H NMR (400 MHz, DMSO) δ 13.86 (s, 1H), 10.33 (s, 1H), 8.00-7.85 (m, 2H), 7.62 (t, J=8.5 Hz, 2H), 7.56-7.29 (m, 5H), 7.28-7.11 (m, 2H), 4.71 (s, 1H), 4.62 (s, 1H), 4.01-3.92 (m, 2H), 3.85 (s, 2H), 3.83 (s, 3H), 1.41 (s, 4.5H), 1.31 (s, 4.5H).

Compound 356 was prepared using INT-36 and General Procedures 16 then 8. Compound 357 was prepared using INT-37 and N,4'-dimethyl-[1,1'-biphenyl]-4-amine using General Procedures 6 then 8. Compound 358 was prepared using INT-37 and (4'-methyl-[1,1'-biphenyl]-4-yl)boronic acid using General Procedures 17 then 8. Compound 359 was prepared using INT-37 and General Procedures 13 then 8. Compounds 360-363 are derived from INT-37.

2-(4'-methyl-[1,1'-biphenyl]-4-yl)-2-oxoethyl 4-((N-(2-(tert-butoxy)-2-oxoethyl)-4-(2-(4-methoxy-2-(trifluoromethyl)phenyl)acetamido)benzamido)methyl)benzoate (INT-38)

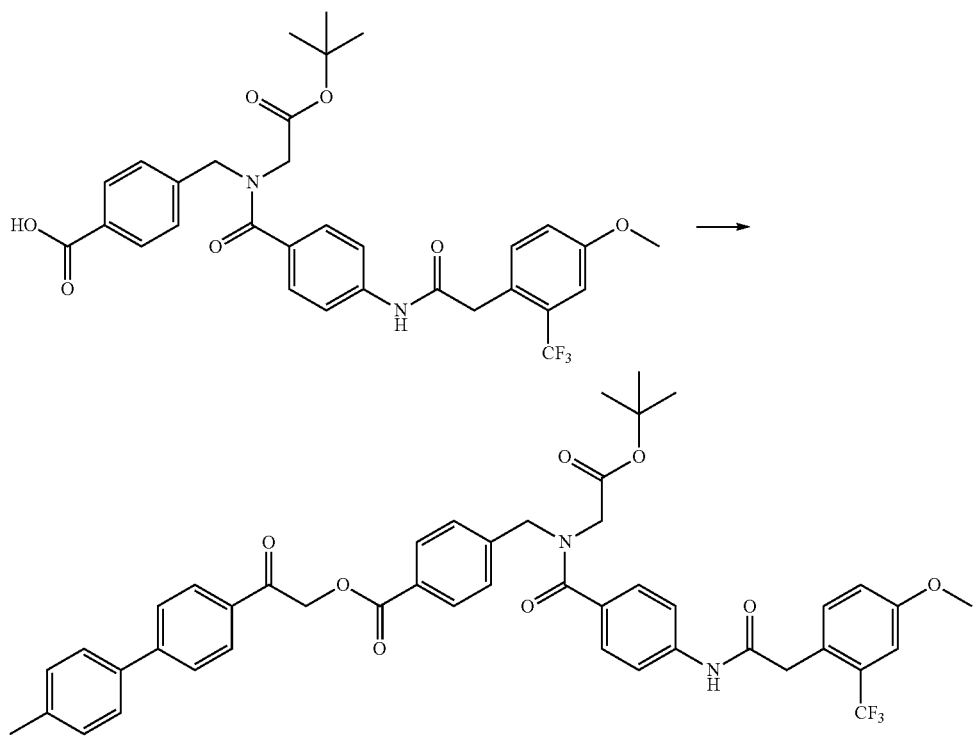

To a stirring suspension of 4-((N-(2-(tert-butoxy)-2-oxoethyl)-4-(2-(4-methoxy-2-(trifluoromethyl)phenyl)acetamido)benzamido)methyl)benzoic acid INT-37 (207 mg, 0.345 mmol) and 2-bromo-1-(4'-methyl-[1,1'-biphenyl]-4-yl)ethanone (100 mg, 0.345 mmol) in acetonitrile (4 mL) at 0° C. was added DIEA (70.0 µl, 0.379 mmol). The reaction mixture was allowed to slowly warm to room temperature and stirred for 16 h. The reaction mixture was poured onto citric acid (50 mL, 0.1 N aqueous solution) and extracted with EA (3×20 mL). The combined organic extracts were washed successively with $NaHCO_3$ (20 mL), brine (20 mL) then dried over $MgSO_4$ and concentrated. The crude product was purified by column chromatography (EA/isohexanes) to yield 254 mg (91%) of 2-(4'-methyl-[1,1'-biphenyl]-4-yl)-2-oxoethyl 4-((N-(2-(tert-butoxy)-2-oxoethyl)-4-(2-(4-methoxy-2-(trifluoromethyl)phenyl)acetamido)benzamido)methyl)benzoate INT-38 as a white foam. LCMS-ESI (m/z) calculated for $C_{46}H_{43}F_3N_2O_8$: 808. found 831 [M+Na]$^+$, $t_R$=3.10 min (Method 10).

2-(4-(2-(4-methoxy-2-(trifluoromethyl)phenyl)
acetamido)-N-(4-(4-(4'-methyl-[1,1'-biphenyl]-4-yl)
oxazol-2-yl)benzyl)benzamido)acetic acid
(Compound 360)

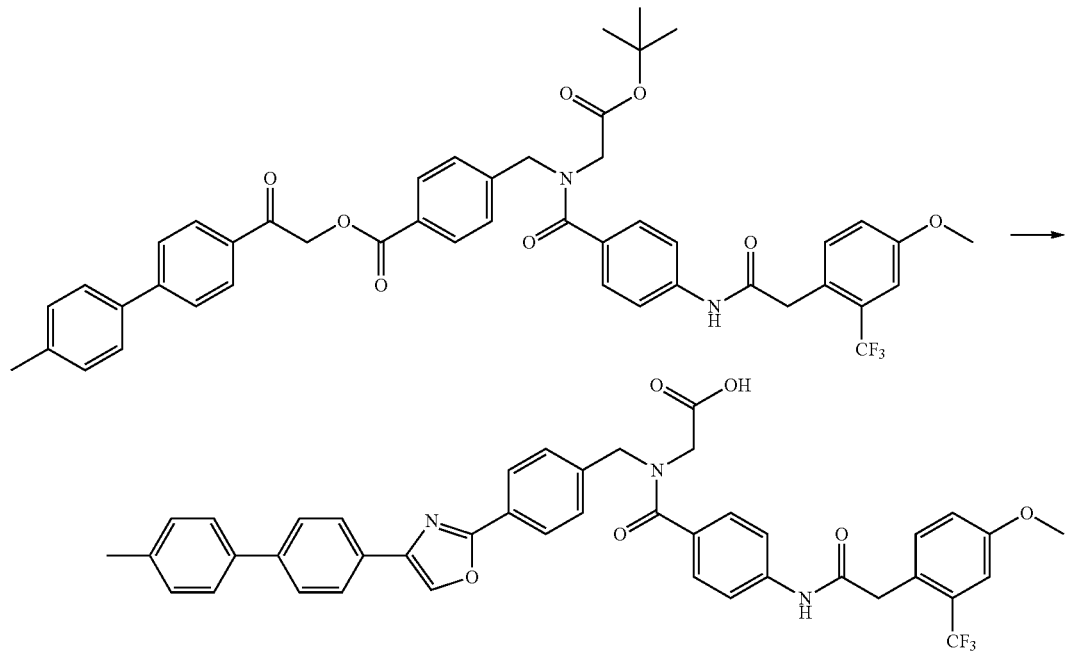

To stirring acetamide (292 mg, 4.95 mmol) at 100° C. was added boron trifluoride etherate (16.0 µl, 0.130 mmol). The temperature was raised to 140° C. and a solution of 2-(4'-methyl-[1,1'-biphenyl]-4-yl)-2-oxoethyl 4-((N-(2-(tert-butoxy)-2-oxoethyl)-4-(2-(4-methoxy-2-(trifluoromethyl)phenyl)acetamido)benzamido)methyl)benzoate INT-38 (100 mg, 0.124 mmol) in DCM (1 mL) was added drop wise under a stream of $N_2$. After 1 h, the reaction mixture was allowed to cool to room temperature and acetonitrile (2 mL) was added. The reaction mixture was stirred at room temperature for 2 h and the precipitate was collected by filtration and washed with acetonitrile (0.5 mL) and isohexanes (2 mL). The isolated precipitate was further re-slurried from DCM (2 mL) to afford 39 mg (43%) of 2-(4-(2-(4-methoxy-2-(trifluoromethyl)phenyl)acetamido)-N-(4-(4-(4'-methyl-[1,1'-biphenyl]-4-yl)oxazol-2-yl)benzyl)benzamido)acetic acid 360 as a white solid. LCMS-ESI (m/z) calculated for $C_{42}H_{34}F_3N_3O_6$: 733. found 734 [M+H]$^+$, $t_R$=9.18 min (Method 9). $^1$H NMR (400 MHz, DMSO) δ 12.84 (s, 1H), 10.34 (s, 1H), 8.78 (s, 1H), 8.10-8.03 (m, 2H), 7.98-7.92 (m, 2H), 7.80-7.73 (m, 2H), 7.68-7.53 (m, 5H), 7.50-7.35 (m, 4H), 7.33-7.27 (d, J=7.8 Hz, 2H), 7.26-7.16 (m, 2H), 4.75 (s, 1H), 4.67 (s, 1H), 4.03 (m, 1H), 3.95 (s, 1H), 3.89-3.79 (m, 5H), 2.37 (s, 3H).

4'-methyl-[1,1'-biphenyl]-4-carbohydrazonamide
(INT-39)

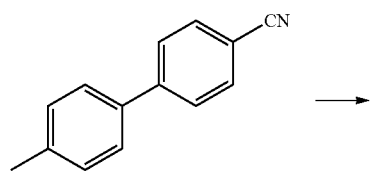

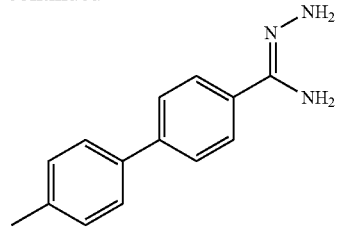

To a stirring solution of hydrazine (3.32 mL, 3.32 mmol, 1 M in THF) in THF (5 mL) at −78° C. was added butyllithium (1.28 mL, 3.05 mmol, 2.5 M in hexanes). After 30 min, a solution of 4'-methyl-[1,1'-biphenyl]-4-carbonitrile (535 mg, 2.77 mmol) in THF (5 mL) was added. The reaction mixture was allowed to warm to room temperature and stirred overnight. The reaction mixture was poured onto water (150 mL) and stirred vigorously for 1 h. The precipitate was isolated by filtration using water (2×20 mL) and isohexanes (3×20 mL) to wash the filter cake. The solid was dried under vacuum to yield 560 mg (90%) of 4'-methyl-[1,1'-biphenyl]-4-carbohydrazonamide INT-39 as a fine yellow solid. LCMS-ESI (m/z) calculated for $C_{14}H_{15}N_3$: 225. found 226 [M+H]$^+$, $t_R$=1.15 min (Method 10).

2-(4-(2-(4-methoxy-2-(trifluoromethyl)phenyl)acet-
amido)-N-(4-(5-(4'-methyl-[1,1'-biphenyl]-4-yl)-1H-
1,2,4-triazol-3-yl)benzyl)benzamido)acetic acid
(Compound 361)

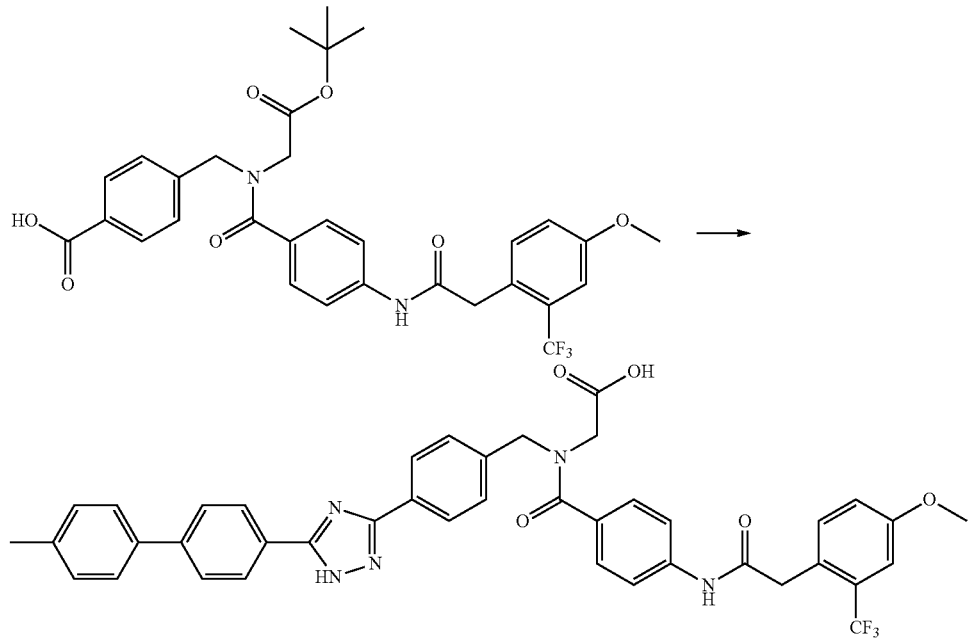

To a stirring solution of 4-((N-(2-(tert-butoxy)-2-oxo-ethyl)-4-(2-(4-methoxy-2-(trifluoromethyl)phenyl)acet-amido)benzamido)methyl)benzoic acid INT-37 (216 mg, 0.360 mmol) in dioxane (4 mL) were added N-methylmorpholine (79.0 µl, 0.719 mmol) and isobutyl chloroformate (49.0 µl, 0.378 mmol). After stirring at room temperature for 1 h, the reaction mixture was added drop wise through a frit to a stirred solution of 4'-methyl-[1,1'-biphenyl]-4-carbohydrazonamide INT-39 (89.0 mg, 0.396 mmol) in DMF (2 mL). After 30 min, the reaction mixture was heated to 120° C. for 1 h. The reaction mixture was allowed to cool to room temperature then poured onto water (50 mL) and extracted with DCM (3×20 mL). The combined organic extracts were washed successively with citric acid (10 mL, 0.1 M aqueous solution) and NaHCO$_3$ (10 mL) then dried over MgSO$_4$ and evaporated. The crude material was purified by column chromatography (EA/isohexanes). The isolated material was dissolved in DCM (2 mL) and treated with TFA (2 mL). The reaction mixture was allowed to stir at room temperature for 2 h then concentrated and purified by preparative HPLC to afford 24 mg (9%) of tert-butyl 2-(4-(2-(4-methoxy-2-(trifluoromethyl)phenyl)acetamido)-N-(4-(5-(4'-methyl-[1,1'-biphenyl]-4-yl)-1H-1,2,4-triazol-3-yl)benzyl)benzamido) acetic acid 361. LCMS-ESI (m/z) calculated for C$_{41}$H$_{34}$F$_3$N$_5$O$_5$: 733. found 734 [M+H]$^+$, t$_R$=7.72 min (Method 9). $^1$H NMR (400 MHz, DMSO) δ 14.54 (s, 1H), 12.84 (s, 1H), 10.34 (s, 1H), 8.25-8.13 (m, 2H), 8.08 (d, J=7.9 Hz, 2H), 7.94-7.73 (m, 2H), 7.70-7.59 (m, 4H), 7.57-7.35 (m, 5H), 7.32 (d, J=7.9 Hz, 2H), 7.25-7.14 (m, 2H), 4.73 (s, 1H), 4.65 (s, 1H), 4.03 (s, 1H), 3.93 (s, 1H), 3.90-3.76 (m, 5H), 2.37 (s, 3H).

N'-hydroxy-4'-methyl-[1,1'-biphenyl]-4-carboximid-
amide (INT-40)

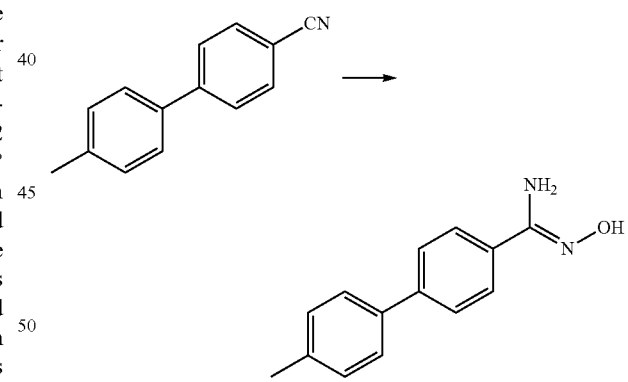

To a stirring solution of 4'-methyl-[1,1'-biphenyl]-4-carbonitrile (524 mg, 2.71 mmol) in DMF (10 mL) were added triethylamine (0.98 mL, 6.78 mmol) and hydroxylamine hydrochloride (471 mg, 6.78 mmol). After stirring at room temperature for 20 h, the reaction mixture was poured into NaHCO$_3$ (50 mL), water (20 mL) and DCM (20 mL) then stirred for 20 min. The precipitate was isolated by filtration using water (2×10 mL) to wash the filter cake. The filter cake was then evaporated with toluene (2×5 mL) and dried under vacuum to afford 435 mg (70%) of N-hydroxy-4'-methyl-[1,1'-biphenyl]-4-carboximidamide INT-40 as a white solid. LCMS-ESI (m/z) calculated for C$_{14}$H$_{14}$N$_2$O: 226. found 227 [M+H]$^+$, t$_R$=1.34 min (Method 10).

tert-butyl 2-(4-(2-(4-methoxy-2-(trifluoromethyl)phenyl)acetamido)-N-(4-(3-(4'-methyl-[1,1'-biphenyl]-4-yl)-1,2,4-oxadiazol-5-yl)benzyl)benzamido)acetate (INT-41)

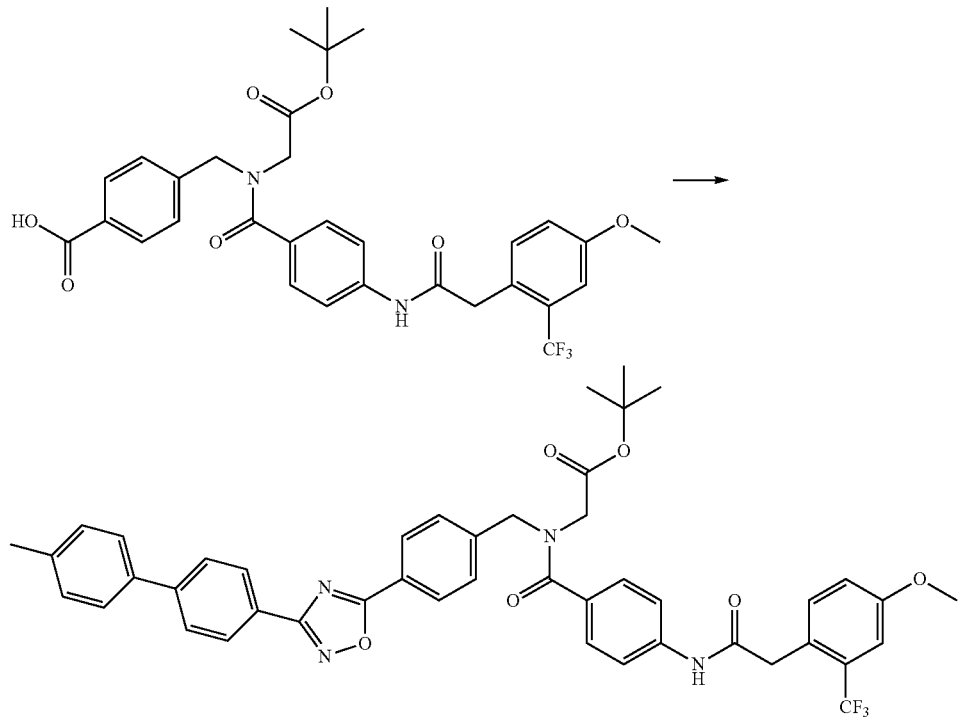

To a stirring solution of 4-((N-(2-(tert-butoxy)-2-oxoethyl)-4-(2-(4-methoxy-2-(trifluoromethyl)phenyl)acetamido)benzamido)methyl)benzoic acid INT-37 (150 mg, 0.25 mmol) in dioxane (4 mL) were added N-methylmorpholine (60.0 μl, 0.55 mmol) and isobutyl chloroformate (34.0 μl, 0.26 mmol). After stirring at room temperature for 1 h, the reaction mixture was added drop wise to a stirring solution of N-hydroxy-4'-methyl-[1,1'-biphenyl]-4-carboximidamide INT-40 (62.0 mg, 0.275 mmol) in dioxane (2 mL) and DMF (2 mL). The reaction mixture was allowed to stir at room temperature for 1 h, then heated to 90° C. for 2 h, and then heated to 120° C. for 16 h. The reaction mixture was allowed to cool to room temperature then poured into NaHCO$_3$ (20 mL) and extracted with DCM (3×20 mL). The combined organic extracts were dried over MgSO$_4$ and concentrated. The crude product was purified by column chromatography (EA/isohexanes) to yield 77 mg (35%) of tert-butyl 2-(4-(2-(4-methoxy-2-(trifluoromethyl)phenyl)acetamido)-N-(4-(3-(4'-methyl-[1,1'-biphenyl]-4-yl)-1,2,4-oxadiazol-5-yl)benzyl)benzamido)acetate INT-41. LCMS-ESI (m/z) calculated for $C_{45}H_{41}F_3N_4O_6$: 791; no m/z observed, $t_R$=3.26 min (Method 10). $^1$H NMR (400 MHz, DMSO) δ 10.34 (s, 1H), 8.35-8.04 (m, 4H), 8.04-7.80 (m, 2H), 7.80-7.28 (m, 11H), 7.28-7.08 (m, 2H), 4.80 (s, 1H), 4.70 (s, 1H), 4.00 (s, 2H), 3.92-3.79 (m, 5H), 2.40 (s, 3H), 1.47 (s, 4.5H), 1.33 (s, 4.5H).

2-(4-(2-(4-methoxy-2-(trifluoromethyl)phenyl)acetamido)-N-(4-(3-(4'-methyl-[1,1'-biphenyl]-4-yl)-1,2,4-oxadiazol-5-yl)benzyl)benzamido)acetic acid (Compound 362)

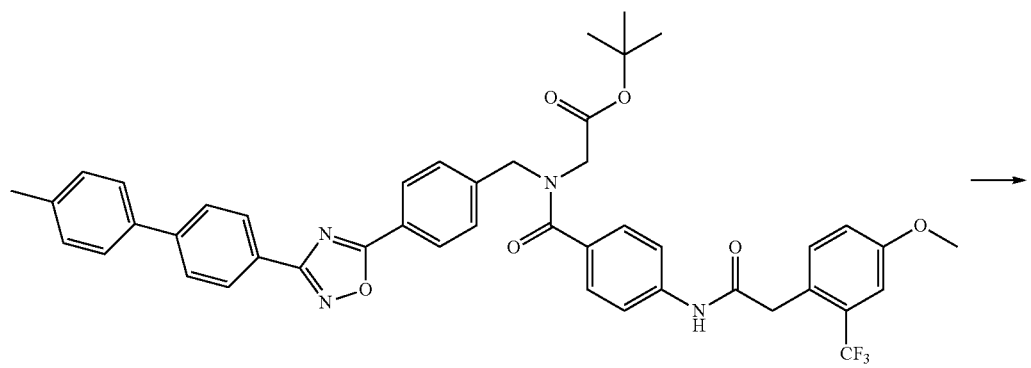

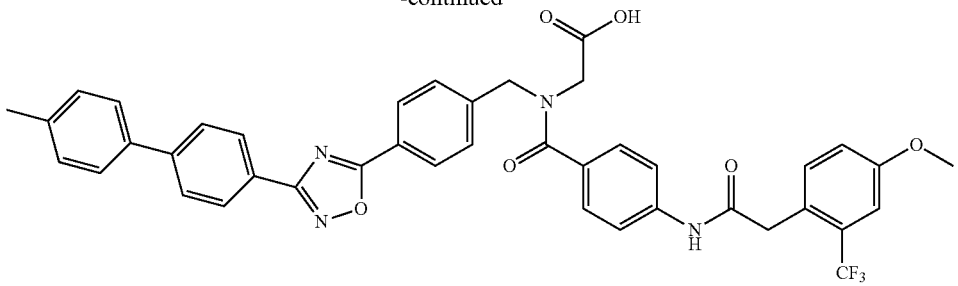

To a stirring solution of tert-butyl 2-(4-(2-(4-methoxy-2-(trifluoromethyl)phenyl)acetamido)-N-(4-(3-(4'-methyl-[1,1'-biphenyl]-4-yl)-1,2,4-oxadiazol-5-yl)benzyl)benzamido)acetate INT-41 (77.0 mg, 0.097 mmol) in DCM (2 mL) was added TFA (2 mL). The reaction mixture was stirred at room temperature for 1 h. The solvent was concentrated and the residue re-slurried from DCM (4 mL), then washed successively with DCM (2 mL) and isohexanes (2 mL) to afford 56 mg (78%) of 2-(4-(2-(4-methoxy-2-(trifluoromethyl)phenyl)acetamido)-N-(4-(3-(4'-methyl-[1,1'-biphenyl]-4-yl)-1,2,4-oxadiazol-5-yl)benzyl)benzamido)acetic acid 362. LCMS-ESI (m/z) calculated for $C_{41}H_{33}F_3N_4O_6$: 734; no ion observed, $t_R$=8.91 min (Method 9). $^1$H NMR (400 MHz, DMSO) δ 12.82 (s, 1H), 10.34 (s, 1H), 8.35-8.04 (m, 4H), 8.04-7.81 (m, 2H), 7.75-7.52 (m, 6H), 7.49-7.30 (m, 5H), 7.26-7.15 (m, 2H), 4.79 (s, 1H), 4.72 (s, 1H), 4.06 (s, 1H), 4.01 (s, 1H), 3.90-3.78 (m, 5H), 2.38 (s, 3H).

2-(4-(2-(4-methoxy-2-(trifluoromethyl)phenyl)acetamido)-N-(4-(3-(p-tolyl)-1,2,4-oxadiazol-5-yl)benzyl)benzamido)acetic acid (Compound 363)

To a stirring solution of 4-((N-(2-(tert-butoxy)-2-oxoethyl)-4-(2-(4-methoxy-2-(trifluoromethyl)phenyl)acetamido)benzamido)methyl)benzoic acid INT-37 (141 mg, 0.235 mmol) and 4-methylmorpholine (57.0 µl, 0.52 mmol) in dioxane (4 mL) was added isobutyl chloroformate (31.0 µl, 0.24 mmol). After 1 h, the reaction mixture was added through a frit to a stirred solution of N-hydroxy-4-methylbenzimidamide (38.8 mg, 0.258 mmol) in DMF (2 mL). After stirring at room temperature for 1 h, the reaction mixture was heated to 120° C. for 2 h. The reaction mixture was allowed to cool to room temperature, diluted with DCM (4 mL), washed with NaHCO₃ (10 mL), split through a hydrophobic frit and evaporated. The crude material was purified by column chromatography (EA/isohexanes). The isolated material was taken up in DCM (2 mL), treated with TFA (2 mL) and allowed to stir for 2 h. The solvents

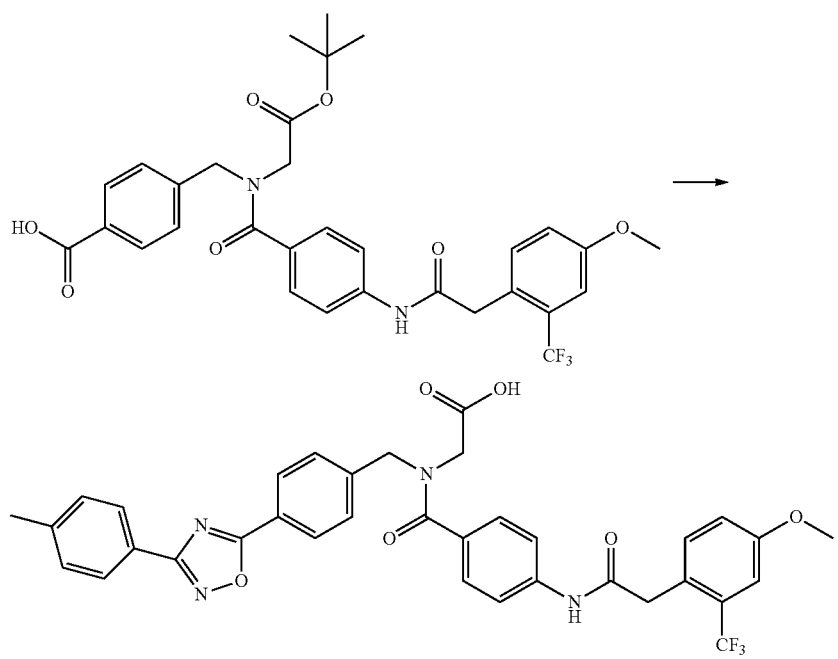

were evaporated and the residue purified by preparative HPLC to afford 22 mg (14%) of 2-(4-(2-(4-methoxy-2-(trifluoromethyl)phenyl)acetamido)-N-(4-(3-(p-tolyl-1,2,4-oxadiazol-5-yl)benzyl)benzamido)acetic acid 363 as a white solid. LCMS-ESI (m/z) calculated for $C_{35}H_{29}F_3N_4O_6$: 658. found 659 [M+H]$^+$, $t_R$=8.01 min (Method 9). $^1$H NMR (400 MHz, DMSO) δ 12.84 (s, 1H), 10.34 (s, 1H), 8.32-8.11 (m, 2H), 8.11-7.86 (m, 2H), 7.71-7.52 (m, 4H), 7.50-7.29 (m, 5H), 7.26-7.16 (m, 2H), 4.78 (s, 1H), 4.71 (s, 1H), 4.05 (s, 1H), 3.99 (s, 1H), 3.92-3.76 (m, 5H), 2.42 (s, 3H).

4-(2-(4-bromophenyl)oxazol-4-yl)benzonitrile (INT-42)

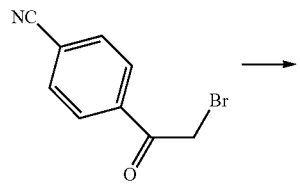

To a stirring solution of 4-(2-bromoacetyl)benzonitrile (7.13 g, 31.8 mmol) in NMP (15 mL) was added 4-bromobenzamide (5.31 g, 26.5 mmol) and the reaction mixture heated to 135° C. for 18 h. The reaction mixture was allowed to cool to room temperature then treated with acetonitrile (25 mL) and stirred for 3 h. The precipitate was collected by filtration and washed with acetonitrile (2×5 mL) to afford 1.51 g (17%) of 4-(2-(4-bromophenyl)oxazol-4-yl)benzonitrile INT-42 as a light brown powder. LCMS-ESI (m/z) calculated for $C_{16}H_9BrN_2O$: 324. found 325 [M+H]$^+$, $t_R$=2.86 min (Method 10). $^1$H NMR (400 MHz, DMSO) δ 8.94 (s, 1H), 8.03 (d, J=8.2 Hz, 2H), 7.98-7.91 (m, 4H), 7.76 (d, J=8.5 Hz, 2H).

4-(2-(4-bromophenyl)oxazol-4-yl)benzaldehyde (INT-43)

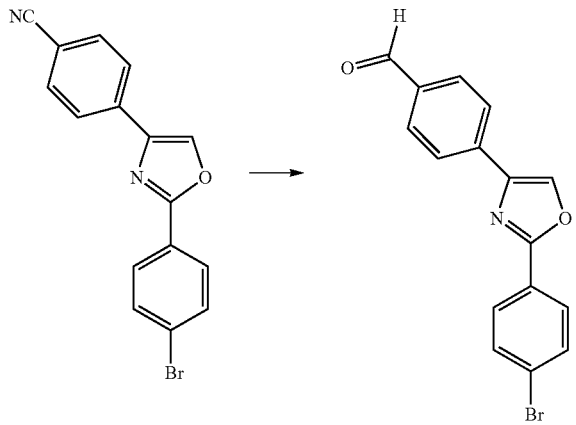 [SMILES: N#Cc1ccc(-c2coc(-c3ccc(Br)cc3)n2)cc1 ; O=Cc1ccc(-c2coc(-c3ccc(Br)cc3)n2)cc1]

To a stirring suspension of 4-(2-(4-bromophenyl)oxazol-4-yl)benzonitrile INT-42 (204 mg, 0.627 mmol) in DCM (30 mL) at −78° C. was added diisobutylaluminum hydride (1.26 mL, 1.26 mmol, 1 M solution in toluene). After 1 h the reaction mixture was poured onto citric acid (50 mL, 0.1 M aqueous solution) and extracted with DCM (2×30 mL). The combined organic extracts were washed successively with water (30 mL) and NaHCO$_3$ (30 mL), dried over MgSO$_4$ and solvents concentrated to afford 198 mg (96%) of 4-(2-(4-bromophenyl)oxazol-4-yl)benzaldehyde INT-43 as an off-white solid. LCMS-ESI (m/z) calculated for $C_{16}H_{10}BrNO_2$: 327. found 328 [M+H]$^+$, $t_R$=3.05 min (Method 5).

tert-butyl 2-((4-(2-(4-bromophenyl)oxazol-4-yl)benzyl)amino)acetate (INT-44)

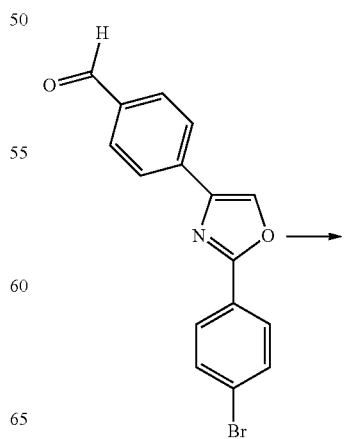

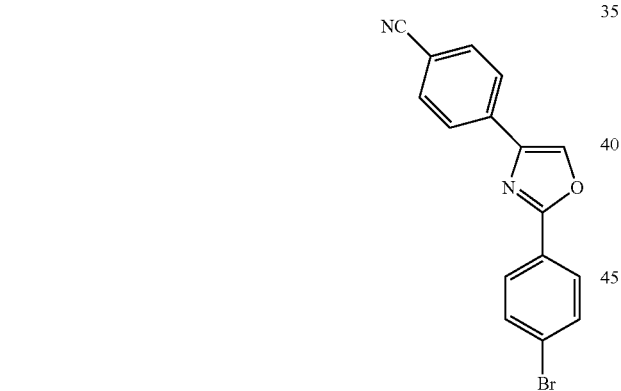

137
-continued

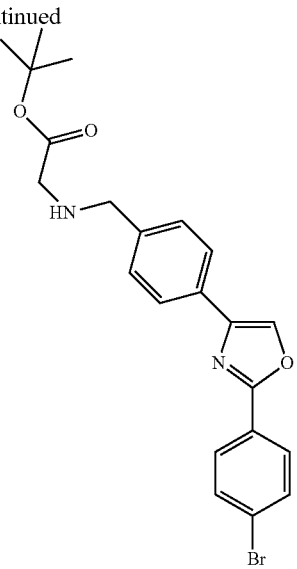

138
-continued

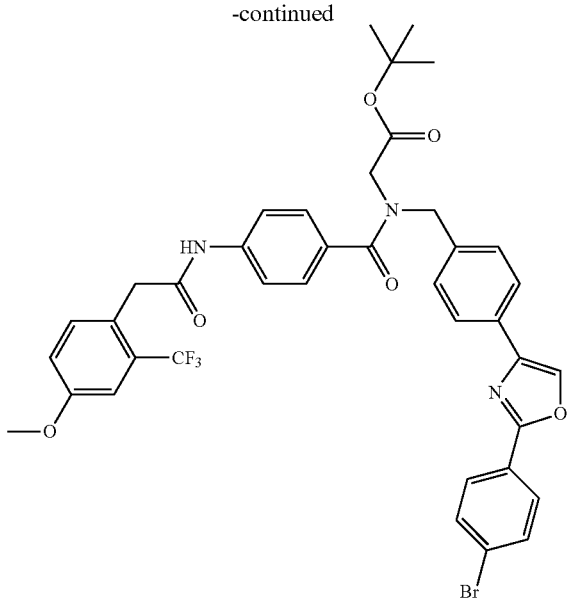

To a stirring suspension of 4-(2-(4-bromophenyl)oxazol-4-yl)benzaldehyde INT-43 (198 mg, 0.603 mmol) in DCM (10 mL) was added tert-butyl glycine hydrochloride (116 mg, 0.694 mmol). After stirring at room temperature for 1 h, tetramethylammonium triacetoxyhydroborate (317 mg, 1.21 mmol) was added and the reaction mixture was stirred for another 1 h. The reaction mixture was quenched with NaHCO$_3$ (10 mL) stirred for 1 h then split through a hydrophobic frit and the organics evaporated. The crude product was purified by column chromatography (NH$_3$/MeOH/DCM) to give 234 mg (88%) of tert-butyl 2-((4-(2-(4-bromophenyl)oxazol-4-yl)benzyl)amino)acetate INT-44 as a yellow solid. LCMS-ESI (m/z) calculated for C$_{22}$H$_{23}$BrN$_2$O$_3$: 442. found 443 [M+H]$^+$, t$_R$=1.85 min (Method 5).

tert-butyl 2-(N-(4-(2-(4-bromophenyl)oxazol-4-yl)benzyl)-4-(2-(4-methoxy-2-(trifluoromethyl)phenyl)acetamido)benzamido)acetate (INT-45)

To a stirring solution of tert-butyl 2-((4-(2-(4-bromophenyl)oxazol-4-yl)benzyl)amino)acetate INT-44 (220 mg, 0.496 mmol), 4-(2-(4-methoxy-2-(trifluoromethyl)phenyl)acetamido)benzoic acid (175 mg, 0.496 mmol) and DIEA (137 µL, 0.744 mmol) in DMF (4 mL) was added HATU (198 mg, 0.521 mmol). The reaction mixture was stirred at room temperature for 16 h then diluted with DCM (4 mL), stirred with NaHCO$_3$ (15 mL) for 15 min, split through a hydrophobic frit and evaporated. The crude product was purified by column chromatography (acetonitrile/DCM) to gave 262 mg (68%) of tert-butyl 2-(N-(4-(2-(4-bromophenyl)oxazol-4-yl)benzyl)-4-(2-(4-methoxy-2-(trifluoromethyl)phenyl)acetamido)benzamido)acetate INT-45 as an off-white solid. LCMS-ESI (m/z) calculated for C$_{39}$H$_{35}$BrF$_3$N$_3$O$_6$: 777. found 778 [M+H]$^+$, t$_R$=3.20 min (Method 5).

Compounds 364 and 365 were prepared using INT-45.

2-(4-(2-(4-methoxy-2-(trifluoromethyl)phenyl)acetamido)-N-(4-(2-(4'-methyl-[1,1'-biphenyl]-4-yl)oxazol-4-yl)benzyl)benzamido)acetic acid (Compound 364)

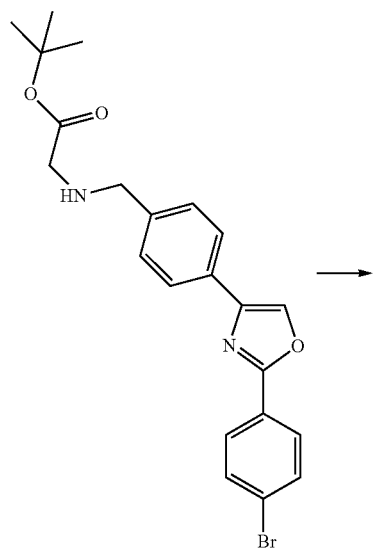

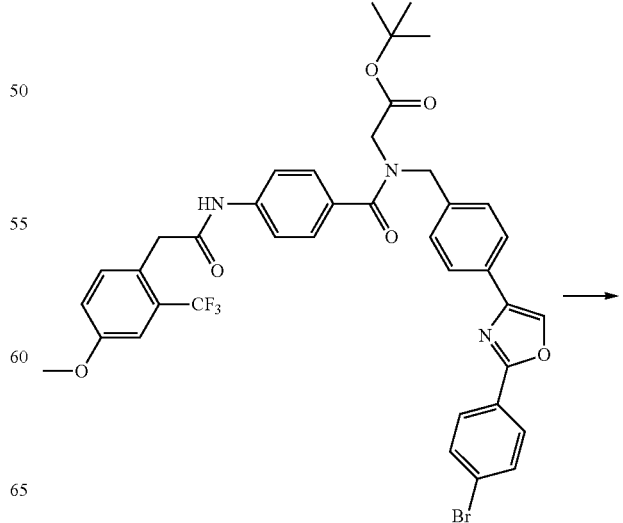

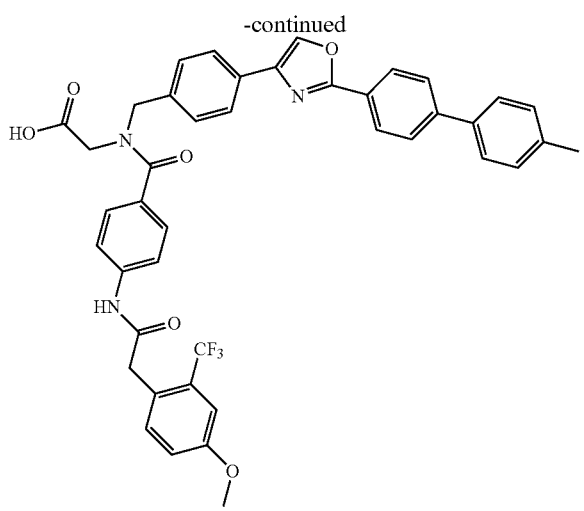

To a stirring solution of tert-butyl 2-(N-(4-(2-(4-bromophenyl)oxazol-4-yl)benzyl)-4-(2-(4-methoxy-2-(trifluoromethyl)phenyl)acetamido)benzamido)acetate INT-45 (118 mg, 0.152 mmol) in THF (1 mL) and acetonitrile (1 mL) were added sodium carbonate (0.30 mL, 0.30 mmol, 1 M aqueous solution) and p-tolylboronic acid (25.0 mg, 0.18 mmol). The reaction mixture was de-gassed and [1,1'-Bis(diphenylphosphino)ferrocene]dichloropalladium (5.50 mg, 7.60 µmol) was added. The reaction mixture was heated in a microwave at 130° C. for 30 min. The reaction mixture was diluted with DCM (4 mL) and NaHCO$_3$ (10 mL), stirred for 15 min and split through a hydrophobic frit. The organics were evaporated and purified by column chromatography (EA/isohexanes) to yield tert-butyl 2-(N-(4-(2-(4-bromophenyl)oxazol-4-yl)benzyl)-4-(2-(4-methoxy-2-(trifluoromethyl)phenyl)acetamido)benzamido)acetate. To tert-butyl 2-(N-(4-(2-(4-bromophenyl)oxazol-4-yl)benzyl)-4-(2-(4-methoxy-2-(trifluoromethyl) phenyl) acetamido) benzamido)acetate in DCM (2 mL) was added TFA (2 mL) and the reaction mixture was stirred at room temperature for 30 min. The reaction mixture was evaporated and re-slurried from acetonitrile (4 mL) to afford 59 mg (53%) of 2-(4-(2-(4-methoxy-2-(trifluoromethyl)phenyl)acetamido)-N-(4-(2-(4'-methyl-[1,1'-biphenyl]-4-yl)oxazol-4-yl) benzyl)benzamido)acetic acid 364 as a white solid. LCMS-ESI (m/z) calculated for C$_{42}$H$_{34}$F$_3$N$_3$O$_6$: 733. found 734 [M+H]$^+$, $t_R$=9.36 min (Method 9). $^1$H NMR (400 MHz, DMSO) δ 12.76 (s, 1H), 10.34 (s, 1H), 8.75 (s, 1H), 8.13 (d, J=6.7 Hz, 2H), 7.90-7.85 (m, 4H), 7.70-7.59 (m, 4H), 7.50-7.42 (m, 2H), 7.41-7.31 (m, 5H), 7.25-7.16 (m, 2H), 4.70 (s, 1H), 4.62 (s, 1H), 4.02 (s, 1H), 3.92 (s, 1H), 3.86 (s, 2H), 3.83 (s, 3H), 2.37 (s, 3H).

2-(4-(heptyloxy)benzyl)-1H-benzo[d]imidazole-5-carbonitrile (INT-46)

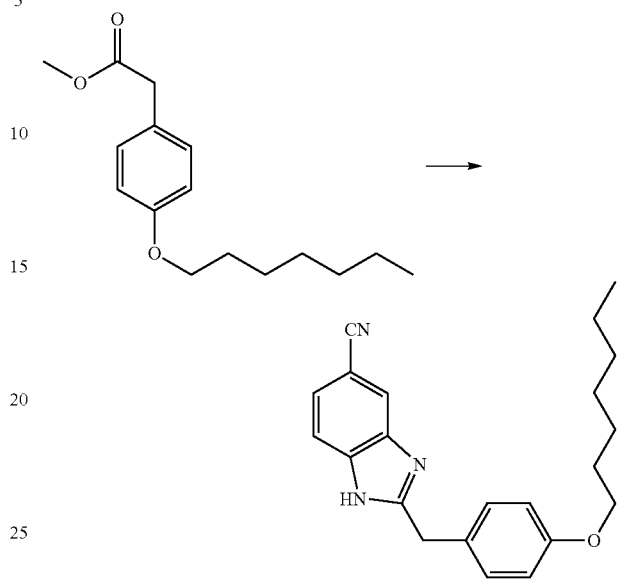

To a stirred solution of 3,4-diaminobenzonitrile (1.08 g, 8.10 mmol) in THF (20 mL) at 0° C. was added trimethylaluminum (4.86 mL, 9.72 mmol, 2 M in hexanes). After 10 min, methyl 2-(4-(heptyloxy)phenyl)acetate (2.36 g, 8.91 mmol) was added and the cooling bath removed. After stirring for 48 h at 60° C., the reaction mixture was allowed to cool to room temperature then poured into a mixture of Rochelle's salt (6.86 g, 24.31 mmol) in water (150 mL) and EA (100 mL) and stirred for 2 h. The layers were split and the aqueous layer further extracted with EA (50 mL). The combined organics were washed successively with water (100 mL) and brine (50 mL), dried over MgSO$_4$ and evaporated. The residue was taken up in xylenes (50 mL), treated with tosic acid (0.154 g, 0.810 mmol) and heated under reflux for 18 h. The reaction mixture was allowed to cool, diluted with EA (100 mL), washed with NaHCO$_3$ (100 mL), dried over MgSO$_4$ and evaporated. The crude material was purified by chromatography (EA/isohexanes) then re-slurried from isohexanes to afford 2.19 g, (78%) of 2-(4-(heptyloxy)benzyl)-1H-benzo[d]imidazole-5-carbonitrile as a white solid INT-46. LCMS-ESI (m/z) calculated for C$_{22}$H$_{25}$N$_3$O: 347. found 348 [M+H]$^+$, $t_R$=2.82 min (Method 5).

2-(4-(heptyloxy)benzyl)-1H-benzo[d]imidazole-5-carbaldehyde (INT-47)

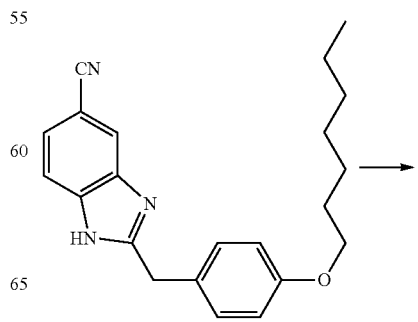

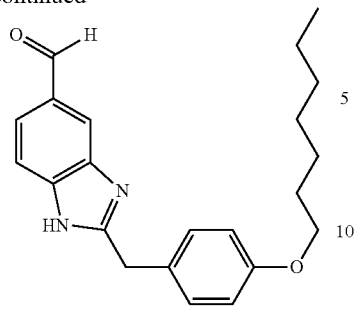

To a stirred solution of 2-(4-(heptyloxy)benzyl)-1H-benzo[d]imidazole-5-carbonitrile INT-46 (1.22 g, 3.51 mmol) in THF (20 mL) at 0° C. was added diisobutylaluminum hydride (12.3 mL, 12.3 mmol, 1 M in toluene). After 2 h the reaction mixture was poured onto Rochelle's salt (7.91 g, 28.0 mmol) in water (100 mL) and EA (50 mL) and stirred for 1 h. The layers were split and the aqueous layer was further extracted with EA (2×30 mL). The combined organics were washed with brine (20 mL) dried over MgSO$_4$ and evaporated. The crude material was purified by chromatography (EA/isohexanes) to afford 571 mg (46%) of 2-(4-(heptyloxy)benzyl)-1H-benzo[d]imidazole-5-carbaldehyde INT-47 as a brown oil. LCMS-ESI (m/z) calculated for $C_{22}H_{26}N_2O_2$: 350. found 351 [M+H]$^+$, $t_R$=2.34 min (Method 5).

tert-butyl 2-(((2-(4-(heptyloxy)benzyl)-1H-benzo[d]imidazol-5-yl)methyl)amino)acetate (INT-48)

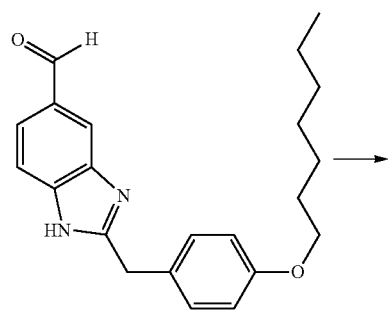

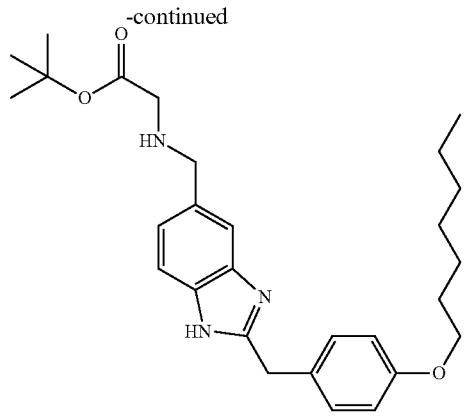

To a stirred solution of 2-(4-(heptyloxy)benzyl)-1H-benzo[d]imidazole-5-carbaldehyde INT-47 (571 mg, 1.63 mmol) in DCM (6 mL) was added tert-butyl 2-aminoacetate hydrochloride (328 mg, 1.96 mmol). After 1 h, sodium triacetoxyhydroborate (691 mg, 3.26 mmol) was added. After stirring at room temperature for 18 h, the reaction mixture was quenched with NaHCO$_3$ (10 mL), stirred for 10 min and split through a hydrophobic frit and evaporated. The crude product was purified by column chromatography (MeOH/EA) to give 228 mg (30%) of tert-butyl 2-(((2-(4-(heptyloxy)benzyl)-1H-benzo[d]imidazol-5-yl)methyl)amino)acetate INT-48 as a pale yellow oil. LCMS-ESI (m/z) calculated for $C_{28}H_{39}N_3O_3$: 465. found 466 [M+H]$^+$, $t_R$=1.17 min (Method 3).

tert-butyl 2-(N-((2-(4-(heptyloxy)benzyl)-1H-benzo[d]imidazol-5-yl)methyl)-4-(2-(4-methoxyphenyl)acetamido)benzamido)acetate (INT-49)

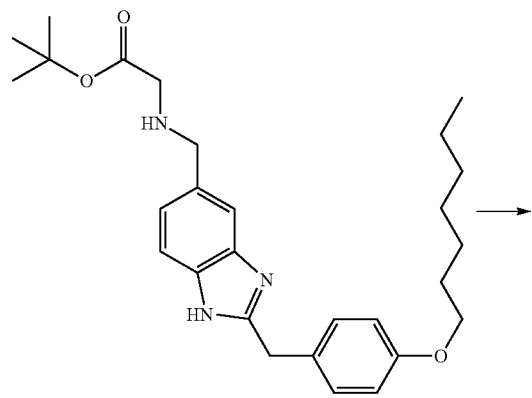

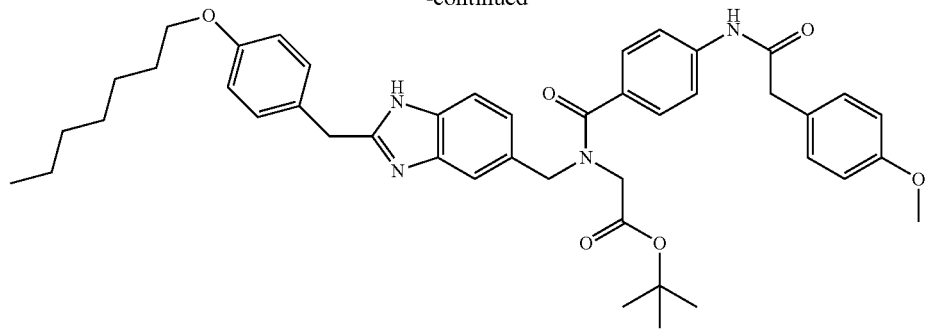

To a stirring solution of 4-(2-(4-methoxyphenyl)acetamido)benzoic acid (142 mg, 0.498 mmol), tert-butyl 2-(((2-(4-(heptyloxy)benzyl)-1H-benzo[d]imidazol-5-yl)methyl) amino)acetate INT-48 (221, 0.475 mmol) and TEA (206 μL, 1.42 mmol) in DMF (2 mL) was added HATU (189 mg, 0.489 mmol). After stirring at room temperature for 1 h, the reaction mixture was diluted with DCM (5 mL) and NaHCO$_3$ (15 mL). The layers were split through a hydrophobic frit and the organics evaporated. The crude product was purified by column chromatography (EA/isohexanes) to give 313 mg (88%) of tert-butyl 2-(N-((2-(4-(heptyloxy)benzyl)-1H-benzo[d]imidazol-5-yl)methyl)-4-(2-(4-methoxyphenyl) acetamido)benzamido)acetate INT-49. LCMS-ESI (m/z) calculated for $C_{44}H_{52}N_4O_6$: 732. found 733[M+H]$^+$, $t_R$=2.09 min (Method 5).

2-(N-((2-(4-(heptyloxy)benzyl)-1H-benzo[d]imidazol-5-yl)methyl)-4-(2-(4-methoxyphenyl) acetamido)benzamido)acetic acid (Compound 366)

To a stirring solution of tert-butyl 2-(N-((2-(4-(heptyloxy)benzyl)-1H-benzo[d]imidazol-5-yl)methyl)-4-(2-(4-methoxyphenyl)acetamido)benzamido)acetate INT-49 (40 mg, 0.055 mmol) in DCM (2 mL) was added TFA (1 mL). After stirring at room temperature for 2 h, the solvents were concentrated and the residue purified by preparative HPLC to afford 15 mg (40%) of 2-(N-((2-(4-(heptyloxy)benzyl)-1H-benzo[d]imidazol-5-yl)methyl)-4-(2-(4-methoxyphenyl)acetamido)benzamido)acetic acid 366 as a white powder. LCMS-ESI (m/z) calculated for $C_{40}H_{44}N_4O_6$: 676. found 677 [M+H]$^+$, $t_R$=6.77 min (Method 4). $^1$H NMR (400 MHz, DMSO) 12.82 (br s, 1H), 12.21 (br s, 1H), 10.29 (s, 1H), 7.65 (d, J=8.2 Hz, 2H), 7.30-7.57 (m, 4H), 7.27-7.15 (m, 4H), 7.15-6.92 (m, 1H), 6.89-6.75 (m, 4H), 4.71 (s, 1H), 4.62 (s, 1H), 4.08 (s, 2H), 3.91 (m, 3H), 3.81-3.69 (m, 4H), 3.57 (s, 2H), 1.73-1.61 (m, 2H), 1.43-1.20 (m, 8H), 0.90-0.80 (m, 3H).

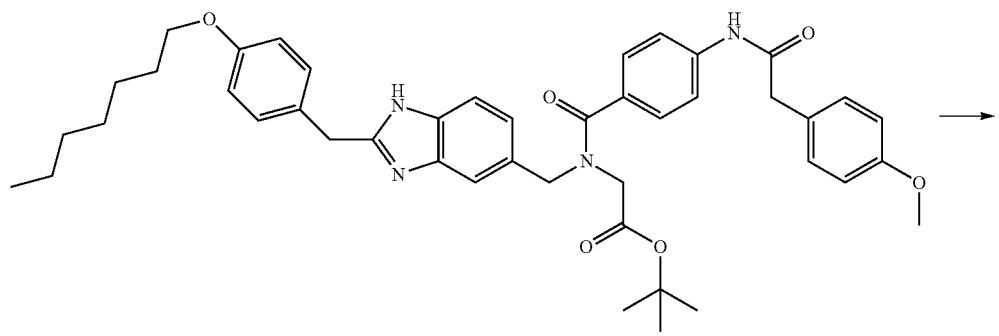

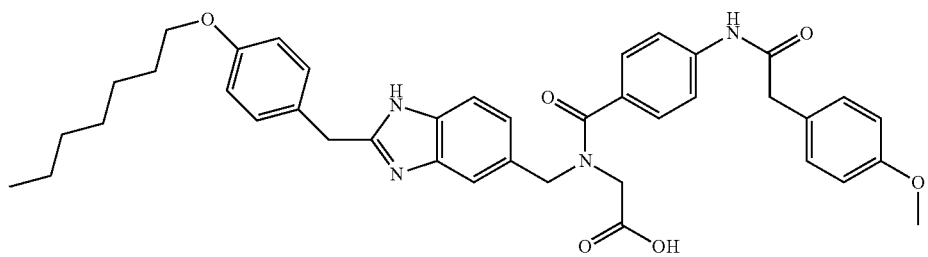

4'-methyl-[1,1'-biphenyl]-4-carbohydrazide (INT-50)

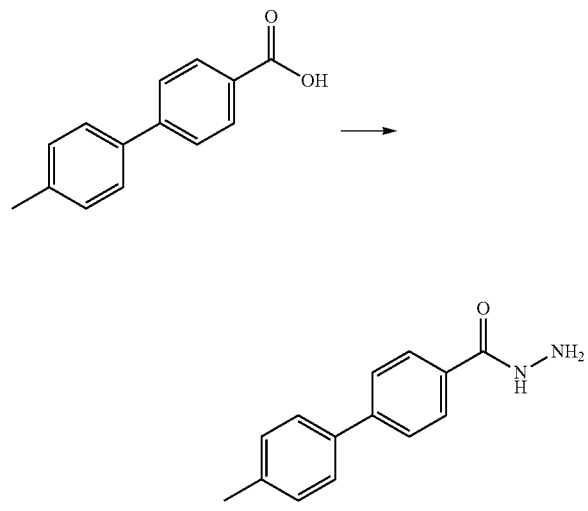

To a stirring solution of 4'-methyl-[1,1'-biphenyl]-4-carboxylic acid (240 mg, 1.13 mmol) and 4-methylmorpholine (131 µL, 1.19 mmol) in THF (3 mL) was added isobutyl chloroformate (147 µL, 1.13 mmol). After 1 h the reaction mixture was added through a syringe filter to a stirring solution of hydrazine (1.24 mL, 1.24 mmol, 1 M in THF) in THF (1 mL). After stirring a further 30 min at room temperature, the reaction mixture was poured into NaHCO$_3$ (20 mL) and extracted with DCM (3×20 mL). The combined organic extracts were dried over MgSO$_4$ and evaporated. The crude product was purified by column chromatography (MeOH/DCM) to give 152 mg (59%) of 4'-methyl-[1,1'-biphenyl]-4-carbohydrazide INT-50 as a white solid. LCMS-ESI (m/z) calculated for C$_{14}$H$_{14}$N$_2$O: 226. found 227 [M+H]$^+$, t$_R$=1.62 min (Method 10).

tert-butyl 2-(4-(2-(4-methoxy-2-(trifluoromethyl)phenyl)acetamido)-N-(4-(2-(4'-methyl-[1,1'-biphenyl]-4-carbonyl)hydrazinecarbonyl)benzyl)benzamido)acetate (INT-51)

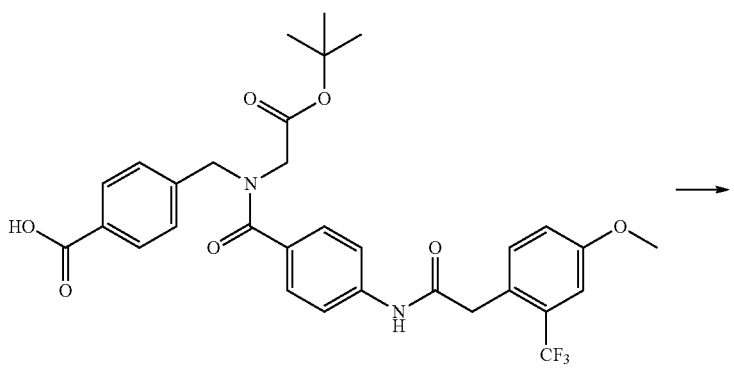

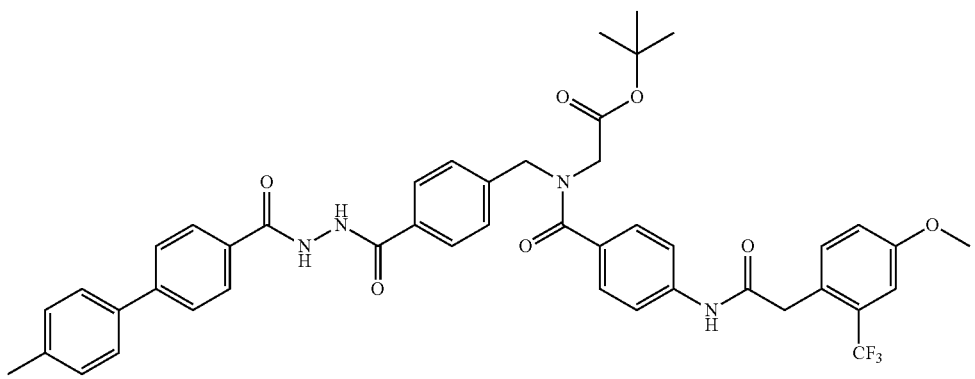

To a stirring solution of 4-((N-(2-(tert-butoxy)-2-oxoethyl)-4-(2-(4-methoxy-2-(trifluoromethyl)phenyl)acetamido)benzamido)methyl)benzoic acid INT-37 (157 mg, 0.26 mmol) and 4-methylmorpholine (63.0 μL, 0.58 mmol) in THF (3 mL) was added isobutyl chloroformate (34.0 μL, 0.26 mmol). After 1 h, the reaction mixture was added to a stirring solution of 4'-methyl-[1,1'-biphenyl]-4-carbohydrazide INT-50 (65.0 mg, 0.29 mmol) in DMF (2 mL). After 2 h, additional 4'-methyl-[1,1'-biphenyl]-4-carbohydrazide INT-50 (12 mg, 0.05 mmol) was added. After stirring at room temperature for 18 h, the reaction mixture was diluted with DCM (4 mL), washed with $NaHCO_3$ (10 mL) and split though a hydrophobic frit. The crude product was purified by column chromatography (EA/isohexanes) to yield 138 mg (65%) of tert-butyl 2-(4-(2-(4-methoxy-2-(trifluoromethyl)phenyl)acetamido)-N-(4-(2-(4'-methyl-[1,1'-biphenyl]-4-carbonyl)hydrazine carbonyl)benzyl)benzamido)acetate INT-51. LCMS-ESI (m/z) calculated for $C_{45}H_{43}F_3N_4O_7$: 808. found 809 [M+H]$^+$, $t_R$=2.75 min (Method 5).

2-(4-(2-(4-methoxy-2-(trifluoromethyl)phenyl)acetamido)-N-(4-(5-(4'-methyl-[1,1'-biphenyl]-4-yl)-1,3,4-oxadiazol-2-yl)benzyl)benzamido)acetic acid (Compound 367)

To a stirring solution of tert-butyl 2-(4-(2-(4-methoxy-2-(trifluoromethyl)phenyl)acetamido)-N-(4-(2-(4'-methyl-[1,1'-biphenyl]-4-carbonyl)hydrazine carbonyl)benzyl)benzamido)acetate INT-51 (138 mg, 0.17 mmol) and triethylamine (37 μL, 0.26 mmol) in DCM (4 mL) was added 2-chloro-1,3-dimethylimidazolinium chloride (32.0 mg, 0.19 mmol). After stirring at room temperature for 16 h, the reaction mixture was warmed to 40° C. After 1 h, additional triethylamine (37.0 μL, 0.26 mmol) was added. After a further 2 h, the reaction mixture was allowed to cool to room temperature then washed with $NaHCO_3$ (10 mL), split through a hydrophobic frit and evaporated. The crude material was purified by column chromatography (EA/isohexanes). The isolated material was diluted with DCM (2 mL), treated with TFA (2 mL) and allowed to stir for 1 h at room temperature. The solvents were concentrated and the residue purified by preparative HPLC to afford 10 mg (8%) of 2-(4-(2-(4-methoxy-2-(trifluoromethyl)phenyl)acetamido)-N-(4-(5-(4'-methyl-[1,1'-biphenyl]-4-yl)-1,3,4-oxadiazol-2-yl)benzyl)benzamido)acetic acid 367 as a white solid. LCMS-ESI (m/z) calculated for $C_{41}H_{33}F_3N_4O_6$: 734. found 735 [M+H]$^+$, $t_R$=8.40 min (Method 9). $^1$H NMR (400 MHz, DMSO) δ 12.96 (s, 1H), 10.36 (s, 1H), 8.26-8.09 (m, 4H), 7.99-7.87 (m, 2H), 7.77-7.50 (m, 6H), 7.47-7.31 (m, 5H), 7.26-7.14 (m, 2H), 4.76 (s, 1H), 4.69 (s, 1H), 4.04 (s, 1H), 3.96 (m, 1H), 3.88-3.77 (m, 5H), 2.38 (s, 3H).

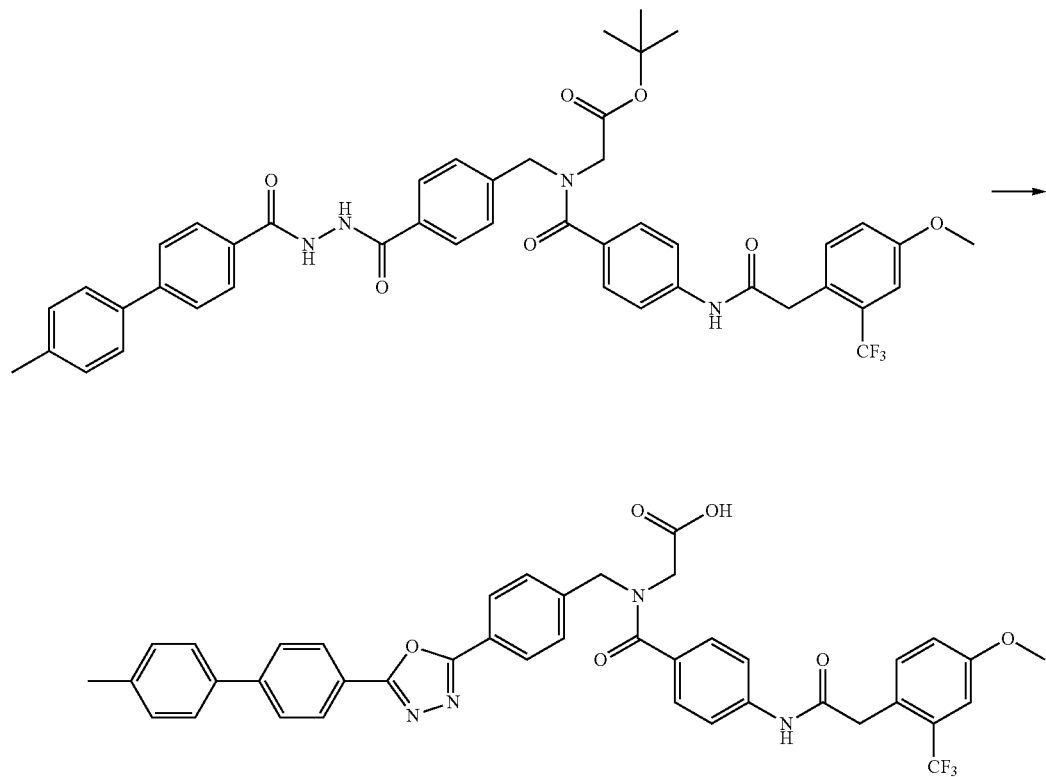

2-(4-(2-(4-methoxy-2-(trifluoromethyl)phenyl)acet-amido)-N-(4-(3-phenyl-1,2,4-oxadiazol-5-yl)benzyl)benzamido)acetic acid (Compound 368)

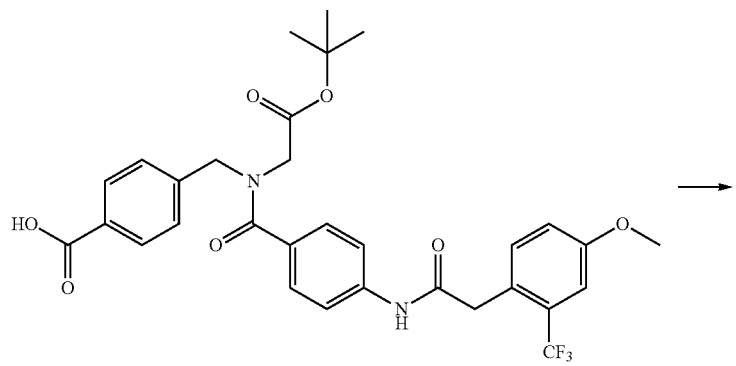

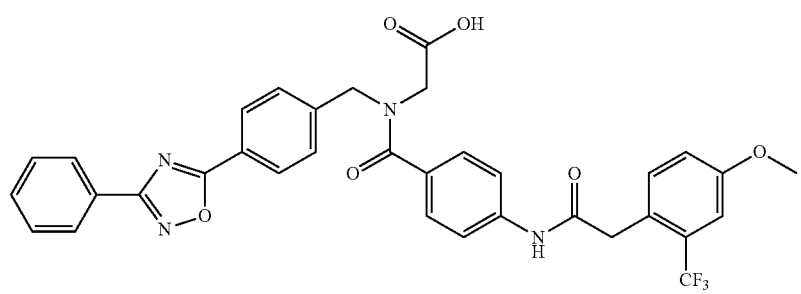

To a stirring solution of 4-((N-(2-(tert-butoxy)-2-oxo-ethyl)-4-(2-(4-methoxy-2-(trifluoromethyl)phenyl)acet-amido)benzamido)methyl)benzoic acid INT-37 (129 mg, 0.22 mmol) and 4-methylmorpholine (52.0 μL, 0.47 mmol) in dioxane (2 mL) was added isobutyl chloroformate (28.0 μL, 0.22 mmol). After 1 h, the reaction mixture was added to a stirring solution of N'-hydroxybenzimidamide (32.0 mg, 0.24 mmol) in DMF (2 mL). After a further 1 h, the reaction mixture was heated to 120° C. for 1 h. The reaction mixture was allowed to cool to room temperature then poured onto citric acid (50 mL, 0.1 M aqueous solution) and extracted with EA(2×20 mL). The combined organic extracts were washed with NaHCO$_3$ (20 mL), dried over MgSO$_4$ and the solvents evaporated. The crude material was purified by column chromatography (EA/isohexanes). The isolated material was dissolved in DCM (2 mL) and treated with TFA (2 mL). After 2 h, the solvents were concentrated and the residue purified by preparative HPLC to afford 19 mg (14%) of 2-(4-(2-(4-methoxy-2-(trifluoromethyl)phenyl)acet-amido)-N-(4-(3-phenyl-1,2,4-oxadiazol-5-yl)benzyl) ben-zamido) acetic acid 368 as a white solid. LCMS-ESI (m/z) calculated for C$_{34}$H$_{27}$F$_3$N$_4$O$_6$: 644. found 645 [M+H]$^+$, t$_R$=7.56 min (Method 9). $^1$H NMR (400 MHz, DMSO) δ 12.85 (s, 1H), 10.34 (s, 1H), 8.22-8.16 (m, 2H), 8.15-8.08 (m, 2H), 7.81-7.49 (m, 7H), 7.49-7.29 (m, 3H), 7.29-7.05 (m, 2H), 4.78 (s, 1H), 4.71 (s, 1H), 4.05 (s, 1H), 3.98 (s, 1H), 3.91-3.77 (s, 5H).

Methyl 4-((4-methoxy-2-(trifluoromethyl)benzyl)carbamoyl)benzoate (INT-52)

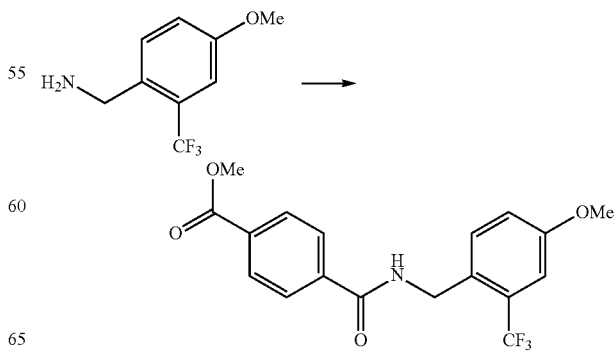

Prepared using General Procedure 6: A solution of monomethyl terephthalate (315 mg, 1.75 mmol), HOBt (395 mg, 2.92 mmol), EDC (562 mg, 2.92 mmol) and DIEA (509 µL, 2.92 mmol) in DMF (10 mL) was stirred at room temperature. After 30 min, 4-methoxy-2-(trifluoromethyl) benzylamine (300 mg, 1.46 mmol) was added as a solution in DMF (2 mL). After stirring for 18 h, the reaction mixture was diluted with NaHCO$_3$ and extracted with EA. The combined organic layers were dried (Na$_2$SO$_4$) and purified by chromatography (EA/hexanes) to provide 418 mg (78%) of methyl 4-((4-methoxy-2-(trifluoromethyl)benzyl)carbamoyl)benzoate INT-52. LCMS-ESI (m/z) calculated for C$_{18}$H$_{16}$F$_3$NO$_4$: 367; no m/z observed, t$_R$=3.42 min (Method 1). $^1$H NMR (400 MHz, CDCl$_3$) δ 8.13-8.04 (m, 2H), 7.85-7.75 (m, 2H), 7.59 (d, J=8.6 Hz, 1H), 7.19 (d, J=2.7 Hz, 1H), 7.05 (dd, J=8.5, 2.7 Hz, 1H), 6.44 (s, 1H), 4.75 (d, J=5.9 Hz, 2H), 3.94 (s, 3H), 3.84 (s, 3H).

4-((4-methoxy-2-(trifluoromethyl)benzyl)carbamoyl) benzoic acid (INT-53)

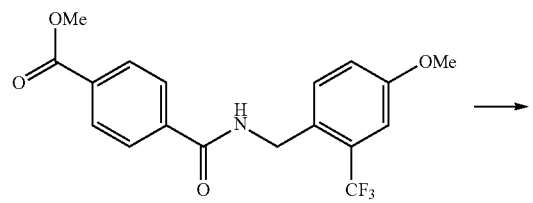

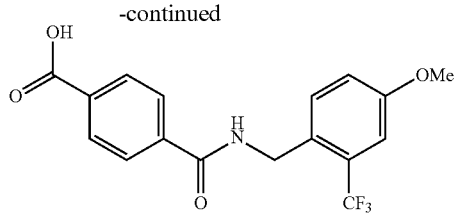

Prepare using General Procedure 9: To a stirring solution of INT-52 (200 mg, 0.54 mmol) in MeOH (5 mL) was added 1 N NaOH (100 µL). The reaction mixture was heated to 50° C. for 18 h, at which time additional 1 N NaOH (200 µL) was added. After stirring an additional 2 h, the reaction mixture was diluted with water, acidified with 1 N HCl and extracted with EA and DCM. The organic layers were combined, dried over Na$_2$SO$_4$, and concentrated to provide 190 mg (99%) of 4-((4-methoxy-2-(trifluoromethyl)benzyl) carbamoyl)benzoic acid INT-53. LCMS-ESI (m/z) calculated for C$_{17}$H$_{14}$F$_3$NO$_4$: 353. found 354 [M+H]$^+$, t$_R$=3.03 min (Method 1).

2-(N-(4-((4-(heptyloxy)benzoyl)oxy)benzyl)-4-((4-methoxy-2-(trifluoromethyl)benzyl) carbamoyl)benzamido)acetic acid (Compound 369)

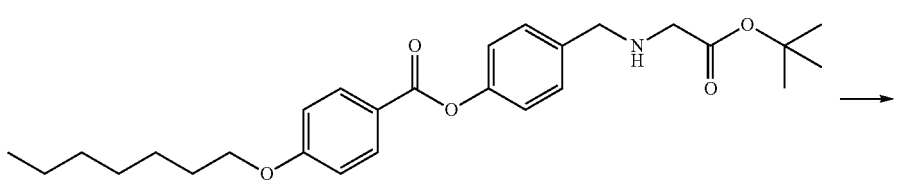

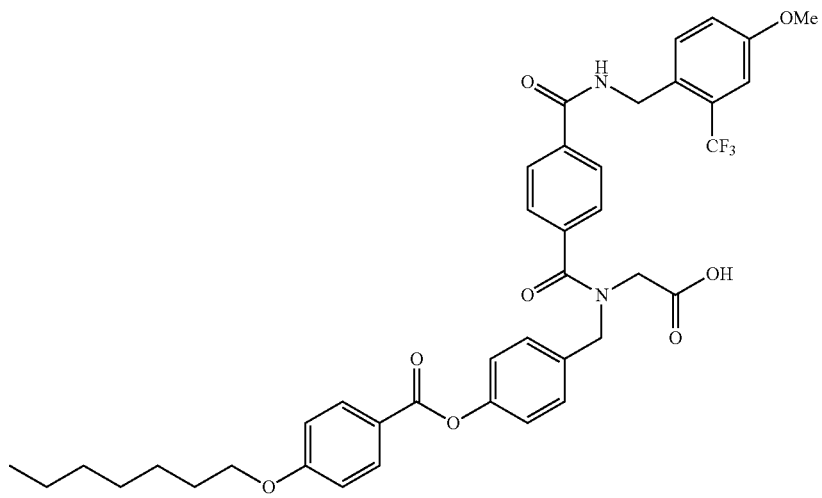

Prepared using General Procedure 6 then 8: To a stirring solution of 4-((4-methoxy-2-(trifluoromethyl)benzyl)carbamoyl)benzoic acid INT-53 (35.5 mg, 0.08 mmol) in DMF (0.5 mL) were added HOBt (19.1 mg, 0.14 mmol), EDC (27.2 mg, 0.14 mmol) and DIEA (24.7 μL, 0.14 mmol). After stirring for 4 h, INT-13 (25.0 mg, 0.07 mmol) was added. After stirring an additional 16 h, the crude reaction mixture was purified by preparative HPLC to provide 28.2 mg (51%) of 4-((N-(2-(tert-butoxy)-2-oxoethyl)-4-((4-methoxy-2-(trifluoromethyl)benzyl)carbamoyl)benzamido)methyl)phenyl 4-(heptyloxy)benzoate, which was dissolved in DCM (1 mL) and TFA (0.2 mL) then stirred for 2.5 h at room temperature. The reaction mixture was concentrated to provide 23 mg (89%) of 2-(N-(4-((4-(heptyloxy)benzoyl)oxy)benzyl)-4-((4-methoxy-2-(trifluoromethyl)benzyl) carbamoyl) benzamido)acetic acid 369. LCMS-ESI (m/z) calculated for $C_{40}H_{41}F_3N_2O_8$: 735; no m/z observed, $t_R$=5.08 min (Method 8). $^1$H NMR (400 MHz, CDCl$_3$) δ 8.10 (dd, J=8.7, 7.2 Hz, 2H), 7.77 (t, J=7.3 Hz, 2H), 7.54-7.44 (m, 2H), 7.40 (dd, J=19.9, 8.4 Hz, 2H), 7.22-7.11 (m, 4H), 7.01-6.87 (m, 3H), 5.75 (s, 2H), 4.80 (d, J=11.1 Hz, 1H), 4.70 (t, J=6.1 Hz, 2H), 4.57 (d, J=29.5 Hz, 1H), 4.16 (s, 1H), 4.04 (t, J=6.6 Hz, 2H), 3.80 (d, J=3.7 Hz, 3H), 1.90-1.72 (m, 2H), 1.54-1.41 (m, 2H), 1.41-1.26 (m, 6H), 0.90 (t, J=6.9 Hz, 3H).

Methyl 4-(2-((4-methoxy-2-(trifluoromethyl)phenyl)amino)-2-oxoethyl)benzoate (INT-54)

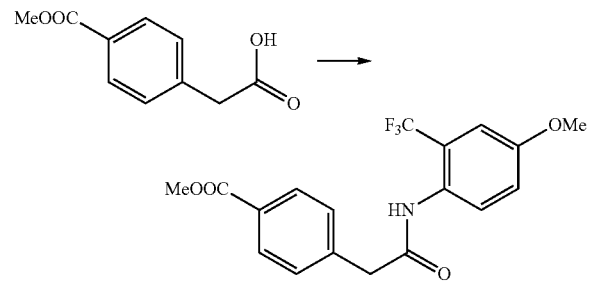

Prepared using General Procedure 6: To a stirring solution of 2-(4-(methoxycarbonyl)phenyl) acetic acid (300 mg, 1.54 mmol) were added HOBt (417 mg, 3.09 mmol), EDC (593 mg, 3.09 mmol) and DIEA (539 μL, 3.09 mmol). After 1.5 h, 4-methoxy-2-(trifluoromethyl)aniline (325 mg, 1.70 mmol) was added. After stirring for 14 h, the mixture was diluted with NaHCO$_3$ and extracted with EA. The combined organic extracts were dried (Na$_2$SO$_4$), concentrated, and purified by chromatography (EA/hexanes) to provide 114 mg (31%) of methyl 4-(2-((4-methoxy-2-(trifluoromethyl)phenyl)amino)-2-oxoethyl)benzoate INT-54. LCMS-ESI (m/z) calculated for $C_{18}H_{16}F_3NO_4$: 367. found 368 [M+H]$^+$, $t_R$=3.27 min (Method 1). $^1$H NMR (400 MHz, CDCl$_3$) δ 8.09 (d, J=8.3 Hz, 2H), 7.91 (d, J=8.4 Hz, 1H), 7.40 (t, J=14.6 Hz, 2H), 7.13 (s, 1H), 7.09-6.96 (m, 2H), 3.92 (d, J=10.8 Hz, 3H), 3.81 (m, 5H).

4-(2-((4-methoxy-2-(trifluoromethyl)phenyl)amino)-2-oxoethyl)benzoic acid (INT-55)

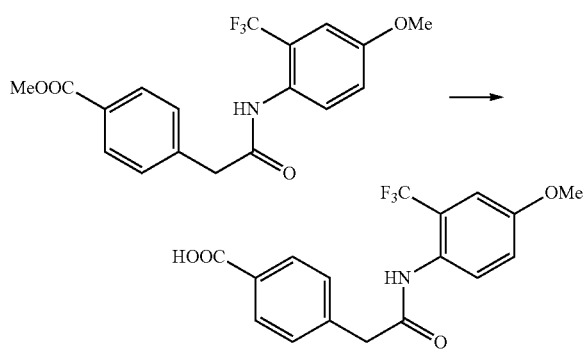

Prepared using General Procedure 9: To a stirring solution of methyl 4-(2-((4-methoxy-2-(trifluoromethyl)phenyl)amino)-2-oxoethyl)benzoate INT-54 (113 mg, 0.31 mmol) in EtOH (10 mL) was added 1 N NaOH (1 mL). The reaction mixture was heated to 50° C. for 3 h, concentrated, diluted with water, acidified with 1 N HCl and extracted with EA and DCM. The organic layers were combined, dried over Na$_2$SO$_4$ and concentrated to provide 97 mg (89%) of 4-(2-((4-methoxy-2-(trifluoromethyl)phenyl)amino)-2-oxoethyl) benzoic acid INT-55. LCMS-ESI (m/z) calculated for $C_{17}H_{14}F_3NO_4$: 353. found 354 [M+H]$^+$, $t_R$=2.84 min (Method 1). $^1$H NMR (400 MHz, CDCl$_3$) δ 8.13 (d, J=8.2 Hz, 2H), 8.04 (d, J=8.0 Hz, 1H), 7.91 (d, J=8.8 Hz, 1H), 7.46 (d, J=8.2 Hz, 1H), 7.13 (s, 1H), 7.05 (m, 2H), 3.82 (m, 5H).

2-(N-(4-((4-(heptyloxy)benzoyl)oxy)benzyl)-4-(2-((4-methoxy-2-(trifluoromethy)phenyl) amino)-2-oxoethyl)benzamido)acetic acid (Compound 370)

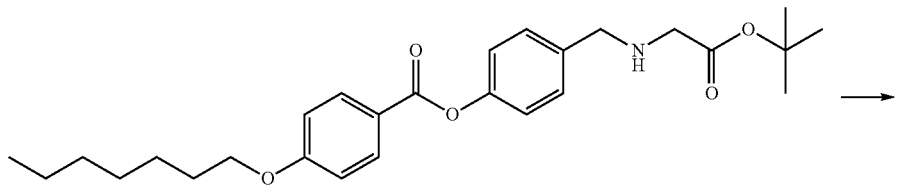

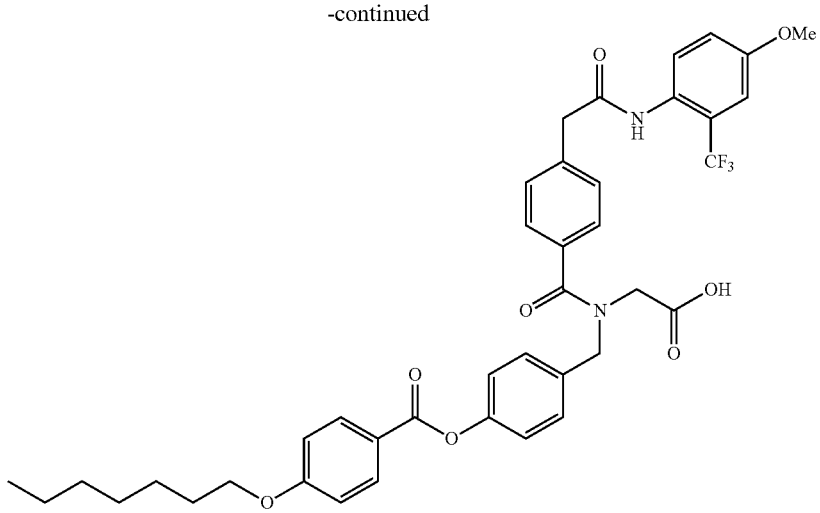

Prepared using General Procedures 6 then 8: To a stirring solution of INT-55 (50 mg, 0.14 mmol) in DMF (1.5 mL) were added HOBt (38.2 mg, 0.28 mmol), EDC (54.3 mg, 0.28 mmol) and DIEA (49.3 µL, 0.28 mmol). After stirring for 1.5 h, INT-13 (71.0 mg, 0.16 mmol) was added. After stirring an additional 16 h, the reaction mixture was diluted with EA and washed with NaHCO₃ and brine. The organic layer was dried (Na₂SO₄) and concentrated to provide 72 mg of crude 4-((N-(2-(tert-butoxy)-2-oxoethyl)-4-(2-((4-methoxy-2-(trifluoromethyl)phenyl)amino)-2-oxoethyl)benzamido)methyl)phenyl 4-(heptyloxy)benzoate, which was dissolved in DCM (5 mL) and TFA (0.3 mL) and stirred for 5 h at room temperature. The mixture was concentrated and purified by prep HPLC to provide 33 mg (32%) of 2-(N-(4-((4-(heptyloxy)benzoyl)oxy)benzyl)-4-(2-((4-methoxy-2-(trifluoromethyl)phenyl)amino)-2-oxoethyl)benzamido)acetic acid 370. LCMS-ESI (m/z) calculated for $C_{40}H_{41}F_3N_2O_8$: 735; no m/z observed. $t_R$=4.31 min (Method 1). ¹H NMR (400 MHz, CDCl₃) δ 9.73 (s, 1H), 8.12 (d, J=8.9 Hz, 2H), 7.82-7.61 (m, 1H), 7.55 (t, J=12.1 Hz, 1H), 7.55-7.30 (m, 4H), 7.22 (dd, J=13.2, 7.3 Hz, 3H), 7.10-6.89 (m, 4H), 4.83 (s, 1H), 4.64 (s, 1H), 4.21 (s, 1H), 4.09-3.97 (m, 2H), 3.89-3.74 (m, 4H), 3.00 (d, J=38.2 Hz, 2H), 1.90-1.75 (m, 2H), 1.56-1.40 (m, 2H), 1.42-1.21 (m, 6H), 0.91 (q, J=6.7 Hz, 3H).

tert-butyl 2-(N-(4-cyanobenzyl)-4-nitrobenzamido)acetate (INT-56)

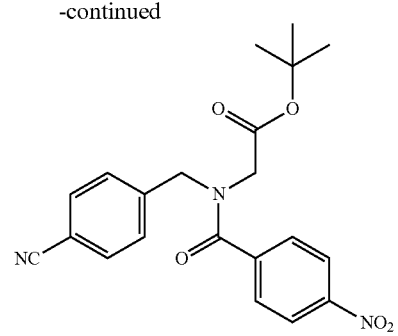

Prepared using General Procedure 7: To a stirred solution of tert-butyl 2-((4-cyanobenzyl)amino)acetate (14.7 g, 47.7 mmol) INT-31 in DCM (150 mL) stirring in a 0° C. in an ice bath was added TEA (9.98 mL, 71.6 mmol) followed by 4-nitrobenzoyl chloride. The reaction mixture was allowed to warm to room temperature over 1.5 h. The reaction mixture was diluted with DCM (300 mL) and washed with NaHCO₃ (2×200 mL). The organics were dried over dried over MgSO₄ and concentrated in vacuo. The crude product was purified by chromatography (MeOH/DCM) followed by evaporation from hexanes to provide 11.5 g (61%) tert-butyl 2-(N-(4-cyanobenzyl)-4-nitrobenzamido)acetate INT-56 as a white powder. LCMS-ESI (m/z) calculated for $C_{21}H_{21}N_3O_5$: 395. found 394 [M–H]⁻, $t_R$=2.33 min broad (Method 10).

tert-butyl 2-(N-(4-(N-hydroxycarbamimidoyl)benzyl)-4-nitrobenzamido)acetate (INT-57)

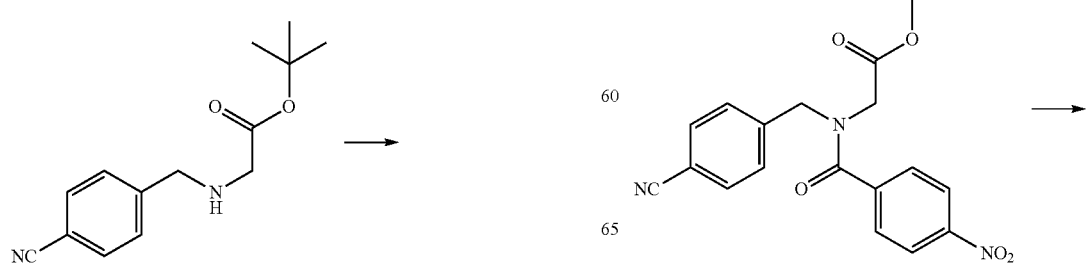

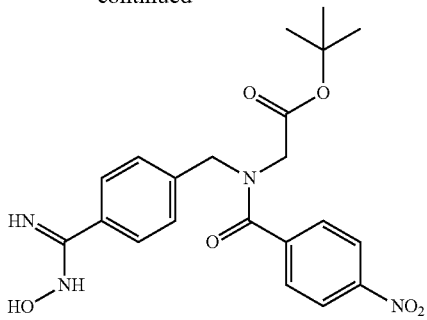

Prepared using General Procedure 19. To a stirred solution of tert-butyl 2-(N-(4-cyanobenzyl)-4-nitrobenzamido)acetate INT-56 (11.5 g, 29.2 mmol) and TEA (10.2 mL, 73.0 mmol) in DMF (50 mL) was added hydroxylamine hydrochloride (5.07 g, 73.0 mmol). After 24 h the reaction mixture was poured onto water (200 mL) and NaHCO$_3$ (200 mL) and extracted into EA (2×250 mL). The organics were washed with brine (3×200 mL), dried over MgSO$_4$ and concentrated in vacuo, evaporating from hexanes, to provide 12.1 g (97%) of tert-butyl 2-(N-(4-(N-hydroxycarbamimidoyl)benzyl)-4-nitrobenzamido)acetate INT-57 as an off-white powder. LCMS-ESI (m/z) calculated for C$_{21}$H$_{24}$N$_4$O$_6$: 428. found 429 [M+H]$^+$, t$_R$=1.42 min (Method 10).

tert-butyl 2-(N-(4-(5-(4'-methyl-[1,1'-biphenyl]-4-yl)-1,2,4-oxadiazol-3-yl)benzyl)-4-nitrobenzamido)acetate (INT-58)

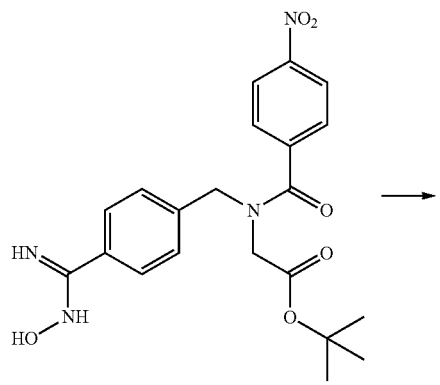

Prepared using General Procedure 20. To a stirred solution of tert-butyl 2-(N-(4-(N-hydroxycarbamimidoyl)benzyl)-4-nitrobenzamido)acetate (7.25 g, 16.6 mmol) INT-57 in dioxanes (25 mL) was added DIEA (3.19 mL, 18.24 mmol) then 4'-methyl-[1,1'-biphenyl]-4-carbonyl chloride (3.83 g, 16.6 mmol). The reaction mixture was stirred at room temperature for 30 mins then at 120° C. for 3 h. The reaction mixture was allowed to cool to room temperature, diluted with EA (400 mL) and washed with brine (500 mL). The organics were pre-absorbed onto silica gel and purified by chromatography (MeCN/DCM) to provide 7.35 g (73%) of tert-butyl 2-(N-(4-(5-(4'-methyl-[1,1'-biphenyl]-4-yl)-1,2,4-oxadiazol-3-yl)benzyl)-4-nitrobenzamido)acetate INT-58 as a white powder. LCMS-ESI (m/z) calculated for C$_{35}$H$_{32}$N$_4$O$_6$: 604. found 549 [M-t-Bu+H]$^+$, t$_R$=3.24 min (Method 10).

tert-butyl 2-(4-amino-N-(4-(5-(4'-methyl-[1,1'-biphenyl]-4-yl)-1,2,4-oxadiazol-3-yl)benzyl)benzamido)acetate (INT-59)

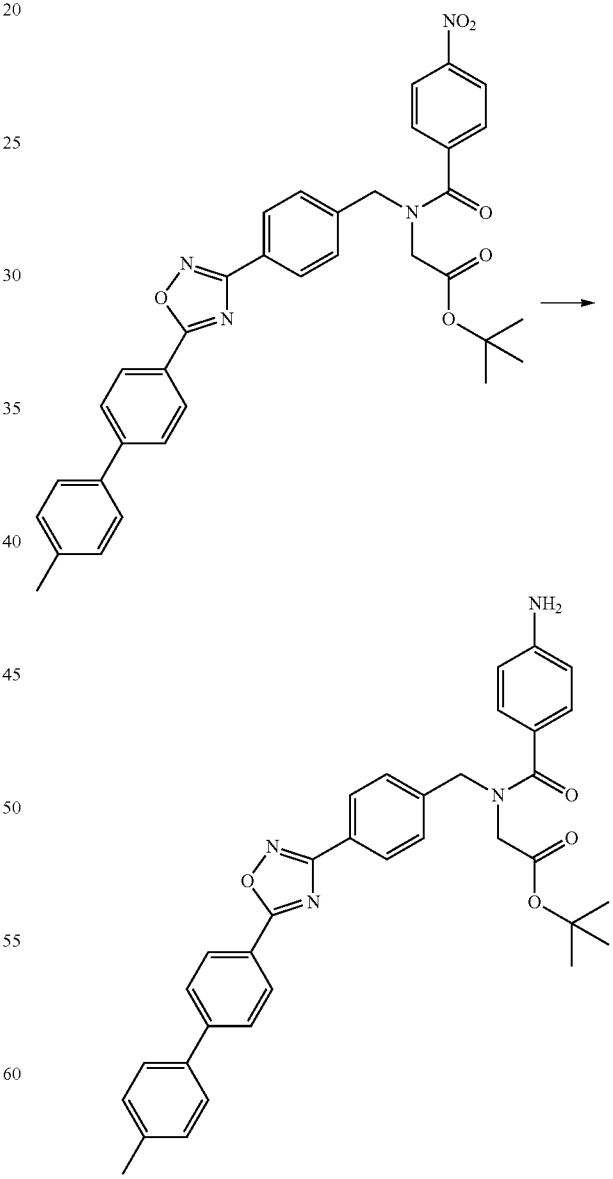

Prepared using General Procedure 5. To a stirred solution of tert-butyl 2-(N-(4-(5-(4'-methyl-[1,1'-biphenyl]-4-yl)-1, 2,4-oxadiazol-3-yl)benzyl)-4-nitrobenzamido)acetate INT-58 (7.25 g, 12.0 mmol) in THF (30 mL) was added water (10 mL) and sodium dithionite (6.26 g, 36.0 mmol) and then heated to 65° C. for 3 h. The reaction mixture was allowed to cool to room temperature and then diluted with brine (300 mL) and extracted into EA (300 mL) and THF (250 mL). The combined organics were dried over MgSO$_4$ and concentrated in vacuo. The solid was dried under vacuum for 18 h to afford 7.17 g (100%) of tert-butyl 2-(4-amino-N-(4-(5-(4'-methyl-[1,1'-biphenyl]-4-yl)-1,2,4-oxadiazol-3-yl)benzyl)benzamido)acetate INT-59 as a pale yellow powder. LCMS-ESI (m/z) calculated for $C_{35}H_{34}N_4O_4$: 574. found 519 [M-t-Bu+H]$^+$, $t_R$=3.12 min (Method 10).

2-(4-(2-(2,5-dimethoxyphenyl)acetamido)-N-(4-(5-(4'-methyl-[1,1'-biphenyl]-4-yl)-1,2,4-oxadiazol-3-yl)benzyl)benzamido)acetic acid (Compound 405)

Prepared using General Procedures 6 and 8: To a stirred solution of tert-butyl 2-(4-amino-N-(4-(5-(4'-methyl-[1,1'-biphenyl]-4-yl)-1,2,4-oxadiazol-3-yl)benzyl)benzamido)acetate INT-59 (250 mg, 0.435 mmol), 2-(2,5-dimethoxyphenyl)acetic acid (85 mg, 0.435 mmol) and TEA (91 μL, 0.653 mmol) in DMF (3 mL) was added HATU (182 mg, 0.479 mmol) at room temperature. After 2 h the reaction mixture was diluted with EA (40 mL) and washed with brine (60 mL). The organic layer was pre-absorbed onto silica gel and purified by chromatography (EA/hexanes) to afford the intermediate ester as a white powder, which was dissolved in DCM (4 mL) and TFA (3 mL) and stirred at room temperature for 3 h. The reaction mixture was concentrated in vacuo and the residue taken up into DMSO (1 mL). Addition of water (30 mL) gave a white precipitate that was isolated by filtration. The damp solid was sonicated in DCM (1 mL) and hexanes (15 mL) and isolated by filtration to provide 73.2 mg (23%) 2-(4-(2-(2,5-dimethoxyphenyl)acetamido)-N-(4-(5-(4'-methyl-[1,1'-biphenyl]-4-yl)-1,2,4-oxadiazol-3-yl)benzyl)benzamido)acetic acid 405 as a white powdery solid. LCMS-ESI (m/z) calculated for $C_{41}H_{36}N_4O_7$: 696. found 697 [M+H]$^+$, $t_R$=8.80 min (Method 9). $^1$H NMR (400 MHz, DMSO) δ 12.75 (s, 1H), 10.25 (s, 1H), 8.32-8.20 (m, 2H), 8.18-8.05 (m, 2H), 8.02-7.92 (m, 2H), 7.78-7.45 (m, 6H), 7.44-7.29 (m, 4H), 6.99-6.74 (m, 3H), 4.76 (s, 1H), 4.69 (s, 1H), 4.04 (s, 1H), 3.98 (s, 1H), 3.75-3.66 (m, 6H), 3.66-3.57 (m, 2H), 2.38 (s, 3H).

2-(4-(2-(2,6-dimethoxyphenyl)acetamido)-N-(4-(5-(4'-methyl-[1,1'-biphenyl]-4-yl)-1,2,4-oxadiazol-3-yl)benzyl)benzamido)acetic acid (Compound 411)

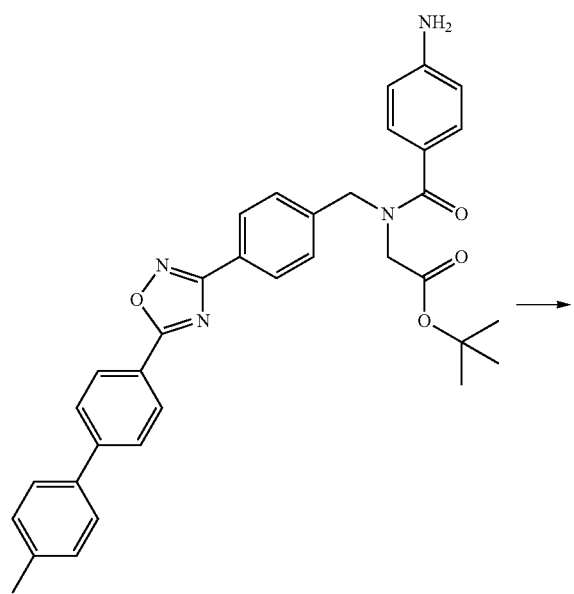

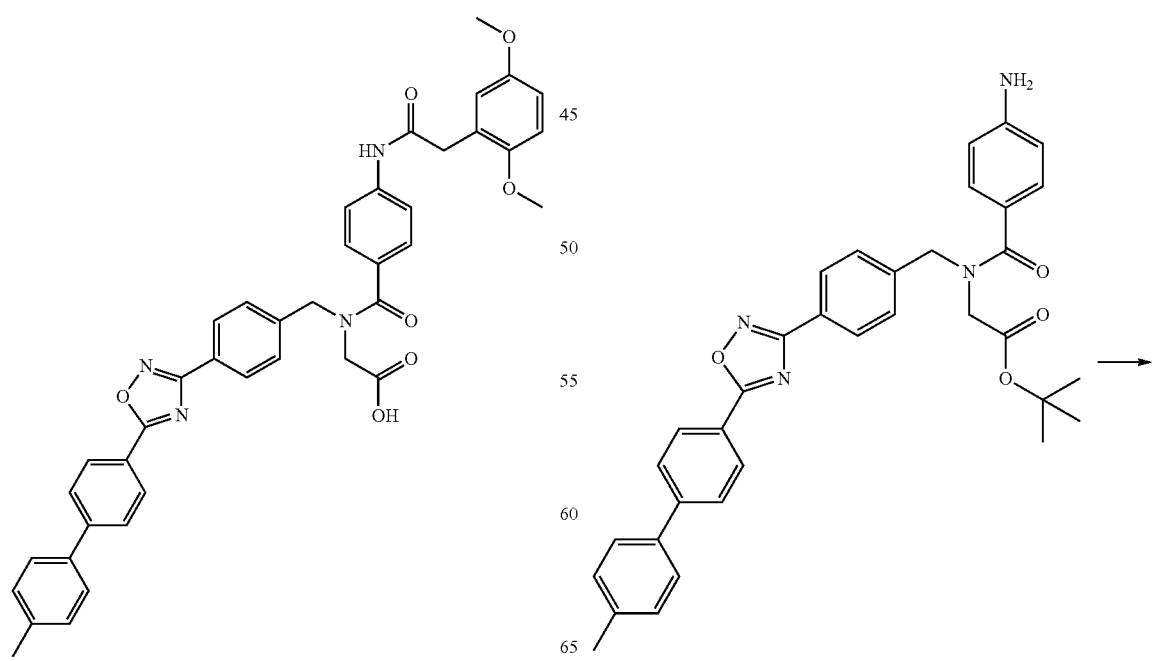

161
-continued

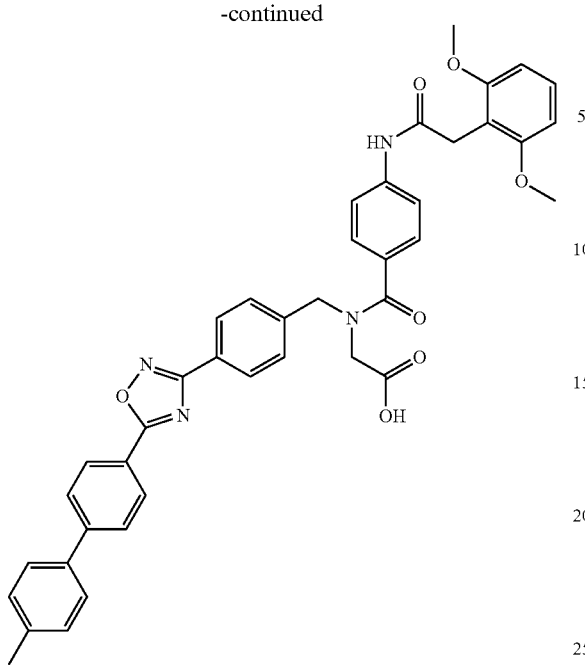

Prepared using General Procedures 6 and 8: To a stirred solution of tert-butyl 2-(4-amino-N-(4-(5-(4'-methyl-[1,1'-biphenyl]-4-yl)-1,2,4-oxadiazol-3-yl)benzyl)benzamido)acetate INT-59 (185 mg, 0.321 mmol), 2-(2,6-dimethoxyphenyl)acetic acid (63 mg, 0.321 mmol) and TEA (67.1 µL, 0.482 mmol) in DMF (3 mL) was added HATU (134 mg, 0.353 mmol) at room temperature. After 2 h the reaction mixture was diluted with EA (30 mL) and washed with brine (60 mL). The organic layer was pre-absorbed onto silica gel and purified by chromatography (acetic acid/EA/hexanes) to afford the intermediate ester as a white powder. The intermediate ester was dissolved in DCM (4 mL) and TFA (3 mL) and stirred at room temperature for 3 h. The reaction mixture was concentrated and the residue taken up into DMSO (1 mL). Addition of water (30 mL) gave a white precipitate that was isolated by filtration. The damp solid was sonicated in DCM (1 mL) and hexanes (15 mL) and isolated by filtration to provide 55 mg (24%) 2-(4-(2-(2,6-dimethoxyphenyl)acetamido)-N-(4-(5-(4'-methyl-[1,1'-biphenyl]-4-yl)-1,2,4-oxadiazol-3-yl)benzyl)benzamido)acetic acid 411 as a white powder. LCMS-ESI (m/z) calculated for $C_{41}H_{36}N_4O_7$: 696. found 697 [M+H]$^+$, $t_R$=9.02 min (Method 9). $^1$H NMR (400 MHz, DMSO) δ 12.80 (s, 1H), 10.18 (s, 1H), 8.32-8.23 (m, 2H), 8.16-8.08 (m, 2H), 8.02-7.94 (m, 2H), 7.77-7.69 (m, 2H), 7.69-7.45 (m, 4H), 7.42-7.32 (m, 4H), 7.26-7.17 (m, 1H), 6.70-6.60 (s, 2H), 4.76 (s, 1H), 4.69 (s, 1H), 4.04 (s, 1H), 3.96 (s, 1H), 3.80 (s, 3H), 3.69 (s, 3H), 3.68 (s, 1H), 3.58 (s, 1H), 2.39 (s, 3H).

162
2-(4-(2-(2,6-difluoro-3-methoxyphenyl)acetamido)-N-(4-(5-(4'-methyl-[1,1'-biphenyl]-4-yl)-1,2,4-oxadiazol-3-yl)benzyl)benzamido)acetic acid (Compound 441)

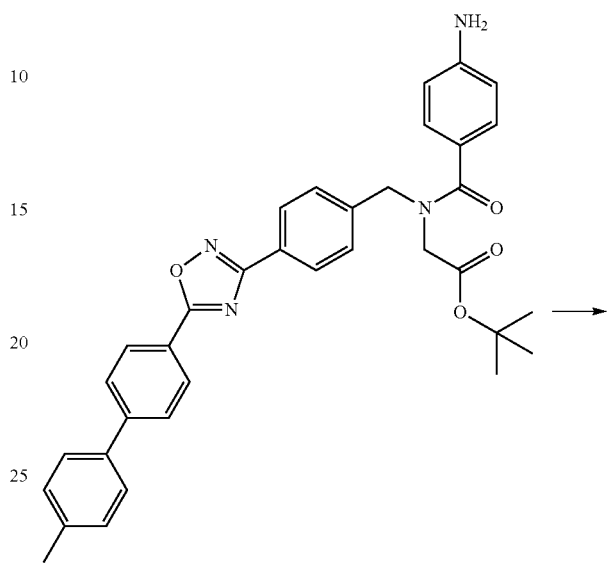

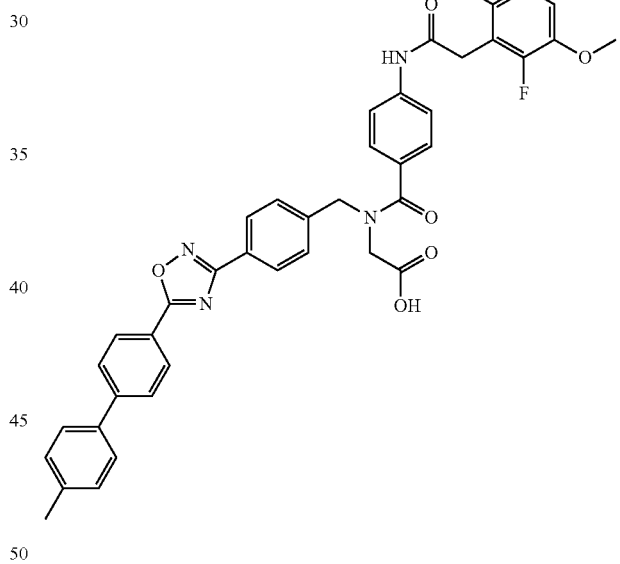

Prepared using General Procedures 7 and 8: To a stirred suspension of 2-(2,6-difluoro-3-methoxyphenyl)acetic acid in DCM (1.5 mL) and DMF (10 µL) was added oxalyl chloride (9.71 µL, 0.111 mmol). After 1 h a solution of tert-butyl 2-(4-amino-N-(4-(5-(4'-methyl-[1,1'-biphenyl]-4-yl)-1,2,4-oxadiazol-3-yl)benzyl)benzamido)acetate INT-59 (50 mg, 0.074 mmol) and TEA (25.8 µL, 0.185 mmol) in DCM (1 mL) was added. After 18 h TFA (1 mL) was added and reaction stirred for 2 h. The solvent was removed from the reaction mixture and the residue purified by preparative HPLC to afford 30 mg (57%) of 2-(4-(2-(2,6-difluoro-3-methoxyphenyl)acetamido)-N-(4-(5-(4'-methyl-[1,1'-biphenyl]-4-yl)-1,2,4-oxadiazol-3-yl)benzyl)benzamido)acetic acid 441. LCMS-ESI (m/z) calculated for $C_{46}H_{32}F_2N_4O_6$: 702. found 703 [M+H]$^+$, $t_R$=8.75 min (Method 9). $^1$H NMR (400 MHz, DMSO) δ 12.79 (s, 1H), 10.26 (s, 1H), 8.31-8.22 (m, 2H), 8.12-8.06 (m, 2H), 8.02-7.92 (m, 2H), 7.74-7.69

(m, 2H), 7.69-7.56 (m, 2H), 7.54-7.45 (m, 1H), 7.42-7.29 (m, 4H), 7.23-7.09 (m, 2H), 6.80-6.66 (m, 1H), 4.76 (s, 1H), 4.67 (s, 1H), 4.04 (s, 1H), 3.97 (s, 1H), 2.92-2.81 (m, 5H), 2.38 (s, 3H).

Compound 395 was prepared using INT-59 and 2-(2-methoxyphenyl)acetic acid using General Procedures 7 then 8. Compound 396 was prepared using INT-59 and 2-(3,5-dimethoxyphenyl)acetic acid using General Procedures 7 then 8. Compound 398 was prepared using INT-59 and 2-(4-methoxy-3-methylphenyl)acetic acid using General Procedures 7 then 8. Compound 399 was prepared using INT-59 and 2-(o-tolyl)acetic acid using General Procedures 7 then 8. Compound 401 was prepared using INT-59 and 2-(2,3-dimethoxyphenyl)acetic acid using General Procedures 7 then 8. Compound 402 was prepared using INT-59 and 2-(2-fluoro-4-methoxyphenyl)acetic acid using General Procedures 7 then 8. Compound 403 was prepared using INT-59 and 2-(4-fluoro-2-methoxyphenyl)acetic acid using General Procedures 7 then 8. Compound 404 was prepared using INT-59 and 2-(3,4-dimethoxyphenyl)acetic acid using General Procedures 7 then 8. Compound 406 was prepared using INT-59 and 2-(3-methoxyphenyl)acetic acid using General Procedures 7 then 8. Compound 407 was prepared using INT-59 and 2-(4-(dimethylamino)-2-(trifluoromethyl)phenyl)acetic acid using General Procedures 7 then 8. Compound 408 was prepared using INT-59 and 2-(4-chloro-2-(trifluoromethyl)phenyl)acetic acid using General Procedures 7 then 8. Compound 409 was prepared using INT-59 and 2-(2-cyano-4-methoxyphenyl)acetic acid using General Procedures 7 then 8. Compound 410 was prepared using INT-59 and 2-(4-methoxy-2-methylphenyl)acetic acid using General Procedures 7 then 8. Compound 415 was prepared using INT-59 and 2-(5-fluoro-2-methoxyphenyl)acetic acid using General Procedures 7 then 8. Compound 416 was prepared using INT-59 and 2-(2,6-difluorophenyl)acetic acid using General Procedures 7 then 8. Compound 417 was prepared using INT-59 and 2-(2-fluoro-6-methoxyphenyl)acetic acid using General Procedures 7 then 8. Compound 418 was prepared using INT-59 and 2-(2-fluorophenyl)acetic acid using General Procedures 7 then 8. Compound 420 was prepared using INT-59 and 2-(3-fluorophenyl)acetic acid using General Procedures 7 then 8. Compound 421 was prepared using INT-59 and 2-(3-(trifluoromethyl)phenyl)acetic acid using General Procedures 7 then 8. Compound 423 was prepared using INT-59 and 2-(3-(trifluoromethyl)phenyl)acetic acid using General Procedures 7 then 8. Compound 431 was prepared using INT-59 and isobutyryl chloride using General Procedures 7 then 8. Compound 433 was prepared using INT-59 and 5-methylthiazole-2-carboxylic acid using General Procedures 7 then 8. Compound 437 was prepared using INT-59 and 2-(2,6-difluoro-4-methoxyphenyl)acetic acid using General Procedures 7 then 8. Compound 439 was prepared using INT-59 and 2-(pyrrolidin-1-yl)acetic acid using General Procedures 6 then 8. Compound 447 was prepared using INT-59 and 2-(2,5-dimethyloxazol-4-yl)acetic acid using General Procedures 6 then 8. Compound 455 was prepared using INT-59 and 2-(2-fluoro-4,5-dimethoxyphenyl)acetic acid using General Procedures 7 then 8. Compound 459 was prepared using INT-59 and 2-(2-fluoro-4,5-dimethoxyphenyl)acetic acid using General Procedures 6 then 8.

tert-butyl 2-((4-cyanobenzyl)amino) (INT-60)

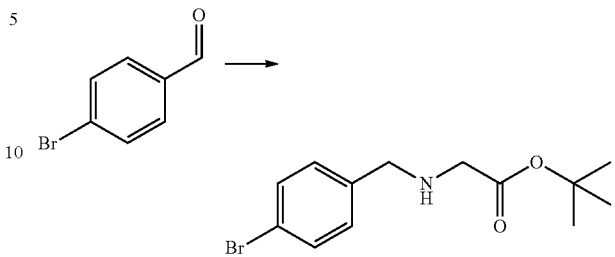

Prepared using General Procedure 12. To a stirred suspension of 4-bromobenzaldehyde (9.88 g, 53.4 mmol) and tert-butyl 2-aminoacetate hydrochloride (8.95 g, 53.4 mmol) in methyl tert-butyl ether (200 mL) were added TEA (8.19 mL, 58.7 mmol) and MgSO$_4$. After stirring at room temperature for 18 h the reaction mixture was filtered and the filtrate concentrated in vacuo. The residue was dissolved in MeOH (200 mL), cooled to 0° C. in an ice bath and sodium borohydride (4.04 g, 107 mmol) was added portionwise. The reaction mixture was allowed to warm to room temperature and was stirred for 18 h. The reaction mixture was quenched with NaHCO$_3$ (200 mL) and after 3 h extracted into EA (300 mL). The organic layer was washed with brine (2×200 mL), dried over MgSO$_4$ and concentrated in vacuo to afford 11.9 g (74%) of tert-butyl 2-((4-bromobenzyl)amino)acetate INT-60. LCMS-ESI (m/z) calculated for $C_{13}H_{18}BrNO_2$: 300. found 300/302 [M+H]$^+$, $t_R$=2.89 min (Method 10).

tert-butyl 2-(N-(4-bromobenzyl)-4-((tert-butoxycarbonyl)amino)benzamido)acetate (INT-61)

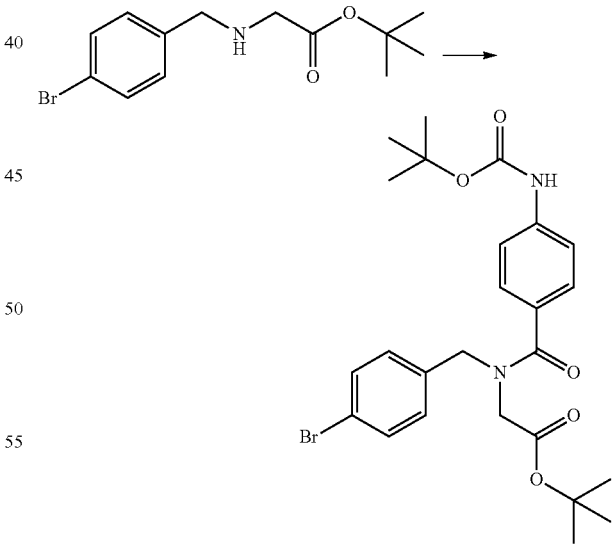

Prepared using General Procedure 6: To a stirred solution of 4-((tert-butoxycarbonyl)amino)benzoic acid (2.0 g, 8.43 mmol), tert-butyl 2-((4-bromobenzyl)amino)acetate INT-60 (2.53 g, 8.43 mmol) and TEA (1.76 mL, 12.6 mmol) in DMF (15 mL) was added HATU (3.53 g, 9.27 mmol) at room temperature. After stirring at room temperature for 2 h the reaction mixture was diluted with EA (150 mL) and washed with brine (200 mL). The organics were concentrated in vacuo and the residue was purified by chromatography (EA/hexanes) to afford 3.97 g (91%) of tert-butyl 2-(N-(4-bromobenzyl)-4-((tert-butoxycarbonyl)amino)benzamido)acetate INT-61 as a viscous oil. LCMS-ESI (m/z) calculated for $C_{25}H_{31}BrN_2O_5$: 519. found: 517/519 [M−H]⁻, $t_R$=2.68 min (Method 10).

General Procedure 21: Preparation of Aryl Acids Via Aryl Bromides and Iodides

To a stirred suspension of lithium formate (3 eq) in DMF was added DIEA (2 eq) and acetic anhydride (2 eq) at room temperature. After 0.5-2 h the reaction mixture was purged with $N_2$ gas then a solution aryl bromide or iodide (1 eq) and $PdCl_2(dppf)$ (0.1 eq) in DMF was added. The reaction mixture was heated at 120° C. for up to 5 h then poured onto 1 M citric acid and extracted with EA. The organics were washed with brine then concentrated and purified by chromatography.

4-((N-(2-(tert-butoxy)-2-oxoethyl)-4-((tert-butoxycarbonyl)amino)benzamido)methyl)benzoic acid (INT-62)

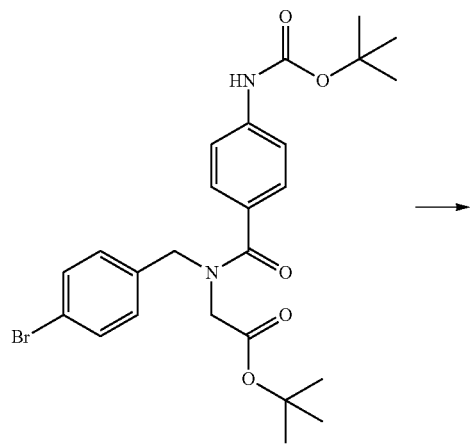

→

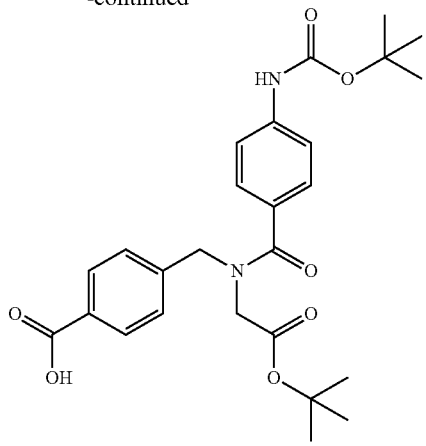

Prepared using General Procedure 21. To a stirred suspension of lithium formate (1.19 g, 22.9 mmol) in DMF (10 mL) was added DIEA (2.67 mL, 15.3 mmol) and acetic anhydride (1.44 mL, 15.3 mmol) at room temperature. After 30 min the reaction mixture was purged with $N_2$ and a solution of tert-butyl 2-(N-(4-bromobenzyl)-4-((tert-butoxycarbonyl)amino)benzamido)acetate INT-61 (3.97 g, 7.64 mmol) and $PdCl_2(dppf)$ (0.559 g, 0.764 mmol) in DMF (5 mL) was added. The reaction mixture was heated for 1 h at 120° C. The reaction mixture was poured onto 1 M citric acid (200 mL) and extracted with EA (200 mL). The organics were washed with brine (200 mL), dried over $MgSO_4$ and concentrated in vacuo. The crude product was purified by chromatography (1% AcOH in EA/hexanes) to afford 2.92 g (79%) of 4-((N-(2-(tert-butoxy)-2-oxoethyl)-4-((tert-butoxycarbonyl)amino)benzamido)methyl)benzoic acid INT-62 as a red-tinged foam. LCMS-ESI (m/z) calculated for $C_{26}H_{32}N_2O_7$: 484. found 430 [M-t-Bu+H]⁺, $t_R$=2.23 min (Method 10).

tert-butyl 2-(4-(((tert-butoxycarbonyl)amino)-N-(4-(3-(4'-methyl-[1,1'-biphenyl]-4-yl)-1,2,4-oxadiazol-5-yl)benzyl)benzamido)acetate (INT-63)

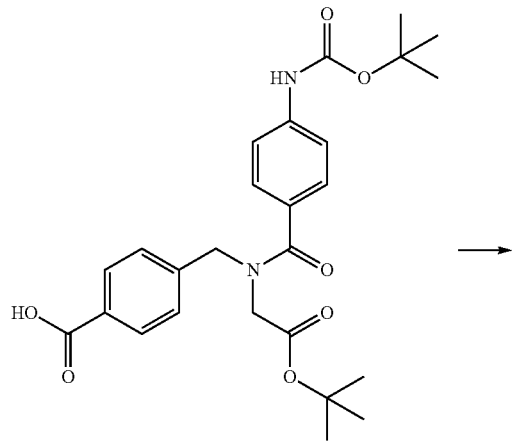

→

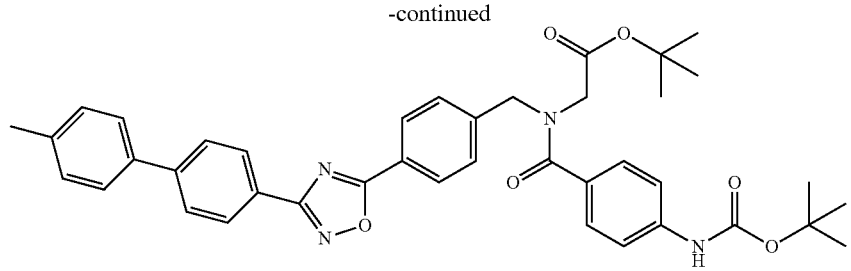

Prepared from INT-62 and INT-40. To a stirred solution of 4-((N-(2-(tert-butoxy)-2-oxoethyl)-4-((tert-butoxycarbonyl)amino)benzamido)methyl)benzoic acid INT-62 (1.57 g, 3.24 mmol) in dioxane (40 mL) and 4-methylmorpholine (0.712 mL, 6.48 mmol) was added isobutyl carbonochloridate (0.420 mL, 3.24 mmol) dropwise. After 30 min the reaction mixture was added to a solution of (Z)—N'-hydroxy-4'-methyl-[1,1'-biphenyl]-4-carboximidamide INT-40 (0.733 g, 3.24 mmol) in DMF (4 mL). After 30 mins the reaction was heated at 110° C. for 2 h. The reaction mixture was cooled to room temperature, diluted with EA (150 mL) and washed with brine (200 mL). The organics were pre-absorbed onto silica gel and purified by chromatography (MeCN/DCM) to afford 659 mg (30%) of tert-butyl 2-(4-((tert-butoxycarbonyl)amino)-N-(4-(3-(4'-methyl-[1,1'-biphenyl]-4-yl)-1,2,4-oxadiazol-5-yl)benzyl)benzamido)acetate INT-63 as a viscous oil. LCMS-ESI (m/z) calculated for $C_{40}H_{42}N_4O_6$: 674; no m/z observed, $t_R$=3.29 min (Method 10).

tert-butyl 2-(4-amino-N-(4-(3-(4'-methyl-[1,1'-biphenyl]-4-yl)-1,2,4-oxadiazol-5-yl)benzyl)benzamido)acetate (INT-64)

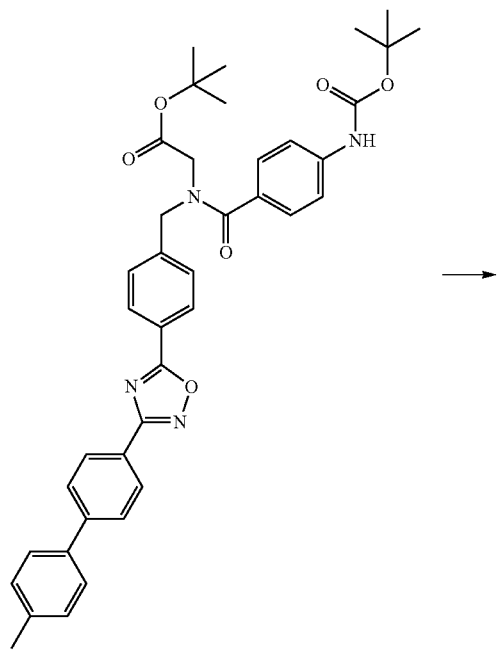

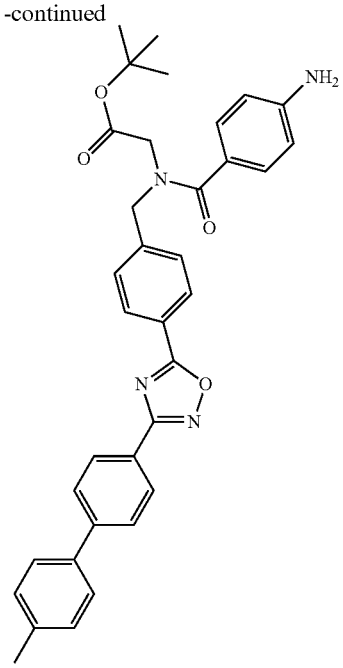

Prepared using General Procedure 8. To a stirred solution of tert-butyl 2-(4-((tert-butoxy carbonyl)amino)-N-(4-(3-(4'-methyl-[1,1'-biphenyl]-4-yl)-1,2,4-oxadiazol-5-yl)benzyl)benzamido)acetate INT-63 (659 mg, 0.977 mmol) in DCM (15 mL) was added TFA (752 µL, 9.77 mmol) at room temperature. After 2 h additional TFA (752 µL, 9.77 mmol) was added and the reaction mixture stirred for a further 3 h at room temperature. The reaction mixture was diluted with toluene (20 mL) and the solvent removed in vacuo. The residue was diluted with EA (100 mL) and washed with NaHCO$_3$ (30 mL). The organics were concentrated in vacuo and the crude product was purified by chromatography (EA/hexanes) to afford 284 mg (50%) of tert-butyl 2-(4-amino-N-(4-(3-(4'-methyl-[1,1'-biphenyl]-4-yl)-1,2,4-oxadiazol-5-yl)benzyl)benzamido)acetate INT-64 as an off-white powder. LCMS-ESI (m/z) calculated for $C_{35}H_{34}N_4O_4$: 574. found 519 [M-t-Bu+H]$^+$, 573 [M−H]$^−$, $t_R$=3.12 min (Method 10).

Compound 454 was prepared from INT-64 and 2-(2-fluoro-4-methoxyphenyl)acetic acid using General Procedures 6 then 9. Compound 456 was prepared from INT-64 and 2-(2-(trifluoromethyl)phenyl)acetic acid using General Procedures 6 then 9.

169 tert-butyl 2-(4-(2-(2,5-dimethoxyphenyl)acetamido)-N-(4-(3-(4'-methyl-[1,1'-biphenyl]-4-yl)-1,2,4-oxadiazol-5-yl)benzyl)benzamido)acetate (INT-65)

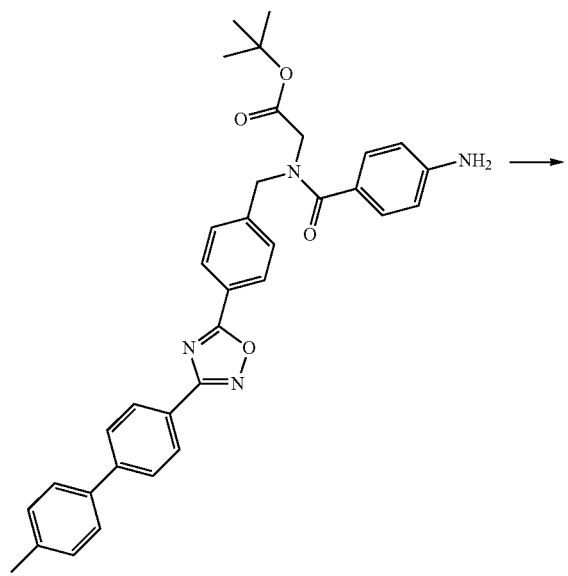

Prepared using General Procedure 6. To a suspension of tert-butyl 2-(4-amino-N-(4-(3-(4'-methyl-[1,1'-biphenyl]-4-yl)-1,2,4-oxadiazol-5-yl)benzyl)benzamido)acetate INT-64 (60 mg, 0.104 mmol) and 2-(2,5-dimethoxyphenyl)acetic acid (20.48 mg, 0.104 mmol) stirring in DMF (2 mL) were added HATU (43.7 mg, 0.115 mmol) and TEA (36.4 μL, 0.261 mmol). After stirring at room temperature for 2 h the reaction mixture was diluted with EA (25 mL) and washed with NaHCO₃ (2×25 mL), 1 M HCl (2×25 mL) and brine (25 mL). The organics were dried over MgSO₄ and concentrated in vacuo. The crude product was purified by chromatography (EA/hexanes) to afford 56 mg (71%) of tert-butyl 2-(4-(2-(2,5-dimethoxyphenyl)acetamido)-N-(4-(3-(4'-methyl-[1,1'-biphenyl]-4-yl)-1,2,4-oxadiazol-5-yl)benzyl)

170 benzamido)acetate INT-65. LCMS-ESI (m/z) calculated for $C_{45}H_{44}N_4O_7$: 752. found 753 [M+H]$^+$, $t_R$=2.76 min (Method 10).

2-(4-(2-(2,5-dimethoxyphenyl)acetamido)-N-(4-(3-(4'-methyl-[1,1'-biphenyl]-4-yl)-1,2,4-oxadiazol-5-yl)benzyl)benzamido)acetic acid (Compound 457)

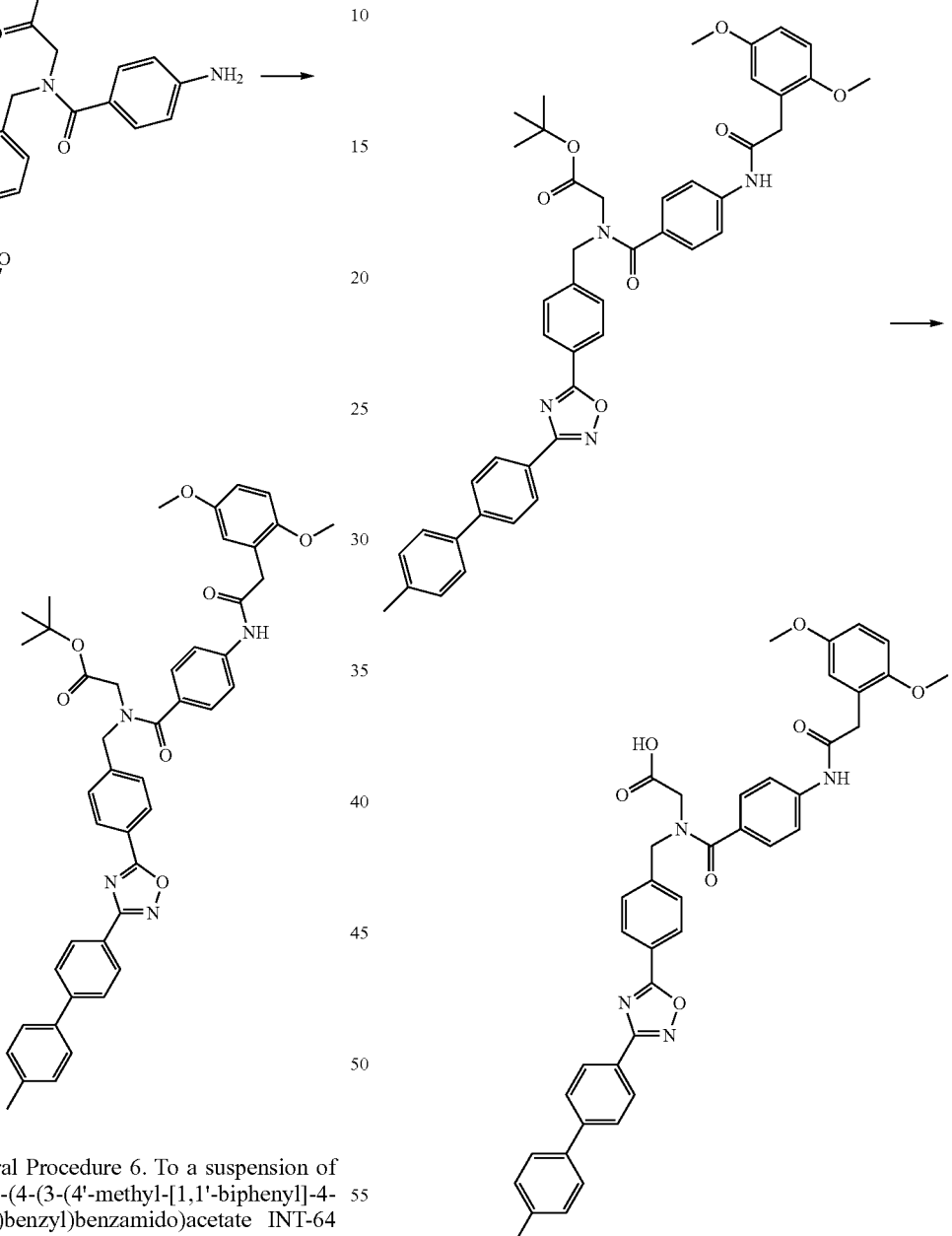

Prepared using General Procedure 9. To a stirring solution of tert-butyl 2-(4-(2-(2,5-dimethoxyphenyl)acetamido)-N-(4-(3-(4'-methyl-[1,1'-biphenyl]-4-yl)-1,2,4-oxadiazol-5-yl)benzyl)benzamido)acetate INT-65 (55 mg, 0.073 mmol) in THF (2 mL) and MeOH (0.25 mL) was added 1 M LiOH (146 μL, 0.146 mmol). The reaction mixture was stirred at room temperature for 20 h and a precipitate was formed. The mixture was filtered under vacuum and the captured solid washed with diethyl ether (5 mL). The captured solid was under vacuum to provide 36 mg (71%) of 2-(4-(2-(2,5-dimethoxyphenyl)acetamido)-N-(4-(3-(4'-methyl-[1,1'-biphenyl]-4-yl)-1,2,4-oxadiazol-5-yl)benzyl)benzamido)acetic acid 457 as a white solid. LCMS-ESI (m/z) calculated for $C_{41}H_{36}N_4O_7$: 696. found 697 [M+H]$^+$, $t_R$=9.84 min (Method 9). $^1$H NMR (400 MHz, DMSO) δ 9.89 (s, 1H), 8.22-8.11 (m, 4H), 7.87 (d, J=8.4 Hz, 2H), 7.66 (d, J=8.1 Hz, 2H), 7.60 (d, J=8.6 Hz, 4H), 7.51 (d, J=8.0 Hz, 2H), 7.33 (d, J=7.9 Hz, 2H), 6.94-6.90 (m, 1H), 6.88 (d, J=3.1 Hz, 1H), 6.83-6.78 (m, 1H), 4.81 (s, 2H), 3.75 (s, 3H), 3.72 (s, 3H), 3.64 (s, 2H), 3.48 (s, 2H), 2.39 (s, 3H).

tert-butyl 2-(4-(2-(2,6-dimethoxyphenyl)acetamido)-N-(4-(3-(4'-methyl-[1,1'-biphenyl]-4-yl)-1,2,4-oxadiazol-5-yl)benzyl)benzamido)acetate (INT-66)

Prepared using General Procedure 6. To a suspension of tert-butyl 2-(4-amino-N-(4-(3-(4'-methyl-[1,1'-biphenyl]-4-yl)-1,2,4-oxadiazol-5-yl)benzyl)benzamido)acetate INT-64 (90 mg, 0.157 mmol) and 2-(2,6-dimethoxyphenyl)acetic acid (30.7 mg, 0.157 mmol) stirring in DMF (2 mL) were added HATU (65.5 mg, 0.172 mmol), DMAP (15 mg, 0.123 mmol) and TEA (54.6 µL, 0.392 mmol). After stirring at room temperature for 18 h 2-(2,6-dimethoxyphenyl)acetic acid (30.7 mg, 0.157 mmol), HATU (65.5 mg, 0.172 mmol) and TEA (21.83 µl, 0.157 mmol) were added. The reaction mixture was stirred at room temperature for 72 h then at 50° C. for 2 h and 60° C. for 2 h. The reaction mixture was cooled to room temperature and more HATU (65.5 mg, 0.172 mmol) was added. After 18 h the reaction mixture was diluted with EA (25 mL) and washed with NaHCO$_3$ (2×25 mL), 1 M HCl (2×25 mL) and brine (25 mL). The combined organics were dried over MgSO$_4$ and concentrated in vacuo. The crude product was purified by chromatography (EA/hexanes) to afford 47 mg (40%) of tert-butyl 2-(4-(2-(2,5-dimethoxyphenyl)acetamido)-N-(4-(3-(4'-methyl-[1,1'-biphenyl]-4-yl)-1,2,4-oxadiazol-5-yl)benzyl)benzamido)acetate INT-66. LCMS-ESI (m/z) calculated for $C_{45}H_{44}N_4O_7$: 752. found 753 [M+H]$^+$, $t_R$=2.79 min (Method 10).

2-(4-(2-(2,6-dimethoxyphenyl)acetamido)-N-(4-(3-(4'-methyl-[1,1'-biphenyl]-4-yl)-1,2,4-oxadiazol-5-yl)benzyl)benzamido)acetic acid (Compound 458)

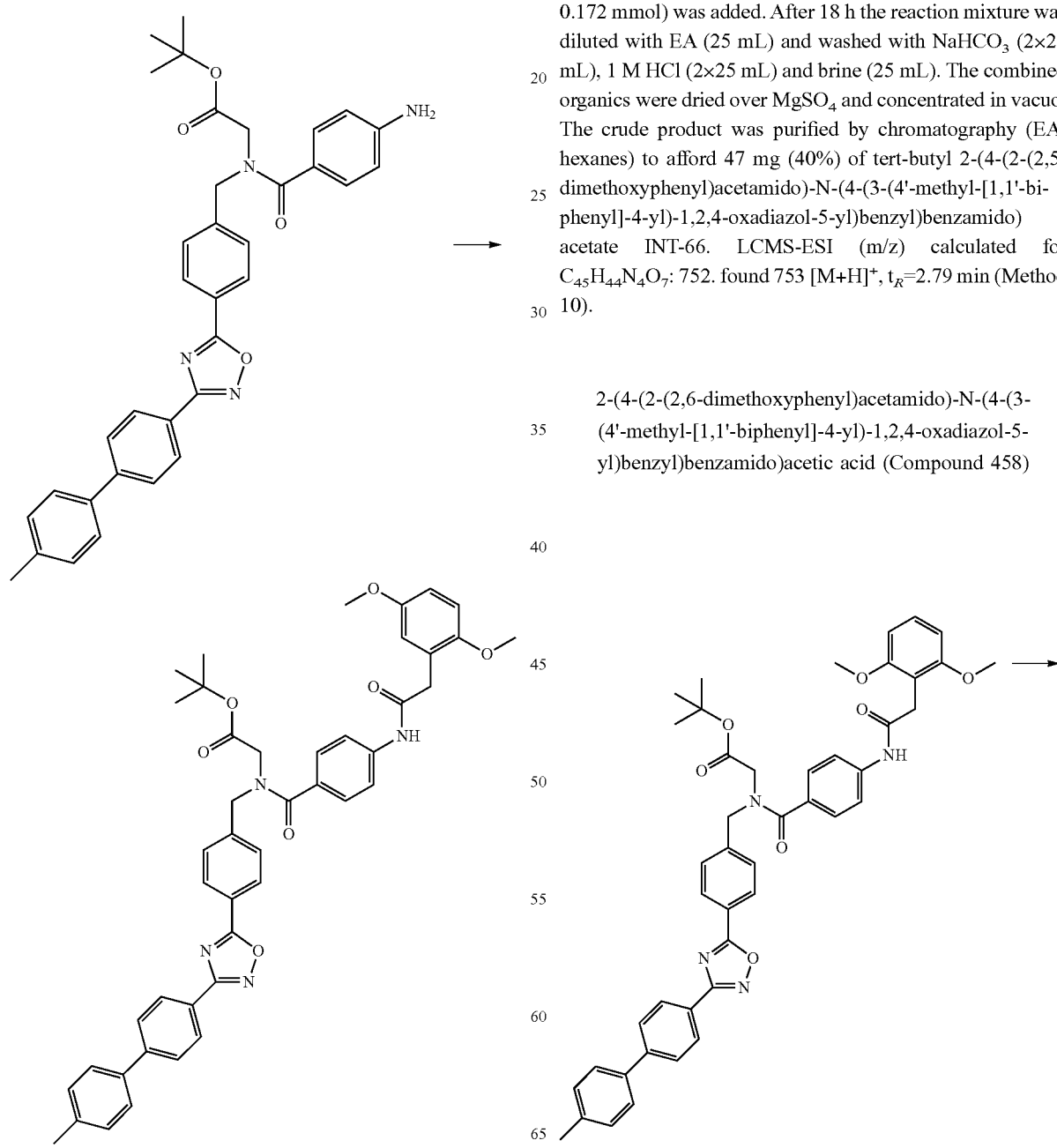

-continued

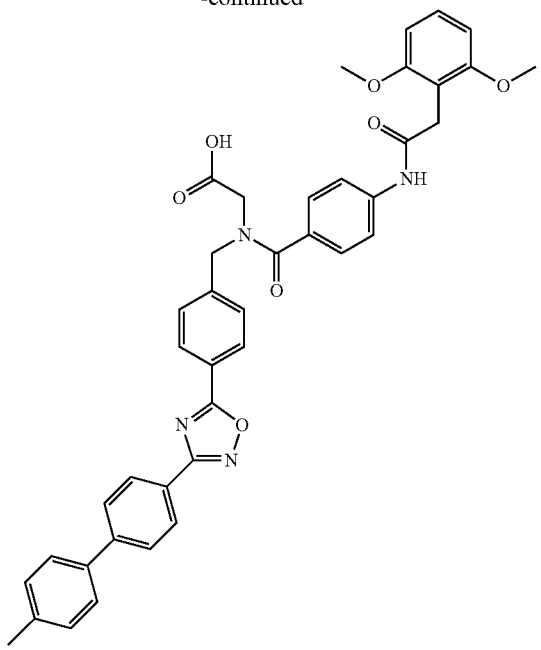

Prepared using General Procedure 9. To a stirring solution of tert-butyl 2-(4-(2-(2,5-dimethoxyphenyl)acetamido)-N-(4-(3-(4'-methyl-[1,1'-biphenyl]-4-yl)-1,2,4-oxadiazol-5-yl)benzyl)benzamido)acetate INT-66 (45 mg, 0.060 mmol) in THF (2 mL) and MeOH (0.25 mL) was added 1 M LiOH (120 μL, 0.120 mmol). The reaction mixture was stirred at room temperature for 20 h and a precipitate was formed. The mixture was filtered under vacuum and the captured solid washed with diethyl ether (5 mL). The captured solid was dried in a vacuum oven to provide 20 mg (48%) of 2-(4-(2-(2,6-dimethoxyphenyl)acetamido)-N-(4-(3-(4'-methyl-[1,1'-biphenyl]-4-yl)-1,2,4-oxadiazol-5-yl)benzyl)benzamido)acetic acid 458. LCMS-ESI (m/z) calculated for $C_{41}H_{36}N_4O_7$: 696. found 697 [M+H]$^+$, $t_R$=9.08 min (Method 9). $^1$H NMR (400 MHz, DMSO) δ 9.70 (s, 1H), 8.22-8.12 (m, 4H), 7.92-7.83 (m, 2H), 7.70-7.64 (m, 2H), 7.63-7.54 (m, 4H), 7.53-7.46 (m, 2H), 7.33 (d, J=7.9 Hz, 2H), 7.22 (t, J=8.3 Hz, 1H), 6.67 (d, J=8.3 Hz, 2H), 4.80 (s, 2H), 3.78 (s, 6H), 3.67 (s, 2H), 3.47 (s, 2H), 2.39 (s, 3H).

Compounds 462-470 and 473-477 were prepared using INT-37 and the appropriate nitrile employing General Procedures 19, 20 then 8.

Compounds 484-489 were prepared using INT-33 and the appropriate carboxylic acid using General Procedures 20 then 8.

2-(4-(2-(4-methoxy-2-(trifluoromethyl)phenyl)acetamido)-N-(4-(5-(p-tolylethynyl)-1,2,4-oxadiazol-3-yl)benzyl)benzamido)acetic acid (Compound 471)

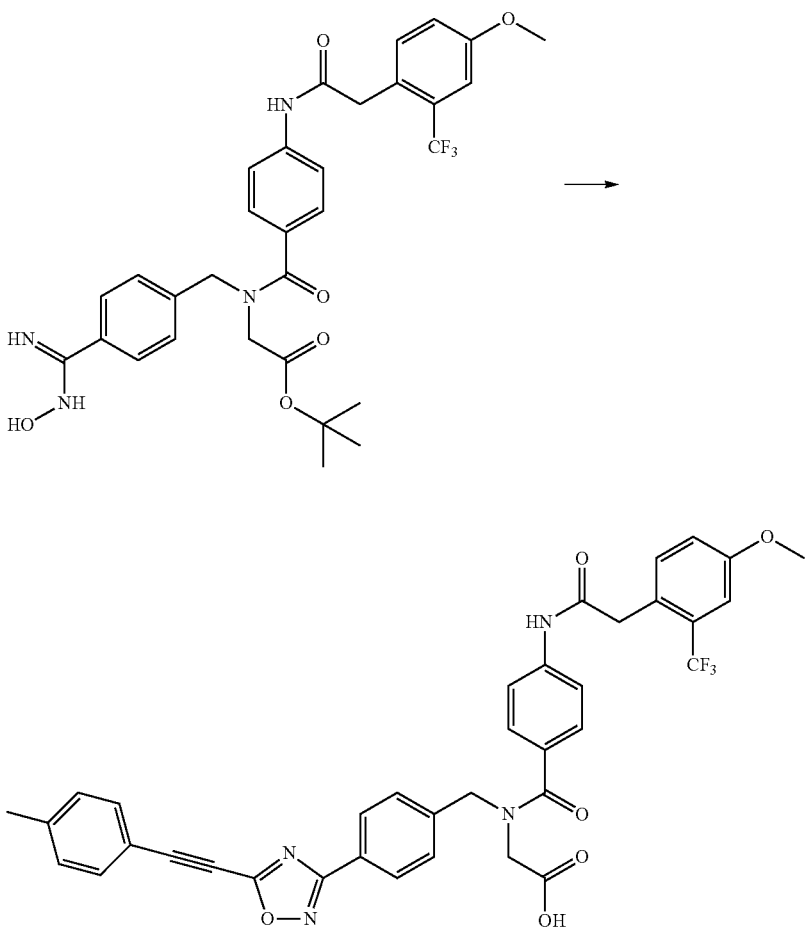

Prepared using General Procedures 20 and 8. To a stirred solution of tert-butyl 2-(N-(4-(N-hydroxycarbamimidoyl)benzyl)-4-(2-(4-methoxy-2-(trifluoromethyl)phenyl)acetamido)benzamido)acetate INT-33 (200 mg, 0.325 mmol) in dioxanes (4 mL) was added DIEA (85 µL, 0.488 mmol) then 3-(p-tolyl)propioloyl chloride (60 mg, 0.36 mmol). The reaction mixture was stirred at room temperature for 30 mins then at 120° C. for 3 h. The reaction mixture was allowed to cool to room temperature, diluted with EA (100 mL) and washed with brine (100 mL). The organics were concentrated and the residue diluted with DCM (5 mL) and TFA (2 mL) was added. The reaction mixture was stirred at room temperature for 2 h. The reaction mixture was concentrated in vacuo and purified by preparative HPLC to afford 44 mg (19%) of 2-(4-(2-(4-methoxy-2-(trifluoromethyl)phenyl)acetamido)-N-(4-(5-(p-tolylethynyl)-1,2,4-oxadiazol-3-yl)benzyl)benzamido)acetic acid 471 as an off-white powder. LCMS-ESI (m/z) calculated for $C_{37}H_{29}F_3N_4O_6$: 682. found 683 [M+H]$^+$, $t_R$=8.49 min (Method 9).

tert-butyl 2-(N-(4-(5-amino-1,2,4-oxadiazol-3-yl)benzyl)-4-nitrobenzamido)acetate (INT-67)

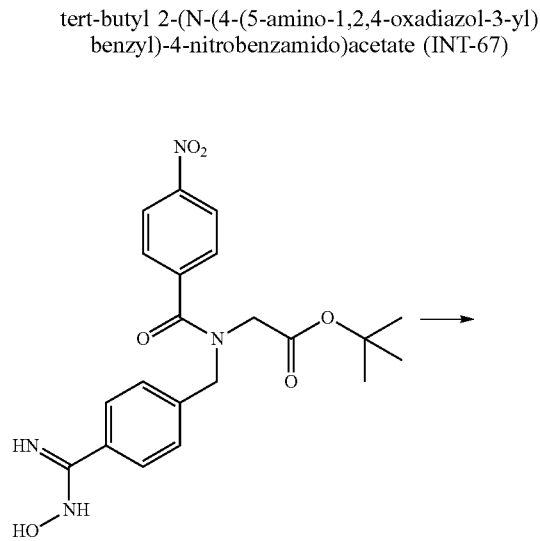

Prepared from INT-57. To a stirring suspension of tert-butyl 2-(N-(4-(N-hydroxycarbamimidoyl)benzyl)-4-nitrobenzamido)acetate INT-57 (820 mg, 1.91 mmol) in dioxane (10 mL) was added 2,2,2-trichloroacetic anhydride (420 µL, 2.30 mmol) and heated to 120° C. for 2 h. To this mixture was added 7 M ammonia in MeOH (10 mL) and stirred at room temperature for 18 h. The reaction mixture was pre-absorbed onto silica gel and purified by chromatography (EA/hexanes) to afford 342 mg (39%) of tert-butyl 2-(N-(4-(5-amino-1,2,4-oxadiazol-3-yl)benzyl)-4-nitrobenzamido)acetate) INT-67 as a white solid. LCMS-ESI (m/z) calculated for $C_{22}H_{23}N_5O_6$: 453. found 454 [M+H]$^+$, $t_R$=2.30 min (Method 10).

tert-butyl 2-(N-(4-(5-(4-methylphenylsulfonamido)-1,2,4-oxadiazol-3-yl)benzyl)-4-nitrobenzamido)acetate (INT-68)

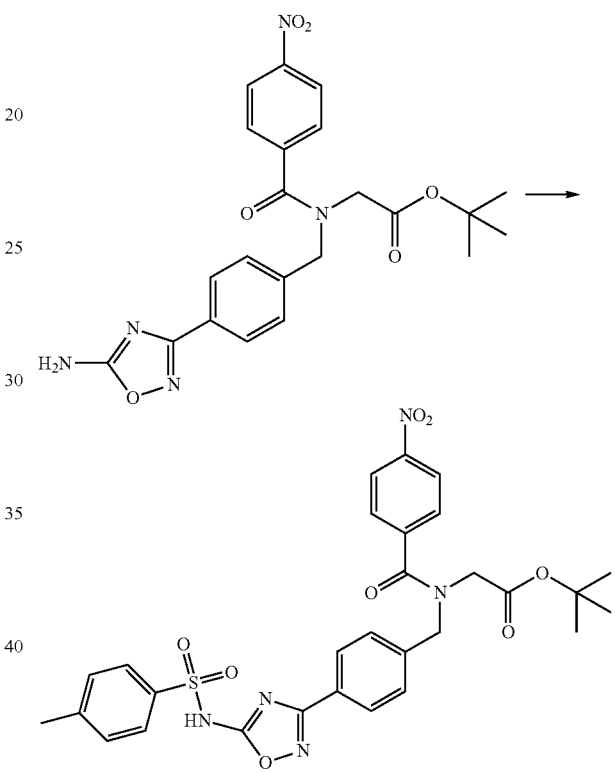

Prepared using General Procedure 10. To a stirring solution of tert-butyl 2-(N-(4-(5-amino-1,2,4-oxadiazol-3-yl)benzyl)-4-nitrobenzamido)acetate INT-67 (150 mg, 0.331 mmol) in THF (3 mL) was added potassium tert-butoxide (599 µL, 0.992 mmol) at room temperature. After 15 mins a solution of 4-methylbenzene-1-sulfonyl chloride (63.1 mg, 0.331 mmol) in THF (1 mL) was added. After 1 h the reaction mixture quenched with 1 M HCl (30 mL) and then extracted with EA (50 mL). The organic layer was concentrated in vacuo and purified by chromatography (EA/hexanes) to provide 20 mg (10%) of tert-butyl 2-(N-(4-(5-(4-methylphenylsulfonamido)-1,2,4-oxadiazol-3-yl)benzyl)-4-nitrobenzamido)acetate INT-68. LCMS-ESI (m/z) calculated for $C_{29}H_{29}N_5O_8S$: 607. found 608 [M+H]$^+$, $t_R$=2.50 min (Method 10).

177 tert-butyl 2-(4-amino-N-(4-(5-(4-methylphenylsulfonamido)-1,2,4-oxadiazol-3-yl)benzyl)benzamido)acetate (INT-69)

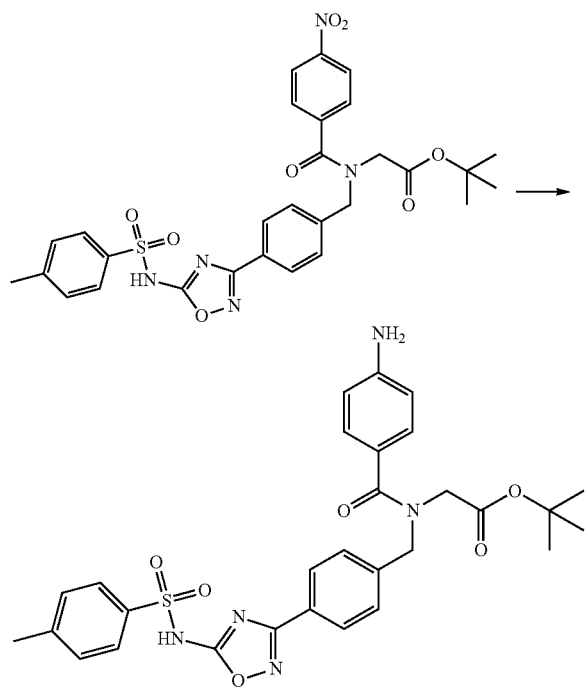

Prepared using General Procedure 5. To a stirred solution of tert-butyl 2-(N-(4-(5-(4-methylphenylsulfonamido)-1,2,4-oxadiazol-3-yl)benzyl)-4-nitrobenzamido)acetate INT-68 (20 mg, 0.033 mmol) in THF (3 mL) and water (1 mL) was added sodium dithionite (17.2 mg, 0.099 mmol) and heated to 65° C. for 2 h. The reaction mixture was extracted with EA (10 mL) and washed with brine (10 mL). The organics were concentrated in vacuo to afford 13 mg (65%) of tert-butyl 2-(4-amino-N-(4-(5-(4-methylphenylsulfonamido)-1,2,4-oxadiazol-3-yl)benzyl)benzamido)acetate INT-69 as a white solid. LCMS-ESI (m/z) calculated for $C_{29}H_{31}N_5O_6S$: 577. found 576 [M−H]⁻, $t_R$=2.41 min (Method 5).

2-(4-(2-(4-methoxy-2-(trifluoromethyl)phenyl)acetamido)-N-(4-(5-(4-methylphenylsulfonamido)-1,2,4-oxadiazol-3-yl)benzyl)benzamido)acetic acid (Compound 480)

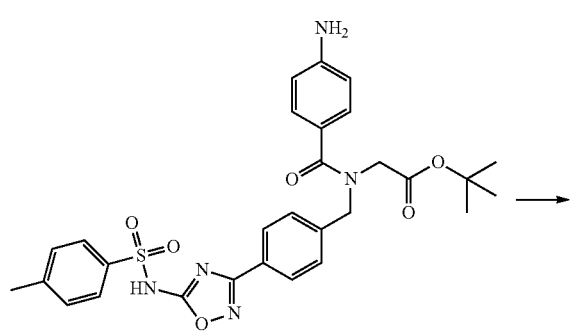

178

-continued

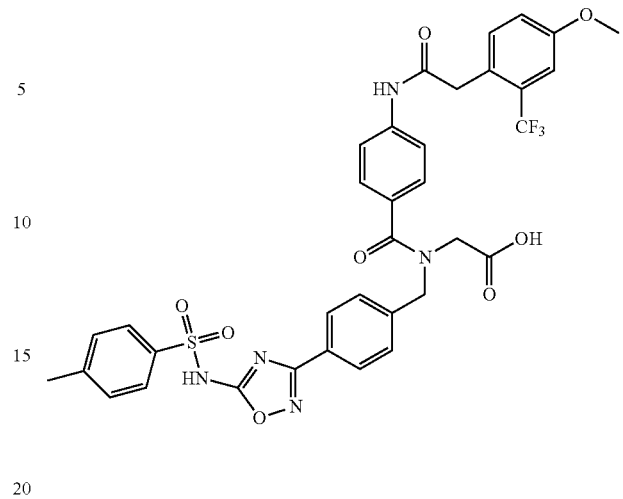

Prepared using General Procedures 7 and 8: To a stirring suspension of 2-(4-methoxy-2-(trifluoromethyl)phenyl)acetic acid (26.4 mg, 0.113 mmol) in DCM (1 mL) and DMF (10 µL) was added oxalyl chloride (9.85 µL, 0.113 mmol) at room temperature. After 1 h the reaction mixture was added to a solution of tert-butyl 2-(4-amino-N-(4-(5-(4-methylphenylsulfonamido)-1,2,4-oxadiazol-3-yl)benzyl)benzamido)acetate INT-69 (13 mg, 0.023 mmol) in DCM (0.5 mL) and TEA (6.27 µL, 0.045 mmol). After stirring at room temperature for 2 h TFA (0.5 mL) was added. The reaction mixture was concentrated in vacuo and purified by preparative HPLC to afford 3.2 mg (18%) of 2-(4-(2-(4-methoxy-2-(trifluoromethyl)phenyl)acetamido)-N-(4-(5-(4-methylphenylsulfonamido)-1,2,4-oxadiazol-3-yl)benzyl)benzamido)acetic acid 480 as an off-white solid. LCMS-ESI (m/z) calculated for $C_{35}H_{30}F_3N_5O_8S$: 737. found 738 [M+H]⁺, $t_R$=5.74 min (Method 9).

Ethyl 2-(2-(4-methoxy-2-(trifluoromethyl)phenyl)acetamido)oxazole-5-carboxylate (INT-70)

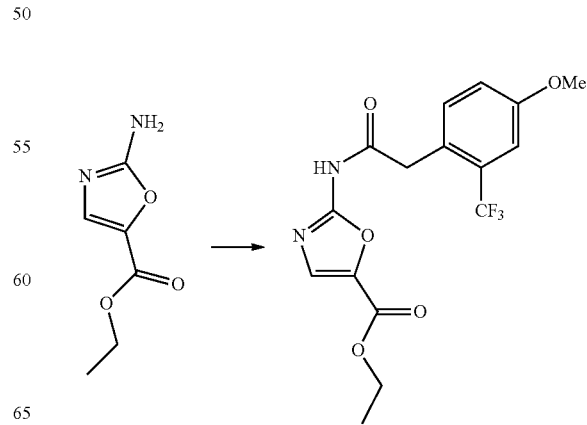

Prepared using General Procedure 6: INT-70 was prepared in a similar fashion to INT-14 using methyl ethyl 2-aminooxazole-5-carboxylate in place of methyl 4-aminobenzoate to yield 2.1 g (67%) of ethyl 2-(2-(4-methoxy-2-(trifluoromethyl)phenyl)acetamido)oxazole-5-carboxylate INT-70 which was used in the next step without purification. LCMS-ESI (m/z) calculated for $C_{16}H_{15}F_3N_2O_5$: 372. found 373, [M+H]$^+$, $t_R$=3.21 min (Method 1).

4-(2-(4-methoxy-2-(trifluoromethyl)phenyl)acetamido)benzoic acid (INT-71)

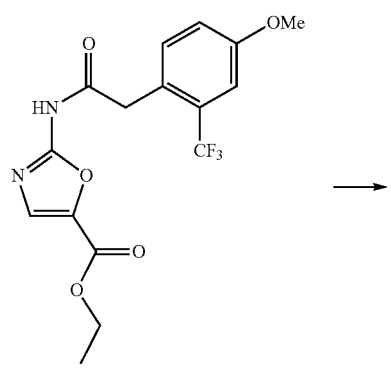

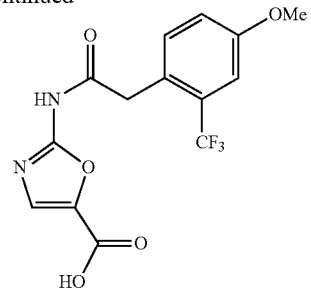

Prepared using General Procedure 9: INT-71 was prepared from INT-70, in a similar fashion to INT-15 to yield 1.78 g (88%) of 4-(2-(4-methoxy-2-(trifluoromethyl)phenyl)acetamido)benzoic acid INT-71 which was used in the next step without purification. LCMS-ESI (m/z) calculated for $C_{14}H_{11}F_3N_2O_5$: 344. found 345, [M+H]$^+$, $t_R$=2.73 min (Method 1).

Compound 491 was prepared using INT-28 and INT-71 employing methods analogous to General Procedures 6 then 8.

Compound 492 was prepared using 2-bromo-1-(4-methoxyphenyl)ethanone, tert-butyl piperazine-1-carboxylate and INT-31 employing methods analogous to General Procedures 4, 8, 9, 6, 19, 20 then 8.

4-(2-(4-methoxy-2-(trifluoromethyl)phenyl)acetamido)-N-(4-(5-(4'-methyl-[1,1'-biphenyl]-4-yl)-1,2,4-oxadiazol-3-yl)benzyl)-N-(2-(methylsulfonamido)-2-oxoethyl)benzamide (Compound 493)

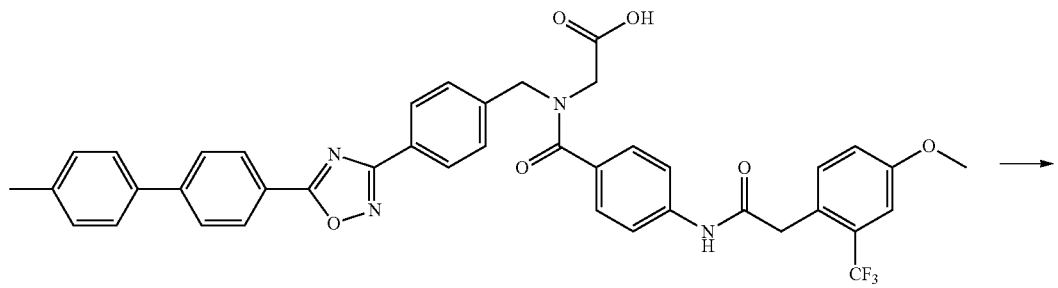

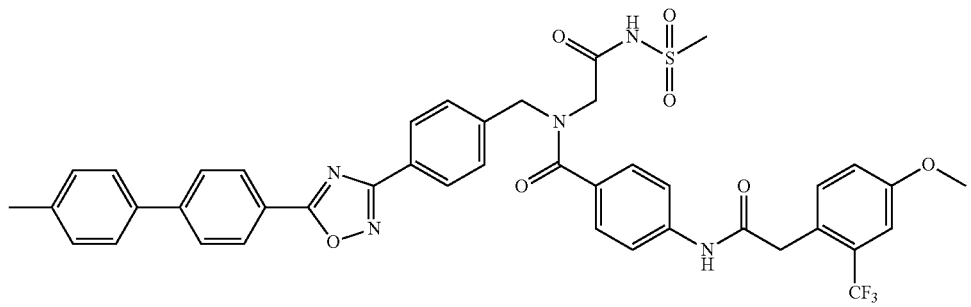

To a stirred solution of 2-(4-(2-(4-methoxy-2-(trifluoromethyl)phenyl)acetamido)-N-(4-(5-(4'-methyl-[1,1'-biphenyl]-4-yl)-1,2,4-oxadiazol-3-yl)benzyl)benzamido)acetic acid 354 (15 mg, 0.02 mmol), methanesulfonamide (2.9 mg, 0.03 mmol) and N,N-dimethylaminopyridine (5 mg, 0.04 mmol) in anhydrous DCM (1 mL) was added dicylcohexylcarbodiimide (6.3 mg). The reaction mixture was stirred at room temperature for 12 h. The reaction was diluted with DCM (2 mL) and washed with saturated NaHCO$_3$ solution (5 mL), brine (5 mL), dried over (MgSO$_4$) then concentrated. The crude product was isolated by HPLC to afford 4-(2-(4-methoxy-2-(trifluoromethyl)phenyl)acetamido)-N-(4-(5-(4'-methyl-[1,1'-biphenyl]-4-yl)-1,2,4-oxadiazol-3-yl)benzyl)-N-(2-(methylsulfonamido)-2-oxoethyl)benzamide 493. LCMS-ESI (m/z) calculated for $C_{42}H_{36}F_3N_5O_7S$: 812; no ion observed, $t_R$=11.03 min (Method 2).

Methyl 2-(2-(4-(2-(4-methoxy-2-(trifluoromethyl)phenyl)acetamido)-N-(4-(5-(4'-methyl-[1,1'-biphenyl]-4-yl)-1,2,4-oxadiazol-3-yl)benzyl)benzamido)acetamido)-2-methylpropanoate (INT-72)

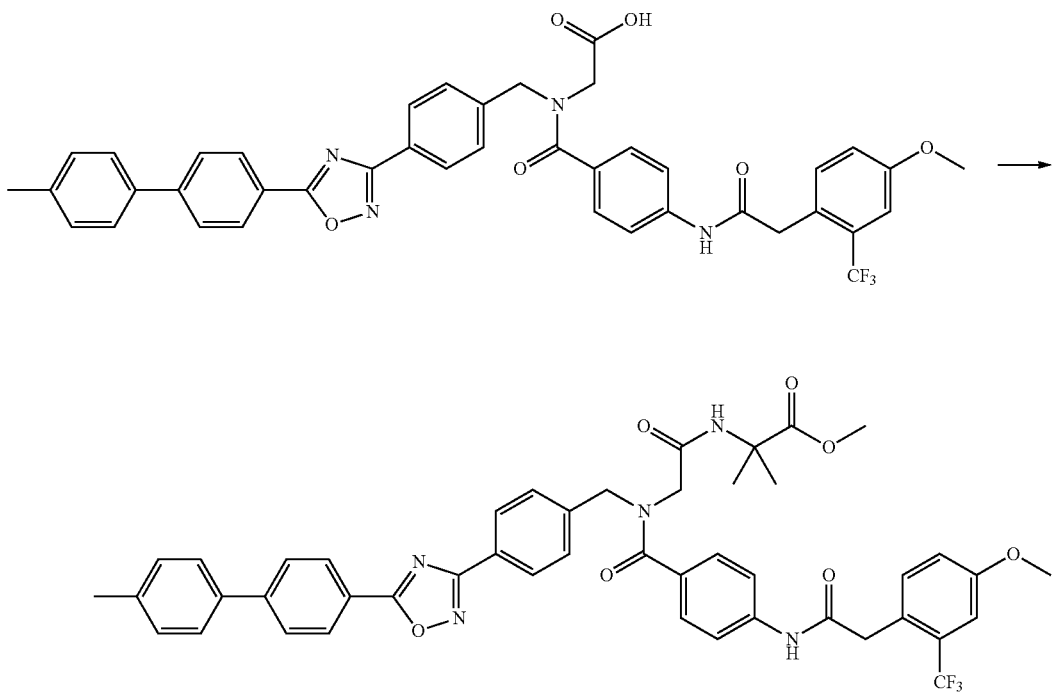

To a stirring solution of 2-(4-(2-(4-methoxy-2-(trifluoromethyl)phenyl)acetamido)-N-(4-(5-(4'-methyl-[1,1'-biphenyl]-4-yl)-1,2,4-oxadiazol-3-yl)benzyl)benzamido)acetic acid 354 (15 mg, 0.02 mmol), methyl 2-amino-2-methylpropanoate (3.6 mg, 0.03 mmol) and HOBt (3.03 mg, 0.02 mmol) in anhydrous DMF (0.5 mL) was added dicyclohexyl carbodiimide (DCC) (4.6 mg, 0.02 mmol) at 0° C. The reaction mixture was stirred at 0° C. for 1 h and allowed stir at room temperature for 36 h. The reaction was quenched with saturated NaHCO$_3$ (2 mL) then extracted with EA (2×3 mL). The combined organic extract was washed with brine (5 mL), dried (MgSO$_4$), filtered and concentrated to afford methyl 2-(2-(4-(2-(4-methoxy-2-(trifluoromethyl)phenyl)acetamido)-N-(4-(5-(4'-methyl-[1,1'-biphenyl]-4-yl)-1,2,4-oxadiazol-3-yl)benzyl)benzamido)acetamido)-2-methylpropanoate INT-72 which was used in the next step without purification. LCMS-ESI (m/z) calculated for $C_{46}H_{42}F_3N_5O_7$: 834; no ion observed, $t_R$=4.44 min (Method 3).

2-(2-(4-(2-(4-methoxy-2-(trifluoromethyl)phenyl)
acetamido)-N-(4-(5-(4'-methyl-[1,1'-biphenyl]-4-yl)-
1,2,4-oxadiazol-3-yl)benzyl)benzamido)acetamido)-
2-methylpropanoic acid (Compound 494)

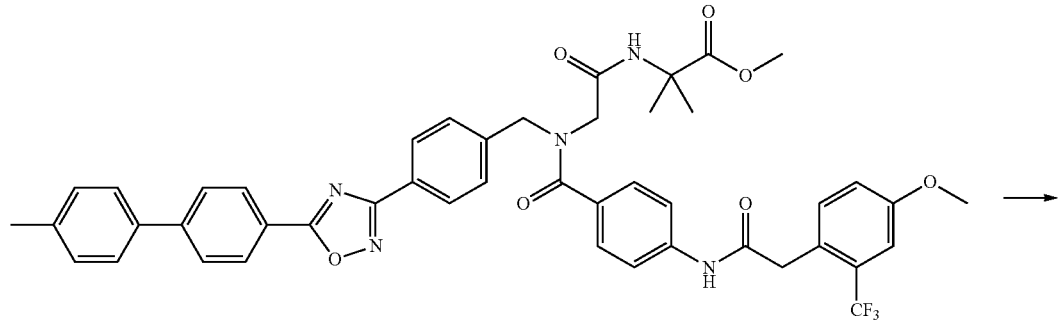

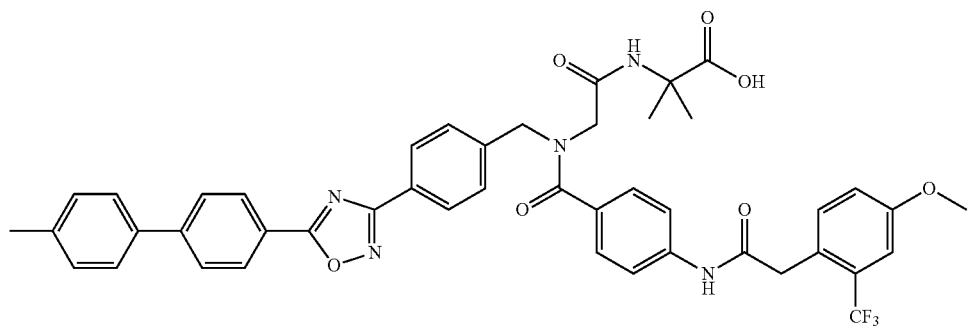

Prepared using General Procedure 9: Compound 494 was prepared from INT-72 and purified by HPLC to afford 5 mg (30%) of 2-(2-(4-(2-(4-methoxy-2-(trifluoromethyl)phenyl)acetamido)-N-(4-(5-(4'-methyl-[1,1'-biphenyl]-4-yl)-1,2,4-oxadiazol-3-yl)benzyl)benzamido)acetamido)-2-methylpropanoic acid. LCMS-ESI (m/z) calculated for $C_{45}H_{40}F_3N_5O_7$: 820. found 821 [M+H]$^+$, $t_R$=11.67 min (Method 2).

methyl 2-((4-cyanobenzyl)amino)acetate (INT-73)

Prepared using General Procedure 13. To a stirred solution of methyl 2-aminoacetate hydrochloride (5.07 g, 40.4 mmol) and 4-(bromomethyl)benzonitrile (7.20 g, 36.7 mmol) in DMF (40 mL) was added potassium carbonate (11.2 g, 81 mmol). After stirring at room temperature for 3 h the reaction mixture was diluted with water (300 mL) and the product extracted into EA (200 mL). The organics were washed with water (200 mL), dried over MgSO$_4$ and concentrated in vacuo. The crude product was purified by chromatography (MeOH/DCM) to afford 1.6 g (21%) of methyl 2-((4-cyanobenzyl)amino)acetate INT-73 as a clear oil. LCMS-ESI (m/z) calculated for $C_{11}H_{12}N_2O_2$: 204. found 205 [M−H]$^+$, $t_R$=0.4 min (Method 10).

methyl 2-((tert-butoxycarbonyl)(4-cyanobenzyl)
amino)acetate (INT-74)

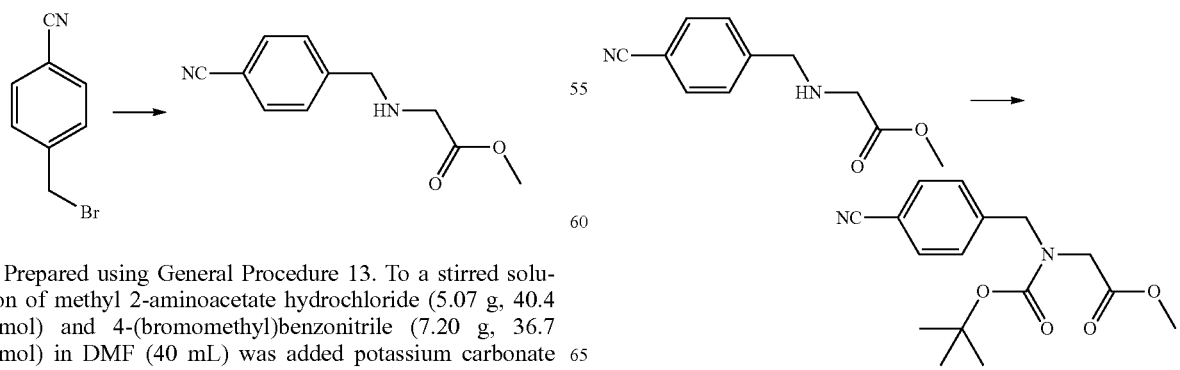

Prepared from INT-73. To a stirred solution of methyl 2-((4-cyanobenzyl)amino)acetate INT-73 (1.6 g, 7.83 mmol) in DCM (30 mL) was added di-tert-butyl dicarbonate (2.70 mL, 11.75 mmol) and DMAP (50 mg). After stirring at room temperature for 2 h the reaction mixture was diluted with DCM (100 mL) and washed with brine (200 mL). The organics were dried over MgSO$_4$ and concentrated in vacuo. The crude product was purified by chromatography (DCM/hexanes) to afford 1.35 g (56%) of methyl 2-((tert-butoxycarbonyl)(4-cyanobenzyl)amino)acetate INT-74 as a viscous orange oil.

methyl 2-((tert-butoxycarbonyl)(4-(N-hydroxycarbamimidoyl)benzyl)amino)acetate (INT-75)

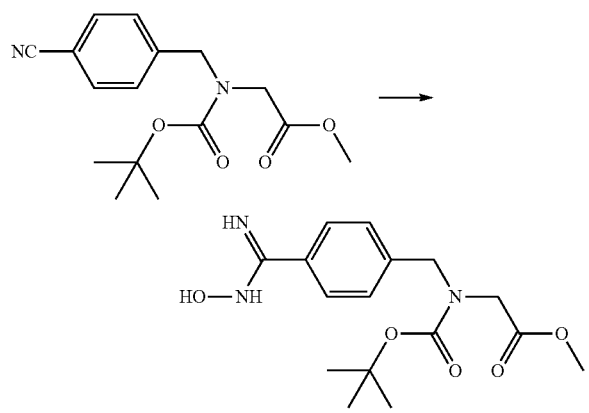

Prepared using General Procedure 19. To a stirring solution of methyl 2-((tert-butoxycarbonyl)(4-cyanobenzyl)amino)acetate INT-74 (1.35 g, 4.44 mmol) in DMF (8 mL) was added TEA (1.546 mL, 11.09 mmol) followed by hydroxylamine hydrochloride (0.771 g, 11.1 mmol). After stirring at room temperature for 48 h the reaction mixture was diluted with EA (100 mL) and the washed with brine (2×150 mL). The crude product was purified by chromatography (MeOH/DCM) to afford 1.28 g (85%) of methyl 2-((tert-butoxycarbonyl)(4-(N-hydroxycarbamimidoyl)benzyl)amino)acetate INT-75 as a viscous oil. LCMS-ESI (m/z) calculated for $C_{16}H_{23}N_3O_5$: 337. found 338 [M−H]$^+$, $t_R$=1.17 min (Method 10).

methyl 2-((tert-butoxycarbonyl)(4-(5-(4'-methyl-[1,1'-biphenyl]-4-yl)-1,2,4-oxadiazol-3-yl)benzyl)amino)acetate (INT-76)

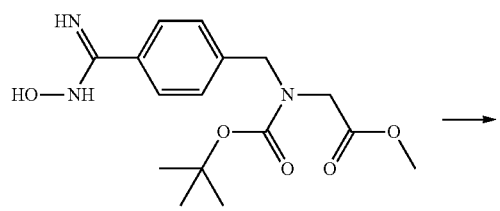

-continued

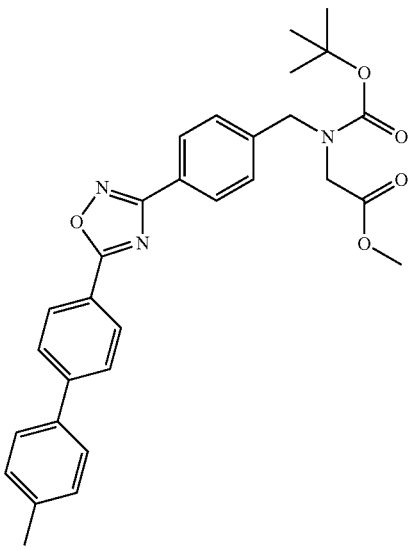

Prepared using General Procedure 20. To a stirring solution of methyl 2-((tert-butoxycarbonyl)(4-(N-hydroxycarbamimidoyl)benzyl)amino)acetate INT-75 (786 mg, 2.33 mmol) and DIEA (448 µL, 2.56 mmol) in dioxanes (15 mL) was added 4'-methyl-[1,1'-biphenyl]-4-carbonyl chloride (591 mg, 2.56 mmol), at room temperature. After 30 min the reaction mixture was heated to 120° C. for 3 h. The reaction mixture was diluted with EA (150 mL) and washed with brine (100 mL). The organics were concentrated in vacuo and the crude product purified by chromatography (MeCN/DCM) to afford 518 mg (43%) of methyl 2-((tert-butoxycarbonyl)(4-(5-(4'-methyl-[1,1'-biphenyl]-4-yl)-1,2,4-oxadiazol-3-yl)benzyl)amino)acetate INT-76 as a white solid.

methyl 2-((4-(5-(4'-methyl-[1,1'-biphenyl]-4-yl)-1,2,4-oxadiazol-3-yl)benzyl)amino)acetate (INT-77)

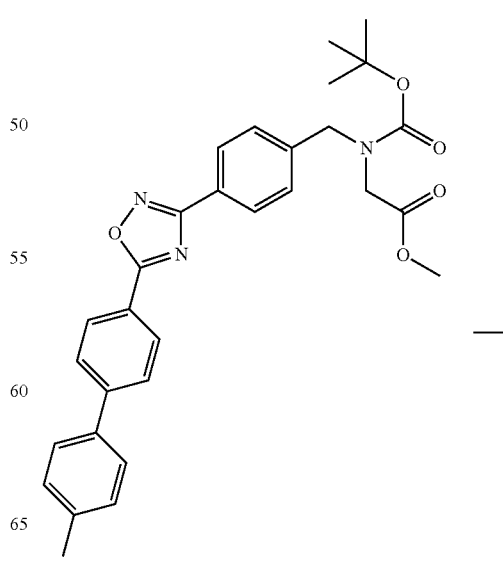

187

-continued

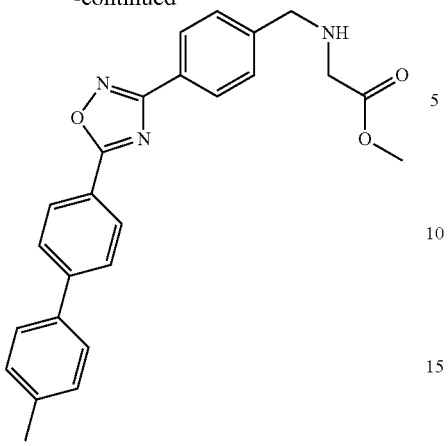

Prepared using General Procedure 8. To a stirring solution of methyl 2-((tert-butoxycarbonyl)(4-(5-(4'-methyl-[1,1'-biphenyl]-4-yl)-1,2,4-oxadiazol-3-yl)benzyl)amino)acetate INT-76 (518 mg, 1.01 mmol) in DCM (10 mL) was added TFA (1 mL) at room temperature. After 2 h the reaction mixture was evaporated to dryness. The crude product was purified by chromatography, eluting with 0.7 M ammonia in MeOH/DCM. The mixture was concentrated in vacuo to afford 272 mg (65%) of methyl 2-((4-(5-(4'-methyl-[1,1'-biphenyl]-4-yl)-1,2,4-oxadiazol-3-yl)benzyl)amino)acetate INT-77 as a white solid. LCMS-ESI (m/z) calculated for $C_{25}H_{23}N_3O_3$: 413. found 414 [M+H]$^+$, $t_R$=1.89 min (Method 10). Compound 495 was prepared from INT-77 and INT-23 using General Procedures 6 then 9. Compound 498 was prepared from INT-77 and INT-15 using General Procedures 6 then 9.

2-fluoro-4-(2-(4-methoxy-2-(trifluoromethyl)phenyl)acetamido)benzoic acid (INT-78)

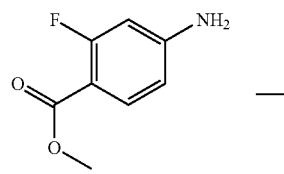

188

-continued

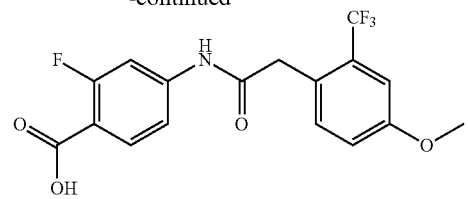

Prepared using General Procedures 6 and 9. To a stirring solution of 2-(4-methoxy-2-(trifluoromethyl)phenyl)acetic acid (500 mg, 2.13 mmol) and methyl 4-amino-2-fluorobenzoate (361 mg, 2.13 mmol) in DMF (5 mL) were added HATU (852 mg, 2.24 mmol) and TEA (744 µl, 5.34 mmol). After stirring at room temperature for 18 h the reaction mixture was diluted with EA (20 mL) and washed with NaHCO$_3$ (2×20 mL) and 1 M HCl (2×20 mL). The organic phase was concentrated in vacuo to afford an orange solid which was dissolved in THF (5 mL) and MeOH (2 mL) and 1 M LiOH (4.3 µL, 4.27 mmol) was added. After stirring at room temperature for 2 h the reaction mixture was concentrated in vacuo, the residue dissolved in water (10 mL) and acidified to pH 1 using 1 M HCl. A white precipitate was formed and the mixture was filtered under vacuum. The captured solid was washed with MeOH (5 mL) to afford a pale brown solid. The solid was triturated with MeOH (5 mL) to afford 198 mg (25%) of 2-fluoro-4-(2-(4-methoxy-2-(trifluoromethyl)phenyl)acetamido)benzoic acid INT-78 as a white solid. LCMS-ESI (m/z) calculated for $C_{17}H_{13}F_4NO_4$: 371. found 372 [M+H]$^+$, $t_R$=1.94 min (Method 10).

methyl 2-(2-fluoro-4-(2-(4-methoxy-2-(trifluoromethyl)phenyl)acetamido)-N-(4-(5-(4'-methyl-[1,1'-biphenyl]-4-yl)-1,2,4-oxadiazol-3-yl)benzyl)benzamido)acetate (INT-79)

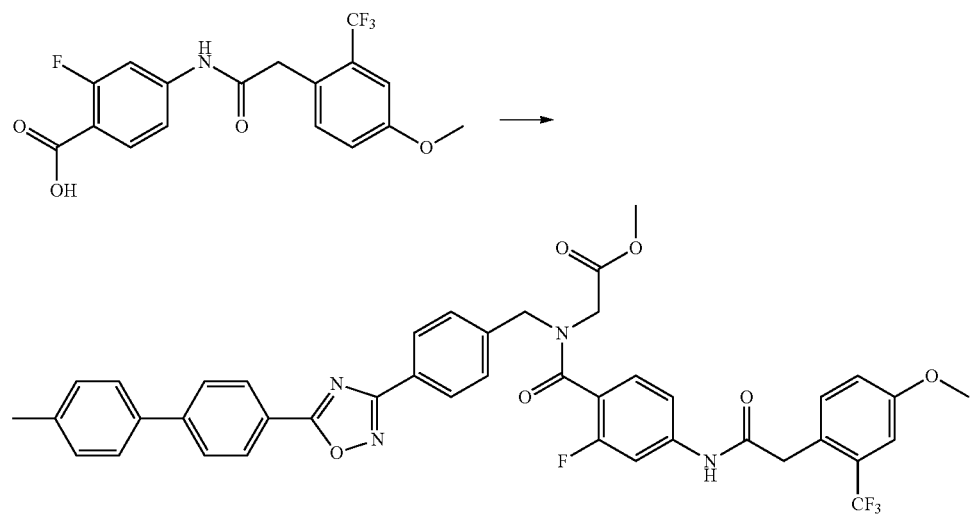

Prepared using General Procedure 6. To a suspension of methyl 2-((4-(5-(4'-methyl-[1,1'-biphenyl]-4-yl)-1,2,4-oxadiazol-3-yl)benzyl)amino)acetate INT-77 (50 mg, 0.121 mmol) and 2-fluoro-4-(2-(4-methoxy-2-(trifluoromethyl)phenyl)acetamido)benzoic acid INT-78 (44.9 mg, 0.121 mmol) in DMF (2 mL) were added HATU (50.6 mg, 0.133 mmol) and TEA (42.1 µL, 0.302 mmol). The reaction mixture was stirred at room temperature. After 60 h the reaction mixture was diluted with EA (20 mL) and washed with NaHCO$_3$ (2×20 mL) and 1 M HCl (2×20 mL). The organics were dried over MgSO$_4$ and concentrated in vacuo to afford 91 mg (98%) of methyl 2-(2-fluoro-4-(2-(4-methoxy-2-(trifluoromethyl)phenyl)acetamido)-N-(4-(5-(4'-methyl-[1,1'-biphenyl]-4-yl)-1,2,4-oxadiazol-3-yl)benzyl)benzamido)acetate INT-79 as a pale yellow solid. LCMS-ESI (m/z) calculated for C$_{42}$H$_{34}$F$_4$N$_4$O$_6$: 766. found 767 [M+H]$^+$, t$_R$=3.27 min (Method 10).

2-(2-fluoro-4-(2-(4-methoxy-2-(trifluoromethyl)phenyl)acetamido)-N-(4-(5-(4'-methyl-[1,1'-biphenyl]-4-yl)-1,2,4-oxadiazol-3-yl)benzyl)benzamido)acetic acid (Compound 496)

Prepared using General Procedure 9. To a stirring solution of methyl 2-(2-fluoro-4-(2-(4-methoxy-2-(trifluoromethyl)phenyl)acetamido)-N-(4-(5-(4'-methyl-[1,1'-biphenyl]-4-yl)-1,2,4-oxadiazol-3-yl)benzyl)benzamido)acetate INT-79 (91 mg, 0.119 mmol) in THF (2 mL) and MeOH (0.25 mL) was added 1 M LiOH (146 µL, 0.146 mmol). The reaction mixture was stirred at room temperature for 18 h. The solvent was removed and the residue suspended in water (5 mL). The mixture was acidified to pH 1 using 1 M HCl, filtered under vacuum and the captured solid washed with MeOH (1 mL). The captured solid was triturated with diethyl ether (3 mL) to afford 25 mg (28%) of 2-(2-fluoro-4-(2-(4-methoxy-2-(trifluoromethyl)phenyl)acetamido)-N-(4-(5-(4'-methyl-[1,1'-biphenyl]-4-yl)-1,2,4-oxadiazol-3-yl)benzyl)benzamido)acetic acid 496. LCMS-ESI (m/z) calculated for C$_{41}$H$_{32}$F$_4$N$_4$O$_6$: 752. found 753 [M+H]$^+$, t$_R$=9.64 min (Method 9). $^1$H NMR (400 MHz, DMSO) δ 10.18 (s, 1H), 8.35-8.18 (m, 2H), 8.07 (d, J=7.8 Hz, 2H), 7.98-7.86 (m, 2H), 7.73-7.65 (m, 2H), 7.64-7.39 (m, 5H), 7.39-7.33 (m, 2H), 7.30 (d, J=8.2 Hz, 1H), 7.25-7.17 (m, 2H), 4.82 (br, 2H), 3.96-3.78 (m, 5H), 3.42 (br, 2H), 2.40 (s, 3H).

6-(2-(4-methoxy-2-(trifluoromethyl)phenyl)acetamido)nicotinic acid (INT-80)

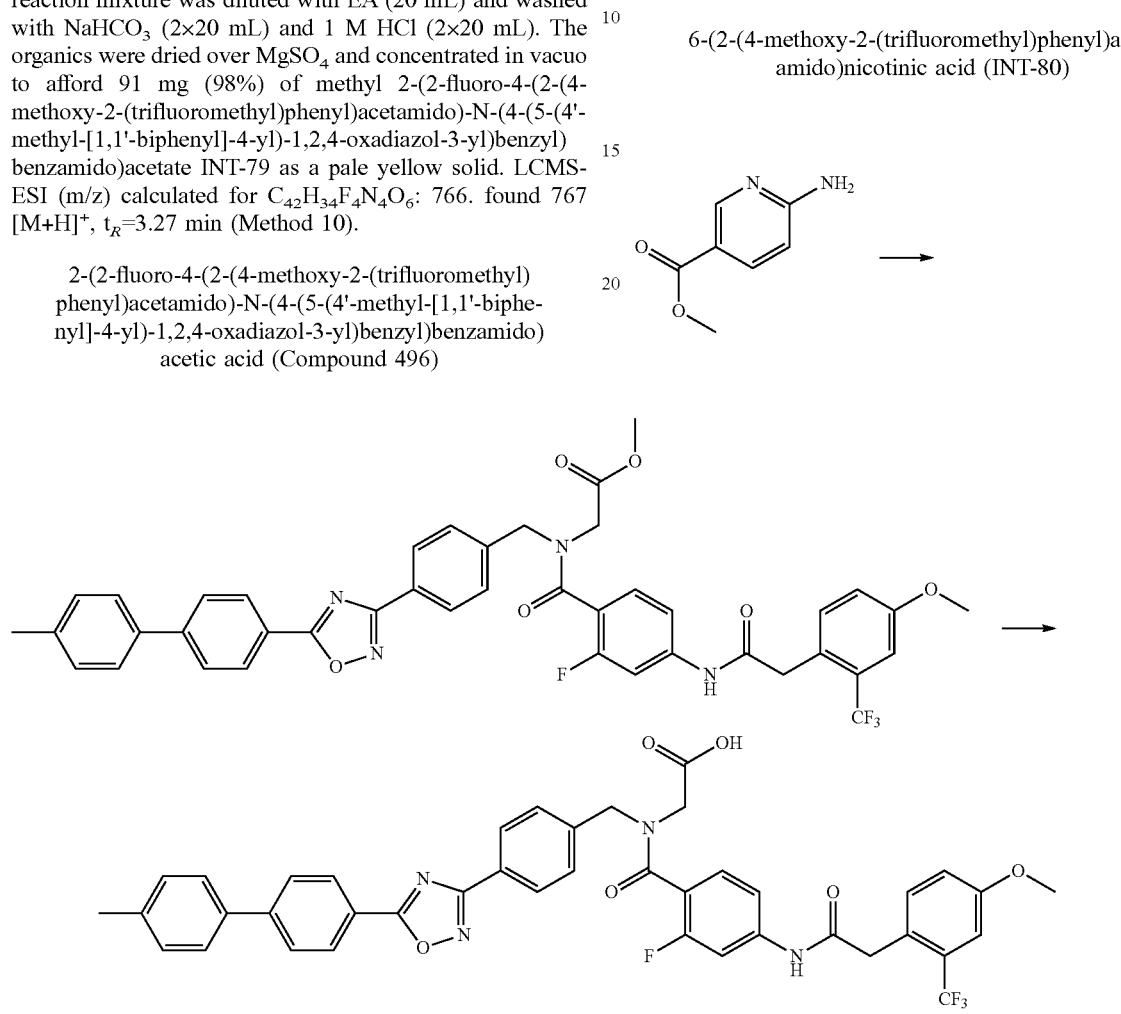

Prepared using General Procedures 6 and 9. To a stirred solution of 2-(4-methoxy-2-(trifluoromethyl)phenyl)acetic acid (500 mg, 2.13 mmol) and methyl 6-aminonicotinate (325 mg, 2.13 mmol) in DMF (5 mL) were added HATU (852 mg, 2.24 mmol) and TEA (744 µL, 5.34 mmol). The reaction mixture was stirred at room temperature. After 1 h the reaction mixture was diluted with EA (30 mL) and washed with brine (2×30 mL). The organics were dried over MgSO₄ and concentrated in vacuo to afford an orange oil which was dissolved in DCM (5 mL) and washed with 1 M HCl (5 mL). The mixture was passed through a phase separation cartridge and the organics concentrated in vacuo to afford an orange oil which was dissolved in THF (5 mL) and MeOH (3 mL). To the reaction mixture was added 1 M LiOH (4.27 mL, 4.27 mmol) and the reaction was stirred at room temperature for 1 h then concentrated in vacuo. The residue was suspended in water (15 mL), acidified to pH 1 using 1 M HCl and the mixture was filtered under vacuum. The crude product was triturated with MeOH (5 mL) and dried in vacuo to afford 97 mg (13%) of 6-(2-(4-methoxy-2-(trifluoromethyl)phenyl)acetamido)nicotinic acid INT-80 as a white solid. LCMS-ESI (m/z) calculated for $C_{16}H_{13}F_3N_2O_4$: 354. found 355 [M+H]⁺, $t_R$=1.84 min (Method 10).

Compound 500 was prepared from INT-77 and INT-80 using General Procedures 6 then 9.

tert-butyl 2-(N-(4-bromobenzyl)-4-(2-(4-methoxy-2-(trifluoromethyl)phenyl)acetamido)benzamido)acetate (INT-81)

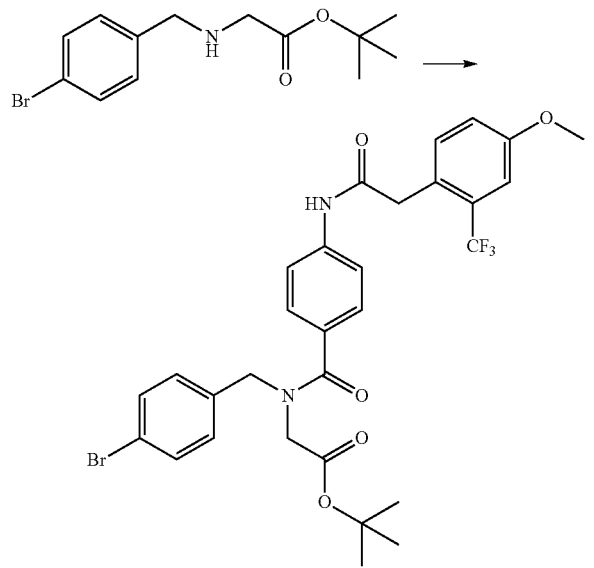

Prepared from INT-60 and INT-18. To a stirring solution of tert-butyl 2-((4-bromobenzyl)amino)acetate INT-60 (2.7 g, 8.99 mmol), 4-(2-(4-methoxy-2-(trifluoromethyl)phenyl)acetamido)benzoic acid INT-18 (3.18 g, 8.99 mmol) and TEA (2.507 mL, 17.99 mmol) in DMF was added PyBOP (4.91 g, 9.44 mmol) at room temperature. After 2 h the reaction mixture was diluted with EA (200 mL) and washed with 1 M HCl (100 mL), NaHCO₃ (200 mL) and brine (200 mL). The organics were dried over MgSO₄, pre-absorbed onto silica gel and purified by chromatography (EA/hexanes) to afford 5.2 g (91%) of tert-butyl 2-(N-(4-bromobenzyl)-4-(2-(4-methoxy-2-(trifluoromethyl)phenyl)acetamido)benzamido)acetate INT-81 as a white foamy solid. LCMS-ESI (m/z) calculated for $C_{30}H_{30}BrF_3N_2O_5$: 635. found 579/581 [M-tBu+H]⁺, $t_R$=2.83 min (Method 10).

tert-butyl 2-(4-(2-(4-methoxy-2-(trifluoromethyl)phenyl)acetamido)-N-(4-(4,4,5,5-tetramethyl-1,3,2-dioxaborolan-2-yl)benzyl)benzamido)acetate (INT-82)

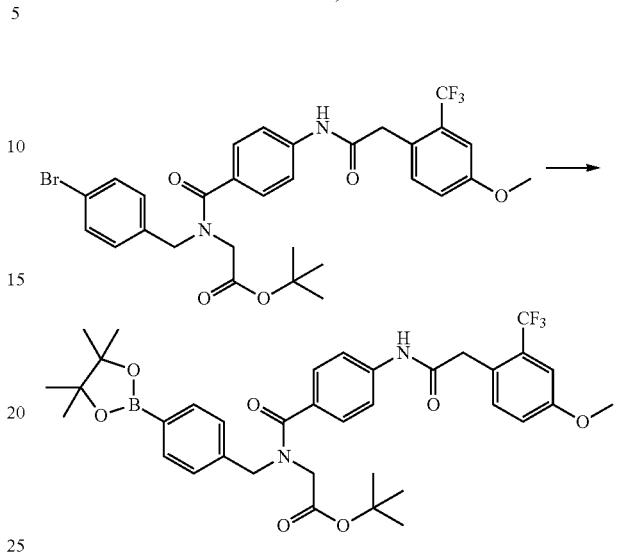

Prepared from INT-81. A solution of tert-butyl 2-(N-(4-bromobenzyl)-4-(2-(4-methoxy-2-(trifluoromethyl)phenyl)acetamido)benzamido)acetate INT-81 (400 mg, 0.629 mmol), 4,4,4',4',5,5,5',5'-octamethyl-2,2'-bi(1,3,2-dioxaborolane) (224 mg, 0.881 mmol), potassium acetate (185 mg, 1.89 mmol) and DMSO (5 mL) was degassed with N₂ gas. PdCl₂(dppf) (23.0 mg, 0.031 mmol) was added and the reaction mixture degassed further. The reaction mixture was heated at 100° C. for 18 h then cooled to room temperature. The reaction mixture was diluted with EA (50 mL) and washed with brine (100 mL). The organics were pre-absorbed onto silica gel and purified by chromatography (EA/hexanes) to afford 325 mg (75%) of tert-butyl 2-(4-(2-(4-methoxy-2-(trifluoromethyl)phenyl)acetamido)-N-(4-(4,4,5,5-tetramethyl-1,3,2-dioxaborolan-2-yl)benzyl)benzamido)acetate INT-82 as a white solid. LCMS-ESI (m/z) calculated for $C_{36}H_{42}BF_3N_2O_7$: 682. found 627 [M-tBu+H]⁺, $t_R$=3.12 min (Method 5).

Compound 505 was prepared from INT-82 and 2-chloroquinazoline using General Procedures 16 then 8. Compound 506 was prepared from INT-82 and 2-chlorobenzo[d]oxazole using General Procedures 16 then 8. Compound 507 was prepared from INT-82 and 2-bromobenzo[d]thiazole using General Procedures 16 then 8. Compound 508 was prepared from INT-82 and 2-chloroquinoxaline using General Procedures 16 then 8.

tert-butyl 2-((4-(1H-benzo[d]imidazol-2-yl)benzyl)amino)acetate (INT-83)

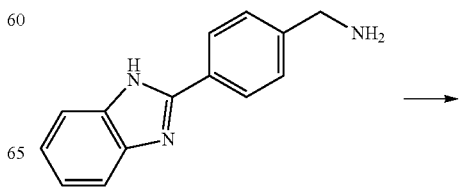

-continued

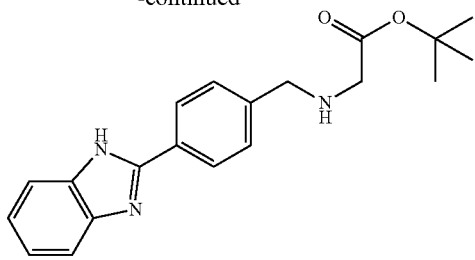

Prepared using General Procedure 13: INT-83 was prepared in a similar fashion to INT-22 from (4-(1H-benzo[d]imidazol-2-yl)phenyl)methanamine. LCMS-ESI (m/z) calculated for $C_{20}H_{23}N_3O_2$: 337. found 338 $[M+H]^+$, $t_R$=1.99 min (Method 1).

Compound 509 was prepared from INT-83 and INT-18 using General Procedures 6 then 8.

1-(4-bromophenyl)-1H-pyrazole (INT-84)

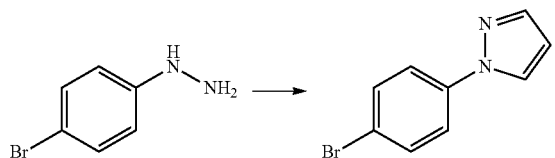 [SMILES: NNc1ccc(Br)cc1 ; Brc1ccc(-n2cccn2)cc1]

To a stirring suspension of (4-bromophenyl)hydrazine hydrochloride (3.28 g, 14.7 mmol) in EtOH (25 mL) was added concentrated HCl (0.147 mL, 1.47 mmol) and 1,1,3,3-tetraethoxypropane (3.87 mL, 16.1 mmol). The reaction mixture was heated at reflux for 2 h then cooled to room temperature. The reaction mixture was poured onto water (150 mL) and hexanes (20 mL) and stirred for 1 h. A brown precipitate was collected by filtration and washed with water (2×10 mL) and hexanes (10 mL). The resultant solid was dried in air then washed with toluene (10 mL) to afford 2 g (61%) of 1-(4-bromophenyl)-1H-pyrazole INT-84 as a light brown powder. LCMS-ESI (m/z) calculated for $C_9H_7BrN_2$: 223. found 223/225 $[M+H]^+$, $t_R$=2.14 min (Method 10).

1-(4'-methyl-[1,1'-biphenyl]-4-yl)-1H-pyrazole (INT-85)

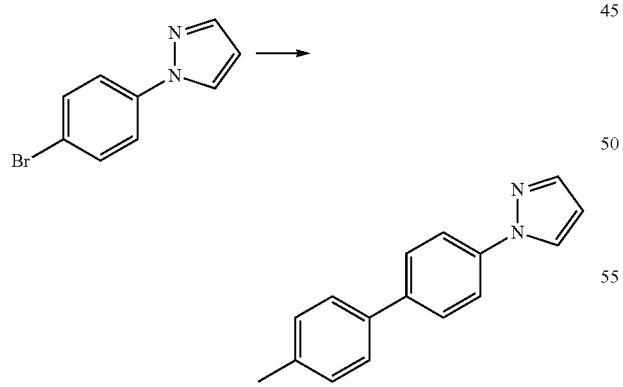

Prepared using General Procedure 16. A stirring mixture of p-tolylboronic acid (391 mg, 2.88 mmol) and 1-(4-bromophenyl)-1H-pyrazole (535 mg, 2.40 mmol) INT-84 in THF (4 mL), MeCN (4 mL) and sodium carbonate (1 M aqueous) (4.8 mL, 4.80 mmol) was de-gassed by bubbling through $N_2$ gas. PdCl$_2$dppf (88 mg, 0.120 mmol) was added and the reaction mixture further de-gassed. The reaction was heated at 130° C. for 30 min in a microwave. The mixture was cooled to room temperature, poured onto water (100 mL) and extracted with EA/THF (2×50/10 mL). The combined organic extracts were washed with brine (50 mL), dried over MgSO$_4$ and concentrated in vacuo. The residue was purified by chromatography (EA/hexanes) to afford 315 mg (56%) of 1-(4'-methyl-[1,1'-biphenyl]-4-yl)-1H-pyrazole INT-85. LCMS-ESI (m/z) calculated for $C_{16}H_{14}N_2$: 234. found 235 $[M+H]^+$, $t_R$=2.60 min (Method 10).

4-bromo-1-(4'-methyl-[1,1'-biphenyl]-4-yl)-1H-pyrazole (INT-86)

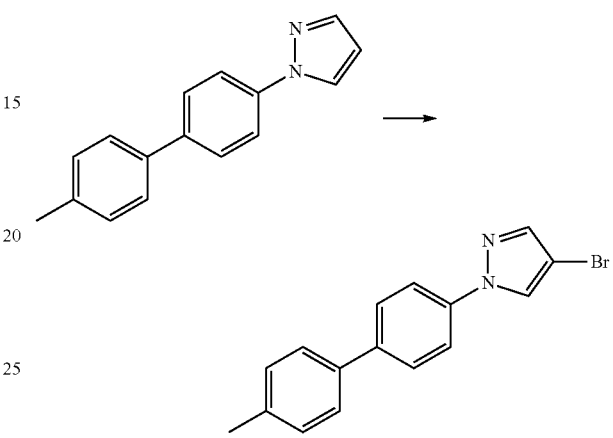

Prepared from INT-85: To a stirring solution of 1-(4'-methyl-[1,1'-biphenyl]-4-yl)-1H-pyrazole (309 mg, 1.319 mmol) INT-85 in DCM (4 mL) was added NBS (258 mg, 1.45 mmol). After stirring at room temperature for 1 h additional THF (4 mL) was added and stirring continued. After 18 h the reaction mixture was concentrated in vacuo and slurried in MeCN (4 mL). The solid was collected by filtration and washed with MeCN (2×2 mL) to provide 360 mg (87%) of 4-bromo-1-(4'-methyl-[1,1'-biphenyl]-4-yl)-1H-pyrazole INT-86. LCMS-ESI (m/z) calculated for $C_{16}H_{13}BrN_2$: 312. found 313 $[M+H]^+$, $t_R$=3.07 min (Method 5).

2-(4-(2-(4-methoxy-2-(trifluoromethyl)phenyl)acetamido)-N-(4-(1-(4'-methyl-[1,1'-biphenyl]-4-yl)-1H-pyrazol-4-yl)benzyl)benzamido)acetic acid (Compound 511)

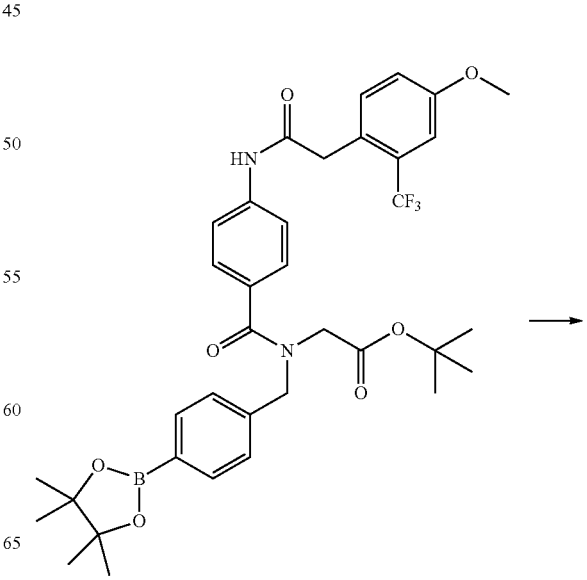

195
-continued

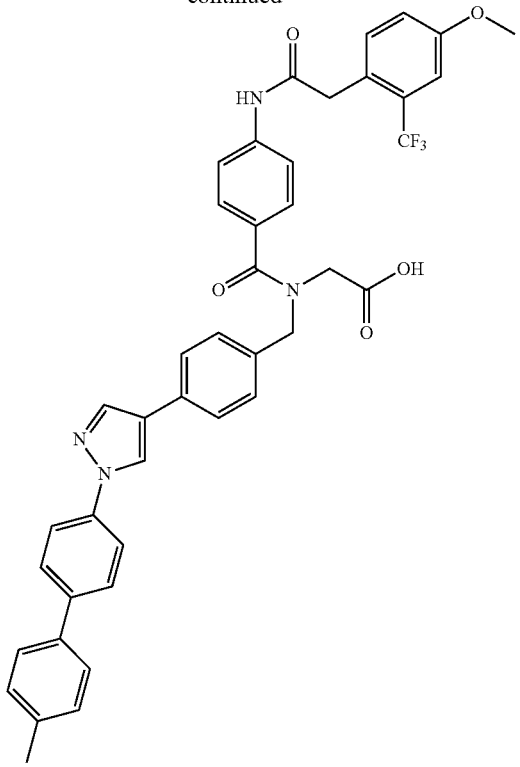

Prepared using General Procedures 16 then 8. A stirring mixture of tert-butyl 24442-(4-methoxy-2-(trifluoromethyl)phenyl)acetamido)-N-(4-(4,4,5,5-tetramethyl-1,3,2-dioxaborolan-2-yl)benzyl)benzamido)acetate INT-82 (155 mg, 0.227 mmol) and 4-bromo-1-(4'-methyl-[1,1'-biphenyl]-4-yl)-1H-pyrazole INT-86 (85 mg, 0.273 mmol) in THF (1.5 mL), MeCN (1.5 mL), water (0.5 mL) and sodium carbonate (130 mg, 0.454 mmol) was de-gassed by bubbling through $N_2$. $PdCl_2dppf$ (16 mg, 0.023 mmol) was added and the reaction mixture further de-gassed. The reaction mixture was heated in a microwave at 110° C. for 50 min, cooled to room temperature and concentrated in vacuo. The residue was diluted in DCM (10 mL) washed with $NaHCO_3$ (5 mL). The organics were concentrated in vacuo and purified by chromatography (EA/hexanes) to afford the intermediate ester, which was dissolved in DCM (2 mL) and TFA (1 mL). After stirring at room temperature for 4 h the reaction mixture was concentrated in vacuo and triturated with water (5 mL). The solid was collected by filtration, washed with hexanes (5 mL) and dried under vacuum to afford 55 mg (33%) of 2-(4-(2-(4-methoxy-2-(trifluoromethyl)phenyl)acetamido)-N-(4-(1-(4'-methyl-[1,1'-biphenyl]-4-yl)-1H-pyrazol-4-yl)benzyl)benzamido)acetic acid 511 as a white solid. LCMS-ESI (m/z) calculated for $C_{42}H_{35}F_3N_4O_5$: 732. found 733 $[M+H]^+$, $t_R$=8.80 min (Method 9).

4-oxo-2-phenyl-3,4-dihydroquinazoline-6-carbonitrile (INT-87)

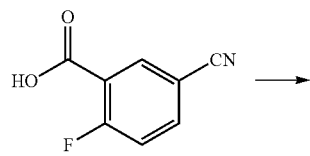

196
-continued

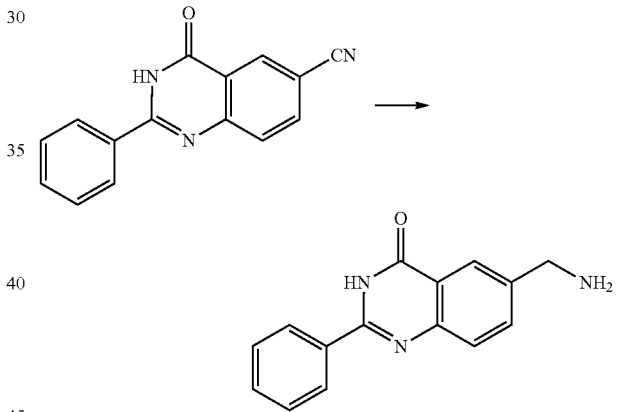

A stirring solution of 5-cyano-2-fluorobenzoic acid (2.02 g, 12.2 mmol) and benzimidamide hydrochloride monohydrate (2.14 g, 12.2 mmol) in DMF (15 mL) was treated with DIEA (5.34 mL, 30.6 mmol) and HATU (4.65 g, 12.2 mmol). The reaction mixture was stirred at room temperature for 30 min then heated at 100° C. for 18 h. The reaction mixture was cooled to room temperature and water (200 mL) was added. A precipitate formed which was isolated by filtration and dried under vacuum to afford 1.66 g (54%) of 4-oxo-2-phenyl-3,4-dihydroquinazoline-6-carbonitrile INT-87 as a light powdery white solid. LCMS-ESI (m/z) calculated for $C_{15}H_9N3O$: 247. found 248 $[M+H]^+$, $t_R$=1.70 min (Method 10).

6-(aminomethyl)-2-phenylquinazolin-4(3H)-one (INT-88)

Prepared from INT-87. To a stirring solution of 4-oxo-2-phenyl-3,4-dihydroquinazoline-6-carbonitrile INT-87 (540 mg, 2.18 mmol) in MeOH (30 mL) and THF (10 mL) was added cobalt(II) chloride hydrate (646 mg, 4.37 mmol) and sodium borohydride (826 mg, 21.8 mmol) portionwise. After stirring at room temperature for 30 min the reaction mixture was quenched with 1 M HCl (5 mL) and filtered through a celite plug, washing with THF (50 mL). The mixture was diluted with EA (100 mL) and washed with $NaHCO_3$ (120 mL) and brine (20 mL). The organics were dried over $MgSO_4$ and concentrated in vacuo to afford 306 mg (56%) of 6-(aminomethyl)-2-phenylquinazolin-4(3H)-one INT-88 as a white powder. LCMS-ESI (m/z) calculated for $C_{15}H_{13}N3O$: 251. found 250 $[M-H]^-$, $t_R$=0.80 min (Method 10).

Compound 512 was prepared using INT-88 and INT-18 using General Procedures 4, 6 then 8.

Selected compounds and their corresponding analytical data are shown in Table 1, where the LCMS data was collected using Methods 2, 3, 4, 6, 8 and 9 (see General Methods).

TABLE 1

| STRUCTURE | COMPOUND NUMBER | LCMS RETENTION TIME (min) |
|---|---|---|
| 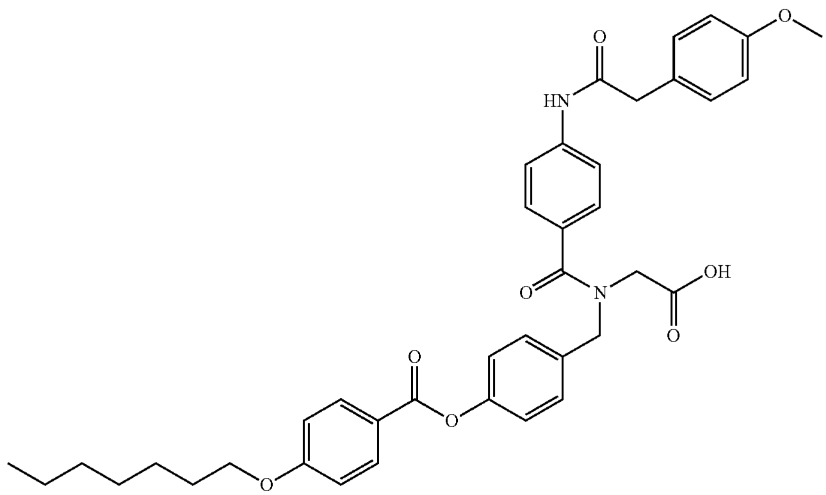 [SMILES: CCCCCCCOc1ccc(C(=O)Oc2ccc(CN(CC(=O)O)C(=O)c3ccc(NC(=O)Cc4ccc(OC)cc4)cc3)cc2)cc1] | 1 | 9.51 |
| 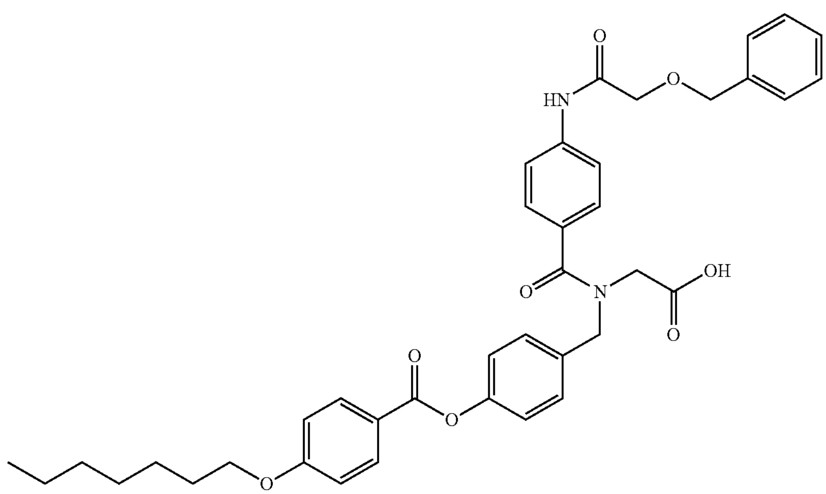 [SMILES: CCCCCCCOc1ccc(C(=O)Oc2ccc(CN(CC(=O)O)C(=O)c3ccc(NC(=O)COCc4ccccc4)cc3)cc2)cc1] | 2 | 9.90 |
| 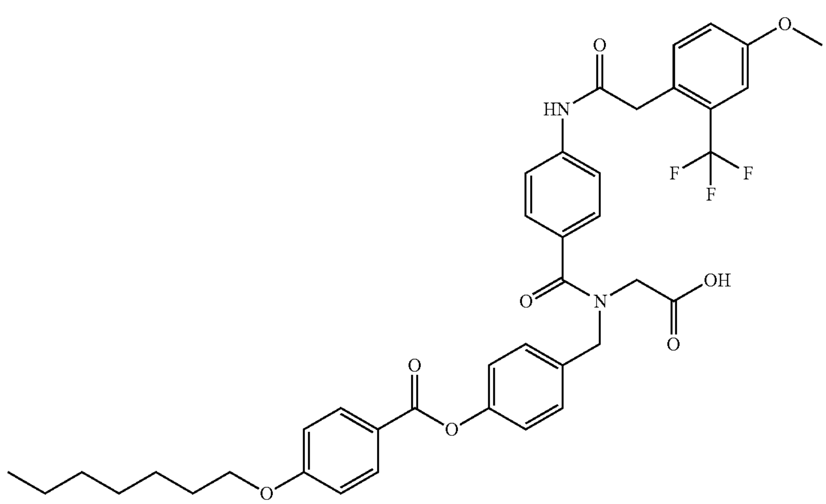 | 3 | 11.42 |

TABLE 1-continued

| STRUCTURE | COMPOUND NUMBER | LCMS RETENTION TIME (min) |
|---|---|---|
| 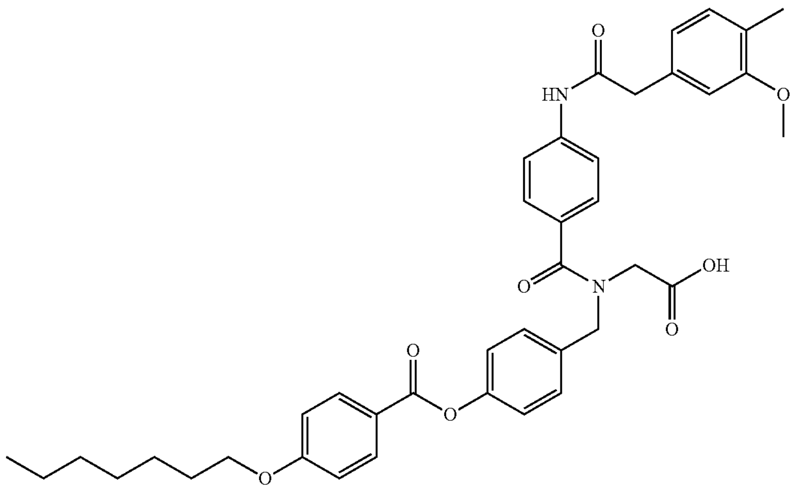 [SMILES: CCCCCCCOc1ccc(C(=O)Oc2ccc(CN(CC(=O)O)C(=O)c3ccc(NC(=O)Cc4ccc(C)c(OC)c4)cc3)cc2)cc1] | 4 | 11.45 |
| 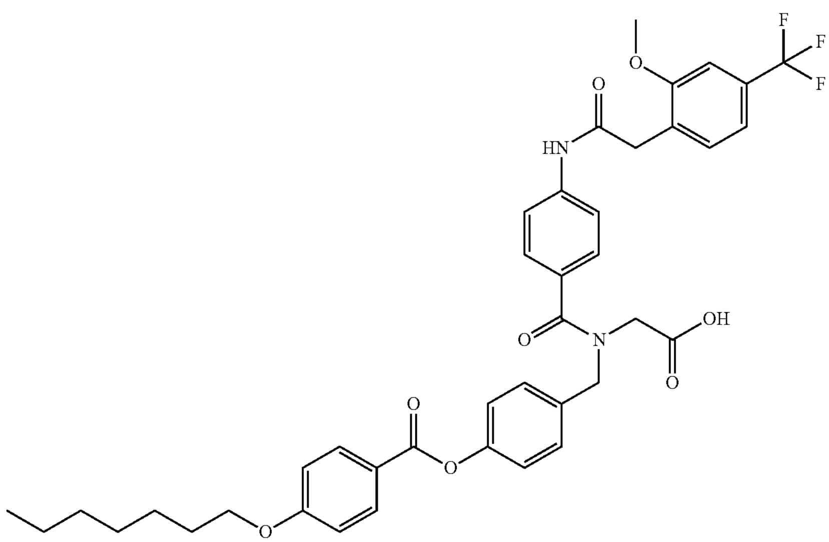 [SMILES: CCCCCCCOc1ccc(C(=O)Oc2ccc(CN(CC(=O)O)C(=O)c3ccc(NC(=O)Cc4ccc(C(F)(F)F)cc4OC)cc3)cc2)cc1] | 5 | 11.51 |
| 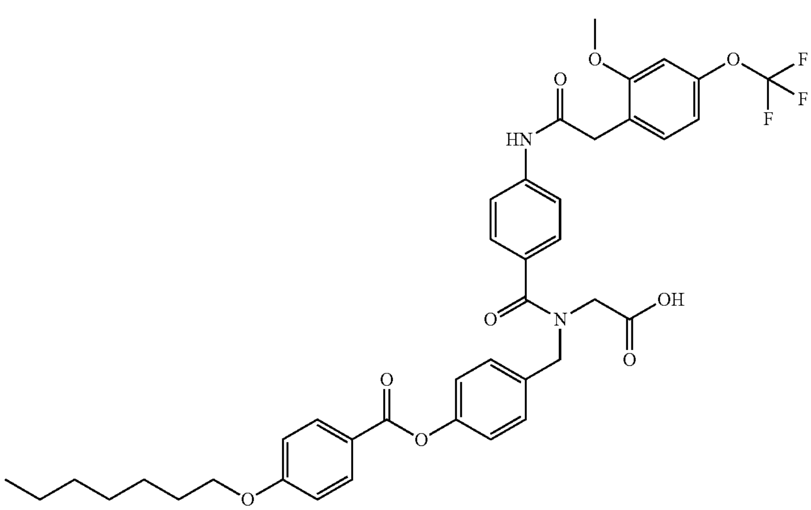 [SMILES: CCCCCCCOc1ccc(C(=O)Oc2ccc(CN(CC(=O)O)C(=O)c3ccc(NC(=O)Cc4ccc(OC(F)(F)F)cc4OC)cc3)cc2)cc1] | 6 | 11.60 |

TABLE 1-continued
| STRUCTURE | COMPOUND NUMBER | LCMS RETENTION TIME (min) |
|---|---|---|
| 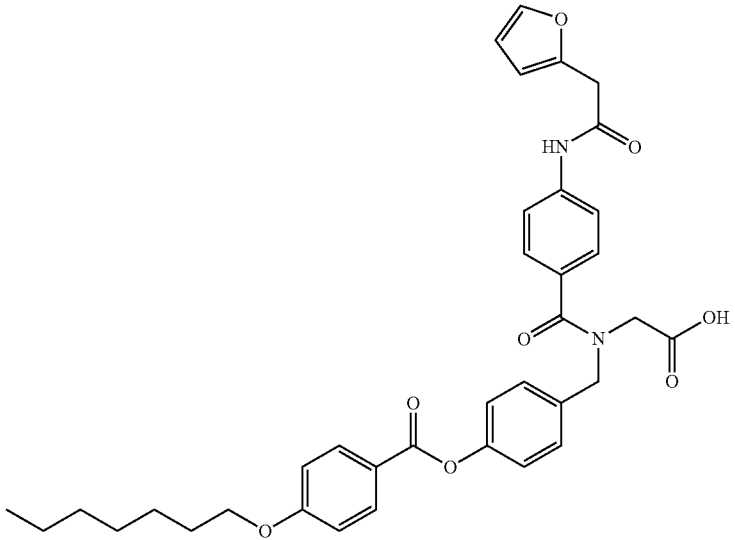 [SMILES: CCCCCCCOc1ccc(C(=O)Oc2ccc(CN(CC(=O)O)C(=O)c3ccc(NC(=O)Cc4ccco4)cc3)cc2)cc1] | 7 | 10.87 |
| 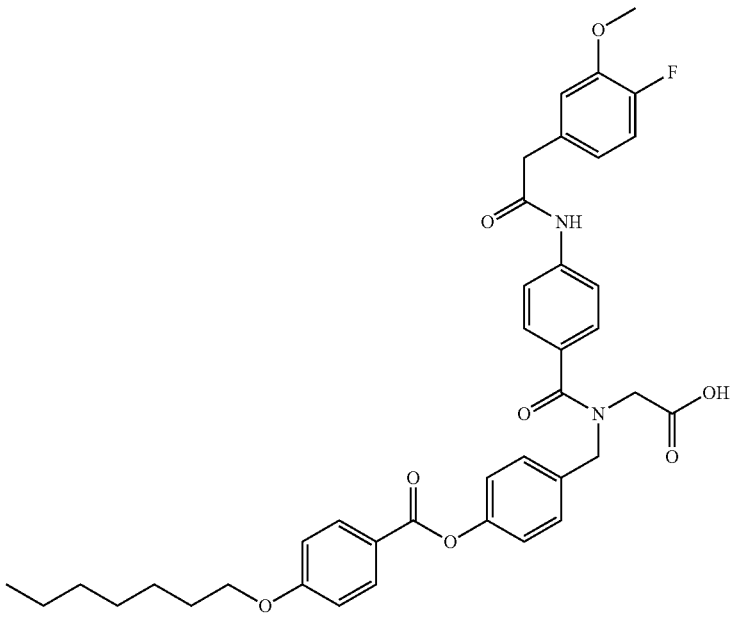 [SMILES: CCCCCCCOc1ccc(C(=O)Oc2ccc(CN(CC(=O)O)C(=O)c3ccc(NC(=O)Cc4ccc(F)c(OC)c4)cc3)cc2)cc1] | 8 | 11.08 |

TABLE 1-continued
| STRUCTURE | COMPOUND NUMBER | LCMS RETENTION TIME (min) |
|---|---|---|
| 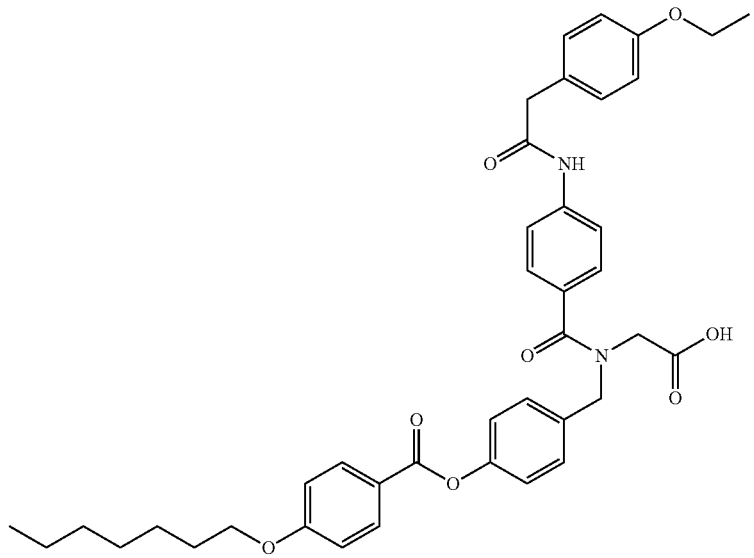 [SMILES: CCCCCCCOc1ccc(C(=O)Oc2ccc(CN(CC(=O)O)C(=O)c3ccc(NC(=O)Cc4ccc(OCC)cc4)cc3)cc2)cc1] | 9 | 11.33 |
| 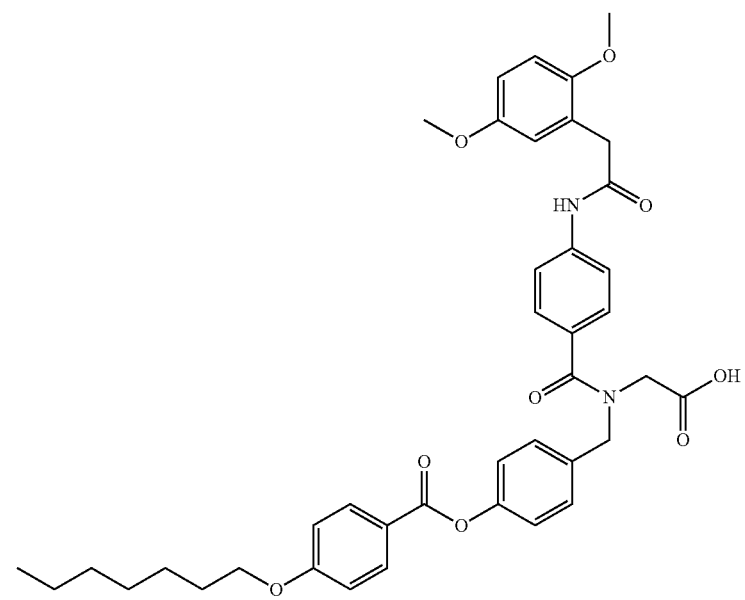 [SMILES: CCCCCCCOc1ccc(C(=O)Oc2ccc(CN(CC(=O)O)C(=O)c3ccc(NC(=O)Cc4cc(OC)ccc4OC)cc3)cc2)cc1] | 10 | 11.15 |

TABLE 1-continued
| STRUCTURE | COMPOUND NUMBER | LCMS RETENTION TIME (min) |
|---|---|---|
| 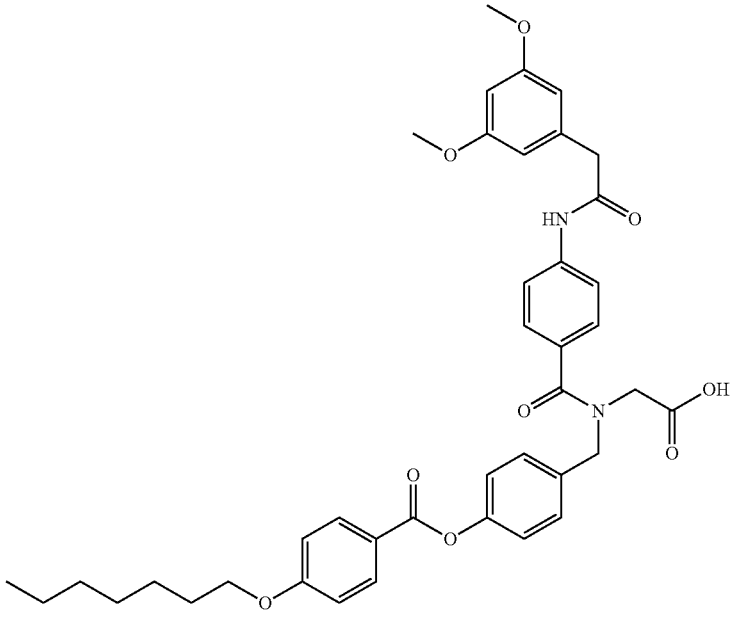 [SMILES: CCCCCCCOc1ccc(C(=O)Oc2ccc(CN(CC(=O)O)C(=O)c3ccc(NC(=O)Cc4cc(OC)cc(OC)c4)cc3)cc2)cc1] | 11 | 11.10 |
| 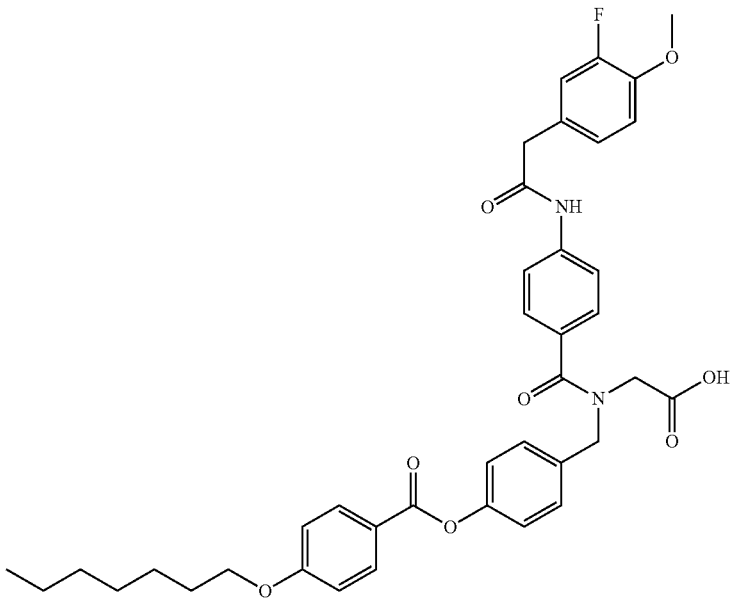 [SMILES: CCCCCCCOc1ccc(C(=O)Oc2ccc(CN(CC(=O)O)C(=O)c3ccc(NC(=O)Cc4ccc(OC)c(F)c4)cc3)cc2)cc1] | 12 | 11.06 |

TABLE 1-continued

| STRUCTURE | COMPOUND NUMBER | LCMS RETENTION TIME (min) |
|---|---|---|
| 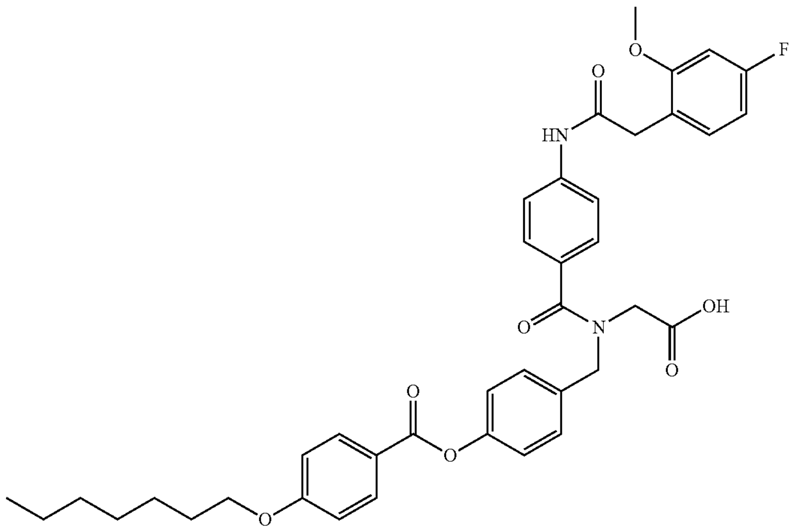 [SMILES: CCCCCCCOc1ccc(C(=O)Oc2ccc(CN(CC(=O)O)C(=O)c3ccc(NC(=O)Cc4ccc(F)cc4OC)cc3)cc2)cc1] | 13 | 11.21 |
| 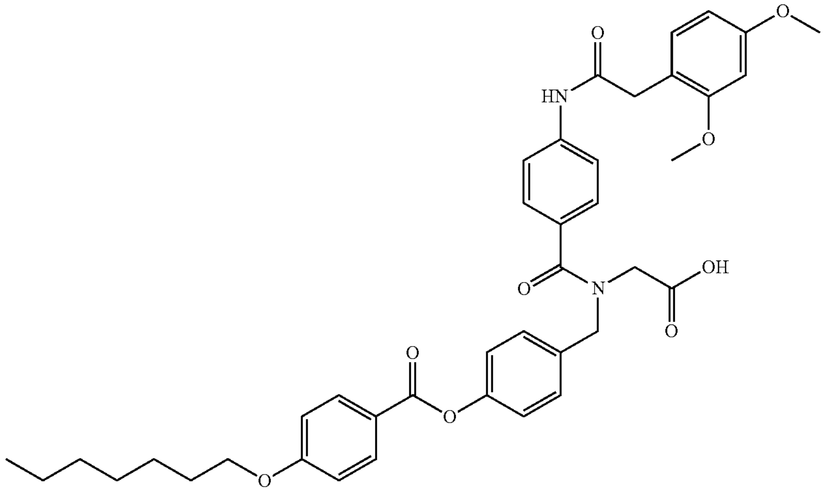 [SMILES: CCCCCCCOc1ccc(C(=O)Oc2ccc(CN(CC(=O)O)C(=O)c3ccc(NC(=O)Cc4ccc(OC)cc4OC)cc3)cc2)cc1] | 14 | 11.15 |
| 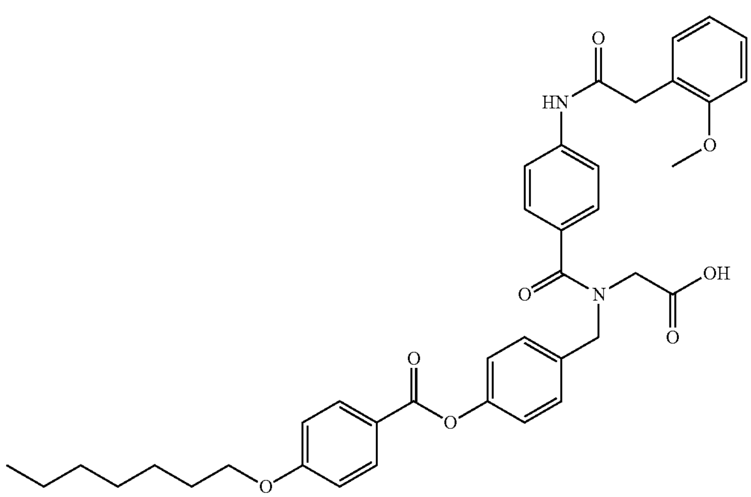 [SMILES: CCCCCCCOc1ccc(C(=O)Oc2ccc(CN(CC(=O)O)C(=O)c3ccc(NC(=O)Cc4ccccc4OC)cc3)cc2)cc1] | 15 | 11.21 |

TABLE 1-continued
| STRUCTURE | COMPOUND NUMBER | LCMS RETENTION TIME (min) |
|---|---|---|
| 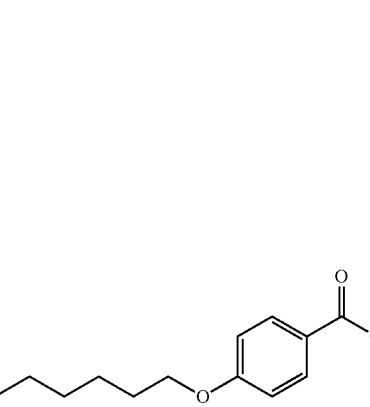 | 16 | 10.43 |
| 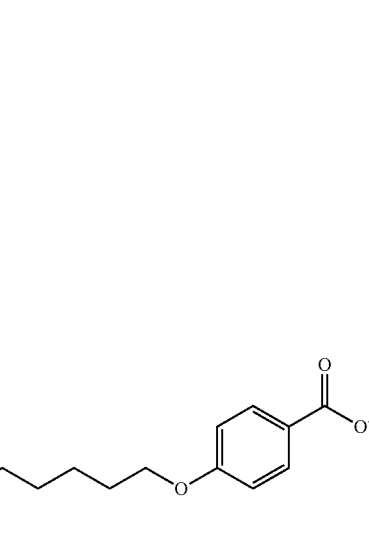 | 17 | 9.96 |
| 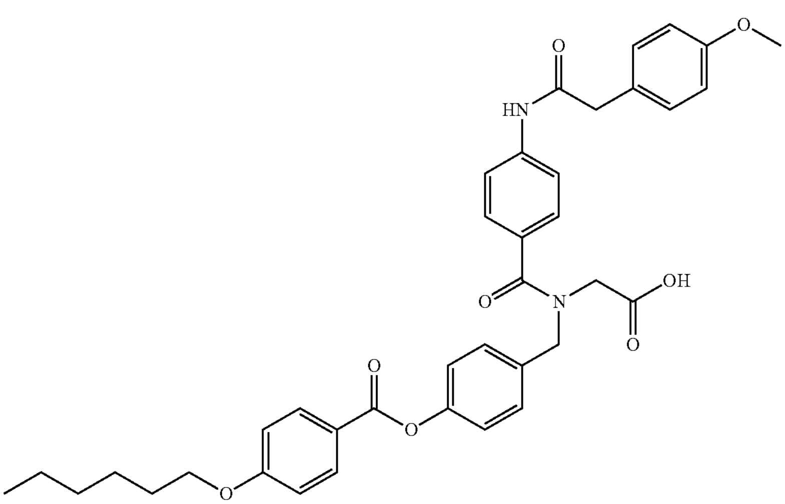 [SMILES: CCCCCCOc1ccc(C(=O)Oc2ccc(CN(CC(=O)O)C(=O)c3ccc(NC(=O)Cc4ccc(OC)cc4)cc3)cc2)cc1] | 18 | 9.01 |

TABLE 1-continued
| STRUCTURE | COMPOUND NUMBER | LCMS RETENTION TIME (min) |
|---|---|---|
| 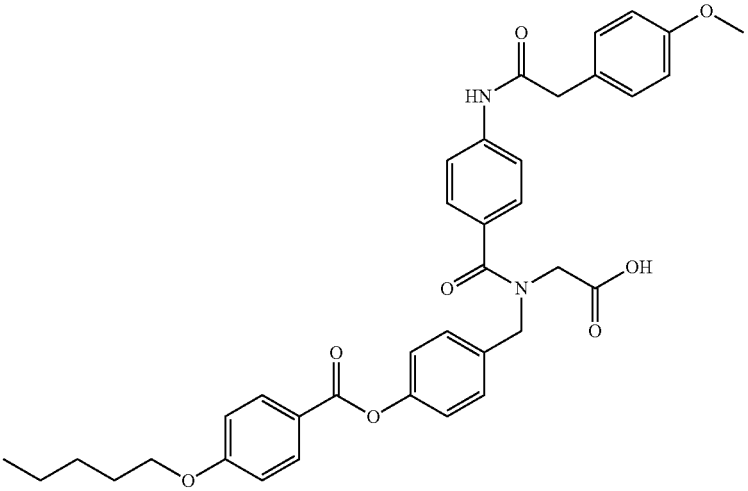 [SMILES: CCCCCOc1ccc(C(=O)Oc2ccc(CN(CC(=O)O)C(=O)c3ccc(NC(=O)Cc4ccc(OC)cc4)cc3)cc2)cc1] | 19 | 8.52 |
| 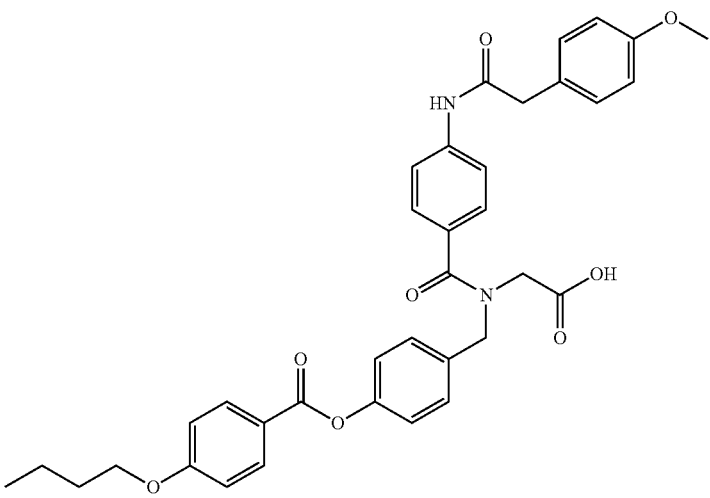 [SMILES: CCCCOc1ccc(C(=O)Oc2ccc(CN(CC(=O)O)C(=O)c3ccc(NC(=O)Cc4ccc(OC)cc4)cc3)cc2)cc1] | 20 | 8.02 |
| 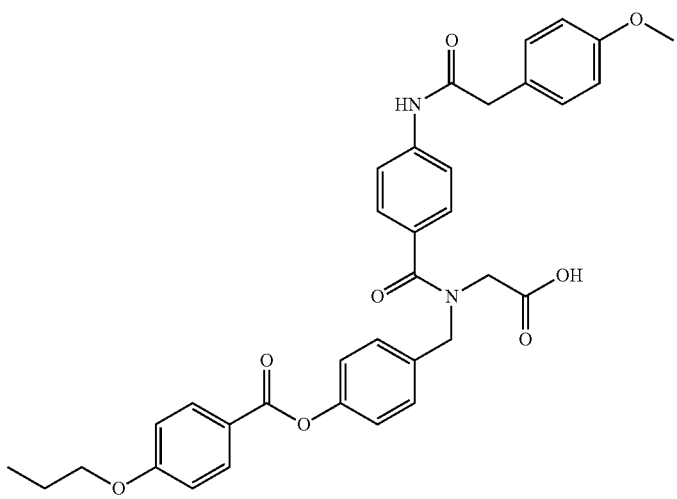 [SMILES: CCCOc1ccc(C(=O)Oc2ccc(CN(CC(=O)O)C(=O)c3ccc(NC(=O)Cc4ccc(OC)cc4)cc3)cc2)cc1] | 21 | 7.49 |

TABLE 1-continued

| STRUCTURE | COMPOUND NUMBER | LCMS RETENTION TIME (min) |
|---|---|---|
| 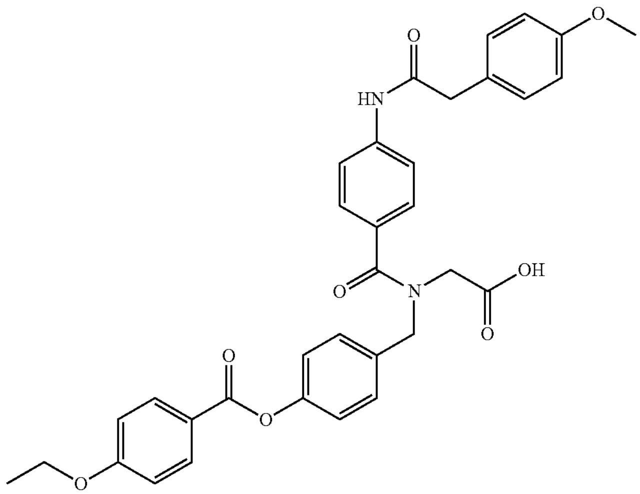 [SMILES: CCOc1ccc(C(=O)Oc2ccc(CN(CC(=O)O)C(=O)c3ccc(NC(=O)Cc4ccc(OC)cc4)cc3)cc2)cc1] | 22 | 6.90 |
| 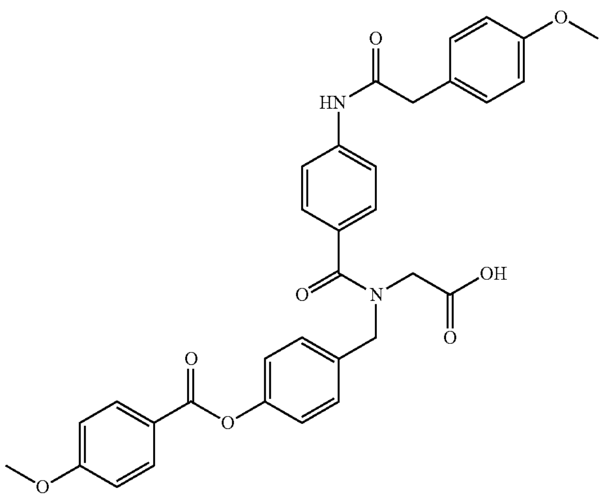 | 23 | 6.36 |
| 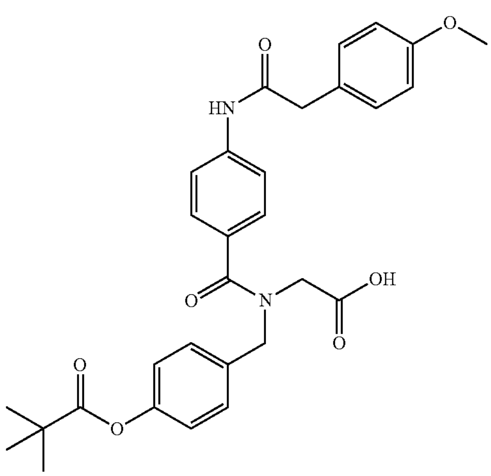 [SMILES: COc1ccc(CC(=O)Nc2ccc(C(=O)N(CC(=O)O)Cc3ccc(OC(=O)C(C)(C)C)cc3)cc2)cc1] | 24 | 6.41 |

TABLE 1-continued

| STRUCTURE | COMPOUND NUMBER | LCMS RETENTION TIME (min) |
|---|---|---|
| 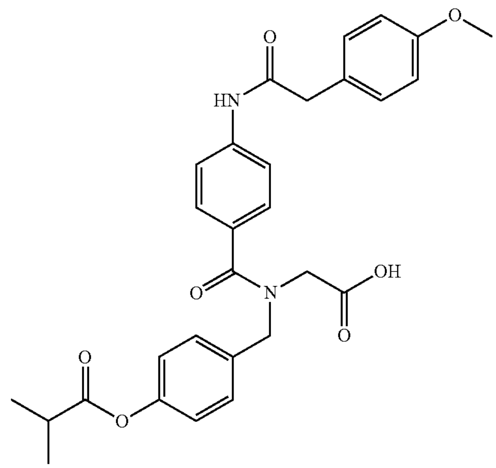 [SMILES: COc1ccc(CC(=O)Nc2ccc(C(=O)N(CC(=O)O)Cc3ccc(OC(=O)C(C)C)cc3)cc2)cc1] | 25 | 5.91 |
| 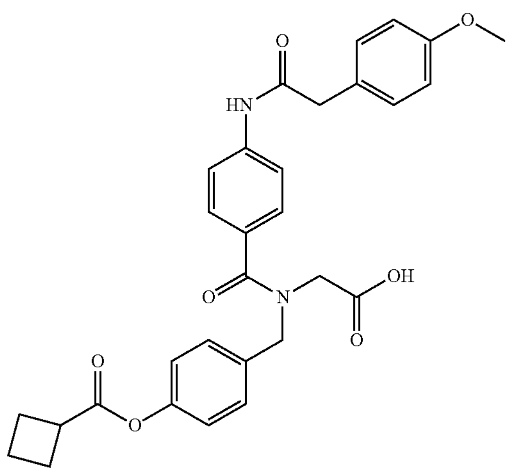 [SMILES: COc1ccc(CC(=O)Nc2ccc(C(=O)N(CC(=O)O)Cc3ccc(OC(=O)C4CCC4)cc3)cc2)cc1] | 26 | 6.09 |
| 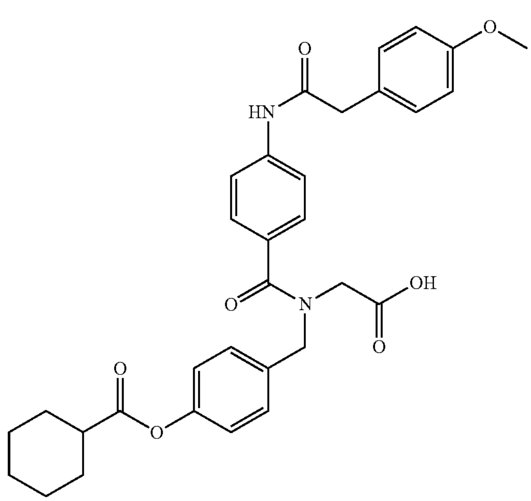 [SMILES: COc1ccc(CC(=O)Nc2ccc(C(=O)N(CC(=O)O)Cc3ccc(OC(=O)C4CCCCC4)cc3)cc2)cc1] | 27 | 7.06 |

TABLE 1-continued

| STRUCTURE | COMPOUND NUMBER | LCMS RETENTION TIME (min) |
|---|---|---|
| 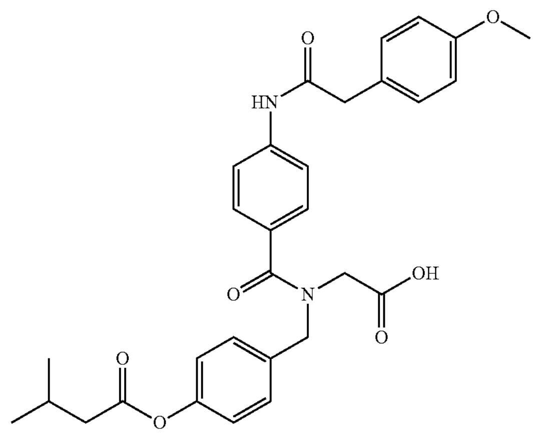 [SMILES: COc1ccc(CC(=O)Nc2ccc(C(=O)N(CC(=O)O)Cc3ccc(OC(=O)CC(C)C)cc3)cc2)cc1] | 28 | 6.42 |
| 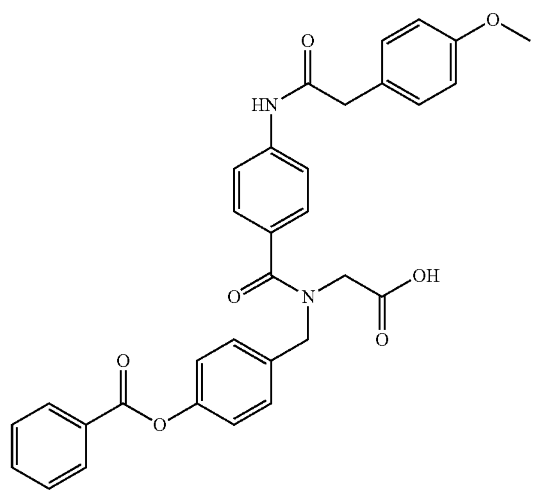 [SMILES: COc1ccc(CC(=O)Nc2ccc(C(=O)N(CC(=O)O)Cc3ccc(OC(=O)c4ccccc4)cc3)cc2)cc1] | 29 | 6.36 |
| 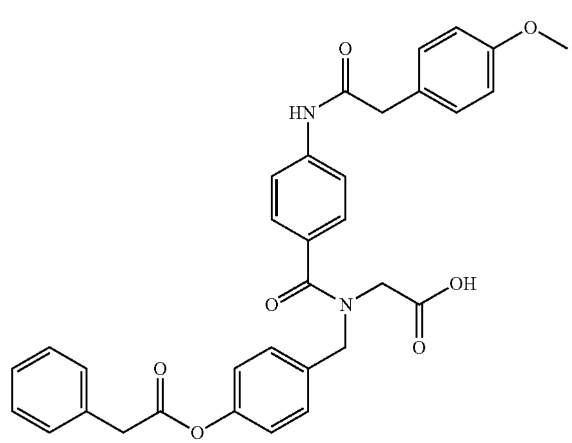 [SMILES: COc1ccc(CC(=O)Nc2ccc(C(=O)N(CC(=O)O)Cc3ccc(OC(=O)Cc4ccccc4)cc3)cc2)cc1] | 30 | 6.37 |

TABLE 1-continued

| STRUCTURE | COMPOUND NUMBER | LCMS RETENTION TIME (min) |
|---|---|---|
| 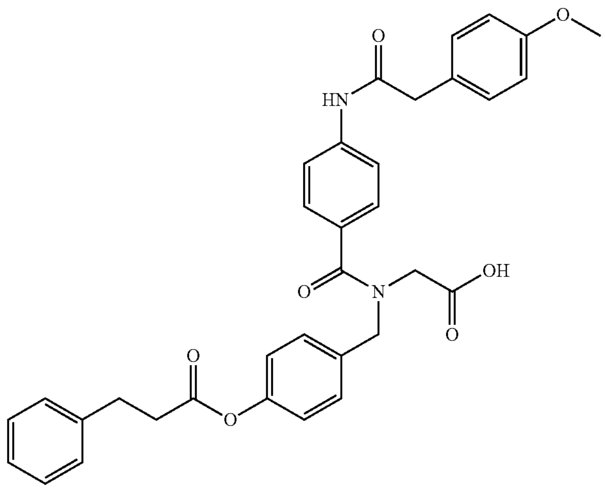 [SMILES: COc1ccc(CC(=O)Nc2ccc(C(=O)N(CC(=O)O)Cc3ccc(OC(=O)CCc4ccccc4)cc3)cc2)cc1] | 31 | 6.74 |
| 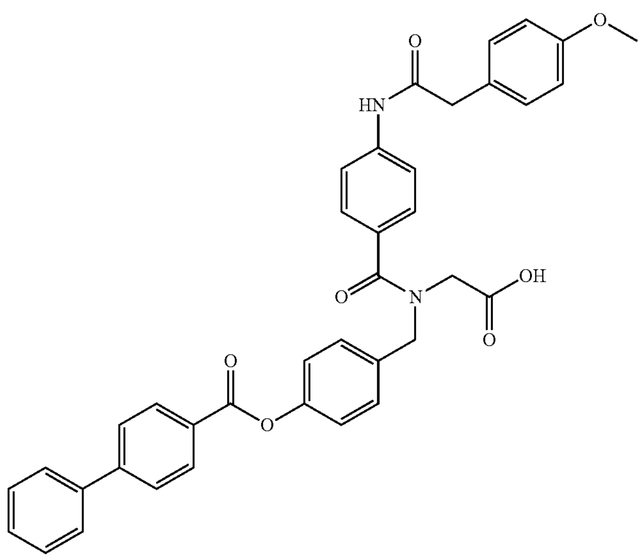 [SMILES: COc1ccc(CC(=O)Nc2ccc(C(=O)N(CC(=O)O)Cc3ccc(OC(=O)c4ccc(-c5ccccc5)cc4)cc3)cc2)cc1] | 32 | 7.83 |
| 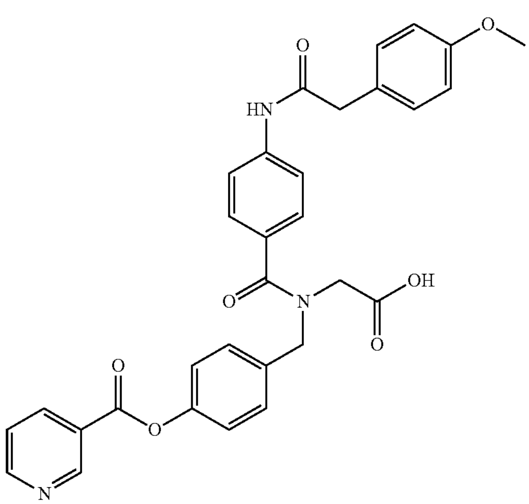 [SMILES: COc1ccc(CC(=O)Nc2ccc(C(=O)N(CC(=O)O)Cc3ccc(OC(=O)c4cccnc4)cc3)cc2)cc1] | 33 | 4.78 |

TABLE 1-continued

| STRUCTURE | COMPOUND NUMBER | LCMS RETENTION TIME (min) |
|---|---|---|
| 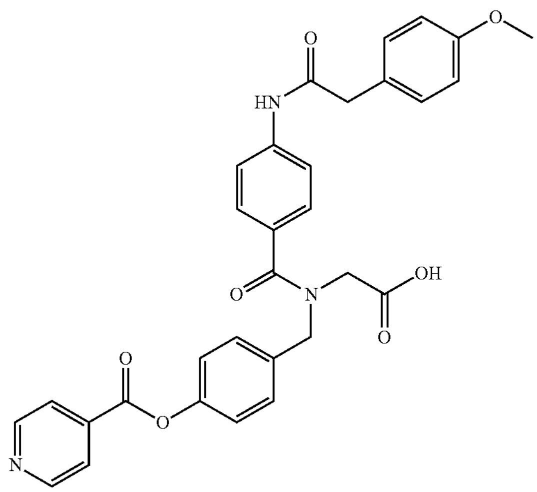 [SMILES: COc1ccc(CC(=O)Nc2ccc(C(=O)N(CC(=O)O)Cc3ccc(OC(=O)c4ccncc4)cc3)cc2)cc1] | 34 | 4.76 |
| 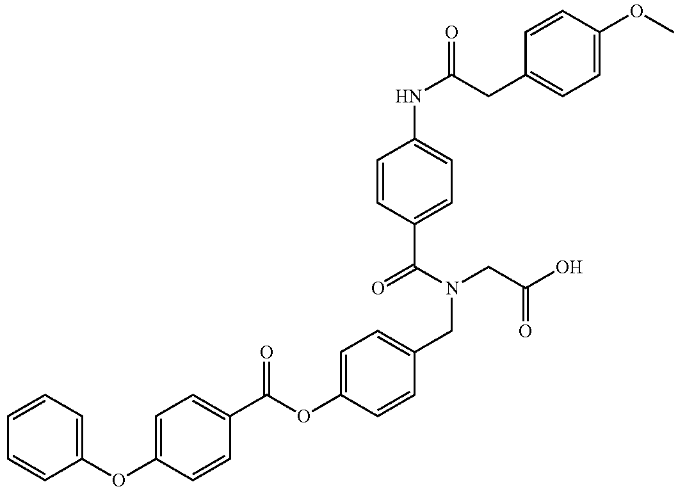 [SMILES: COc1ccc(CC(=O)Nc2ccc(C(=O)N(CC(=O)O)Cc3ccc(OC(=O)c4ccc(Oc5ccccc5)cc4)cc3)cc2)cc1] | 35 | 7.81 |
| 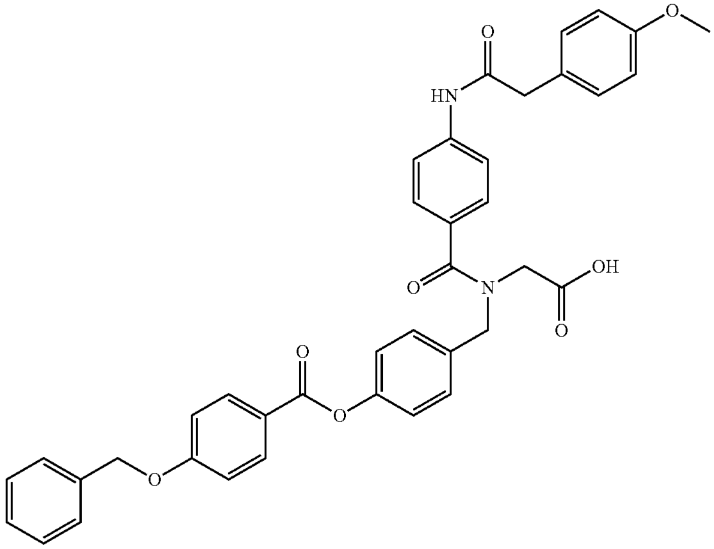 [SMILES: COc1ccc(CC(=O)Nc2ccc(C(=O)N(CC(=O)O)Cc3ccc(OC(=O)c4ccc(OCc5ccccc5)cc4)cc3)cc2)cc1] | 36 | 7.75 |

TABLE 1-continued
| STRUCTURE | COMPOUND NUMBER | LCMS RETENTION TIME (min) |
|---|---|---|
| 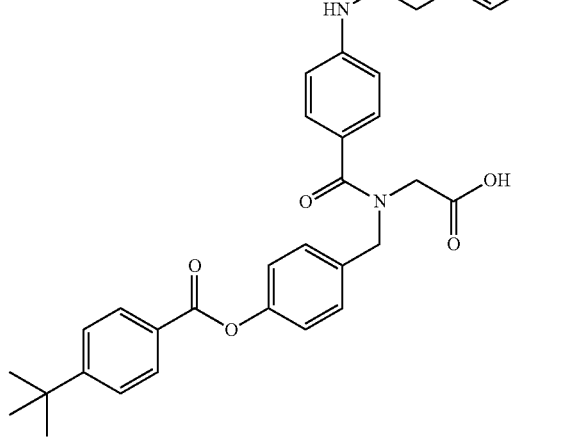 | 37 | 8.06 |
| 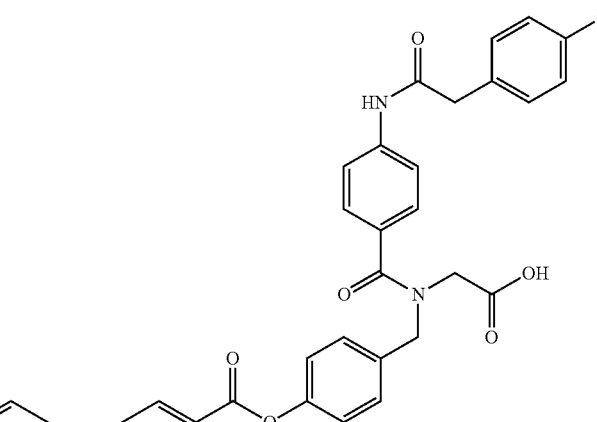 | 38 | 7.91 |
| 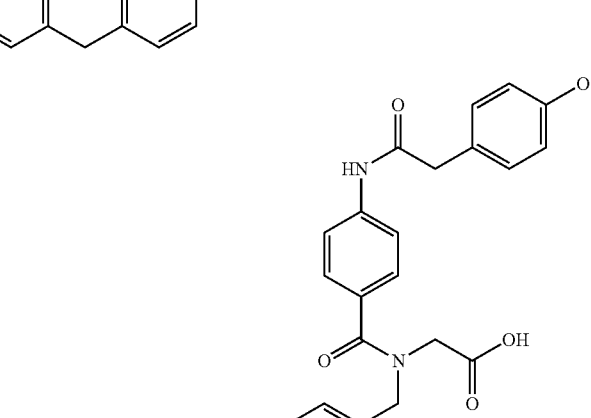 | 39 | 8.92 |

TABLE 1-continued

| STRUCTURE | COMPOUND NUMBER | LCMS RETENTION TIME (min) |
|---|---|---|
| 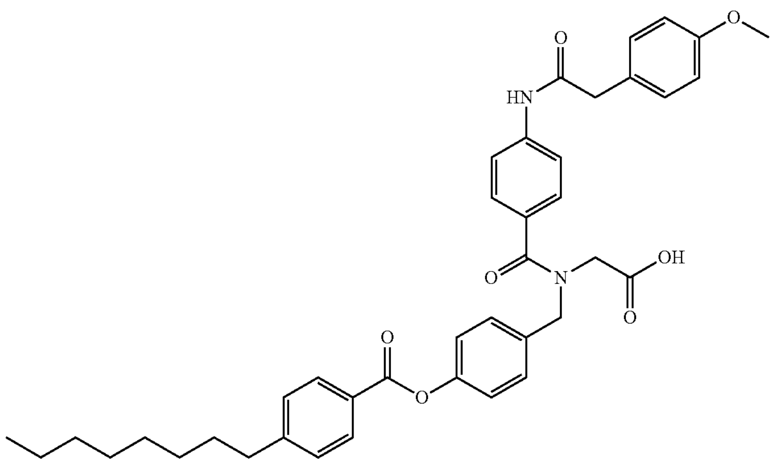 [SMILES: CCCCCCCCc1ccc(C(=O)Oc2ccc(CN(CC(=O)O)C(=O)c3ccc(NC(=O)Cc4ccc(OC)cc4)cc3)cc2)cc1] | 40 | 10.33 |
| 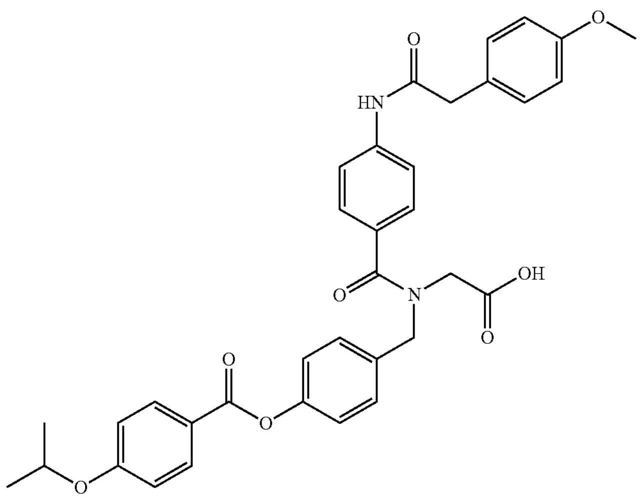 [SMILES: COc1ccc(CC(=O)Nc2ccc(C(=O)N(CC(=O)O)Cc3ccc(OC(=O)c4ccc(OC(C)C)cc4)cc3)cc2)cc1] | 41 | 7.29 |
| 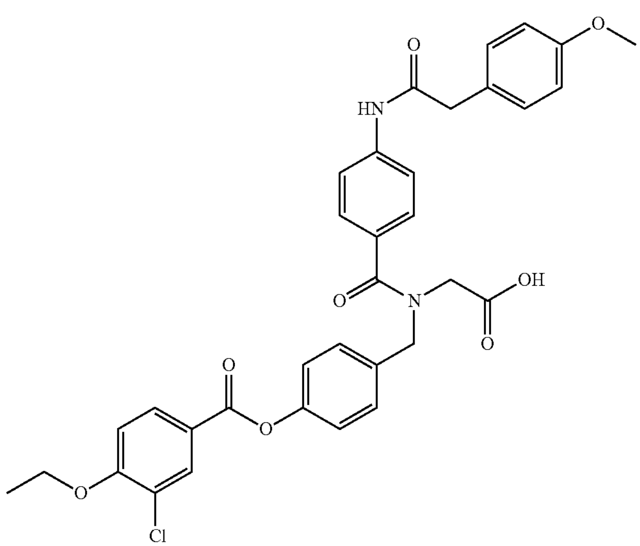 [SMILES: CCOc1ccc(C(=O)Oc2ccc(CN(CC(=O)O)C(=O)c3ccc(NC(=O)Cc4ccc(OC)cc4)cc3)cc2)cc1Cl] | 42 | 7.38 |

TABLE 1-continued

| STRUCTURE | COMPOUND NUMBER | LCMS RETENTION TIME (min) |
|---|---|---|
| 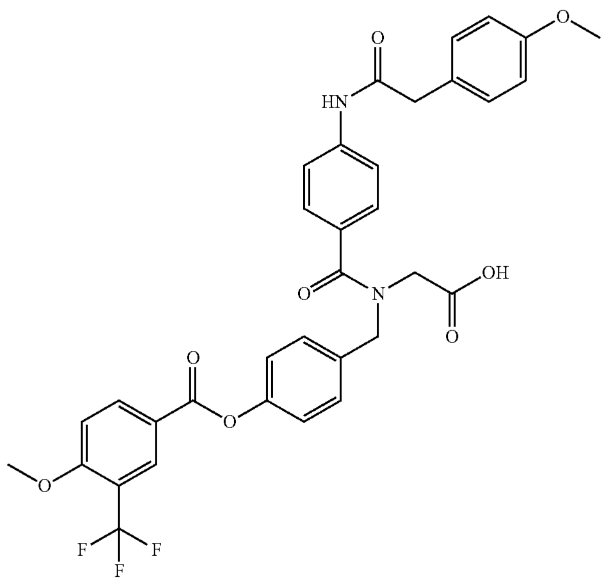 | 43 | 7.05 |
| 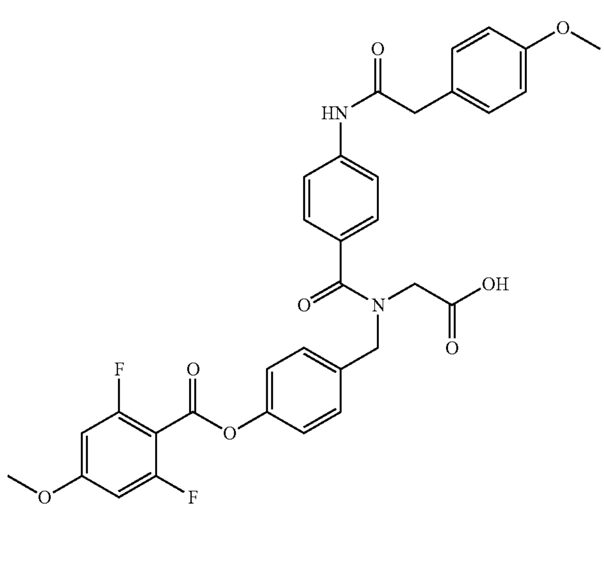 | 44 | 6.45 |

TABLE 1-continued

| STRUCTURE | COMPOUND NUMBER | LCMS RETENTION TIME (min) |
|---|---|---|
| 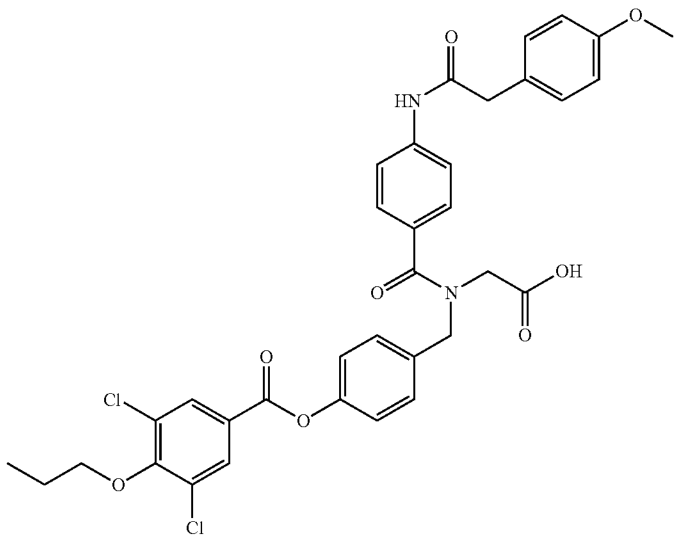 [SMILES: CCCOc1c(Cl)cc(C(=O)Oc2ccc(CN(CC(=O)O)C(=O)c3ccc(NC(=O)Cc4ccc(OC)cc4)cc3)cc2)cc1Cl] | 45 | 8.73 |
| 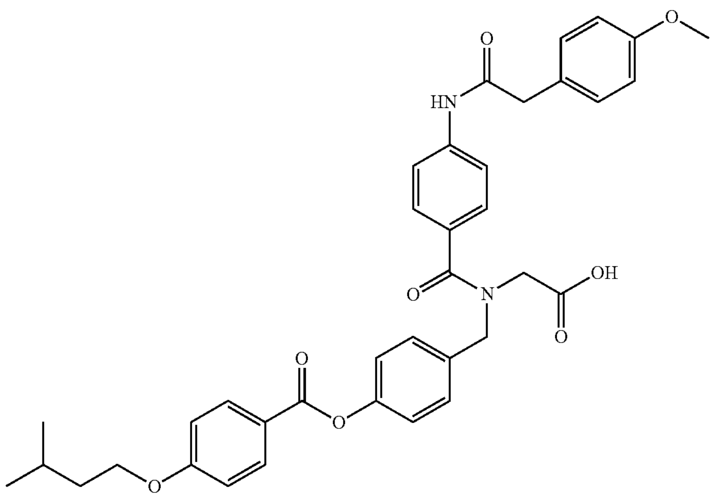 [SMILES: COc1ccc(CC(=O)Nc2ccc(C(=O)N(CC(=O)O)Cc3ccc(OC(=O)c4ccc(OCCC(C)C)cc4)cc3)cc2)cc1] | 46 | 8.44 |
| 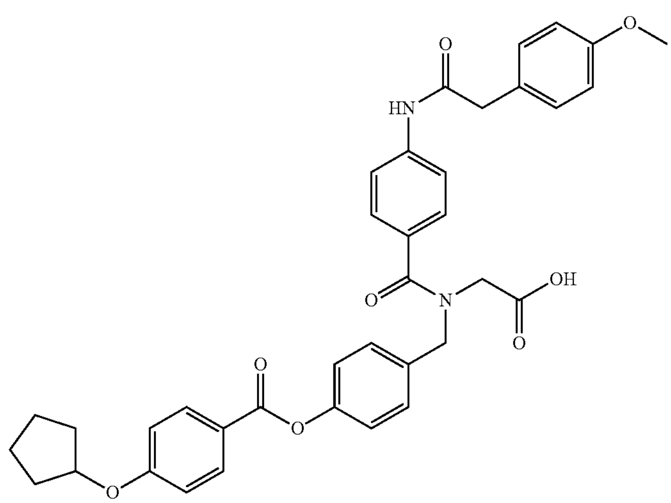 [SMILES: COc1ccc(CC(=O)Nc2ccc(C(=O)N(CC(=O)O)Cc3ccc(OC(=O)c4ccc(OC5CCCC5)cc4)cc3)cc2)cc1] | 47 | 8.08 |

TABLE 1-continued
| STRUCTURE | COMPOUND NUMBER | LCMS RETENTION TIME (min) |
|---|---|---|
| 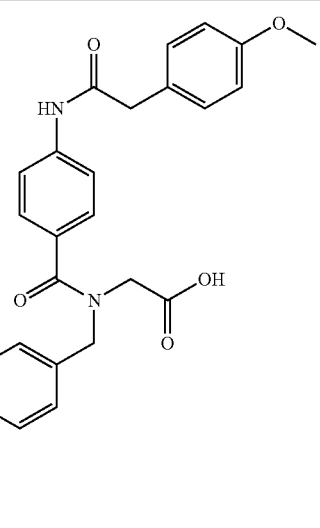 | 48 | 5.05 |
| 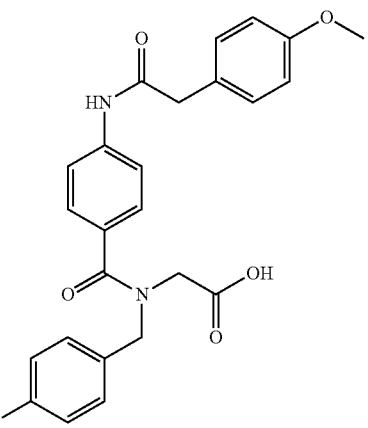 | 49 | 5.57 |
| 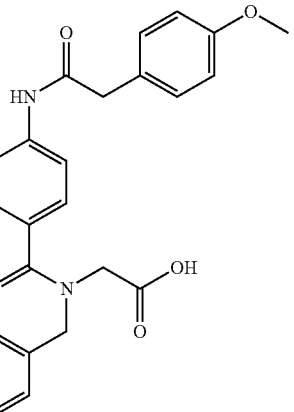 | 50 | 4.71 |

TABLE 1-continued
| STRUCTURE | COMPOUND NUMBER | LCMS RETENTION TIME (min) |
|---|---|---|
| 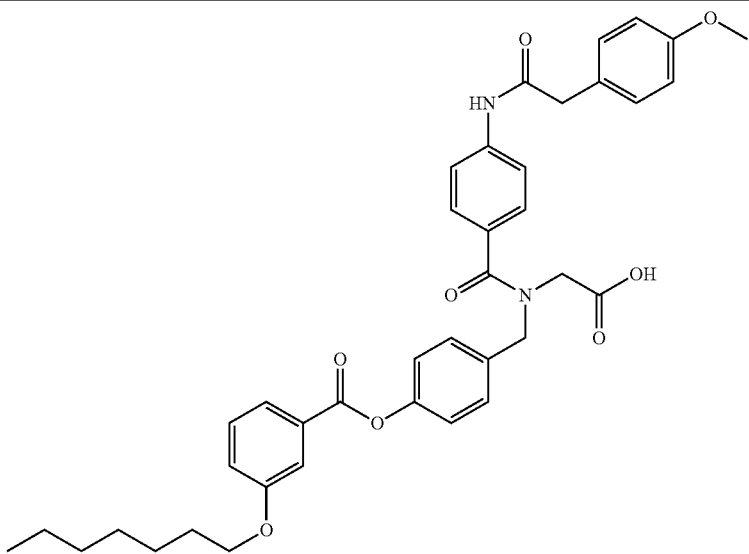 | 51 | 9.49 |
| 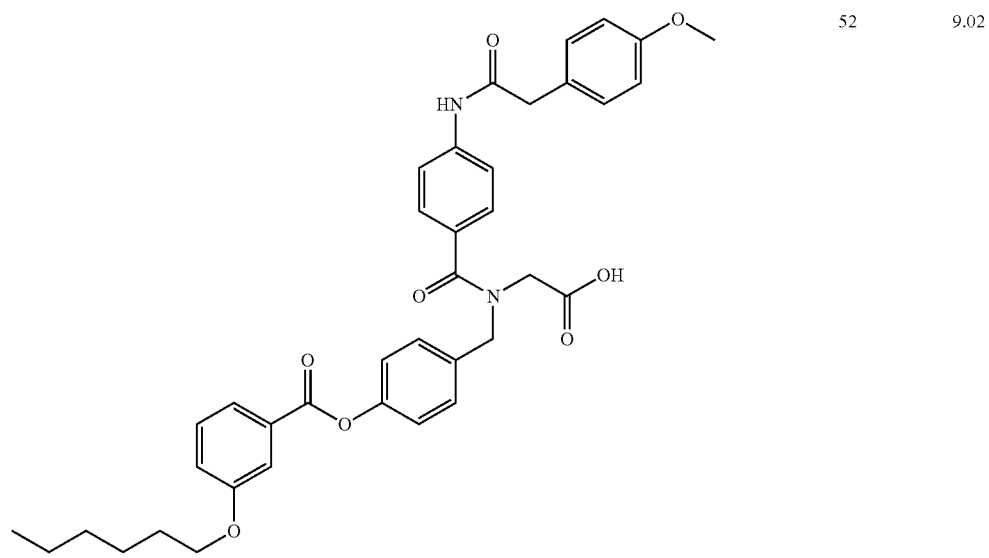 | 52 | 9.02 |

TABLE 1-continued
| STRUCTURE | COMPOUND NUMBER | LCMS RETENTION TIME (min) |
|---|---|---|
| 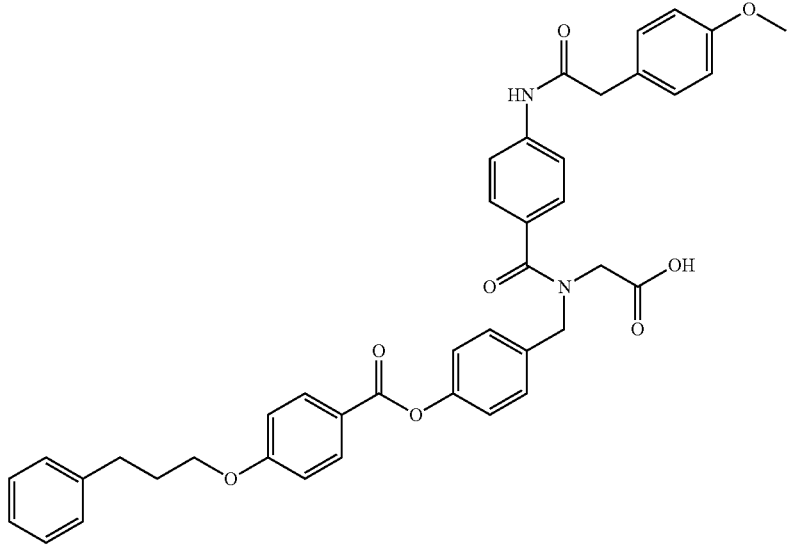 [SMILES: COc1ccc(CC(=O)Nc2ccc(C(=O)N(CC(=O)O)Cc3ccc(OC(=O)c4ccc(OCCCc5ccccc5)cc4)cc3)cc2)cc1] | 53 | 8.49 |
| 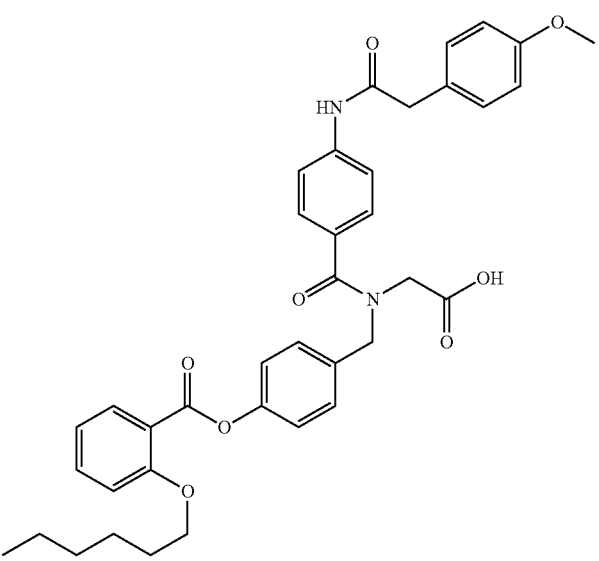 [SMILES: CCCCCCOc1ccccc1C(=O)Oc1ccc(CN(CC(=O)O)C(=O)c2ccc(NC(=O)Cc3ccc(OC)cc3)cc2)cc1] | 54 | 8.30 |

TABLE 1-continued

| STRUCTURE | COMPOUND NUMBER | LCMS RETENTION TIME (min) |
|---|---|---|
| 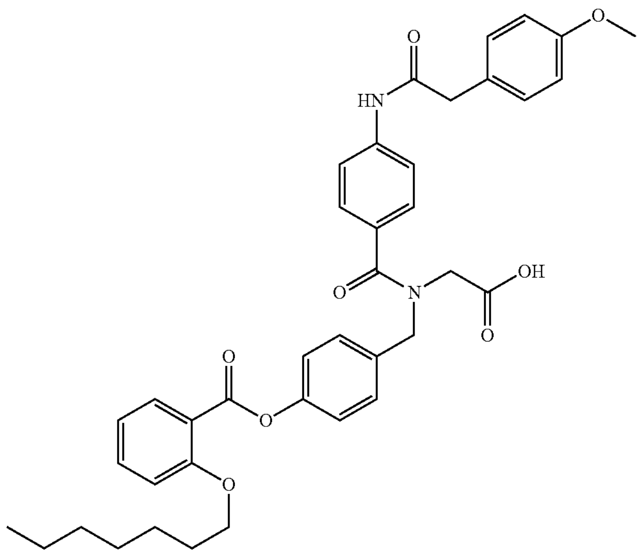 [SMILES: CCCCCCCOc1ccccc1C(=O)Oc1ccc(CN(CC(=O)O)C(=O)c2ccc(NC(=O)Cc3ccc(OC)cc3)cc2)cc1] | 55 | 8.72 |
| 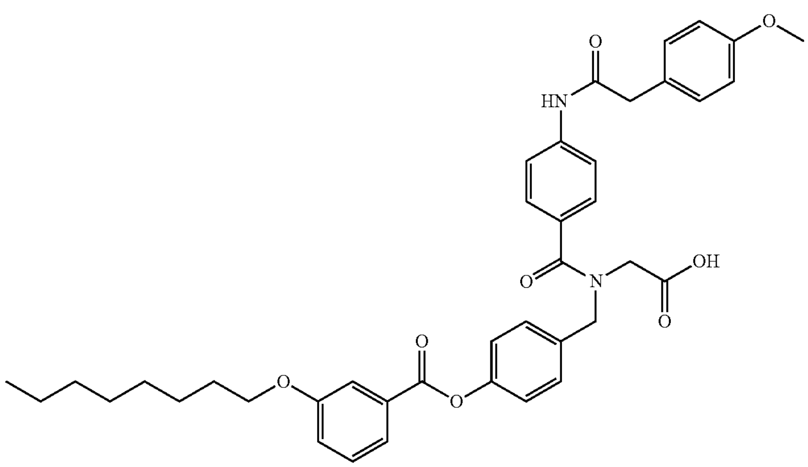 [SMILES: CCCCCCCCOc1cccc(C(=O)Oc2ccc(CN(CC(=O)O)C(=O)c3ccc(NC(=O)Cc4ccc(OC)cc4)cc3)cc2)c1] | 56 | 9.98 |
| 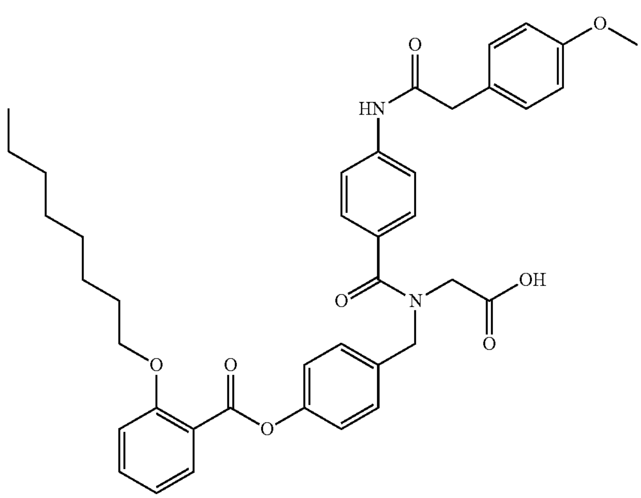 [SMILES: CCCCCCCCOc1ccccc1C(=O)Oc1ccc(CN(CC(=O)O)C(=O)c2ccc(NC(=O)Cc3ccc(OC)cc3)cc2)cc1] | 57 | 9.46 |

TABLE 1-continued

| STRUCTURE | COMPOUND NUMBER | LCMS RETENTION TIME (min) |
|---|---|---|
| 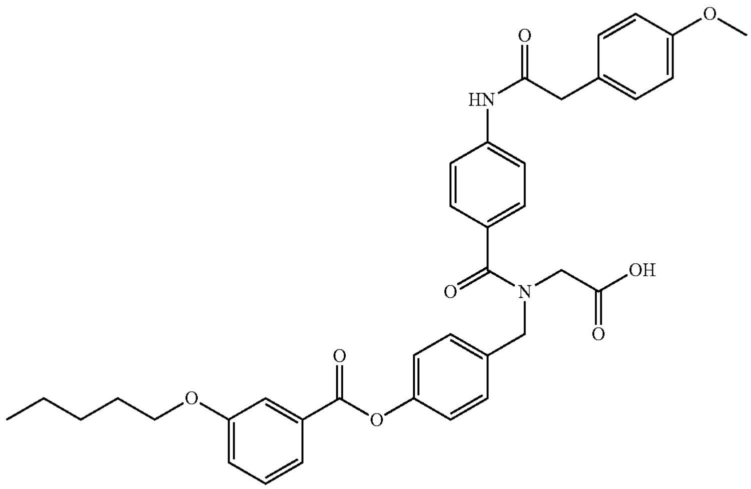 [SMILES: CCCCCOc1cccc(C(=O)Oc2ccc(CN(CC(=O)O)C(=O)c3ccc(NC(=O)Cc4ccc(OC)cc4)cc3)cc2)c1] | 58 | 8.53 |
| 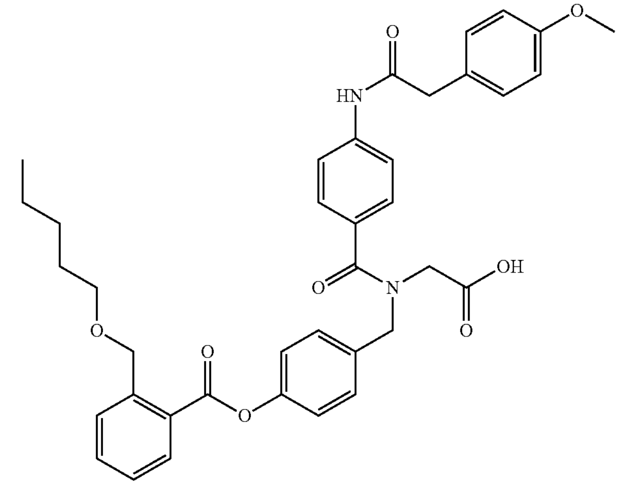 [SMILES: CCCCCOCc1ccccc1C(=O)Oc1ccc(CN(CC(=O)O)C(=O)c2ccc(NC(=O)Cc3ccc(OC)cc3)cc2)cc1] | 59 | 7.88 |
| 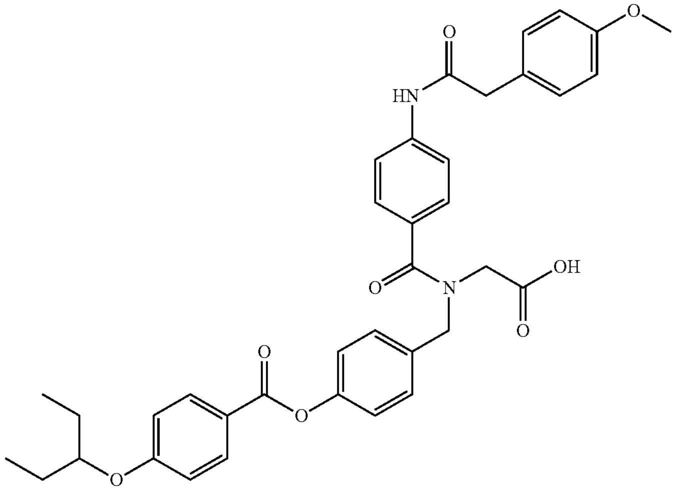 [SMILES: CCC(CC)Oc1ccc(C(=O)Oc2ccc(CN(CC(=O)O)C(=O)c3ccc(NC(=O)Cc4ccc(OC)cc4)cc3)cc2)cc1] | 60 | 8.30 |

TABLE 1-continued

| STRUCTURE | COMPOUND NUMBER | LCMS RETENTION TIME (min) |
|---|---|---|
| 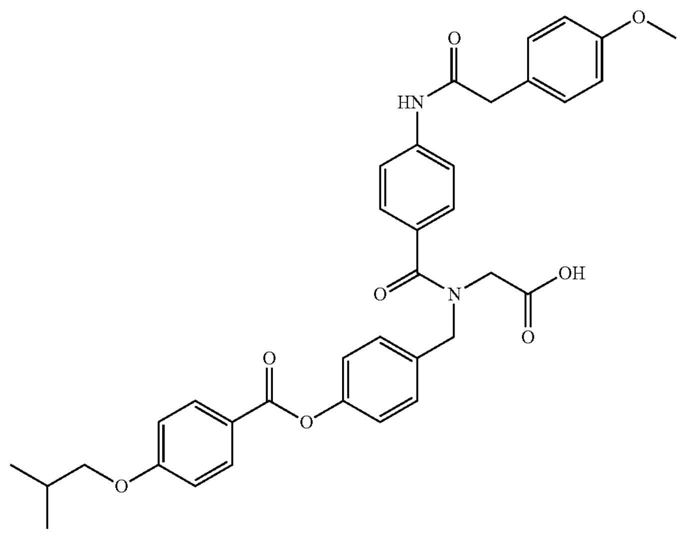 [SMILES: COc1ccc(CC(=O)Nc2ccc(C(=O)N(CC(=O)O)Cc3ccc(OC(=O)c4ccc(OCC(C)C)cc4)cc3)cc2)cc1] | 61 | 8.03 |
| 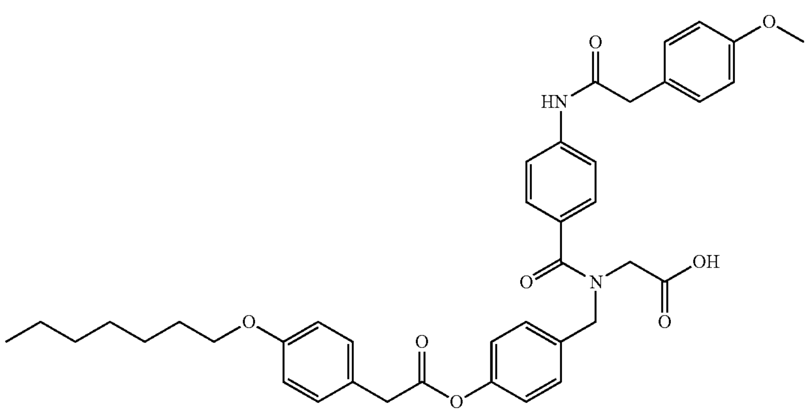 [SMILES: CCCCCCCOc1ccc(CC(=O)Oc2ccc(CN(CC(=O)O)C(=O)c3ccc(NC(=O)Cc4ccc(OC)cc4)cc3)cc2)cc1] | 62 | 9.28 |
| 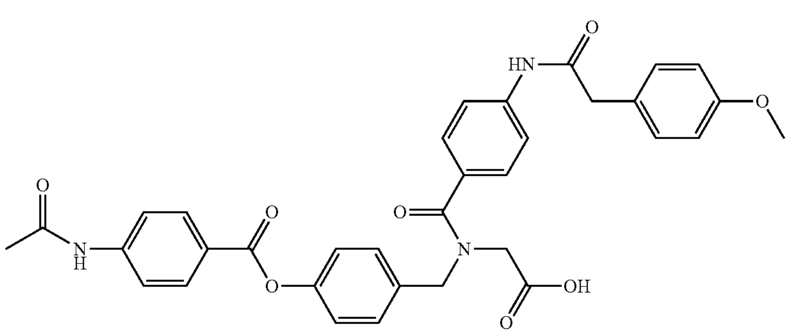 [SMILES: COc1ccc(CC(=O)Nc2ccc(C(=O)N(CC(=O)O)Cc3ccc(OC(=O)c4ccc(NC(C)=O)cc4)cc3)cc2)cc1] | 63 | 5.07 |
| 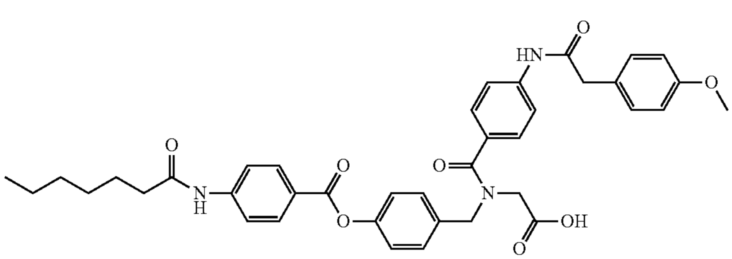 [SMILES: CCCCCCC(=O)Nc1ccc(C(=O)Oc2ccc(CN(CC(=O)O)C(=O)c3ccc(NC(=O)Cc4ccc(OC)cc4)cc3)cc2)cc1] | 64 | 7.49 |

TABLE 1-continued

| STRUCTURE | COMPOUND NUMBER | LCMS RETENTION TIME (min) |
|---|---|---|
| 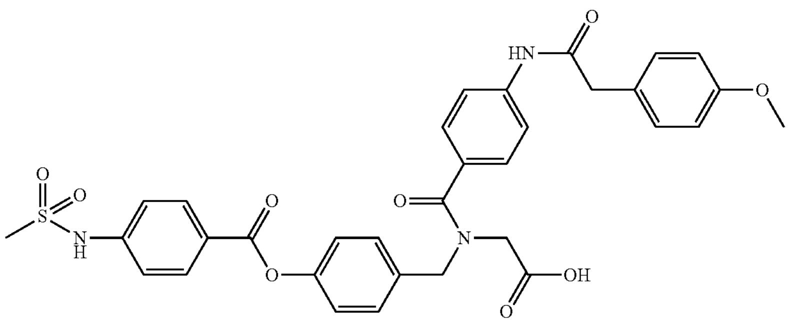 | 65 | 5.77 |
| 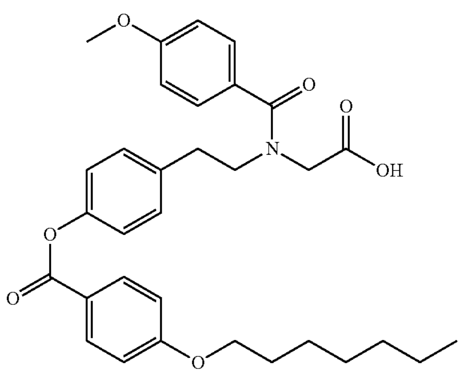 [SMILES: CCCCCCCOc1ccc(C(=O)Oc2ccc(CCN(CC(=O)O)C(=O)c3ccc(OC)cc3)cc2)cc1] | 66 | 9.66 |
| 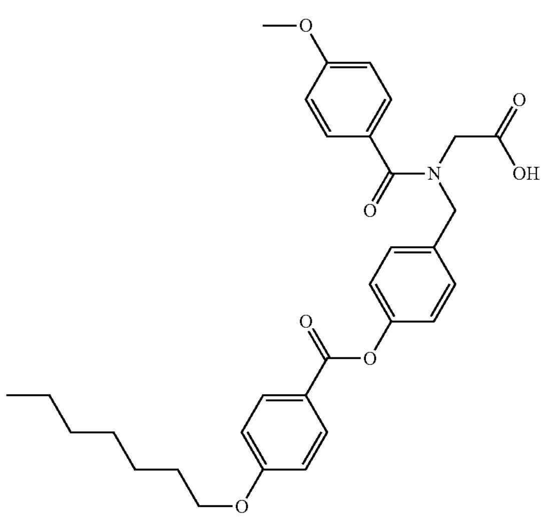 [SMILES: CCCCCCCOc1ccc(C(=O)Oc2ccc(CN(CC(=O)O)C(=O)c3ccc(OC)cc3)cc2)cc1] | 67 | 9.54 |

TABLE 1-continued
| STRUCTURE | COMPOUND NUMBER | LCMS RETENTION TIME (min) |
|---|---|---|
| 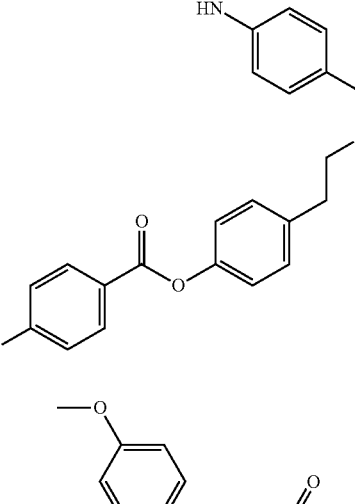 | 68 | 10.28 |
| 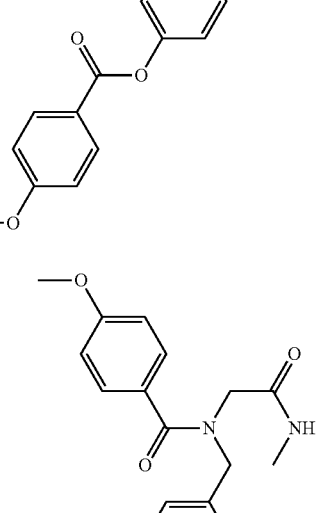 | 69 | 9.00 |
| 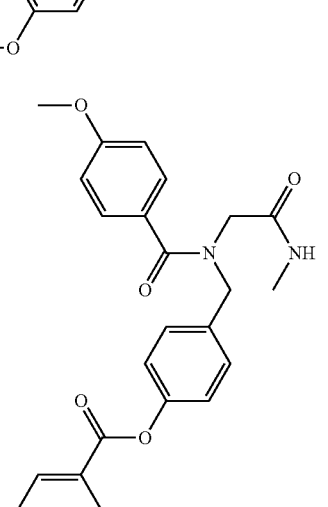 | 70 | 9.30 |

TABLE 1-continued

| STRUCTURE | COMPOUND NUMBER | LCMS RETENTION TIME (min) |
|---|---|---|
| 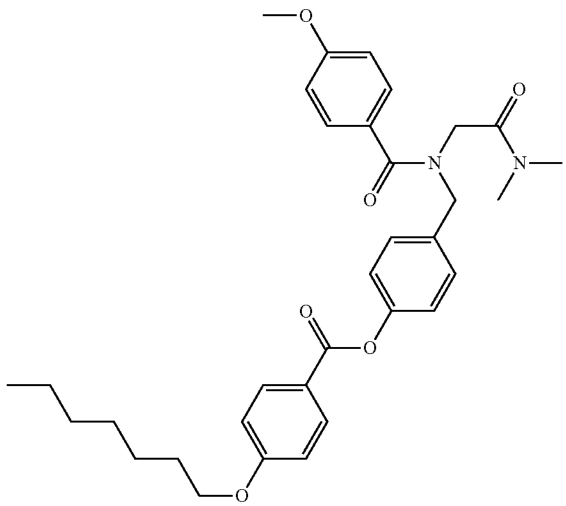 [SMILES: CCCCCCCOc1ccc(C(=O)Oc2ccc(CN(CC(=O)N(C)C)C(=O)c3ccc(OC)cc3)cc2)cc1] | 71 | 9.71 |
| 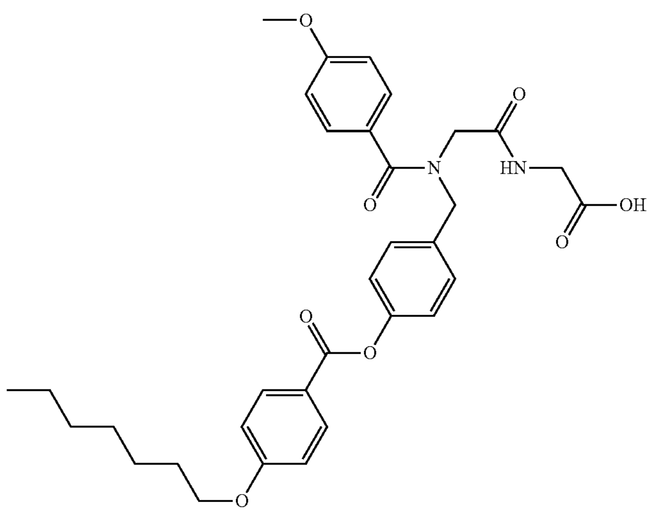 [SMILES: CCCCCCCOc1ccc(C(=O)Oc2ccc(CN(CC(=O)NCC(=O)O)C(=O)c3ccc(OC)cc3)cc2)cc1] | 72 | 8.86 |
| 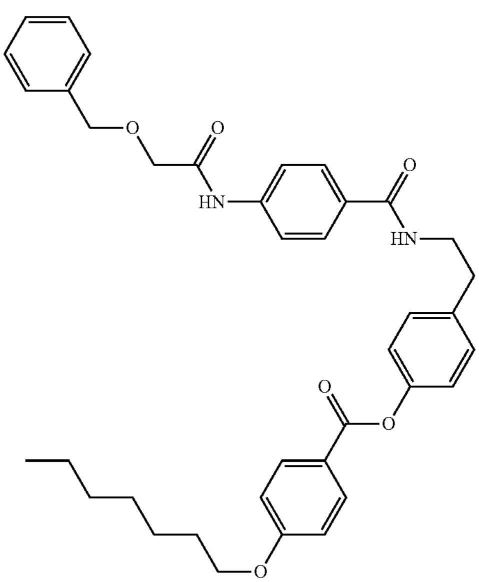 [SMILES: CCCCCCCOc1ccc(C(=O)Oc2ccc(CCNC(=O)c3ccc(NC(=O)COCc4ccccc4)cc3)cc2)cc1] | 73 | 10.90 |

| STRUCTURE | COMPOUND NUMBER | LCMS RETENTION TIME (min) |
|---|---|---|
| 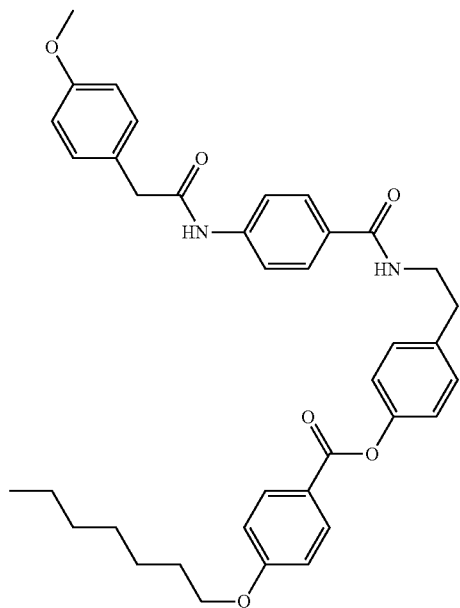 [SMILES: CCCCCCCOc1ccc(C(=O)Oc2ccc(CCNC(=O)c3ccc(NC(=O)Cc4ccc(OC)cc4)cc3)cc2)cc1] | 74 | 10.49 |
| 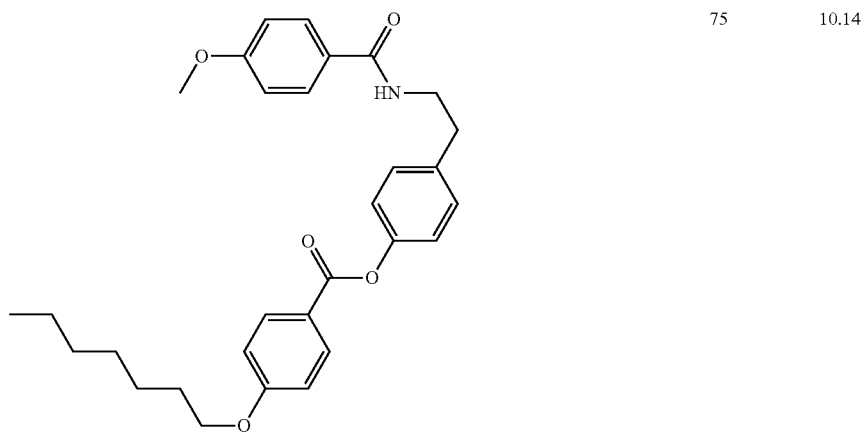 | 75 | 10.14 |

TABLE 1-continued
| STRUCTURE | COMPOUND NUMBER | LCMS RETENTION TIME (min) |
|---|---|---|
| 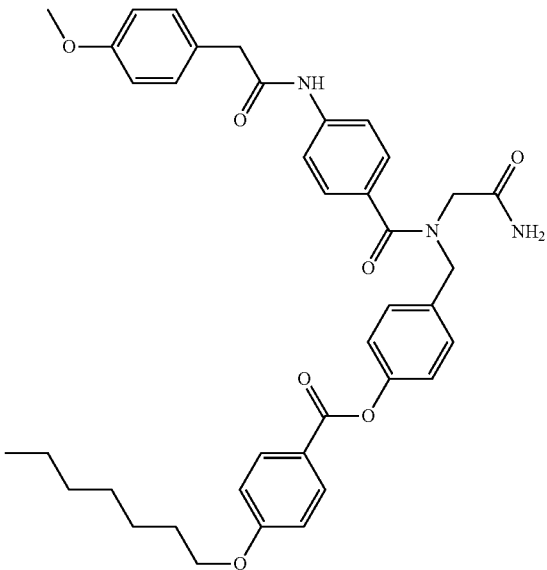 [SMILES: CCCCCCCOc1ccc(C(=O)Oc2ccc(CN(CC(N)=O)C(=O)c3ccc(NC(=O)Cc4ccc(OC)cc4)cc3)cc2)cc1] | 76 | 9.07 |
| 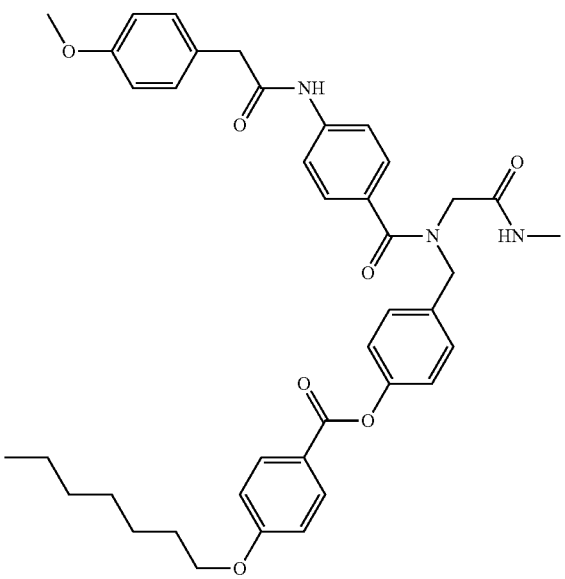 [SMILES: CCCCCCCOc1ccc(C(=O)Oc2ccc(CN(CC(=O)NC)C(=O)c3ccc(NC(=O)Cc4ccc(OC)cc4)cc3)cc2)cc1] | 77 | 9.34 |

TABLE 1-continued
| STRUCTURE | COMPOUND NUMBER | LCMS RETENTION TIME (min) |
|---|---|---|
| 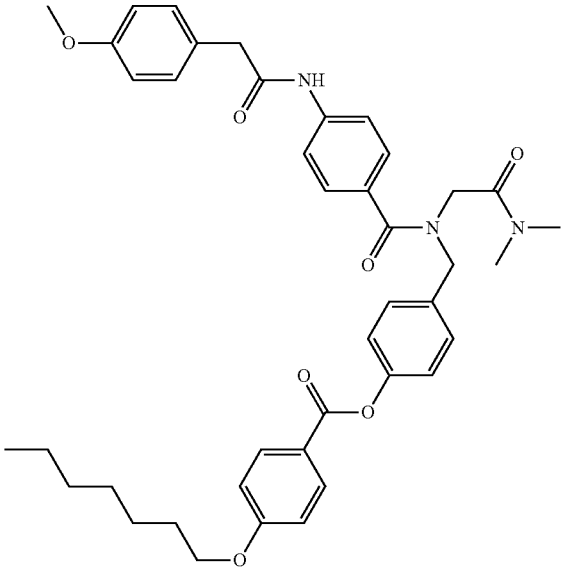 [SMILES: CCCCCCCOc1ccc(C(=O)Oc2ccc(CN(CC(=O)N(C)C)C(=O)c3ccc(NC(=O)Cc4ccc(OC)cc4)cc3)cc2)cc1] | 78 | 9.71 |
| 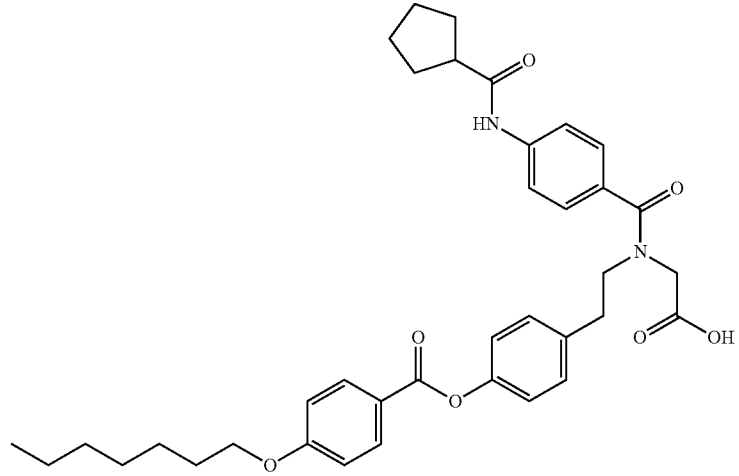 [SMILES: CCCCCCCOc1ccc(C(=O)Oc2ccc(CCN(CC(=O)O)C(=O)c3ccc(NC(=O)C4CCCC4)cc3)cc2)cc1] | 79 | 9.93 |

TABLE 1-continued

| STRUCTURE | COMPOUND NUMBER | LCMS RETENTION TIME (min) |
|---|---|---|
| 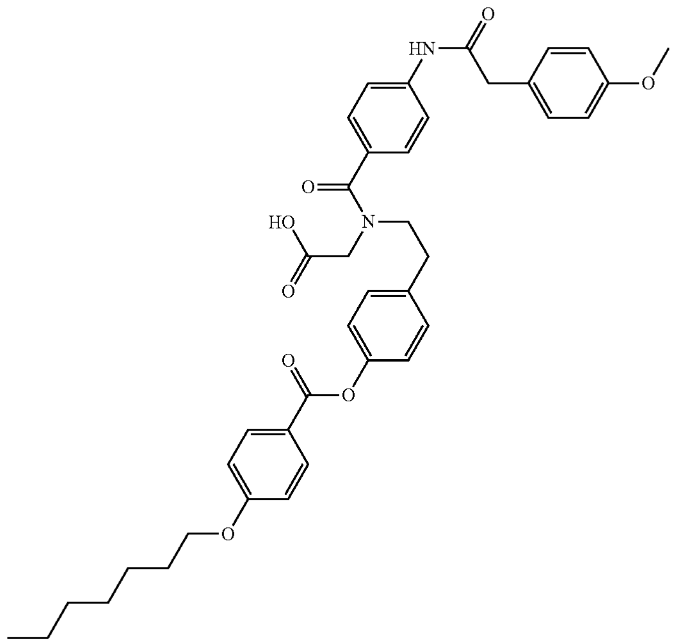 [SMILES: CCCCCCCOc1ccc(C(=O)Oc2ccc(CCN(CC(=O)O)C(=O)c3ccc(NC(=O)Cc4ccc(OC)cc4)cc3)cc2)cc1] | 80 | 9.64 |
| 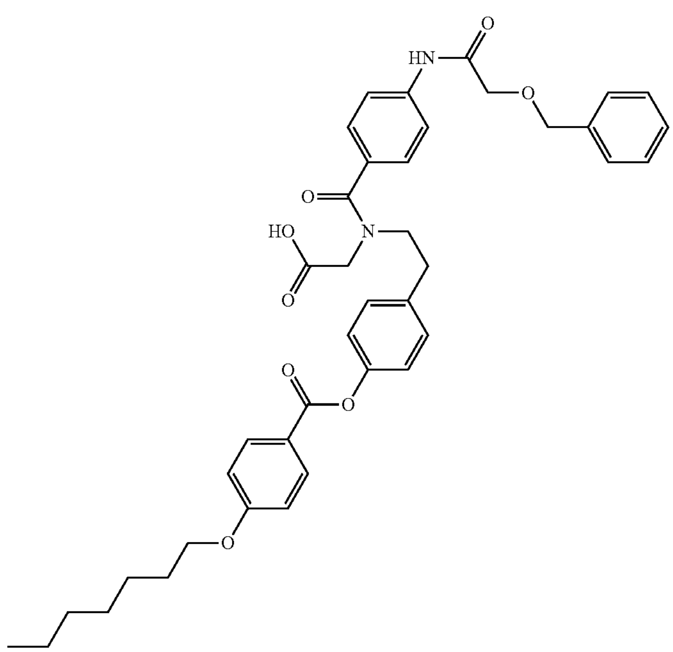 [SMILES: CCCCCCCOc1ccc(C(=O)Oc2ccc(CCN(CC(=O)O)C(=O)c3ccc(NC(=O)COCc4ccccc4)cc3)cc2)cc1] | 81 | 10.02 |

TABLE 1-continued
| STRUCTURE | COMPOUND NUMBER | LCMS RETENTION TIME (min) |
|---|---|---|
| 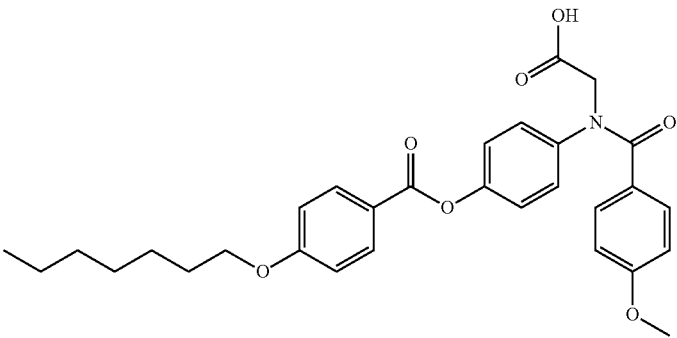 [SMILES: CCCCCCCOc1ccc(C(=O)Oc2ccc(N(CC(=O)O)C(=O)c3ccc(OC)cc3)cc2)cc1] | 82 | 9.08 |
| 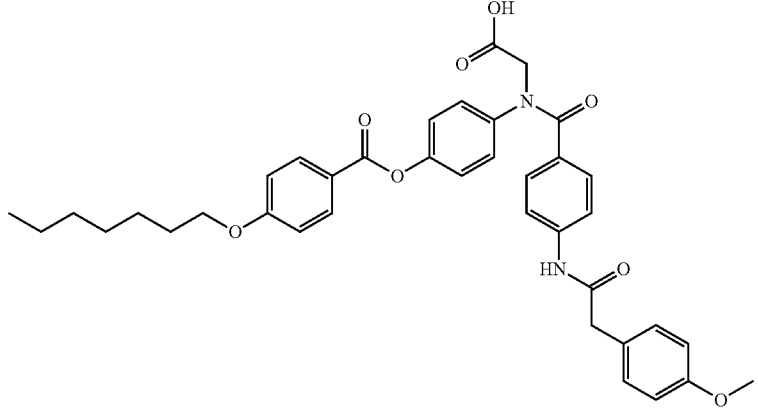 [SMILES: CCCCCCCOc1ccc(C(=O)Oc2ccc(N(CC(=O)O)C(=O)c3ccc(NC(=O)Cc4ccc(OC)cc4)cc3)cc2)cc1] | 83 | 8.77 |
| 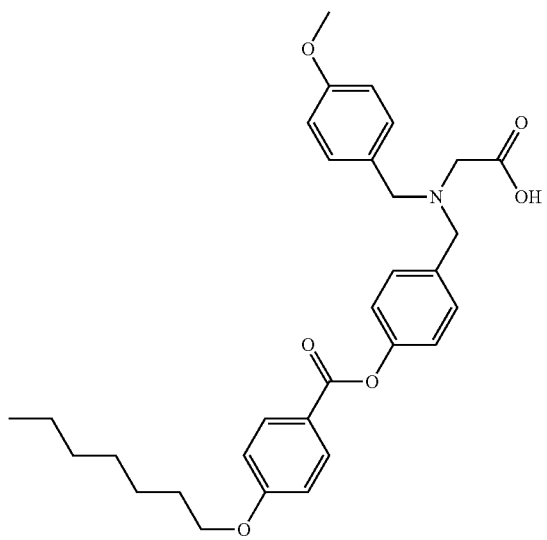 [SMILES: CCCCCCCOc1ccc(C(=O)Oc2ccc(CN(CC(=O)O)Cc3ccc(OC)cc3)cc2)cc1] | 84 | 7.85 |

TABLE 1-continued

| STRUCTURE | COMPOUND NUMBER | LCMS RETENTION TIME (min) |
|---|---|---|
| 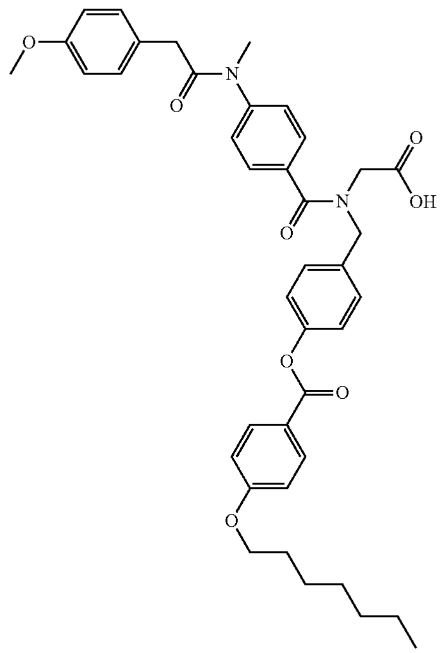 [SMILES: CCCCCCCOc1ccc(C(=O)Oc2ccc(CN(CC(=O)O)C(=O)c3ccc(N(C)C(=O)Cc4ccc(OC)cc4)cc3)cc2)cc1] | 85 | 9.43 |
| 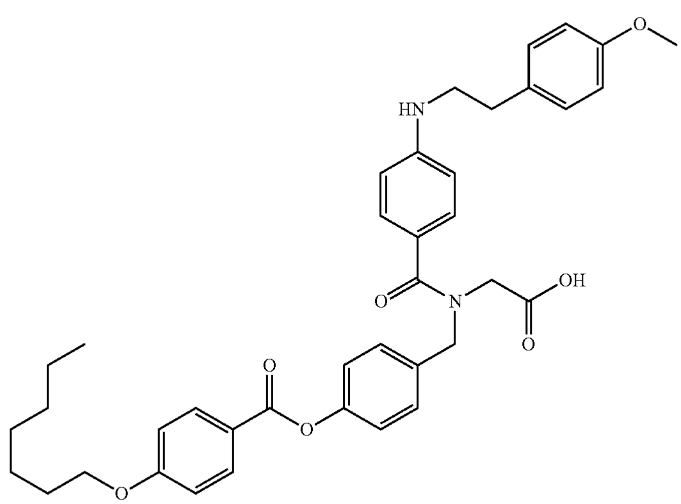 [SMILES: CCCCCCCOc1ccc(C(=O)Oc2ccc(CN(CC(=O)O)C(=O)c3ccc(NCCc4ccc(OC)cc4)cc3)cc2)cc1] | 86 | 3.14 |

TABLE 1-continued

| STRUCTURE | COMPOUND NUMBER | LCMS RETENTION TIME (min) |
|---|---|---|
| 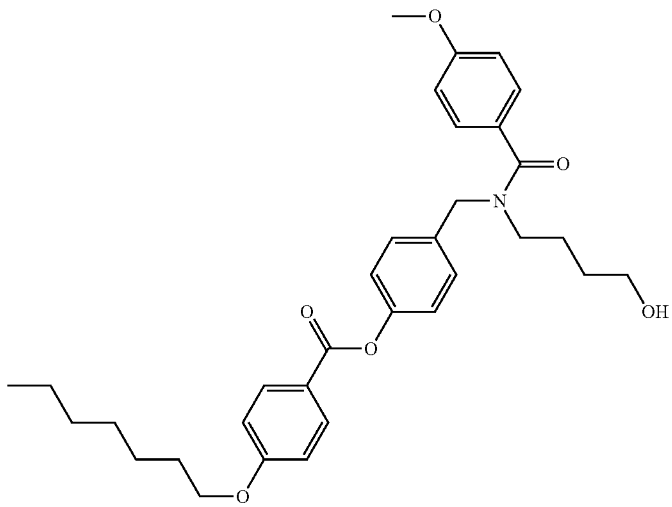 [SMILES: CCCCCCCOc1ccc(C(=O)Oc2ccc(CN(CCCCO)C(=O)c3ccc(OC)cc3)cc2)cc1] | 87 | 3.07 |
| 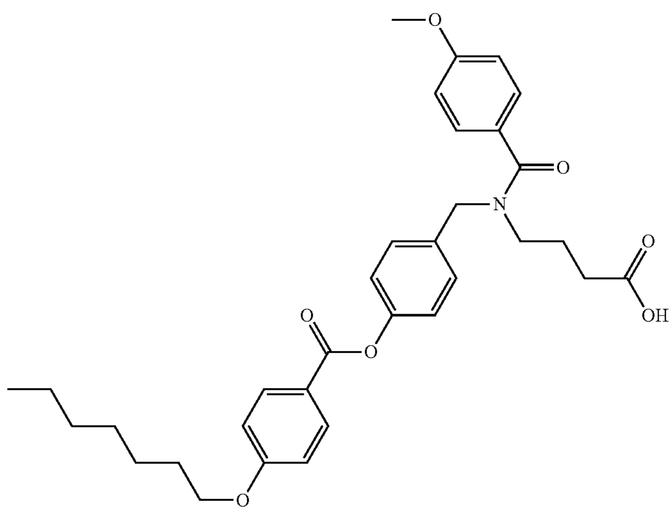 [SMILES: CCCCCCCOc1ccc(C(=O)Oc2ccc(CN(CCCC(=O)O)C(=O)c3ccc(OC)cc3)cc2)cc1] | 88 | 9.53 |
| 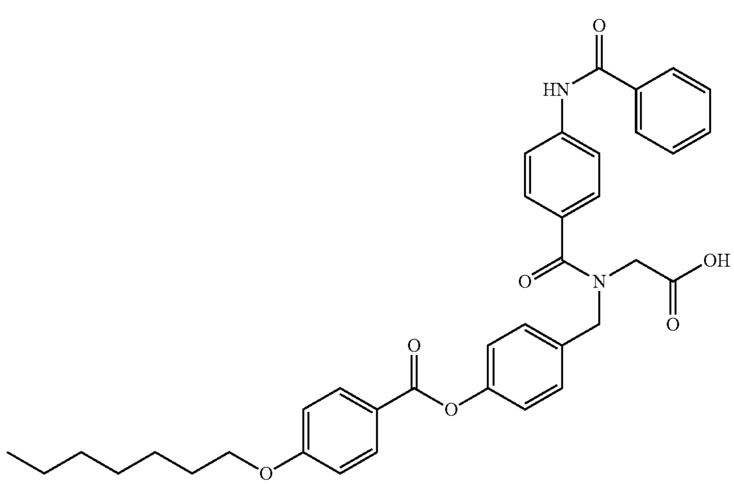 [SMILES: CCCCCCCOc1ccc(C(=O)Oc2ccc(CN(CC(=O)O)C(=O)c3ccc(NC(=O)c4ccccc4)cc3)cc2)cc1] | 89 | 10.94 |

TABLE 1-continued

| STRUCTURE | COMPOUND NUMBER | LCMS RETENTION TIME (min) |
|---|---|---|
| 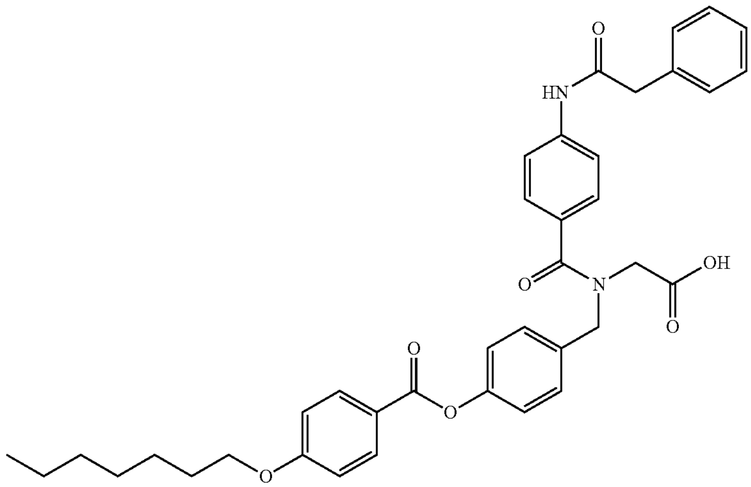 [SMILES: CCCCCCCOc1ccc(C(=O)Oc2ccc(CN(CC(=O)O)C(=O)c3ccc(NC(=O)Cc4ccccc4)cc3)cc2)cc1] | 90 | 10.92 |
| 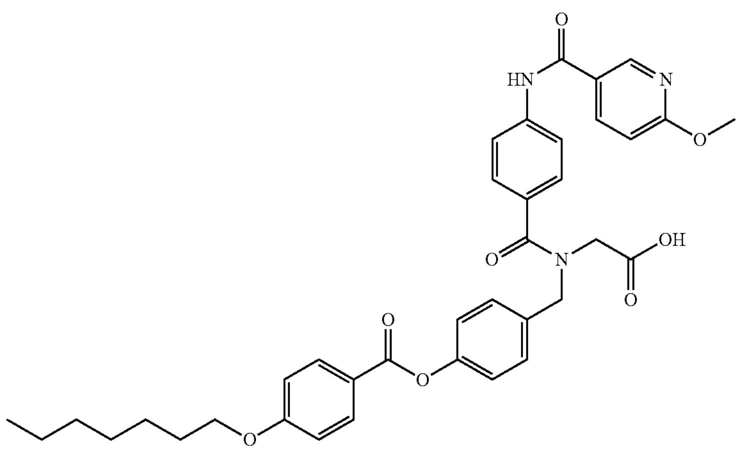 [SMILES: CCCCCCCOc1ccc(C(=O)Oc2ccc(CN(CC(=O)O)C(=O)c3ccc(NC(=O)c4ccc(OC)nc4)cc3)cc2)cc1] | 91 | 11.08 |
| 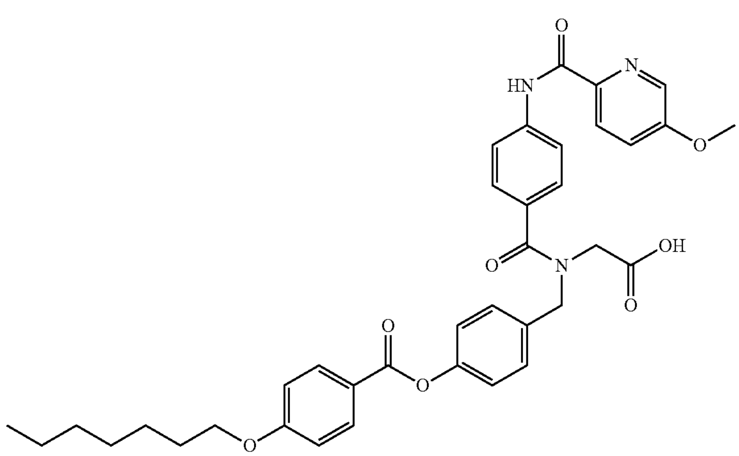 [SMILES: CCCCCCCOc1ccc(C(=O)Oc2ccc(CN(CC(=O)O)C(=O)c3ccc(NC(=O)c4ccc(OC)cn4)cc3)cc2)cc1] | 92 | 11.27 |

TABLE 1-continued
| STRUCTURE | COMPOUND NUMBER | LCMS RETENTION TIME (min) |
|---|---|---|
| 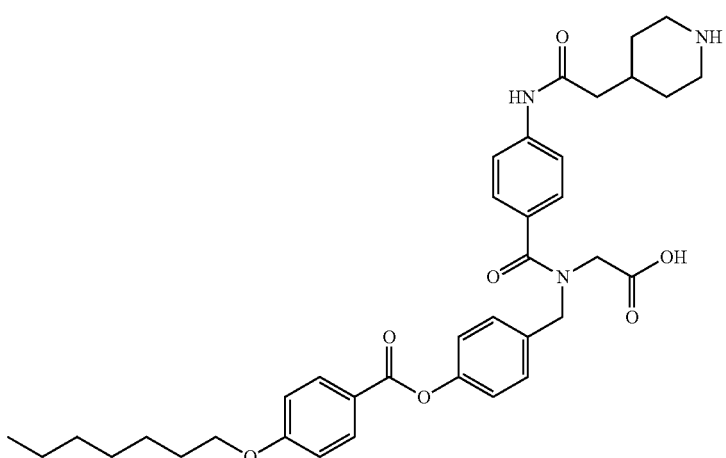 | 93 | 7.95 |
| 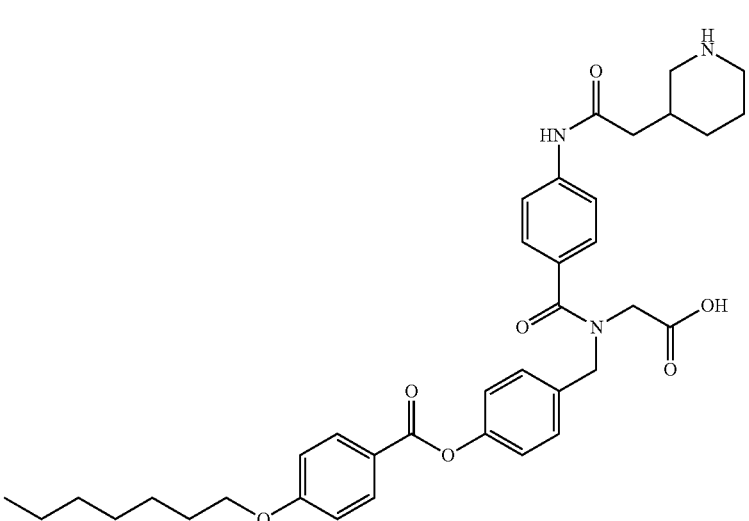 [SMILES: CCCCCCCOc1ccc(C(=O)Oc2ccc(CN(CC(=O)O)C(=O)c3ccc(NC(=O)CC4CCCNC4)cc3)cc2)cc1] | 94 | 7.90 |
| 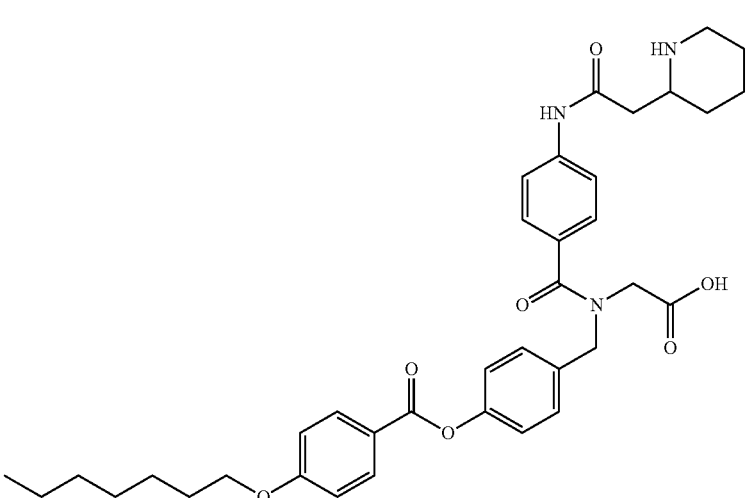 | 95 | 8.19 |

TABLE 1-continued
| STRUCTURE | COMPOUND NUMBER | LCMS RETENTION TIME (min) |
|---|---|---|
| 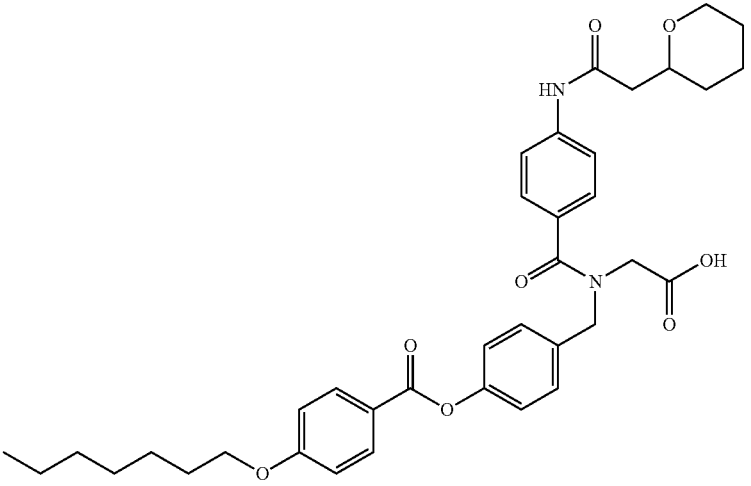 [SMILES: CCCCCCCOc1ccc(C(=O)Oc2ccc(CN(CC(=O)O)C(=O)c3ccc(NC(=O)CC4CCCCO4)cc3)cc2)cc1] | 96 | 11.03 |
| 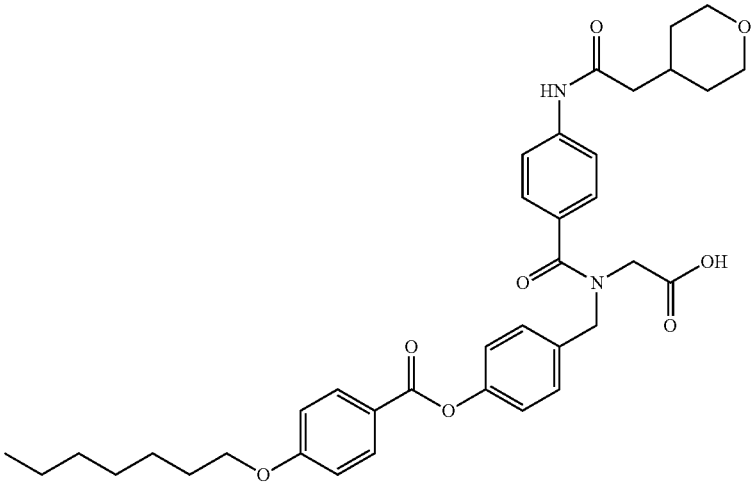 [SMILES: CCCCCCCOc1ccc(C(=O)Oc2ccc(CN(CC(=O)O)C(=O)c3ccc(NC(=O)CC4CCOCC4)cc3)cc2)cc1] | 97 | 10.55 |
| 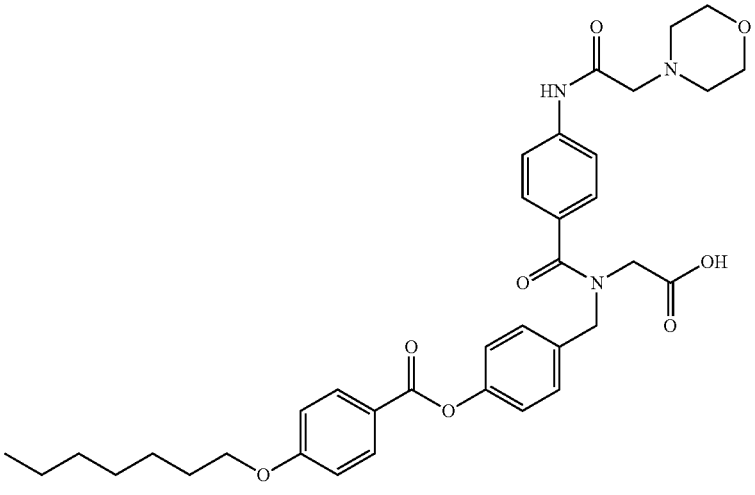 [SMILES: CCCCCCCOc1ccc(C(=O)Oc2ccc(CN(CC(=O)O)C(=O)c3ccc(NC(=O)CN4CCOCC4)cc3)cc2)cc1] | 98 | 8.05 |

TABLE 1-continued

| STRUCTURE | COMPOUND NUMBER | LCMS RETENTION TIME (min) |
|---|---|---|
| 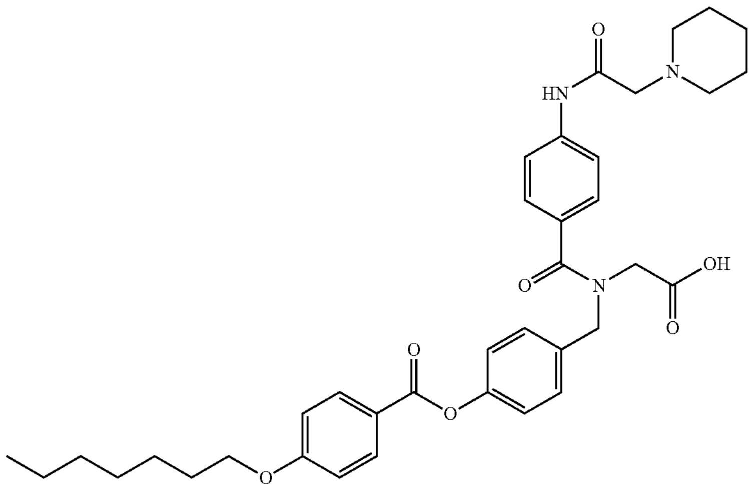 [SMILES: CCCCCCCOc1ccc(C(=O)Oc2ccc(CN(CC(=O)O)C(=O)c3ccc(NC(=O)CN4CCCCC4)cc3)cc2)cc1] | 99 | 7.94 |
| 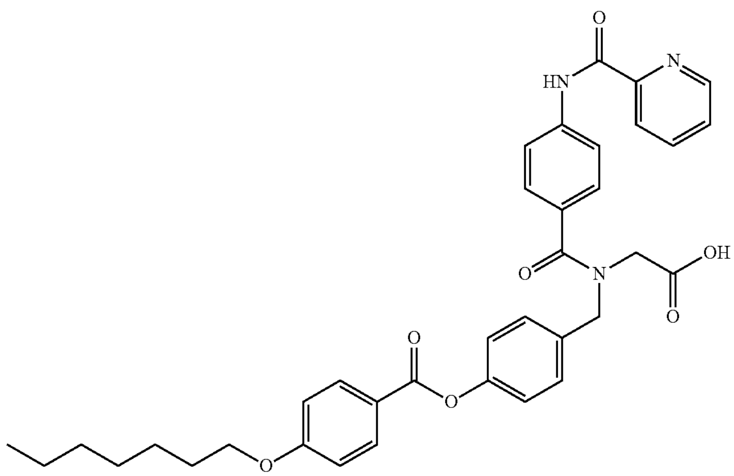 [SMILES: CCCCCCCOc1ccc(C(=O)Oc2ccc(CN(CC(=O)O)C(=O)c3ccc(NC(=O)c4ccccn4)cc3)cc2)cc1] | 100 | 11.20 |
| 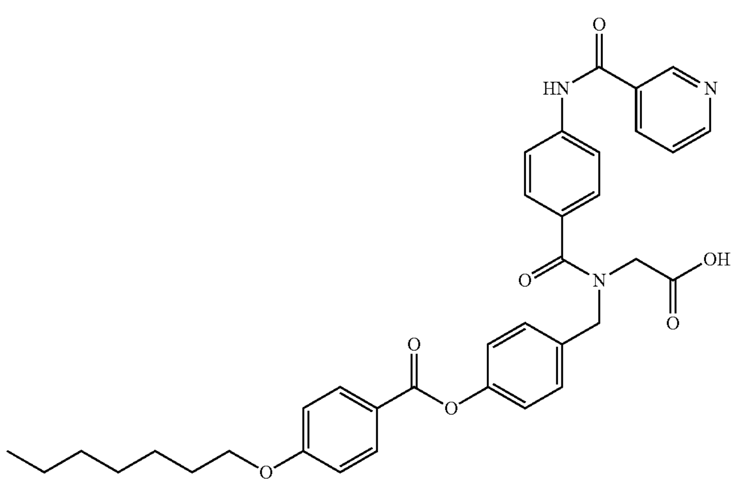 [SMILES: CCCCCCCOc1ccc(C(=O)Oc2ccc(CN(CC(=O)O)C(=O)c3ccc(NC(=O)c4cccnc4)cc3)cc2)cc1] | 101 | 10.28 |

TABLE 1-continued
| STRUCTURE | COMPOUND NUMBER | LCMS RETENTION TIME (min) |
|---|---|---|
| 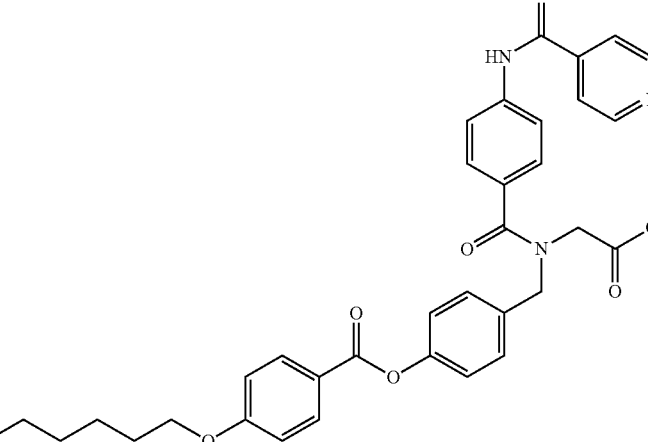 | 102 | 10.21 |
| 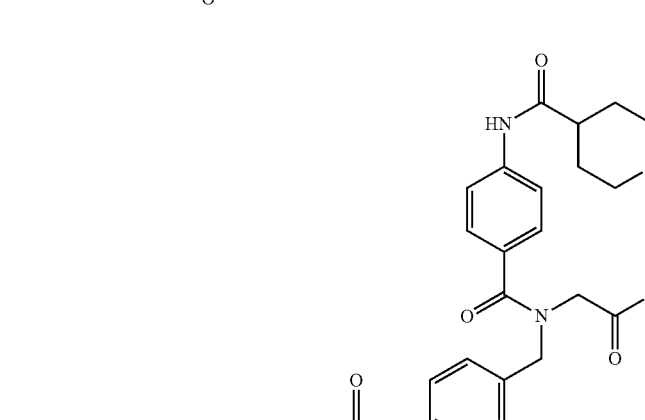 | 103 | 7.91 |
| 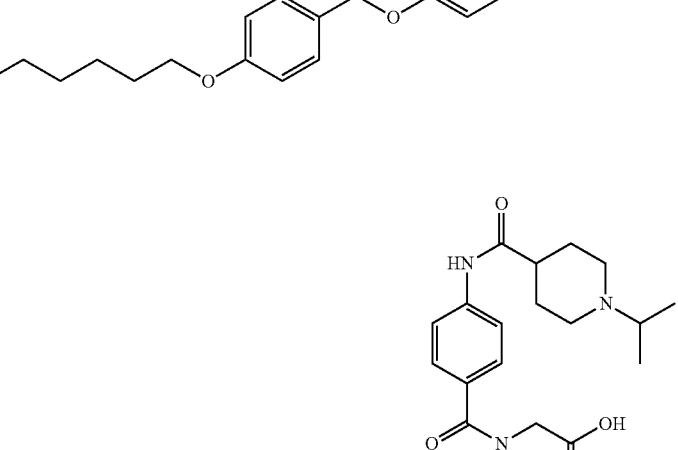 | 104 | 8.24 |

TABLE 1-continued
| STRUCTURE | COMPOUND NUMBER | LCMS RETENTION TIME (min) |
|---|---|---|
| 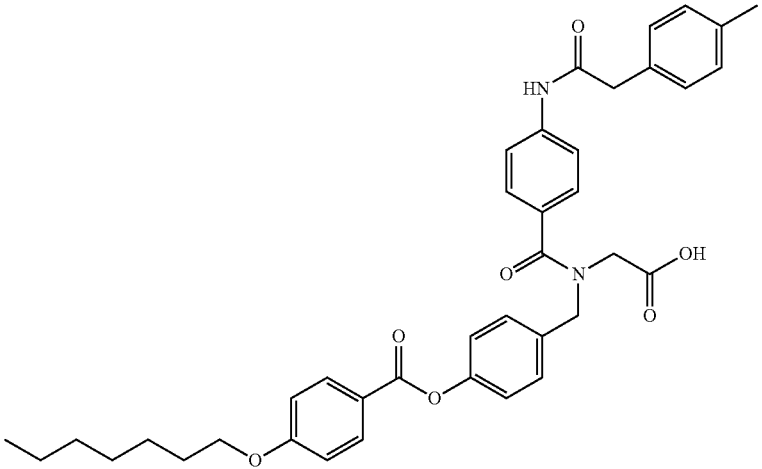 [SMILES: CCCCCCCOc1ccc(C(=O)Oc2ccc(CN(CC(=O)O)C(=O)c3ccc(NC(=O)Cc4ccc(C)cc4)cc3)cc2)cc1] | 105 | 11.39 |
| 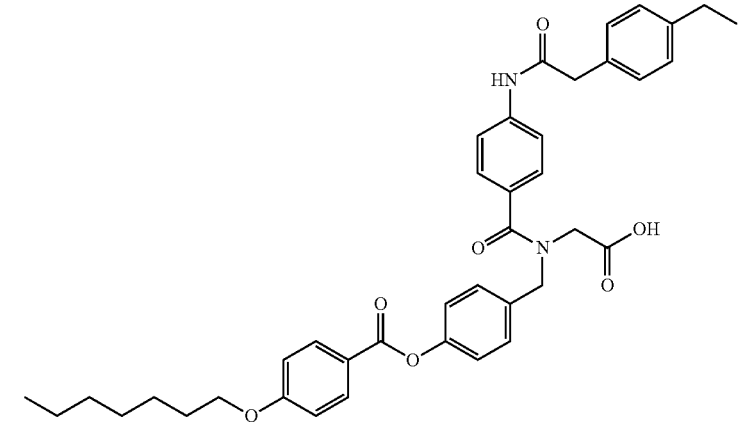 [SMILES: CCCCCCCOc1ccc(C(=O)Oc2ccc(CN(CC(=O)O)C(=O)c3ccc(NC(=O)Cc4ccc(CC)cc4)cc3)cc2)cc1] | 106 | 11.63 |
| 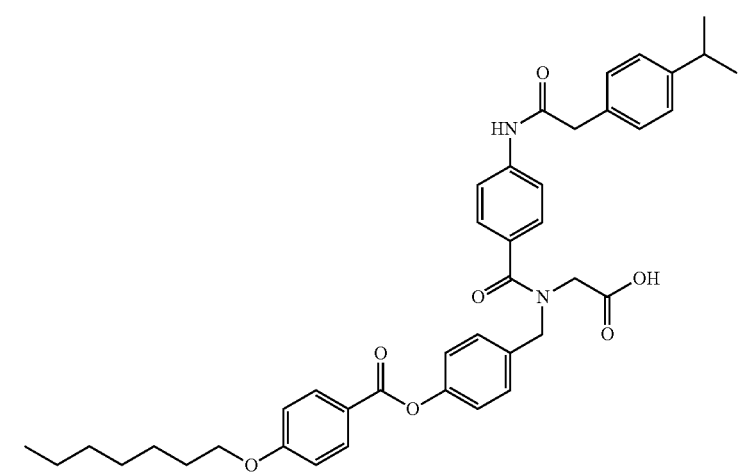 | 107 | 11.82 |

TABLE 1-continued

| STRUCTURE | COMPOUND NUMBER | LCMS RETENTION TIME (min) |
|---|---|---|
| 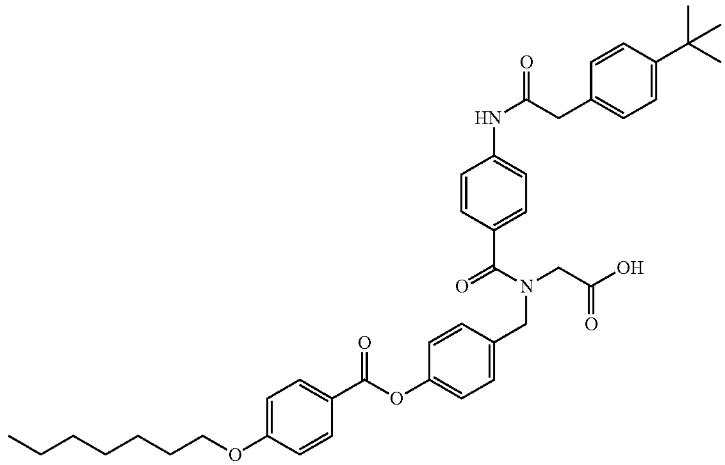 [SMILES: CCCCCCCOc1ccc(C(=O)Oc2ccc(CN(CC(=O)O)C(=O)c3ccc(NC(=O)Cc4ccc(C(C)(C)C)cc4)cc3)cc2)cc1] | 108 | 12.00 |
| 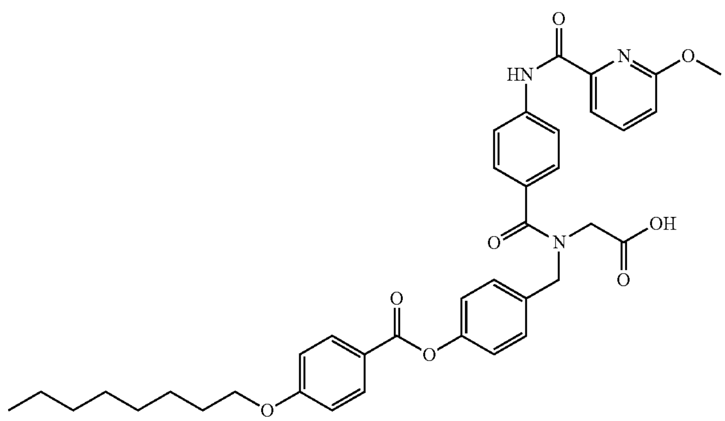 [SMILES: CCCCCCCCOc1ccc(C(=O)Oc2ccc(CN(CC(=O)O)C(=O)c3ccc(NC(=O)c4cccc(OC)n4)cc3)cc2)cc1] | 109 | 11.57 |
| 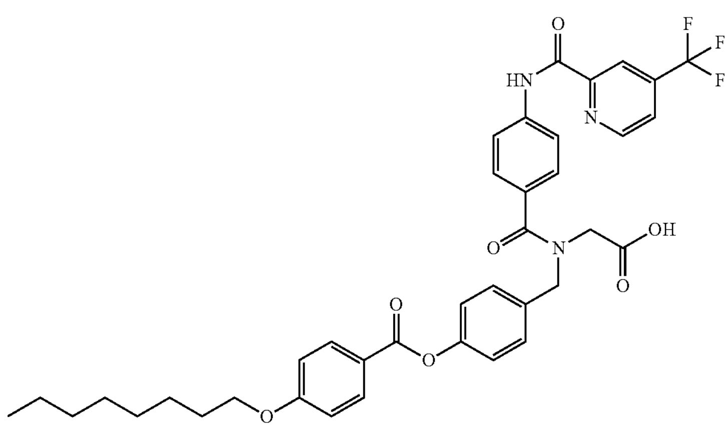 [SMILES: CCCCCCCCOc1ccc(C(=O)Oc2ccc(CN(CC(=O)O)C(=O)c3ccc(NC(=O)c4cc(C(F)(F)F)ccn4)cc3)cc2)cc1] | 110 | 11.66 |

TABLE 1-continued

| STRUCTURE | COMPOUND NUMBER | LCMS RETENTION TIME (min) |
|---|---|---|
| *(structure)* | 111 | 11.54 |
| *(structure)* | 112 | 11.63 |
| *(structure)* | 113 | 11.51 |

TABLE 1-continued

| STRUCTURE | COMPOUND NUMBER | LCMS RETENTION TIME (min) |
|---|---|---|
| 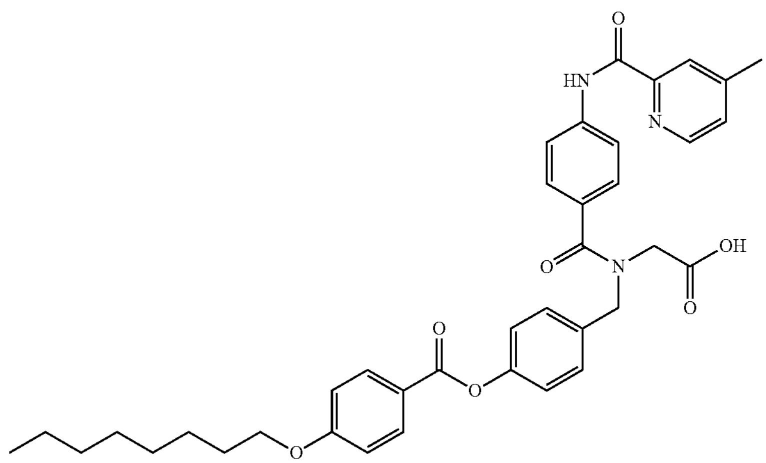 [SMILES: CCCCCCCCOc1ccc(C(=O)Oc2ccc(CN(CC(=O)O)C(=O)c3ccc(NC(=O)c4cc(C)ccn4)cc3)cc2)cc1] | 114 | 11.50 |
| 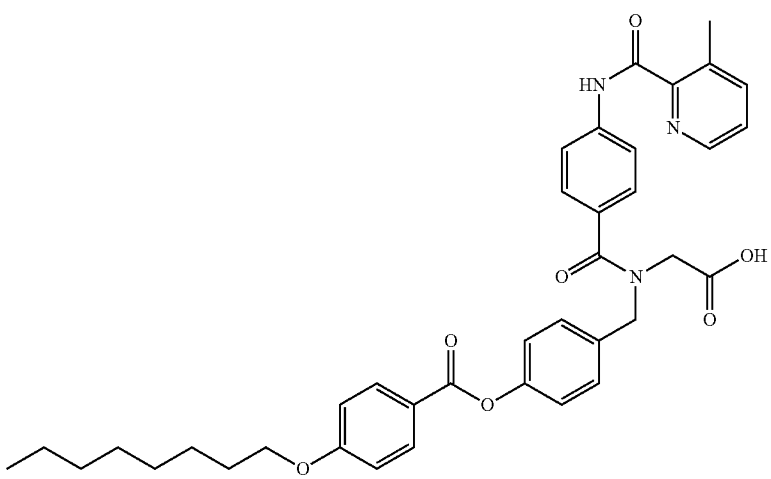 [SMILES: CCCCCCCCOc1ccc(C(=O)Oc2ccc(CN(CC(=O)O)C(=O)c3ccc(NC(=O)c4ncccc4C)cc3)cc2)cc1] | 115 | 11.53 |
| 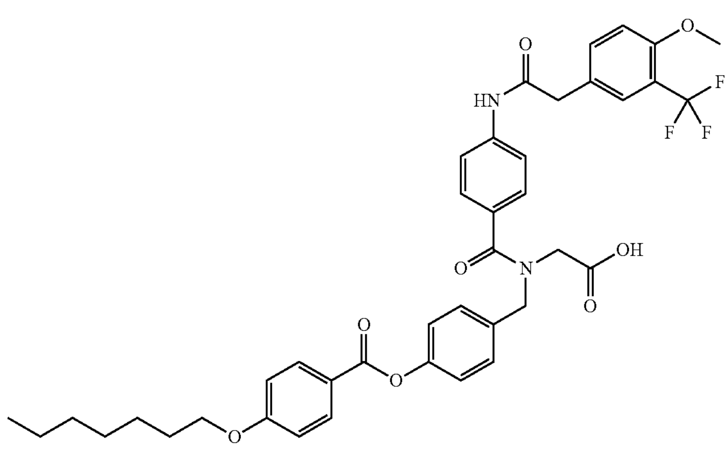 [SMILES: CCCCCCCOc1ccc(C(=O)Oc2ccc(CN(CC(=O)O)C(=O)c3ccc(NC(=O)Cc4ccc(OC)c(C(F)(F)F)c4)cc3)cc2)cc1] | 116 | 11.31 |

TABLE 1-continued

| STRUCTURE | COMPOUND NUMBER | LCMS RETENTION TIME (min) |
|---|---|---|
| 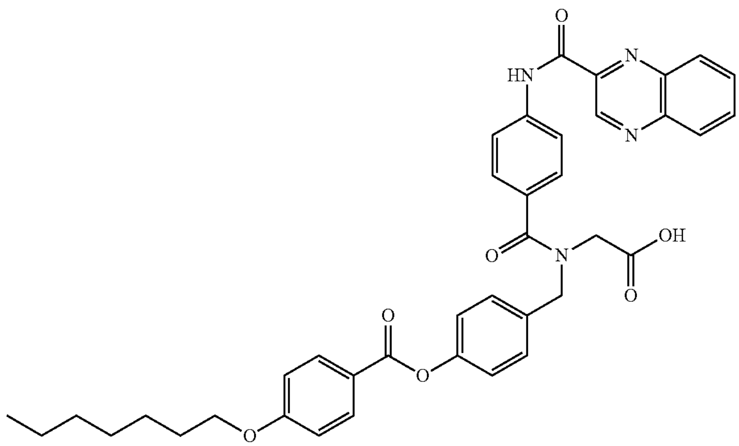 [SMILES: CCCCCCCOc1ccc(C(=O)Oc2ccc(CN(CC(=O)O)C(=O)c3ccc(NC(=O)c4cnc5ccccc5n4)cc3)cc2)cc1] | 117 | 11.36 |
| 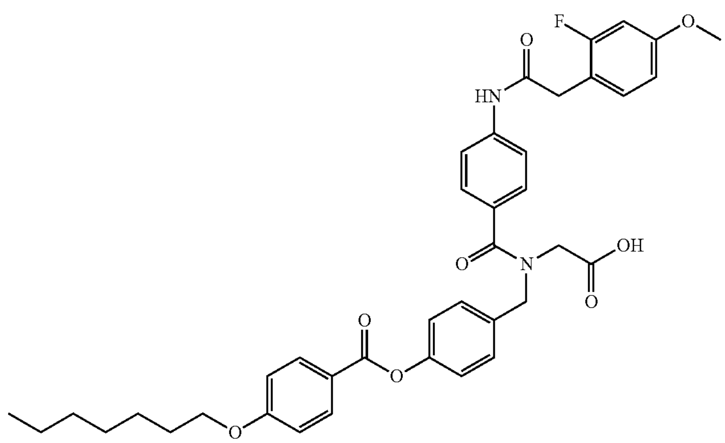 [SMILES: CCCCCCCOc1ccc(C(=O)Oc2ccc(CN(CC(=O)O)C(=O)c3ccc(NC(=O)Cc4ccc(OC)cc4F)cc3)cc2)cc1] | 118 | 11.12 |
| 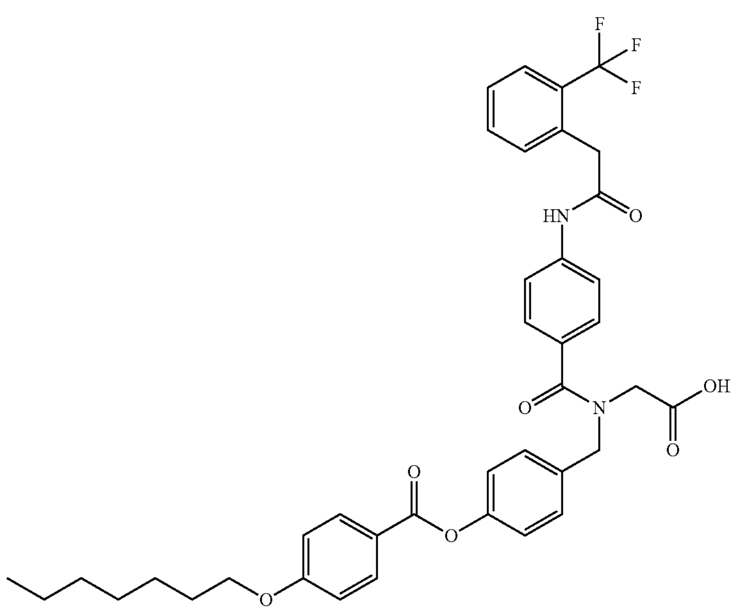 [SMILES: CCCCCCCOc1ccc(C(=O)Oc2ccc(CN(CC(=O)O)C(=O)c3ccc(NC(=O)Cc4ccccc4C(F)(F)F)cc3)cc2)cc1] | 119 | 11.39 |

TABLE 1-continued
| STRUCTURE | COMPOUND NUMBER | LCMS RETENTION TIME (min) |
|---|---|---|
| 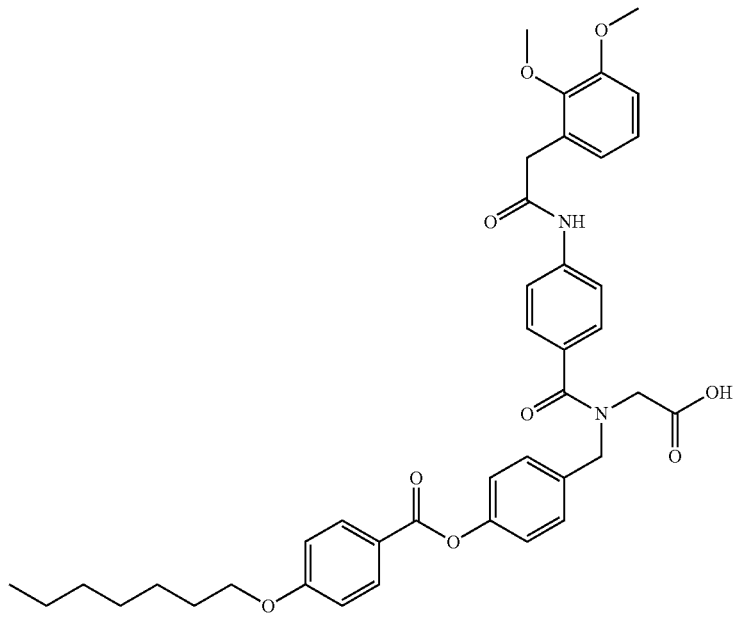 [SMILES: CCCCCCCOc1ccc(C(=O)Oc2ccc(CN(CC(=O)O)C(=O)c3ccc(NC(=O)Cc4cccc(OC)c4OC)cc3)cc2)cc1] | 120 | 11.13 |
| 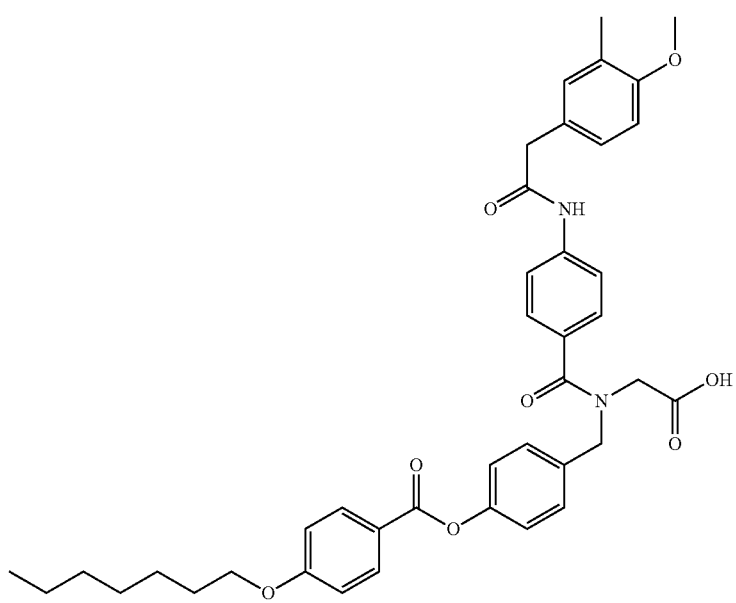 [SMILES: CCCCCCCOc1ccc(C(=O)Oc2ccc(CN(CC(=O)O)C(=O)c3ccc(NC(=O)Cc4ccc(OC)c(C)c4)cc3)cc2)cc1] | 121 | 11.35 |

TABLE 1-continued
| STRUCTURE | COMPOUND NUMBER | LCMS RETENTION TIME (min) |
|---|---|---|
| 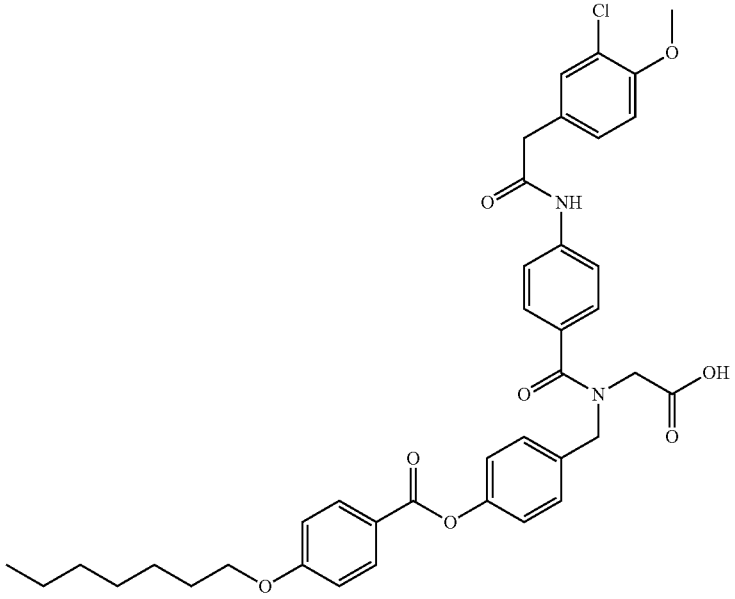 | 122 | 11.22 |
| 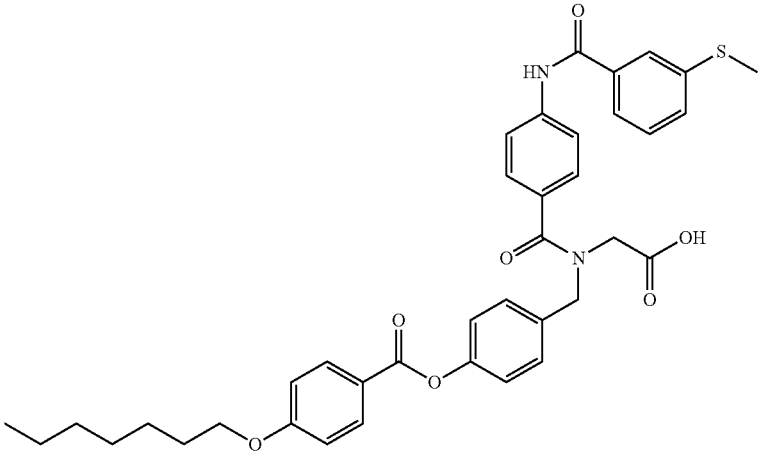 [SMILES: CCCCCCCOc1ccc(C(=O)Oc2ccc(CN(CC(=O)O)C(=O)c3ccc(NC(=O)c4cccc(SC)c4)cc3)cc2)cc1] | 123 | 11.44 |
| 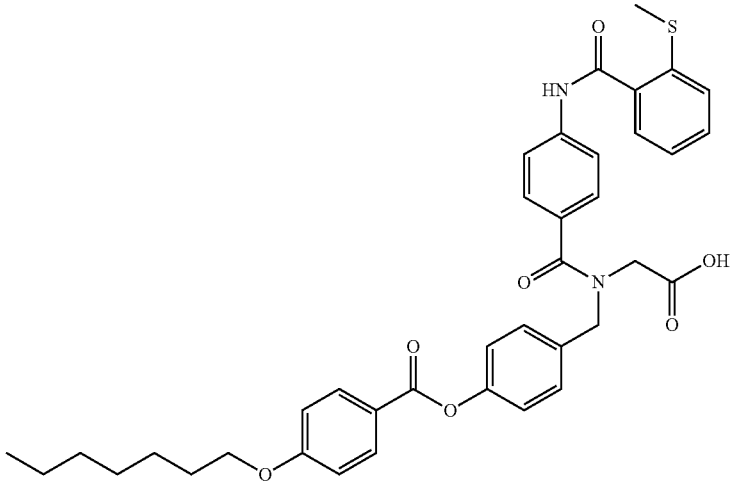 [SMILES: CCCCCCCOc1ccc(C(=O)Oc2ccc(CN(CC(=O)O)C(=O)c3ccc(NC(=O)c4ccccc4SC)cc3)cc2)cc1] | 124 | 11.18 |

TABLE 1-continued

| STRUCTURE | COMPOUND NUMBER | LCMS RETENTION TIME (min) |
|---|---|---|
| 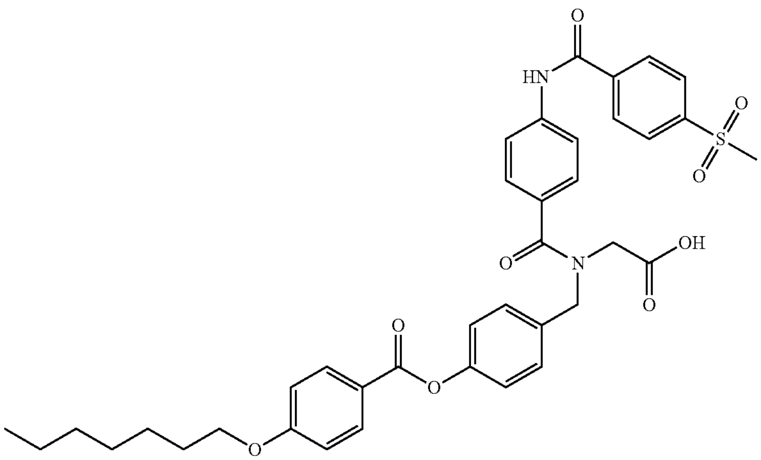 [SMILES: CCCCCCCOc1ccc(C(=O)Oc2ccc(CN(CC(=O)O)C(=O)c3ccc(NC(=O)c4ccc(S(C)(=O)=O)cc4)cc3)cc2)cc1] | 125 | 10.54 |
| 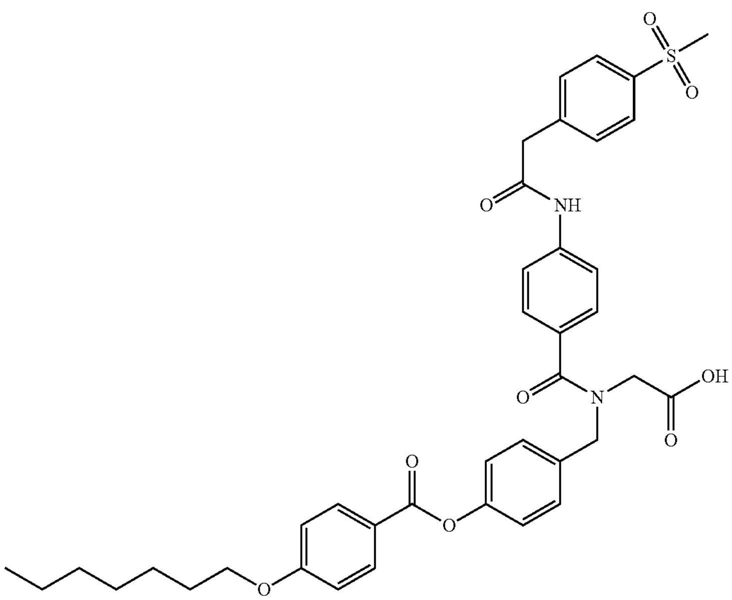 [SMILES: CCCCCCCOc1ccc(C(=O)Oc2ccc(CN(CC(=O)O)C(=O)c3ccc(NC(=O)Cc4ccc(S(C)(=O)=O)cc4)cc3)cc2)cc1] | 126 | 10.38 |
| 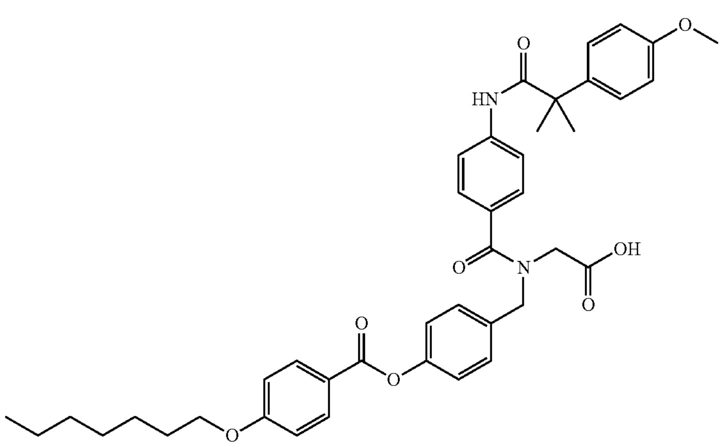 [SMILES: CCCCCCCOc1ccc(C(=O)Oc2ccc(CN(CC(=O)O)C(=O)c3ccc(NC(=O)C(C)(C)c4ccc(OC)cc4)cc3)cc2)cc1] | 127 | 11.57 |

TABLE 1-continued

| STRUCTURE | COMPOUND NUMBER | LCMS RETENTION TIME (min) |
|---|---|---|
| 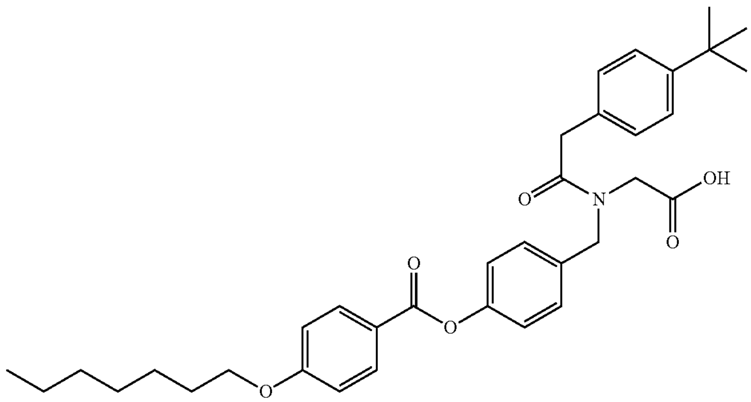 [SMILES: CCCCCCCOc1ccc(C(=O)Oc2ccc(CN(CC(=O)O)C(=O)Cc3ccc(C(C)(C)C)cc3)cc2)cc1] | 128 | 10.91 |
| 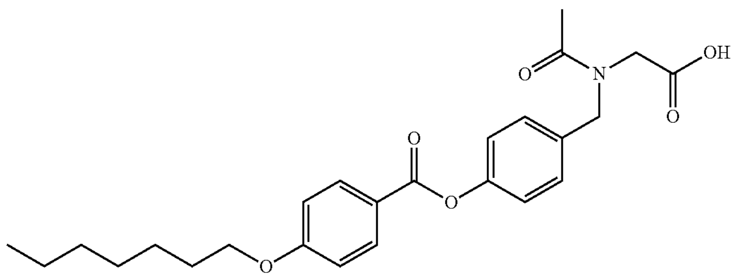 [SMILES: CCCCCCCOc1ccc(C(=O)Oc2ccc(CN(CC(=O)O)C(C)=O)cc2)cc1] | 129 | 8.26 |
| 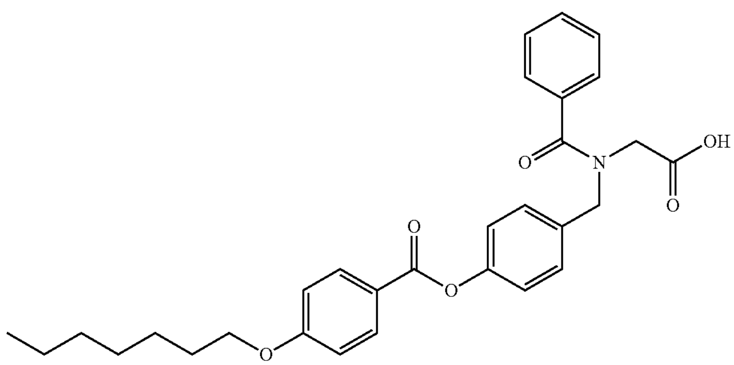 [SMILES: CCCCCCCOc1ccc(C(=O)Oc2ccc(CN(CC(=O)O)C(=O)c3ccccc3)cc2)cc1] | 130 | 9.39 |
| 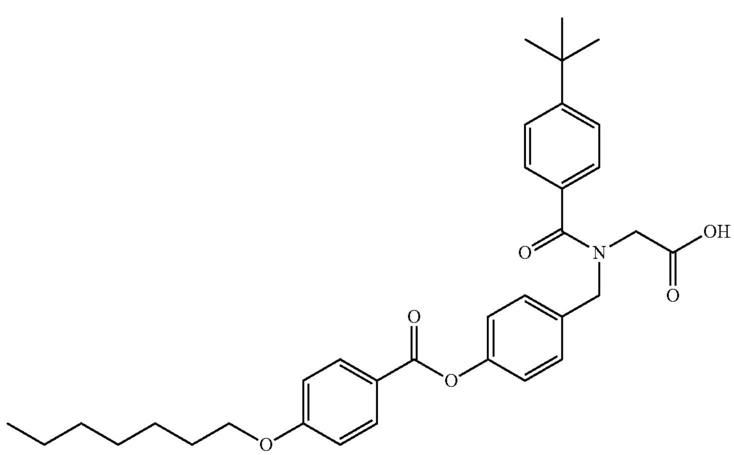 [SMILES: CCCCCCCOc1ccc(C(=O)Oc2ccc(CN(CC(=O)O)C(=O)c3ccc(C(C)(C)C)cc3)cc2)cc1] | 131 | 10.80 |

TABLE 1-continued
| STRUCTURE | COMPOUND NUMBER | LCMS RETENTION TIME (min) |
|---|---|---|
| 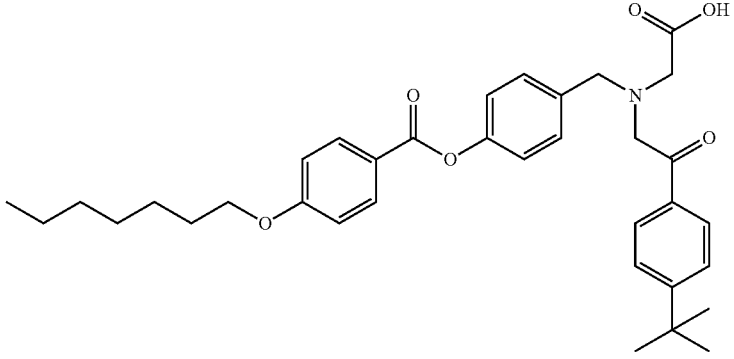 [SMILES: CCCCCCCOc1ccc(C(=O)Oc2ccc(CN(CC(=O)O)CC(=O)c3ccc(C(C)(C)C)cc3)cc2)cc1] | 132 | 10.01 |
| 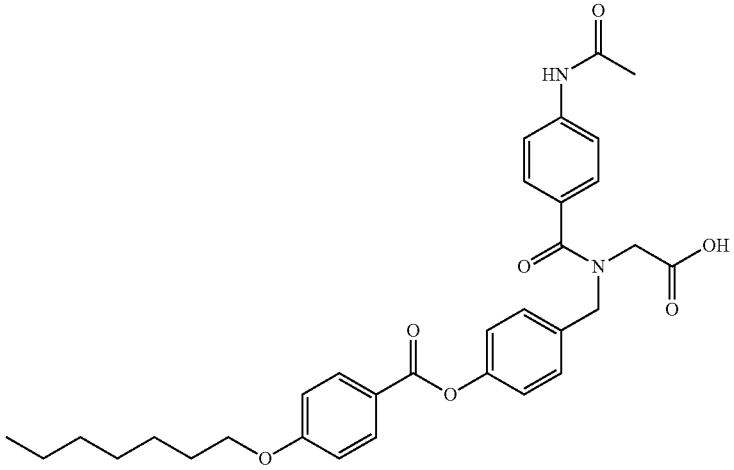 [SMILES: CCCCCCCOc1ccc(C(=O)Oc2ccc(CN(CC(=O)O)C(=O)c3ccc(NC(C)=O)cc3)cc2)cc1] | 133 | 10.37 |
| 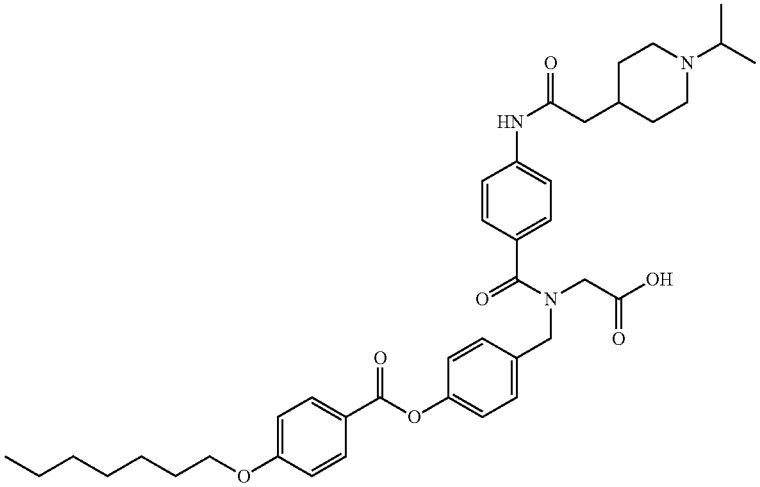 [SMILES: CCCCCCCOc1ccc(C(=O)Oc2ccc(CN(CC(=O)O)C(=O)c3ccc(NC(=O)CC4CCN(C(C)C)CC4)cc3)cc2)cc1] | 134 | 7.80 |

TABLE 1-continued

| STRUCTURE | COMPOUND NUMBER | LCMS RETENTION TIME (min) |
|---|---|---|
| 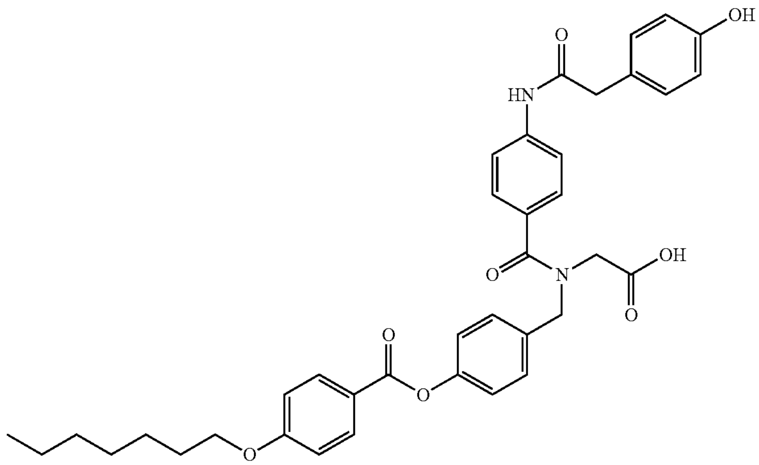 [SMILES: CCCCCCCOc1ccc(C(=O)Oc2ccc(CN(CC(=O)O)C(=O)c3ccc(NC(=O)Cc4ccc(O)cc4)cc3)cc2)cc1] | 135 | 10.36 |
| 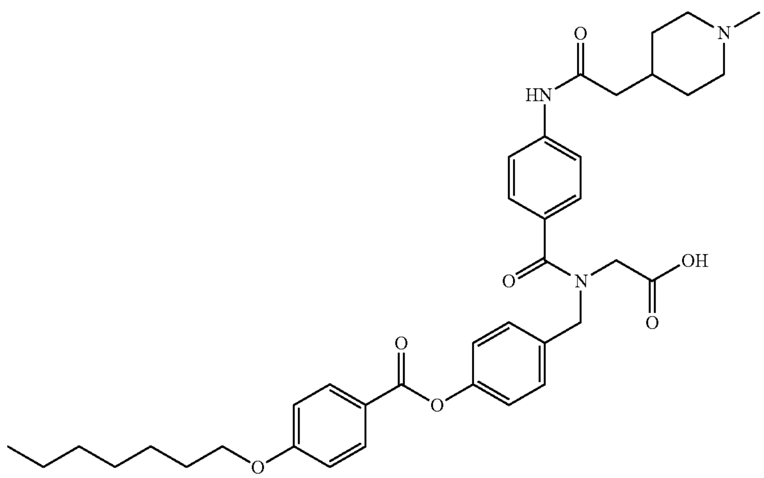 [SMILES: CCCCCCCOc1ccc(C(=O)Oc2ccc(CN(CC(=O)O)C(=O)c3ccc(NC(=O)CC4CCN(C)CC4)cc3)cc2)cc1] | 136 | 7.93 |
| 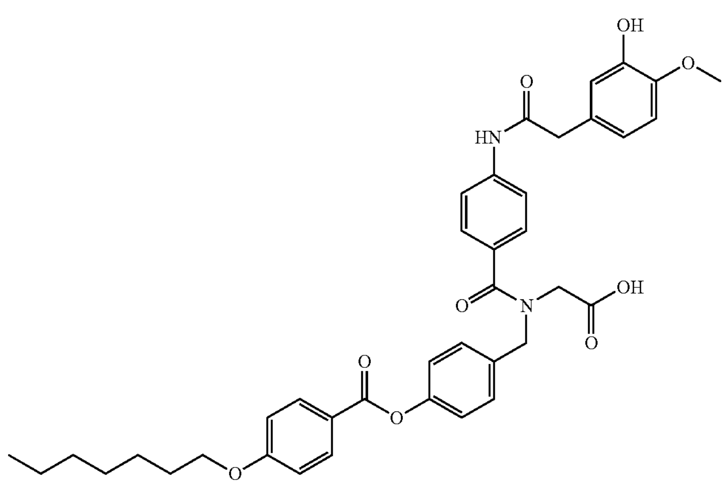 [SMILES: CCCCCCCOc1ccc(C(=O)Oc2ccc(CN(CC(=O)O)C(=O)c3ccc(NC(=O)Cc4ccc(OC)c(O)c4)cc3)cc2)cc1] | 137 | 10.47 |

TABLE 1-continued
| STRUCTURE | COMPOUND NUMBER | LCMS RETENTION TIME (min) |
|---|---|---|
| 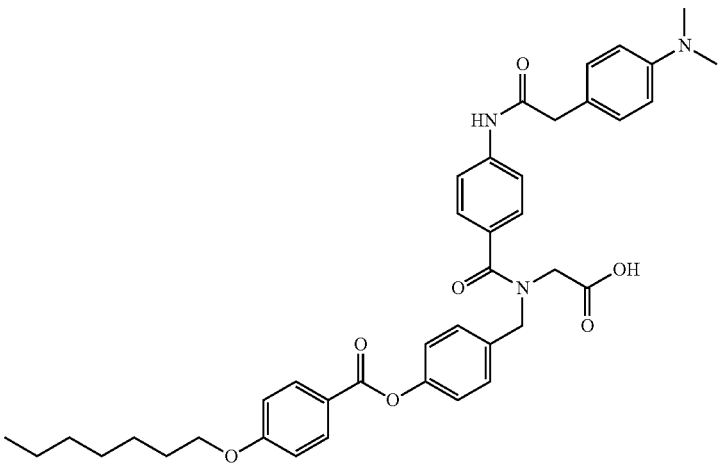 [SMILES: CCCCCCCOc1ccc(C(=O)Oc2ccc(CN(CC(=O)O)C(=O)c3ccc(NC(=O)Cc4ccc(N(C)C)cc4)cc3)cc2)cc1] | 138 | 10.03 |
| 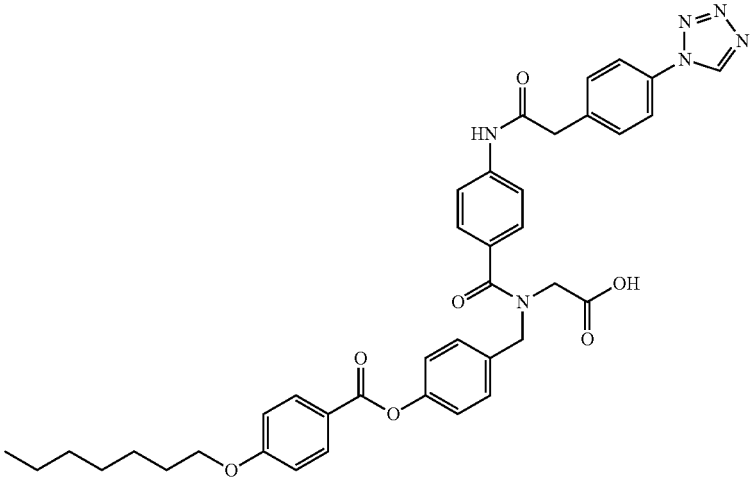 [SMILES: CCCCCCCOc1ccc(C(=O)Oc2ccc(CN(CC(=O)O)C(=O)c3ccc(NC(=O)Cc4ccc(-n5cnnn5)cc4)cc3)cc2)cc1] | 139 | 10.46 |
| 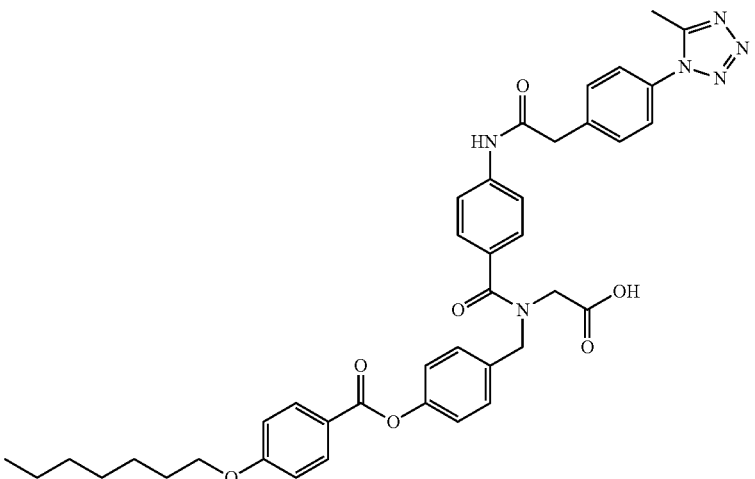 | 140 | 10.41 |

TABLE 1-continued

| STRUCTURE | COMPOUND NUMBER | LCMS RETENTION TIME (min) |
|---|---|---|
| 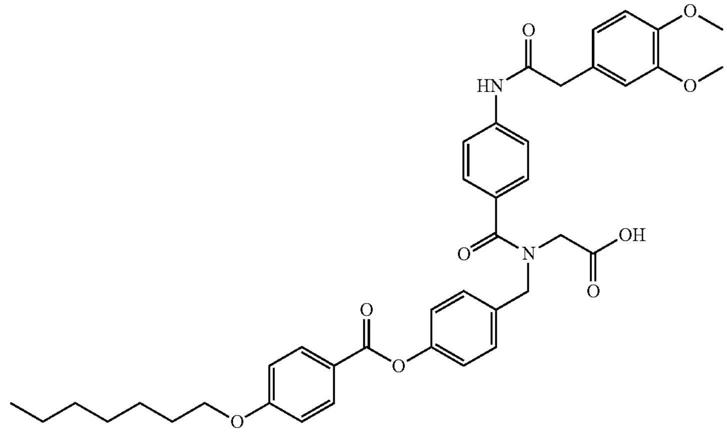 [SMILES: CCCCCCCOc1ccc(C(=O)Oc2ccc(CN(CC(=O)O)C(=O)c3ccc(NC(=O)Cc4ccc(OC)c(OC)c4)cc3)cc2)cc1] | 141 | 10.74 |
| 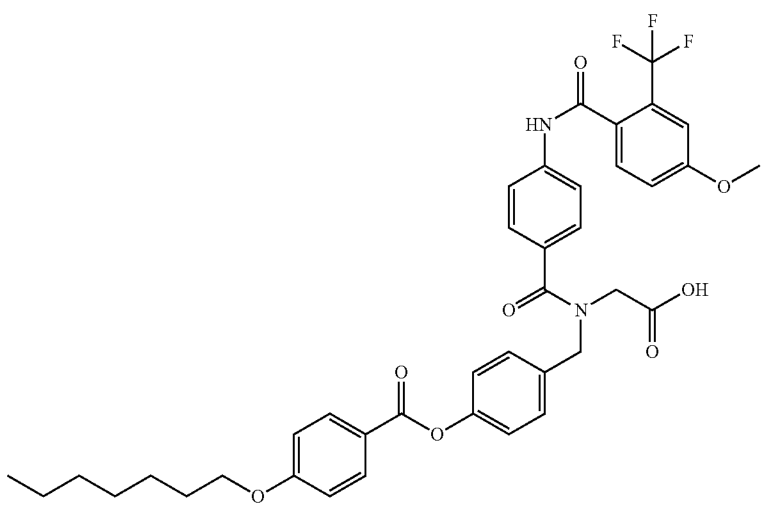 [SMILES: CCCCCCCOc1ccc(C(=O)Oc2ccc(CN(CC(=O)O)C(=O)c3ccc(NC(=O)c4ccc(OC)cc4C(F)(F)F)cc3)cc2)cc1] | 142 | 11.24 |
| 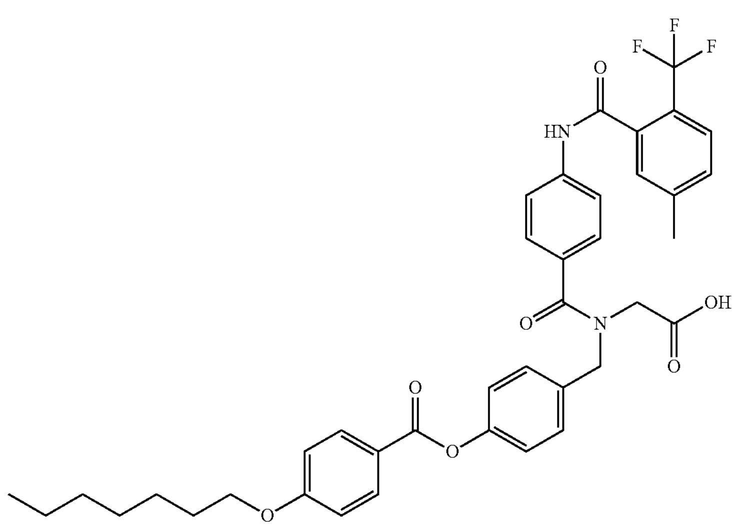 [SMILES: CCCCCCCOc1ccc(C(=O)Oc2ccc(CN(CC(=O)O)C(=O)c3ccc(NC(=O)c4cc(C)ccc4C(F)(F)F)cc3)cc2)cc1] | 143 | 11.14 |

TABLE 1-continued
| STRUCTURE | COMPOUND NUMBER | LCMS RETENTION TIME (min) |
|---|---|---|
| 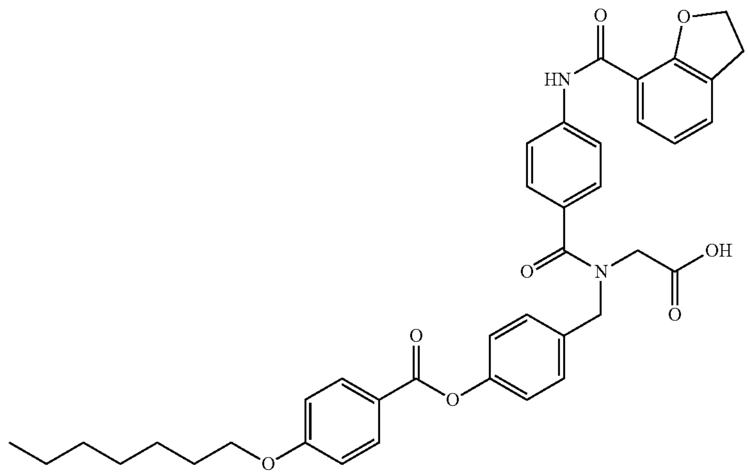 [SMILES: CCCCCCCOc1ccc(C(=O)Oc2ccc(CN(CC(=O)O)C(=O)c3ccc(NC(=O)c4cccc5c4OCC5)cc3)cc2)cc1] | 144 | 11.10 |
| 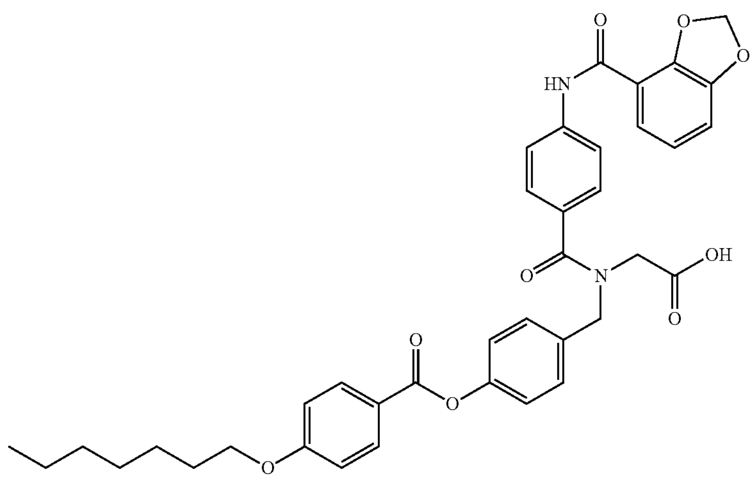 [SMILES: CCCCCCCOc1ccc(C(=O)Oc2ccc(CN(CC(=O)O)C(=O)c3ccc(NC(=O)c4cccc5c4OCO5)cc3)cc2)cc1] | 145 | 11.02 |
| 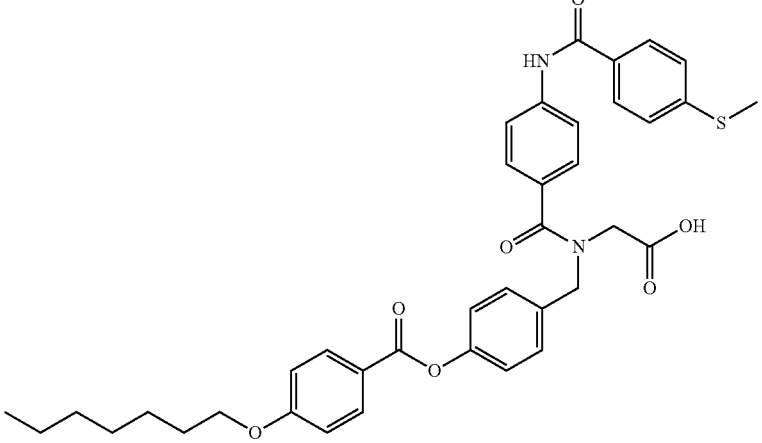 | 146 | 11.41 |

TABLE 1-continued
| STRUCTURE | COMPOUND NUMBER | LCMS RETENTION TIME (min) |
|---|---|---|
| 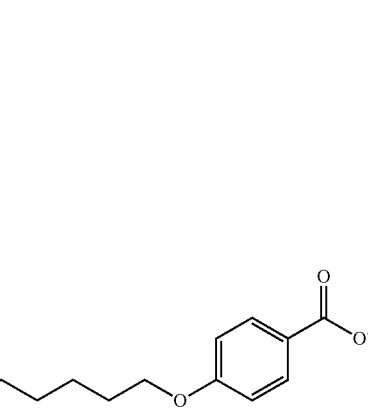 | 147 | 11.27 |
| 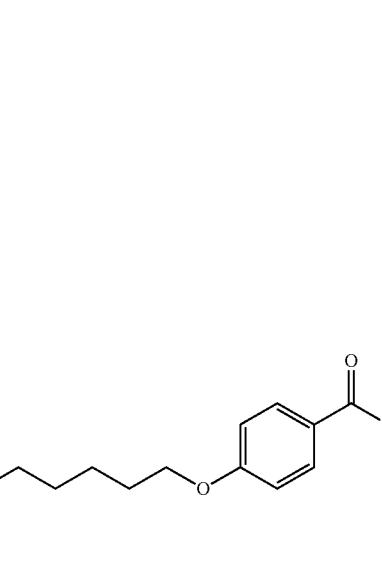 | 148 | 11.08 |
| 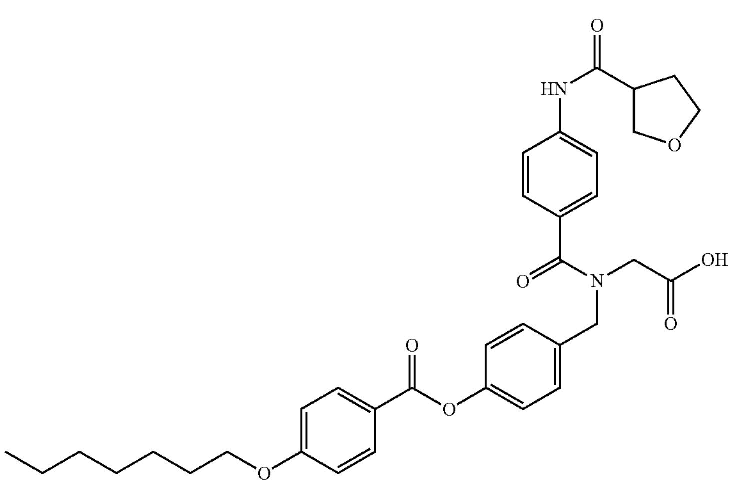 [SMILES: CCCCCCCOc1ccc(C(=O)Oc2ccc(CN(CC(=O)O)C(=O)c3ccc(NC(=O)C4CCOC4)cc3)cc2)cc1] | 149 | 10.44 |

TABLE 1-continued

| STRUCTURE | COMPOUND NUMBER | LCMS RETENTION TIME (min) |
|---|---|---|
| 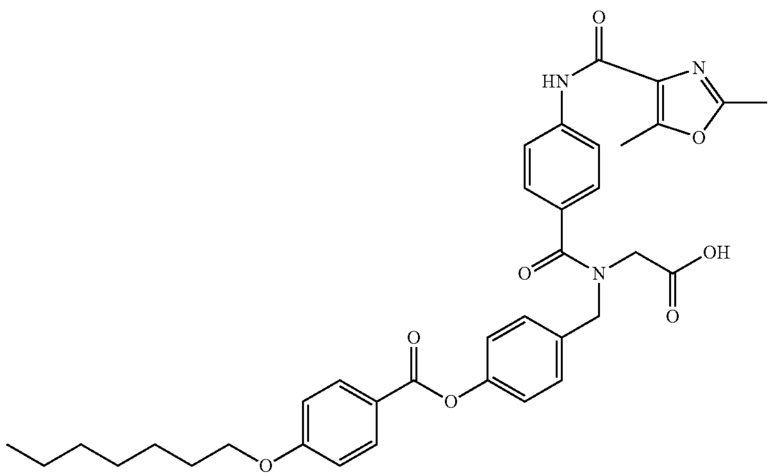 [SMILES: CCCCCCCOc1ccc(C(=O)Oc2ccc(CN(CC(=O)O)C(=O)c3ccc(NC(=O)c4nc(C)oc4C)cc3)cc2)cc1] | 150 | 11.29 |
| 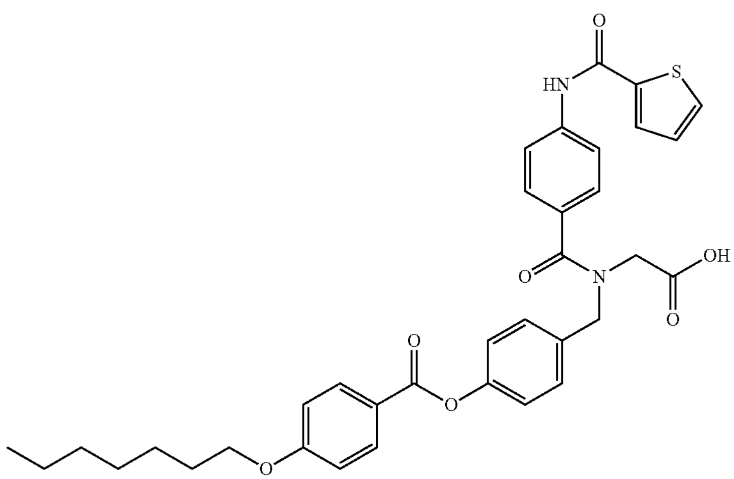 [SMILES: CCCCCCCOc1ccc(C(=O)Oc2ccc(CN(CC(=O)O)C(=O)c3ccc(NC(=O)c4cccs4)cc3)cc2)cc1] | 151 | 11.09 |
| 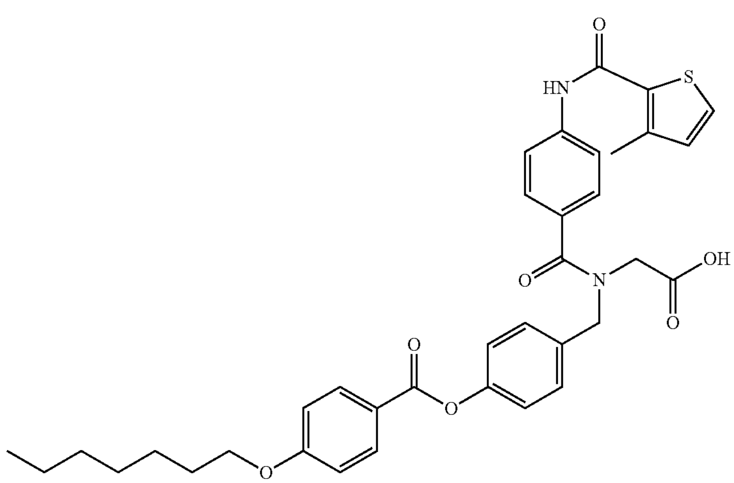 [SMILES: CCCCCCCOc1ccc(C(=O)Oc2ccc(CN(CC(=O)O)C(=O)c3ccc(NC(=O)c4sccc4C)cc3)cc2)cc1] | 152 | 10.80 |

TABLE 1-continued
| STRUCTURE | COMPOUND NUMBER | LCMS RETENTION TIME (min) |
|---|---|---|
| 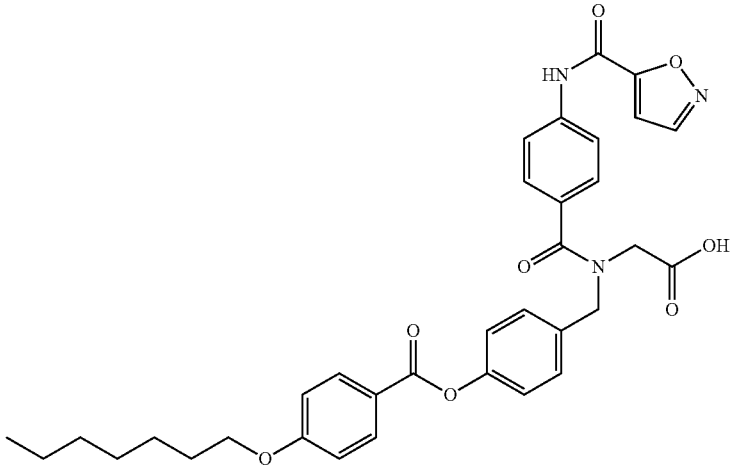 [SMILES: CCCCCCCOc1ccc(C(=O)Oc2ccc(CN(CC(=O)O)C(=O)c3ccc(NC(=O)c4ccno4)cc3)cc2)cc1] | 153 | 10.67 |
| 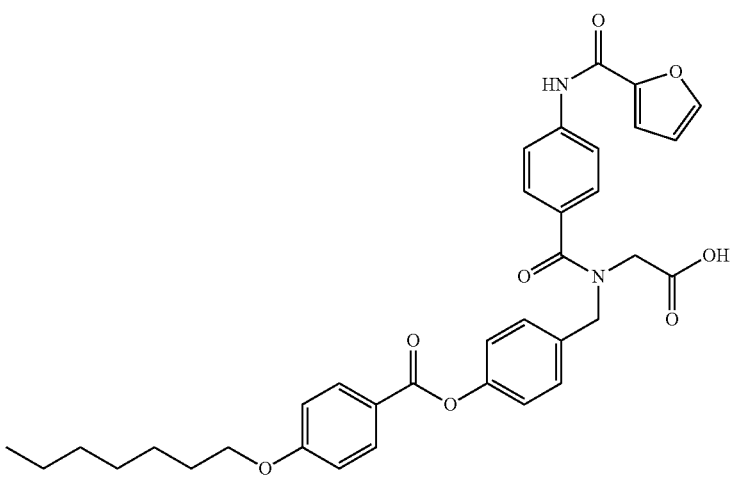 [SMILES: CCCCCCCOc1ccc(C(=O)Oc2ccc(CN(CC(=O)O)C(=O)c3ccc(NC(=O)c4ccco4)cc3)cc2)cc1] | 154 | 10.81 |
| 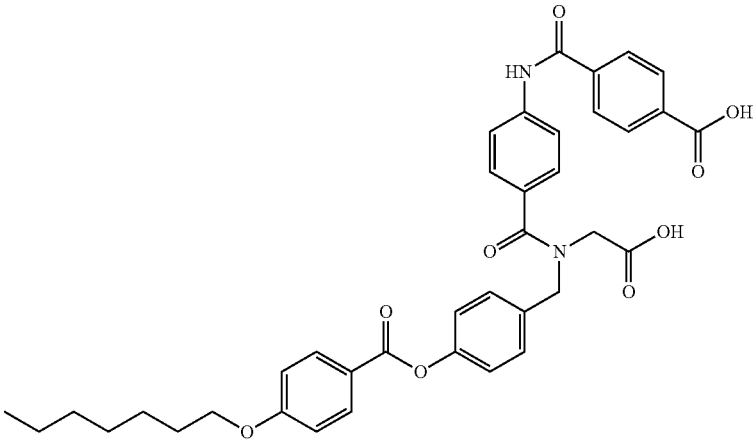 [SMILES: CCCCCCCOc1ccc(C(=O)Oc2ccc(CN(CC(=O)O)C(=O)c3ccc(NC(=O)c4ccc(C(=O)O)cc4)cc3)cc2)cc1] | 155 | 11.00 |

TABLE 1-continued
| STRUCTURE | COMPOUND NUMBER | LCMS RETENTION TIME (min) |
|---|---|---|
| 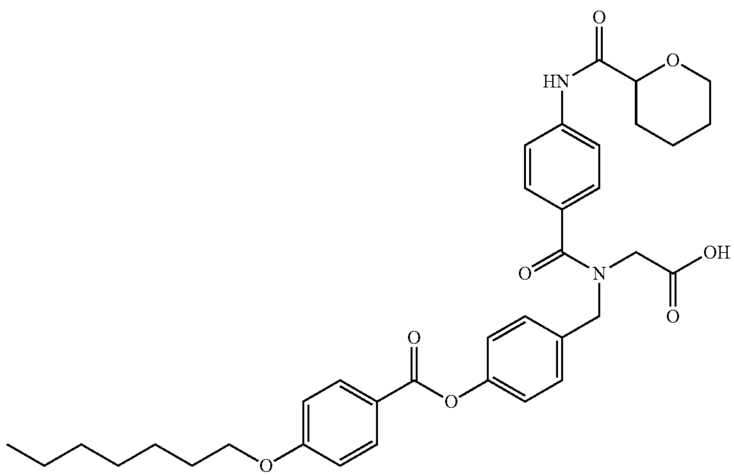 [SMILES: CCCCCCCOc1ccc(C(=O)Oc2ccc(CN(CC(=O)O)C(=O)c3ccc(NC(=O)C4CCCCO4)cc3)cc2)cc1] | 156 | 11.04 |
| 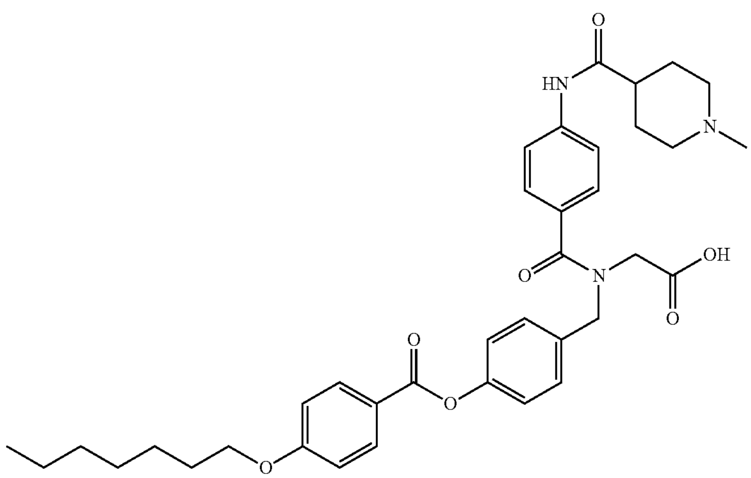 [SMILES: CCCCCCCOc1ccc(C(=O)Oc2ccc(CN(CC(=O)O)C(=O)c3ccc(NC(=O)C4CCN(C)CC4)cc3)cc2)cc1] | 157 | 10.49 |
| 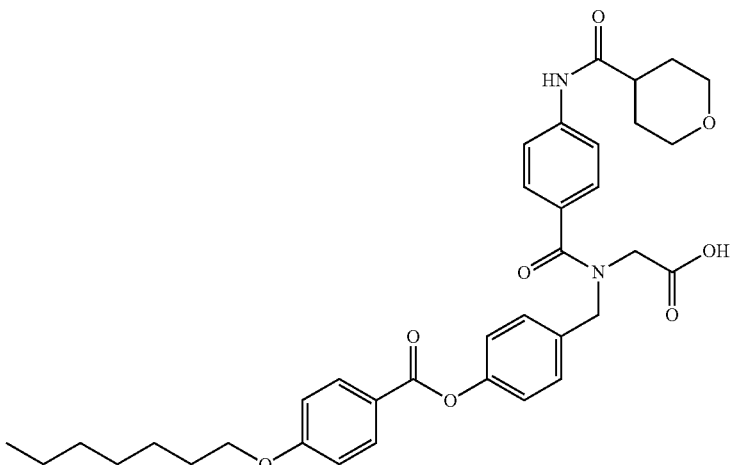 | 158 | 10.46 |

TABLE 1-continued

| STRUCTURE | COMPOUND NUMBER | LCMS RETENTION TIME (min) |
|---|---|---|
| 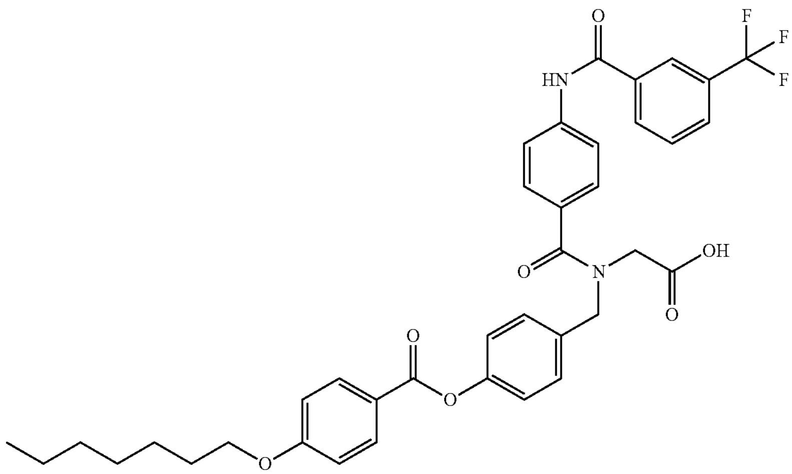 [SMILES: CCCCCCCOc1ccc(C(=O)Oc2ccc(CN(CC(=O)O)C(=O)c3ccc(NC(=O)c4cccc(C(F)(F)F)c4)cc3)cc2)cc1] | 159 | 10.52 |
| 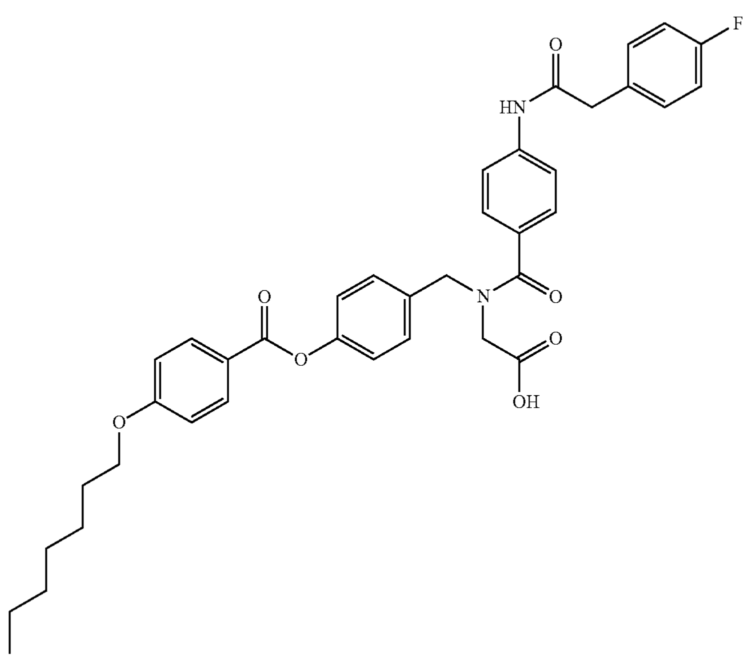 [SMILES: CCCCCCCOc1ccc(C(=O)Oc2ccc(CN(CC(=O)O)C(=O)c3ccc(NC(=O)Cc4ccc(F)cc4)cc3)cc2)cc1] | 160 | 11.07 |

TABLE 1-continued
| STRUCTURE | COMPOUND NUMBER | LCMS RETENTION TIME (min) |
|---|---|---|
| 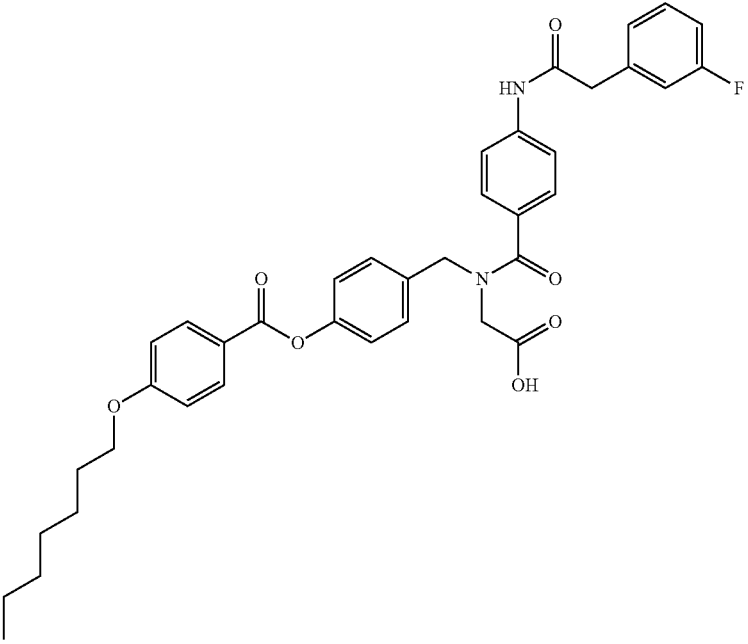 [SMILES: CCCCCCCOc1ccc(C(=O)Oc2ccc(CN(CC(=O)O)C(=O)c3ccc(NC(=O)Cc4cccc(F)c4)cc3)cc2)cc1] | 161 | 11.10 |
| 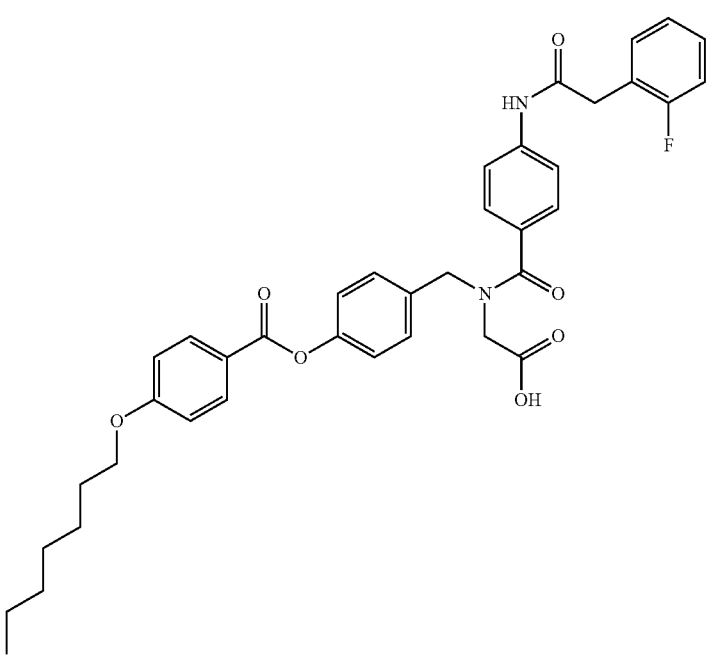 [SMILES: CCCCCCCOc1ccc(C(=O)Oc2ccc(CN(CC(=O)O)C(=O)c3ccc(NC(=O)Cc4ccccc4F)cc3)cc2)cc1] | 162 | 11.08 |

TABLE 1-continued
| STRUCTURE | COMPOUND NUMBER | LCMS RETENTION TIME (min) |
|---|---|---|
| 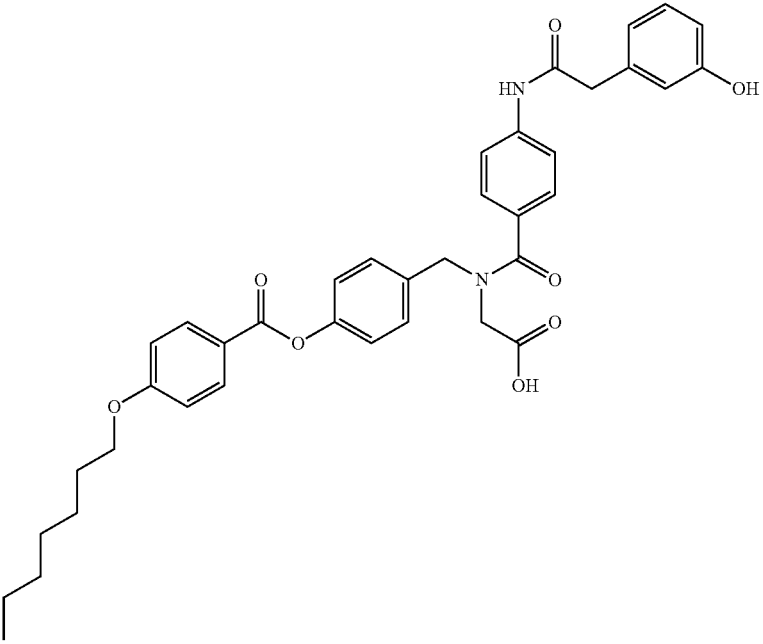 [SMILES: CCCCCCCOc1ccc(C(=O)Oc2ccc(CN(CC(=O)O)C(=O)c3ccc(NC(=O)Cc4cccc(O)c4)cc3)cc2)cc1] | 163 | 10.44 |
| 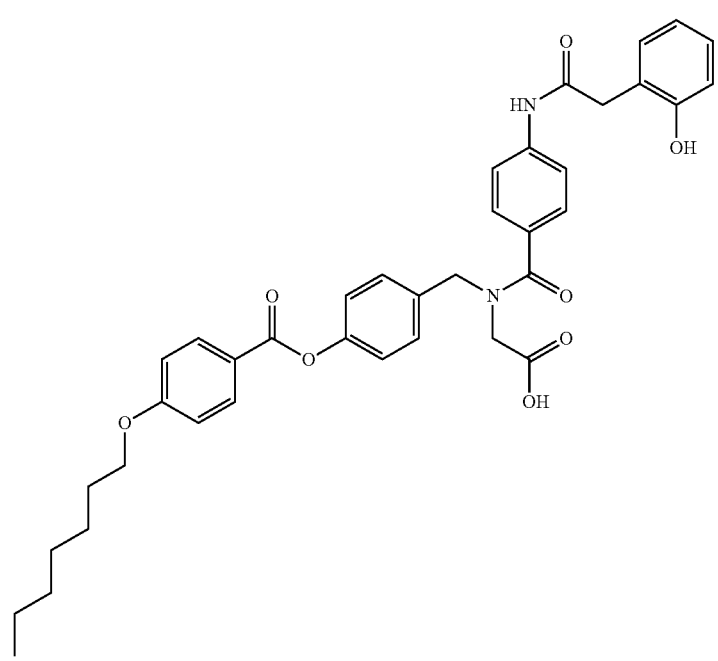 [SMILES: CCCCCCCOc1ccc(C(=O)Oc2ccc(CN(CC(=O)O)C(=O)c3ccc(NC(=O)Cc4ccccc4O)cc3)cc2)cc1] | 164 | 10.35 |

TABLE 1-continued
| STRUCTURE | COMPOUND NUMBER | LCMS RETENTION TIME (min) |
|---|---|---|
| 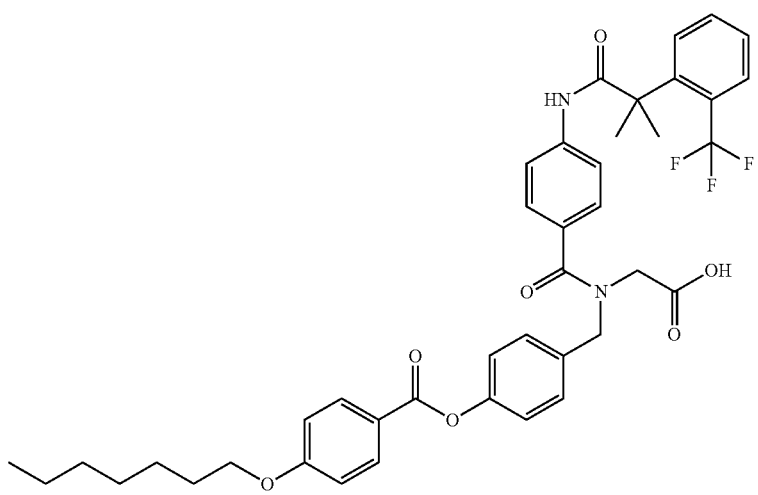 [SMILES: CCCCCCCOc1ccc(C(=O)Oc2ccc(CN(CC(=O)O)C(=O)c3ccc(NC(=O)C(C)(C)c4ccccc4C(F)(F)F)cc3)cc2)cc1] | 165 | 11.55 |
| 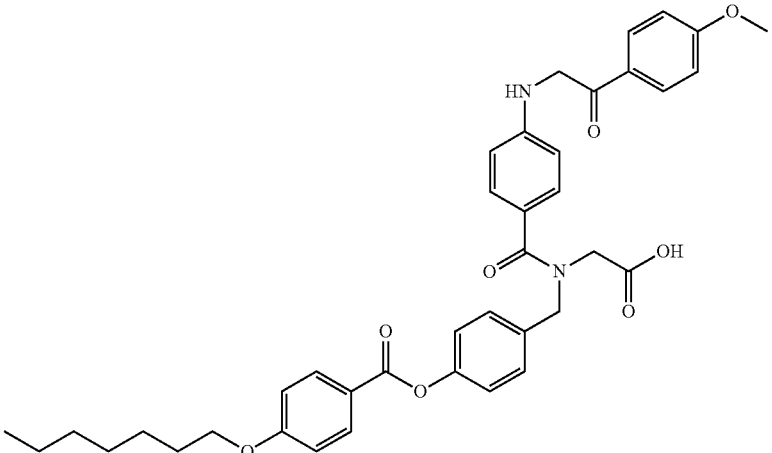 | 166 | 11.43 |
| 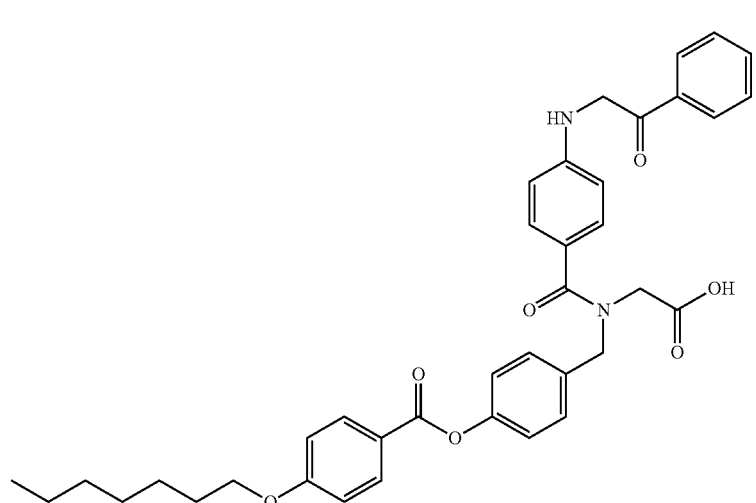 | 167 | 11.44 |

TABLE 1-continued
| STRUCTURE | COMPOUND NUMBER | LCMS RETENTION TIME (min) |
|---|---|---|
| 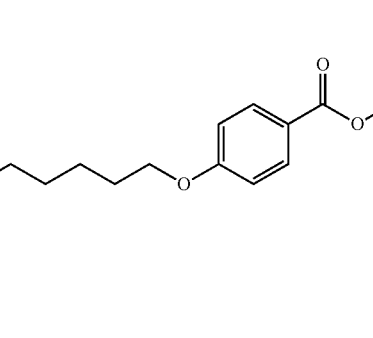 | 168 | 11.79 |
| 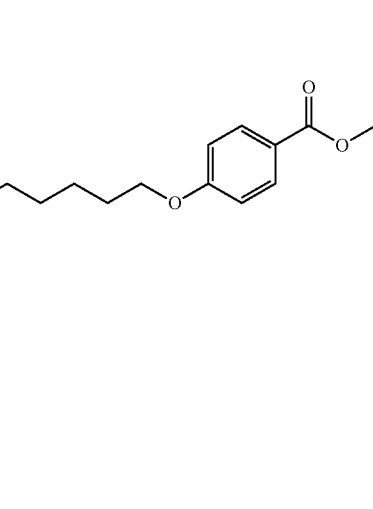 | 169 | 11.26 |
| 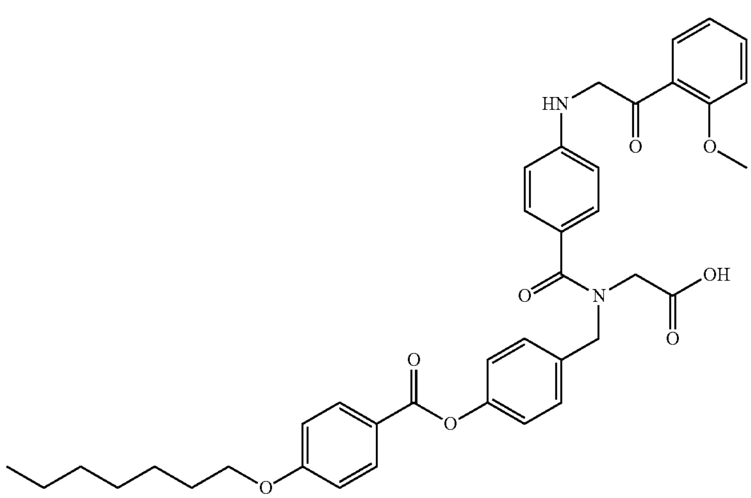 [SMILES: CCCCCCCOc1ccc(C(=O)Oc2ccc(CN(CC(=O)O)C(=O)c3ccc(NCC(=O)c4ccccc4OC)cc3)cc2)cc1] | 170 | 11.53 |

TABLE 1-continued

| STRUCTURE | COMPOUND NUMBER | LCMS RETENTION TIME (min) |
|---|---|---|
| 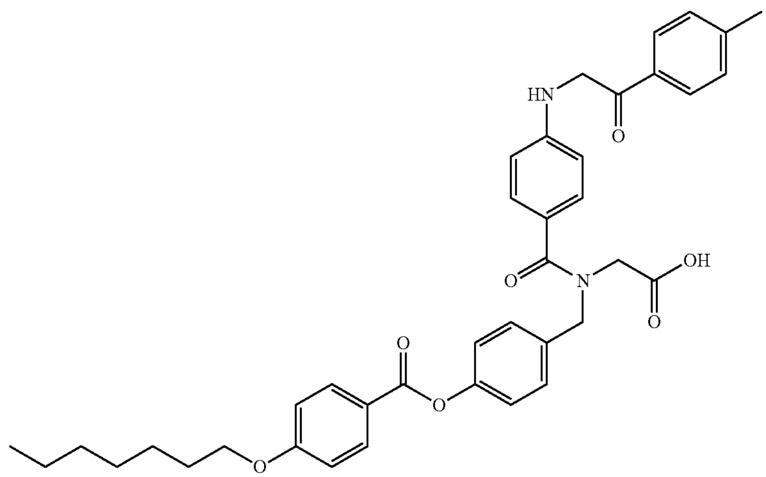 [SMILES: CCCCCCCOc1ccc(C(=O)Oc2ccc(CN(CC(=O)O)C(=O)c3ccc(NCC(=O)c4ccc(C)cc4)cc3)cc2)cc1] | 171 | 11.69 |
| 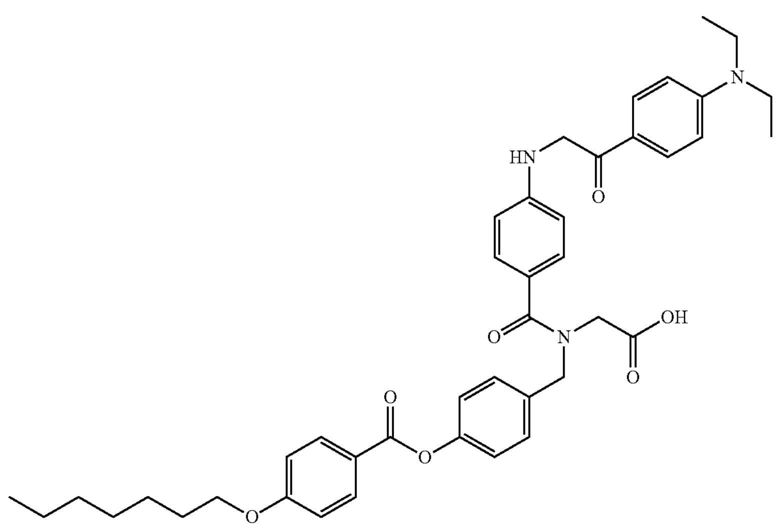 [SMILES: CCCCCCCOc1ccc(C(=O)Oc2ccc(CN(CC(=O)O)C(=O)c3ccc(NCC(=O)c4ccc(N(CC)CC)cc4)cc3)cc2)cc1] | 172 | 11.99 |
| 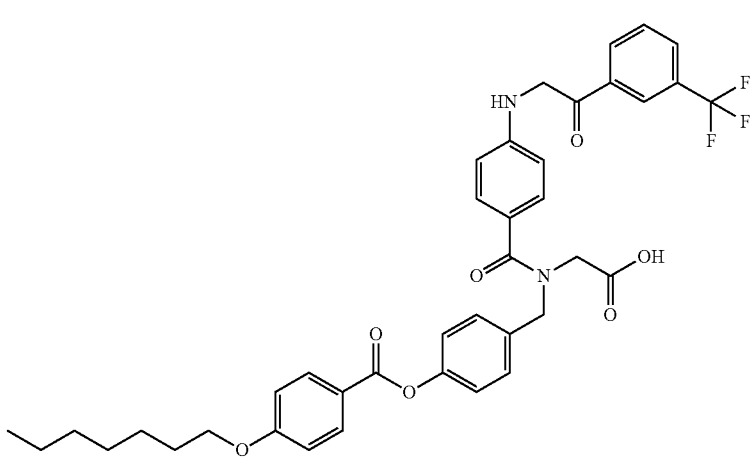 [SMILES: CCCCCCCOc1ccc(C(=O)Oc2ccc(CN(CC(=O)O)C(=O)c3ccc(NCC(=O)c4cccc(C(F)(F)F)c4)cc3)cc2)cc1] | 173 | 11.08 |

TABLE 1-continued
| STRUCTURE | COMPOUND NUMBER | LCMS RETENTION TIME (min) |
|---|---|---|
| 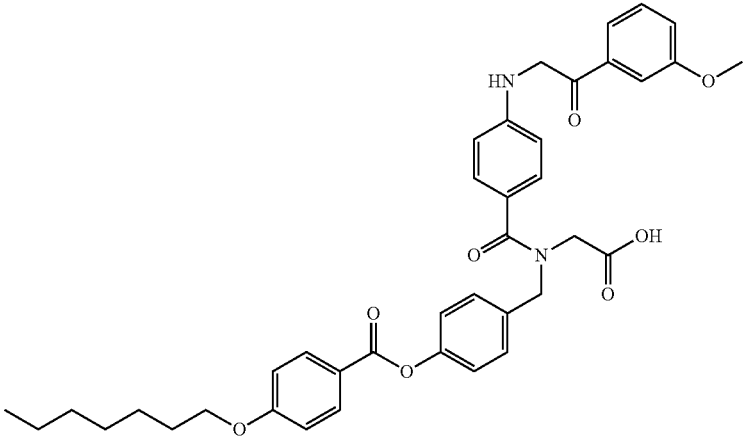 [SMILES: CCCCCCCOc1ccc(C(=O)Oc2ccc(CN(CC(=O)O)C(=O)c3ccc(NCC(=O)c4cccc(OC)c4)cc3)cc2)cc1] | 174 | 11.47 |
| 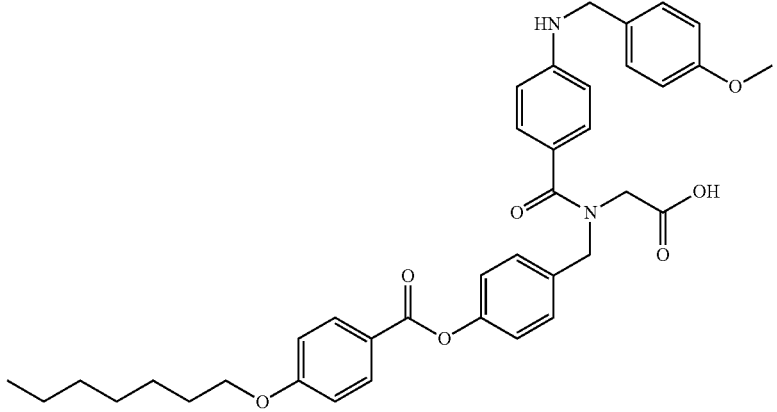 [SMILES: CCCCCCCOc1ccc(C(=O)Oc2ccc(CN(CC(=O)O)C(=O)c3ccc(NCc4ccc(OC)cc4)cc3)cc2)cc1] | 175 | 11.46 |
| 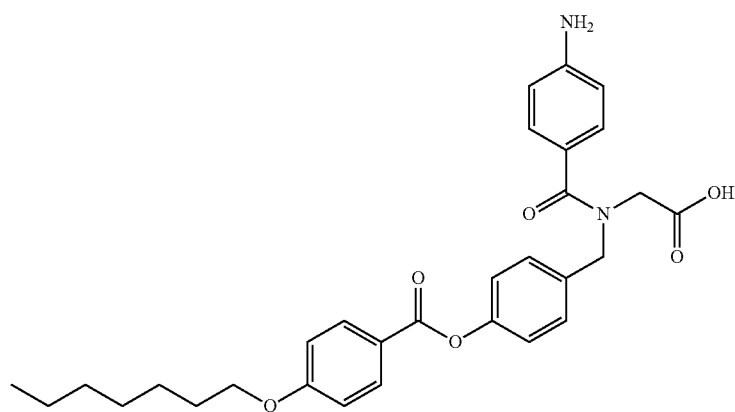 [SMILES: CCCCCCCOc1ccc(C(=O)Oc2ccc(CN(CC(=O)O)C(=O)c3ccc(N)cc3)cc2)cc1] | 176 | 10.46 |

TABLE 1-continued
| STRUCTURE | COMPOUND NUMBER | LCMS RETENTION TIME (min) |
|---|---|---|
| 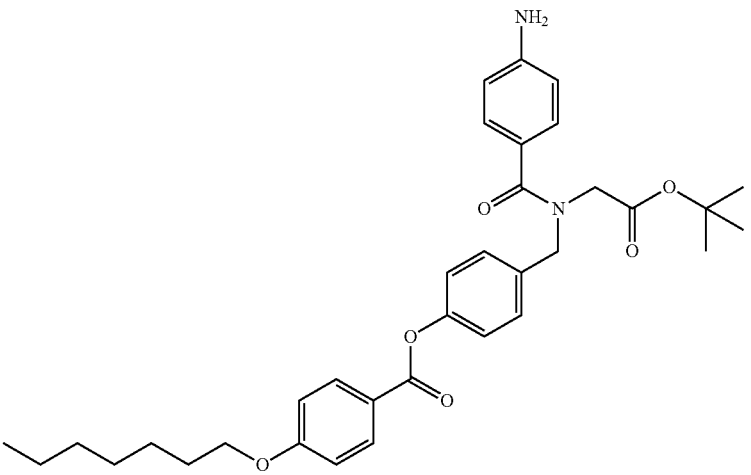 [SMILES: CCCCCCCOc1ccc(C(=O)Oc2ccc(CN(CC(=O)OC(C)(C)C)C(=O)c3ccc(N)cc3)cc2)cc1] | 177 | 10.48 |
| 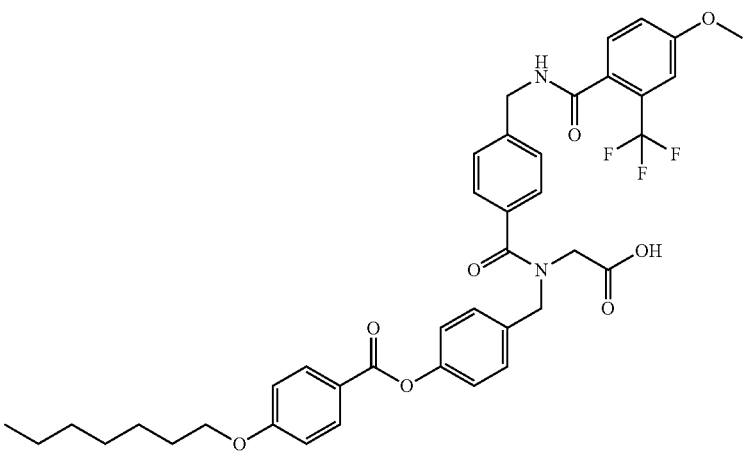 [SMILES: CCCCCCCOc1ccc(C(=O)Oc2ccc(CN(CC(=O)O)C(=O)c3ccc(CNC(=O)c4ccc(OC)cc4C(F)(F)F)cc3)cc2)cc1] | 178 | 11.09 |
| 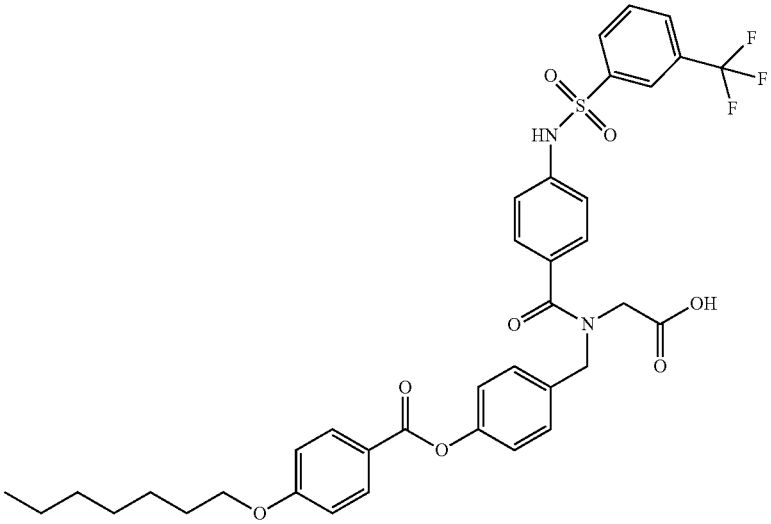 [SMILES: CCCCCCCOc1ccc(C(=O)Oc2ccc(CN(CC(=O)O)C(=O)c3ccc(NS(=O)(=O)c4cccc(C(F)(F)F)c4)cc3)cc2)cc1] | 179 | 11.31 |

TABLE 1-continued
| STRUCTURE | COMPOUND NUMBER | LCMS RETENTION TIME (min) |
|---|---|---|
| 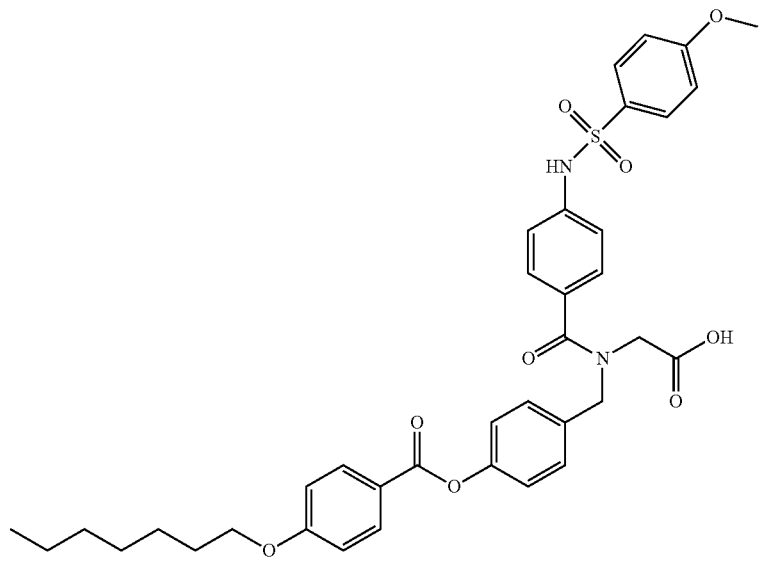 [SMILES: CCCCCCCOc1ccc(C(=O)Oc2ccc(CN(CC(=O)O)C(=O)c3ccc(NS(=O)(=O)c4ccc(OC)cc4)cc3)cc2)cc1] | 180 | 11.71 |
| 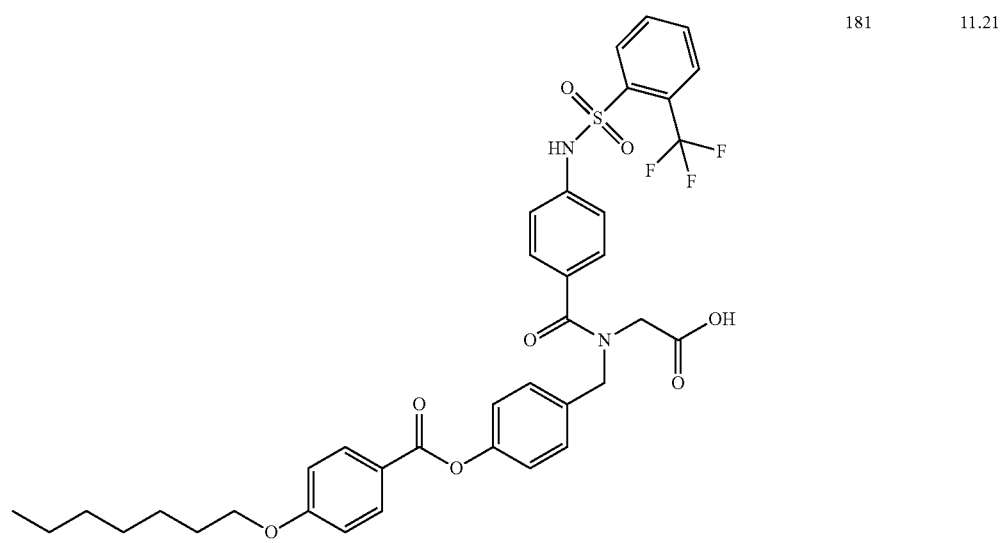 | 181 | 11.21 |

TABLE 1-continued
| STRUCTURE | COMPOUND NUMBER | LCMS RETENTION TIME (min) |
|---|---|---|
| 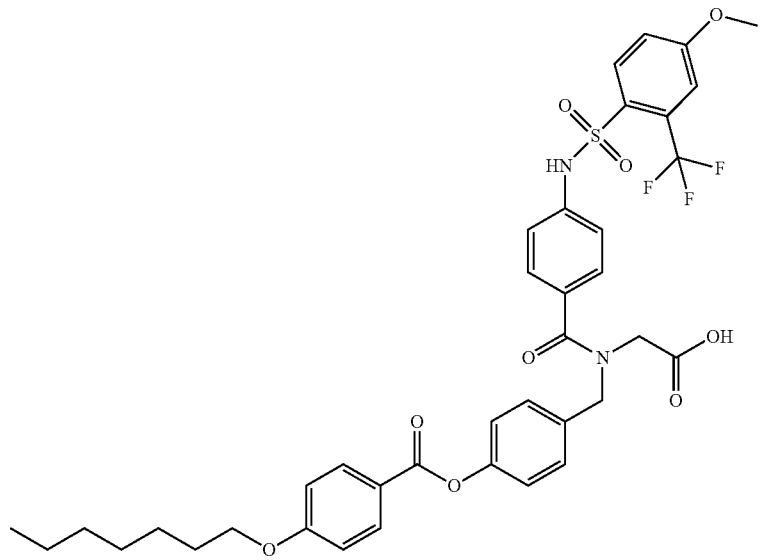 [SMILES: CCCCCCCOc1ccc(C(=O)Oc2ccc(CN(CC(=O)O)C(=O)c3ccc(NS(=O)(=O)c4ccc(OC)cc4C(F)(F)F)cc3)cc2)cc1] | 182 | 11.27 |
| 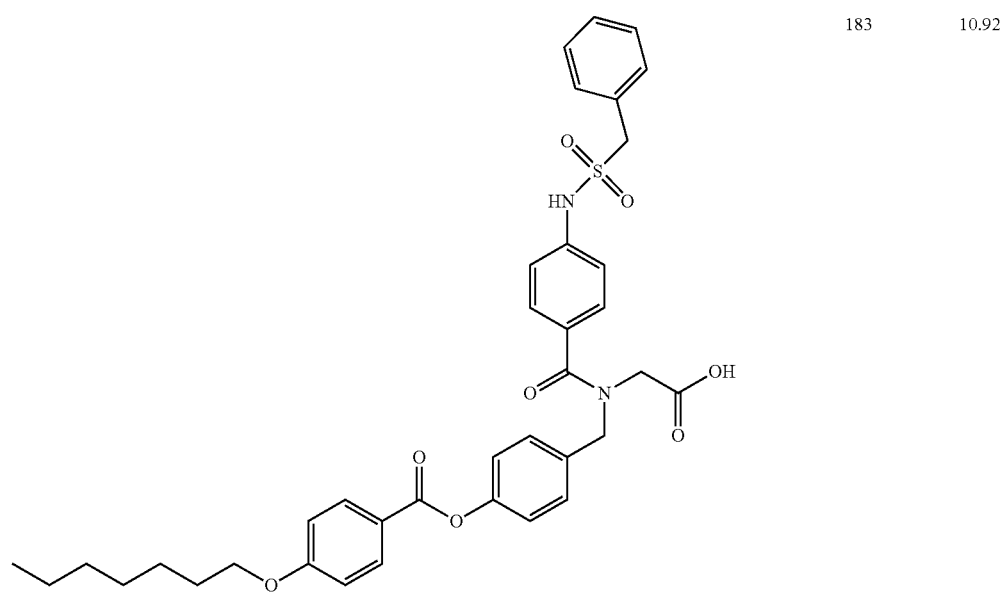 | 183 | 10.92 |

TABLE 1-continued
| STRUCTURE | COMPOUND NUMBER | LCMS RETENTION TIME (min) |
|---|---|---|
| 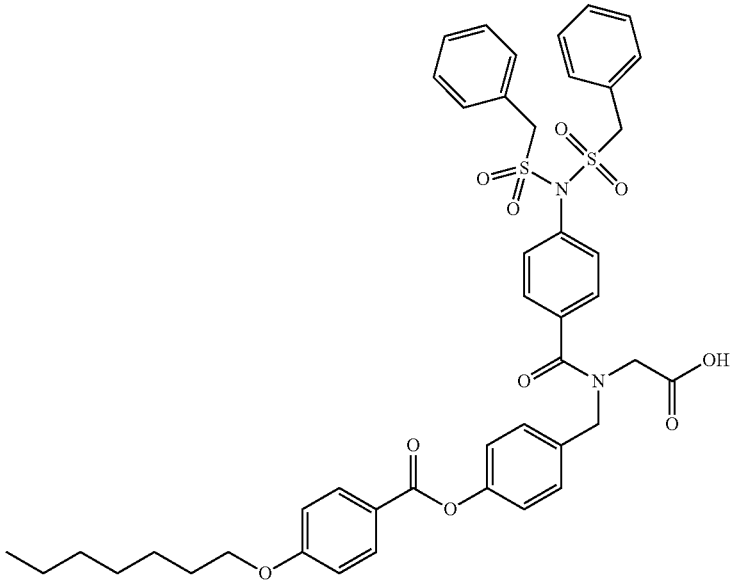 [SMILES: CCCCCCCOc1ccc(C(=O)Oc2ccc(CN(CC(=O)O)C(=O)c3ccc(N(S(=O)(=O)Cc4ccccc4)S(=O)(=O)Cc4ccccc4)cc3)cc2)cc1] | 184 | 11.53 |
| 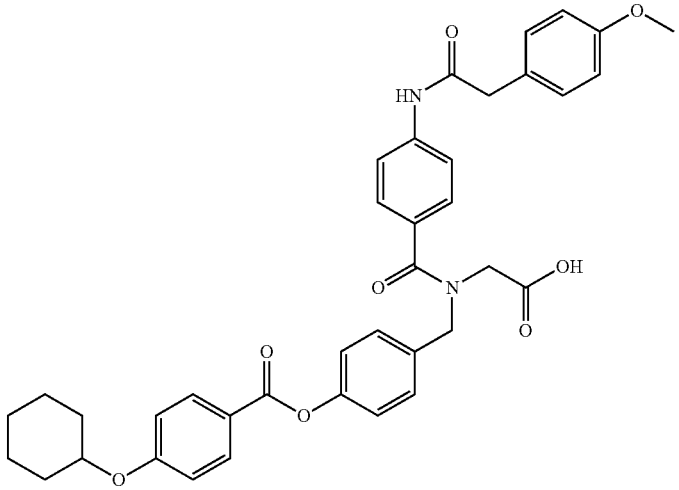 [SMILES: COc1ccc(CC(=O)Nc2ccc(C(=O)N(CC(=O)O)Cc3ccc(OC(=O)c4ccc(OC5CCCCC5)cc4)cc3)cc2)cc1] | 185 | 8.07 |
| 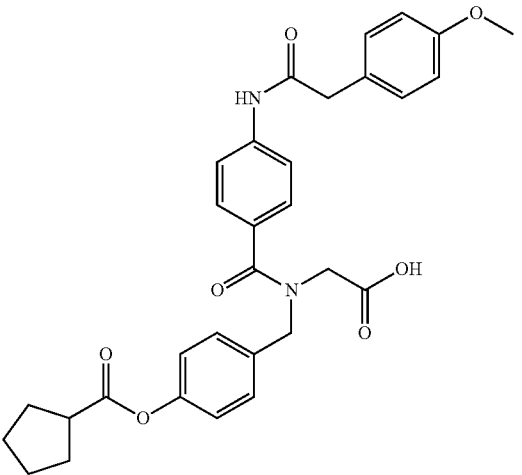 [SMILES: COc1ccc(CC(=O)Nc2ccc(C(=O)N(CC(=O)O)Cc3ccc(OC(=O)C4CCCC4)cc3)cc2)cc1] | 186 | 6.05 |

TABLE 1-continued
| STRUCTURE | COMPOUND NUMBER | LCMS RETENTION TIME (min) |
|---|---|---|
| 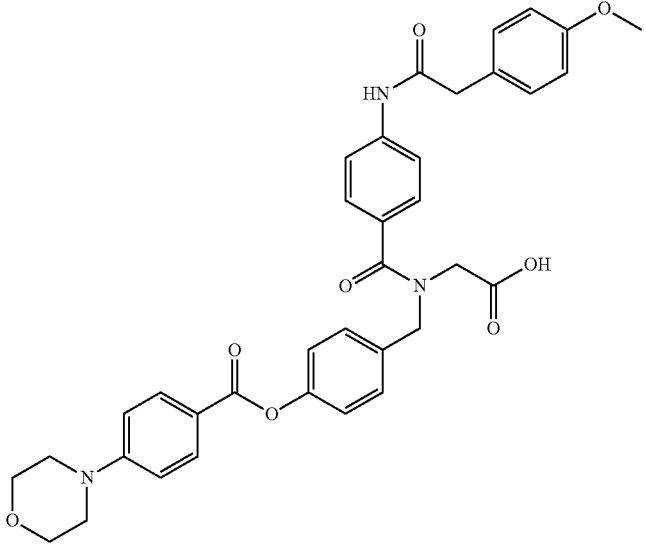 [SMILES: COc1ccc(CC(=O)Nc2ccc(C(=O)N(CC(=O)O)Cc3ccc(OC(=O)c4ccc(N5CCOCC5)cc4)cc3)cc2)cc1] | 187 | 5.58 |
| 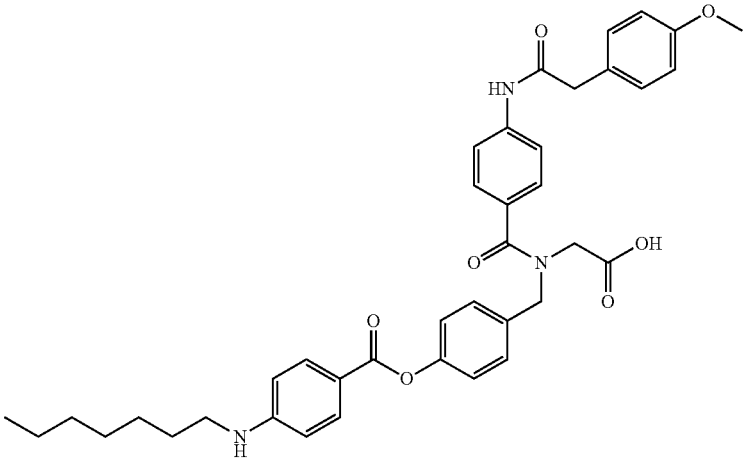 [SMILES: CCCCCCCNc1ccc(C(=O)Oc2ccc(CN(CC(=O)O)C(=O)c3ccc(NC(=O)Cc4ccc(OC)cc4)cc3)cc2)cc1] | 188 | 8.90 |
| 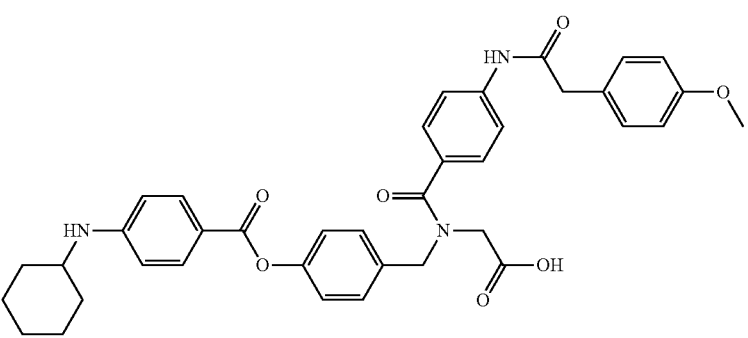 [SMILES: COc1ccc(CC(=O)Nc2ccc(C(=O)N(CC(=O)O)Cc3ccc(OC(=O)c4ccc(NC5CCCCC5)cc4)cc3)cc2)cc1] | 189 | 7.73 |

TABLE 1-continued
| STRUCTURE | COMPOUND NUMBER | LCMS RETENTION TIME (min) |
|---|---|---|
| 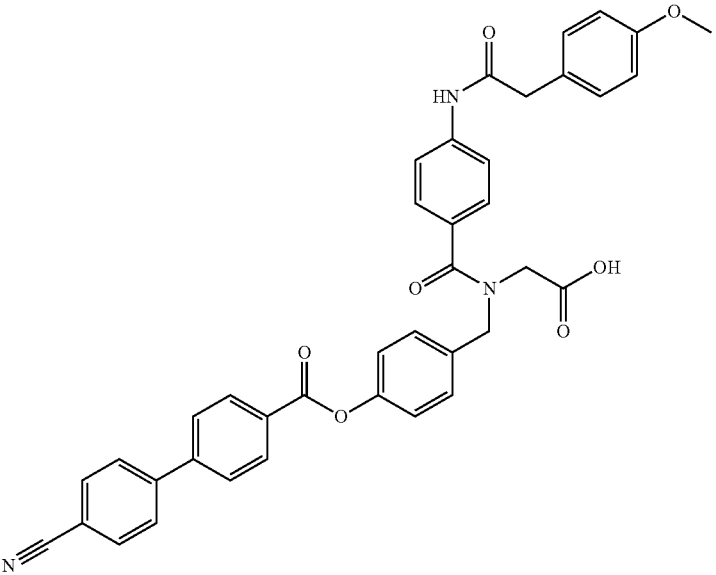 [SMILES: COc1ccc(CC(=O)Nc2ccc(C(=O)N(CC(=O)O)Cc3ccc(OC(=O)c4ccc(-c5ccc(C#N)cc5)cc4)cc3)cc2)cc1] | 190 | 8.90 |
| 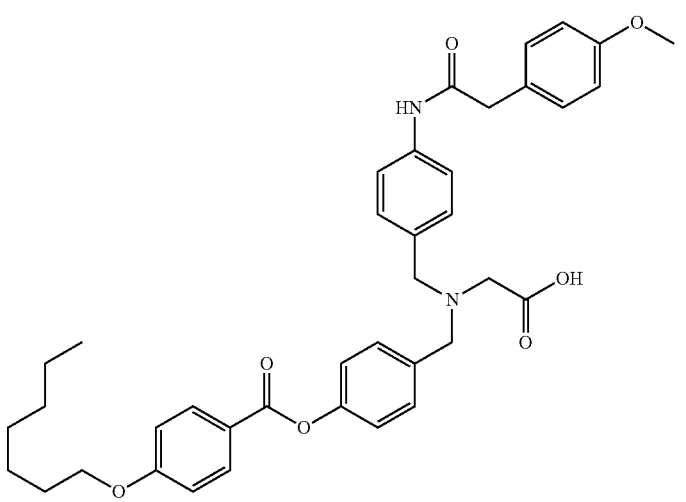 [SMILES: CCCCCCCOc1ccc(C(=O)Oc2ccc(CN(CC(=O)O)Cc3ccc(NC(=O)Cc4ccc(OC)cc4)cc3)cc2)cc1] | 191 | 7.61 |

TABLE 1-continued

| STRUCTURE | COMPOUND NUMBER | LCMS RETENTION TIME (min) |
|---|---|---|
| 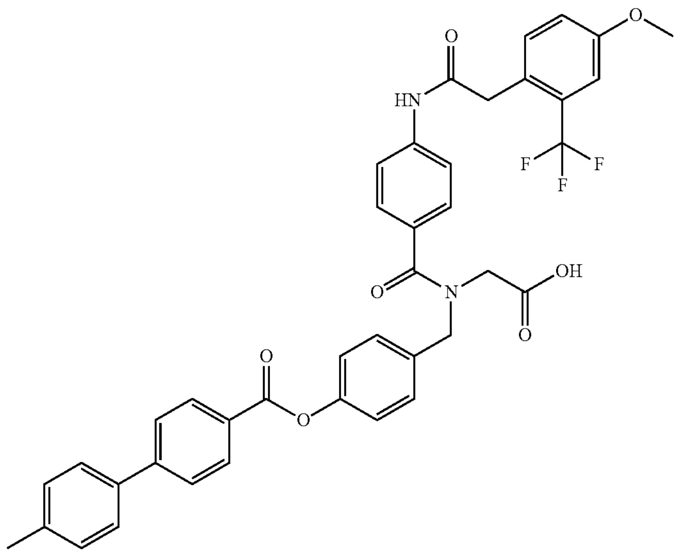 | 192 | 8.81 |
| 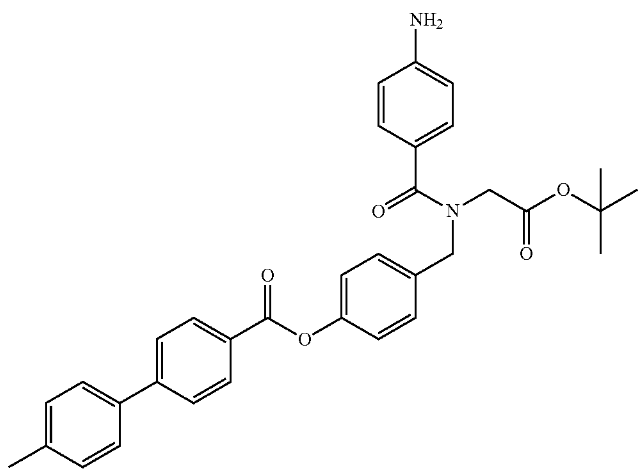 [SMILES: Cc1ccc(-c2ccc(C(=O)Oc3ccc(CN(CC(=O)OC(C)(C)C)C(=O)c4ccc(N)cc4)cc3)cc2)cc1] | 193 | 2.98 |
| 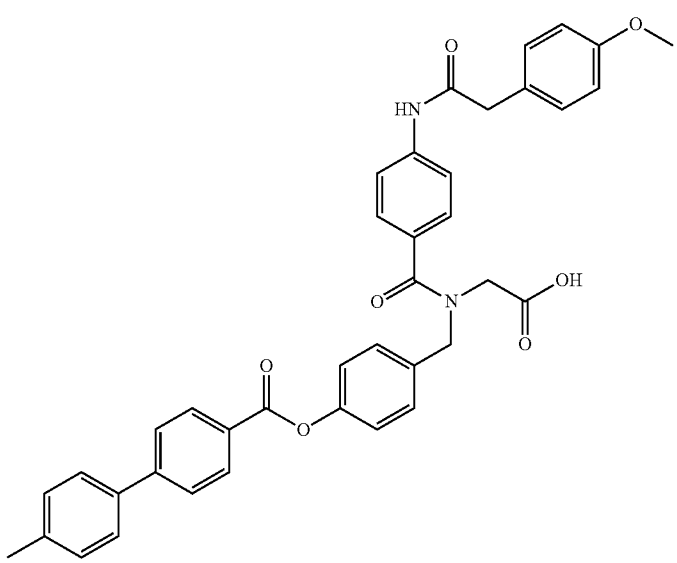 | 194 | 9.96 |

TABLE 1-continued

| STRUCTURE | COMPOUND NUMBER | LCMS RETENTION TIME (min) |
|---|---|---|
| 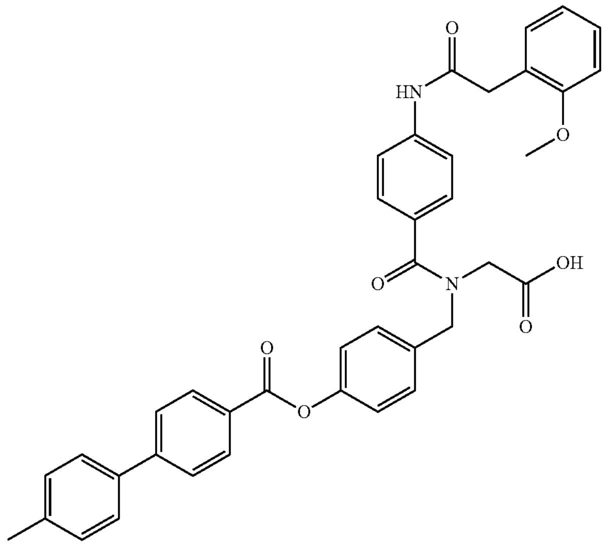 [SMILES: COc1ccccc1CC(=O)Nc1ccc(C(=O)N(CC(=O)O)Cc2ccc(OC(=O)c3ccc(-c4ccc(C)cc4)cc3)cc2)cc1] | 195 | 10.10 |
| 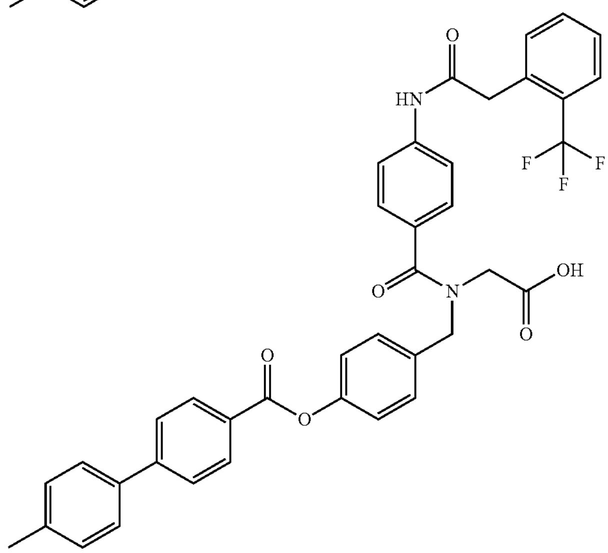 | 196 | 10.36 |
| 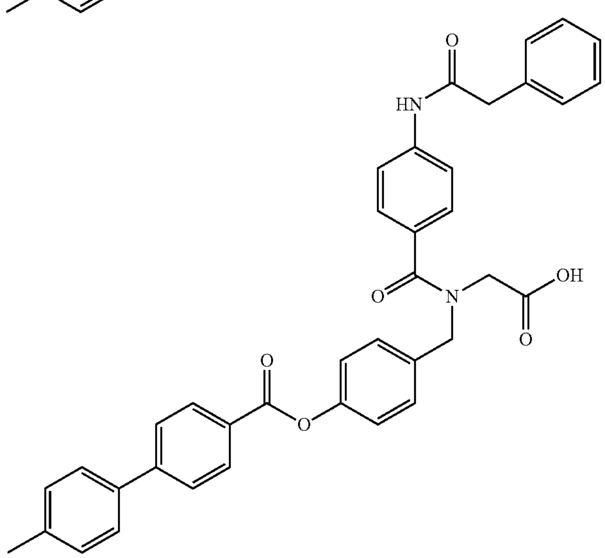 | 197 | 10.09 |

TABLE 1-continued
| STRUCTURE | COMPOUND NUMBER | LCMS RETENTION TIME (min) |
|---|---|---|
| 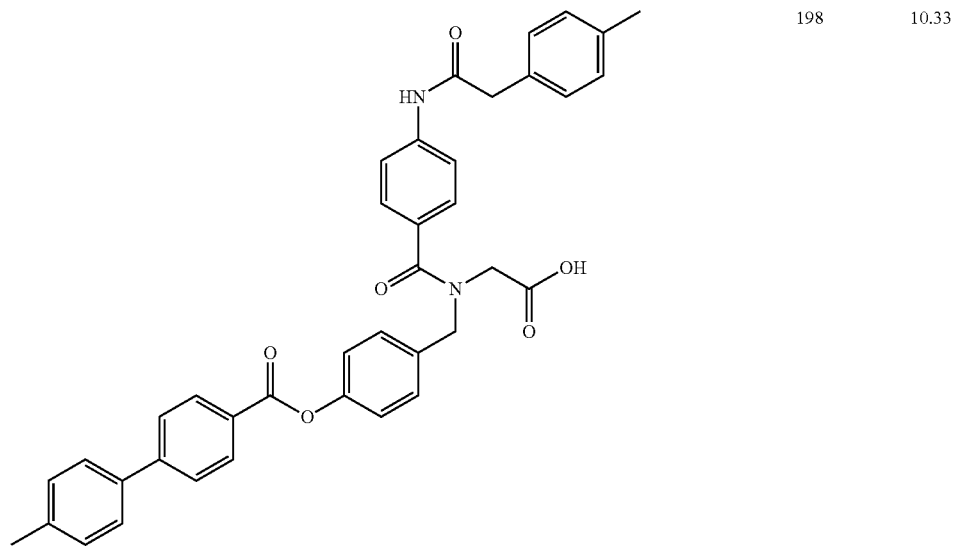 | 198 | 10.33 |
| 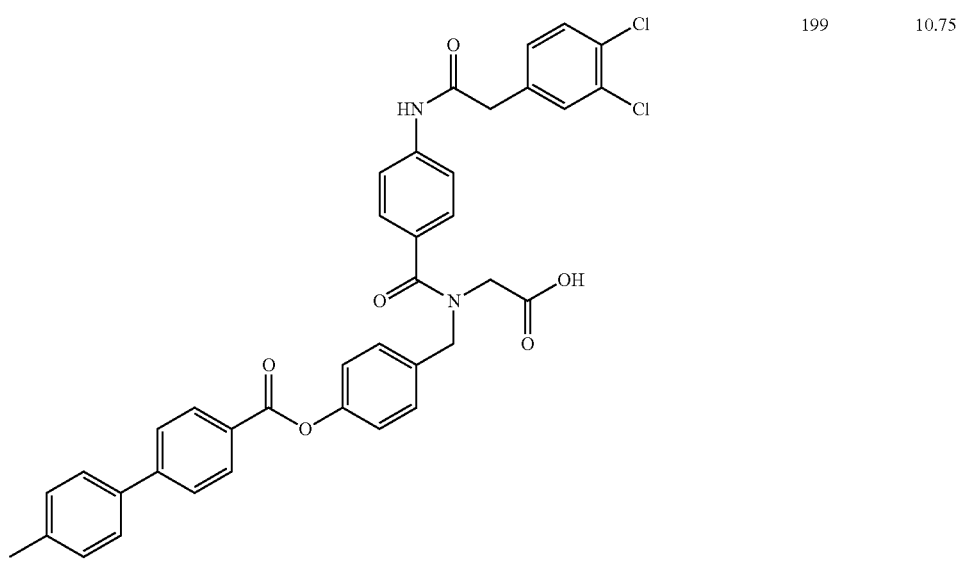 | 199 | 10.75 |

TABLE 1-continued
| STRUCTURE | COMPOUND NUMBER | LCMS RETENTION TIME (min) |
|---|---|---|
| 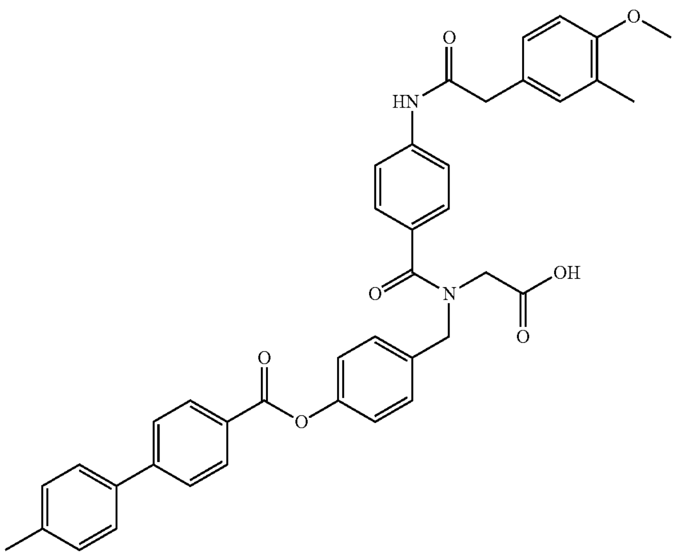 | 200 | 10.33 |
| 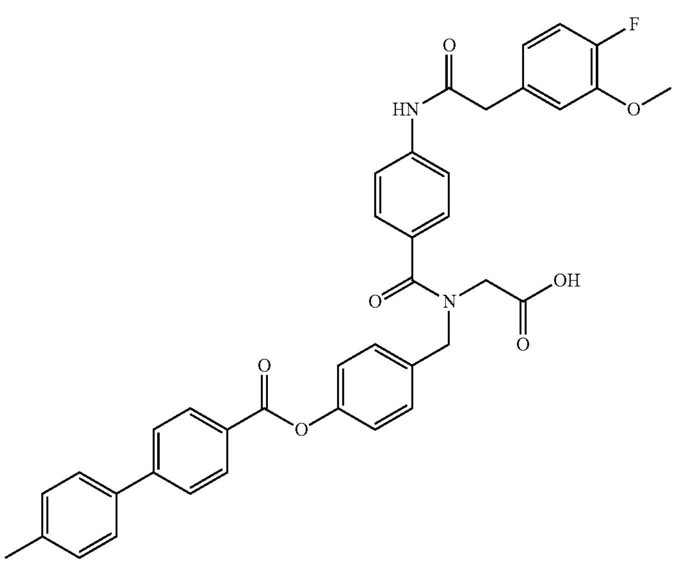 | 201 | 10.01 |

TABLE 1-continued
| STRUCTURE | COMPOUND NUMBER | LCMS RETENTION TIME (min) |
|---|---|---|
| 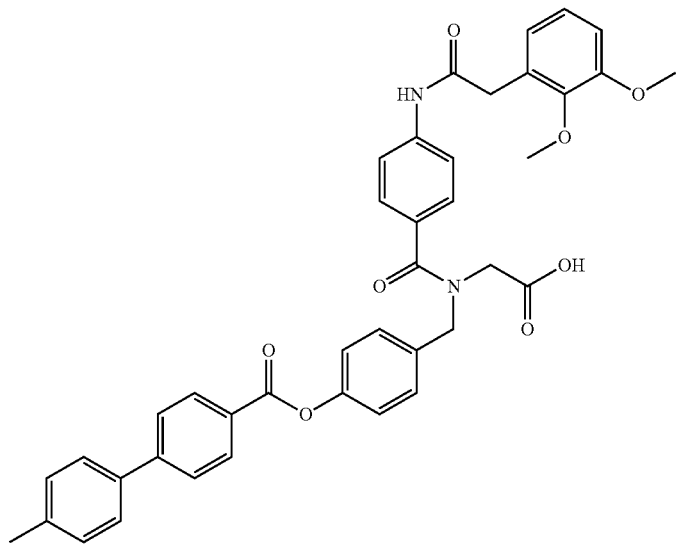 | 202 | 10.03 |
| 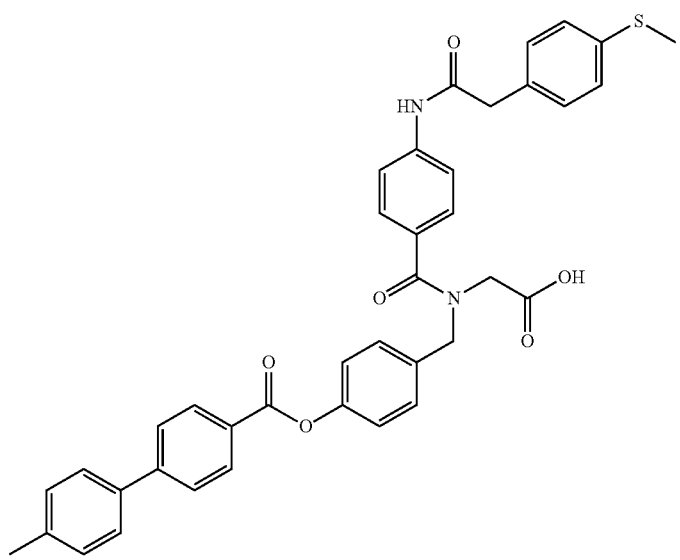 | 203 | 10.32 |

TABLE 1-continued

| STRUCTURE | COMPOUND NUMBER | LCMS RETENTION TIME (min) |
|---|---|---|
| 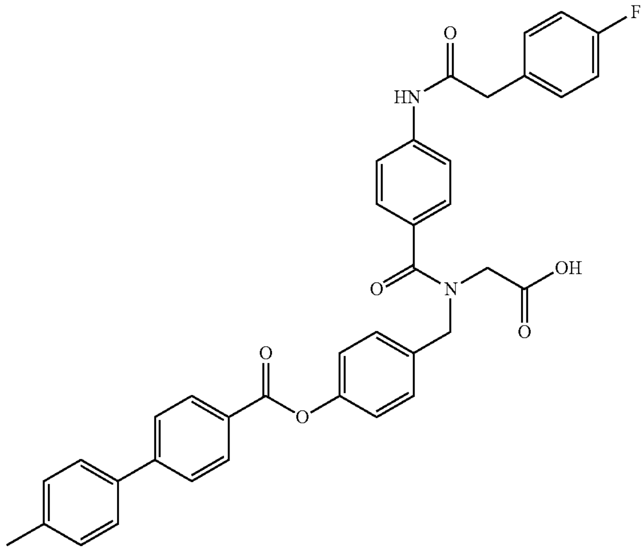 [SMILES: Cc1ccc(-c2ccc(C(=O)Oc3ccc(CN(CC(=O)O)C(=O)c4ccc(NC(=O)Cc5ccc(F)cc5)cc4)cc3)cc2)cc1] | 204 | 10.13 |
| 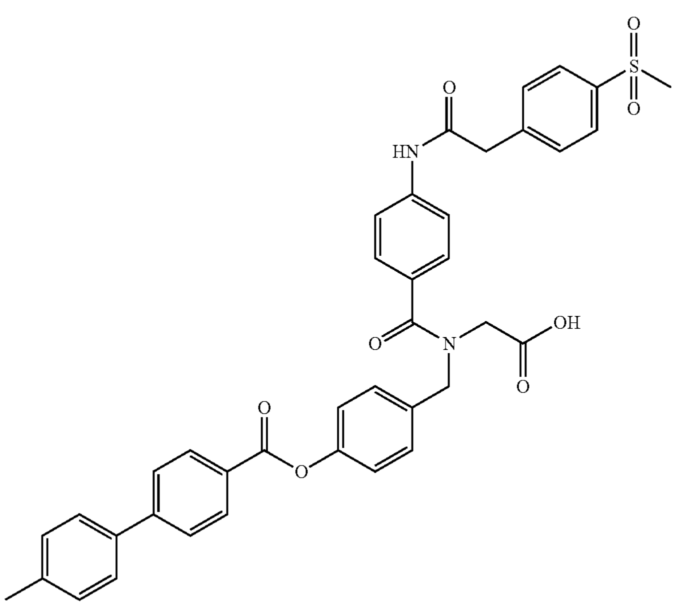 | 205 | 9.27 |

TABLE 1-continued

| STRUCTURE | COMPOUND NUMBER | LCMS RETENTION TIME (min) |
|---|---|---|
| 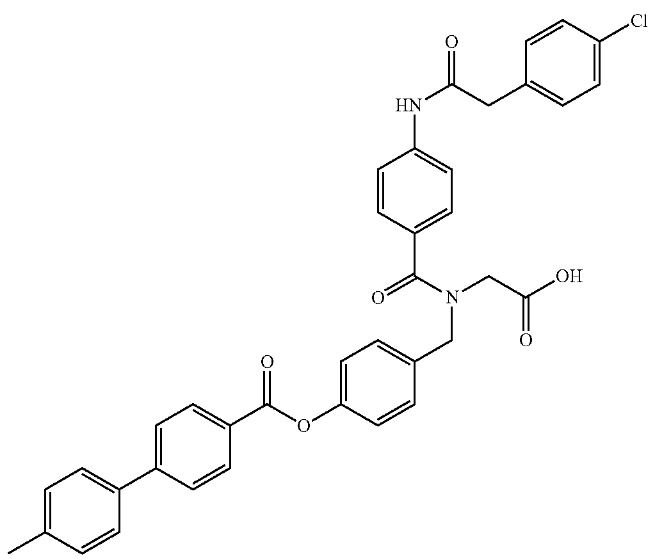 [SMILES: Cc1ccc(-c2ccc(C(=O)Oc3ccc(CN(CC(=O)O)C(=O)c4ccc(NC(=O)Cc5ccc(Cl)cc5)cc4)cc3)cc2)cc1] | 206 | 10.33 |
| 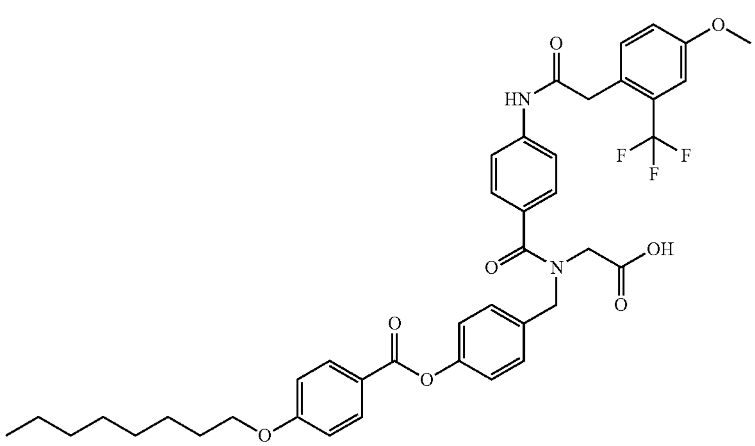 [SMILES: CCCCCCCCOc1ccc(C(=O)Oc2ccc(CN(CC(=O)O)C(=O)c3ccc(NC(=O)Cc4ccc(OC)cc4C(F)(F)F)cc3)cc2)cc1] | 207 | 10.48 |
| 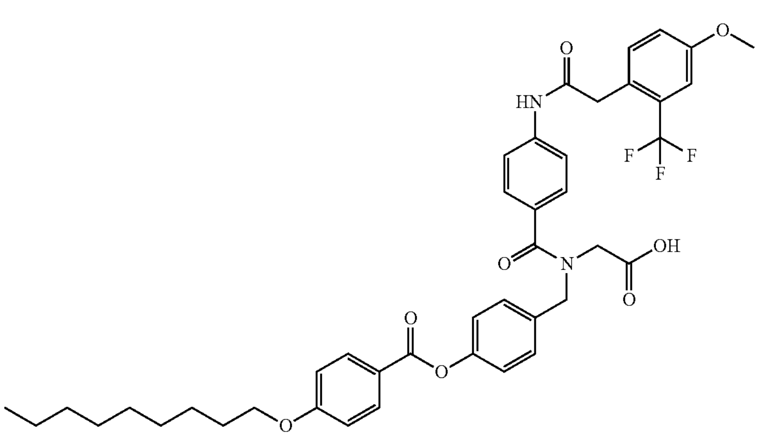 [SMILES: CCCCCCCCCOc1ccc(C(=O)Oc2ccc(CN(CC(=O)O)C(=O)c3ccc(NC(=O)Cc4ccc(OC)cc4C(F)(F)F)cc3)cc2)cc1] | 208 | 10.83 |

TABLE 1-continued
| STRUCTURE | COMPOUND NUMBER | LCMS RETENTION TIME (min) |
|---|---|---|
| 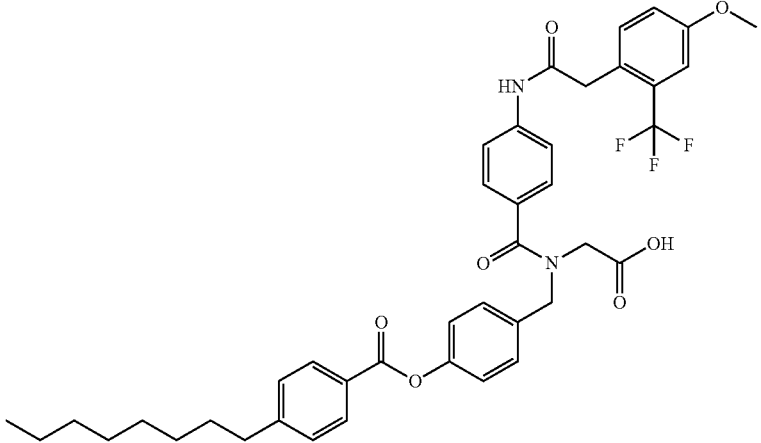 [SMILES: CCCCCCCCc1ccc(C(=O)Oc2ccc(CN(CC(=O)O)C(=O)c3ccc(NC(=O)Cc4ccc(OC)cc4C(F)(F)F)cc3)cc2)cc1] | 209 | 10.73 |
| 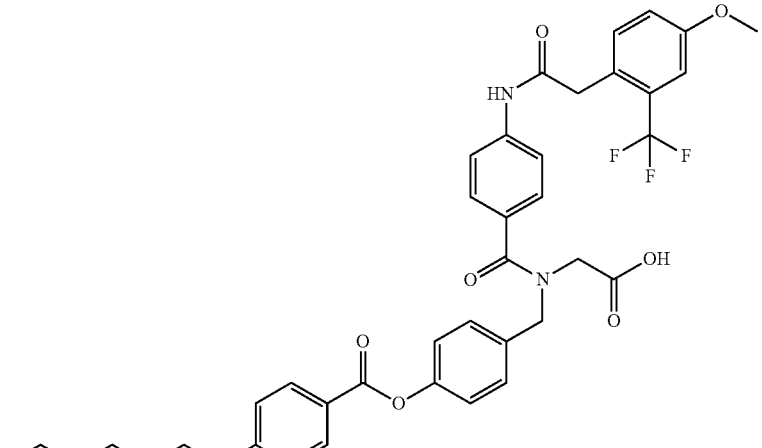 | 210 | 9.51 |
| 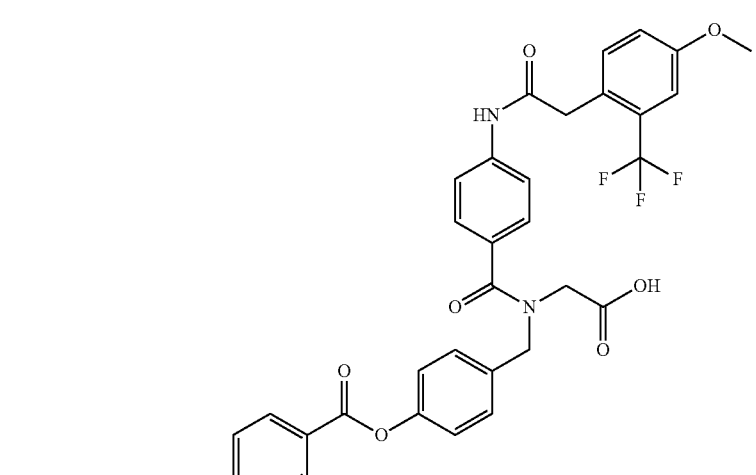 | 211 | 9.04 |

TABLE 1-continued
| STRUCTURE | COMPOUND NUMBER | LCMS RETENTION TIME (min) |
|---|---|---|
| 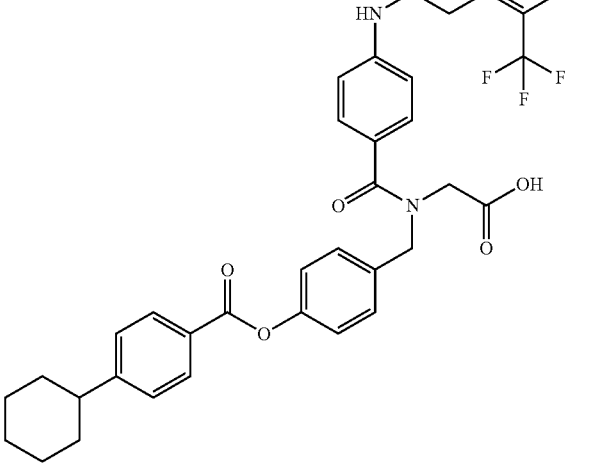 | 212 | 9.44 |
| 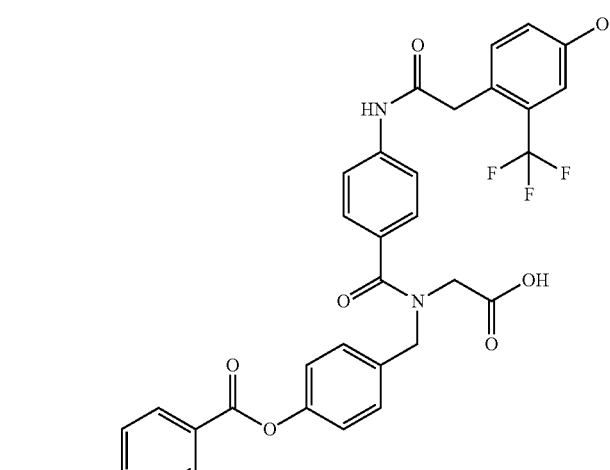 | 213 | 8.57 |
| 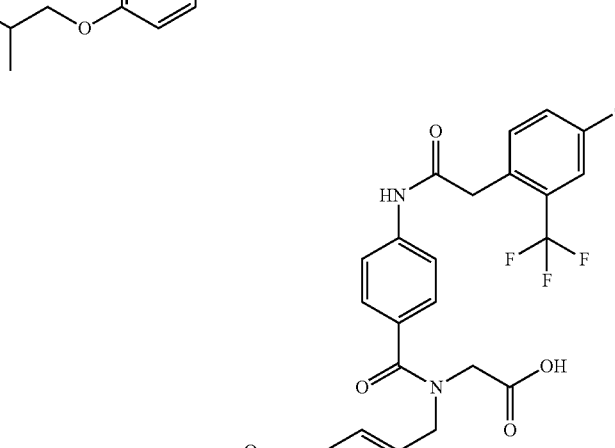 | 214 | 8.96 |

TABLE 1-continued
| STRUCTURE | COMPOUND NUMBER | LCMS RETENTION TIME (min) |
|---|---|---|
| 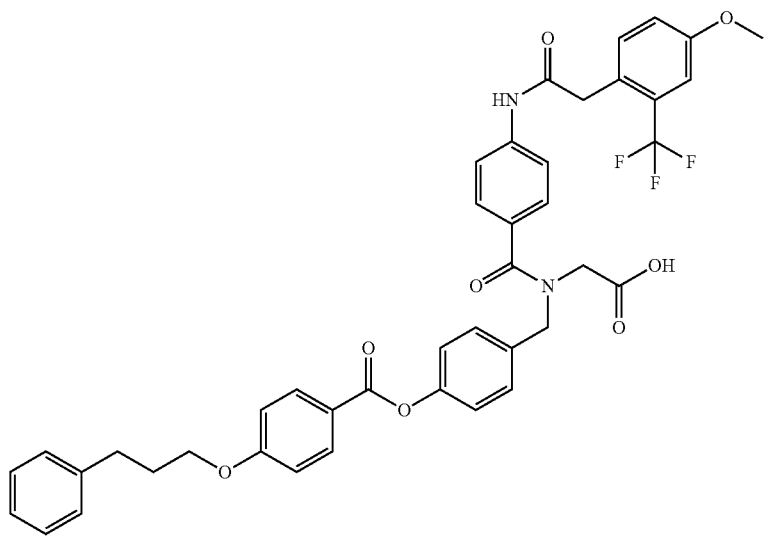 [SMILES: COc1ccc(CC(=O)Nc2ccc(C(=O)N(CC(=O)O)Cc3ccc(OC(=O)c4ccc(OCCCc5ccccc5)cc4)cc3)cc2)c(C(F)(F)F)c1] | 215 | 8.97 |
| 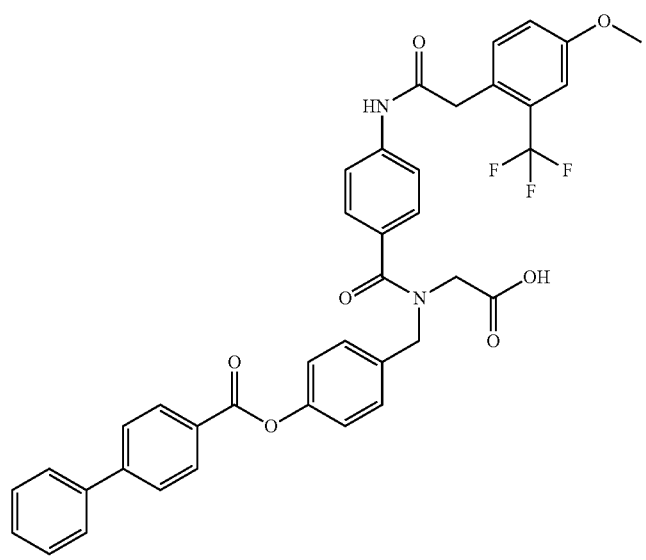 | 216 | 8.37 |

TABLE 1-continued

| STRUCTURE | COMPOUND NUMBER | LCMS RETENTION TIME (min) |
|---|---|---|
| 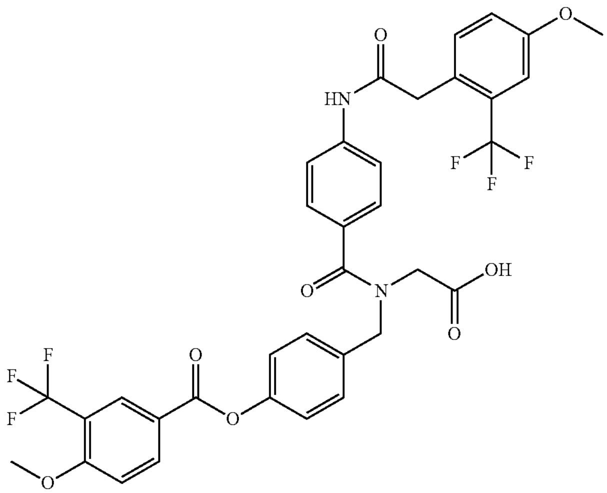 | 217 | 7.62 |
| 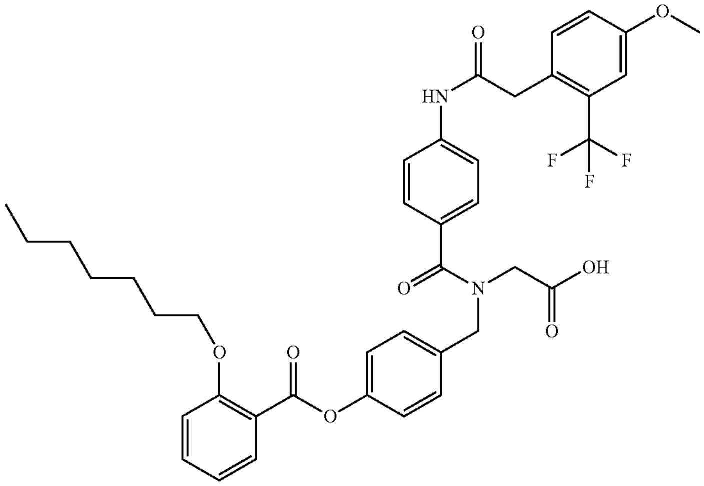 [SMILES: CCCCCCCOc1ccccc1C(=O)Oc1ccc(CN(CC(=O)O)C(=O)c2ccc(NC(=O)Cc3ccc(OC)cc3C(F)(F)F)cc2)cc1] | 218 | 9.22 |
| 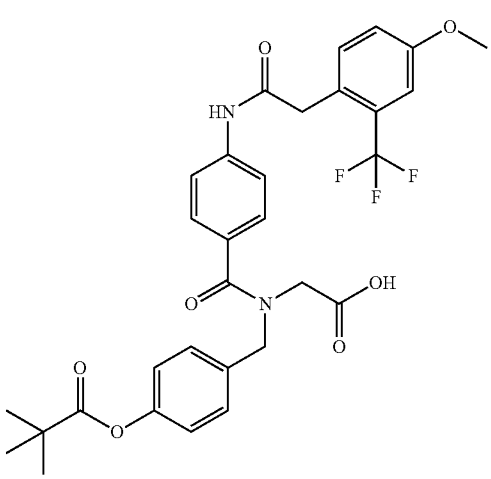 [SMILES: COc1ccc(CC(=O)Nc2ccc(C(=O)N(CC(=O)O)Cc3ccc(OC(=O)C(C)(C)C)cc3)cc2)c(C(F)(F)F)c1] | 219 | 7.11 |

TABLE 1-continued

| STRUCTURE | COMPOUND NUMBER | LCMS RETENTION TIME (min) |
|---|---|---|
| 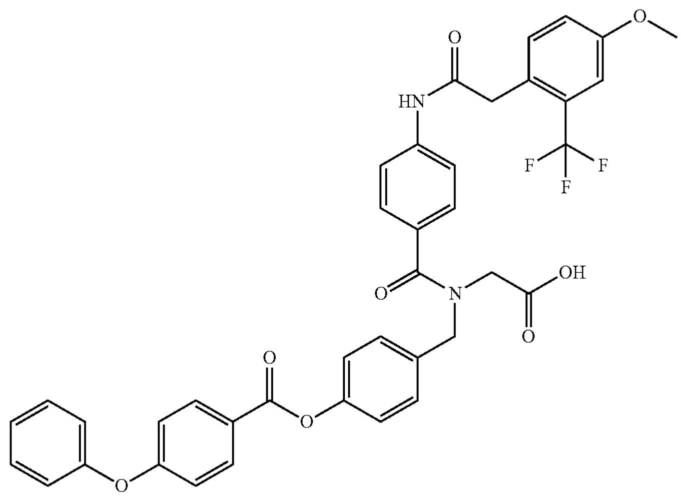 [SMILES: COc1ccc(CC(=O)Nc2ccc(C(=O)N(CC(=O)O)Cc3ccc(OC(=O)c4ccc(Oc5ccccc5)cc4)cc3)cc2)c(C(F)(F)F)c1] | 220 | 8.34 |
| 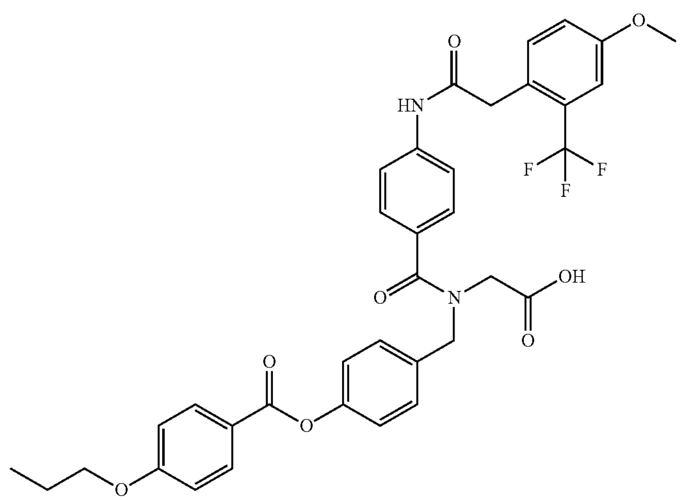 [SMILES: CCCOc1ccc(C(=O)Oc2ccc(CN(CC(=O)O)C(=O)c3ccc(NC(=O)Cc4ccc(OC)cc4C(F)(F)F)cc3)cc2)cc1] | 221 | 8.07 |
| 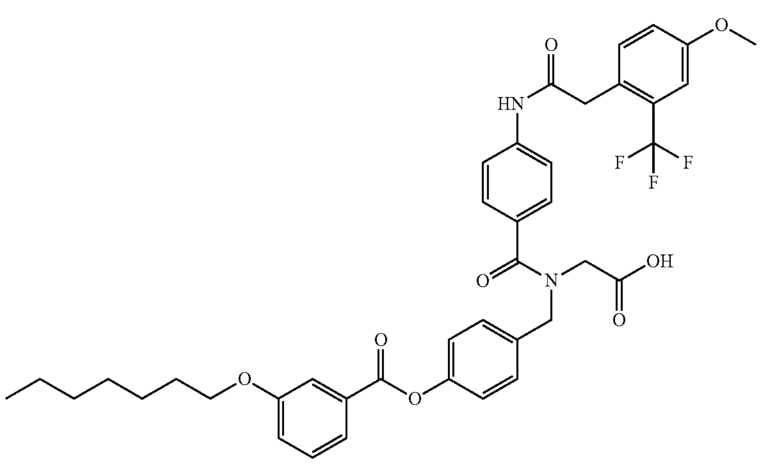 [SMILES: CCCCCCCOc1cccc(C(=O)Oc2ccc(CN(CC(=O)O)C(=O)c3ccc(NC(=O)Cc4ccc(OC)cc4C(F)(F)F)cc3)cc2)c1] | 222 | 9.96 |

TABLE 1-continued
| STRUCTURE | COMPOUND NUMBER | LCMS RETENTION TIME (min) |
|---|---|---|
| 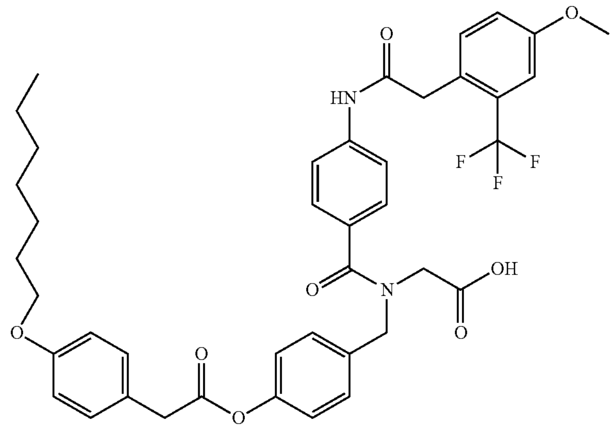 [SMILES: CCCCCCCOc1ccc(CC(=O)Oc2ccc(CN(CC(=O)O)C(=O)c3ccc(NC(=O)Cc4ccc(OC)cc4C(F)(F)F)cc3)cc2)cc1] | 223 | 9.74 |
| 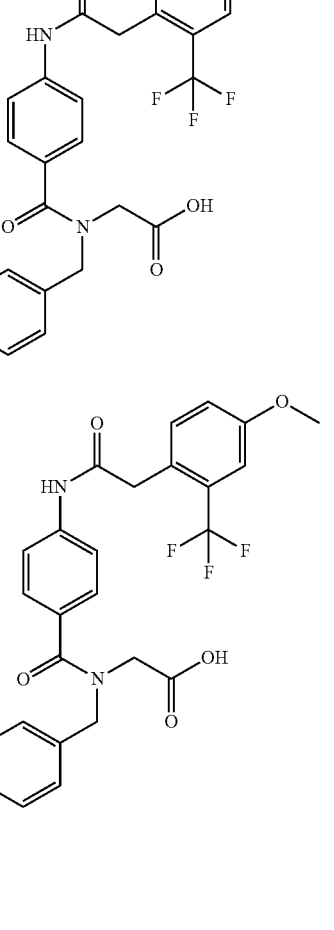 | 224 | 7.67 |
| 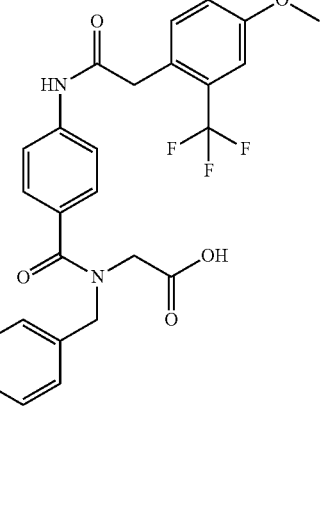 | 225 | 8.19 |

TABLE 1-continued

| STRUCTURE | COMPOUND NUMBER | LCMS RETENTION TIME (min) |
|---|---|---|
| 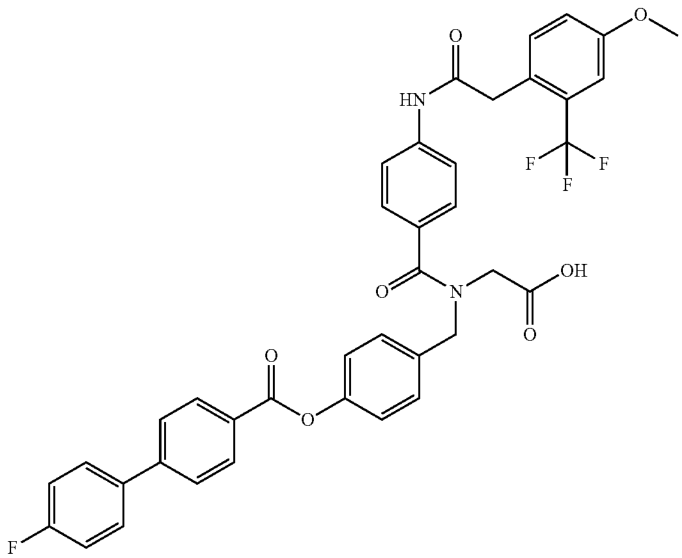 [SMILES: COc1ccc(CC(=O)Nc2ccc(C(=O)N(CC(=O)O)Cc3ccc(OC(=O)c4ccc(-c5ccc(F)cc5)cc4)cc3)cc2)c(C(F)(F)F)c1] | 226 | 8.36 |
| 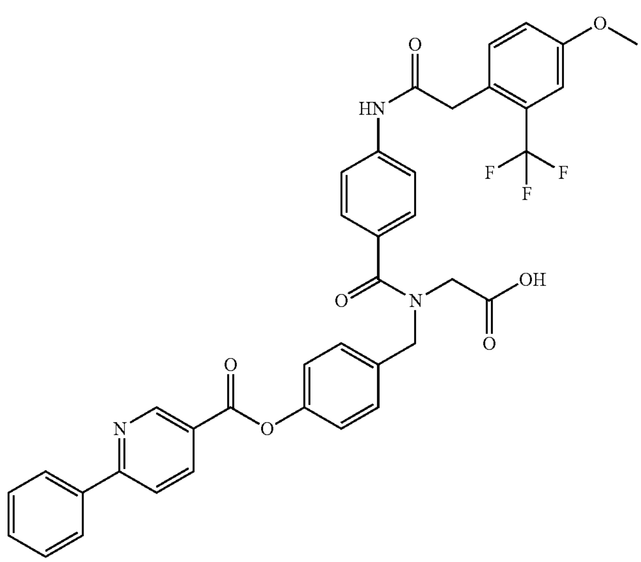 [SMILES: COc1ccc(CC(=O)Nc2ccc(C(=O)N(CC(=O)O)Cc3ccc(OC(=O)c4ccc(-c5ccccc5)nc4)cc3)cc2)c(C(F)(F)F)c1] | 227 | 7.62 |

TABLE 1-continued

| STRUCTURE | COMPOUND NUMBER | LCMS RETENTION TIME (min) |
|---|---|---|
| 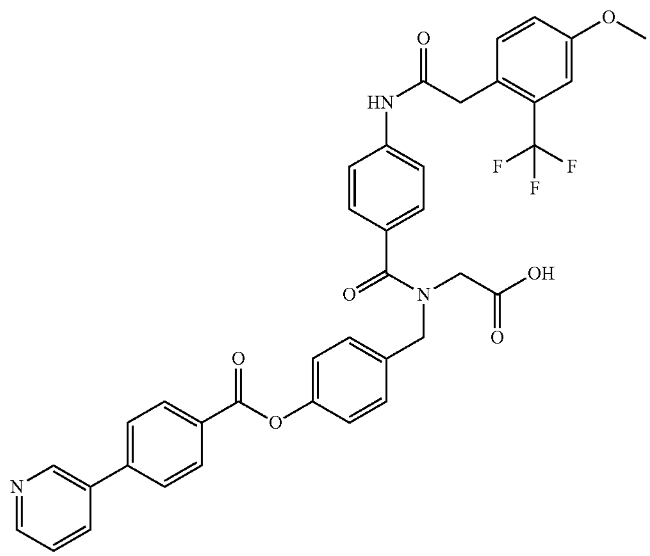 [SMILES: COc1ccc(CC(=O)Nc2ccc(C(=O)N(CC(=O)O)Cc3ccc(OC(=O)c4ccc(-c5cccnc5)cc4)cc3)cc2)c(C(F)(F)F)c1] | 228 | 5.85 |
| 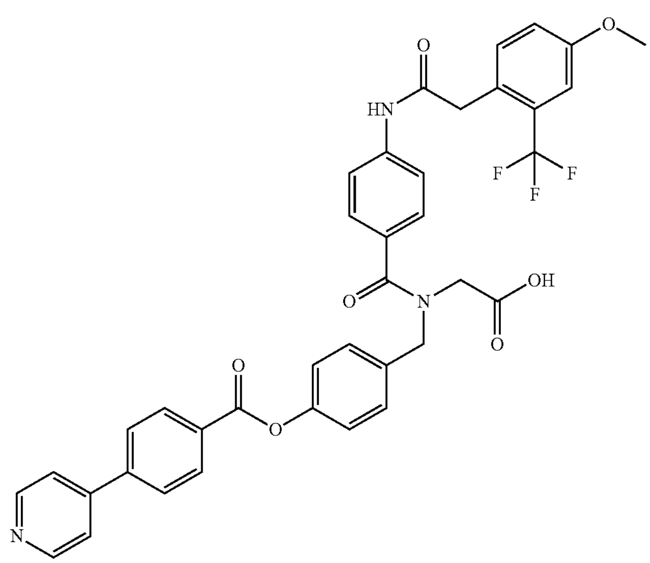 [SMILES: COc1ccc(CC(=O)Nc2ccc(C(=O)N(CC(=O)O)Cc3ccc(OC(=O)c4ccc(-c5ccncc5)cc4)cc3)cc2)c(C(F)(F)F)c1] | 229 | 5.35 |

TABLE 1-continued

| STRUCTURE | COMPOUND NUMBER | LCMS RETENTION TIME (min) |
|---|---|---|
| (structure) | 230 | 6.11 |
| (structure) | 231 | 5.54 |
| (structure) | 232 | 7.98 |

TABLE 1-continued
| STRUCTURE | COMPOUND NUMBER | LCMS RETENTION TIME (min) |
|---|---|---|
| 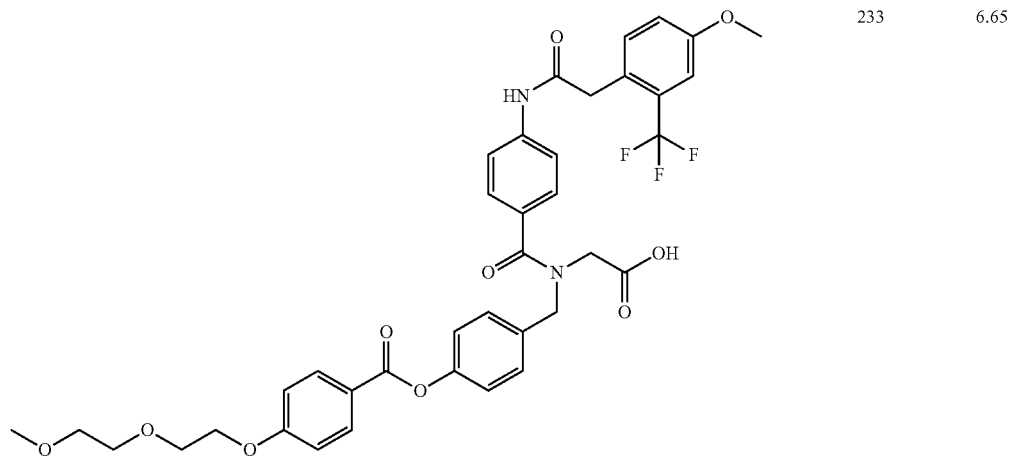 | 233 | 6.65 |
| 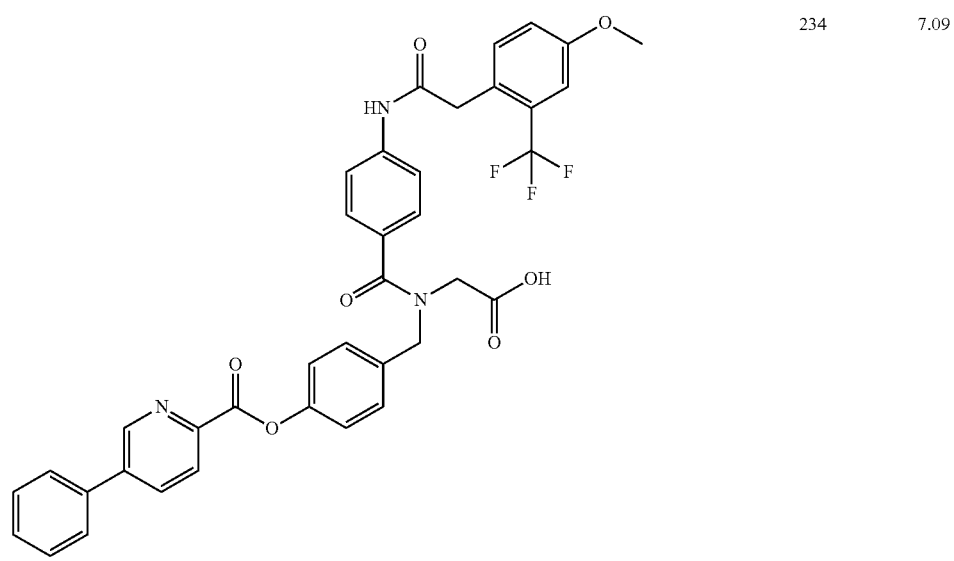 | 234 | 7.09 |

TABLE 1-continued
| STRUCTURE | COMPOUND NUMBER | LCMS RETENTION TIME (min) |
|---|---|---|
| 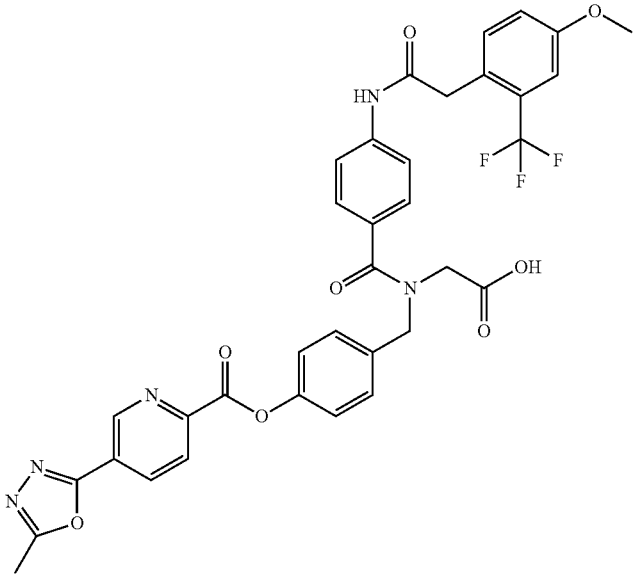 [SMILES: COc1ccc(CC(=O)Nc2ccc(C(=O)N(CC(=O)O)Cc3ccc(OC(=O)c4ccc(-c5nnc(C)o5)cn4)cc3)cc2)c(C(F)(F)F)c1] | 235 | 6.17 |
| 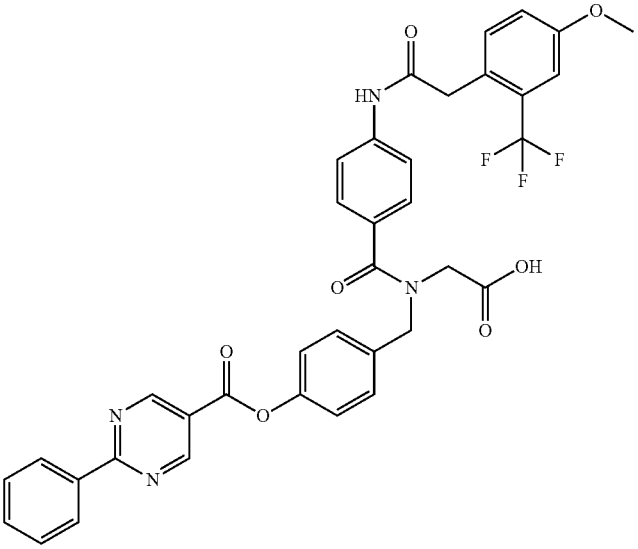 [SMILES: COc1ccc(CC(=O)Nc2ccc(C(=O)N(CC(=O)O)Cc3ccc(OC(=O)c4cnc(-c5ccccc5)nc4)cc3)cc2)c(C(F)(F)F)c1] | 236 | 7.74 |

TABLE 1-continued
| STRUCTURE | COMPOUND NUMBER | LCMS RETENTION TIME (min) |
|---|---|---|
| 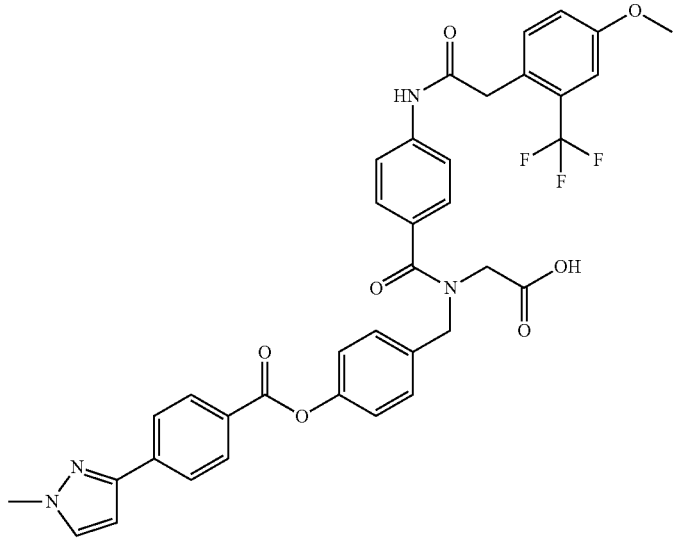 | 237 | 6.67 |
| 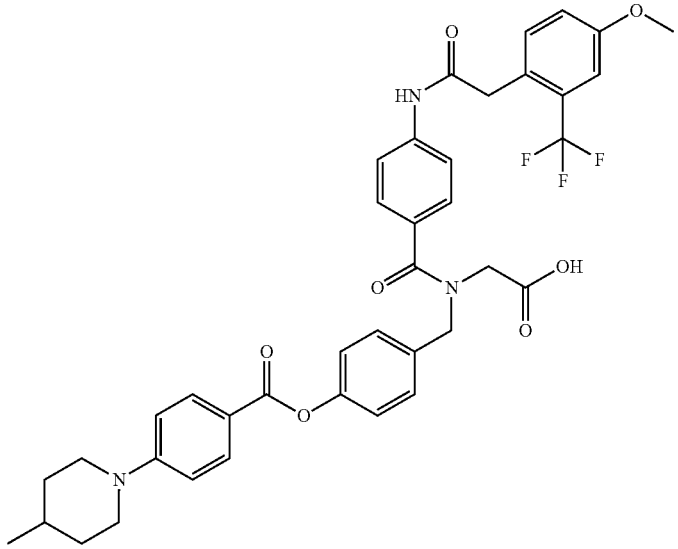 | 238 | 8.71 |

TABLE 1-continued
| STRUCTURE | COMPOUND NUMBER | LCMS RETENTION TIME (min) |
|---|---|---|
| 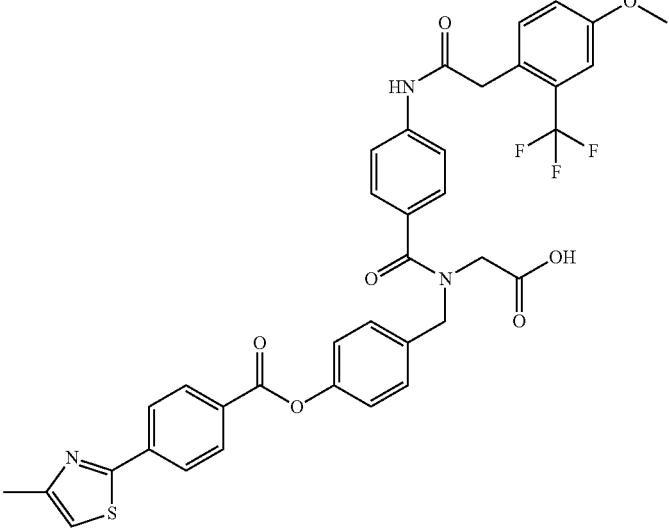 | 239 | 7.71 |
| 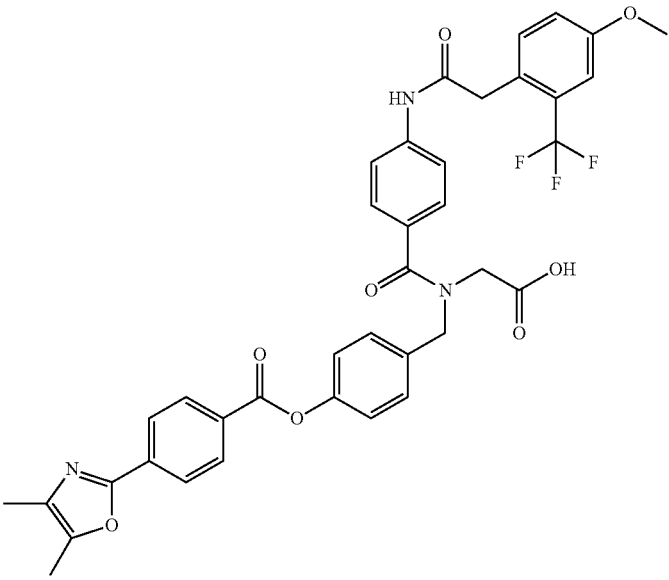 | 240 | 7.59 |

TABLE 1-continued

| STRUCTURE | COMPOUND NUMBER | LCMS RETENTION TIME (min) |
|---|---|---|
| 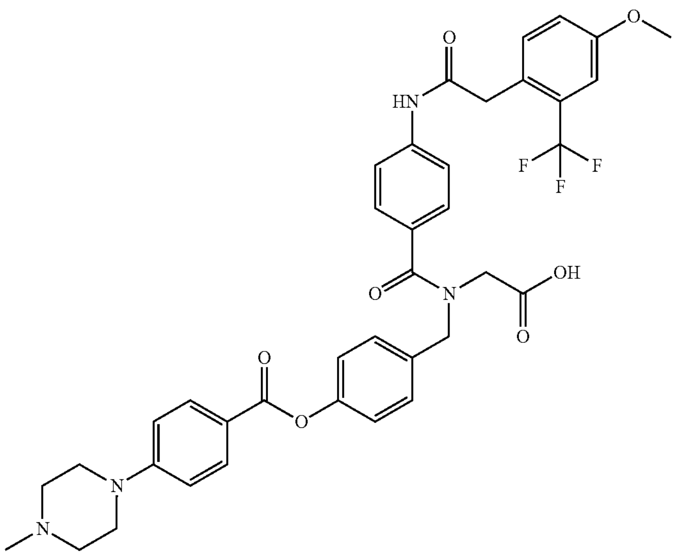 | 241 | 4.31 |
| 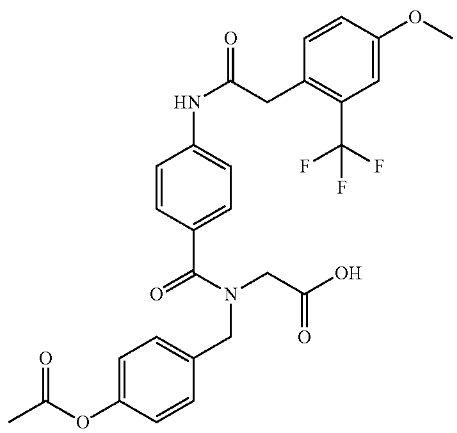 [SMILES: COc1ccc(CC(=O)Nc2ccc(C(=O)N(CC(=O)O)Cc3ccc(OC(C)=O)cc3)cc2)c(C(F)(F)F)c1] | 242 | 5.61 |
| 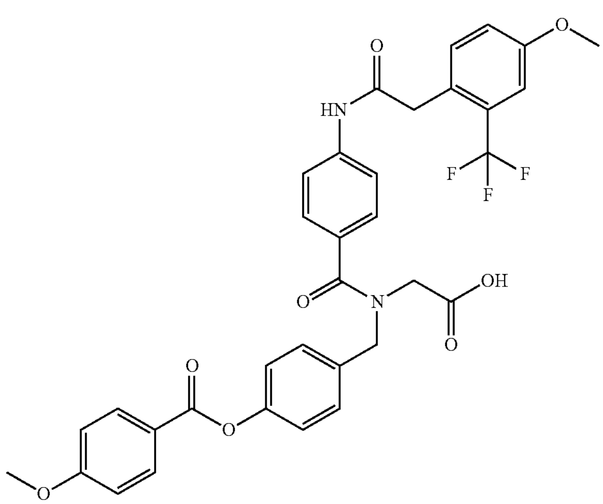 | 243 | 7.47 |

TABLE 1-continued
| STRUCTURE | COMPOUND NUMBER | LCMS RETENTION TIME (min) |
|---|---|---|
| 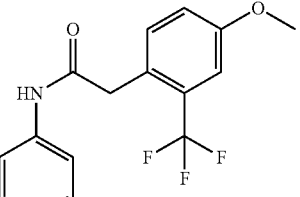 | 244 | 6.66 |
| 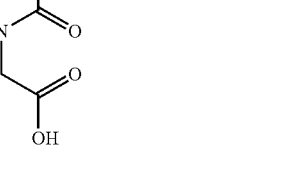 | 245 | 7.19 |
| 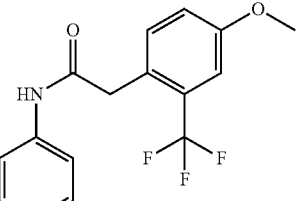 | 246 | 8.20 |

TABLE 1-continued
| STRUCTURE | COMPOUND NUMBER | LCMS RETENTION TIME (min) |
|---|---|---|
| 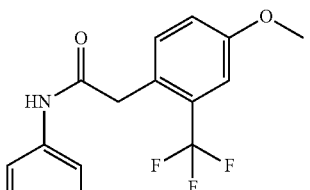 | 247 | 6.58 |
| 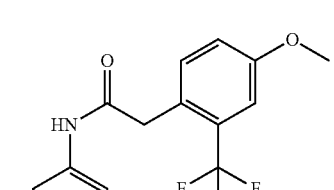 | 248 | 7.67 |
| 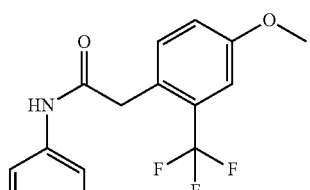 | 249 | 5.52 |

TABLE 1-continued
| STRUCTURE | COMPOUND NUMBER | LCMS RETENTION TIME (min) |
|---|---|---|
| 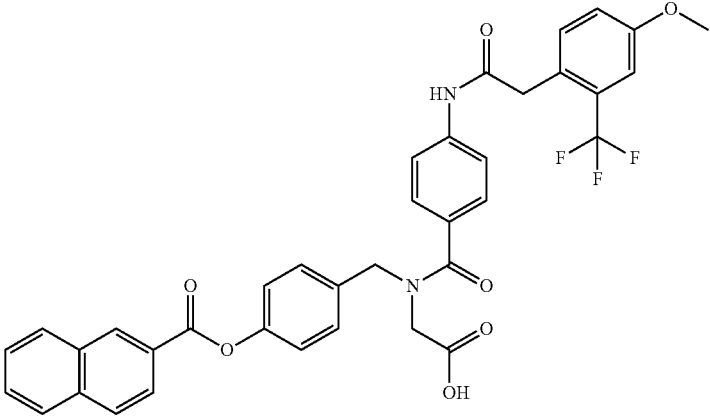 [SMILES: COc1ccc(CC(=O)Nc2ccc(C(=O)N(CC(=O)O)Cc3ccc(OC(=O)c4ccc5ccccc5c4)cc3)cc2)c(C(F)(F)F)c1] | 250 | 7.88 |
| 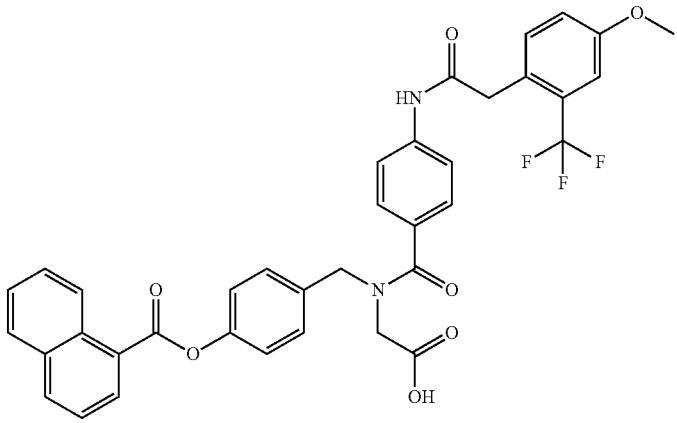 [SMILES: COc1ccc(CC(=O)Nc2ccc(C(=O)N(CC(=O)O)Cc3ccc(OC(=O)c4cccc5ccccc45)cc3)cc2)c(C(F)(F)F)c1] | 251 | 7.79 |
| 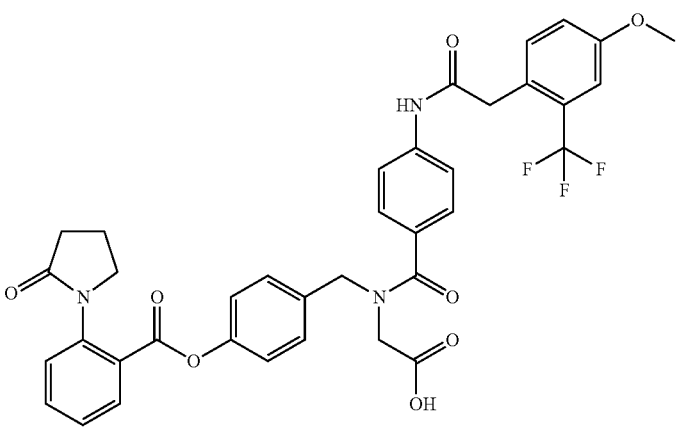 [SMILES: COc1ccc(CC(=O)Nc2ccc(C(=O)N(CC(=O)O)Cc3ccc(OC(=O)c4ccccc4N4CCCC4=O)cc3)cc2)c(C(F)(F)F)c1] | 252 | 5.98 |

TABLE 1-continued

| STRUCTURE | COMPOUND NUMBER | LCMS RETENTION TIME (min) |
|---|---|---|
| 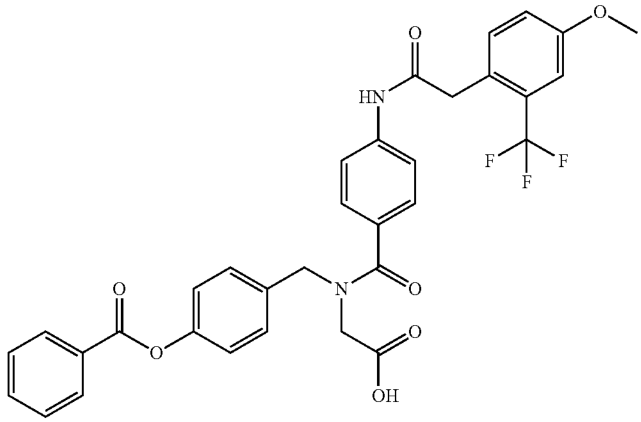 [SMILES: COc1ccc(CC(=O)Nc2ccc(C(=O)N(CC(=O)O)Cc3ccc(OC(=O)c4ccccc4)cc3)cc2)c(C(F)(F)F)c1] | 253 | 7.06 |
| 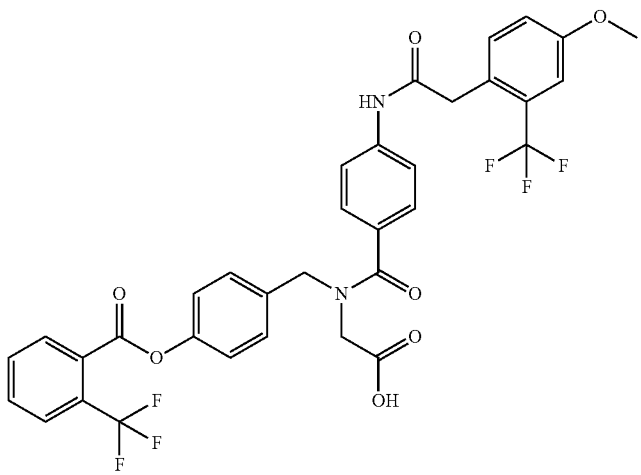 [SMILES: COc1ccc(CC(=O)Nc2ccc(C(=O)N(CC(=O)O)Cc3ccc(OC(=O)c4ccccc4C(F)(F)F)cc3)cc2)c(C(F)(F)F)c1] | 254 | 7.38 |
| 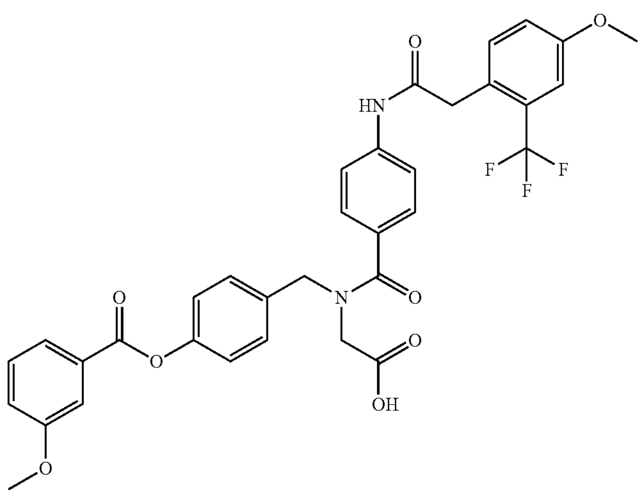 [SMILES: COc1cccc(C(=O)Oc2ccc(CN(CC(=O)O)C(=O)c3ccc(NC(=O)Cc4ccc(OC)cc4C(F)(F)F)cc3)cc2)c1] | 255 | 7.07 |

TABLE 1-continued

| STRUCTURE | COMPOUND NUMBER | LCMS RETENTION TIME (min) |
|---|---|---|
| 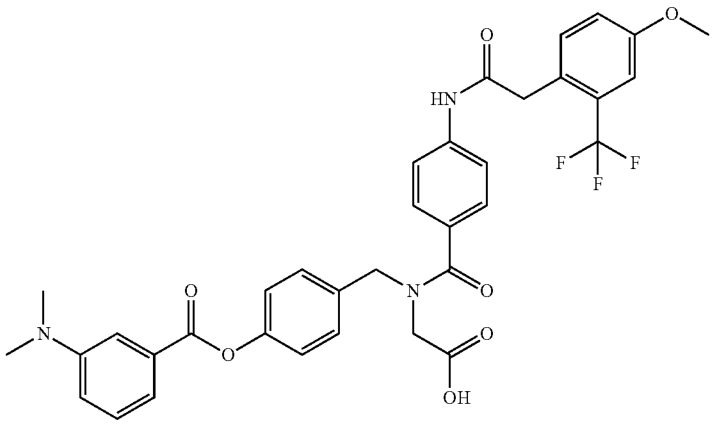 | 256 | 7.26 |
| 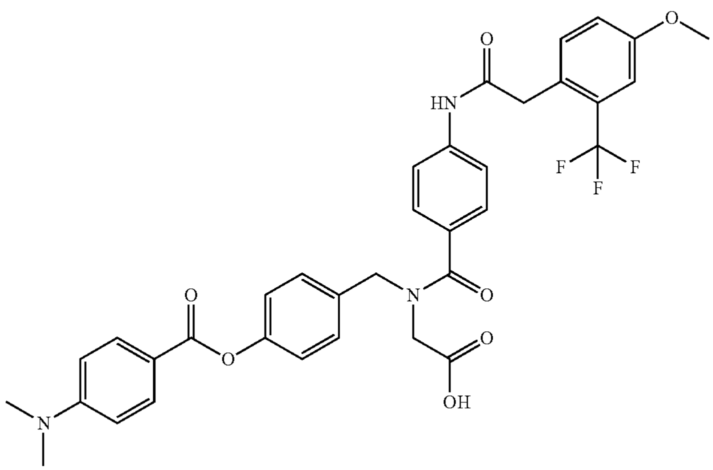 | 257 | 7.23 |
| 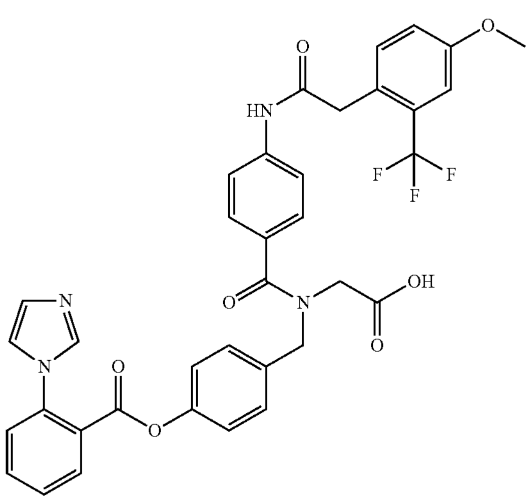 [SMILES: COc1ccc(CC(=O)Nc2ccc(C(=O)N(CC(=O)O)Cc3ccc(OC(=O)c4ccccc4-n4ccnc4)cc3)cc2)c(C(F)(F)F)c1] | 258 | 4.46 |

TABLE 1-continued

| STRUCTURE | COMPOUND NUMBER | LCMS RETENTION TIME (min) |
|---|---|---|
| 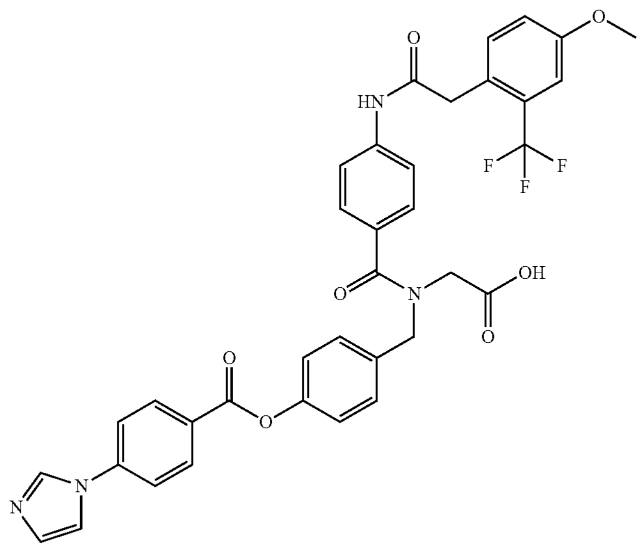 [SMILES: COc1ccc(CC(=O)Nc2ccc(C(=O)N(CC(=O)O)Cc3ccc(OC(=O)c4ccc(-n5ccnc5)cc4)cc3)cc2)c(C(F)(F)F)c1] | 259 | 4.44 |
| 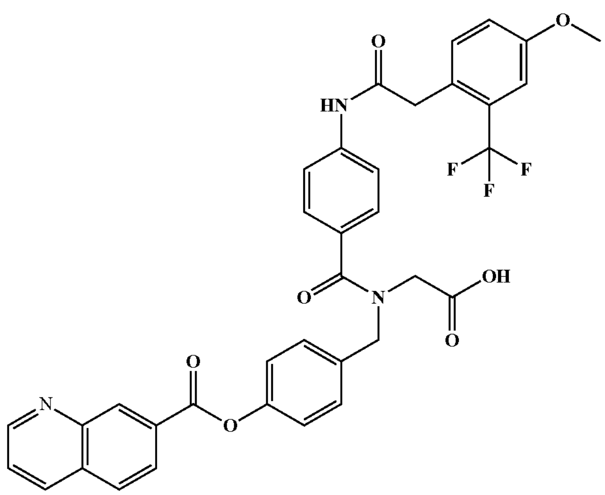 [SMILES: COc1ccc(CC(=O)Nc2ccc(C(=O)N(CC(=O)O)Cc3ccc(OC(=O)c4ccc5cccnc5c4)cc3)cc2)c(C(F)(F)F)c1] | 260 | 6.23 |
| 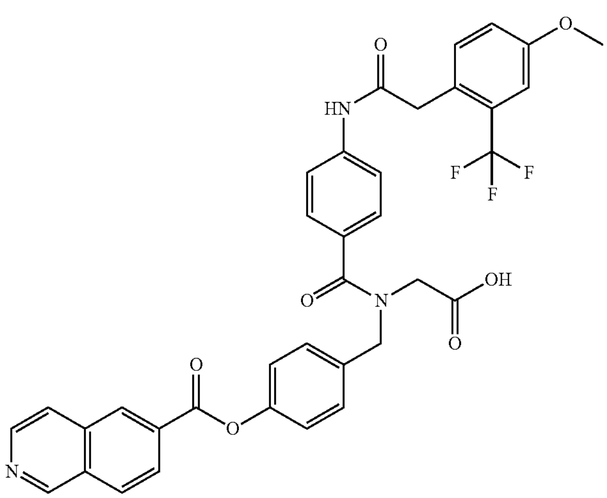 [SMILES: COc1ccc(CC(=O)Nc2ccc(C(=O)N(CC(=O)O)Cc3ccc(OC(=O)c4ccc5cnccc5c4)cc3)cc2)c(C(F)(F)F)c1] | 261 | 5.64 |

TABLE 1-continued
| STRUCTURE | COMPOUND NUMBER | LCMS RETENTION TIME (min) |
|---|---|---|
| 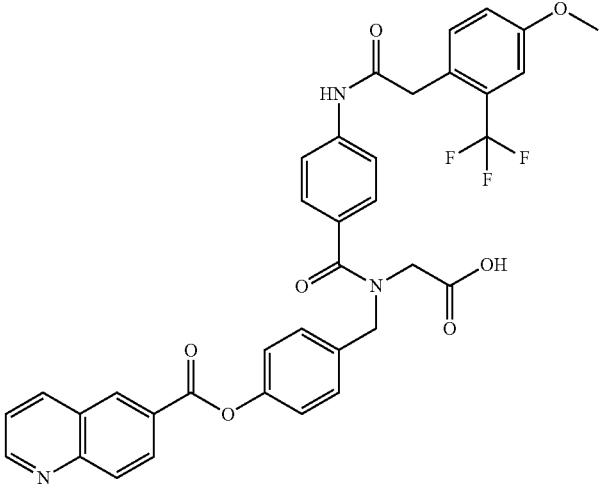 [SMILES: COc1ccc(CC(=O)Nc2ccc(C(=O)N(CC(=O)O)Cc3ccc(OC(=O)c4ccc5ncccc5c4)cc3)cc2)c(C(F)(F)F)c1] | 262 | 6.08 |
| 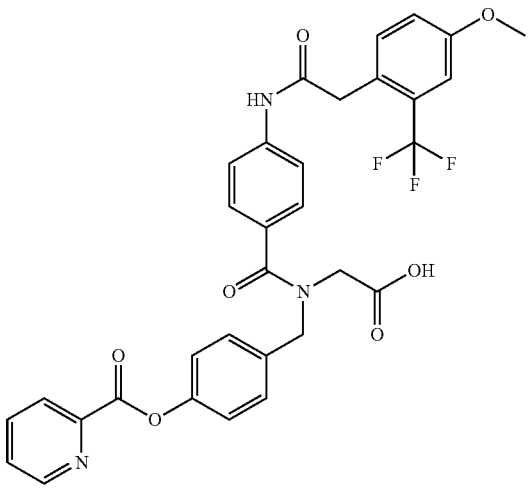 [SMILES: COc1ccc(CC(=O)Nc2ccc(C(=O)N(CC(=O)O)Cc3ccc(OC(=O)c4ccccn4)cc3)cc2)c(C(F)(F)F)c1] | 263 | 5.50 |
| 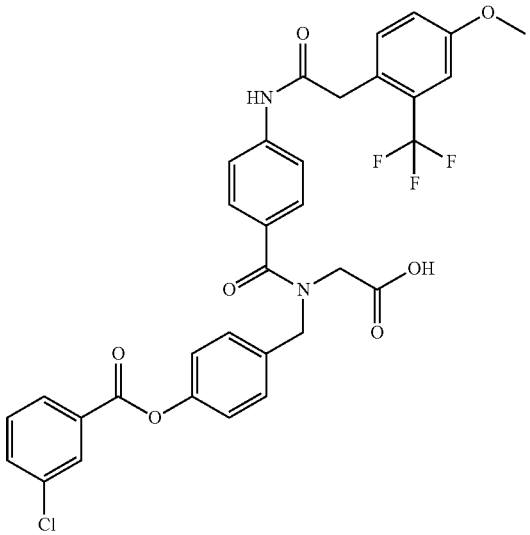 [SMILES: COc1ccc(CC(=O)Nc2ccc(C(=O)N(CC(=O)O)Cc3ccc(OC(=O)c4cccc(Cl)c4)cc3)cc2)c(C(F)(F)F)c1] | 264 | 7.60 |

TABLE 1-continued

| STRUCTURE | COMPOUND NUMBER | LCMS RETENTION TIME (min) |
|---|---|---|
| 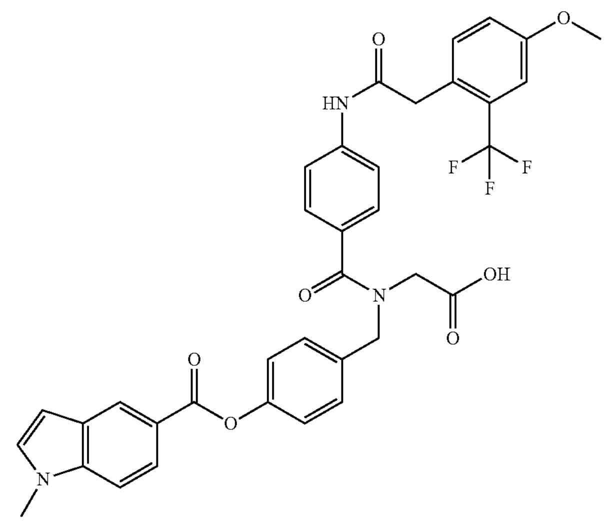 [SMILES: COc1ccc(CC(=O)Nc2ccc(C(=O)N(CC(=O)O)Cc3ccc(OC(=O)c4ccc5c(ccn5C)c4)cc3)cc2)c(C(F)(F)F)c1] | 265 | 7.10 |
| 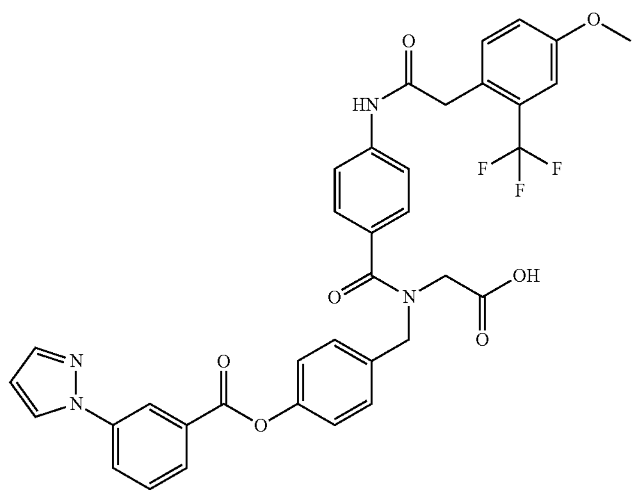 [SMILES: COc1ccc(CC(=O)Nc2ccc(C(=O)N(CC(=O)O)Cc3ccc(OC(=O)c4cccc(-n5cccn5)c4)cc3)cc2)c(C(F)(F)F)c1] | 266 | 6.92 |
| 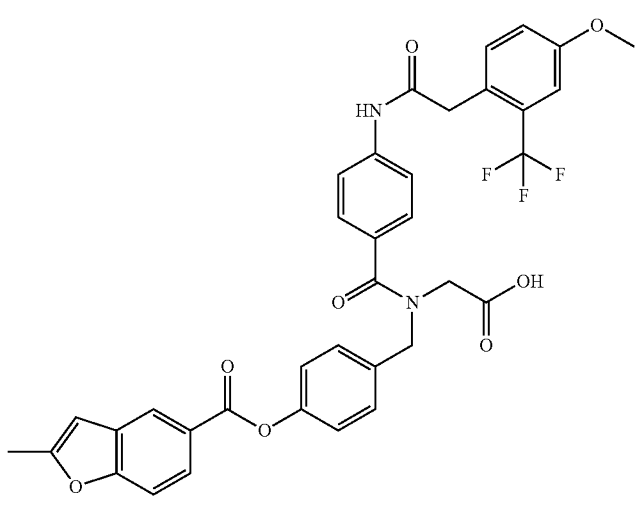 | 267 | 7.77 |

TABLE 1-continued

| STRUCTURE | COMPOUND NUMBER | LCMS RETENTION TIME (min) |
|---|---|---|
| 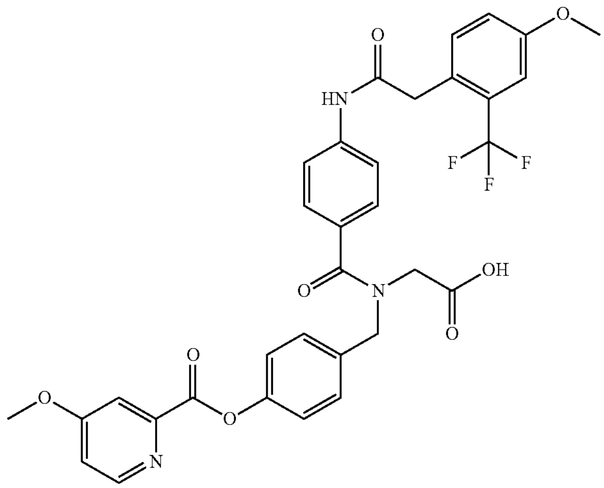 | 268 | 5.58 |
| 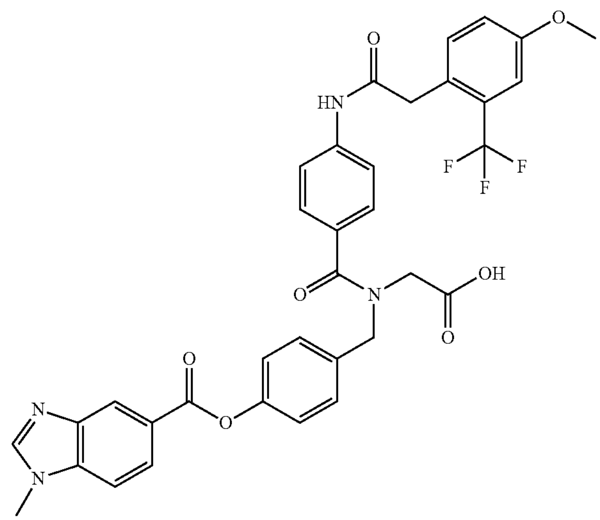 [SMILES: COc1ccc(CC(=O)Nc2ccc(C(=O)N(CC(=O)O)Cc3ccc(OC(=O)c4ccc5c(c4)ncn5C)cc3)cc2)c(C(F)(F)F)c1] | 269 | 5.04 |
| 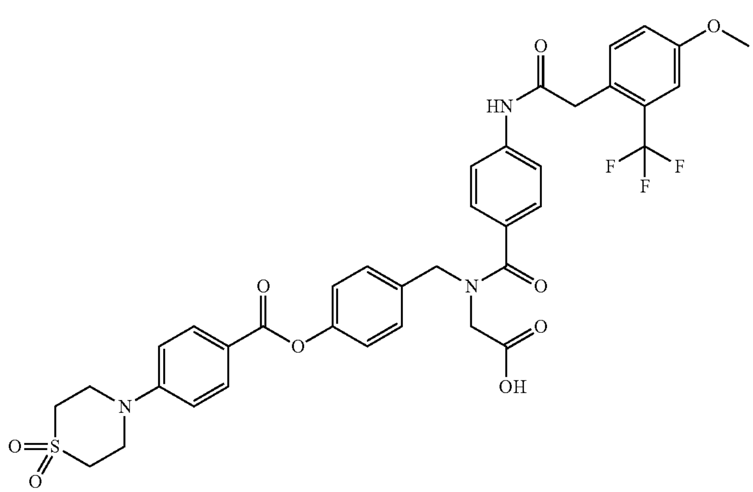 [SMILES: COc1ccc(CC(=O)Nc2ccc(C(=O)N(CC(=O)O)Cc3ccc(OC(=O)c4ccc(N5CCS(=O)(=O)CC5)cc4)cc3)cc2)c(C(F)(F)F)c1] | 270 | 5.91 |

TABLE 1-continued

| STRUCTURE | COMPOUND NUMBER | LCMS RETENTION TIME (min) |
|---|---|---|
| *(structure)* | 271 | 6.84 |
| *(structure)* | 272 | 10.02 |
| *(structure)* | 273 | 7.48 |

TABLE 1-continued
| STRUCTURE | COMPOUND NUMBER | LCMS RETENTION TIME (min) |
|---|---|---|
| 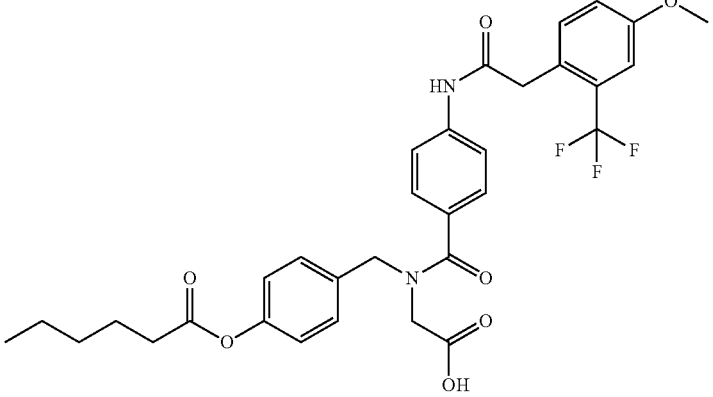 | 274 | 7.63 |
| 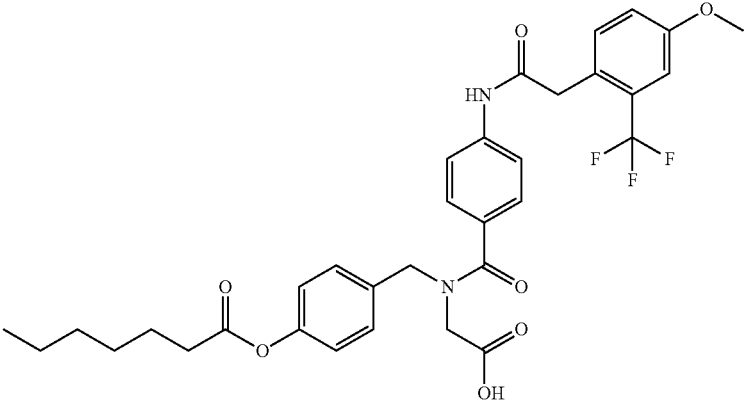 [SMILES: CCCCCCC(=O)Oc1ccc(CN(CC(=O)O)C(=O)c2ccc(NC(=O)Cc3ccc(OC)cc3C(F)(F)F)cc2)cc1] | 275 | 8.12 |
| 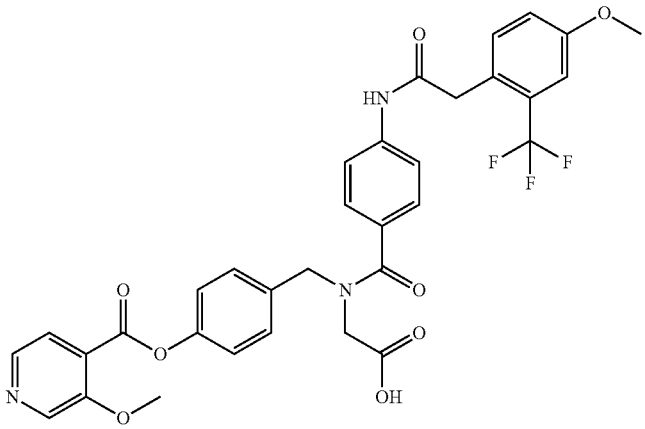 [SMILES: COc1ccc(CC(=O)Nc2ccc(C(=O)N(CC(=O)O)Cc3ccc(OC(=O)c4ccncc4OC)cc3)cc2)c(C(F)(F)F)c1] | 276 | 5.49 |

TABLE 1-continued

| STRUCTURE | COMPOUND NUMBER | LCMS RETENTION TIME (min) |
|---|---|---|
| 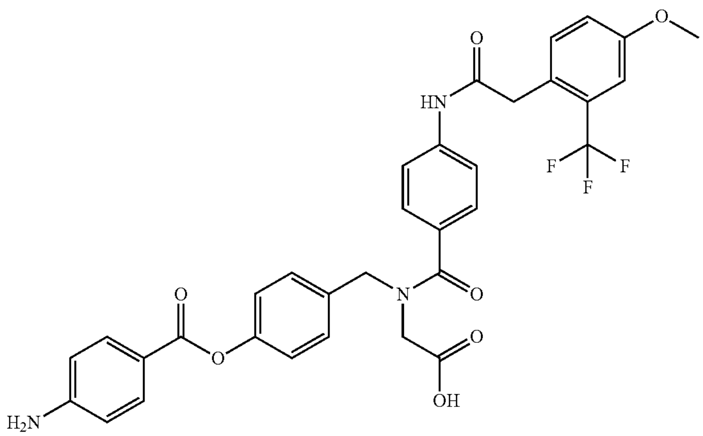 [SMILES: COc1ccc(CC(=O)Nc2ccc(C(=O)N(CC(=O)O)Cc3ccc(OC(=O)c4ccc(N)cc4)cc3)cc2)c(C(F)(F)F)c1] | 277 | 5.85 |
| 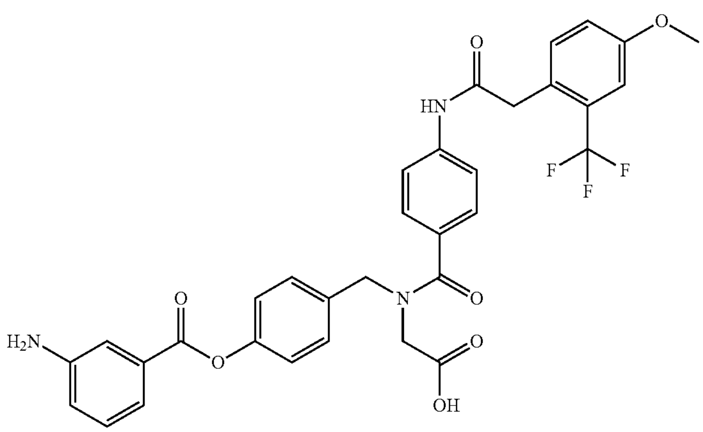 [SMILES: COc1ccc(CC(=O)Nc2ccc(C(=O)N(CC(=O)O)Cc3ccc(OC(=O)c4cccc(N)c4)cc3)cc2)c(C(F)(F)F)c1] | 278 | 5.81 |
| 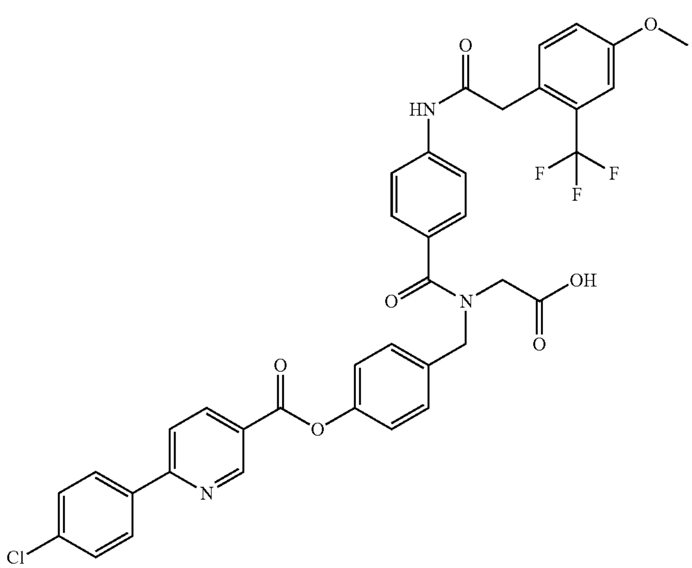 [SMILES: COc1ccc(CC(=O)Nc2ccc(C(=O)N(CC(=O)O)Cc3ccc(OC(=O)c4ccc(-c5ccc(Cl)cc5)nc4)cc3)cc2)c(C(F)(F)F)c1] | 279 | 8.16 |

TABLE 1-continued

| STRUCTURE | COMPOUND NUMBER | LCMS RETENTION TIME (min) |
|---|---|---|
| 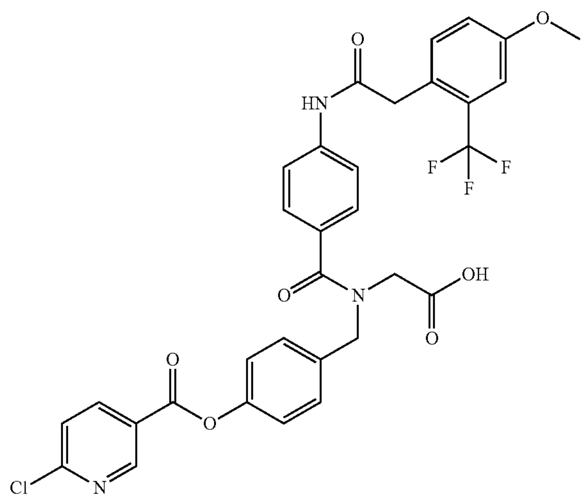 [SMILES: COc1ccc(CC(=O)Nc2ccc(C(=O)N(CC(=O)O)Cc3ccc(OC(=O)c4ccc(Cl)nc4)cc3)cc2)c(C(F)(F)F)c1] | 280 | 6.46 |
| 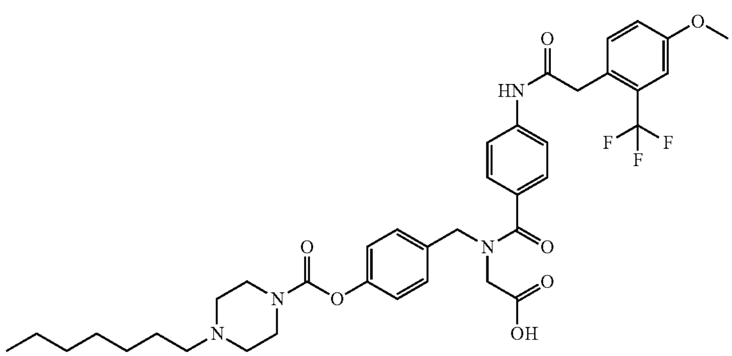 [SMILES: CCCCCCCN1CCN(C(=O)Oc2ccc(CN(CC(=O)O)C(=O)c3ccc(NC(=O)Cc4ccc(OC)cc4C(F)(F)F)cc3)cc2)CC1] | 281 | 5.67 |
| 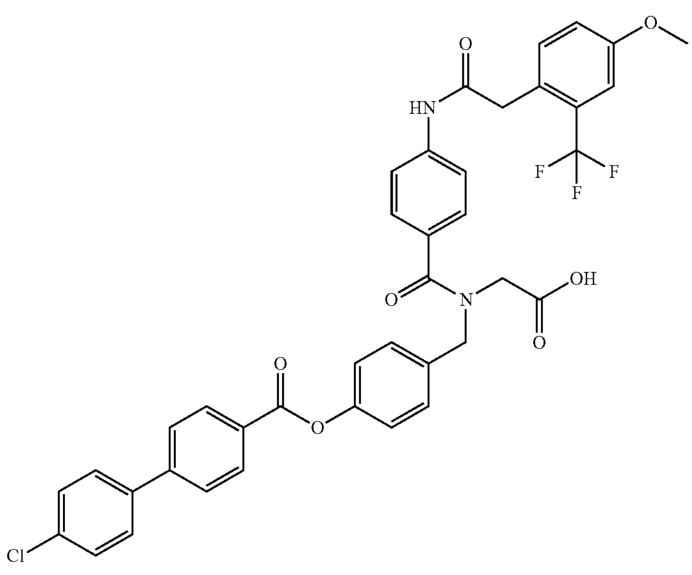 [SMILES: COc1ccc(CC(=O)Nc2ccc(C(=O)N(CC(=O)O)Cc3ccc(OC(=O)c4ccc(-c5ccc(Cl)cc5)cc4)cc3)cc2)c(C(F)(F)F)c1] | 282 | 8.89 |

TABLE 1-continued

| STRUCTURE | COMPOUND NUMBER | LCMS RETENTION TIME (min) |
|---|---|---|
| 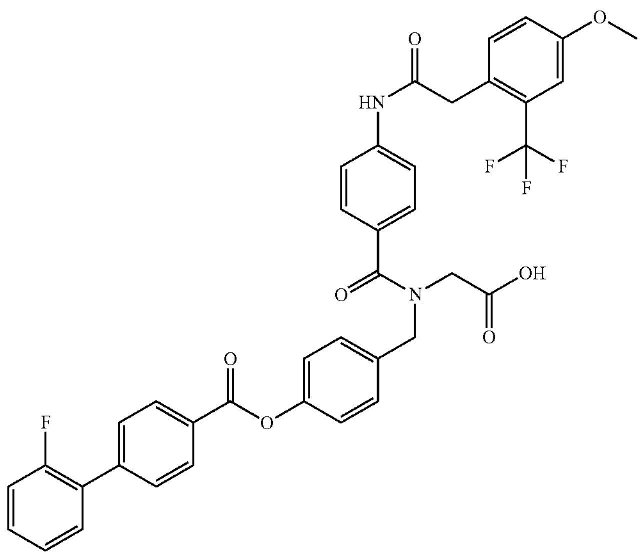 [SMILES: COc1ccc(CC(=O)Nc2ccc(C(=O)N(CC(=O)O)Cc3ccc(OC(=O)c4ccc(-c5ccccc5F)cc4)cc3)cc2)c(C(F)(F)F)c1] | 283 | 8.27 |
| 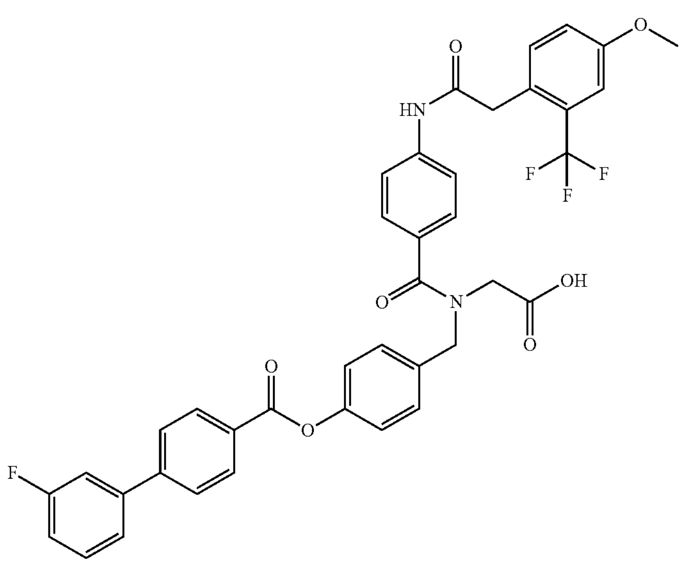 [SMILES: COc1ccc(CC(=O)Nc2ccc(C(=O)N(CC(=O)O)Cc3ccc(OC(=O)c4ccc(-c5cccc(F)c5)cc4)cc3)cc2)c(C(F)(F)F)c1] | 284 | 8.34 |

TABLE 1-continued

| STRUCTURE | COMPOUND NUMBER | LCMS RETENTION TIME (min) |
|---|---|---|
| 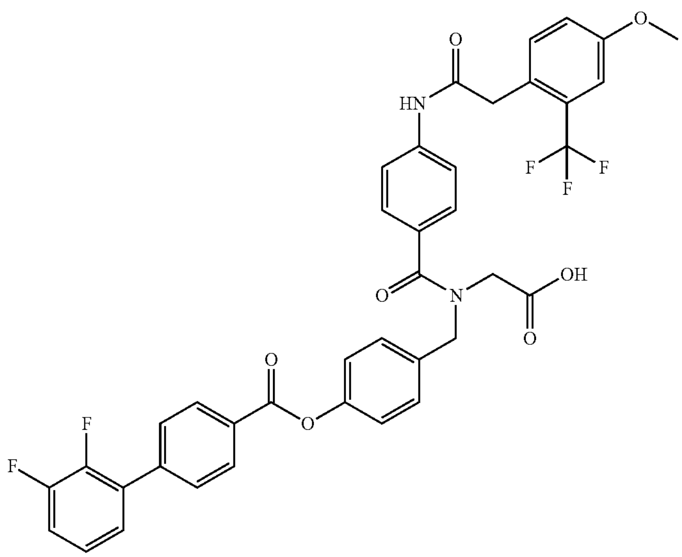 [SMILES: COc1ccc(CC(=O)Nc2ccc(C(=O)N(CC(=O)O)Cc3ccc(OC(=O)c4ccc(-c5cccc(F)c5F)cc4)cc3)cc2)c(C(F)(F)F)c1] | 285 | 8.32 |
| 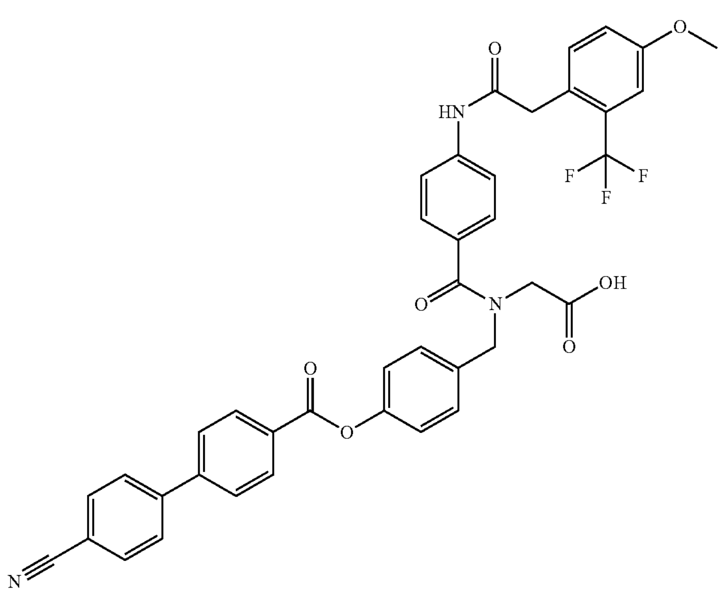 [SMILES: COc1ccc(CC(=O)Nc2ccc(C(=O)N(CC(=O)O)Cc3ccc(OC(=O)c4ccc(-c5ccc(C#N)cc5)cc4)cc3)cc2)c(C(F)(F)F)c1] | 286 | 7.58 |

TABLE 1-continued

| STRUCTURE | COMPOUND NUMBER | LCMS RETENTION TIME (min) |
|---|---|---|
| 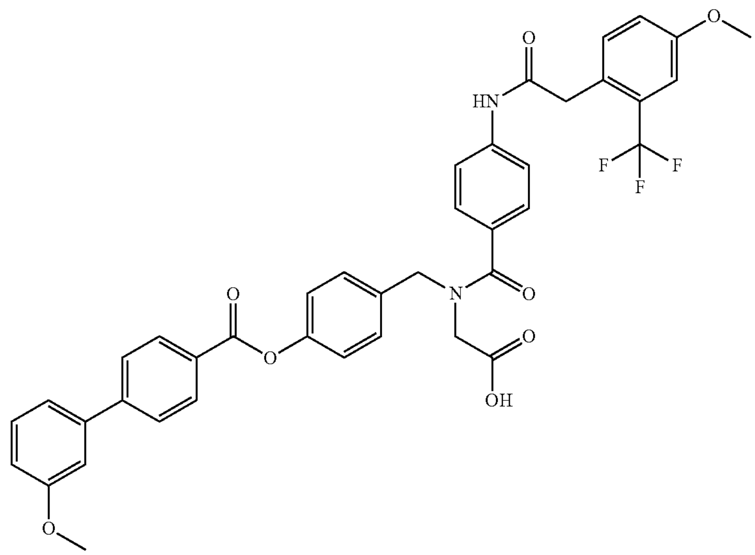 [SMILES: COc1cccc(-c2ccc(C(=O)Oc3ccc(CN(CC(=O)O)C(=O)c4ccc(NC(=O)Cc5ccc(OC)cc5C(F)(F)F)cc4)cc3)cc2)c1] | 287 | 8.22 |
| 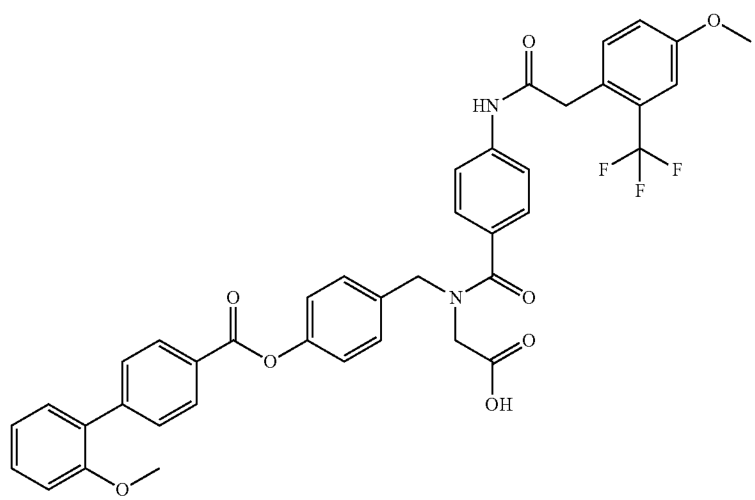 [SMILES: COc1ccc(CC(=O)Nc2ccc(C(=O)N(CC(=O)O)Cc3ccc(OC(=O)c4ccc(-c5ccccc5OC)cc4)cc3)cc2)c(C(F)(F)F)c1] | 288 | 8.25 |
| 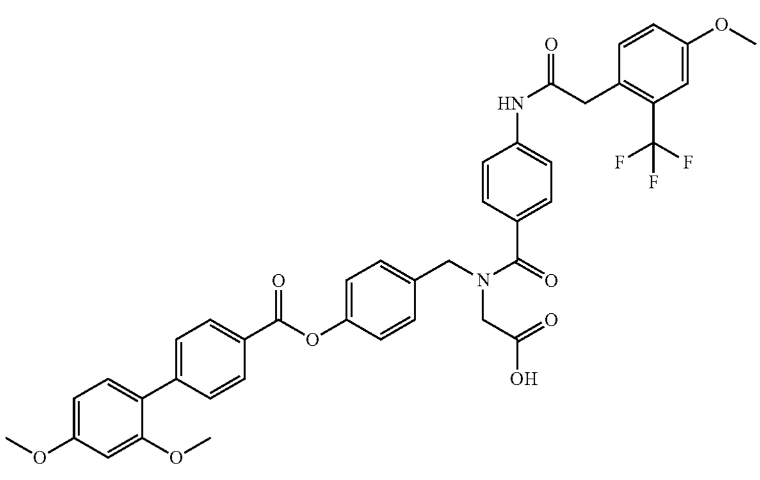 | 289 | 8.12 |

TABLE 1-continued
| STRUCTURE | COMPOUND NUMBER | LCMS RETENTION TIME (min) |
|---|---|---|
| 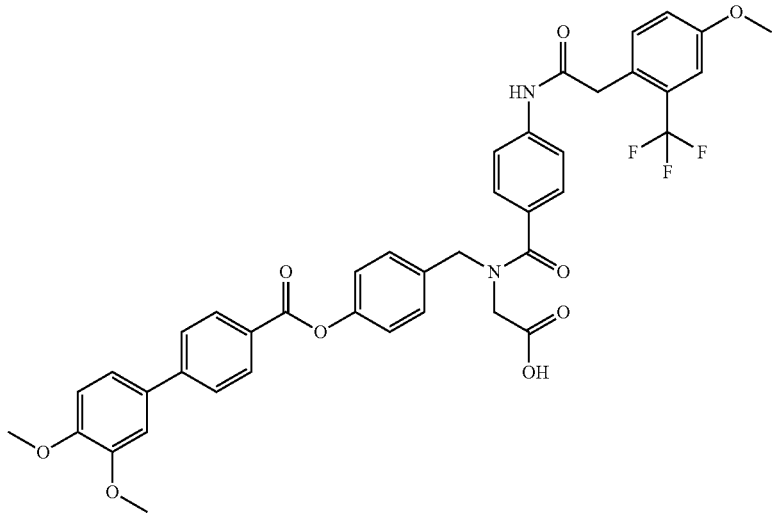 | 290 | 7.53 |
| 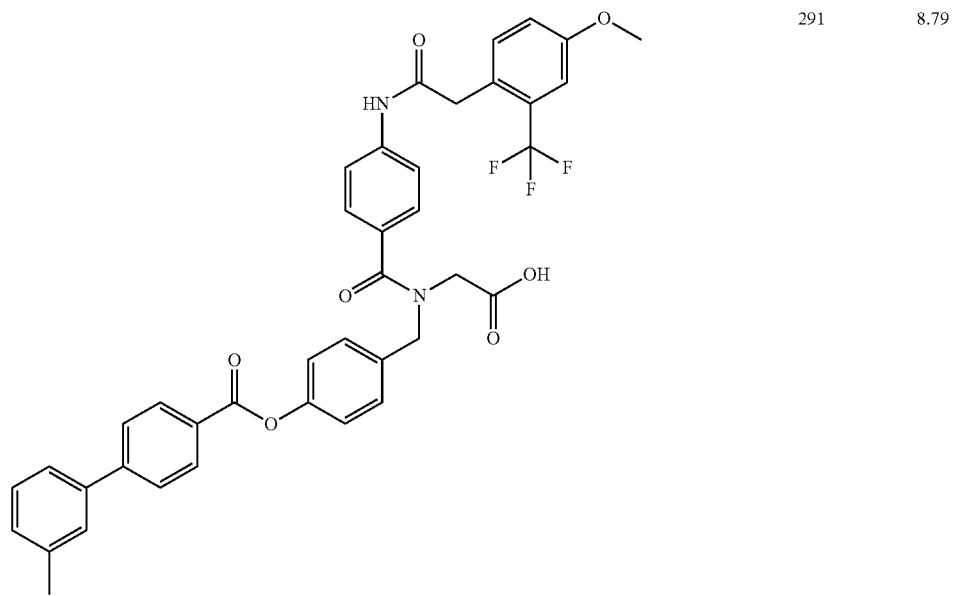 | 291 | 8.79 |

TABLE 1-continued

| STRUCTURE | COMPOUND NUMBER | LCMS RETENTION TIME (min) |
|---|---|---|
| 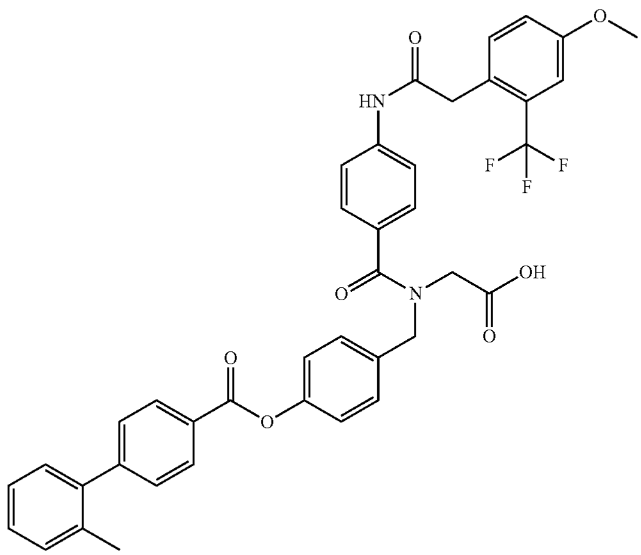 [SMILES: COc1ccc(CC(=O)Nc2ccc(C(=O)N(CC(=O)O)Cc3ccc(OC(=O)c4ccc(-c5ccccc5C)cc4)cc3)cc2)c(C(F)(F)F)c1] | 292 | 8.70 |
| 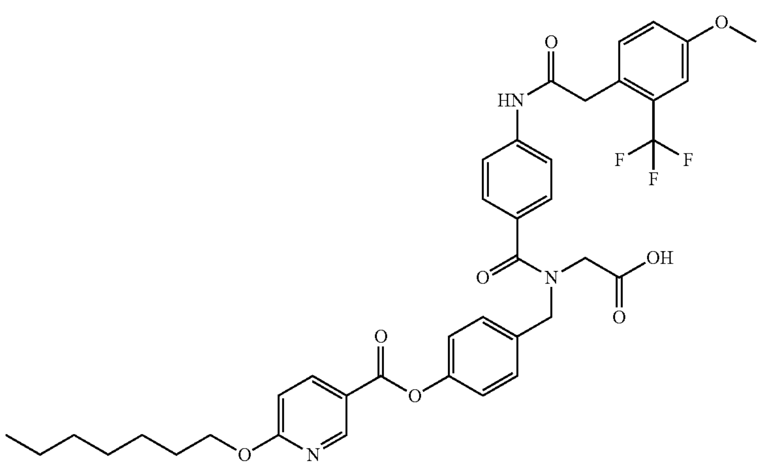 [SMILES: CCCCCCCOc1ccc(C(=O)Oc2ccc(CN(CC(=O)O)C(=O)c3ccc(NC(=O)Cc4ccc(OC)cc4C(F)(F)F)cc3)cc2)cn1] | 293 | 9.75 |
| 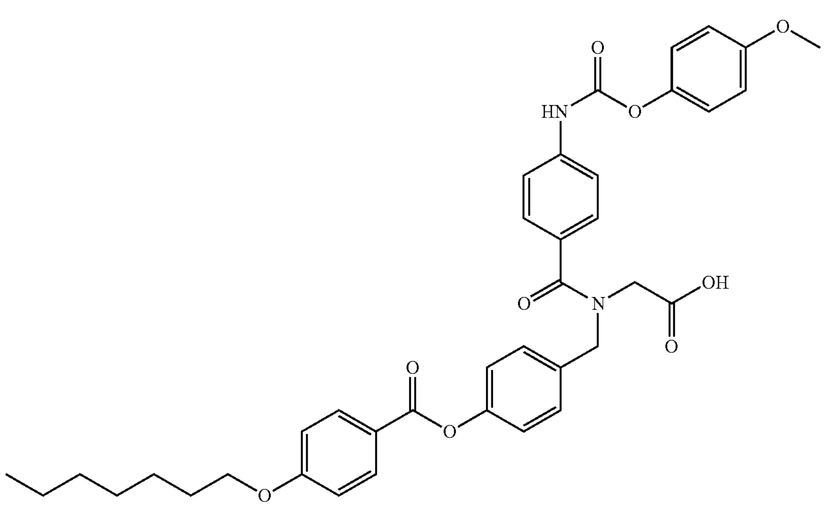 [SMILES: CCCCCCCOc1ccc(C(=O)Oc2ccc(CN(CC(=O)O)C(=O)c3ccc(NC(=O)Oc4ccc(OC)cc4)cc3)cc2)cc1] | 294 | 11.19 |

TABLE 1-continued

| STRUCTURE | COMPOUND NUMBER | LCMS RETENTION TIME (min) |
|---|---|---|
| 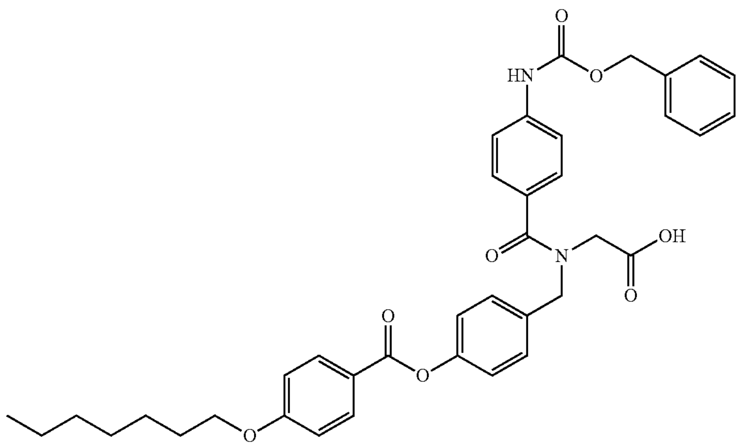 [SMILES: CCCCCCCOc1ccc(C(=O)Oc2ccc(CN(CC(=O)O)C(=O)c3ccc(NC(=O)OCc4ccccc4)cc3)cc2)cc1] | 295 | 11.45 |
| 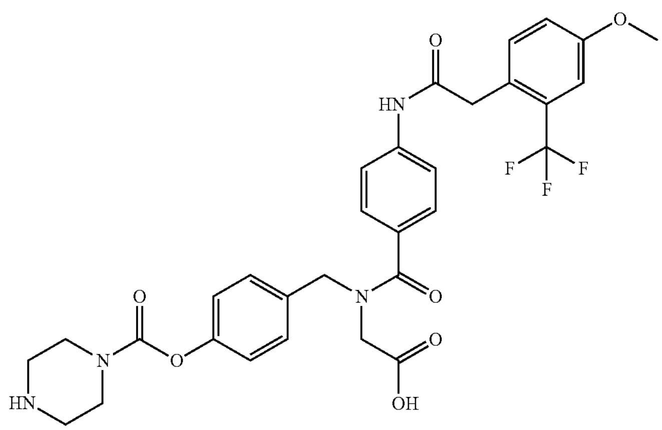 [SMILES: COc1ccc(CC(=O)Nc2ccc(C(=O)N(CC(=O)O)Cc3ccc(OC(=O)N4CCNCC4)cc3)cc2)c(C(F)(F)F)c1] | 296 | 3.51 |
| 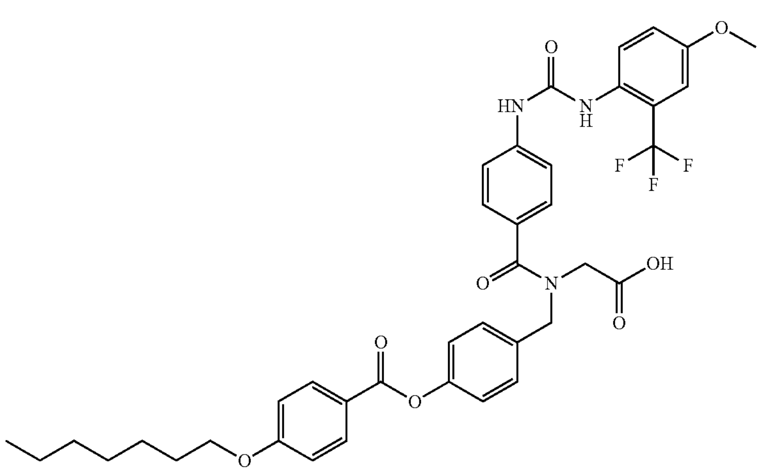 [SMILES: CCCCCCCOc1ccc(C(=O)Oc2ccc(CN(CC(=O)O)C(=O)c3ccc(NC(=O)Nc4ccc(OC)cc4C(F)(F)F)cc3)cc2)cc1] | 297 | 11.20 |

TABLE 1-continued

| STRUCTURE | COMPOUND NUMBER | LCMS RETENTION TIME (min) |
|---|---|---|
| 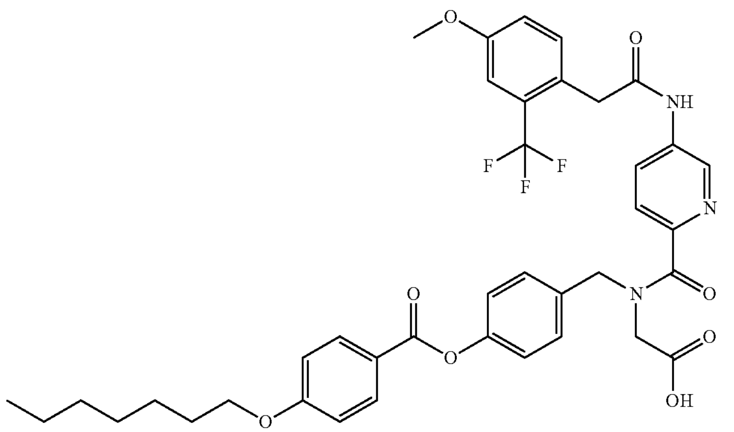 [SMILES: CCCCCCCOc1ccc(C(=O)Oc2ccc(CN(CC(=O)O)C(=O)c3ccc(NC(=O)Cc4ccc(OC)cc4C(F)(F)F)cn3)cc2)cc1] | 298 | 11.36 |
| 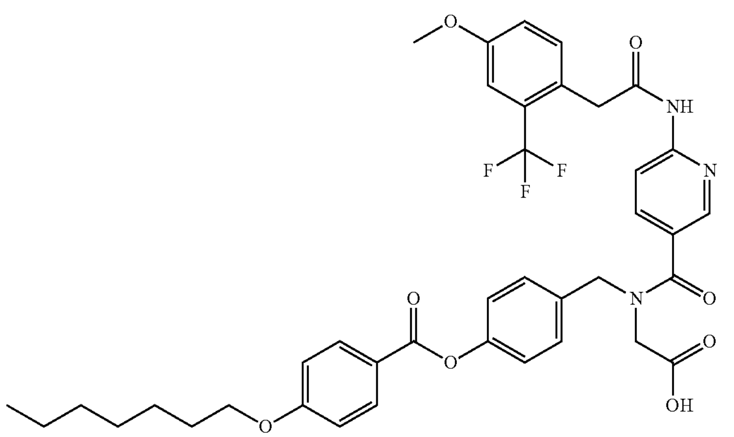 [SMILES: CCCCCCCOc1ccc(C(=O)Oc2ccc(CN(CC(=O)O)C(=O)c3ccc(NC(=O)Cc4ccc(OC)cc4C(F)(F)F)nc3)cc2)cc1] | 299 | 11.41 |
| 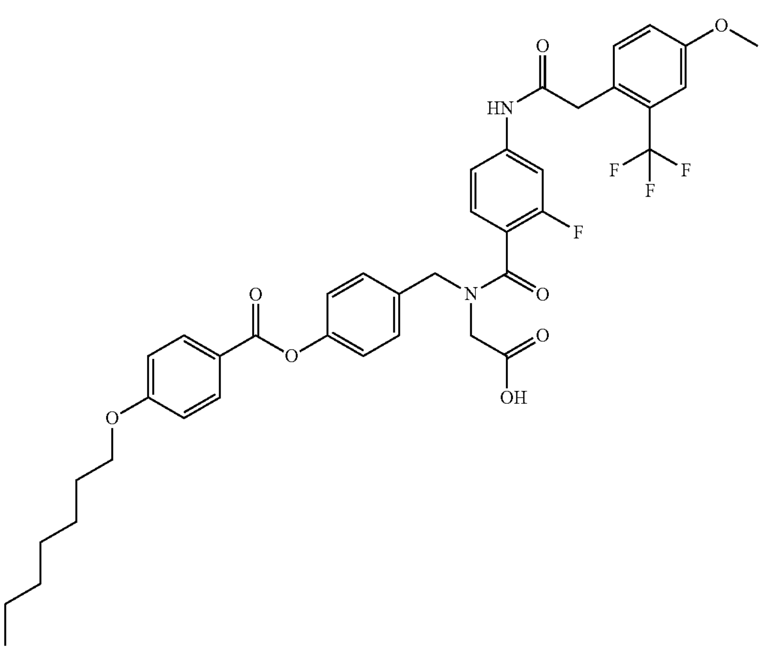 [SMILES: CCCCCCCOc1ccc(C(=O)Oc2ccc(CN(CC(=O)O)C(=O)c3ccc(NC(=O)Cc4ccc(OC)cc4C(F)(F)F)cc3F)cc2)cc1] | 300 | 11.43 |

… TABLE 1-continued
| STRUCTURE | COMPOUND NUMBER | LCMS RETENTION TIME (min) |
|---|---|---|
| 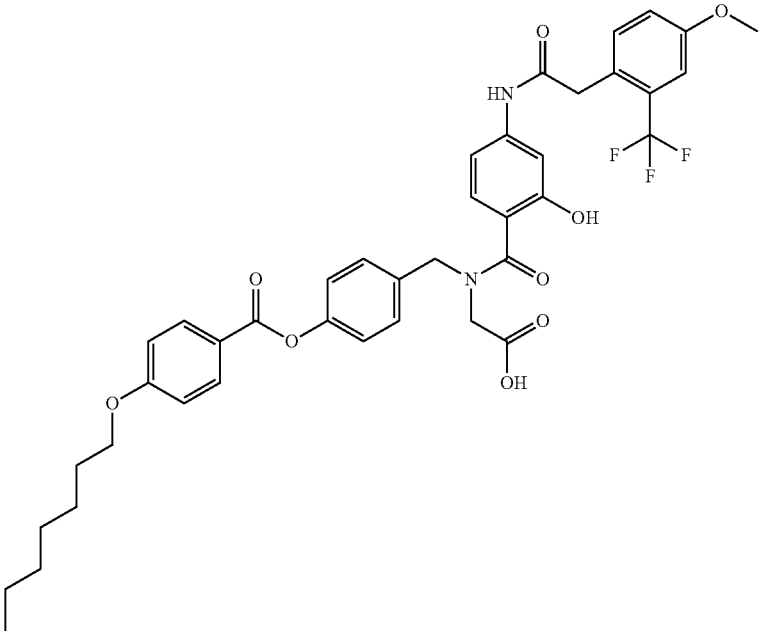 [SMILES: CCCCCCCOc1ccc(C(=O)Oc2ccc(CN(CC(=O)O)C(=O)c3ccc(NC(=O)Cc4ccc(OC)cc4C(F)(F)F)cc3O)cc2)cc1] | 301 | 11.69 |
| 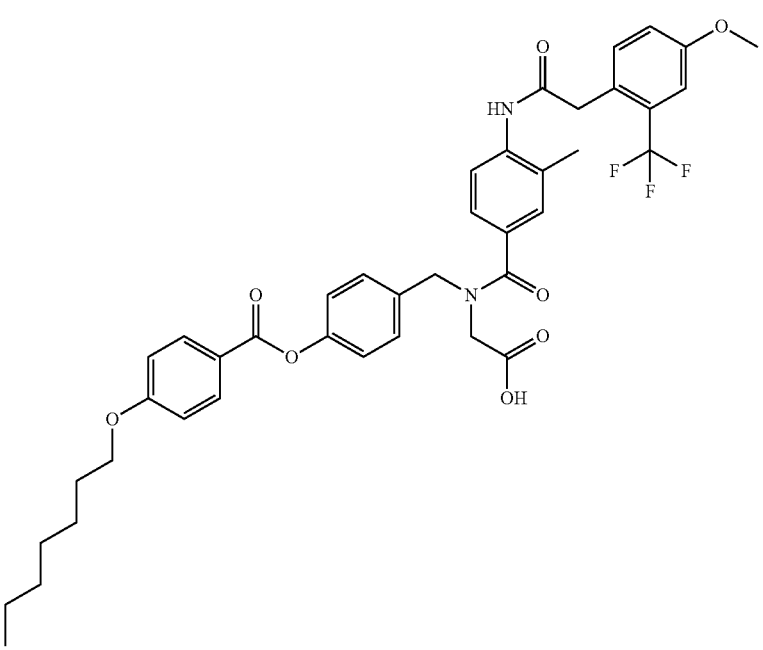 | 302 | 11.71 |

TABLE 1-continued
| STRUCTURE | COMPOUND NUMBER | LCMS RETENTION TIME (min) |
|---|---|---|
| 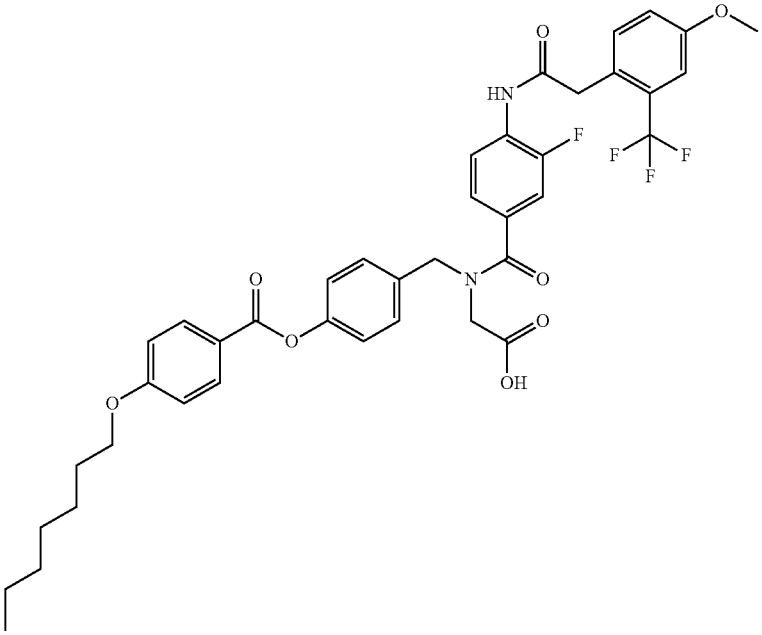 [SMILES: CCCCCCCOc1ccc(C(=O)Oc2ccc(CN(CC(=O)O)C(=O)c3ccc(NC(=O)Cc4ccc(OC)cc4C(F)(F)F)c(C)c3)cc2)cc1] | 303 | 11.96 |
| 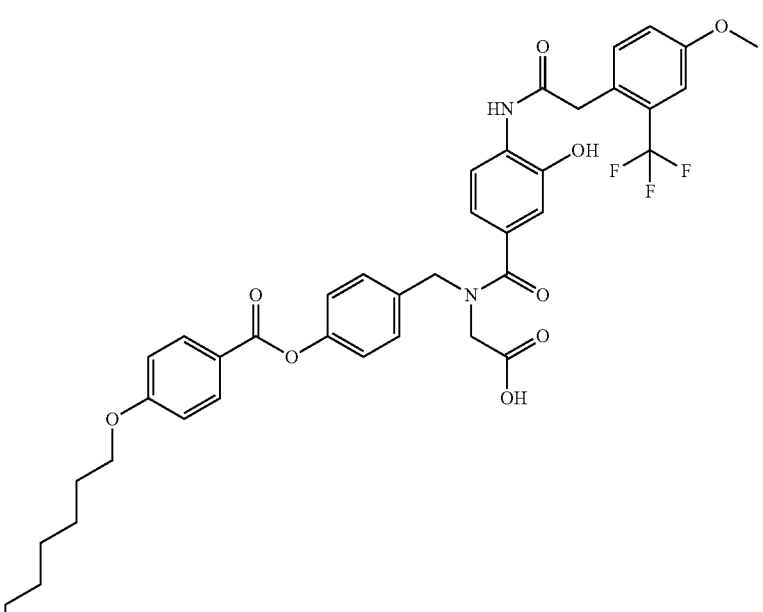 | 304 | 11.49 |

TABLE 1-continued

| STRUCTURE | COMPOUND NUMBER | LCMS RETENTION TIME (min) |
|---|---|---|
| 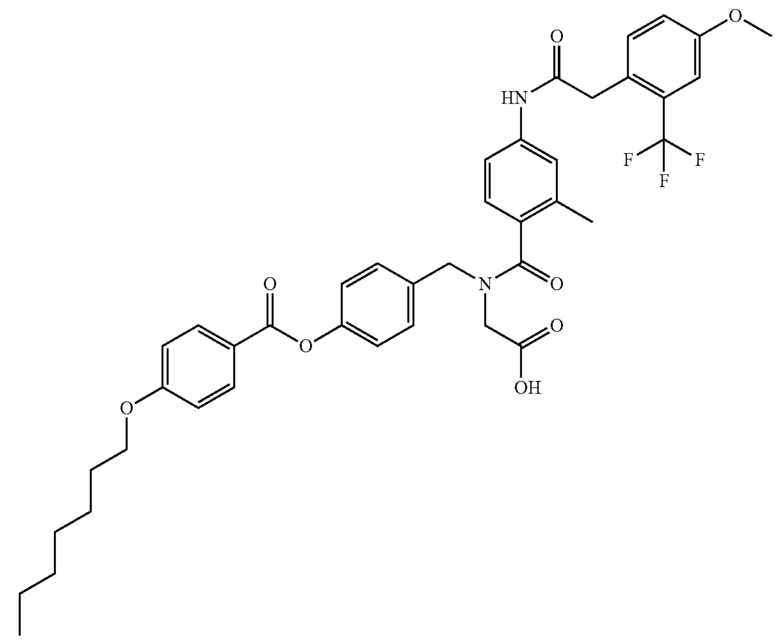 | 305 | 11.13 |
| 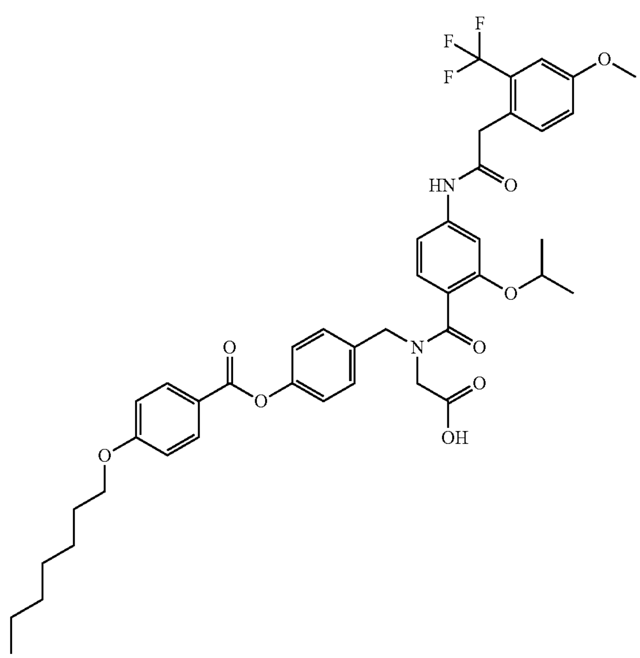 [SMILES: CCCCCCCOc1ccc(C(=O)Oc2ccc(CN(CC(=O)O)C(=O)c3ccc(NC(=O)Cc4ccc(OC)cc4C(F)(F)F)cc3OC(C)C)cc2)cc1] | 306 | 11.34 |

TABLE 1-continued
| STRUCTURE | COMPOUND NUMBER | LCMS RETENTION TIME (min) |
|---|---|---|
| 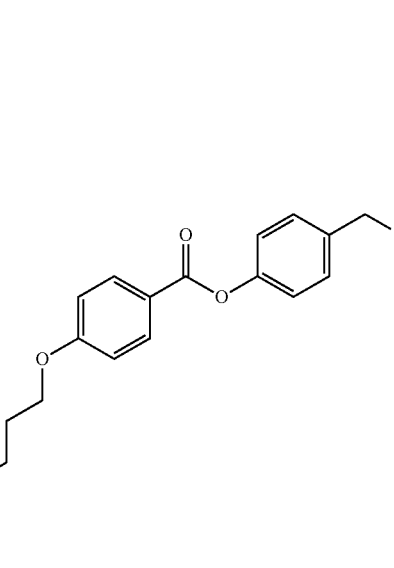 | 307 | 11.34 |
| 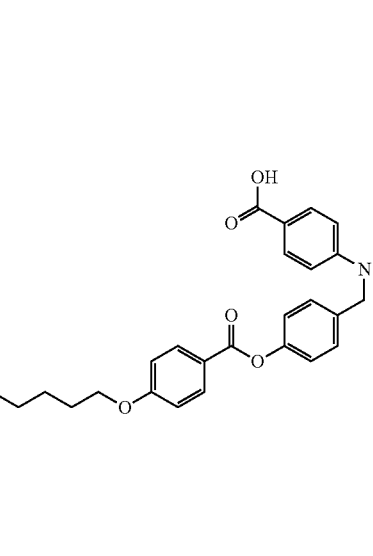 | 308 | 11.02 |
| 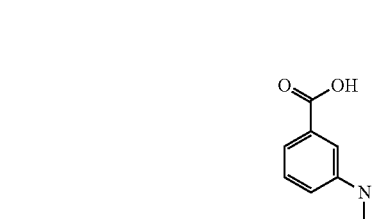 | 309 | 11.03 |

TABLE 1-continued
| STRUCTURE | COMPOUND NUMBER | LCMS RETENTION TIME (min) |
|---|---|---|
| 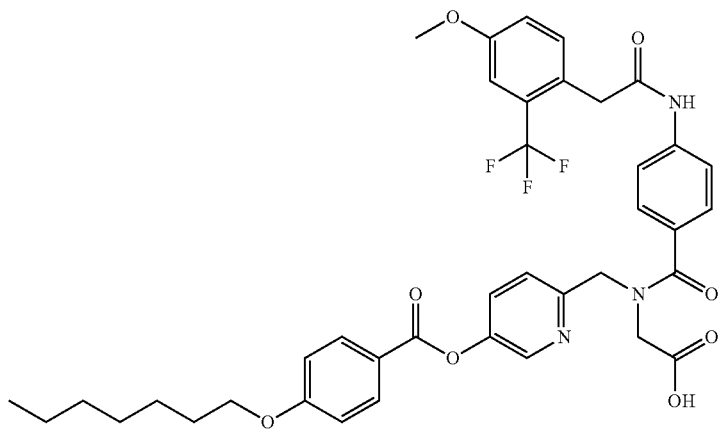 [SMILES: CCCCCCCOc1ccc(C(=O)Oc2ccc(CN(CC(=O)O)C(=O)c3ccc(NC(=O)Cc4ccc(OC)cc4C(F)(F)F)cc3)nc2)cc1] | 310 | 11.01 |
| 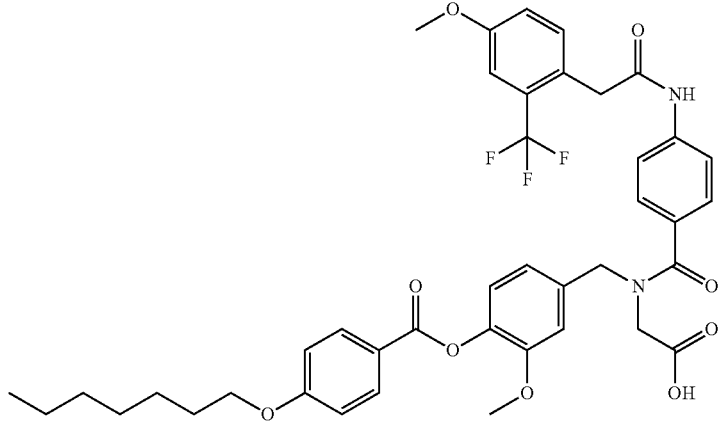 [SMILES: CCCCCCCOc1ccc(C(=O)Oc2ccc(CN(CC(=O)O)C(=O)c3ccc(NC(=O)Cc4ccc(OC)cc4C(F)(F)F)cc3)cc2OC)cc1] | 311 | 9.89 |
| 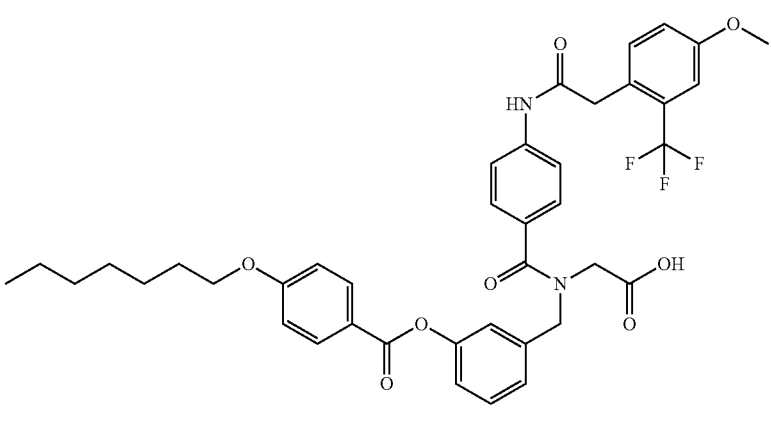 [SMILES: CCCCCCCOc1ccc(C(=O)Oc2cccc(CN(CC(=O)O)C(=O)c3ccc(NC(=O)Cc4ccc(OC)cc4C(F)(F)F)cc3)c2)cc1] | 312 | 9.93 |

TABLE 1-continued

| STRUCTURE | COMPOUND NUMBER | LCMS RETENTION TIME (min) |
|---|---|---|
| 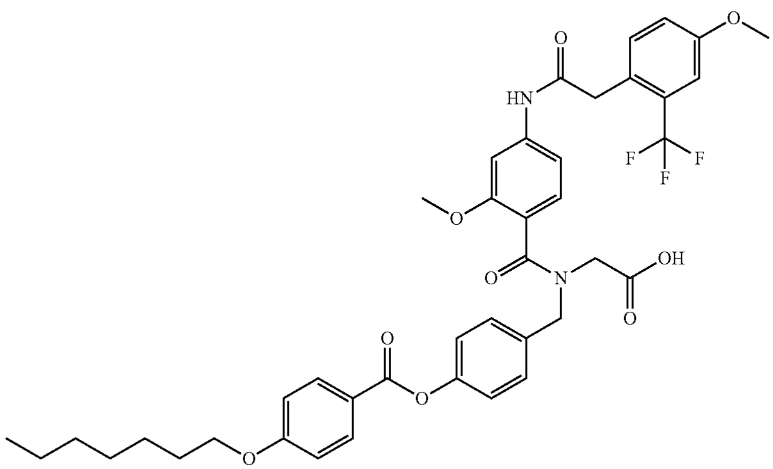 [SMILES: CCCCCCCOc1ccc(C(=O)Oc2ccc(CN(CC(=O)O)C(=O)c3ccc(NC(=O)Cc4ccc(OC)cc4C(F)(F)F)cc3OC)cc2)cc1] | 313 | 9.93 |
| 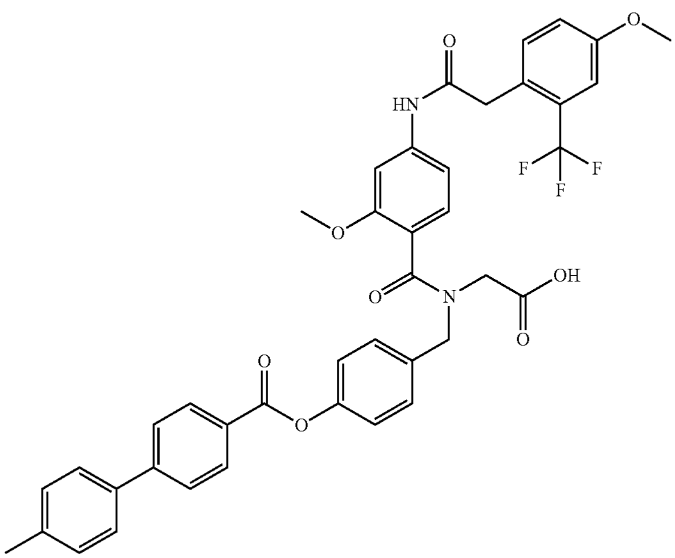 | 314 | 8.78 |
| 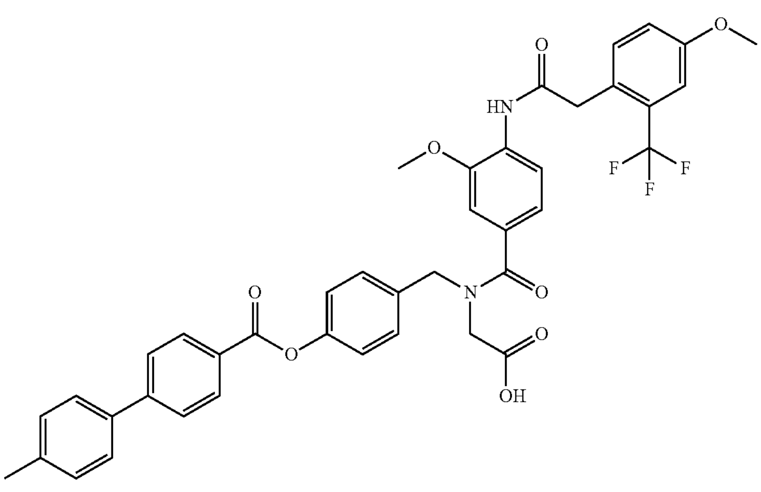 | 315 | 9.14 |

TABLE 1-continued

| STRUCTURE | COMPOUND NUMBER | LCMS RETENTION TIME (min) |
|---|---|---|
| [structure] | 316 | 10.02 |
| [structure] | 317 | 11.06 |
| [structure] | 318 | 11.03 |
| [structure] | 319 | 10.80 |
| [structure] | 320 | 11.14 |

TABLE 1-continued
| STRUCTURE | COMPOUND NUMBER | LCMS RETENTION TIME (min) |
|---|---|---|
| 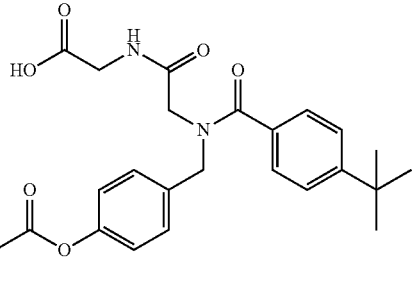 | 321 | 10.14 |
| 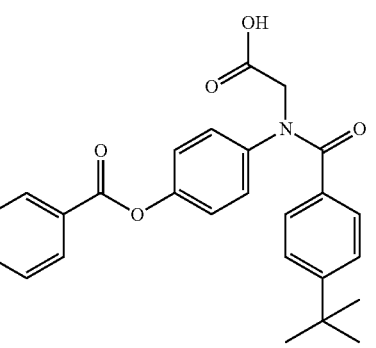 | 322 | 10.74 |
| 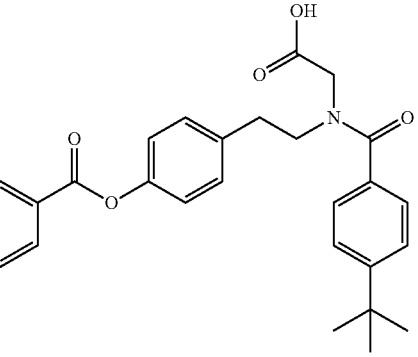 | 323 | 10.91 |
| 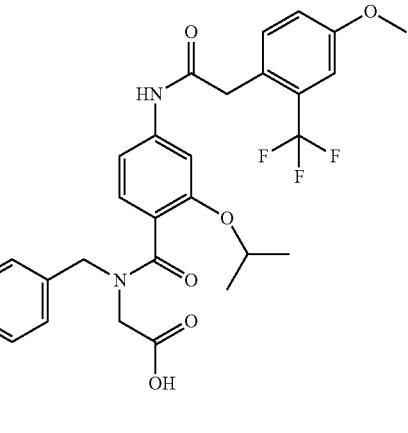 | 324 | 10.82 |

TABLE 1-continued
| STRUCTURE | COMPOUND NUMBER | LCMS RETENTION TIME (min) |
|---|---|---|
| 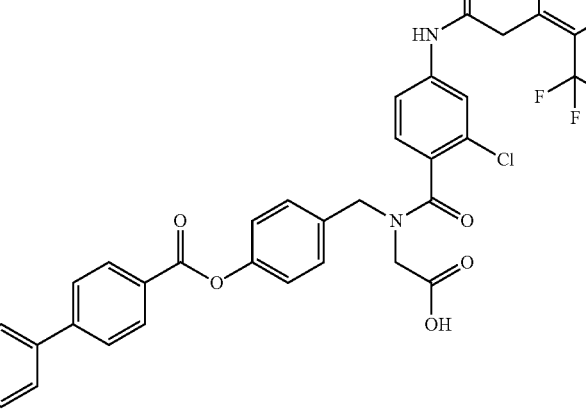 | 325 | 10.71 |
| 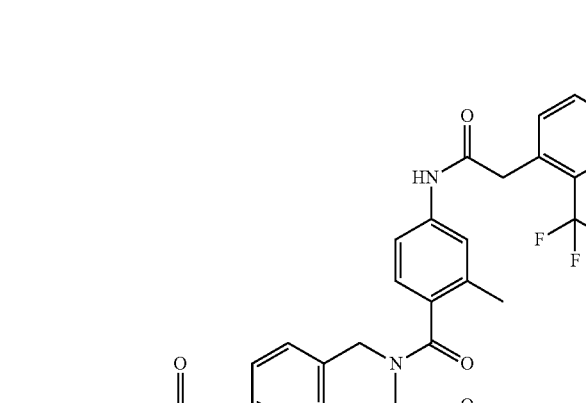 | 326 | 10.42 |
| 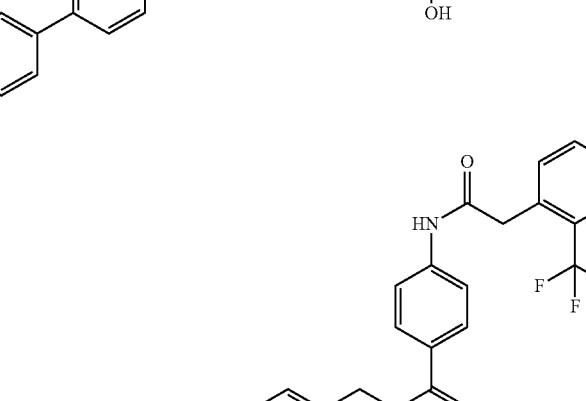 | 327 | 7.34 |

TABLE 1-continued

| STRUCTURE | COMPOUND NUMBER | LCMS RETENTION TIME (min) |
|---|---|---|
| 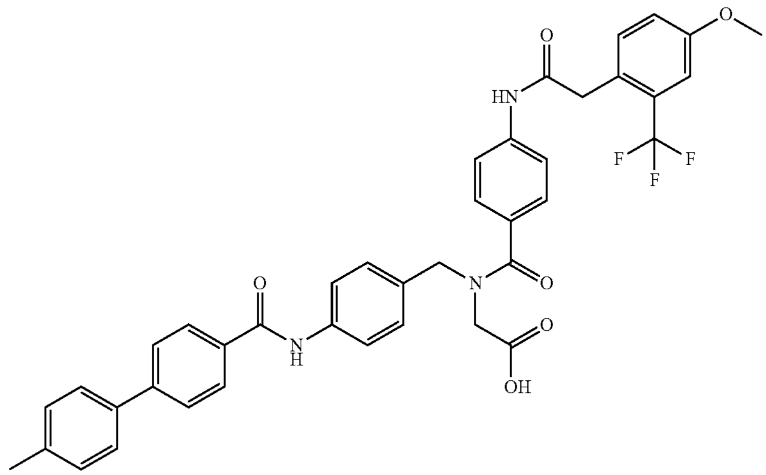 | 328 | 7.76 |
| 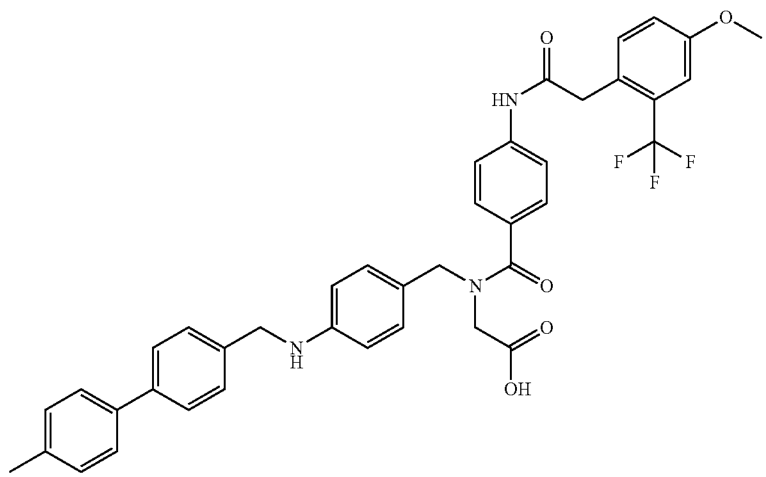 | 329 | 8.25 |
| 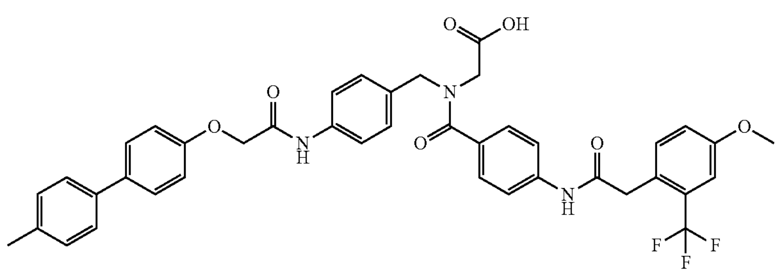 | 330 | 7.96 |
| 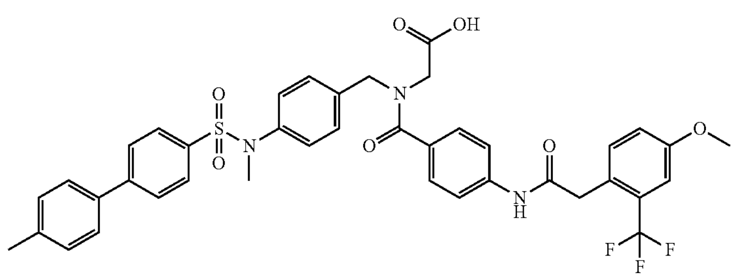 | 331 | 8.11 |

TABLE 1-continued

| STRUCTURE | COMPOUND NUMBER | LCMS RETENTION TIME (min) |
|---|---|---|
| 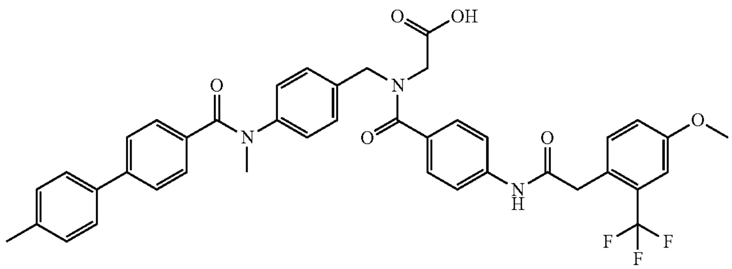 | 332 | 7.19 |
| 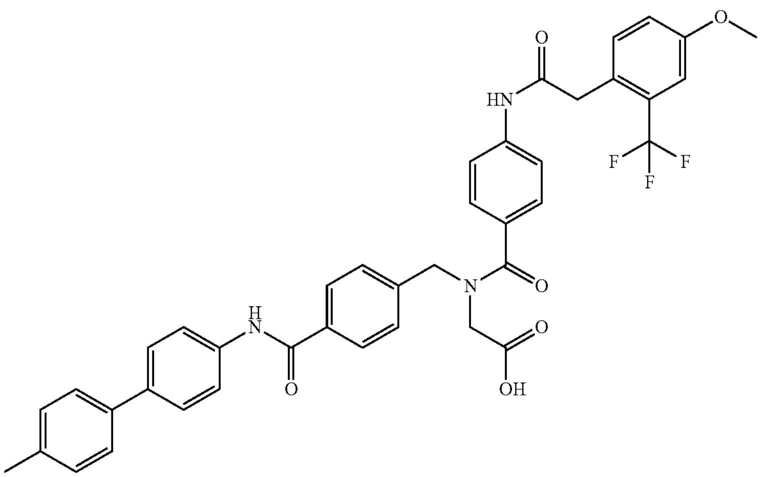 | 333 | 7.83 |
| 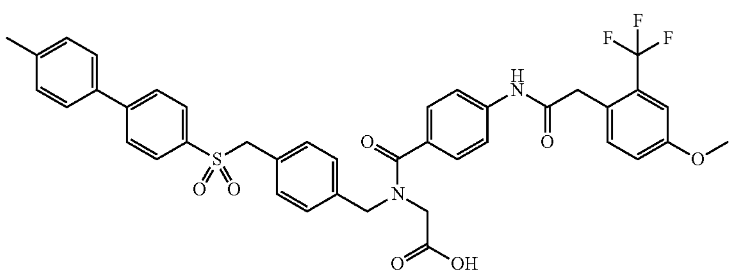 | 334 | 7.57 |
| 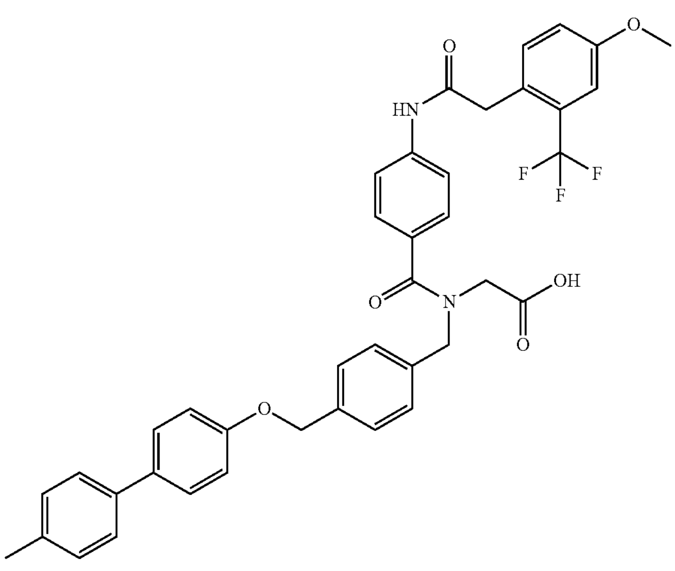 | 335 | 8.83 |

TABLE 1-continued

| STRUCTURE | COMPOUND NUMBER | LCMS RETENTION TIME (min) |
|---|---|---|
| 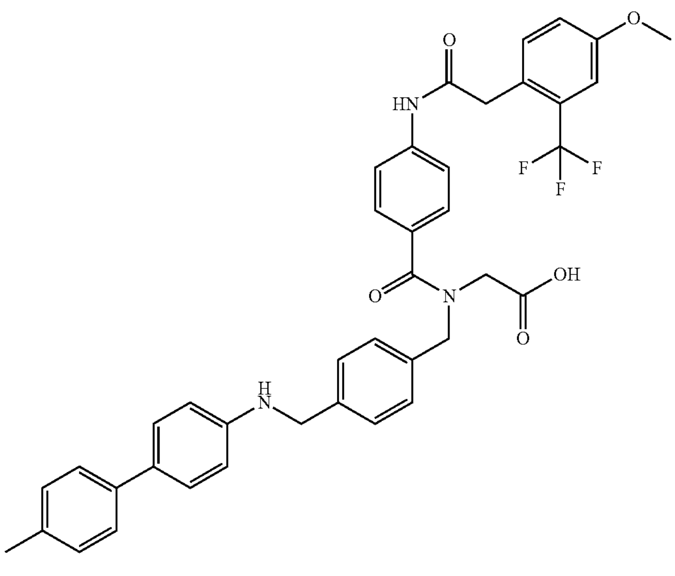 | 336 | 8.31 |
| 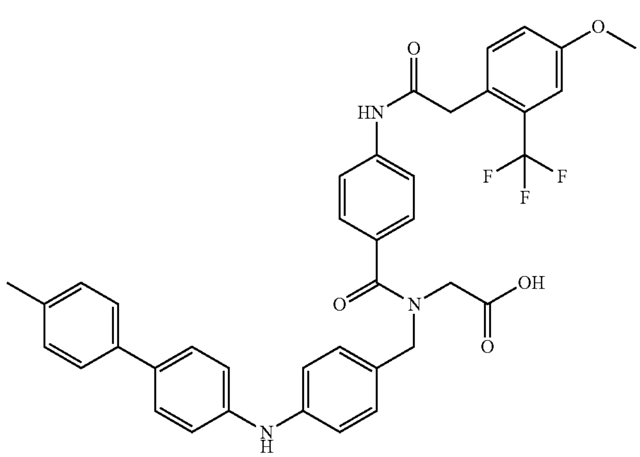 | 337 | 8.38 |
| 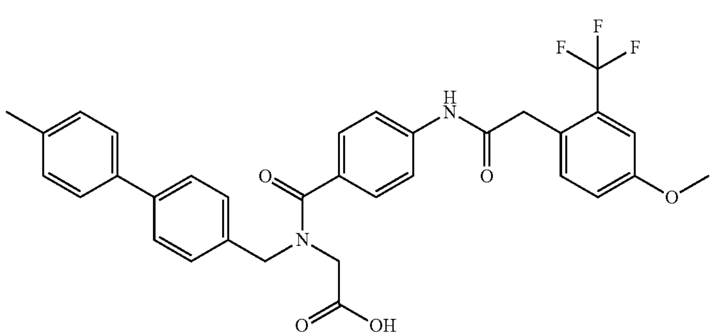 | 338 | 7.62 |

TABLE 1-continued
| STRUCTURE | COMPOUND NUMBER | LCMS RETENTION TIME (min) |
|---|---|---|
| 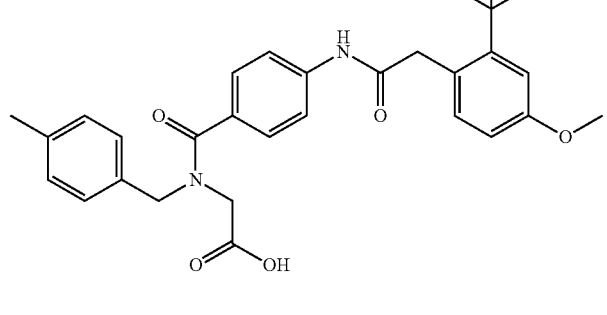 | 339 | 6.26 |
| 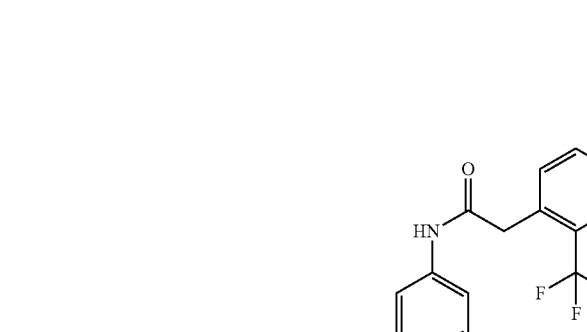 | 340 | 8.84 |
| 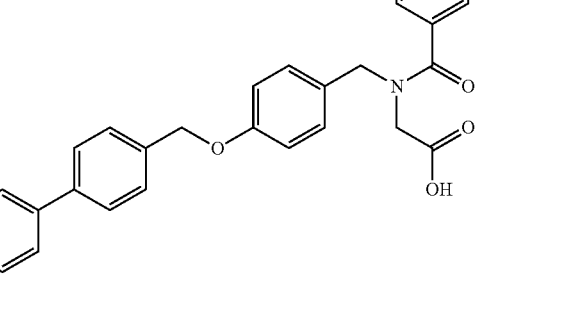 | 341 | 8.86 |

TABLE 1-continued

| STRUCTURE | COMPOUND NUMBER | LCMS RETENTION TIME (min) |
|---|---|---|
| 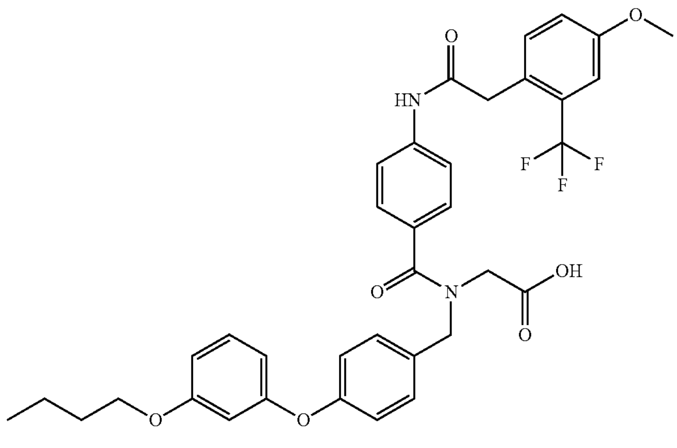 [SMILES: CCCCOc1cccc(Oc2ccc(CN(CC(=O)O)C(=O)c3ccc(NC(=O)Cc4ccc(OC)cc4C(F)(F)F)cc3)cc2)c1] | 342 | 8.52 |
| 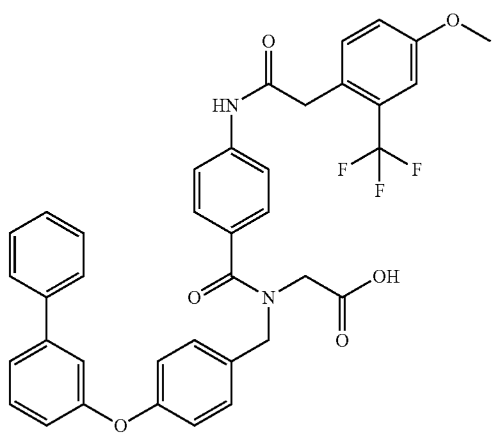 [SMILES: COc1ccc(CC(=O)Nc2ccc(C(=O)N(CC(=O)O)Cc3ccc(Oc4cccc(-c5ccccc5)c4)cc3)cc2)c(C(F)(F)F)c1] | 343 | 8.31 |
| 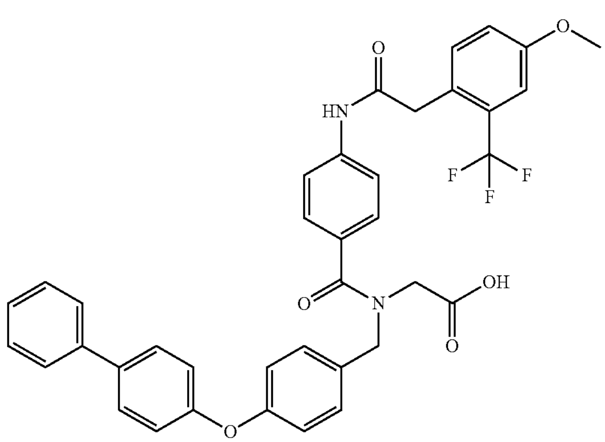 [SMILES: COc1ccc(CC(=O)Nc2ccc(C(=O)N(CC(=O)O)Cc3ccc(Oc4ccc(-c5ccccc5)cc4)cc3)cc2)c(C(F)(F)F)c1] | 344 | 8.35 |

TABLE 1-continued
| STRUCTURE | COMPOUND NUMBER | LCMS RETENTION TIME (min) |
|---|---|---|
| 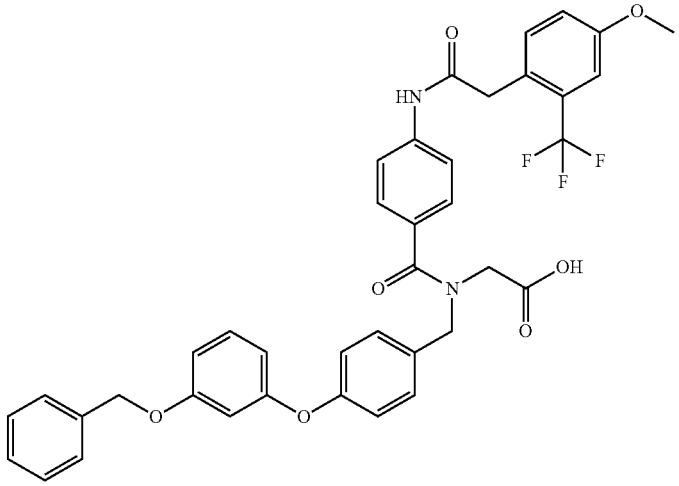 [SMILES: COc1ccc(CC(=O)Nc2ccc(C(=O)N(CC(=O)O)Cc3ccc(Oc4cccc(OCc5ccccc5)c4)cc3)cc2)c(C(F)(F)F)c1] | 345 | 8.24 |
| 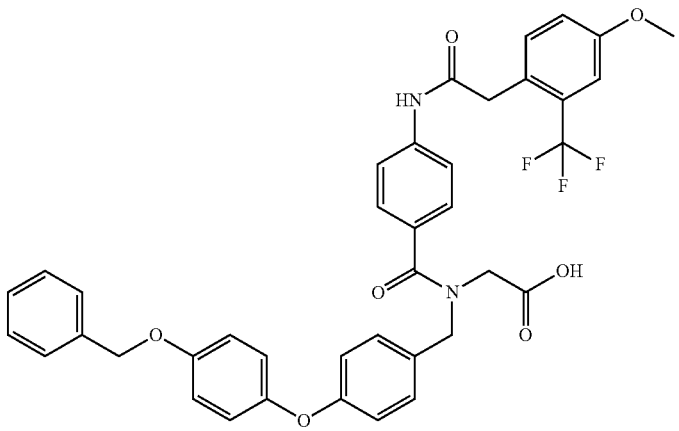 [SMILES: COc1ccc(CC(=O)Nc2ccc(C(=O)N(CC(=O)O)Cc3ccc(Oc4ccc(OCc5ccccc5)cc4)cc3)cc2)c(C(F)(F)F)c1] | 346 | 8.26 |
| 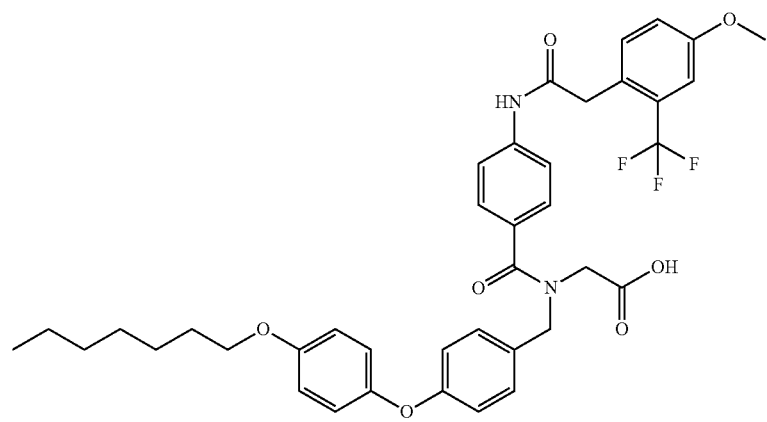 [SMILES: CCCCCCCOc1ccc(Oc2ccc(CN(CC(=O)O)C(=O)c3ccc(NC(=O)Cc4ccc(OC)cc4C(F)(F)F)cc3)cc2)cc1] | 347 | 9.96 |

TABLE 1-continued

| STRUCTURE | COMPOUND NUMBER | LCMS RETENTION TIME (min) |
| --- | --- | --- |
| 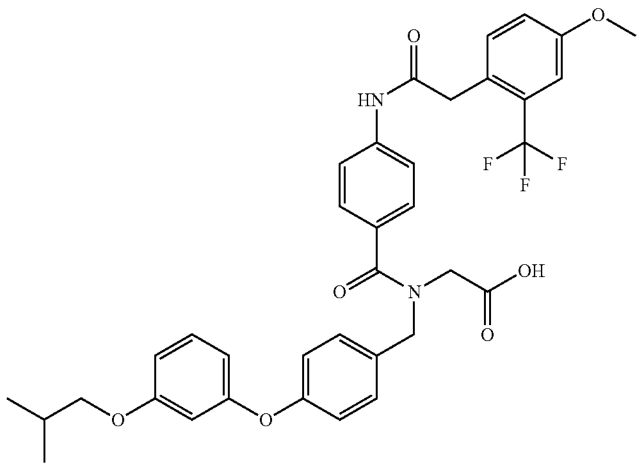 [SMILES: COc1ccc(CC(=O)Nc2ccc(C(=O)N(CC(=O)O)Cc3ccc(Oc4cccc(OCC(C)C)c4)cc3)cc2)c(C(F)(F)F)c1] | 348 | 8.54 |
| 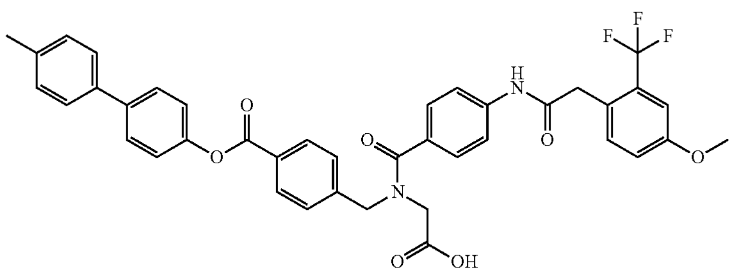 | 349 | 8.68 |
| 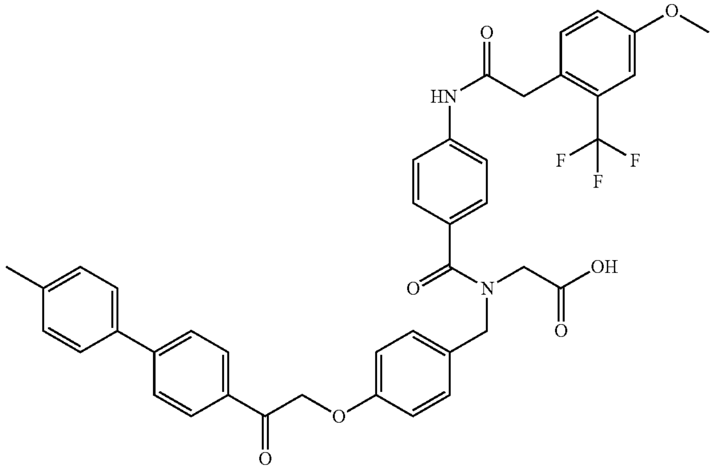 | 350 | 8.25 |

TABLE 1-continued

| STRUCTURE | COMPOUND NUMBER | LCMS RETENTION TIME (min) |
|---|---|---|
| 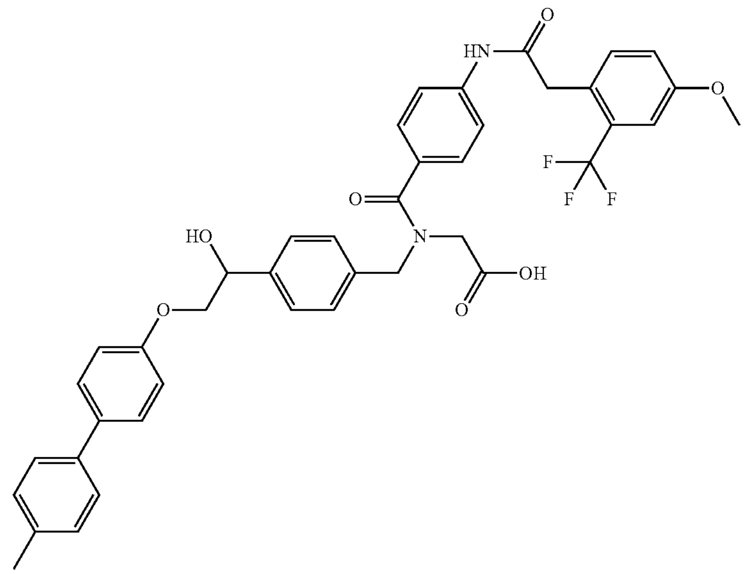 [SMILES: COc1ccc(CC(=O)Nc2ccc(C(=O)N(CC(=O)O)Cc3ccc(C(O)COc4ccc(-c5ccc(C)cc5)cc4)cc3)cc2)c(C(F)(F)F)c1] | 351 | 7.88 |
| 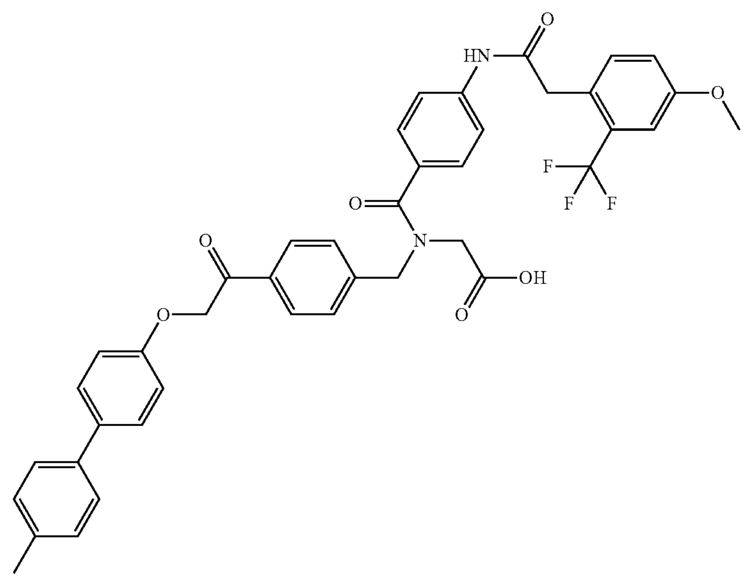 [SMILES: COc1ccc(CC(=O)Nc2ccc(C(=O)N(CC(=O)O)Cc3ccc(C(=O)COc4ccc(-c5ccc(C)cc5)cc4)cc3)cc2)c(C(F)(F)F)c1] | 352 | 8.27 |
| 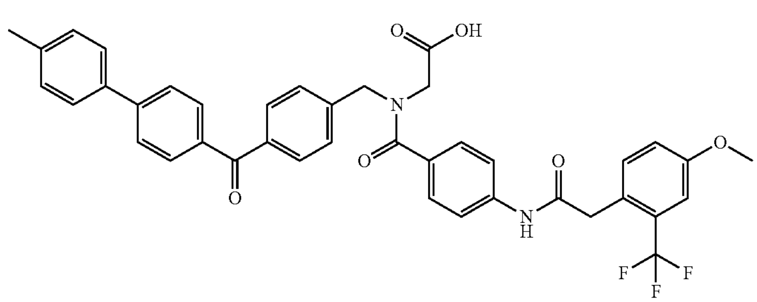 | 353 | 8.26 |

TABLE 1-continued

| STRUCTURE | COMPOUND NUMBER | LCMS RETENTION TIME (min) |
|---|---|---|
| 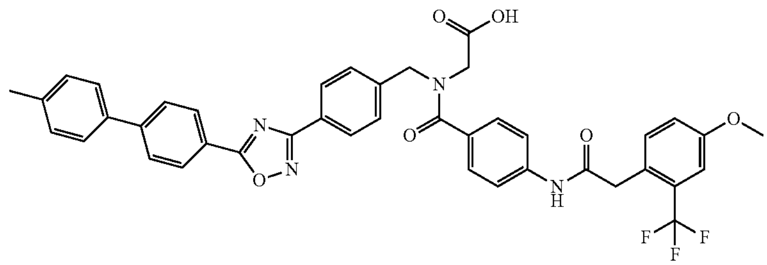 | 354 | 9.40 |
| 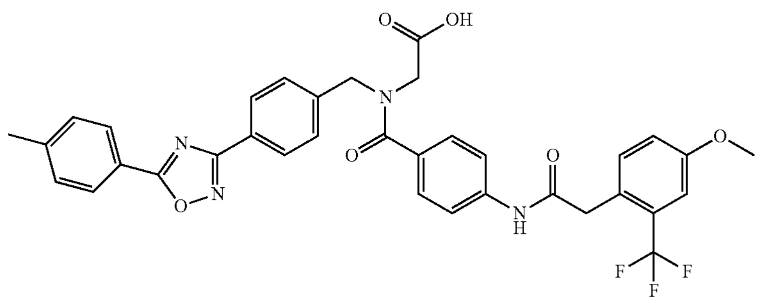 | 355 | 7.97 |
| 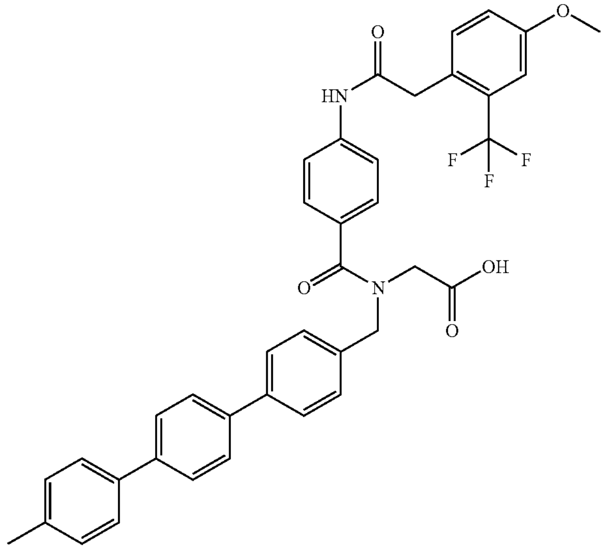 | 356 | 8.88 |
| 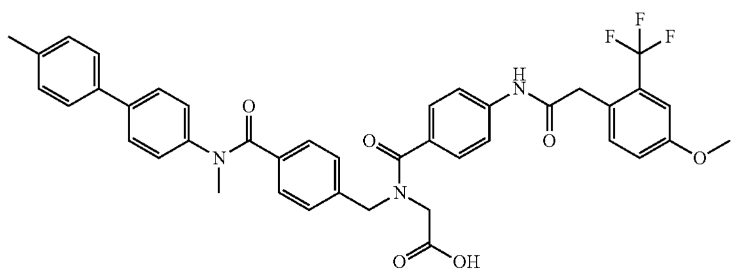 | 357 | 7.51 |

TABLE 1-continued
| STRUCTURE | COMPOUND NUMBER | LCMS RETENTION TIME (min) |
|---|---|---|
| 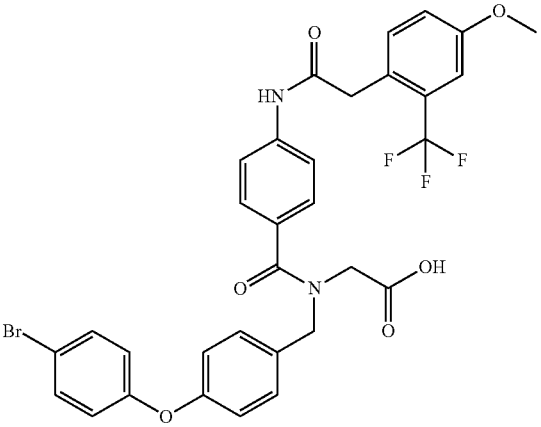 [SMILES: COc1ccc(CC(=O)Nc2ccc(C(=O)N(CC(=O)O)Cc3ccc(Oc4ccc(Br)cc4)cc3)cc2)c(C(F)(F)F)c1] | 358 | 7.90 |
| 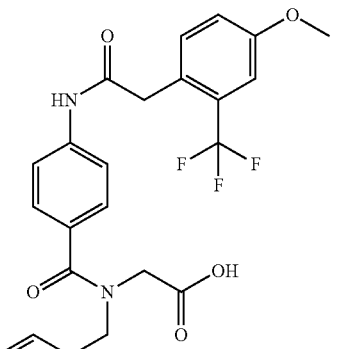 | 359 | 8.48 |
| 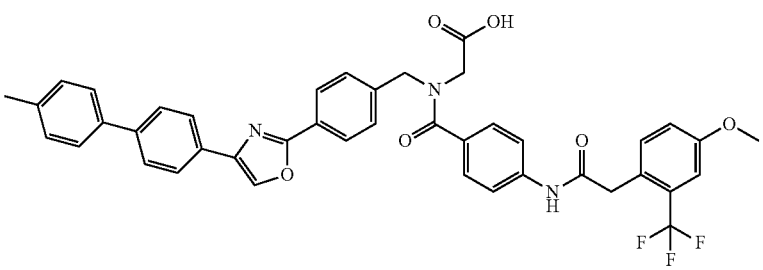 | 360 | 9.18 |
| 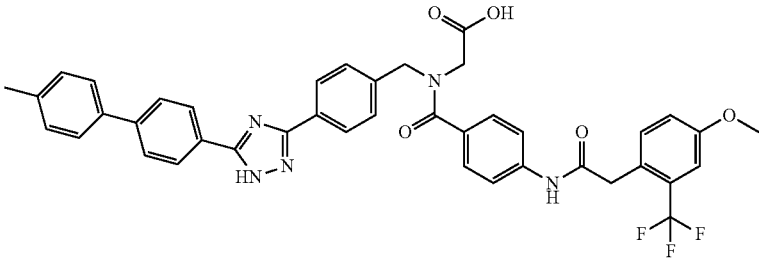 | 361 | 7.72 |

TABLE 1-continued

| STRUCTURE | COMPOUND NUMBER | LCMS RETENTION TIME (min) |
|---|---|---|
| 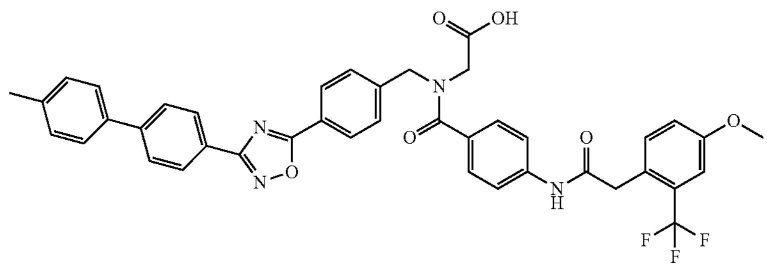 | 362 | 8.91 |
| 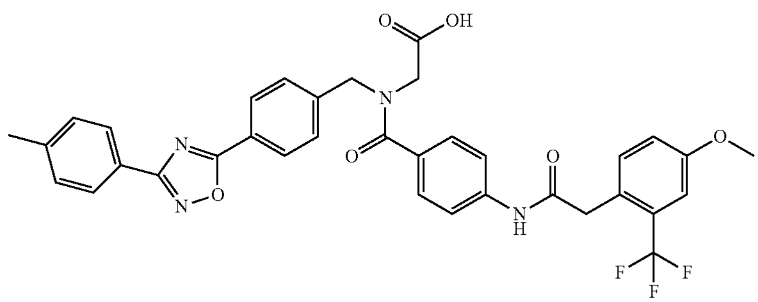 | 363 | 8.01 |
| 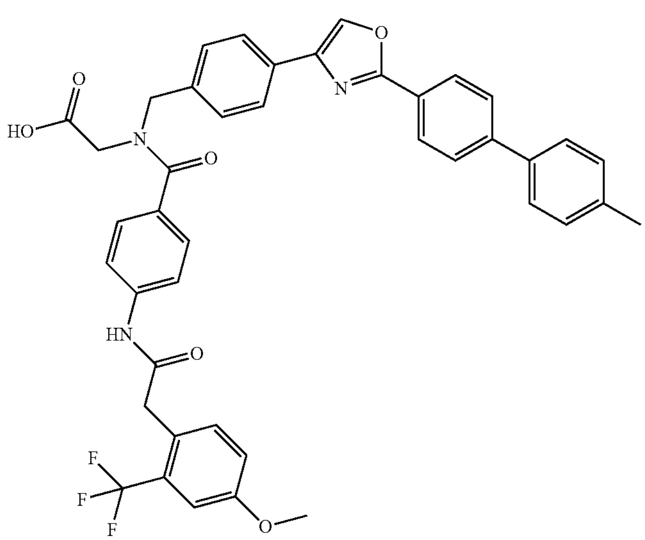 [SMILES: COc1ccc(CC(=O)Nc2ccc(C(=O)N(CC(=O)O)Cc3ccc(-c4coc(-c5ccc(-c6ccc(C)cc6)cc5)n4)cc3)cc2)c(C(F)(F)F)c1] | 364 | 9.38 |

TABLE 1-continued

| STRUCTURE | COMPOUND NUMBER | LCMS RETENTION TIME (min) |
|---|---|---|
| 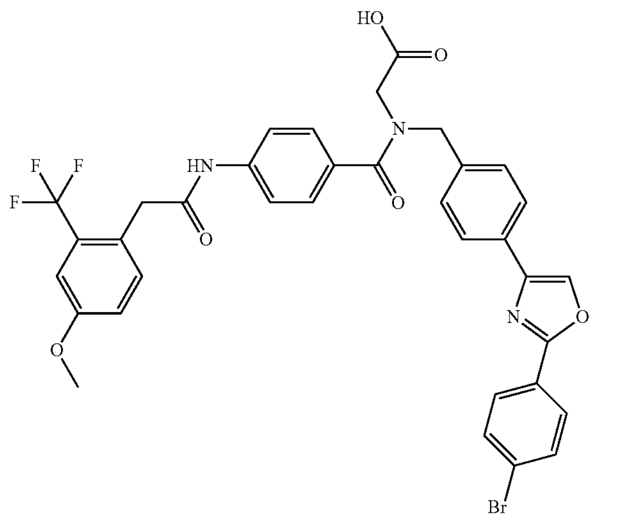 [SMILES: COc1ccc(CC(=O)Nc2ccc(C(=O)N(CC(=O)O)Cc3ccc(-c4coc(-c5ccc(Br)cc5)n4)cc3)cc2)c(C(F)(F)F)c1] | 365 | 8.42 |
| 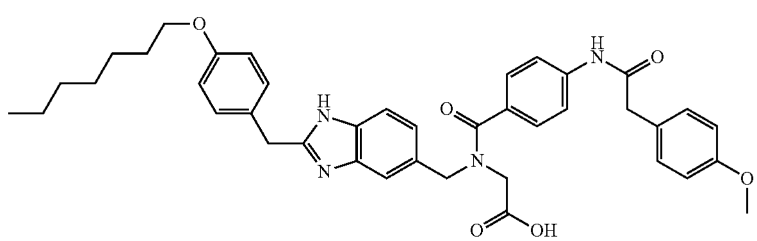 [SMILES: CCCCCCCOc1ccc(Cc2nc3cc(CN(CC(=O)O)C(=O)c4ccc(NC(=O)Cc5ccc(OC)cc5)cc4)ccc3[nH]2)cc1] | 366 | 6.77 |
| 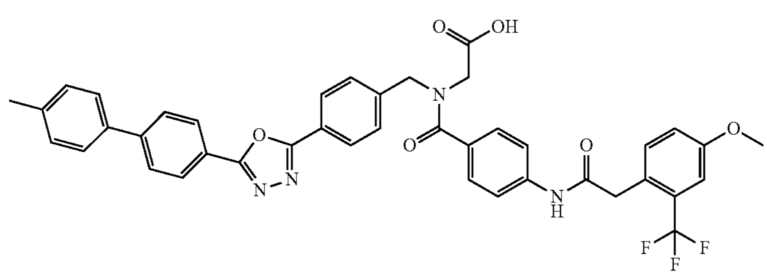 | 367 | 8.40 |
| 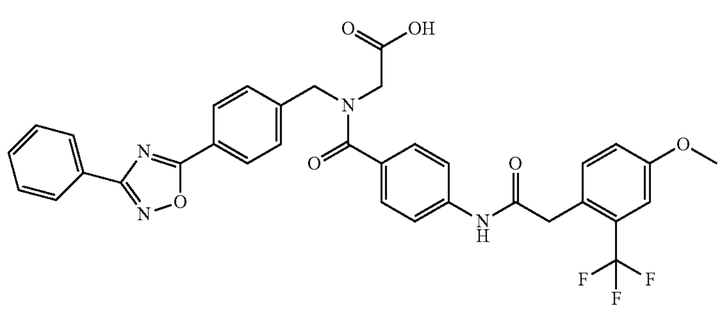 [SMILES: COc1ccc(CC(=O)Nc2ccc(C(=O)N(CC(=O)O)Cc3ccc(-c4nc(-c5ccccc5)no4)cc3)cc2)c(C(F)(F)F)c1] | 368 | 7.56 |

TABLE 1-continued

| STRUCTURE | COMPOUND NUMBER | LCMS RETENTION TIME (min) |
|---|---|---|
| 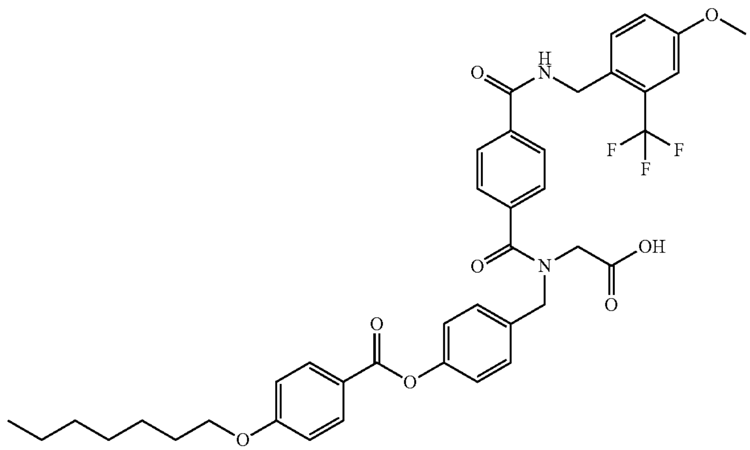 [SMILES: CCCCCCCOc1ccc(C(=O)Oc2ccc(CN(CC(=O)O)C(=O)c3ccc(C(=O)NCc4ccc(OC)cc4C(F)(F)F)cc3)cc2)cc1] | 369 | 11.42 |
| 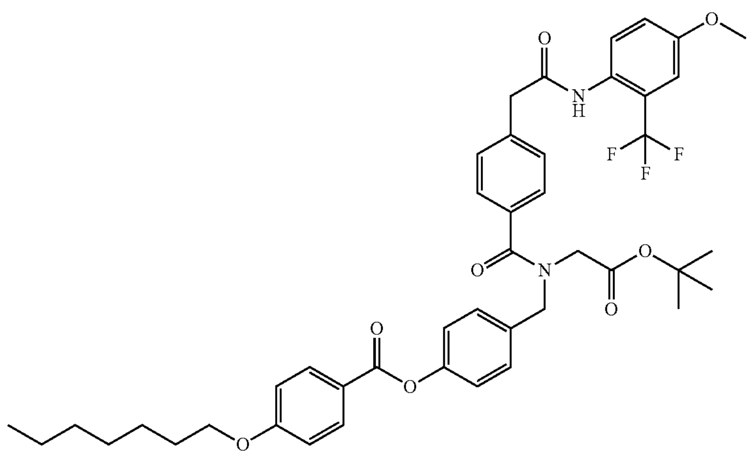 [SMILES: CCCCCCCOc1ccc(C(=O)Oc2ccc(CN(CC(=O)OC(C)(C)C)C(=O)c3ccc(CC(=O)Nc4ccc(OC)cc4C(F)(F)F)cc3)cc2)cc1] | 370 | 11.08 |
| 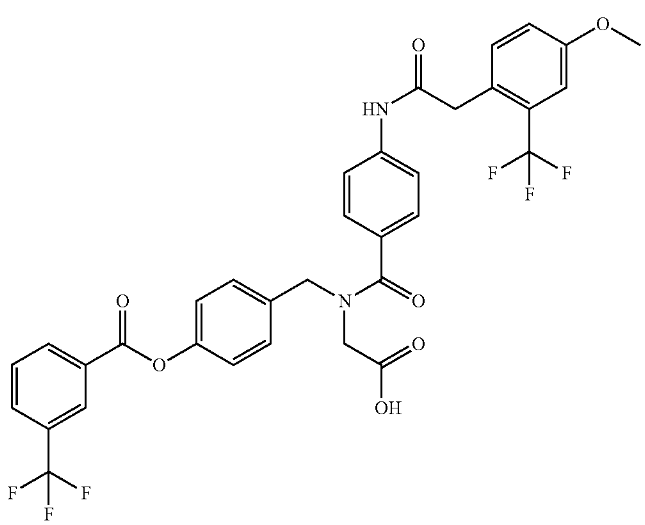 [SMILES: COc1ccc(CC(=O)Nc2ccc(C(=O)N(CC(=O)O)Cc3ccc(OC(=O)c4cccc(C(F)(F)F)c4)cc3)cc2)c(C(F)(F)F)c1] | 371 | 7.69 |

TABLE 1-continued

| STRUCTURE | COMPOUND NUMBER | LCMS RETENTION TIME (min) |
|---|---|---|
| (structure) | 372 | 6.62 |
| (structure) | 373 | 6.31 |
| (structure) | 374 | 5.97 |

TABLE 1-continued
| STRUCTURE | COMPOUND NUMBER | LCMS RETENTION TIME (min) |
|---|---|---|
| 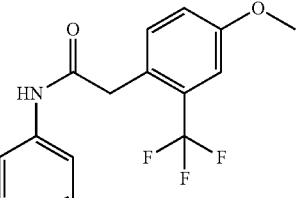 | 375 | 6.53 |
| 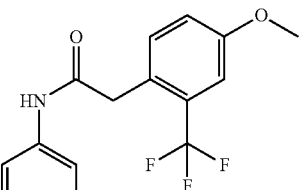 | 376 | 6.70 |
| 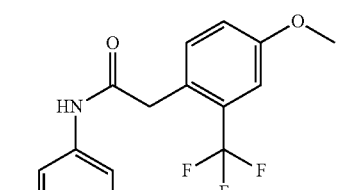 | 377 | 7.08 |

TABLE 1-continued
| STRUCTURE | COMPOUND NUMBER | LCMS RETENTION TIME (min) |
|---|---|---|
| 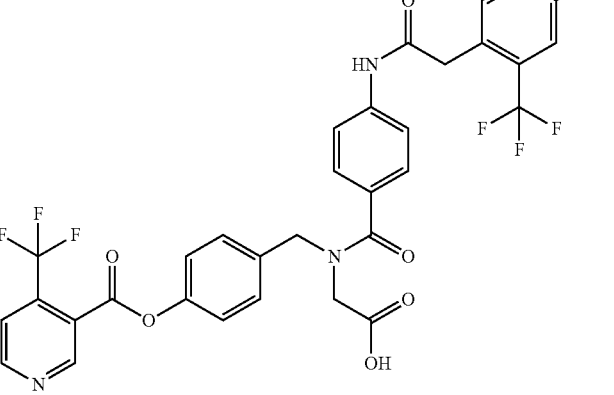 | 378 | 6.49 |
| 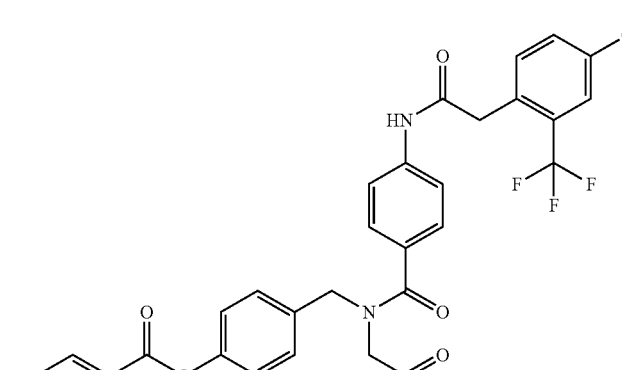 | 379 | 6.73 |
| 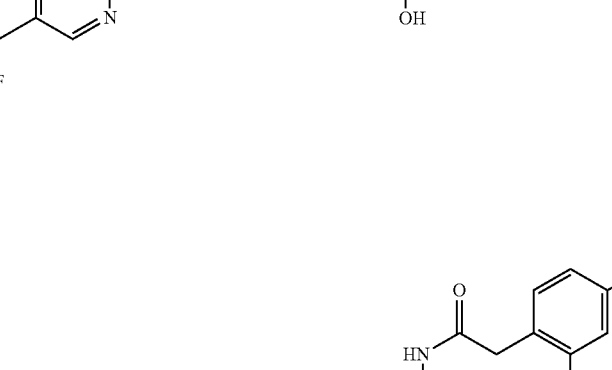 | 380 | 7.38 |

TABLE 1-continued

| STRUCTURE | COMPOUND NUMBER | LCMS RETENTION TIME (min) |
|---|---|---|
| 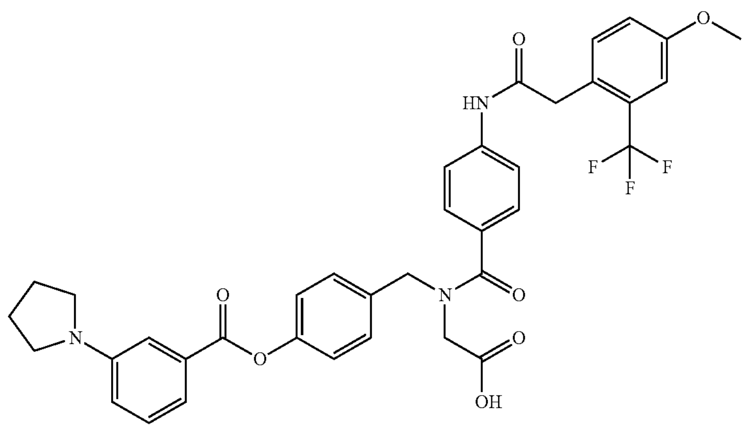 [SMILES: COc1ccc(CC(=O)Nc2ccc(C(=O)N(CC(=O)O)Cc3ccc(OC(=O)c4cccc(N5CCCC5)c4)cc3)cc2)c(C(F)(F)F)c1] | 381 | 8.18 |
| 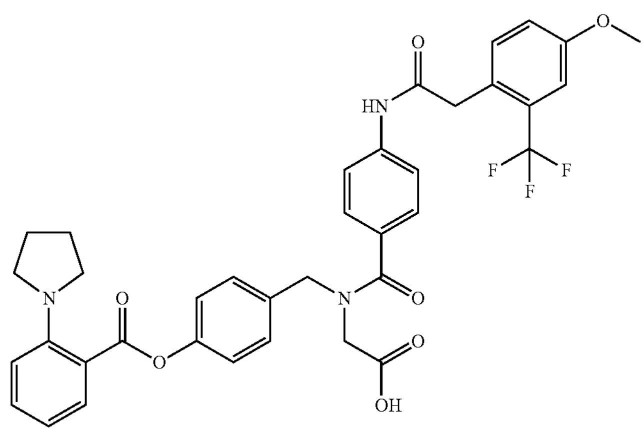 [SMILES: COc1ccc(CC(=O)Nc2ccc(C(=O)N(CC(=O)O)Cc3ccc(OC(=O)c4ccccc4N4CCCC4)cc3)cc2)c(C(F)(F)F)c1] | 382 | 7.59 |
| 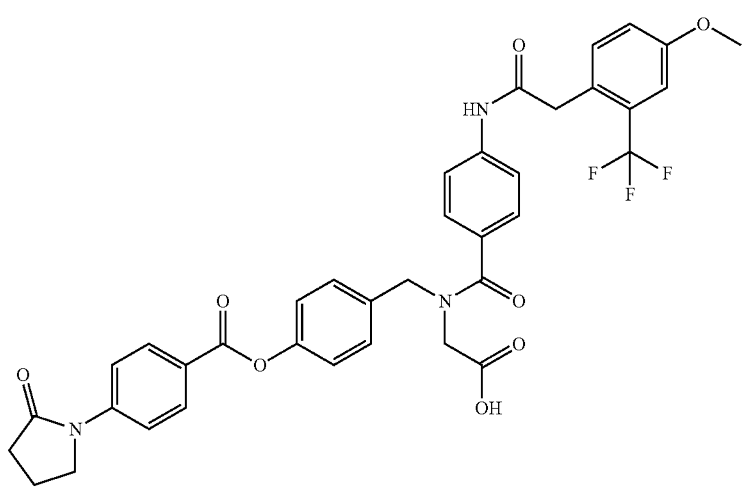 [SMILES: COc1ccc(CC(=O)Nc2ccc(C(=O)N(CC(=O)O)Cc3ccc(OC(=O)c4ccc(N5CCCC5=O)cc4)cc3)cc2)c(C(F)(F)F)c1] | 383 | 6.26 |

TABLE 1-continued

| STRUCTURE | COMPOUND NUMBER | LCMS RETENTION TIME (min) |
|---|---|---|
| 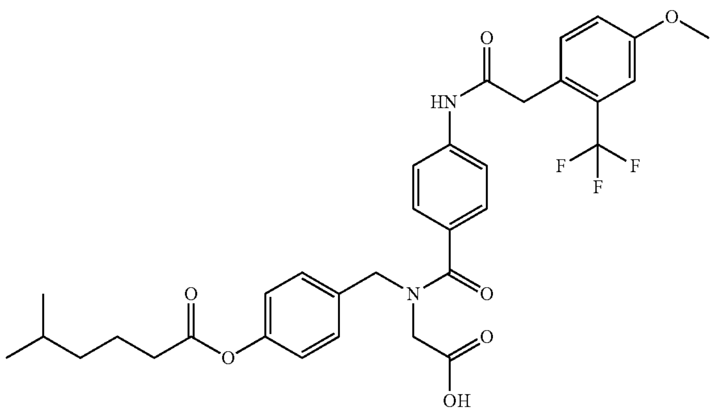 [SMILES: COc1ccc(CC(=O)Nc2ccc(C(=O)N(CC(=O)O)Cc3ccc(OC(=O)CCCC(C)C)cc3)cc2)c(C(F)(F)F)c1] | 384 | 8.02 |
| 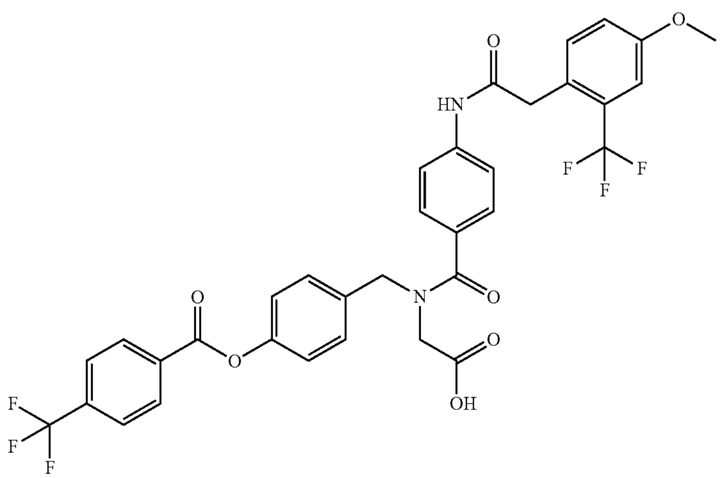 [SMILES: COc1ccc(CC(=O)Nc2ccc(C(=O)N(CC(=O)O)Cc3ccc(OC(=O)c4ccc(C(F)(F)F)cc4)cc3)cc2)c(C(F)(F)F)c1] | 385 | 7.81 |
| 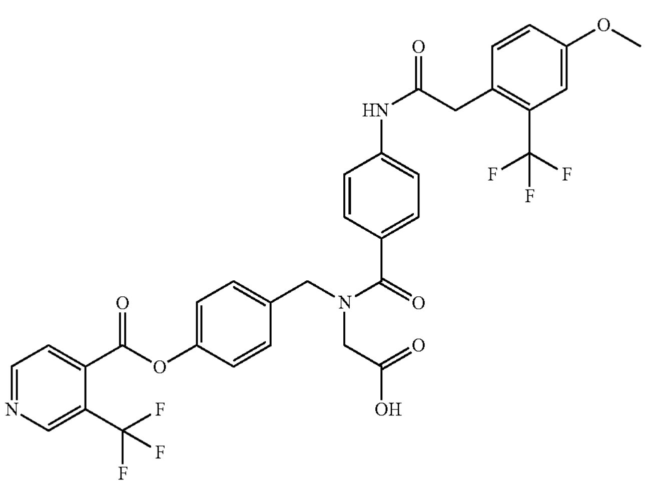 [SMILES: COc1ccc(CC(=O)Nc2ccc(C(=O)N(CC(=O)O)Cc3ccc(OC(=O)c4ccncc4C(F)(F)F)cc3)cc2)c(C(F)(F)F)c1] | 386 | 6.53 |

TABLE 1-continued

| STRUCTURE | COMPOUND NUMBER | LCMS RETENTION TIME (min) |
|---|---|---|
| 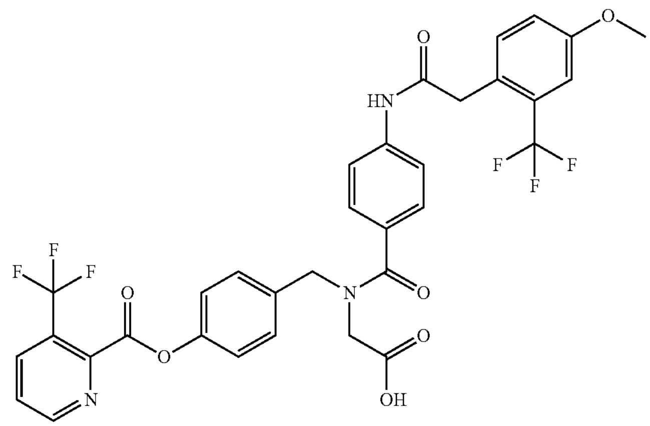 [SMILES: COc1ccc(CC(=O)Nc2ccc(C(=O)N(CC(=O)O)Cc3ccc(OC(=O)c4ncccc4C(F)(F)F)cc3)cc2)c(C(F)(F)F)c1] | 387 | 6.45 |
| 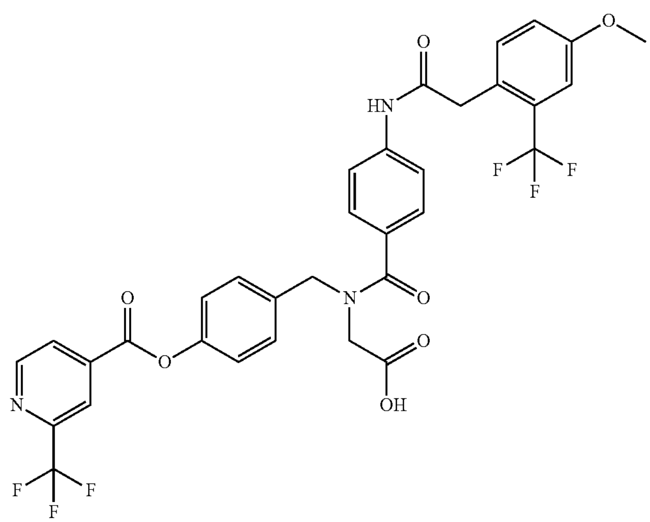 [SMILES: COc1ccc(CC(=O)Nc2ccc(C(=O)N(CC(=O)O)Cc3ccc(OC(=O)c4ccnc(C(F)(F)F)c4)cc3)cc2)c(C(F)(F)F)c1] | 388 | 7.01 |
| 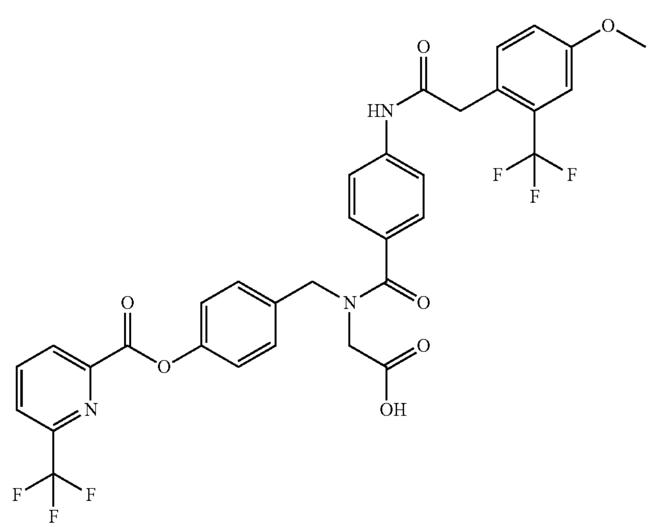 [SMILES: COc1ccc(CC(=O)Nc2ccc(C(=O)N(CC(=O)O)Cc3ccc(OC(=O)c4cccc(C(F)(F)F)n4)cc3)cc2)c(C(F)(F)F)c1] | 389 | 6.76 |

TABLE 1-continued

| STRUCTURE | COMPOUND NUMBER | LCMS RETENTION TIME (min) |
|---|---|---|
| 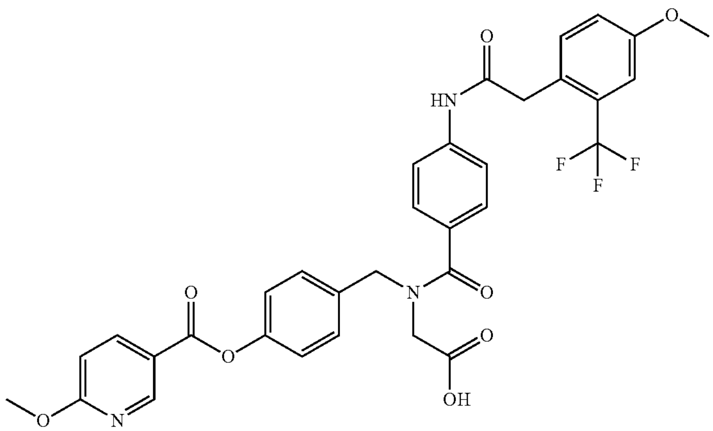 | 390 | 6.69 |
| 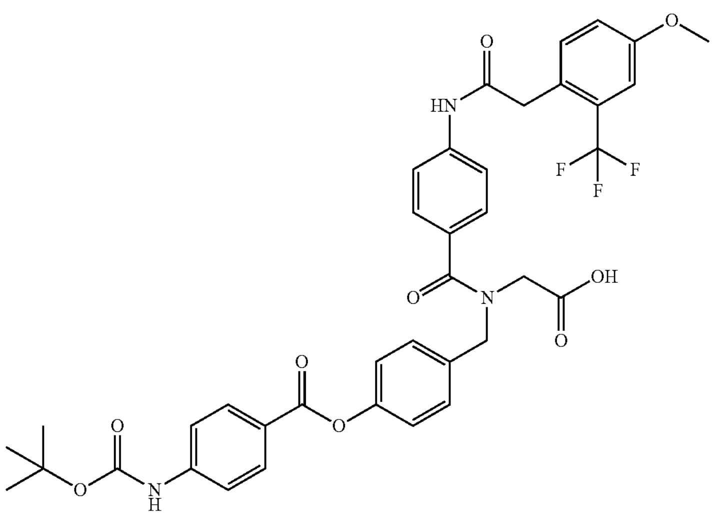 [SMILES: COc1ccc(CC(=O)Nc2ccc(C(=O)N(CC(=O)O)Cc3ccc(OC(=O)c4ccc(NC(=O)OC(C)(C)C)cc4)cc3)cc2)c(C(F)(F)F)c1] | 391 | 7.58 |
| 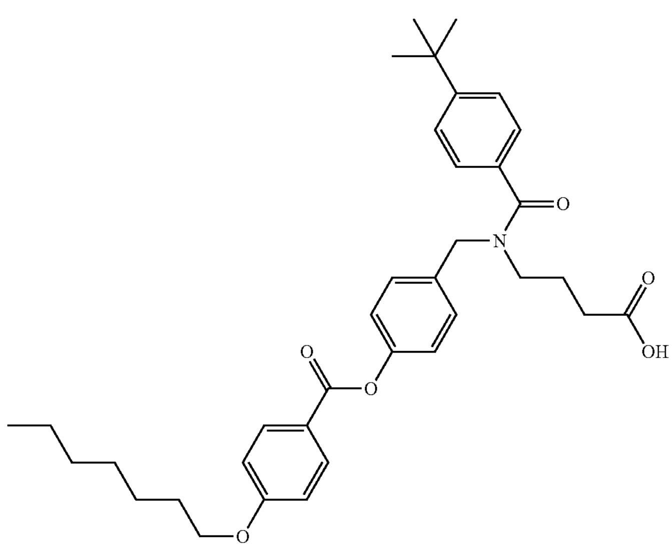 [SMILES: CCCCCCCOc1ccc(C(=O)Oc2ccc(CN(CCCC(=O)O)C(=O)c3ccc(C(C)(C)C)cc3)cc2)cc1] | 392 | 10.73 |

TABLE 1-continued

| STRUCTURE | COMPOUND NUMBER | LCMS RETENTION TIME (min) |
|---|---|---|
| (structure) | 393 | 9.32 |
| (structure) | 394 | 8.66 |
| (structure) | 395 | 8.85 |
| (structure) | 396 | 8.74 |
| (structure) | 397 | 9.11 |
| (structure) | 398 | 9.07 |

TABLE 1-continued
| STRUCTURE | COMPOUND NUMBER | LCMS RETENTION TIME (min) |
|---|---|---|
| 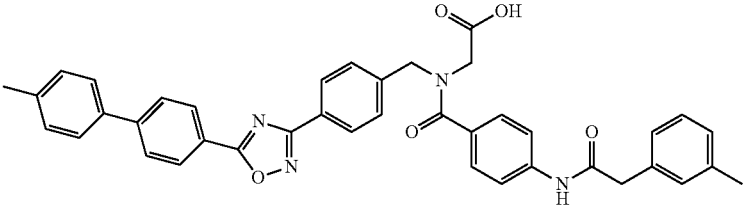 | 399 | 9.15 |
| 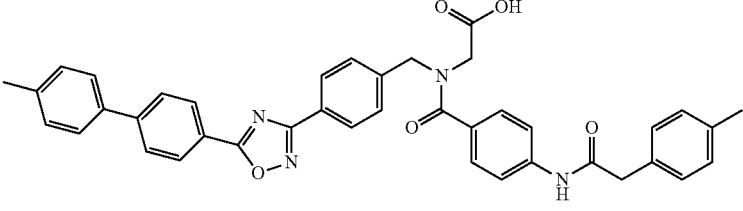 | 400 | 9.13 |
| 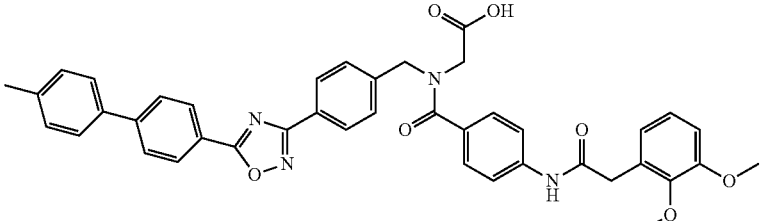 | 401 | 8.76 |
| 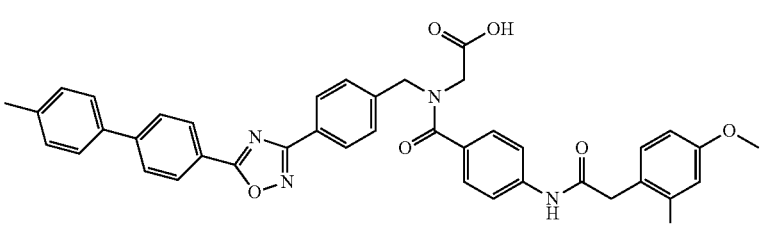 | 402 | 8.82 |
| 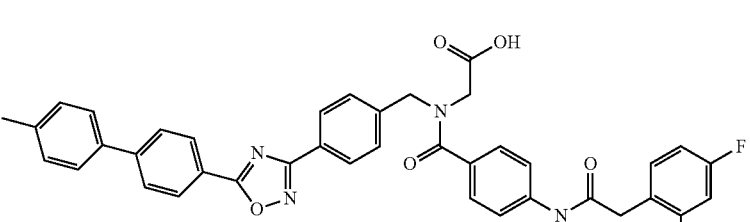 | 403 | 8.74 |
| 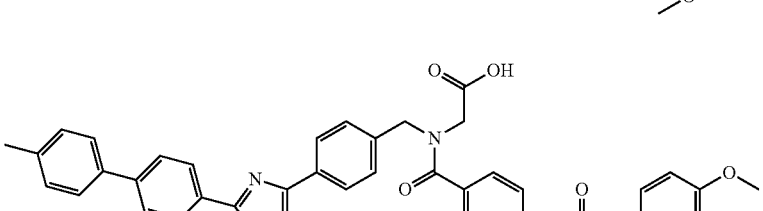 | 404 | 8.29 |

TABLE 1-continued

| STRUCTURE | COMPOUND NUMBER | LCMS RETENTION TIME (min) |
|---|---|---|
| 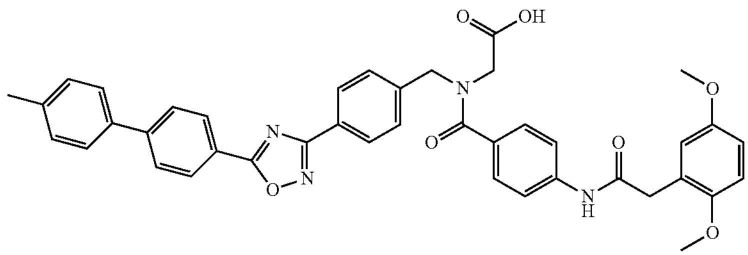 [SMILES: COc1ccc(OC)c(CC(=O)Nc2ccc(C(=O)N(CC(=O)O)Cc3ccc(-c4noc(-c5ccc(-c6ccc(C)cc6)cc5)n4)cc3)cc2)c1] | 405 | 8.80 |
| 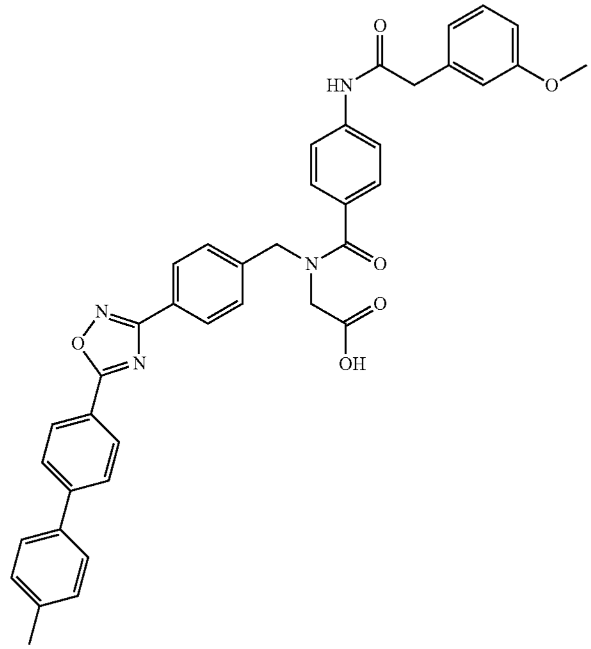 [SMILES: COc1cccc(CC(=O)Nc2ccc(C(=O)N(CC(=O)O)Cc3ccc(-c4noc(-c5ccc(-c6ccc(C)cc6)cc5)n4)cc3)cc2)c1] | 406 | 8.71 |
| 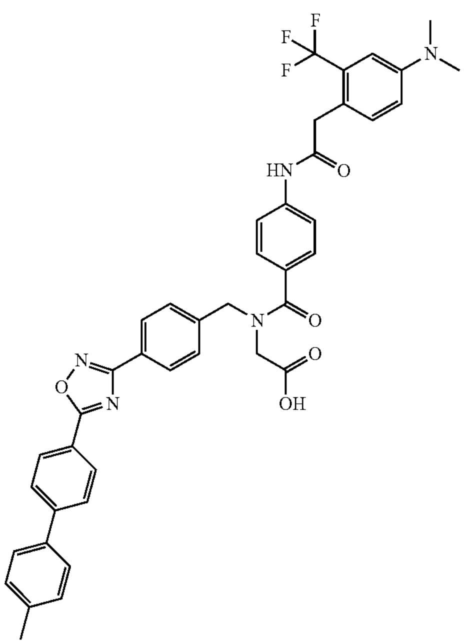 [SMILES: Cc1ccc(-c2ccc(-c3nc(-c4ccc(CN(CC(=O)O)C(=O)c5ccc(NC(=O)Cc6ccc(N(C)C)cc6C(F)(F)F)cc5)cc4)no3)cc2)cc1] | 407 | 9.60 |

TABLE 1-continued

| STRUCTURE | COMPOUND NUMBER | LCMS RETENTION TIME (min) |
|---|---|---|
| 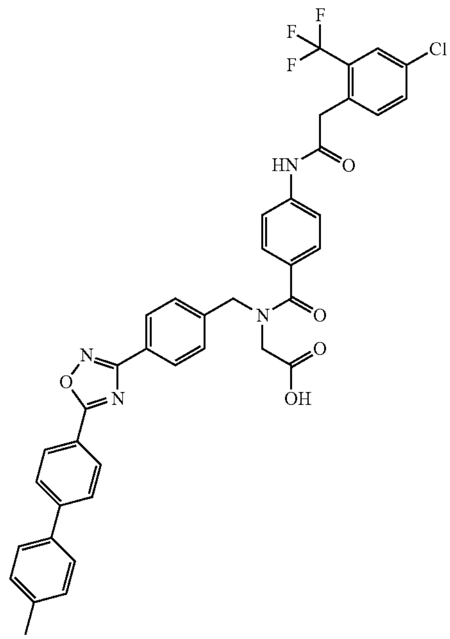 [SMILES: Cc1ccc(-c2ccc(-c3nc(-c4ccc(CN(CC(=O)O)C(=O)c5ccc(NC(=O)Cc6ccc(Cl)cc6C(F)(F)F)cc5)cc4)no3)cc2)cc1] | 408 | 9.84 |
| 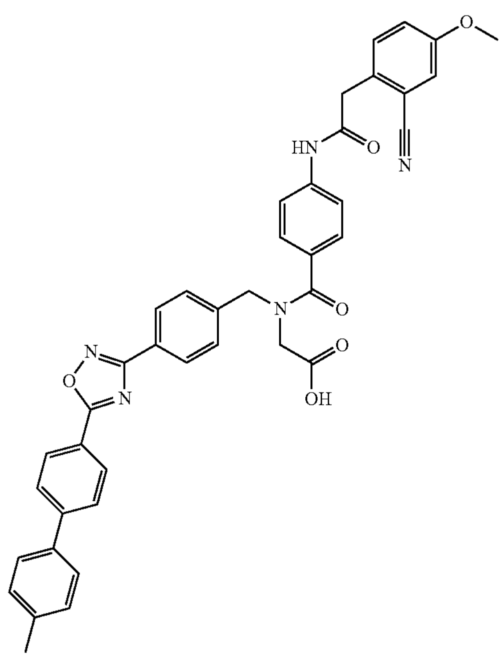 [SMILES: COc1ccc(CC(=O)Nc2ccc(C(=O)N(CC(=O)O)Cc3ccc(-c4noc(-c5ccc(-c6ccc(C)cc6)cc5)n4)cc3)cc2)c(C#N)c1] | 409 | 8.63 |

TABLE 1-continued
| STRUCTURE | COMPOUND NUMBER | LCMS RETENTION TIME (min) |
|---|---|---|
| 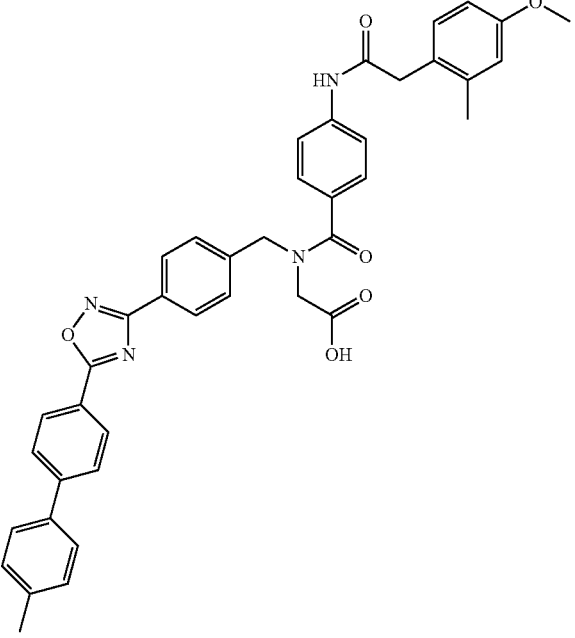 | 410 | 8.95 |
| 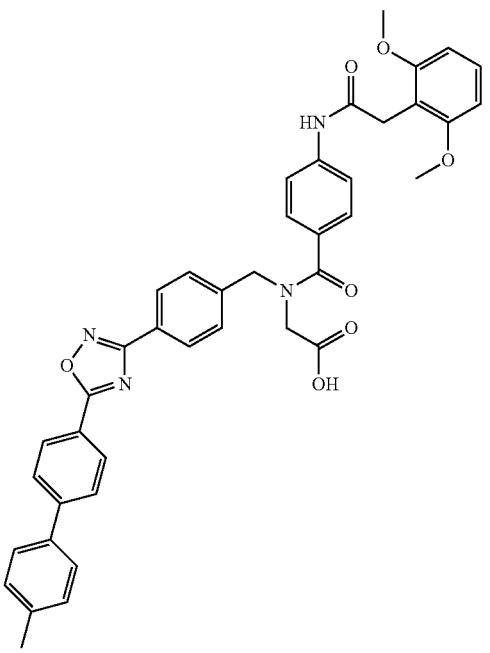 [SMILES: COc1cccc(OC)c1CC(=O)Nc1ccc(C(=O)N(CC(=O)O)Cc2ccc(-c3noc(-c4ccc(-c5ccc(C)cc5)cc4)n3)cc2)cc1] | 411 | 9.02 |

TABLE 1-continued

| STRUCTURE | COMPOUND NUMBER | LCMS RETENTION TIME (min) |
|---|---|---|
| 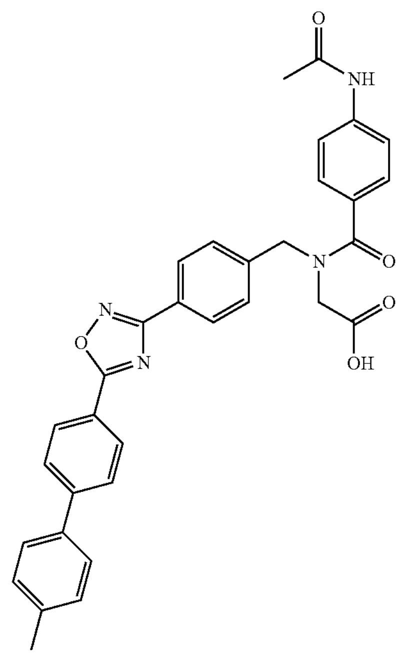 [SMILES: CC(=O)Nc1ccc(C(=O)N(CC(=O)O)Cc2ccc(-c3noc(-c4ccc(-c5ccc(C)cc5)cc4)n3)cc2)cc1] | 412 | 7.46 |
| 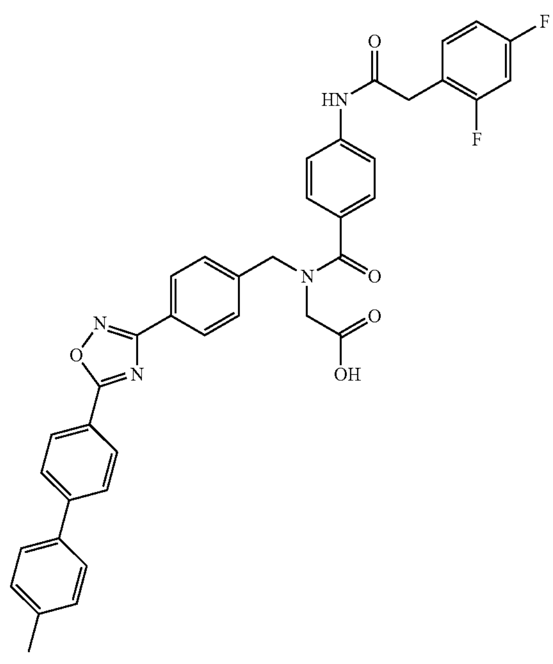 [SMILES: Cc1ccc(-c2ccc(-c3nc(-c4ccc(CN(CC(=O)O)C(=O)c5ccc(NC(=O)Cc6ccc(F)cc6F)cc5)cc4)no3)cc2)cc1] | 413 | 8.91 |

TABLE 1-continued

| STRUCTURE | COMPOUND NUMBER | LCMS RETENTION TIME (min) |
|---|---|---|
| 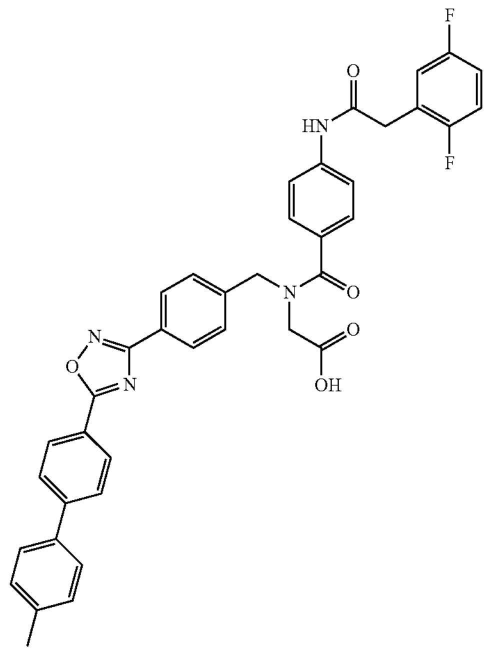 [SMILES: Cc1ccc(-c2ccc(-c3nc(-c4ccc(CN(CC(=O)O)C(=O)c5ccc(NC(=O)Cc6cc(F)ccc6F)cc5)cc4)no3)cc2)cc1] | 414 | 8.88 |
| 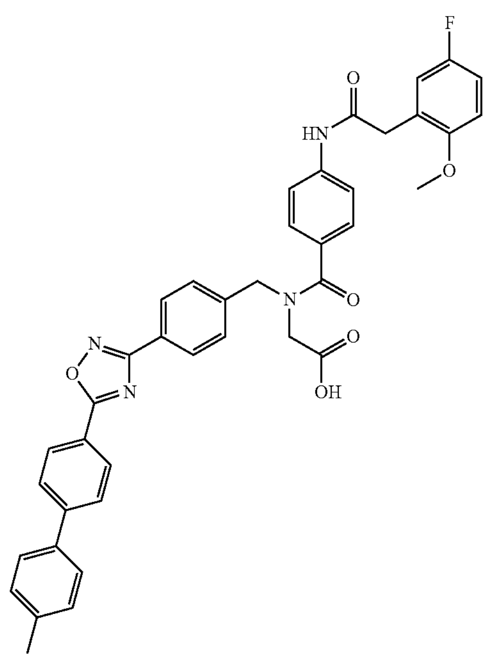 | 415 | 8.90 |

TABLE 1-continued

| STRUCTURE | COMPOUND NUMBER | LCMS RETENTION TIME (min) |
|---|---|---|
| 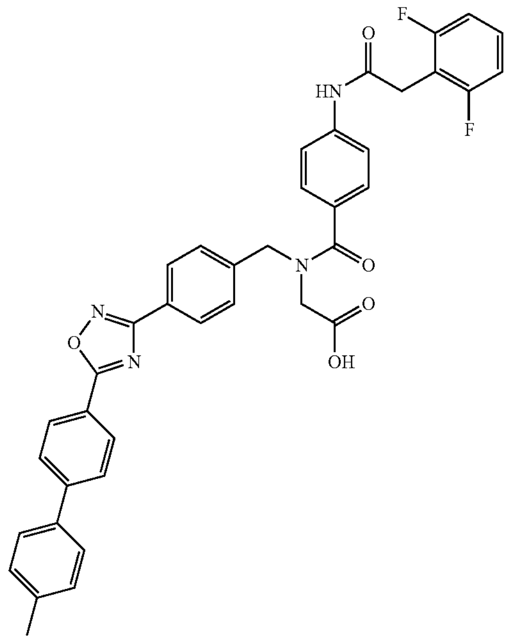 [SMILES: Cc1ccc(-c2ccc(-c3nc(-c4ccc(CN(CC(=O)O)C(=O)c5ccc(NC(=O)Cc6c(F)cccc6F)cc5)cc4)no3)cc2)cc1] | 416 | 8.84 |
| 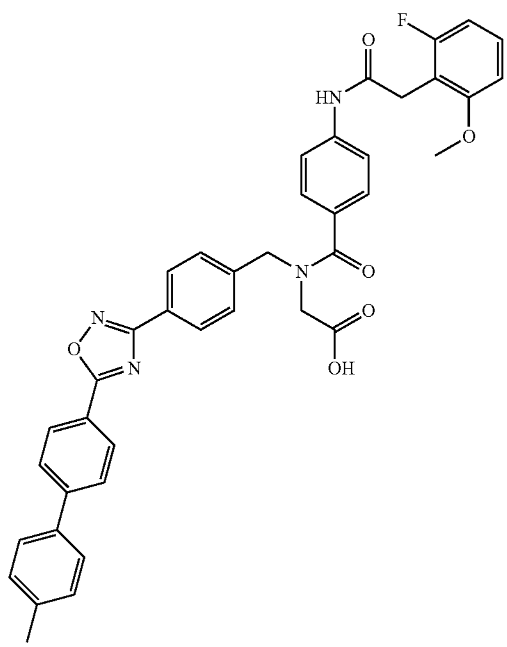 [SMILES: COc1cccc(F)c1CC(=O)Nc1ccc(C(=O)N(CC(=O)O)Cc2ccc(-c3noc(-c4ccc(-c5ccc(C)cc5)cc4)n3)cc2)cc1] | 417 | 8.91 |
| 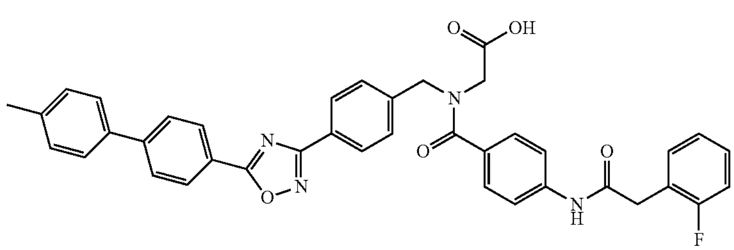 [SMILES: Cc1ccc(-c2ccc(-c3nc(-c4ccc(CN(CC(=O)O)C(=O)c5ccc(NC(=O)Cc6ccccc6F)cc5)cc4)no3)cc2)cc1] | 418 | 8.81 |

TABLE 1-continued

| STRUCTURE | COMPOUND NUMBER | LCMS RETENTION TIME (min) |
|---|---|---|
| 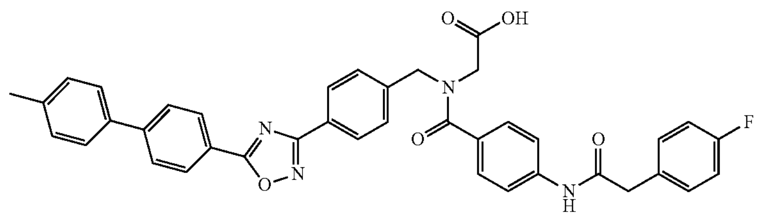 [SMILES: Cc1ccc(-c2ccc(-c3nc(-c4ccc(CN(CC(=O)O)C(=O)c5ccc(NC(=O)Cc6ccc(F)cc6)cc5)cc4)no3)cc2)cc1] | 419 | 8.85 |
| 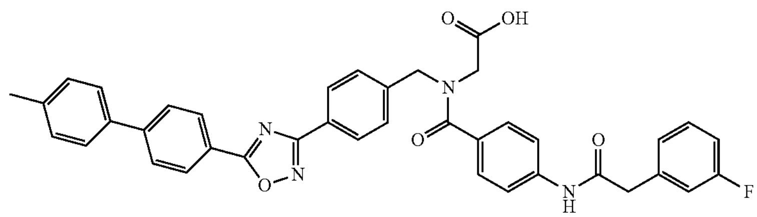 [SMILES: Cc1ccc(-c2ccc(-c3nc(-c4ccc(CN(CC(=O)O)C(=O)c5ccc(NC(=O)Cc6cccc(F)c6)cc5)cc4)no3)cc2)cc1] | 420 | 8.88 |
| 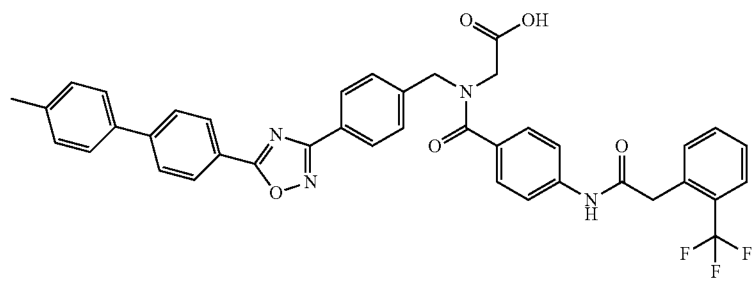 [SMILES: Cc1ccc(-c2ccc(-c3nc(-c4ccc(CN(CC(=O)O)C(=O)c5ccc(NC(=O)Cc6ccccc6C(F)(F)F)cc5)cc4)no3)cc2)cc1] | 421 | 9.29 |
| 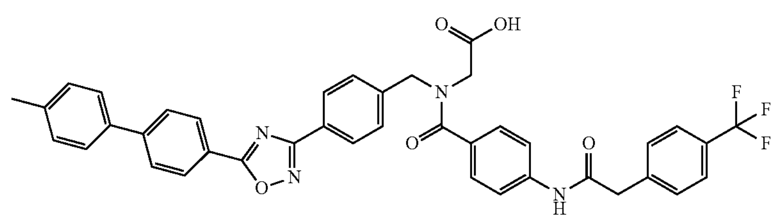 [SMILES: Cc1ccc(-c2ccc(-c3nc(-c4ccc(CN(CC(=O)O)C(=O)c5ccc(NC(=O)Cc6ccc(C(F)(F)F)cc6)cc5)cc4)no3)cc2)cc1] | 422 | 9.43 |
| 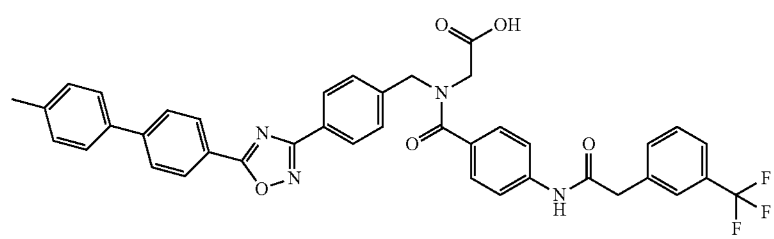 [SMILES: Cc1ccc(-c2ccc(-c3nc(-c4ccc(CN(CC(=O)O)C(=O)c5ccc(NC(=O)Cc6cccc(C(F)(F)F)c6)cc5)cc4)no3)cc2)cc1] | 423 | 9.44 |
| 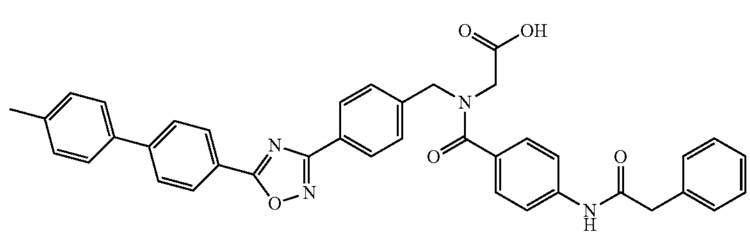 [SMILES: Cc1ccc(-c2ccc(-c3nc(-c4ccc(CN(CC(=O)O)C(=O)c5ccc(NC(=O)Cc6ccccc6)cc5)cc4)no3)cc2)cc1] | 424 | 9.46 |

TABLE 1-continued

| STRUCTURE | COMPOUND NUMBER | LCMS RETENTION TIME (min) |
|---|---|---|
| 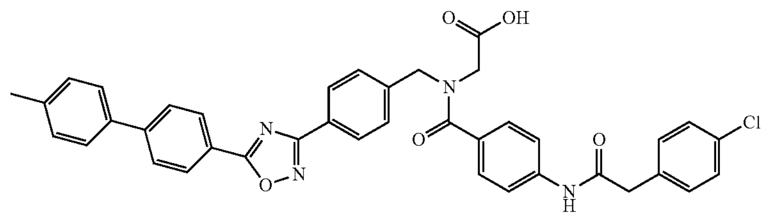 [SMILES: Cc1ccc(-c2ccc(-c3nc(-c4ccc(CN(CC(=O)O)C(=O)c5ccc(NC(=O)Cc6ccc(Cl)cc6)cc5)cc4)no3)cc2)cc1] | 425 | 9.26 |
| 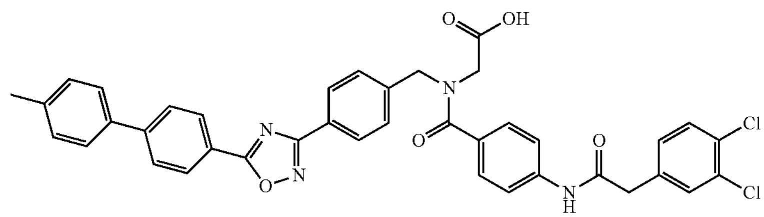 [SMILES: Cc1ccc(-c2ccc(-c3nc(-c4ccc(CN(CC(=O)O)C(=O)c5ccc(NC(=O)Cc6ccc(Cl)c(Cl)c6)cc5)cc4)no3)cc2)cc1] | 426 | 9.71 |
| 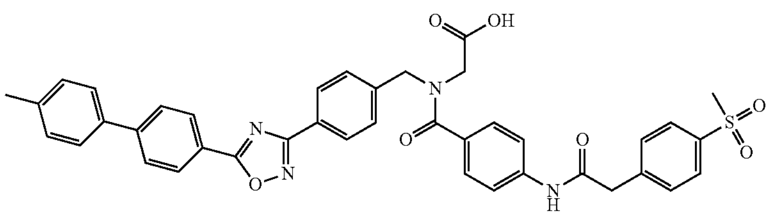 [SMILES: Cc1ccc(-c2ccc(-c3nc(-c4ccc(CN(CC(=O)O)C(=O)c5ccc(NC(=O)Cc6ccc(S(C)(=O)=O)cc6)cc5)cc4)no3)cc2)cc1] | 427 | 7.84 |
| 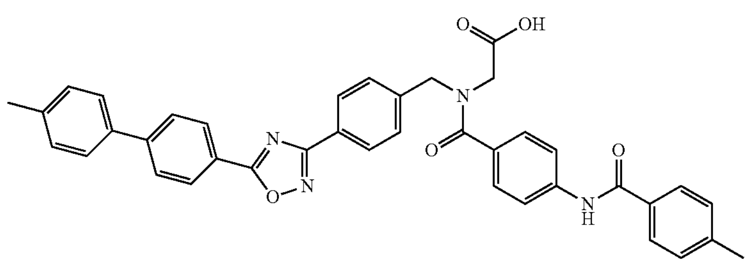 | 428 | 9.11 |
| 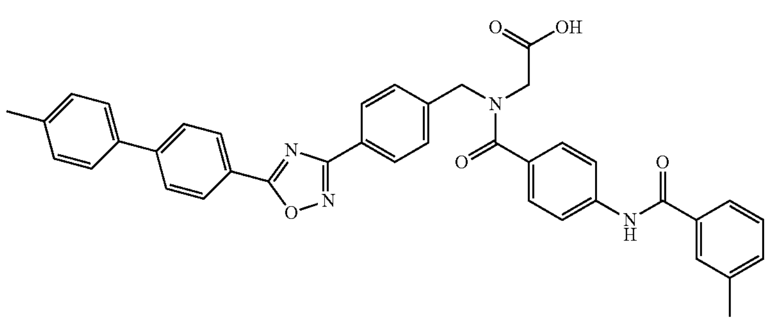 [SMILES: Cc1ccc(-c2ccc(-c3nc(-c4ccc(CN(CC(=O)O)C(=O)c5ccc(NC(=O)c6cccc(C)c6)cc5)cc4)no3)cc2)cc1] | 429 | 9.15 |
| 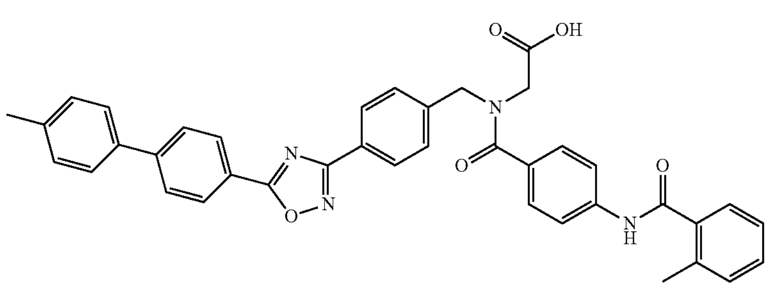 [SMILES: Cc1ccc(-c2ccc(-c3nc(-c4ccc(CN(CC(=O)O)C(=O)c5ccc(NC(=O)c6ccccc6C)cc5)cc4)no3)cc2)cc1] | 430 | 8.94 |

TABLE 1-continued

| STRUCTURE | COMPOUND NUMBER | LCMS RETENTION TIME (min) |
|---|---|---|
| 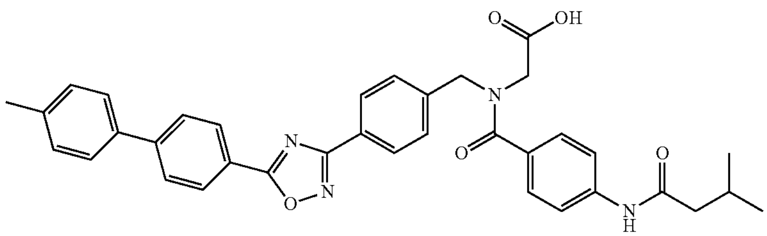 [SMILES: Cc1ccc(-c2ccc(-c3nc(-c4ccc(CN(CC(=O)O)C(=O)c5ccc(NC(=O)CC(C)C)cc5)cc4)no3)cc2)cc1] | 431 | 8.70 |
| 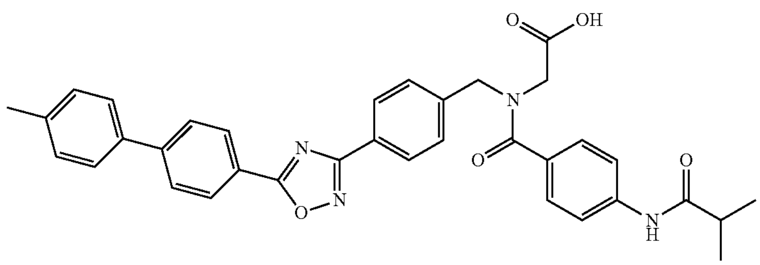 [SMILES: Cc1ccc(-c2ccc(-c3nc(-c4ccc(CN(CC(=O)O)C(=O)c5ccc(NC(=O)C(C)C)cc5)cc4)no3)cc2)cc1] | 432 | 8.34 |
| 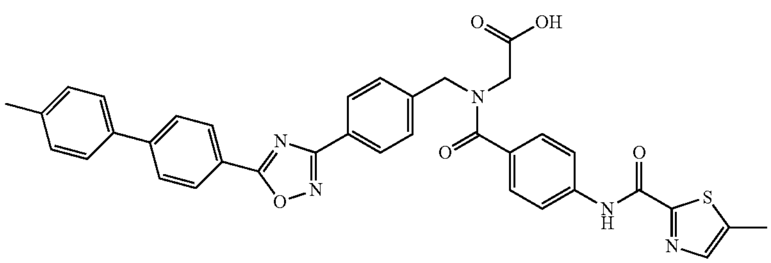 | 433 | 8.95 |
| 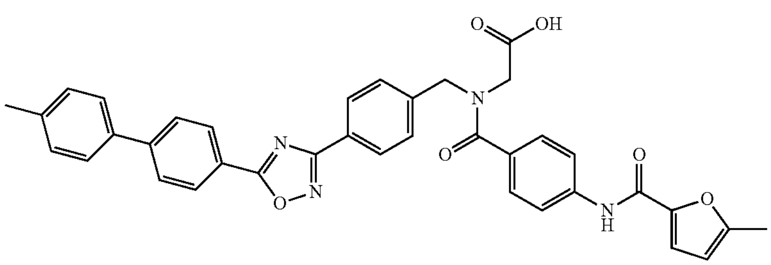 | 434 | 8.52 |
| 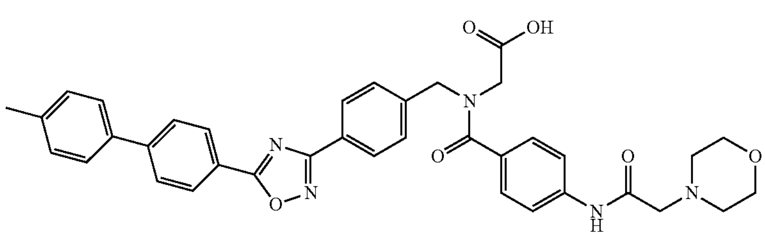 [SMILES: Cc1ccc(-c2ccc(-c3nc(-c4ccc(CN(CC(=O)O)C(=O)c5ccc(NC(=O)CN6CCOCC6)cc5)cc4)no3)cc2)cc1] | 435 | 5.98 |
| 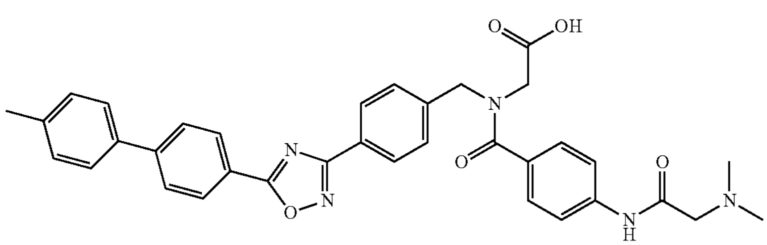 | 436 | 5.91 |

TABLE 1-continued
| STRUCTURE | COMPOUND NUMBER | LCMS RETENTION TIME (min) |
|---|---|---|
| 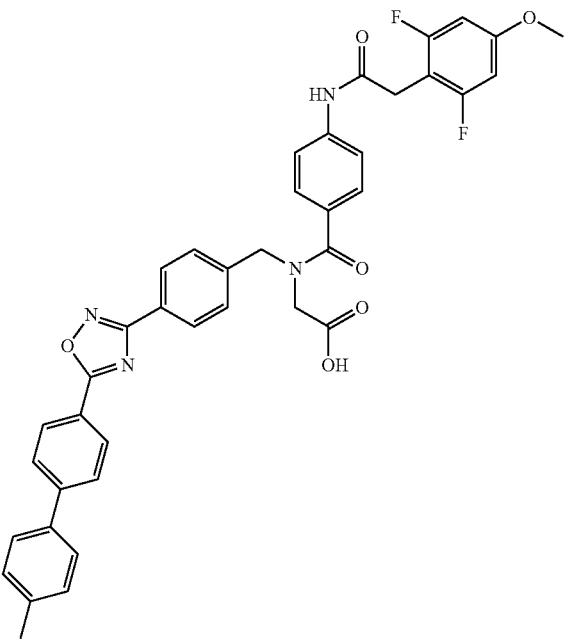 [SMILES: COc1cc(F)c(CC(=O)Nc2ccc(C(=O)N(CC(=O)O)Cc3ccc(-c4noc(-c5ccc(-c6ccc(C)cc6)cc5)n4)cc3)cc2)c(F)c1] | 437 | 9.03 |
| 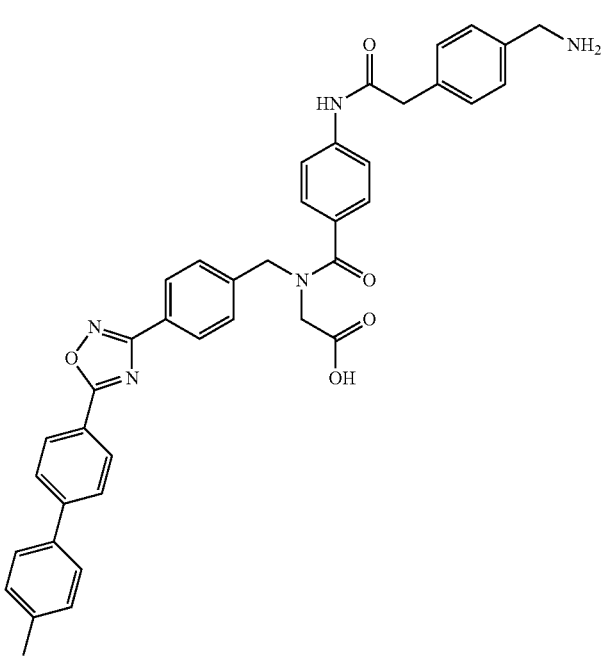 [SMILES: Cc1ccc(-c2ccc(-c3nc(-c4ccc(CN(CC(=O)O)C(=O)c5ccc(NC(=O)Cc6ccc(CN)cc6)cc5)cc4)no3)cc2)cc1] | 438 | 5.74 |

TABLE 1-continued
| STRUCTURE | COMPOUND NUMBER | LCMS RETENTION TIME (min) |
|---|---|---|
| 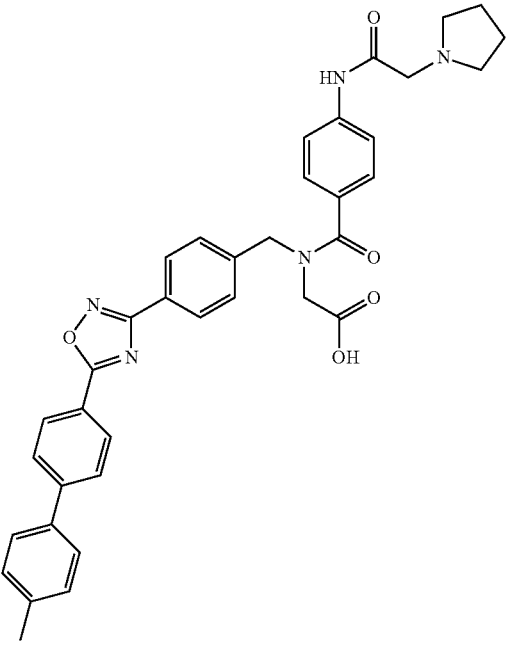 [SMILES: Cc1ccc(-c2ccc(-c3nc(-c4ccc(CN(CC(=O)O)C(=O)c5ccc(NC(=O)CN6CCCC6)cc5)cc4)no3)cc2)cc1] | 439 | 5.99 |
| 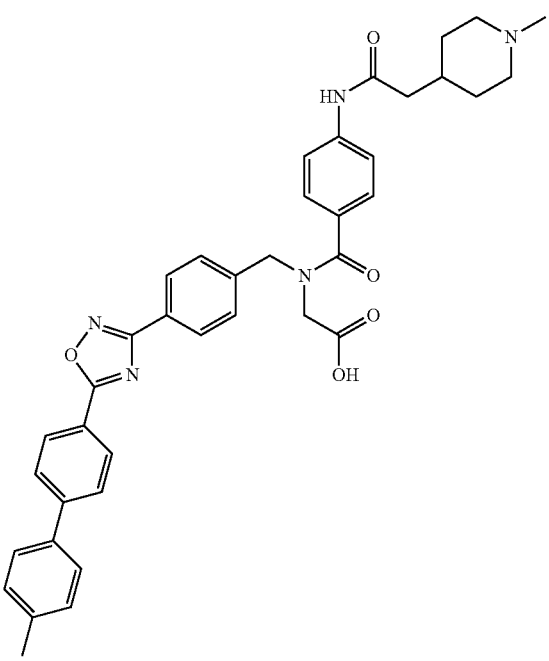 [SMILES: Cc1ccc(-c2ccc(-c3nc(-c4ccc(CN(CC(=O)O)C(=O)c5ccc(NC(=O)CC6CCN(C)CC6)cc5)cc4)no3)cc2)cc1] | 440 | 5.27 |

TABLE 1-continued
| STRUCTURE | COMPOUND NUMBER | LCMS RETENTION TIME (min) |
|---|---|---|
| 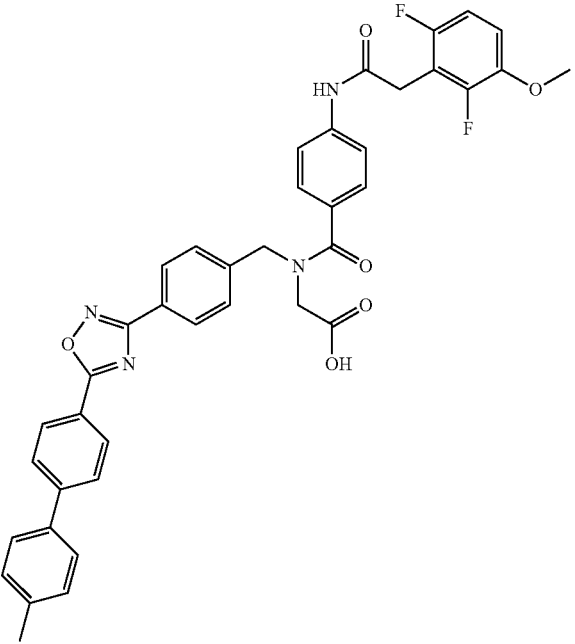 [SMILES: COc1ccc(F)c(CC(=O)Nc2ccc(C(=O)N(CC(=O)O)Cc3ccc(-c4noc(-c5ccc(-c6ccc(C)cc6)cc5)n4)cc3)cc2)c1F] | 441 | 8.75 |
| 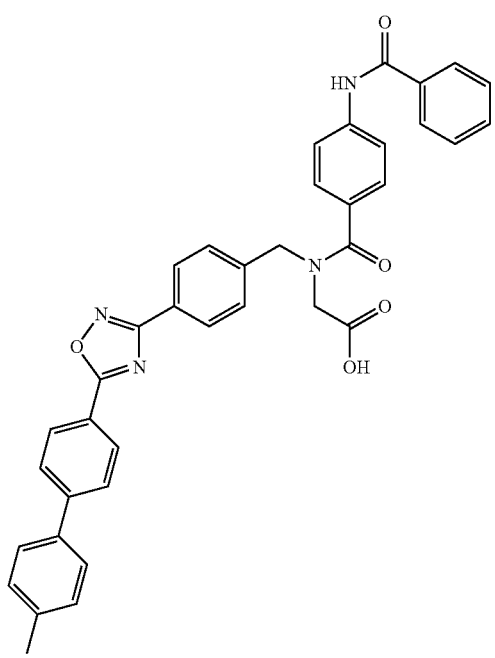 [SMILES: Cc1ccc(-c2ccc(-c3nc(-c4ccc(CN(CC(=O)O)C(=O)c5ccc(NC(=O)c6ccccc6)cc5)cc4)no3)cc2)cc1] | 442 | 8.68 |

TABLE 1-continued
| STRUCTURE | COMPOUND NUMBER | LCMS RETENTION TIME (min) |
|---|---|---|
| 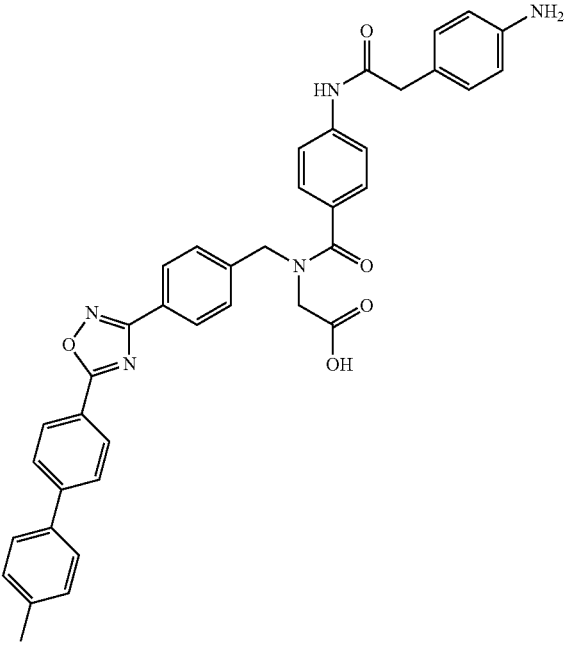 [SMILES: Cc1ccc(-c2ccc(-c3nc(-c4ccc(CN(CC(=O)O)C(=O)c5ccc(NC(=O)Cc6ccc(N)cc6)cc5)cc4)no3)cc2)cc1] | 443 | 6.46 |
| 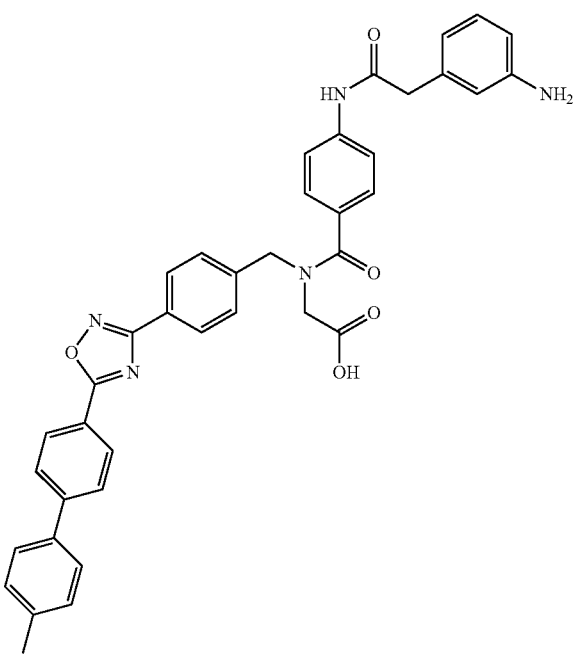 [SMILES: Cc1ccc(-c2ccc(-c3nc(-c4ccc(CN(CC(=O)O)C(=O)c5ccc(NC(=O)Cc6cccc(N)c6)cc5)cc4)no3)cc2)cc1] | 444 | 6.82 |

TABLE 1-continued

| STRUCTURE | COMPOUND NUMBER | LCMS RETENTION TIME (min) |
|---|---|---|
| 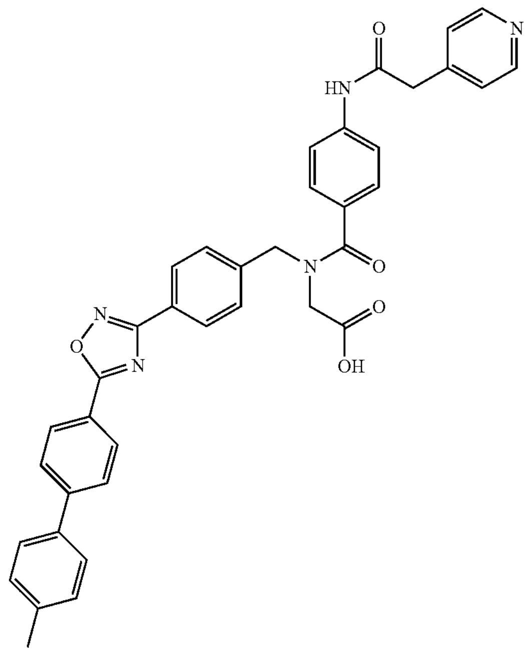 [SMILES: Cc1ccc(-c2ccc(-c3nc(-c4ccc(CN(CC(=O)O)C(=O)c5ccc(NC(=O)Cc6ccncc6)cc5)cc4)no3)cc2)cc1] | 445 | 5.58 |
| 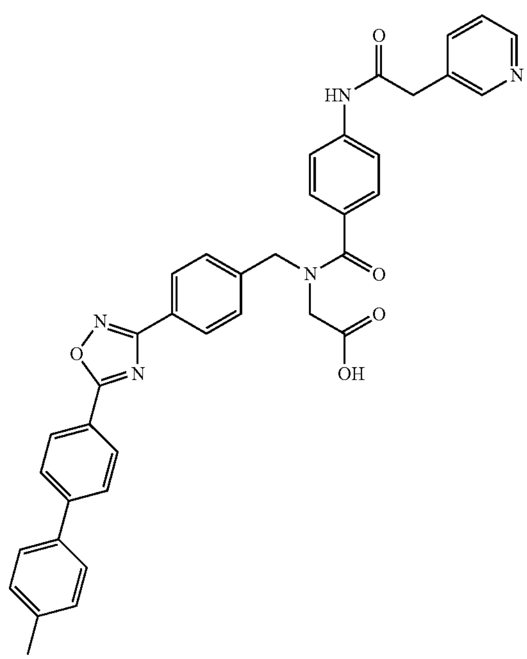 [SMILES: Cc1ccc(-c2ccc(-c3nc(-c4ccc(CN(CC(=O)O)C(=O)c5ccc(NC(=O)Cc6cccnc6)cc5)cc4)no3)cc2)cc1] | 446 | 5.91 |

TABLE 1-continued
| STRUCTURE | COMPOUND NUMBER | LCMS RETENTION TIME (min) |
|---|---|---|
| 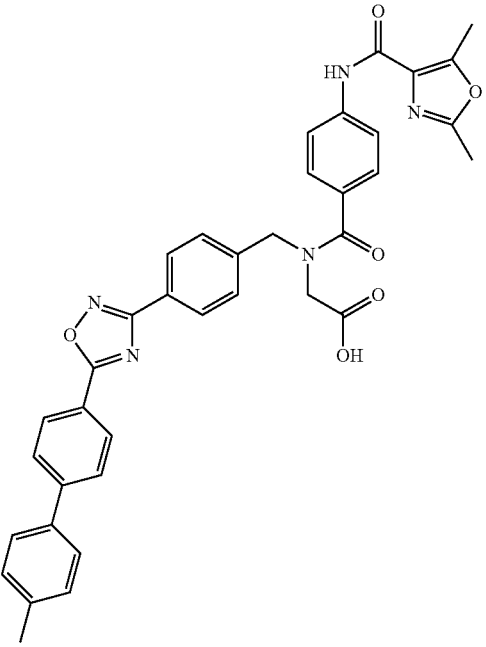 [SMILES: Cc1ccc(-c2ccc(-c3nc(-c4ccc(CN(CC(=O)O)C(=O)c5ccc(NC(=O)c6nc(C)oc6C)cc5)cc4)no3)cc2)cc1] | 447 | 8.85 |
| 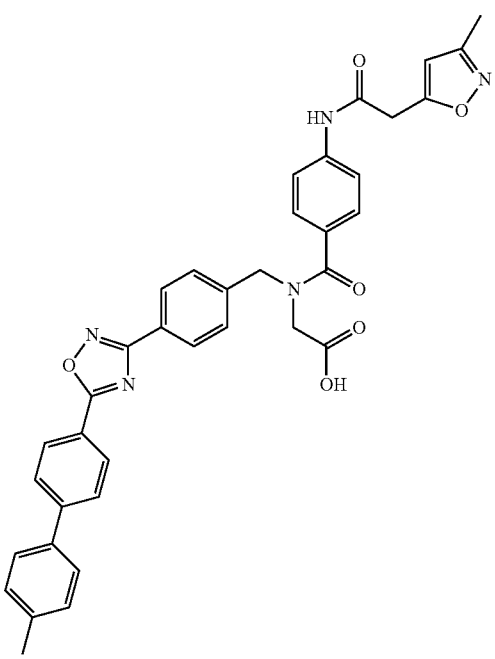 [SMILES: Cc1ccc(-c2ccc(-c3nc(-c4ccc(CN(CC(=O)O)C(=O)c5ccc(NC(=O)Cc6cc(C)no6)cc5)cc4)no3)cc2)cc1] | 448 | 7.92 |

TABLE 1-continued
| STRUCTURE | COMPOUND NUMBER | LCMS RETENTION TIME (min) |
|---|---|---|
| 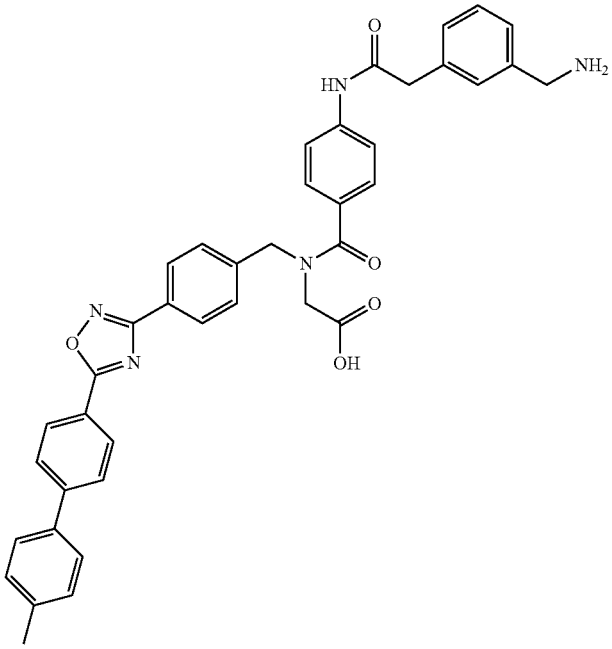 [SMILES: Cc1ccc(-c2ccc(-c3nc(-c4ccc(CN(CC(=O)O)C(=O)c5ccc(NC(=O)Cc6cccc(CN)c6)cc5)cc4)no3)cc2)cc1] | 449 | 5.46 |
| 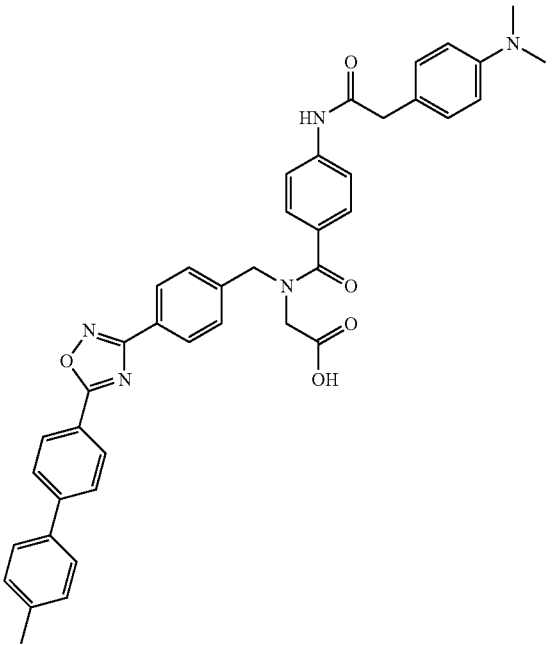 [SMILES: Cc1ccc(-c2ccc(-c3nc(-c4ccc(CN(CC(=O)O)C(=O)c5ccc(NC(=O)Cc6ccc(N(C)C)cc6)cc5)cc4)no3)cc2)cc1] | 450 | 7.33 |

TABLE 1-continued
| STRUCTURE | COMPOUND NUMBER | LCMS RETENTION TIME (min) |
|---|---|---|
| 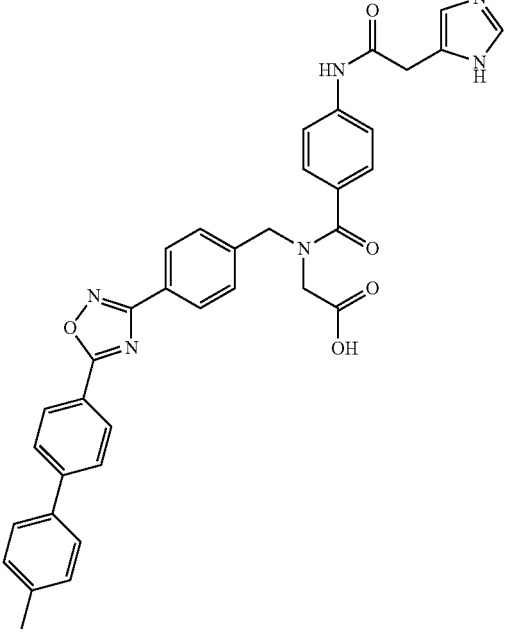 | 451 | 4.89 |
| 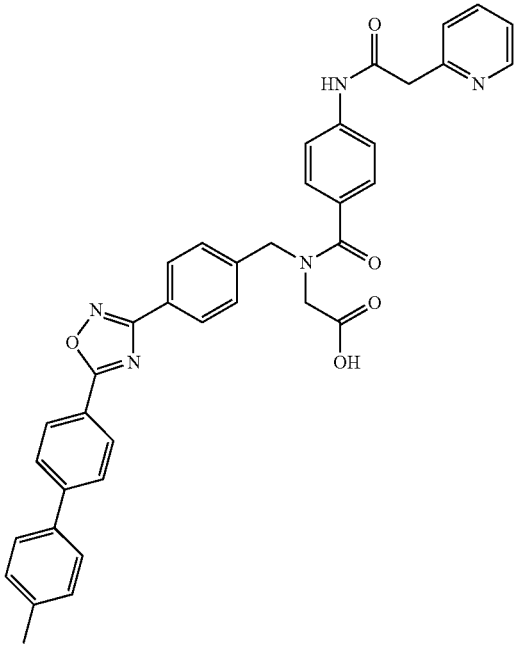 [SMILES: Cc1ccc(-c2ccc(-c3nc(-c4ccc(CN(CC(=O)O)C(=O)c5ccc(NC(=O)Cc6ccccn6)cc5)cc4)no3)cc2)cc1] | 452 | 6.63 |

TABLE 1-continued

| STRUCTURE | COMPOUND NUMBER | LCMS RETENTION TIME (min) |
|---|---|---|
| 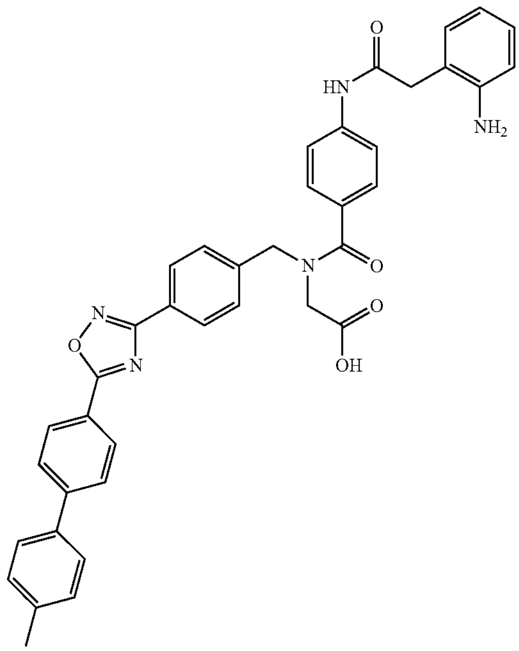 [SMILES: Cc1ccc(-c2ccc(-c3nc(-c4ccc(CN(CC(=O)O)C(=O)c5ccc(NC(=O)Cc6ccccc6N)cc5)cc4)no3)cc2)cc1] | 453 | 6.50 |
| 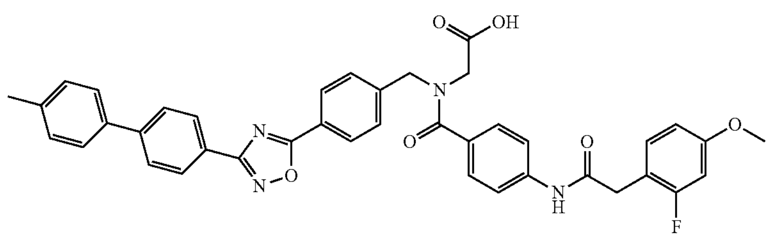 | 454 | 8.92 |
| 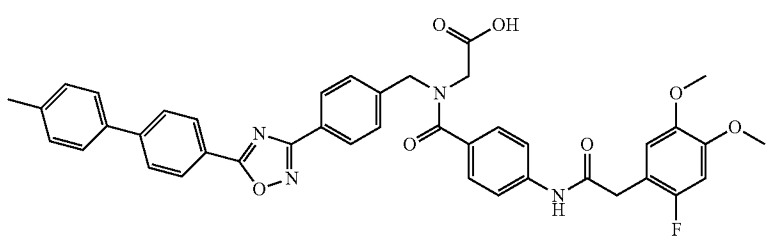 | 455 | 8.49 |
| 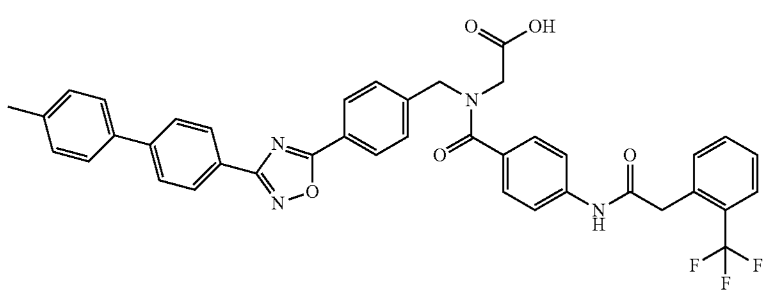 [SMILES: Cc1ccc(-c2ccc(-c3noc(-c4ccc(CN(CC(=O)O)C(=O)c5ccc(NC(=O)Cc6ccccc6C(F)(F)F)cc5)cc4)n3)cc2)cc1] | 456 | 9.37 |

TABLE 1-continued

| STRUCTURE | COMPOUND NUMBER | LCMS RETENTION TIME (min) |
|---|---|---|
| 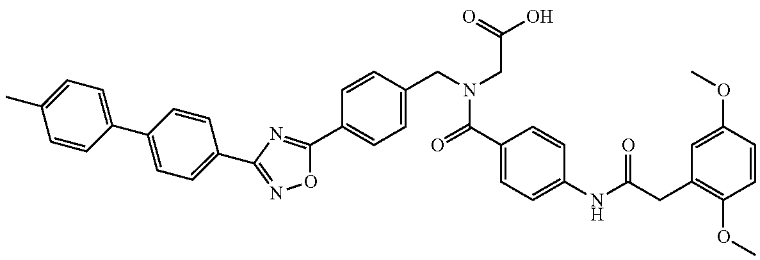 | 457 | 8.94 |
| 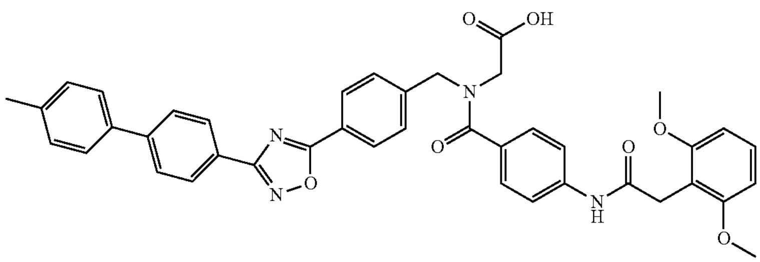 | 458 | 9.08 |
| 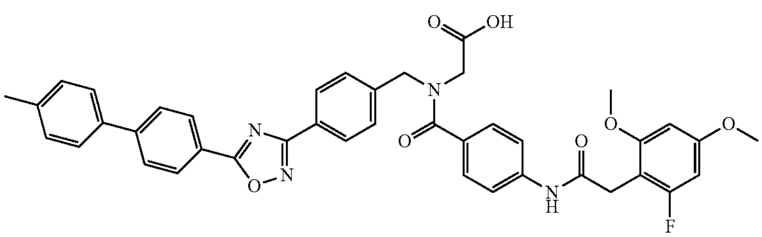 | 459 | 9.01 |
| 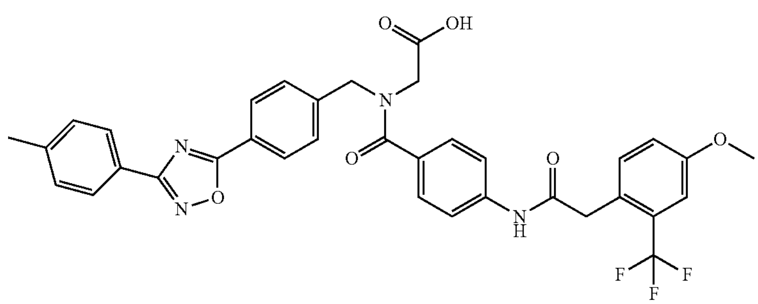 | 460 | 7.83 |
| 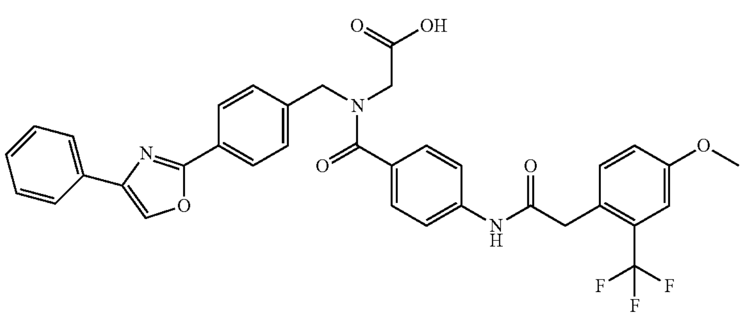 | 461 | 7.38 |

TABLE 1-continued

| STRUCTURE | COMPOUND NUMBER | LCMS RETENTION TIME (min) |
|---|---|---|
| (structure) | 462 | 9.72 |
| (structure) | 463 | 9.66 |
| (structure) | 464 | 9.66 |
| (structure) | 465 | 8.44 |
| (structure) | 466 | 7.72 |

TABLE 1-continued

| STRUCTURE | COMPOUND NUMBER | LCMS RETENTION TIME (min) |
|---|---|---|
| 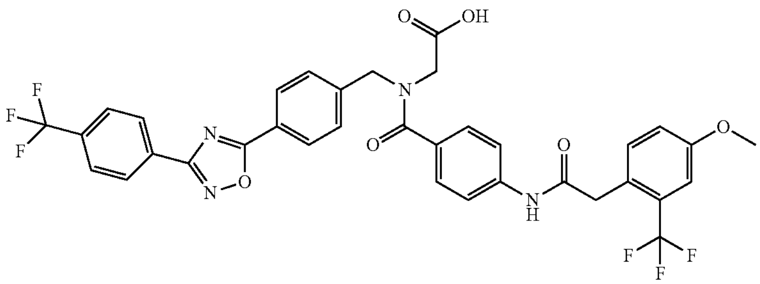 | 467 | 10.04 |
| 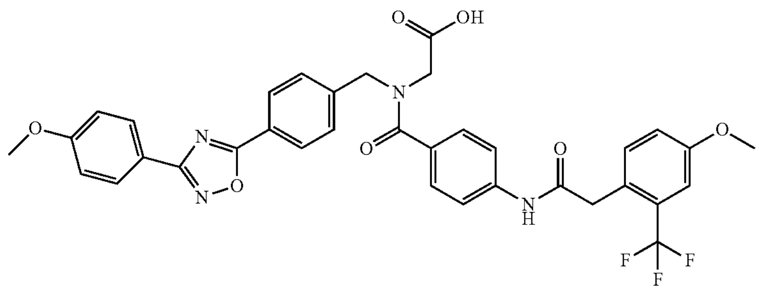 [SMILES: CCc1ccc(-c2noc(-c3ccc(CN(CC(=O)O)C(=O)c4ccc(NC(=O)Cc5ccc(OC)cc5C(F)(F)F)cc4)cc3)n2)cc1] | 468 | 9.13 |
| 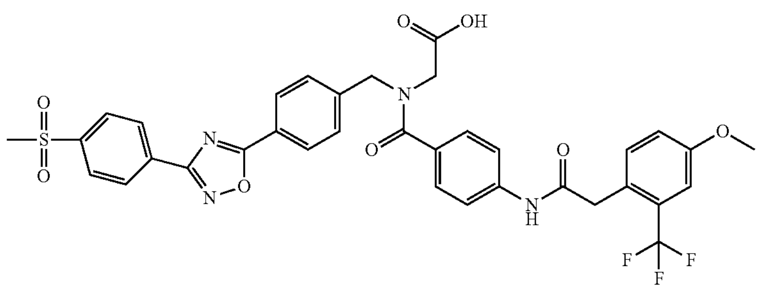 | 469 | 8.46 |
| 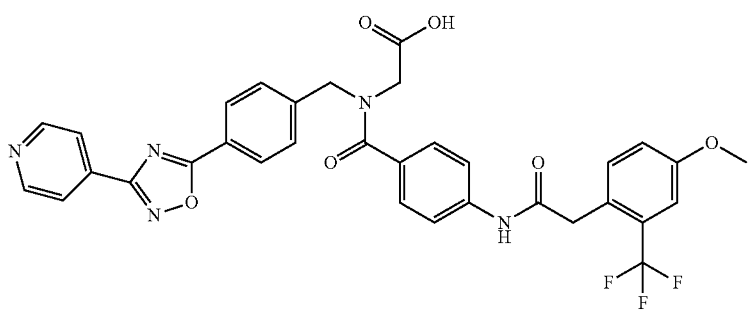 [SMILES: COc1ccc(CC(=O)Nc2ccc(C(=O)N(CC(=O)O)Cc3ccc(-c4nc(-c5ccncc5)no4)cc3)cc2)c(C(F)(F)F)c1] | 470 | 7.88 |
| 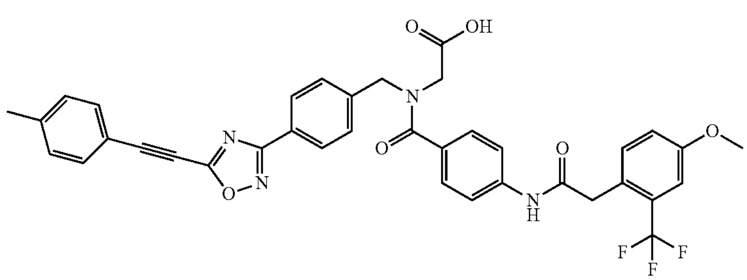 | 471 | 8.49 |

TABLE 1-continued

| STRUCTURE | COMPOUND NUMBER | LCMS RETENTION TIME (min) |
|---|---|---|
| 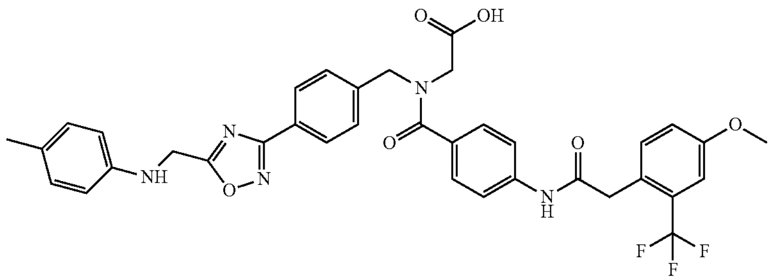 | 472 | 7.29 |
| 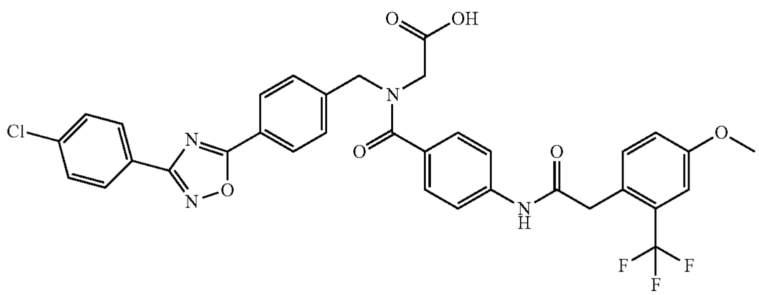 [SMILES: COc1ccc(CC(=O)Nc2ccc(C(=O)N(CC(=O)O)Cc3ccc(-c4nc(-c5ccc(Cl)cc5)no4)cc3)cc2)c(C(F)(F)F)c1] | 473 | 9.59 |
| 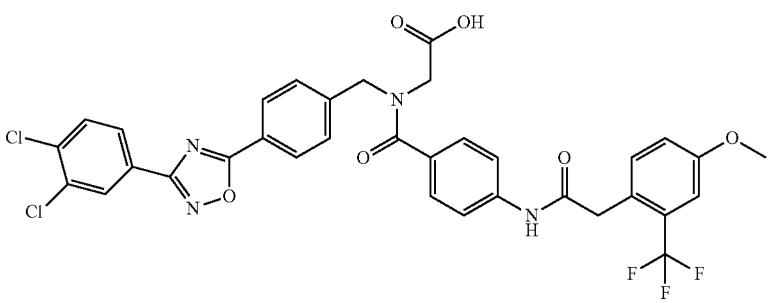 [SMILES: COc1ccc(CC(=O)Nc2ccc(C(=O)N(CC(=O)O)Cc3ccc(-c4nc(-c5ccc(Cl)c(Cl)c5)no4)cc3)cc2)c(C(F)(F)F)c1] | 474 | 10.09 |
| 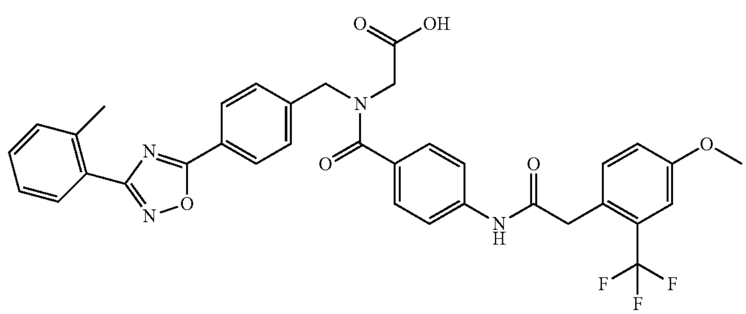 [SMILES: COc1ccc(CC(=O)Nc2ccc(C(=O)N(CC(=O)O)Cc3ccc(-c4nc(-c5ccccc5C)no4)cc3)cc2)c(C(F)(F)F)c1] | 475 | 9.37 |
| 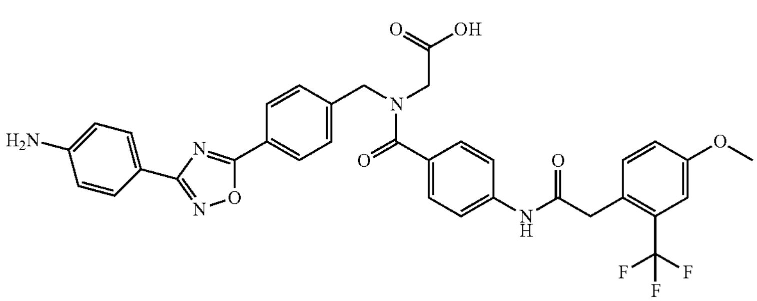 [SMILES: COc1ccc(CC(=O)Nc2ccc(C(=O)N(CC(=O)O)Cc3ccc(-c4nc(-c5ccc(N)cc5)no4)cc3)cc2)c(C(F)(F)F)c1] | 476 | 7.78 |

TABLE 1-continued

| STRUCTURE | COMPOUND NUMBER | LCMS RETENTION TIME (min) |
|---|---|---|
| 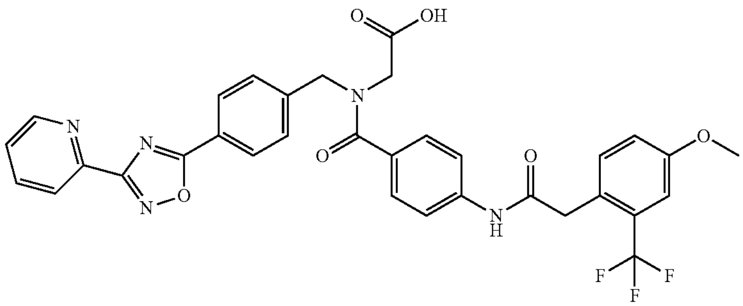 | 477 | 8.00 |
| 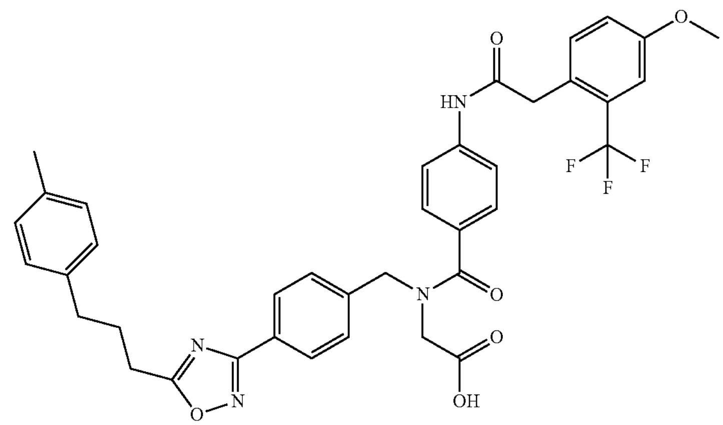 [SMILES: COc1ccc(CC(=O)Nc2ccc(C(=O)N(CC(=O)O)Cc3ccc(-c4noc(CCCc5ccc(C)cc5)n4)cc3)cc2)c(C(F)(F)F)c1] | 478 | 8.30 |
| 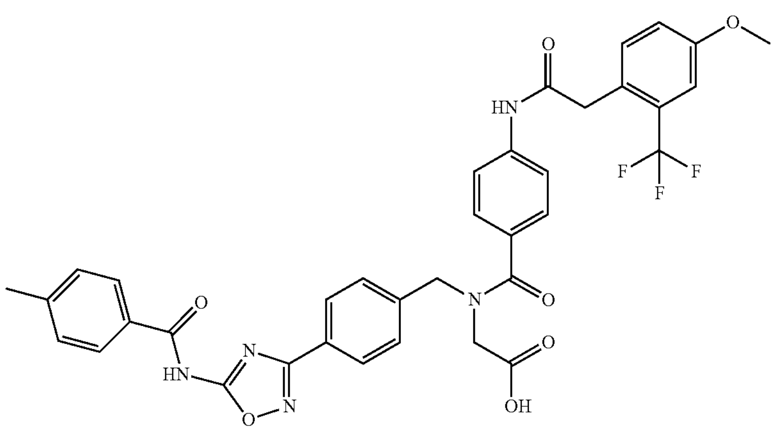 | 479 | 6.54 |
| 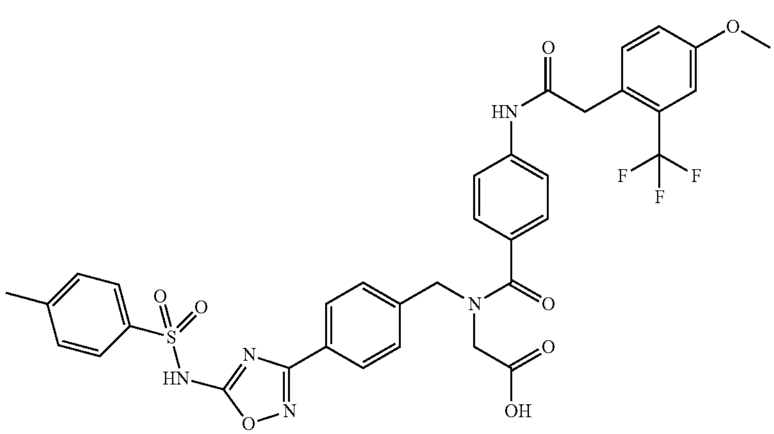 | 480 | 5.74 |

TABLE 1-continued

| STRUCTURE | COMPOUND NUMBER | LCMS RETENTION TIME (min) |
|---|---|---|
| 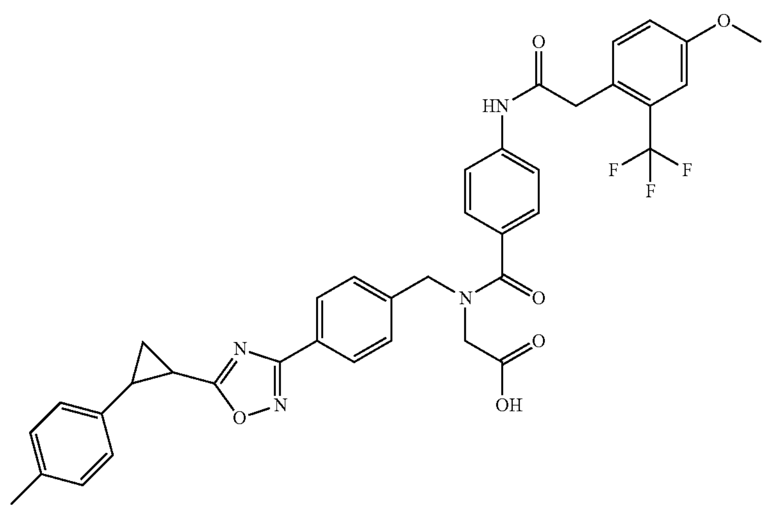 | 481 | 8.26 |
| 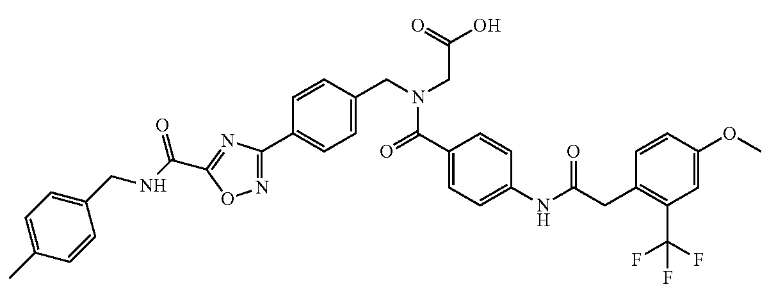 | 482 | 7.11 |
| 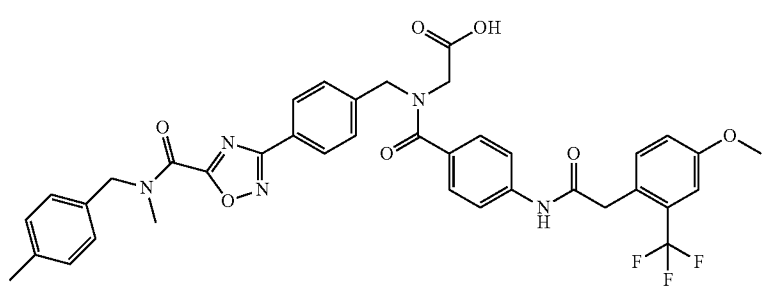 | 483 | 7.41 |

TABLE 1-continued
| STRUCTURE | COMPOUND NUMBER | LCMS RETENTION TIME (min) |
|---|---|---|
| 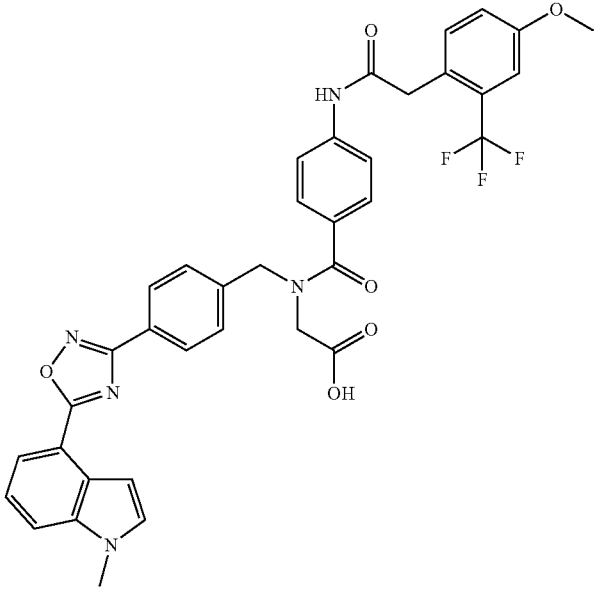 [SMILES: COc1ccc(CC(=O)Nc2ccc(C(=O)N(CC(=O)O)Cc3ccc(-c4noc(-c5cccc6c5ccn6C)n4)cc3)cc2)c(C(F)(F)F)c1] | 484 | 9.39 |
| 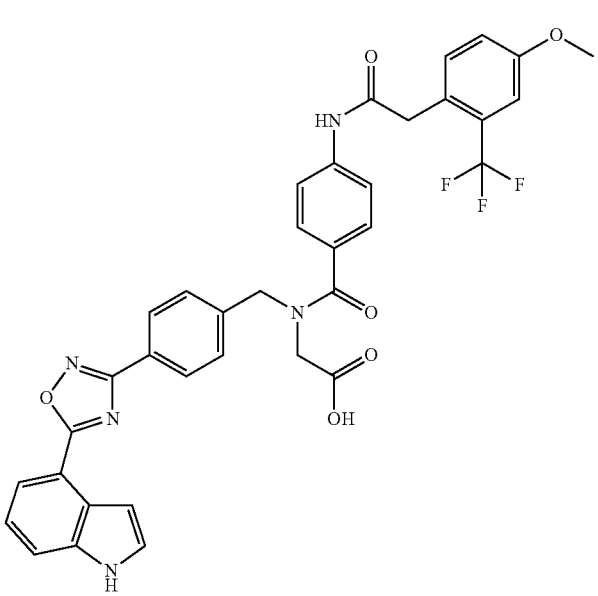 [SMILES: COc1ccc(CC(=O)Nc2ccc(C(=O)N(CC(=O)O)Cc3ccc(-c4noc(-c5cccc6[nH]ccc56)n4)cc3)cc2)c(C(F)(F)F)c1] | 485 | 8.60 |

TABLE 1-continued
| STRUCTURE | COMPOUND NUMBER | LCMS RETENTION TIME (min) |
|---|---|---|
| 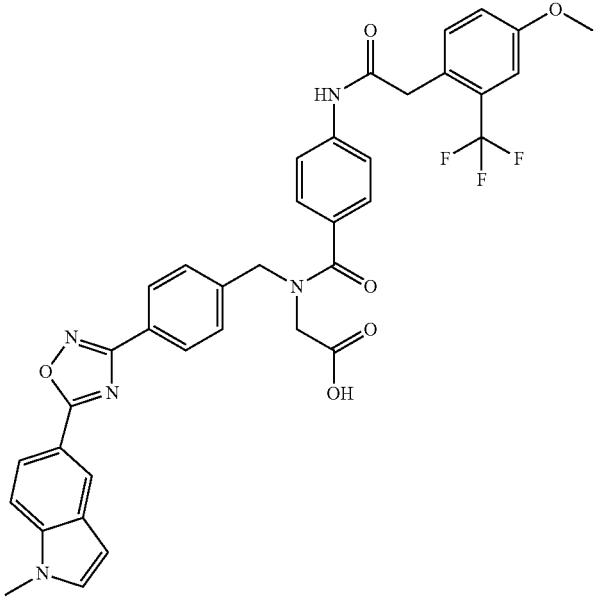 | 486 | 9.37 |
| 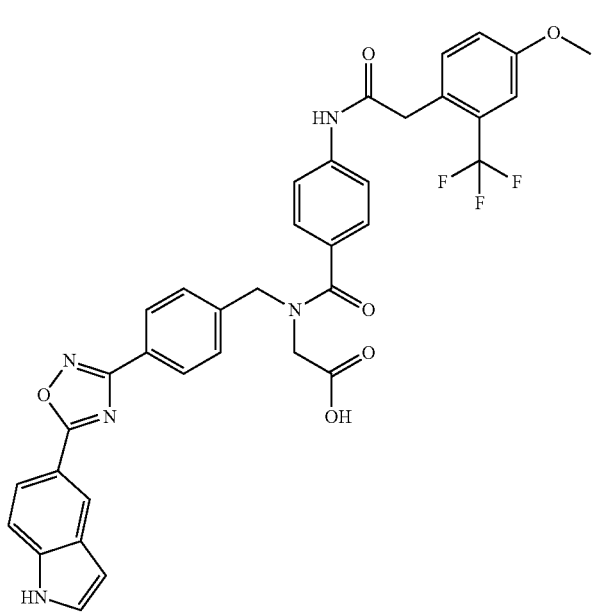 [SMILES: COc1ccc(CC(=O)Nc2ccc(C(=O)N(CC(=O)O)Cc3ccc(-c4noc(-c5ccc6[nH]ccc6c5)n4)cc3)cc2)c(C(F)(F)F)c1] | 487 | 8.70 |

TABLE 1-continued

| STRUCTURE | COMPOUND NUMBER | LCMS RETENTION TIME (min) |
|---|---|---|
| 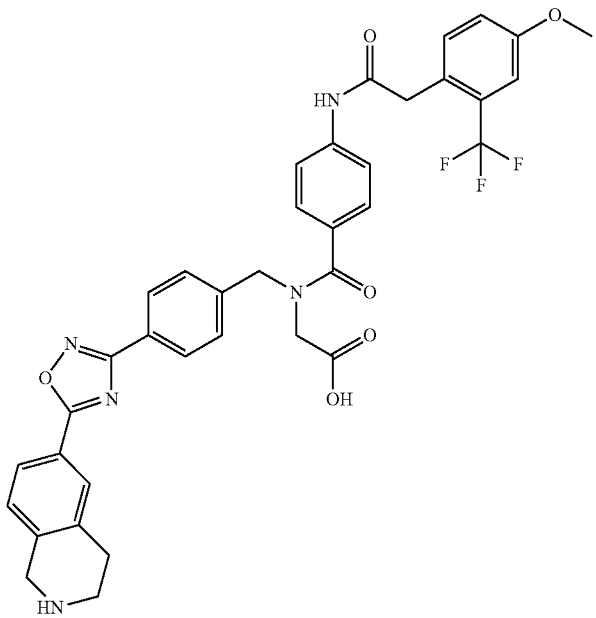 [SMILES: COc1ccc(CC(=O)Nc2ccc(C(=O)N(CC(=O)O)Cc3ccc(-c4noc(-c5ccc6c(c5)CCNC6)n4)cc3)cc2)c(C(F)(F)F)c1] | 488 | 6.55 |
| 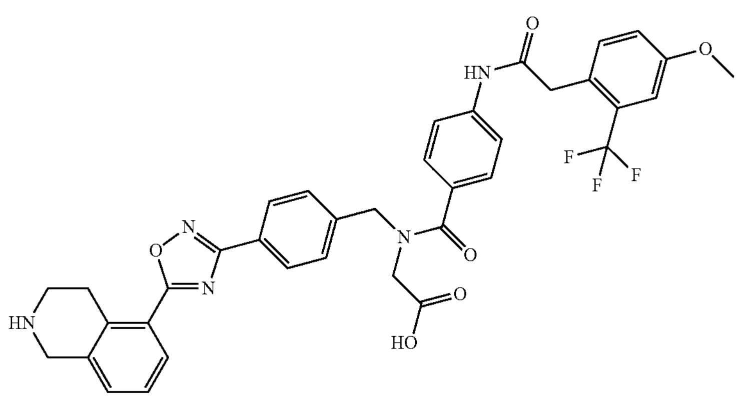 [SMILES: COc1ccc(CC(=O)Nc2ccc(C(=O)N(CC(=O)O)Cc3ccc(-c4noc(-c5cccc6c5CCNC6)n4)cc3)cc2)c(C(F)(F)F)c1] | 489 | 6.66 |
| 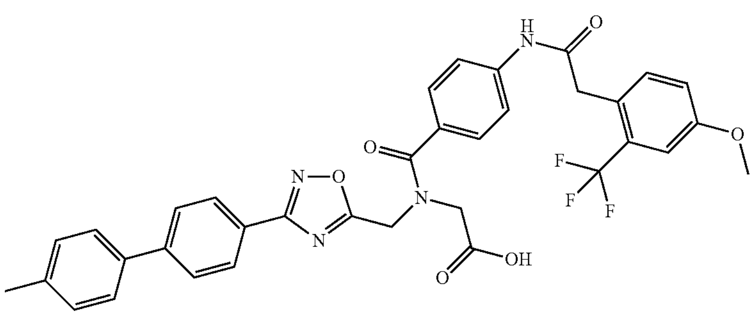 | 490 | 8.04 |

TABLE 1-continued

| STRUCTURE | COMPOUND NUMBER | LCMS RETENTION TIME (min) |
|---|---|---|
| 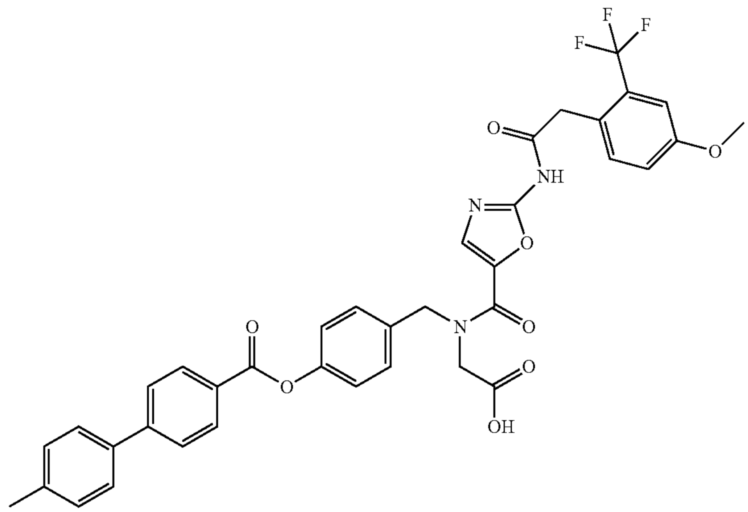 | 491 | 9.82 |
| 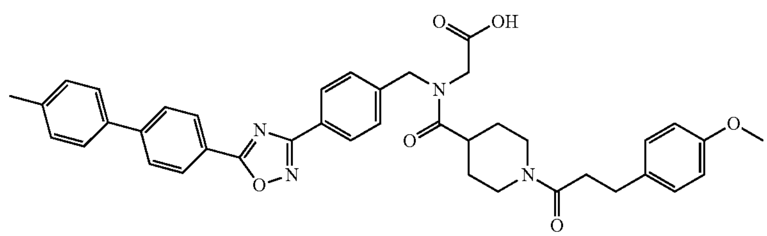 | 492 | 10.05 |
| 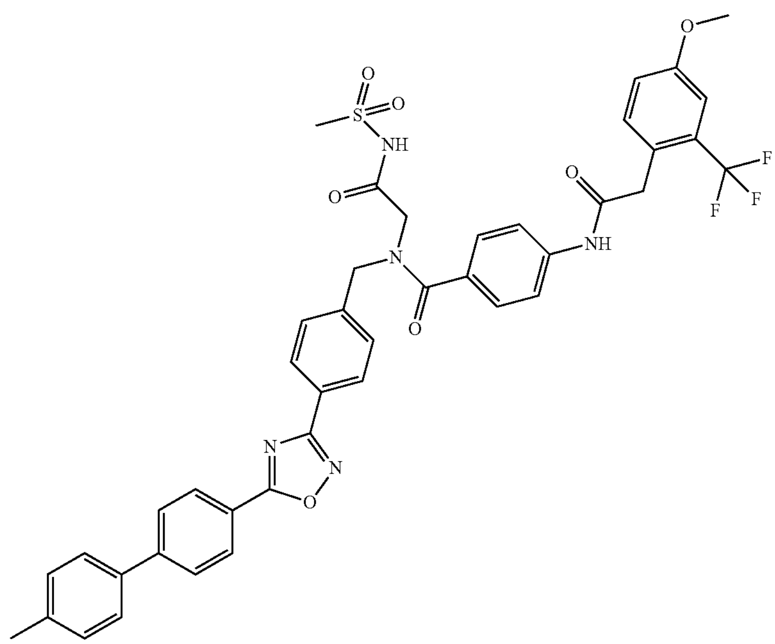 [SMILES: COc1ccc(CC(=O)Nc2ccc(C(=O)N(CC(=O)NS(C)(=O)=O)Cc3ccc(-c4noc(-c5ccc(-c6ccc(C)cc6)cc5)n4)cc3)cc2)c(C(F)(F)F)c1] | 493 | 11.03 |

TABLE 1-continued

| STRUCTURE | COMPOUND NUMBER | LCMS RETENTION TIME (min) |
|---|---|---|
| 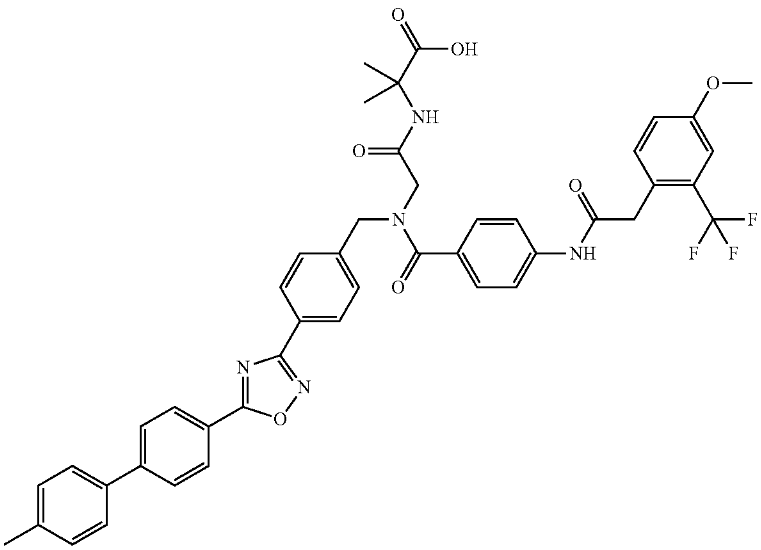 [SMILES: COc1ccc(CC(=O)Nc2ccc(C(=O)N(CC(=O)NC(C)(C)C(=O)O)Cc3ccc(-c4noc(-c5ccc(-c6ccc(C)cc6)cc5)n4)cc3)cc2)c(C(F)(F)F)c1] | 494 | 11.67 |
| 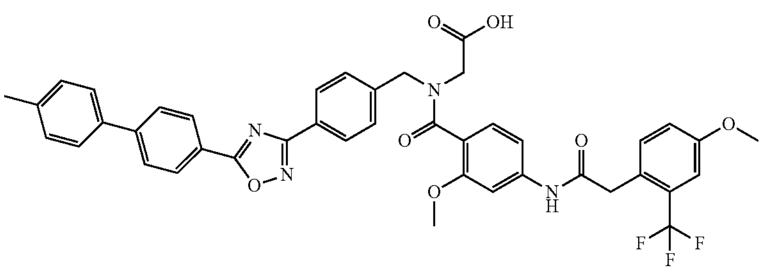 | 495 | 9.49 |
| 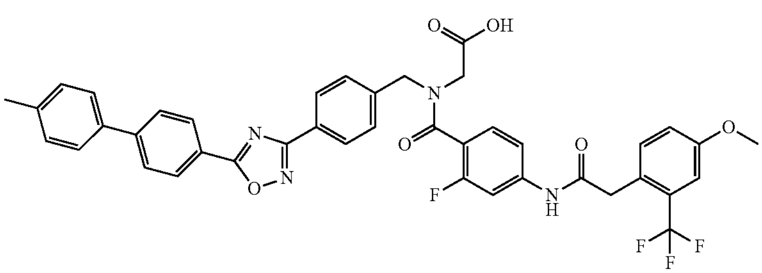 | 496 | 9.64 |
| 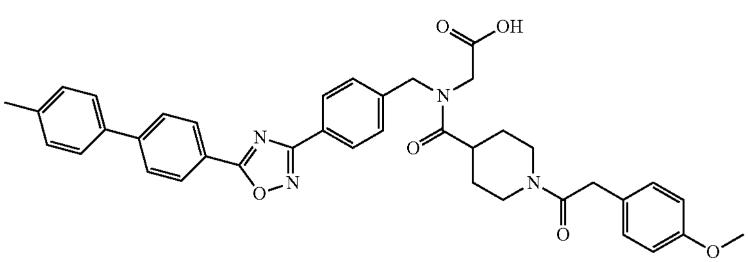 | 497 | 10.02 |

TABLE 1-continued

| STRUCTURE | COMPOUND NUMBER | LCMS RETENTION TIME (min) |
|---|---|---|
| 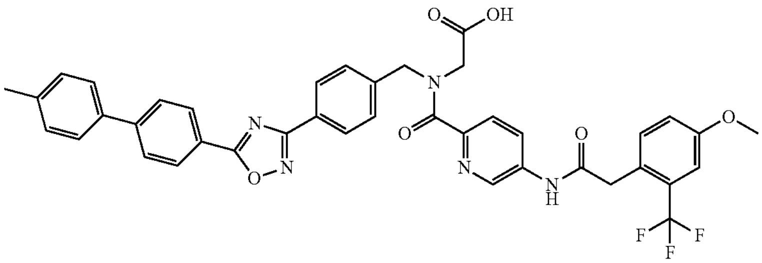 | 498 | 9.27 |
| 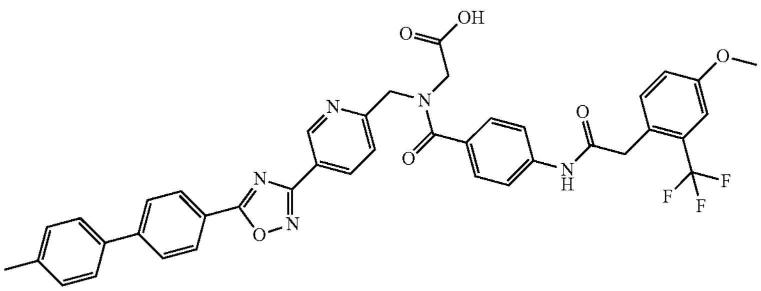 | 499 | 8.82 |
| 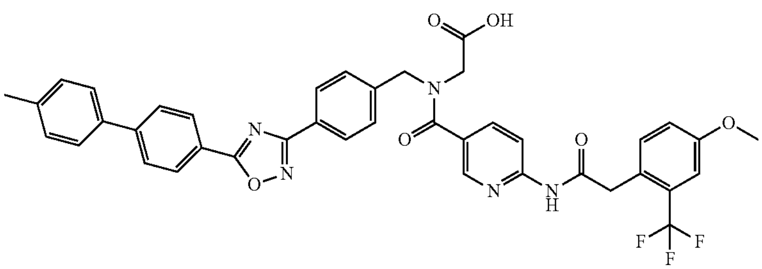 | 500 | 9.35 |
| 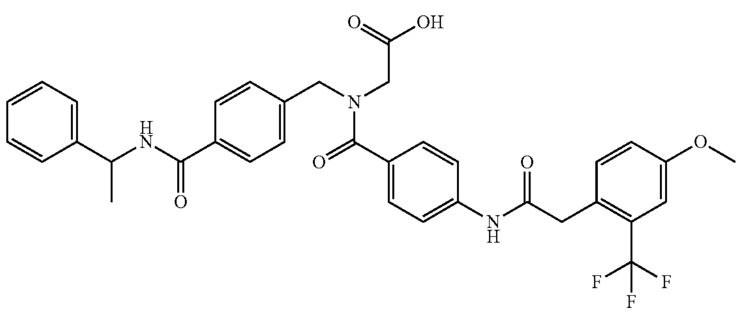 [SMILES: COc1ccc(CC(=O)Nc2ccc(C(=O)N(CC(=O)O)Cc3ccc(C(=O)NC(C)c4ccccc4)cc3)cc2)c(C(F)(F)F)c1] | 501 | 6.22 |
| 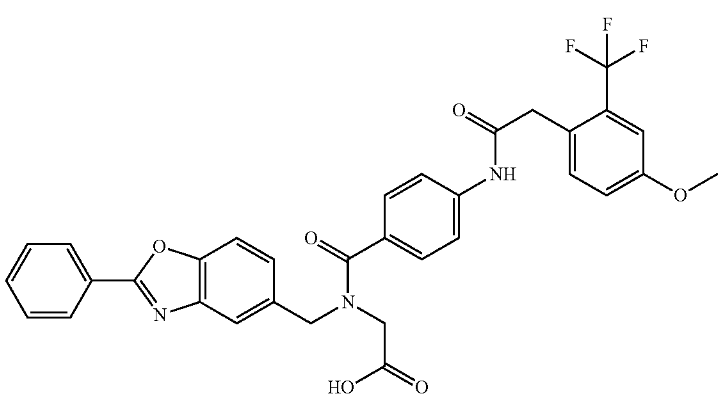 [SMILES: COc1ccc(CC(=O)Nc2ccc(C(=O)N(CC(=O)O)Cc3ccc4oc(-c5ccccc5)nc4c3)cc2)c(C(F)(F)F)c1] | 502 | 6.88 |

TABLE 1-continued

| STRUCTURE | COMPOUND NUMBER | LCMS RETENTION TIME (min) |
|---|---|---|
| 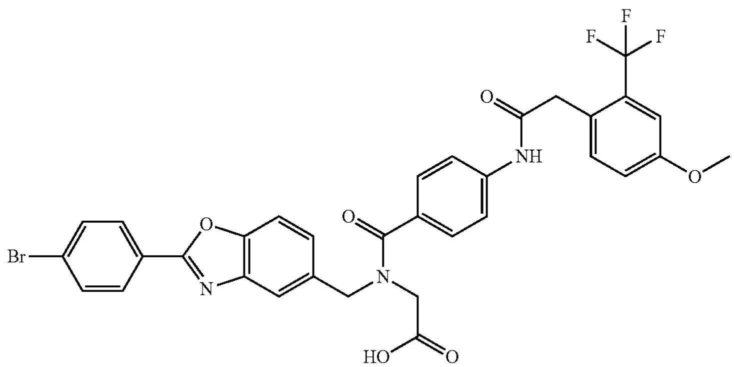 [SMILES: COc1ccc(CC(=O)Nc2ccc(C(=O)N(CC(=O)O)Cc3ccc4oc(-c5ccc(Br)cc5)nc4c3)cc2)c(C(F)(F)F)c1] | 503 | 7.76 |
| 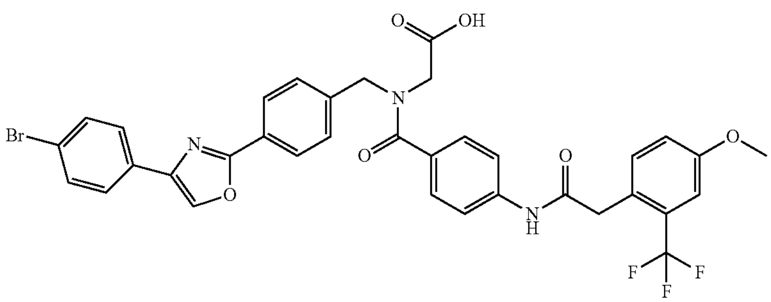 | 504 | 8.23 |
| 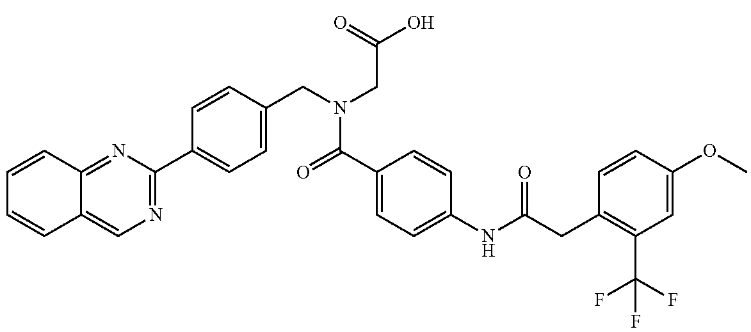 [SMILES: COc1ccc(CC(=O)Nc2ccc(C(=O)N(CC(=O)O)Cc3ccc(-c4ncc5ccccc5n4)cc3)cc2)c(C(F)(F)F)c1] | 505 | 8.59 |
| 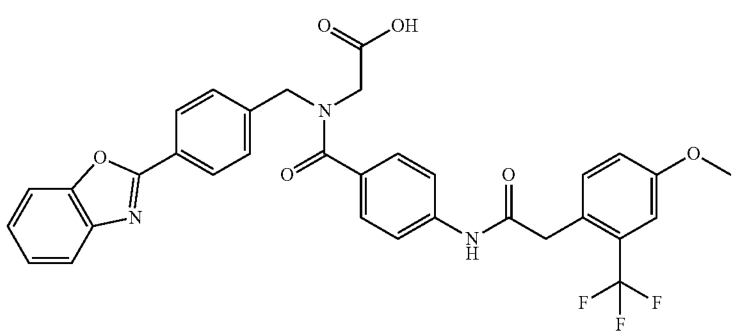 [SMILES: COc1ccc(CC(=O)Nc2ccc(C(=O)N(CC(=O)O)Cc3ccc(-c4nc5ccccc5o4)cc3)cc2)c(C(F)(F)F)c1] | 506 | 8.63 |

TABLE 1-continued
| STRUCTURE | COMPOUND NUMBER | LCMS RETENTION TIME (min) |
|---|---|---|
| 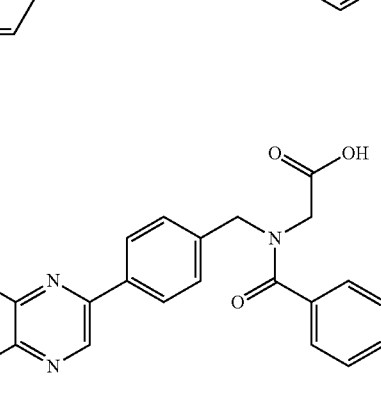 | 507 | 9.01 |
| 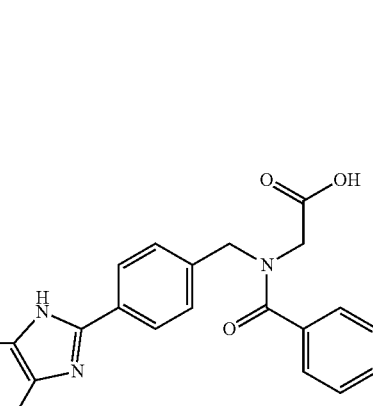 | 508 | 8.30 |
| 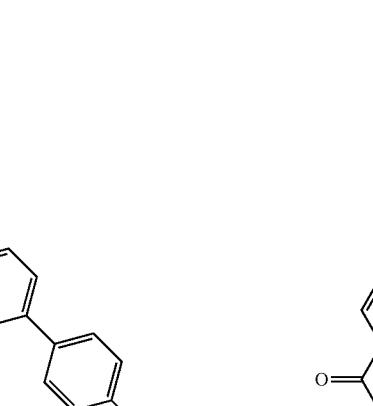 | 509 | 6.52 |
| 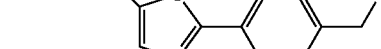 | 510 | 8.91 |

TABLE 1-continued
| STRUCTURE | COMPOUND NUMBER | LCMS RETENTION TIME (min) |
|---|---|---|
| 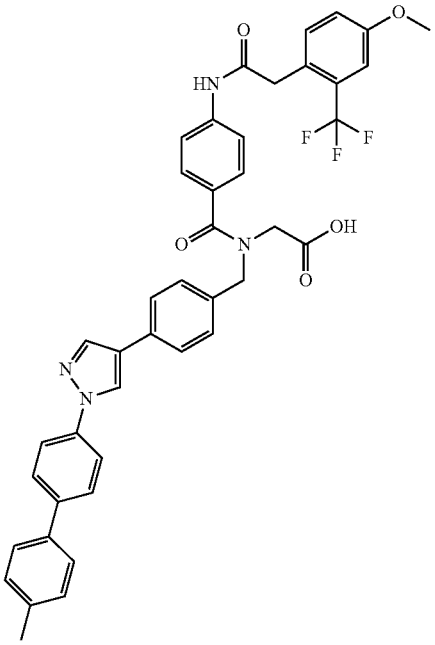 [SMILES: COc1ccc(CC(=O)Nc2ccc(C(=O)N(CC(=O)O)Cc3ccc(-c4cnn(-c5ccc(-c6ccc(C)cc6)cc5)c4)cc3)cc2)c(C(F)(F)F)c1] | 511 | 8.80 |
| 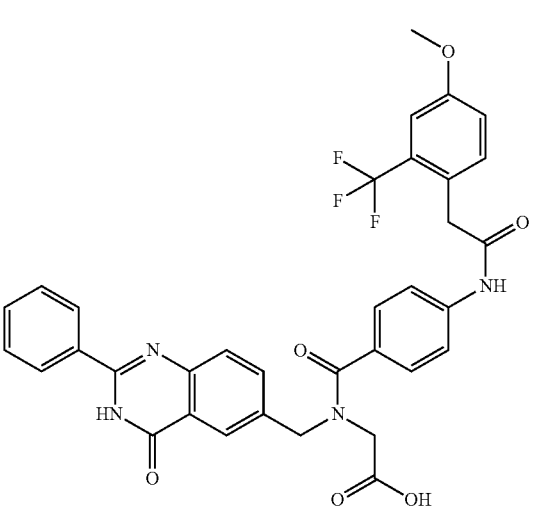 [SMILES: COc1ccc(CC(=O)Nc2ccc(C(=O)N(CC(=O)O)Cc3ccc4nc(-c5ccccc5)[nH]c(=O)c4c3)cc2)c(C(F)(F)F)c1] | 512 | 5.65 |

TABLE 1-continued
| STRUCTURE | COMPOUND NUMBER | LCMS RETENTION TIME (min) |
|---|---|---|
| 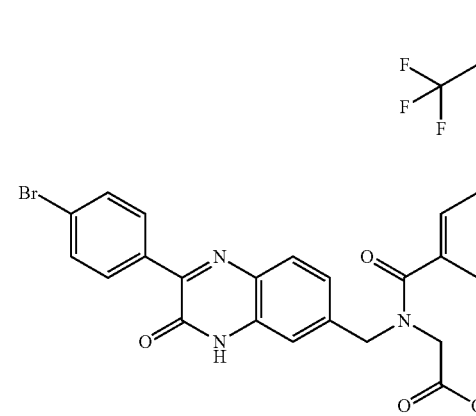 | 513 | 7.03 |
| 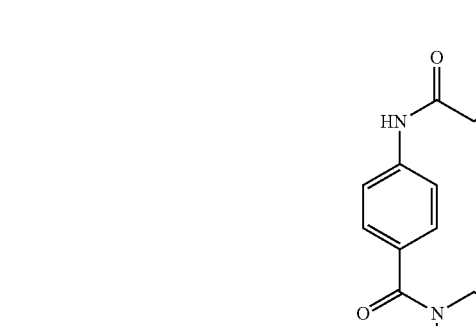 | 514 | 9.08 |
| 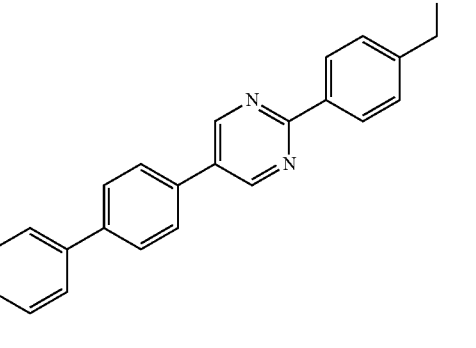 | 515 | 6.79 |

Biological Assays

Assay Procedures
GLP-1 PAM Shift cAMP Assay: Dose Response of Peptide Ligand in Presence of Fixed Concentration of Compound A GLP-1R expressing CRE-bla CHO-K1 cell line was purchased from Invitrogen. Cells were seeded into 384-well white flat bottom plates at 5000 cells/well/20 μl growth media (DMEM-High glucose, 10% dialyzed FBS, 0.1 mM NEAA, 25 mM Hepes, 100 U/mL penicillin/100 μg/mL streptomycin, 5 μg/mL Blasticidin, 600 μg/mL Hygromycin) and incubated for 18 h at 37° C. in 5% $CO_2$. Growth medium was replaced with 12 μL assay buffer (Hanks Balanced Salt solution, 10 mM Hepes, 0.1% BSA, pH7.4). A 5× peptide dose response curve (12-point) was generated in assay buffer containing 1.5 mM IBMX, 12.5% DMSO, and 50 μM compound. Peptide ligand was either GLP-1(9-36) or RP-101868. The 5× peptide dose response plus compound mix was added (3 μL) and cells were incubated for 30 min at 37° C. Direct detection of cAMP was carried out using DiscoveRx HitHunter cAMP kit according to manufacturer's instructions and luminescence was read using a SpectraMax M5 plate reader. Luminescence was analyzed by non-linear regression to determine the $EC_{50}$ and Emax. A GLP-1(7-36) dose response was included to determine maximum efficacy.

$EC_{20}$GLP-1(9-36) PAM cAMP Assay: Dose Response of Compound in the Presence of Fixed Concentration of GLP-1 (9-36)

GLP-1R CRE-bla CHO-K1 cells were seeded into 384-well white flat bottom plates at 10,000 cells/well/20 μL growth medium (DMEM-High glucose, 10% dialyzed FBS, 0.1 mM NEAA, 25 mM Hepes, 100 U/mL penicillin/100 μg/mL streptomycin, 5 μg/mL Blasticidin, 600 μg/mL Hygromycin) and incubated for 18 h at 37° C. in 5% $CO_2$. Growth medium was replaced with 12 μL assay buffer (Hanks Balanced Salt solution, 10 mM Hepes, 0.1% BSA, pH7.4). A 5× compound dose response curve (12-point) was generated in assay buffer containing 1.5 mM IBMX, 12.5% DMSO. GLP-1(9-36) was diluted to 4.2 μM in assay buffer containing 1.5 mM IBMX and 12.5% DMSO. The 5× compound dose response was added (3 μL), followed by 0.5 μL of GLP-1(9-36) and cells were incubated for 30 min at 37° C. Direct detection of cAMP was carried out using DiscoveRx HitHunter cAMP kit according to manufacturer's instructions and luminescence was read using a SpectraMax M5 plate reader. Luminescence was converted to total cAMP using a cAMP standard curve and data was analyzed by non-linear regression to determine the $EC_{50}$ and Emax.

Peptide Sequences:

```
                                      (SEQ ID NO: 1)
GLP-1 (7-36): HAEGTFTSDVSSYLEGQAAKEFIAWLVKGR-NH2

(SEQ ID NO: 2)
GLP-1 (9-36): EGTFTSDVSSYLEGQAAKEFIAWLVKGR-NH2

(SEQ ID NO: 3)
RP-101868: GEGTFTS-Nle-LSKQMEEEAVRLFIEWLKNGR-NH2
```

GLP-1 (7-36) was purchased from GenScript. GLP-1 (9-36) and RP-101868 (Ex RPG-14) were purchased from Biopeptide Co., Inc.

Reported GLP-1 Activity

Activity data for selected GLP-1 modulators is displayed in Table 2. The GLP-1 (9-36) PAM Activity range is denoted as follows: + denotes activity <10 nM, ++ denotes activity between 10 to 100 nM, and +++ denotes activity between 100 to 1000 nM, and ++++ denotes activity >1000 nM. N/A denotes not available. The $EC_{20}$ GLP-1 (9-36) PAM Activity range is denoted as follows: + denotes activity <1++ denotes activity between 1 to 5 μM, and +++ denotes activity between 5 to 10 μM, and ++++ denotes activity >10 μM. N/A denotes not available.

TABLE 2

| COMPOUND NUMBER | GLP-1 (9-36) PAM Activity | $EC_{20}$ GLP-1 (9-36) PAM Activity |
|---|---|---|
| 1 | ++ | ++ |
| 2 | ++ | N/A |
| 3 | + | ++ |
| 4 | ++ | ++ |
| 5 | ++ | ++ |
| 6 | ++ | ++ |
| 7 | +++ | N/A |
| 8 | ++ | +++ |
| 9 | ++ | +++ |
| 10 | ++ | ++ |
| 11 | ++ | ++ |
| 12 | ++ | +++ |
| 13 | ++ | ++ |
| 14 | ++ | +++ |
| 15 | ++ | +++ |
| 16 | ++ | ++ |
| 17 | ++ | ++ |
| 18 | ++ | ++ |
| 19 | ++ | ++++ |
| 20 | +++ | ++++ |
| 21 | +++ | ++++ |
| 22 | +++ | ++++ |
| 23 | ++++ | ++++ |
| 24 | ++++ | N/A |
| 25 | ++++ | N/A |
| 26 | ++++ | N/A |
| 27 | ++++ | N/A |
| 28 | ++++ | N/A |
| 29 | ++++ | N/A |
| 30 | ++++ | N/A |
| 31 | +++ | N/A |
| 32 | ++ | ++++ |
| 33 | ++++ | N/A |
| 34 | ++++ | N/A |
| 35 | +++ | N/A |
| 36 | +++ | N/A |
| 37 | +++ | N/A |
| 38 | +++ | N/A |
| 39 | ++ | ++ |
| 40 | ++ | ++ |
| 41 | +++ | N/A |
| 42 | +++ | N/A |
| 43 | ++++ | N/A |
| 44 | ++++ | N/A |
| 45 | +++ | N/A |
| 46 | ++ | +++ |
| 47 | +++ | N/A |
| 48 | ++++ | N/A |
| 49 | ++++ | N/A |
| 50 | ++++ | N/A |
| 51 | +++ | N/A |
| 52 | +++ | N/A |
| 53 | ++ | ++++ |
| 54 | ++++ | N/A |
| 55 | ++++ | N/A |
| 56 | +++ | N/A |
| 57 | +++ | N/A |
| 58 | +++ | N/A |
| 59 | +++ | N/A |
| 60 | +++ | N/A |
| 61 | ++ | ++++ |
| 62 | +++ | N/A |
| 63 | ++++ | N/A |
| 64 | +++ | N/A |

TABLE 2-continued

| COMPOUND NUMBER | GLP-1 (9-36) PAM Activity | EC$_{20}$ GLP-1 (9-36) PAM Activity |
|---|---|---|
| 65 | +++ | N/A |
| 66 | +++ | ++++ |
| 67 | +++ | ++++ |
| 68 | N/A | N/A |
| 69 | ++++ | N/A |
| 70 | +++ | N/A |
| 71 | +++ | N/A |
| 72 | +++ | N/A |
| 73 | +++ | ++++ |
| 74 | ++++ | ++++ |
| 75 | ++++ | ++++ |
| 76 | +++ | ++++ |
| 77 | +++ | N/A |
| 78 | +++ | N/A |
| 79 | N/A | N/A |
| 80 | +++ | ++++ |
| 81 | ++ | N/A |
| 82 | ++++ | ++++ |
| 83 | ++++ | ++++ |
| 84 | ++++ | N/A |
| 85 | +++ | ++++ |
| 86 | ++ | ++ |
| 87 | +++ | N/A |
| 88 | +++ | ++++ |
| 89 | +++ | ++++ |
| 90 | +++ | ++++ |
| 91 | ++++ | N/A |
| 92 | +++ | ++++ |
| 93 | +++ | ++++ |
| 94 | +++ | N/A |
| 95 | +++ | N/A |
| 96 | +++ | N/A |
| 97 | +++ | N/A |
| 98 | +++ | N/A |
| 99 | +++ | N/A |
| 100 | +++ | N/A |
| 101 | +++ | N/A |
| 102 | +++ | N/A |
| 103 | +++ | N/A |
| 104 | +++ | N/A |
| 105 | +++ | +++ |
| 106 | ++ | ++ |
| 107 | ++ | ++ |
| 108 | ++ | ++ |
| 109 | ++++ | N/A |
| 110 | ++++ | N/A |
| 111 | +++ | N/A |
| 112 | ++++ | N/A |
| 113 | +++ | N/A |
| 114 | +++ | N/A |
| 115 | ++++ | N/A |
| 116 | ++ | +++ |
| 117 | +++ | N/A |
| 118 | ++ | ++++ |
| 119 | ++ | ++ |
| 120 | ++ | +++ |
| 121 | ++ | ++ |
| 122 | ++ | ++ |
| 123 | ++ | N/A |
| 124 | ++ | ++++ |
| 125 | +++ | N/A |
| 126 | +++ | N/A |
| 127 | ++ | ++ |
| 128 | +++ | ++++ |
| 129 | +++ | N/A |
| 130 | +++ | N/A |
| 131 | +++ | ++++ |
| 132 | +++ | N/A |
| 133 | +++ | ++++ |
| 134 | +++ | N/A |
| 135 | +++ | N/A |
| 136 | +++ | N/A |
| 137 | +++ | N/A |
| 138 | +++ | N/A |
| 139 | ++++ | N/A |
| 140 | ++++ | N/A |
| 141 | +++ | N/A |
| 142 | +++ | N/A |
| 143 | +++ | N/A |
| 144 | +++ | N/A |
| 145 | +++ | N/A |
| 146 | +++ | N/A |
| 147 | +++ | N/A |
| 148 | +++ | N/A |
| 149 | +++ | N/A |
| 150 | +++ | +++ |
| 151 | +++ | N/A |
| 152 | +++ | N/A |
| 153 | +++ | N/A |
| 154 | +++ | N/A |
| 155 | +++ | N/A |
| 156 | +++ | N/A |
| 157 | +++ | N/A |
| 158 | +++ | N/A |
| 159 | +++ | N/A |
| 160 | +++ | ++++ |
| 161 | +++ | ++++ |
| 162 | +++ | +++ |
| 163 | +++ | N/A |
| 164 | +++ | N/A |
| 165 | +++ | ++++ |
| 166 | +++ | +++ |
| 167 | +++ | N/A |
| 168 | ++++ | N/A |
| 169 | ++++ | N/A |
| 170 | +++ | N/A |
| 171 | +++ | N/A |
| 172 | +++ | N/A |
| 173 | ++++ | N/A |
| 174 | +++ | N/A |
| 175 | +++ | ++++ |
| 176 | +++ | N/A |
| 177 | +++ | ++++ |
| 178 | +++ | ++++ |
| 179 | +++ | N/A |
| 180 | +++ | N/A |
| 181 | +++ | ++++ |
| 182 | +++ | ++++ |
| 183 | +++ | N/A |
| 184 | +++ | N/A |
| 185 | +++ | N/A |
| 186 | +++ | N/A |
| 187 | +++ | N/A |
| 188 | ++ | +++ |
| 189 | ++++ | N/A |
| 190 | +++ | N/A |
| 191 | +++ | N/A |
| 192 | ++ | ++ |
| 193 | ++++ | N/A |
| 194 | ++ | +++ |
| 195 | ++ | ++ |
| 196 | ++ | ++ |
| 197 | +++ | +++ |
| 198 | ++ | ++ |
| 199 | ++ | ++ |
| 200 | ++ | ++ |
| 201 | ++ | ++ |
| 202 | ++ | ++ |
| 203 | ++ | ++ |
| 204 | +++ | ++ |
| 205 | +++ | N/A |
| 206 | ++ | ++ |
| 207 | ++ | N/A |
| 208 | ++ | N/A |
| 209 | ++ | ++ |
| 210 | ++ | N/A |
| 211 | ++ | N/A |
| 212 | ++ | ++ |

TABLE 2-continued

| COMPOUND NUMBER | GLP-1 (9-36) PAM Activity | $EC_{20}$ GLP-1 (9-36) PAM Activity |
|---|---|---|
| 213 | ++ | N/A |
| 214 | ++ | +++ |
| 215 | ++ | +++ |
| 216 | ++ | ++ |
| 217 | +++ | N/A |
| 218 | +++ | N/A |
| 219 | ++++ | N/A |
| 220 | +++ | N/A |
| 221 | +++ | N/A |
| 222 | +++ | N/A |
| 223 | +++ | N/A |
| 224 | ++++ | ++++ |
| 225 | ++ | ++ |
| 226 | ++ | +++ |
| 227 | +++ | N/A |
| 228 | +++ | N/A |
| 229 | +++ | ++++ |
| 230 | +++ | N/A |
| 231 | +++ | N/A |
| 232 | +++ | ++++ |
| 233 | +++ | N/A |
| 234 | +++ | N/A |
| 235 | +++ | ++++ |
| 236 | +++ | N/A |
| 237 | +++ | N/A |
| 238 | ++ | +++ |
| 239 | +++ | N/A |
| 240 | +++ | N/A |
| 241 | +++ | N/A |
| 242 | ++++ | ++++ |
| 243 | +++ | ++++ |
| 244 | +++ | N/A |
| 245 | +++ | N/A |
| 246 | +++ | ++++ |
| 247 | ++++ | N/A |
| 248 | +++ | ++++ |
| 249 | +++ | N/A |
| 250 | +++ | N/A |
| 251 | +++ | N/A |
| 252 | ++++ | N/A |
| 253 | +++ | N/A |
| 254 | +++ | N/A |
| 255 | +++ | N/A |
| 256 | +++ | N/A |
| 257 | +++ | N/A |
| 258 | +++ | N/A |
| 259 | +++ | N/A |
| 260 | +++ | N/A |
| 261 | +++ | N/A |
| 262 | +++ | N/A |
| 263 | +++ | N/A |
| 264 | +++ | N/A |
| 265 | +++ | N/A |
| 266 | +++ | N/A |
| 267 | +++ | +++ |
| 268 | +++ | N/A |
| 269 | +++ | N/A |
| 270 | ++++ | N/A |
| 271 | +++ | N/A |
| 272 | ++ | ++ |
| 273 | +++ | N/A |
| 274 | +++ | N/A |
| 275 | +++ | N/A |
| 276 | ++++ | N/A |
| 277 | ++++ | N/A |
| 278 | +++ | N/A |
| 279 | ++ | ++ |
| 280 | +++ | N/A |
| 281 | +++ | ++++ |
| 282 | ++ | ++ |
| 283 | ++ | ++ |
| 284 | ++ | ++ |
| 285 | ++ | ++ |
| 286 | +++ | N/A |
| 287 | ++ | ++++ |
| 288 | +++ | ++ |
| 289 | +++ | ++++ |
| 290 | +++ | ++ |
| 291 | ++ | ++ |
| 292 | +++ | ++ |
| 293 | ++ | ++ |
| 294 | +++ | +++ |
| 295 | +++ | N/A |
| 296 | ++++ | N/A |
| 297 | ++ | ++ |
| 298 | ++ | ++ |
| 299 | ++ | ++ |
| 300 | ++ | + |
| 301 | +++ | ++++ |
| 302 | ++ | ++ |
| 303 | ++ | ++ |
| 304 | +++ | +++ |
| 305 | ++ | ++ |
| 306 | ++ | ++ |
| 307 | ++ | ++ |
| 308 | +++ | ++ |
| 309 | +++ | + |
| 310 | ++ | ++ |
| 311 | ++ | ++ |
| 312 | ++ | N/A |
| 313 | ++ | + |
| 314 | ++ | + |
| 315 | ++ | ++ |
| 316 | ++ | ++ |
| 317 | +++ | N/A |
| 318 | ++++ | N/A |
| 319 | ++ | ++++ |
| 320 | ++ | ++ |
| 321 | ++ | ++ |
| 322 | +++ | N/A |
| 323 | +++ | ++ |
| 324 | ++ | + |
| 325 | ++ | + |
| 326 | ++ | + |
| 327 | +++ | N/A |
| 328 | +++ | ++++ |
| 329 | +++ | ++++ |
| 330 | +++ | ++++ |
| 331 | ++++ | N/A |
| 332 | +++ | N/A |
| 333 | ++ | +++ |
| 334 | +++ | ++++ |
| 335 | ++ | ++++ |
| 336 | ++ | ++++ |
| 337 | +++ | N/A |
| 338 | +++ | ++++ |
| 339 | ++++ | N/A |
| 340 | ++ | ++++ |
| 341 | +++ | ++++ |
| 342 | +++ | N/A |
| 343 | +++ | N/A |
| 344 | +++ | N/A |
| 345 | +++ | N/A |
| 346 | +++ | N/A |
| 347 | +++ | ++++ |
| 348 | +++ | N/A |
| 349 | ++ | + |
| 350 | +++ | ++++ |
| 351 | +++ | ++++ |
| 352 | +++ | ++++ |
| 353 | +++ | N/A |
| 354 | ++ | + |
| 355 | ++ | ++ |
| 356 | ++ | ++ |
| 357 | +++ | N/A |
| 358 | +++ | N/A |
| 359 | ++ | ++ |
| 360 | ++ | + |

TABLE 2-continued

| COMPOUND NUMBER | GLP-1 (9-36) PAM Activity | EC$_{20}$ GLP-1 (9-36) PAM Activity |
|---|---|---|
| 361 | ++ | ++ |
| 362 | ++ | + |
| 363 | ++ | ++ |
| 364 | ++ | + |
| 365 | ++ | ++ |
| 366 | +++ | N/A |
| 367 | ++ | ++ |
| 368 | ++ | +++ |
| 369 | ++ | ++ |
| 370 | +++ | ++++ |
| 371 | +++ | N/A |
| 372 | +++ | N/A |
| 373 | +++ | N/A |
| 374 | ++++ | N/A |
| 375 | +++ | N/A |
| 376 | +++ | N/A |
| 377 | ++++ | N/A |
| 378 | +++ | N/A |
| 379 | +++ | N/A |
| 380 | +++ | N/A |
| 381 | +++ | N/A |
| 382 | +++ | N/A |
| 383 | +++ | N/A |
| 384 | +++ | N/A |
| 385 | +++ | ++++ |
| 386 | +++ | N/A |
| 387 | ++++ | N/A |
| 388 | +++ | N/A |
| 389 | ++++ | N/A |
| 390 | +++ | N/A |
| 391 | +++ | ++++ |
| 392 | +++ | N/A |
| 393 | ++ | ++ |
| 394 | N/A | ++ |
| 395 | N/A | + |
| 396 | N/A | + |
| 397 | N/A | ++ |
| 398 | N/A | + |
| 399 | N/A | + |
| 400 | N/A | ++ |
| 401 | N/A | + |
| 402 | N/A | + |
| 403 | N/A | + |
| 404 | N/A | + |
| 405 | N/A | + |
| 406 | N/A | + |
| 407 | N/A | + |
| 408 | N/A | + |
| 409 | N/A | + |
| 410 | N/A | + |
| 411 | N/A | + |
| 412 | N/A | ++++ |
| 413 | N/A | ++ |
| 414 | N/A | ++ |
| 415 | N/A | + |
| 416 | N/A | + |
| 417 | N/A | + |
| 418 | N/A | + |
| 419 | N/A | ++++ |
| 420 | N/A | + |
| 421 | N/A | + |
| 422 | N/A | ++++ |
| 423 | N/A | + |
| 424 | N/A | ++ |
| 425 | N/A | ++++ |
| 426 | N/A | ++ |
| 427 | N/A | ++++ |
| 428 | N/A | ++++ |
| 429 | N/A | ++ |
| 430 | N/A | ++ |
| 431 | N/A | + |
| 432 | N/A | ++++ |
| 433 | N/A | ++++ |
| 434 | N/A | ++++ |
| 435 | N/A | ++++ |
| 436 | N/A | ++++ |
| 437 | N/A | + |
| 438 | N/A | ++++ |
| 439 | N/A | ++++ |
| 440 | N/A | ++++ |
| 441 | N/A | + |
| 442 | N/A | + |
| 443 | N/A | ++++ |
| 444 | N/A | ++++ |
| 445 | N/A | ++++ |
| 446 | N/A | ++++ |
| 447 | N/A | + |
| 448 | N/A | ++++ |
| 449 | N/A | +++ |
| 450 | N/A | ++ |
| 451 | N/A | ++++ |
| 452 | N/A | + |
| 453 | N/A | ++ |
| 454 | N/A | + |
| 455 | N/A | + |
| 456 | N/A | + |
| 457 | N/A | + |
| 458 | N/A | + |
| 459 | N/A | + |
| 460 | N/A | ++++ |
| 461 | N/A | ++++ |
| 462 | N/A | +++ |
| 463 | N/A | ++ |
| 464 | N/A | ++++ |
| 465 | N/A | ++++ |
| 466 | N/A | ++++ |
| 467 | N/A | ++ |
| 468 | N/A | +++ |
| 469 | N/A | ++++ |
| 470 | N/A | ++++ |
| 471 | N/A | ++ |
| 472 | N/A | ++++ |
| 473 | N/A | +++ |
| 474 | N/A | ++ |
| 475 | N/A | ++ |
| 476 | N/A | ++++ |
| 477 | N/A | ++++ |
| 478 | N/A | ++++ |
| 479 | N/A | ++++ |
| 480 | N/A | ++++ |
| 481 | N/A | ++++ |
| 482 | N/A | ++++ |
| 483 | N/A | ++++ |
| 484 | N/A | ++++ |
| 485 | N/A | ++++ |
| 486 | N/A | +++ |
| 487 | N/A | ++++ |
| 488 | N/A | ++++ |
| 489 | N/A | ++++ |
| 490 | N/A | ++++ |
| 491 | N/A | ++ |
| 492 | N/A | + |
| 493 | N/A | + |
| 494 | N/A | + |
| 495 | N/A | + |
| 496 | N/A | + |
| 497 | N/A | ++ |
| 498 | N/A | + |
| 499 | N/A | ++ |
| 500 | N/A | + |
| 501 | N/A | ++++ |
| 502 | N/A | ++++ |
| 503 | N/A | ++++ |
| 504 | N/A | ++ |
| 505 | N/A | ++++ |
| 506 | N/A | ++++ |
| 507 | N/A | ++++ |
| 508 | N/A | ++++ |

TABLE 2-continued

| COMPOUND NUMBER | GLP-1 (9-36) PAM Activity | EC$_{20}$ GLP-1 (9-36) PAM Activity |
|---|---|---|
| 509 | N/A | ++++ |
| 510 | N/A | ++ |
| 511 | N/A | + |
| 512 | N/A | ++++ |
| 513 | N/A | ++++ |
| 514 | N/A | ++ |
| 515 | N/A | ++++ |

Reported GLP-1 Activity

Activity data for selected GLP-1 modulators is displayed in Table 3. The GLP-1 (RP-101868) PAM Activity range is denoted as follows: + denotes activity <10 nM, ++ denotes activity between 10 to 100 nM, and +++ denotes activity between 100 to 1000 nM, and ++++ denotes activity >1000 nM. N/A denotes not available.

TABLE 3

| COMPOUND NUMBER | GLP-1 (RP-101868) PAM Activity |
|---|---|
| 1 | + |
| 2 | ++ |
| 73 | +++ |
| 74 | ++++ |
| 79 | +++ |
| 80 | ++ |
| 81 | +++ |

Pharmacokinetic Assay

Determination of Absolute Oral Bioavailability in Rats

All pharmacokinetic studies were conducted in fasted female Sprague-Dawely rats (Simonsen Laboratories or Harlan Laboratories). Rats were housed in an ALAAC accredited facility and the research was approved by the facilities Institutional Animal Care and Use Committee (IACUC). The animals were acclimated to the laboratory for at least 48 h prior to initiation of experiments.

Compounds were formulated in 20% hydroxy beta cyclodextrin or 20% captisol and 80%-25 mM NaPO$_4$ Buffer (pH 8) (intravenous infusion), or 5% DMSO/5% Tween20 and 90% water (oral gavage or intraperitoneal injection). The concentration of the dosing solutions was verified by HPLC-UV. For intravenous dosing, compounds were administered into the tail vein to manually restrained animals (n=3 rats/compound). The intravenous dose was 1 mg/kg. Oral dosing was by gavage using a standard stainless steel gavage needle (n=2-4 rats/compound). The oral solution dose was 5 mg/kg. For compounds 1 and 3, the oral solution dose was 30 mg/kg. For both routes of administration, blood was collected into BD Microtainer tubes with Dipotassium EDTA as the anticoagulantant eight time-points after dosing with the final sample drawn 24 h post dose Plasma was separated by centrifugation and transferred to a polypropylene 96-well plate and kept at 4° C. until analysis.

Proteins were precipitated by adding 150 μL acetonitrile to 50 μL of plasma. Plates were mixed for 1 min on a plate shaker to facilitate protein precipitation and then centrifuged at 3,000 rpm for 10 min to pellet protein. The supernatant was transferred to a clean plate and centrifuged at 3,000 rpm for 10 min to pellet any remaining solid material prior to LC/MS/MS analysis. Calibration curve standards were prepared by spiking 54 compound stock in DMSO into rat plasma from untreated animals. An eight point standard curve spanning a range of 0.14 nM to 300 nM was included with each bio-analytical run. The standards were processed identically to the rat pharmacokinetic samples.

Concentrations in the rat pharmacokinetic samples were determined using a standardized HPLC-LC/MS/MS method relative to the eight point standard curve. The system consisted of a Leap CTC Pal injector, Agilent 1200 HPLC with binary pump coupled with an Applied Biosystems 4000 QTrap. Compounds were chromatographed on a Phenomenex Luna C8(2) 20×2 mm 2 um Mercury Cartridge with Security Guard. A gradient method was used with mobile phase A consisting of 0.1% formic acid in water and mobile phase B consisting of 0.1% formic acid in acetonitrile at flow rates varying from 0.7 to 0.8 mL/min. Ions were generated in positive ionization mode using an electrospray ionization (ESI) interface. Multiple reaction monitoring (MRM) methods were developed specific to each compound. The heated nebulizer was set at 500° C. with a nebulizer current of 5.1 μA. Collision energies used to generate daughter ions ranged between 29 and 80 V. Peak area obtained from MRM of the mass transitions specific for each compound were used for quantification. The limit of quantification of the method was typically 1.2 nM. Data were collected and analyzed using Analyst software version 1.5.1. Blood concentration versus time data were analyzed using non-compartmental methods (WinNonlin Phoenix version 6.2; model 200 for oral or intraperitoneal dosing and model 202 for intravenous infusion). Absolute oral bioavailability (%) was calculated using the following expression: (Oral AUC×IV Dose)/(IV AUC×Oral Dose)×100.

Activity data and PK data for selected GLP-1 modulators is displayed in Table 4. N/A denotes not available.

TABLE 4

| COMPOUND NUMBER | EC$_{20}$ GLP-1 (9-36) PAM Activity EC$_{50}$ (μM) | EC$_{20}$ GLP-1 (9-36) PAM Activity max cAMP (nM) | Rat-Oral Bioavailability (%) |
|---|---|---|---|
| 1 | 3.6 | 240 | <1.0 |
| 3 | 1.3 | 284 | <1.0 |
| 4 | 2.4 | 371 | N/A |
| 16 | 1.2 | 293 | N/A |
| 17 | 1.5 | 281 | N/A |
| 18 | 3.1 | 182 | N/A |
| 39 | 2.5 | 273 | N/A |
| 40 | 2.1 | 397 | N/A |
| 46 | 7.0 | 252 | N/A |
| 192 | 1.3 | 248 | N/A |
| 314 | 0.5 | 307 | N/A |
| 354 | 0.3 | 297 | 2.0 |
| 355 | 2.9 | 266 | 2.0 |
| 360 | 0.5 | 290 | 2.0 |
| 361 | 2.7 | 234 | N/A |
| 362 | 0.3 | 281 | 8.0 |
| 363 | 3.2 | 237 | 3.0 |
| 364 | 0.4 | 278 | 10.0 |
| 405 | 0.3 | 206 | 8.0 |
| 411 | 0.2 | 258 | 10.0 |
| 441 | 0.5 | 167 | 5.0 |
| 457 | 0.2 | 266 | 19.4 |
| 458 | 0.2 | 302 | 14.8 |
| 496 | 0.5 | 310 | 7.0 |

We claim:
1. A method of treating type II diabetes in a subject in need thereof, said method comprising administering to said subject a pharmaceutical composition comprising a compound having a structure of Formula I:

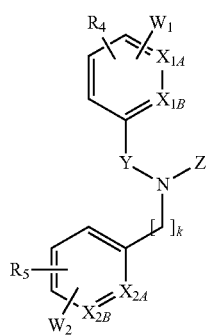

or a pharmaceutically acceptable salt thereof, wherein
each of $X_{1A}$, $X_{1B}$, $X_{2A}$ and $X_{2B}$ is CH;
$R_4$ is H, alkyl, alkoxy, alkyl substituted with one or more $R_{43}$, halogen, perhaloalkyl, perhaloalkoxy, —CN, —$OR_{40}$, or —$NR_{41}R_{42}$;
$W_1$ is -$L_1$-$CH_2$-$R_1$;
$L_1$ is —NH—C(O)—;
$R_1$ is $R_{13}$;
each $R_{10}$, $R_{11}$ and $R_{12}$ is independently H or alkyl;
$R_{13}$ is phenyl, where any ring atom of $R_{13}$ may be optionally substituted with one or more $R_{14}$ or $R_{15}$;
each $R_{14}$ is independently H, alkyl, halo, hydroxy, cyano, alkoxy, perhaloalkyl, perhaloalkoxy, —$OR_{10}$, —$(CH_2)_n$—$COOR_{10}$, —$SR_{10}$, —SO—$R_{10}$, —$SO_2R_{10}$, —$(CH_2)_n$—$NR_{11}R_{12}$, —$NHCO(CH_2)_n$—$R_{12}$, —$N(R_{11})CO(CH_2)_n$—$R_{12}$, or —$NH(CH_2)_n$—$R_{12}$;
each $R_{15}$ is cycloalkyl, heterocyclylalkyl, aryl, heteroaryl, or a fused bicycle of any two of such ring moieties, where any ring atom of $R_{15}$ may be optionally substituted with one or more $R_{14}$;
$R_5$ is independently H, alkyl, alkoxy, alkyl substituted with one or more $R_{53}$, halogen, perhaloalkyl, perhaloalkoxy, —CN, —$OR_{50}$, or —$NR_{51}R_{52}$;
$W_2$ is -$L_2$-$R_2$;
$L_2$ is 1,2,4-oxadiazol-3-yl;
each $R_a$ and $R_b$ is independently H, hydroxy, methyl, or both $R_a$ and $R_b$ attached to the same carbon are, taken together, oxo, or cycloalkyl;
$R_2$ is $R_{26}$, —O—$(CH_2)_n$—$R_{26}$, $R_{23}$ or -$L_4$-$R_{23}$;
$L_4$ is —O—$(CH_2)_n$—, —C≡C—, —C(O)$NR_{20}$—$(CH_2)_n$—, —$N(R_{20})$—C(O)—$(CH_2)_n$—, —$N(R_{20})$—$S(O_2)$—, —$S(O_2)$—$NR_{20}$—, or cyclopropylene;
each $R_{20}$ is independently H or alkyl;
$R_{23}$ is cycloalkyl, heterocyclylalkyl, aryl, heteroaryl, or a fused bicycle of any two of such ring moieties, or $R_{23}$ and $R_{20}$ taken together with the N atom to which they are attached form a heterocyclic ring optionally fused with aryl or heteroaryl, where any ring atom of $R_{23}$ may be optionally substituted with one or more of $R_{24}$ and wherein one ring atom of $R_{23}$ is optionally substituted with -$L_3$-$R_{25}$;

each $R_{24}$ is independently H, halo, alkyl, hydroxy, oxo, cyano, alkoxy, perhaloalkyl, perhaloalkoxy, nitro or amino, —O—$(CH_2)_n$—$R_{21}$, —$(CH_2)_n$—O—$R_{21}$, —O$(CH_2)_n$—O—$R_{21}$, —$(CH_2)_n$—$NR_{21}R_{22}$, —$(CH_2)_n$—$N(R_{21})CO(CH_2)_n$—$R_{21}$, —$(CH_2)_n$—N$(R_{21})SO_2(CH_2)_n$—$R_{21}$, —$(CH_2)_n$—$SO_2$—$N(R_{21})$—$(CH_2)_n$—$R_{21}$, —$(CH_2)_n$—$CO(CH_2)_n$—$R_{21}$, —$(CH_2)_m$—COO—$R_{21}$, —O—$(CH_2)_n$—COO—$R_{21}$ or —$(CH_2)_m$—OCO—$R_{21}$;
each $R_{21}$ and $R_{22}$ is independently H, alkyl, or —$(CH_2)_n$—COOH, or $R_{21}$ and $R_{22}$ taken together with the nitrogen atom to which they are attached form a 3- to 7-membered heterocyclic ring;
$L_3$ is null, —O—, —$(CH_2)_n$—O—$(CH_2)_n$—, or —$(CH_2)_n$—$NR_{20}$—$(CH_2)_n$—;
each $R_{25}$ is independently cycloalkyl, heterocyclylalkyl, aryl, or heteroaryl, or a fused bicycle of any two of such ring moieties 1, where any ring atom of $R_{25}$ may be optionally substituted with one or more of $R_{24}$;
$R_{26}$ is H, alkyl, alkoxy, oxo, hydroxy, or hydroxy substituted alkyl;
Y is —C(O)—, —$CH_2$—, —C(O)—$CH_2$—, or —$CH_2$—C(O)—;
Z is —$(CR_aR_b)_n$—C(O)—$R_3$, —$(CR_aR_b)_n$—$R_3$, —$R_{34}$—C(O)—$R_3$, or H;
$R_3$ is —$OR_{30}$, —$NR_{31}R_{32}$ or —(CO)$NHSO_2R_{30}$;
each $R_{30}$ is independently H or alkyl;
each $R_{31}$ and $R_{32}$ is independently H or $C_1$-$C_6$ alkyl optionally substituted with one or more $R_{33}$, or $R_{31}$ and $R_{32}$ taken together with the N atom to which they are attached form a 3- to 7-membered heterocyclic ring;
each $R_{33}$ is independently halo, hydroxyl, alkoxy, perhaloalkyl, perhaloalkoxy, carboxyl, —COO—$R_{30}$, or —$OR_{30}$;
$R_{34}$ is cycloalkyl, heterocyclylalkyl, aryl, or heteroaryl, where any ring atom of $R_{34}$ may be optionally substituted with one or more $R_{35}$;
each $R_{35}$ is independently H, alkyl, halo, hydroxy, cyano, alkoxy or perhaloalkyl;
each $R_{40}$ and $R_{50}$ is independently H or alkyl;
each $R_{41}$ and $R_{42}$ is independently H, alkyl, —$(CH_2)_n$—COO—$R_{40}$, —C(O)—$R_{40}$, aryl, or heteroaryl, or $R_{41}$ and $R_{42}$ taken together with the N atom to which they are attached form a 3- to 7-membered heterocyclic ring;
each $R_{51}$ and $R_{52}$ is independently H or alkyl, —$(CH_2)_n$—COO—$R_{50}$, —C(O)—$R_{50}$, aryl, heteroaryl, or $R_{51}$ and $R_{52}$ taken together with the N atom to which they are attached form a 3- to 7-membered heterocyclic ring;
each $R_{43}$ is independently H, halo, hydroxyl, —$NR_{41}R_{42}$, or alkoxy;
each $R_{53}$ is independently H, halo, hydroxyl, —$NR_{51}R_{52}$, or alkoxy;
k is 1, 2, 3 or 4;
each m is independently 0 or 1;
each n is independently 0, 1, 2, 3 or 4;
wherein each occurrence of heterocyclyl is independently an aromatic or non-aromatic ring moiety, mono-cyclic or fused poly-cyclic, containing 3 to 20 ring members and with at least one heteroatom selected from N, O, S and P; and wherein each occurrence of heteroaryl is independently an aromatic ring moiety, mono-cylic or fused poly-cyclic, containing 5 to 20 ring members and with at least one heteroatom selected from N, O, S and P, and in the case of a fused poly-cyclic heteroaryl at least one ring is aromatic.

2. The method of claim 1 wherein the subject is a human being.

3. The method of claim 1, wherein the compound has the structure of Formula II:

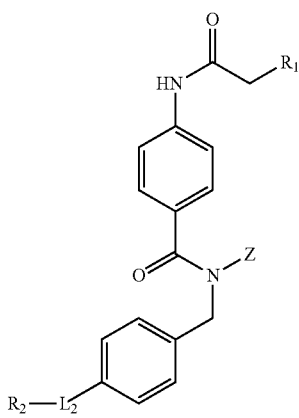

or a pharmaceutically acceptable salt thereof, wherein
$R_1$ is $R_{13}$;
each $R_{10}$, $R_{11}$ and $R_{12}$ is independently H or alkyl;
$R_{13}$ is phenyl, where any ring atom of $R_{13}$ may be optionally substituted with one or more $R_{14}$ or $R_{15}$;
each $R_{14}$ is independently H, alkyl, halo, hydroxy, cyano, alkoxy, perhaloalkyl, perhaloalkoxy, —$OR_{10}$, —$(CH_2)_n$—$COOR_{10}$, —$SR_{10}$, —$SO$—$R_{10}$, —$SO_2R_{10}$, —$NR_{11}R_{12}$, —$NHCO(CH_2)_n$—$R_{12}$, —$N(R_{11})CO(CH_2)_n$—$R_{12}$, or —$NH(CH_2)_nR_{12}$;
each $R_{15}$ is cycloalkyl, heterocyclylalkyl, aryl, heteroaryl, or a fused bicycle of any two of such ring moieties, where any ring atom of $R_{15}$ may be optionally substituted with one or more $R_{14}$;
$L_2$ is 1,2,4-oxadiazol-3-yl;
$R_2$ is $R_{26}$, —O—$(CH_2)_n$—$R_{26}$, $R_{23}$ or —O—$(CH_2)_n$—$R_{23}$;
each $R_{20}$ is independently H or alkyl;
$R_{23}$ is cycloalkyl, heterocyclylalkyl, aryl, heteroaryl, or a fused bicycle of any two of such ring moieties;
each $R_{24}$ is independently H, halo, alkyl, hydroxy, oxo, cyano, alkoxy, perhaloalkyl, perhaloalkoxy, nitro or amino, —O—$(CH_2)_n$—$R_{21}$, —$(CH_2)_n$—O—$R_{21}$, —O—$(CH_2)_n$—O—$R_{21}$, —$(CH_2)_n$—$NR_{21}R_{22}$, —$(CH_2)_n$—N($R_{21}$)CO($CH_2)_n$—$R_{21}$, —$(CH_2)_n$—N($R_{21}$)$SO_2(CH_2)_n$—$R_{21}$, —$(CH_2)_n$—$SO_2$—N($R_{21}$)—$(CH_2)_n$—$R_{21}$, —$(CH_2)_n$—CO($CH_2)_n$—$R_{21}$, —$(CH_2)_m$—COO—$R_{21}$, —O—$(CH_2)_n$—COO—$R_{21}$ or —$(CH_2)_m$—OCO—$R_{21}$;
each $R_{21}$ and $R_{22}$ is independently H, alkyl, —$(CH_2)_n$—COOH, or $R_{21}$ and $R_{22}$ taken together with the nitrogen atom to which they are attached form a 3- to 7-membered heterocyclic ring;
$L_3$ is null, —O—, —$(CH_2)_n$—O—$(CH_2)_n$—, or —$(CH_2)_b$—$NR_{20}$—$(CH_2)_n$—;

each $R_{25}$ is independently cycloalkyl, heterocyclylalkyl, aryl, or heteroaryl, or a fused bicycle of any two of such ring moieties 1, where any ring atom of $R_{25}$ may be optionally substituted with one or more of $R_{24}$;
each $R_{26}$ is independently H, alkyl, alkoxy, oxo, hydroxy, or hydroxy substituted alkyl;
Z is —$(CH_2)_n$—C(O)—$R_3$, —$(CH_2)_n$—$R_3$, —$R_{34}$—C(O)—$R_3$ or H;
$R_{34}$ is cycloalkyl, heterocyclylalkyl, aryl, or heteroaryl, where any ring atom of $R_{34}$ may be optionally substituted with one or more $R_{35}$;
each $R_{35}$ is independently H, alkyl, halo, hydroxy, cyano, alkoxy or perhaloalkyl;
$R_3$ is —$OR_{30}$, or —$NR_{31}R_{32}$;
each $R_{30}$ is independently H or alkyl;
each $R_{31}$ and $R_{32}$ is independently H or $C_1$-$C_6$ alkyl optionally substituted with one or more $R_{33}$, or $R_{31}$ and $R_{32}$ taken together with the N atom to which they are attached form a 3- to 7-membered heterocyclic ring;
each $R_{33}$ is independently halo, hydroxyl, alkoxy, perhaloalkyl, perhaloalkoxy, carboxyl, —COO—$R_{30}$, or —$OR_{30}$;
each m is independently 0 or 1;
each n is independently 0, 1, 2, 3 or 4;
wherein each occurrence of heterocyclyl is independently an aromatic or non-aromatic ring moiety, mono-cyclic or fused poly-cyclic, containing 3 to 20 ring members and with at least one heteroatom selected from N, O, S and P; and
wherein each occurrence of heteroaryl is independently an aromatic ring moiety, mono-cylic or fused poly-cyclic, containing 5 to 20 ring members and with at least one heteroatom selected from N, O, S and P, and in the case of a fused poly-cyclic heteroaryl at least one ring is aromatic.

4. The method of claim 3 wherein $R_1$ is substituted with one or more substituents selected independently from the group consisting of methyl, ethyl, isopropyl, t-butyl, —$CF_3$, methoxy, ethoxy, hydroxyl, —$OCF_3$, halogen, methylthio, and —$SO_2CH_3$.

5. The method of claim 4 wherein $R_1$ is substituted with one or more substituents selected independently from the group consisting of methyl, methoxy, and —$CF_3$.

6. The method of claim 4 wherein $R_1$ is

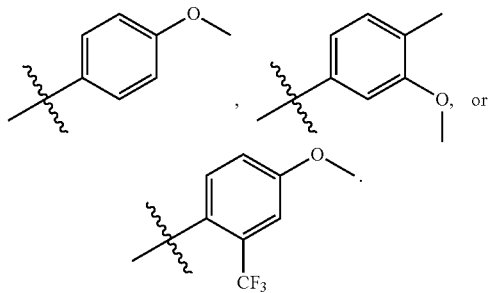

7. The method of claim 1 wherein the compound is selected from one of the following compounds:

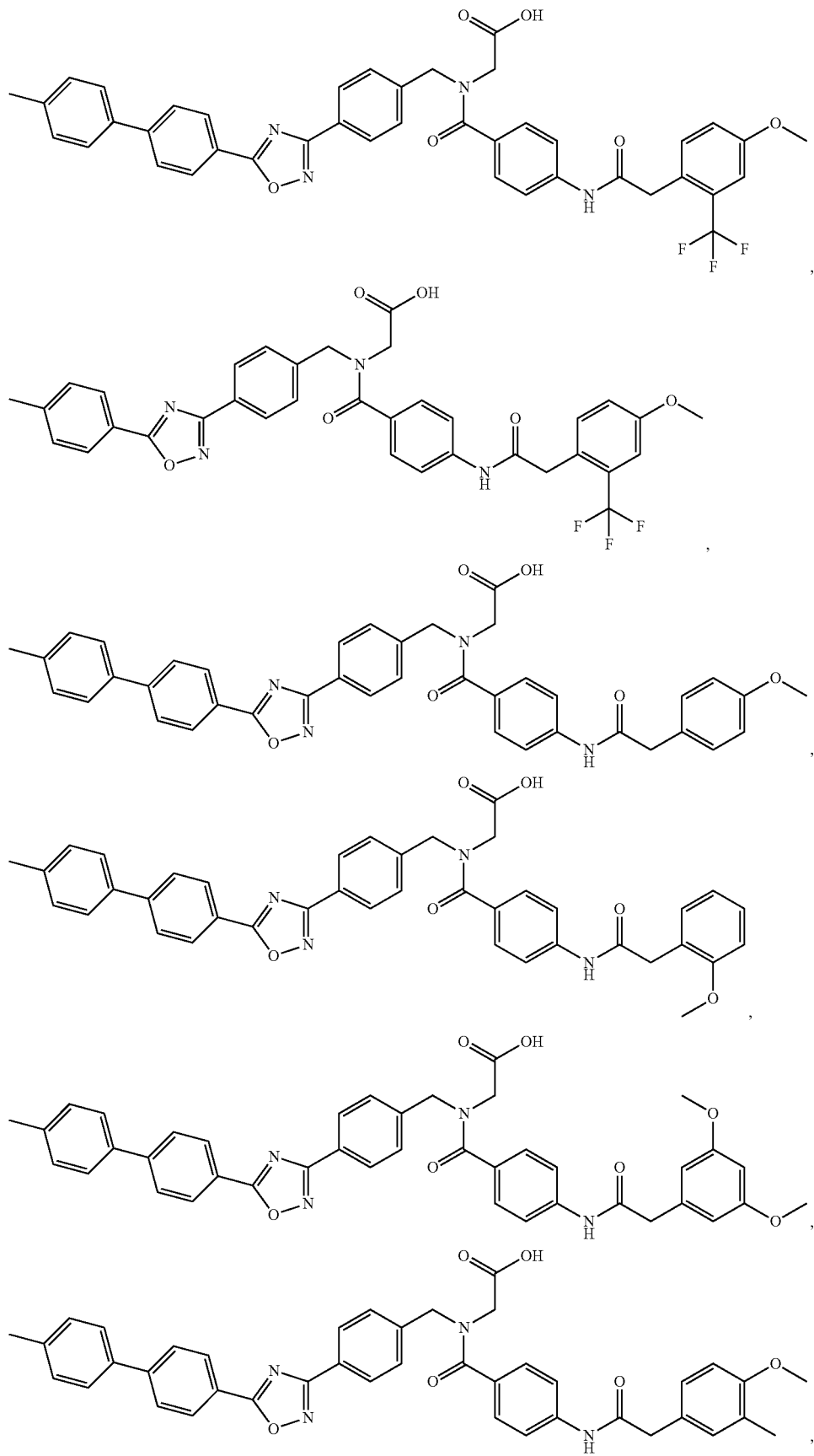

-continued
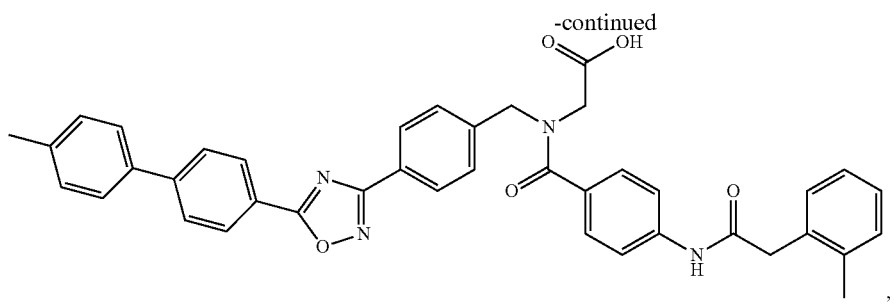
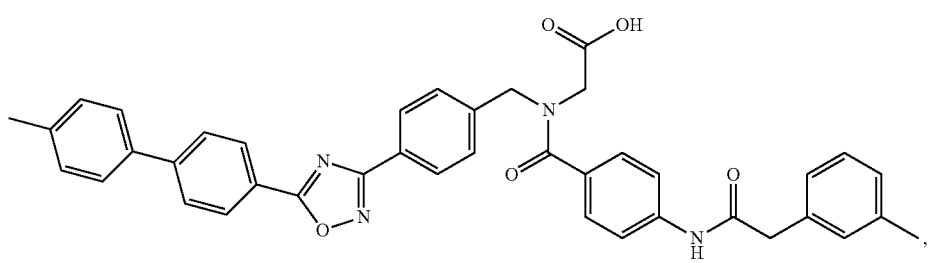
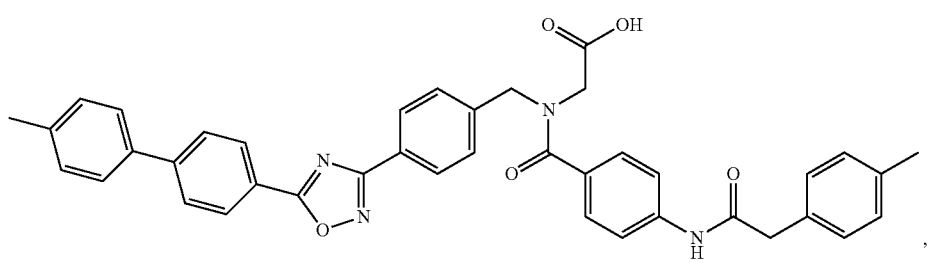
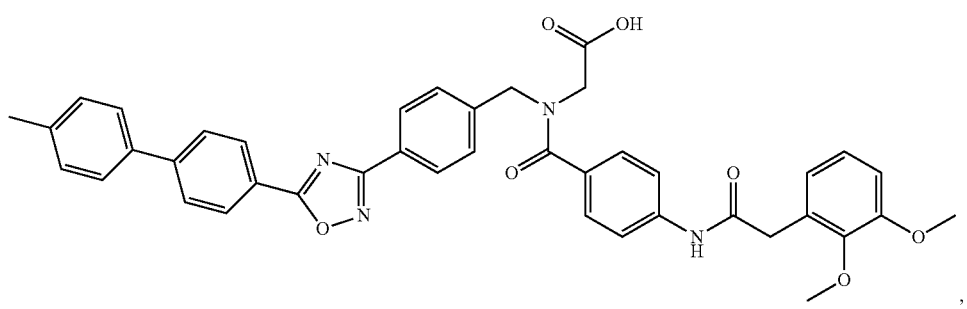
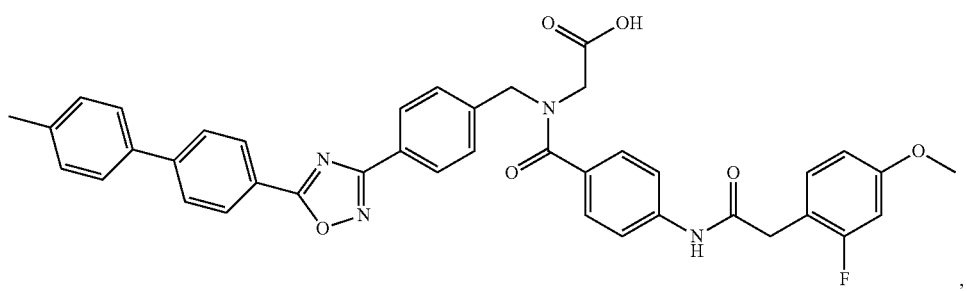

-continued
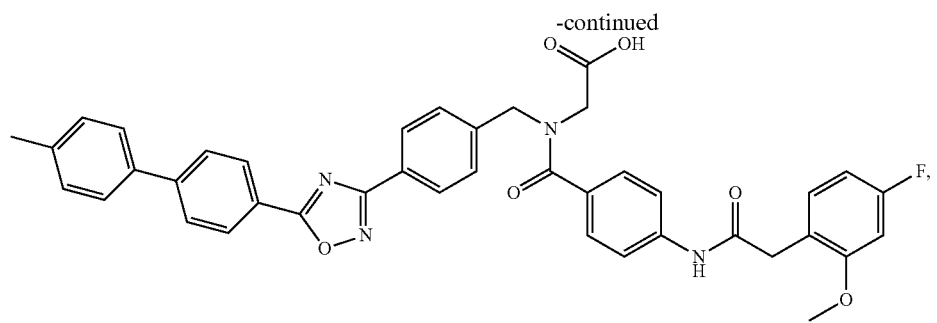
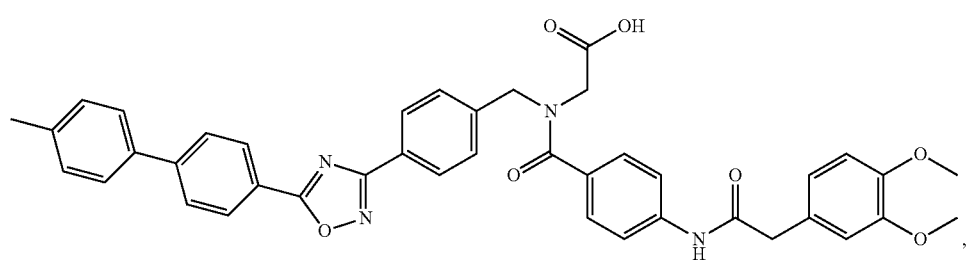
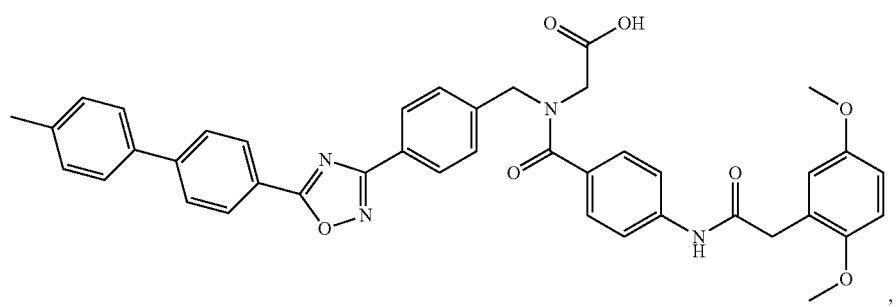
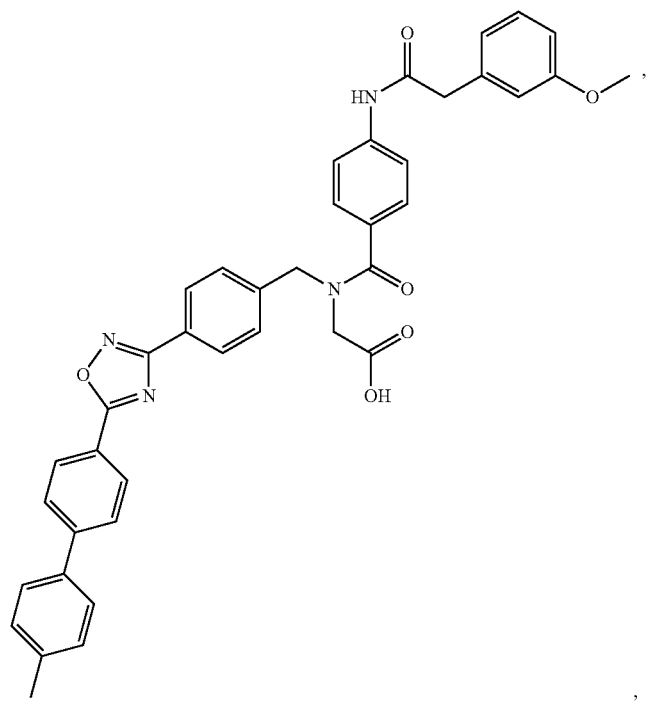

569
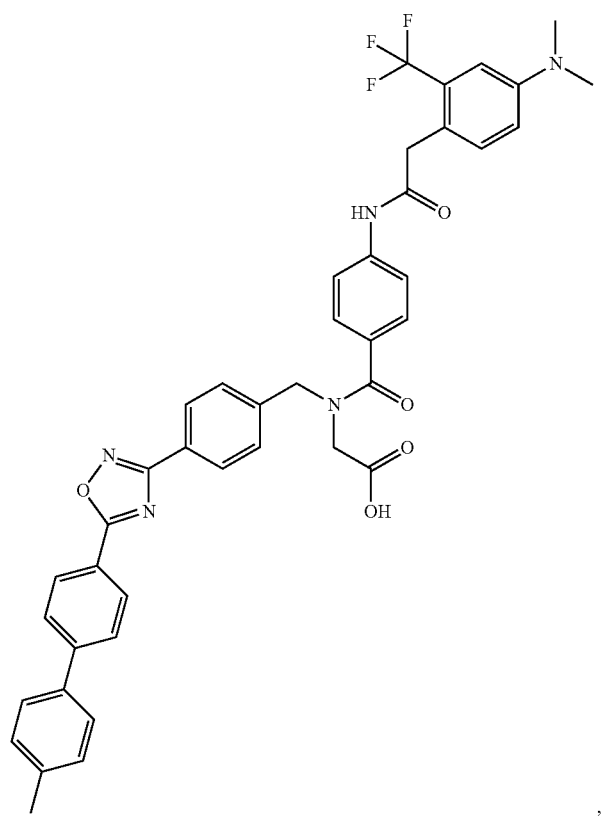
570
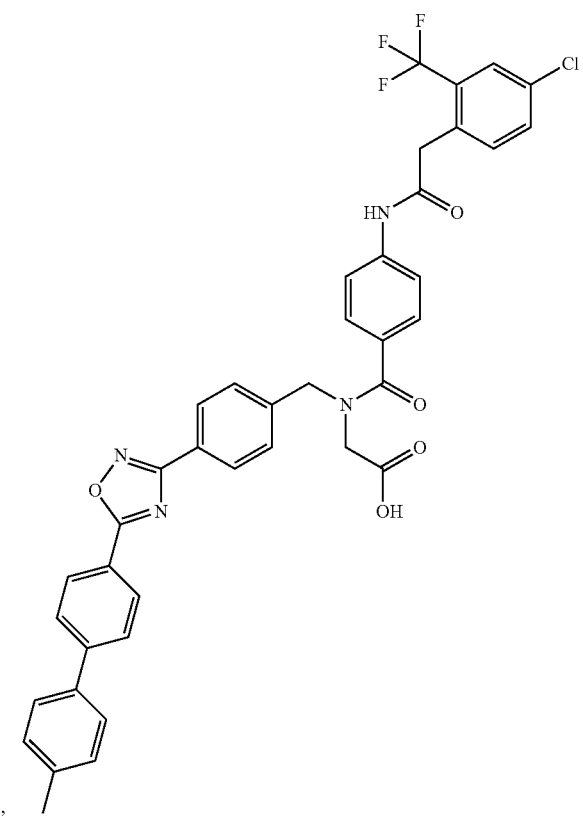
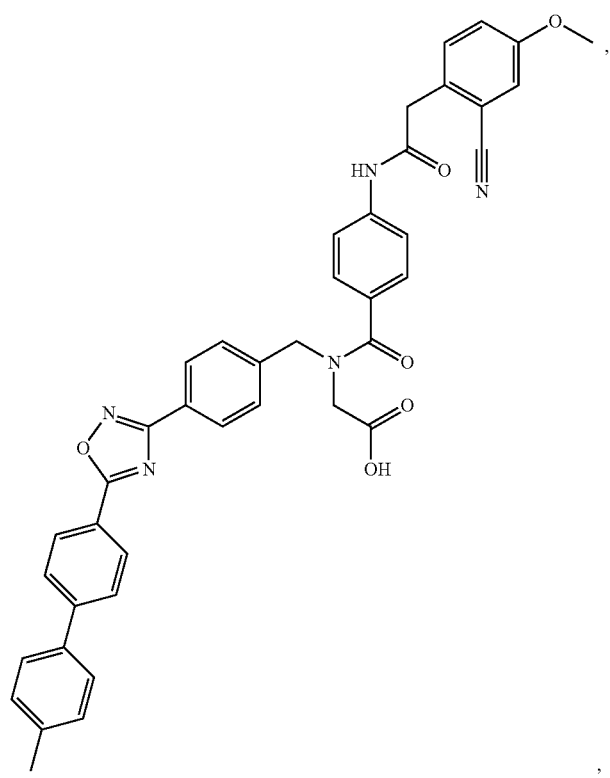

-continued
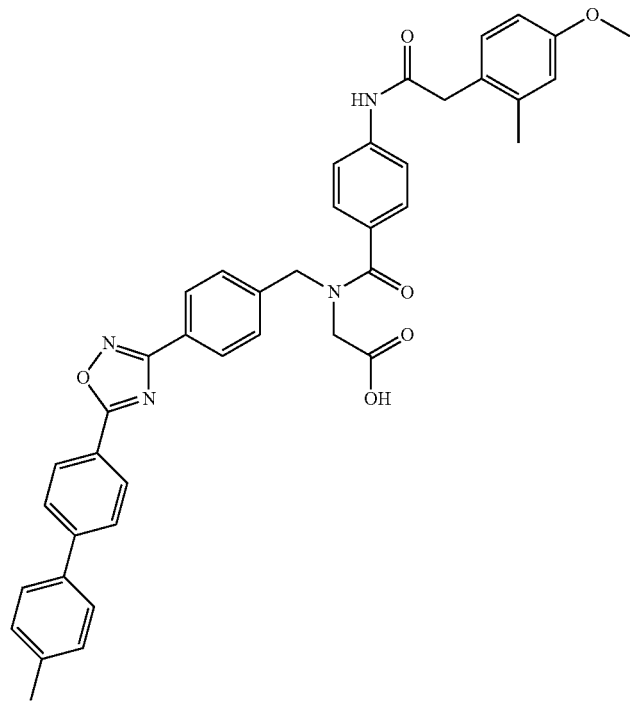
571
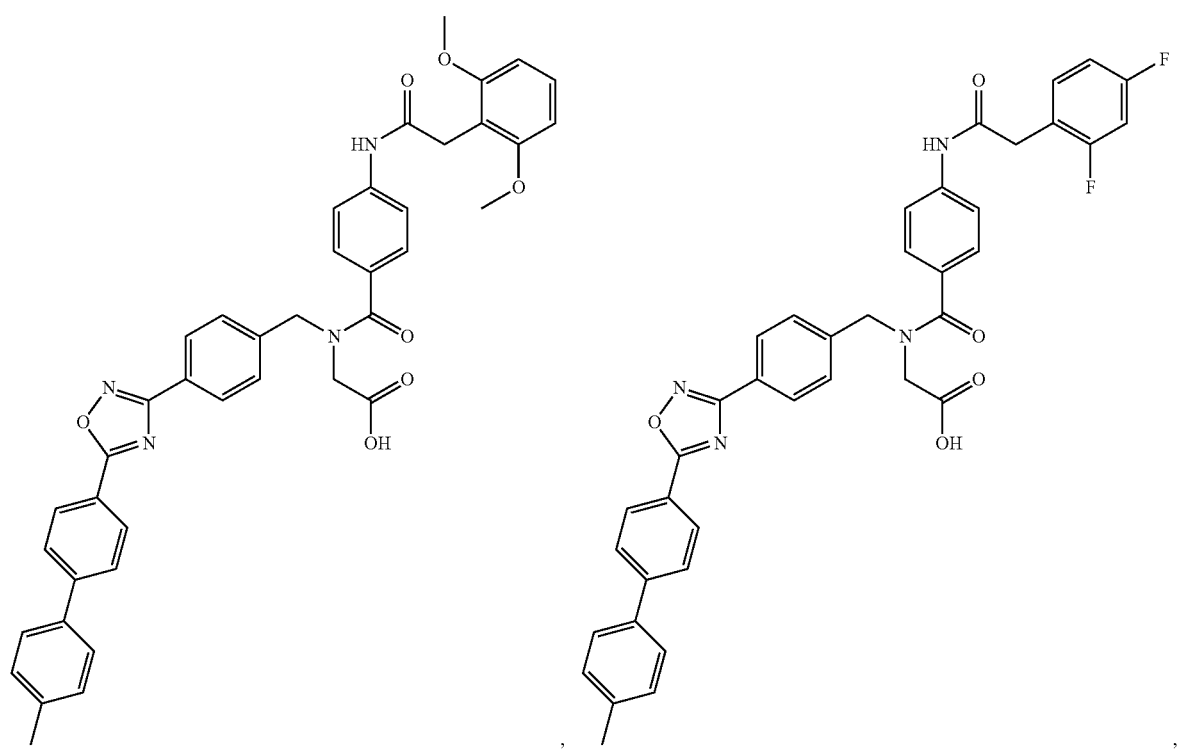
572

573
574
-continued
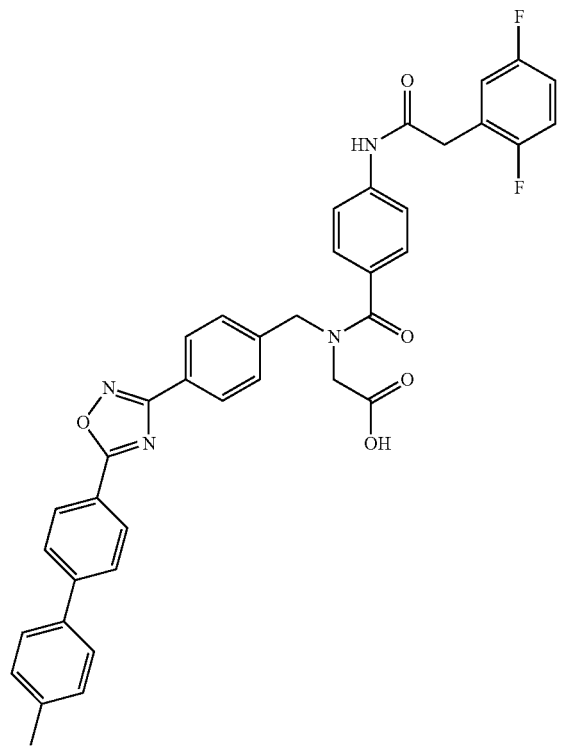
,
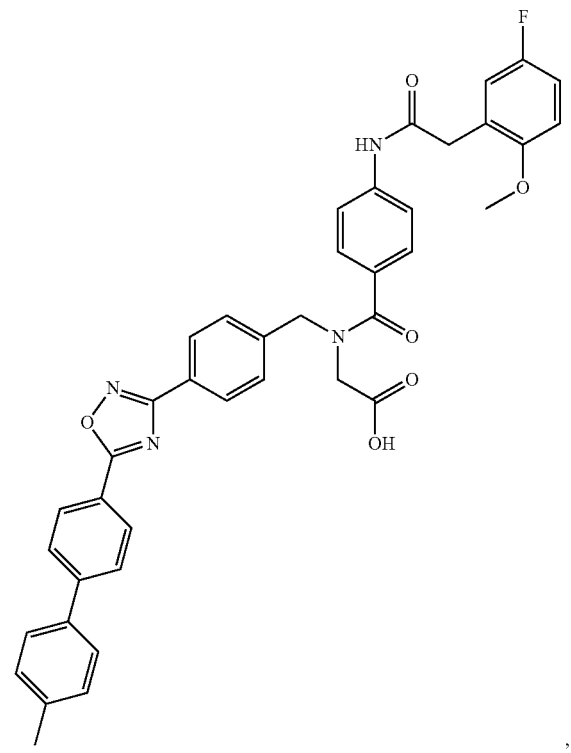
,
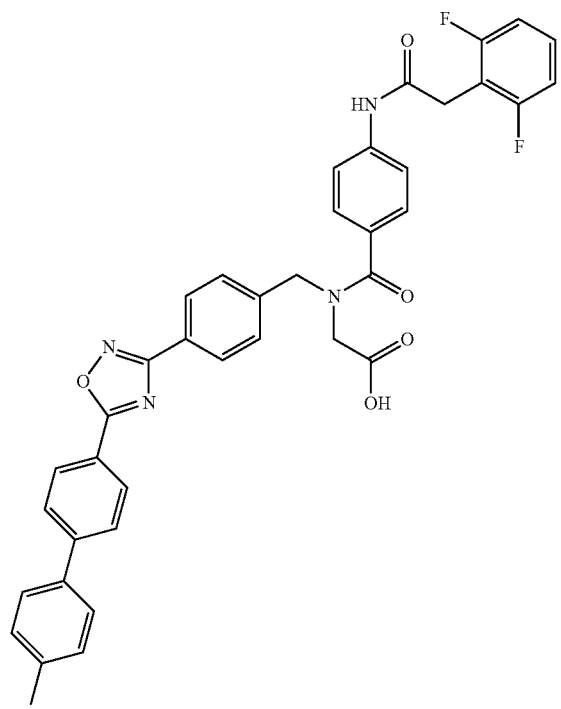
,
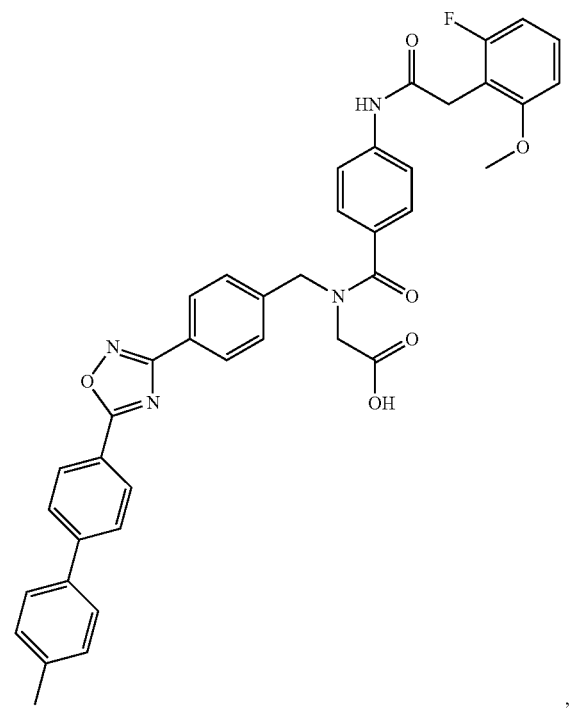
,

-continued
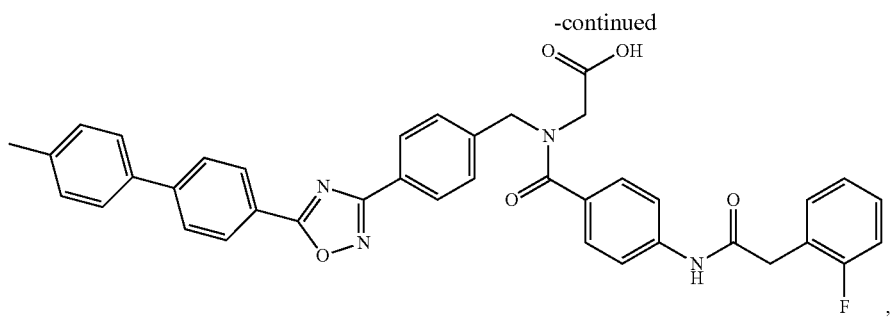
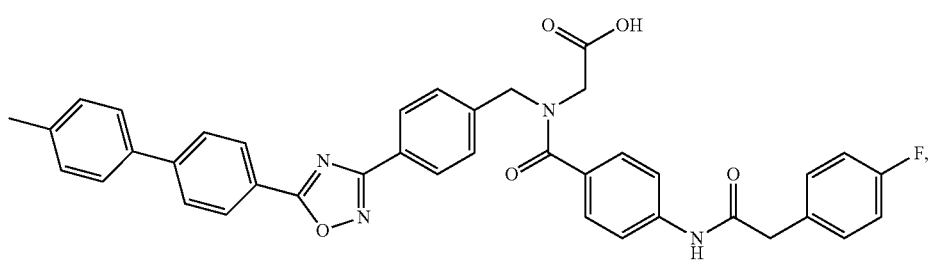
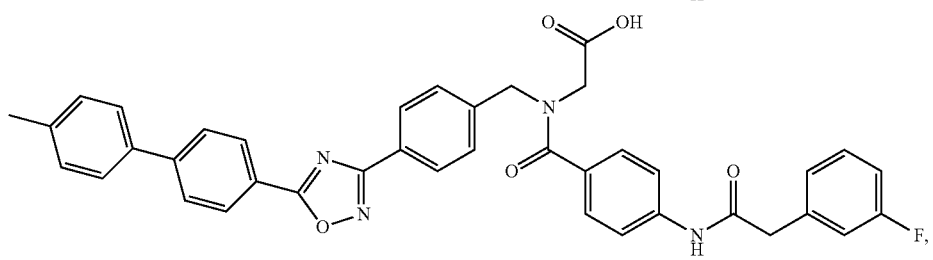
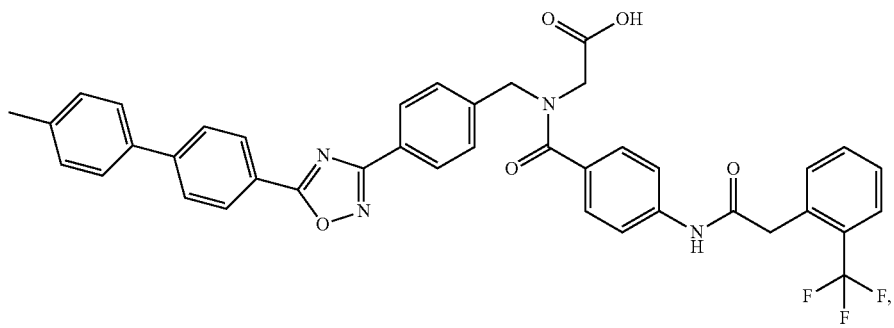
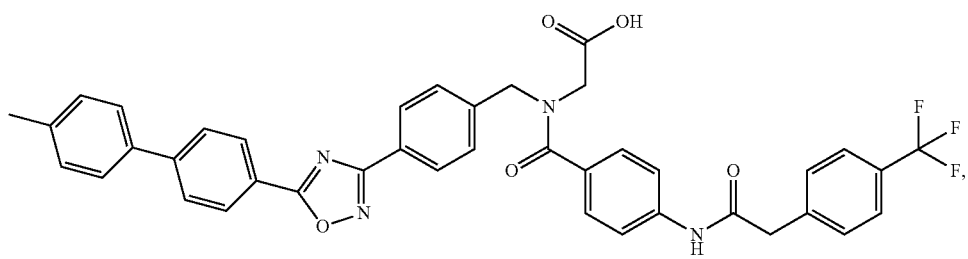
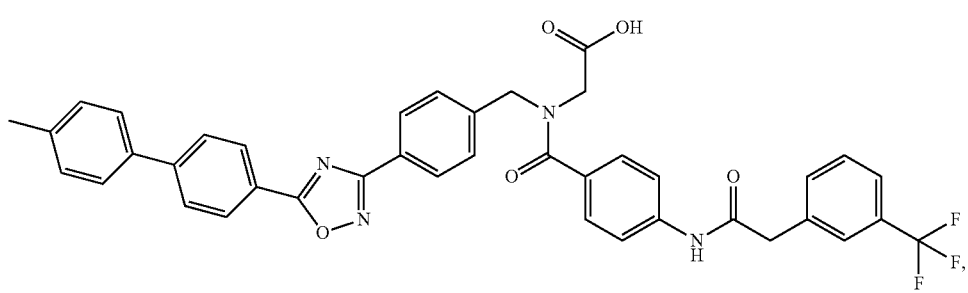

-continued
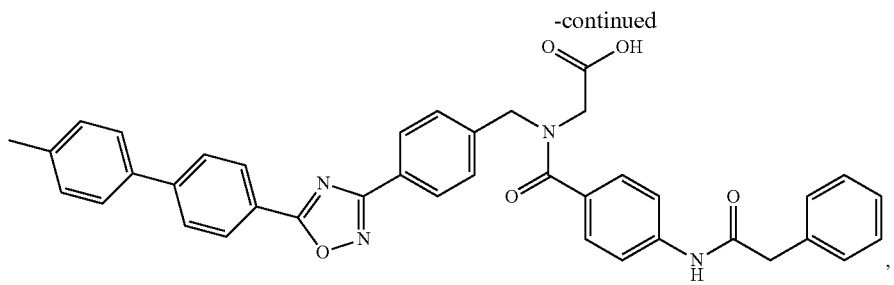
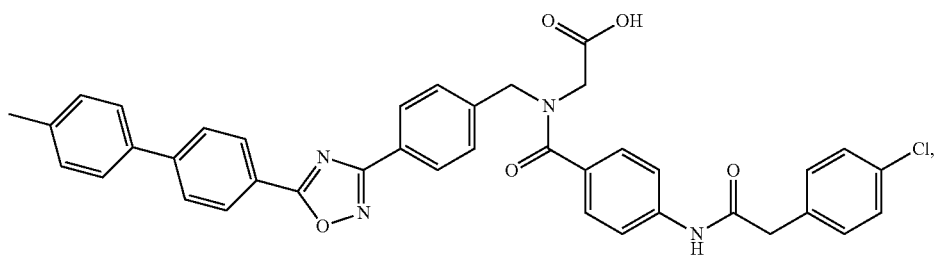
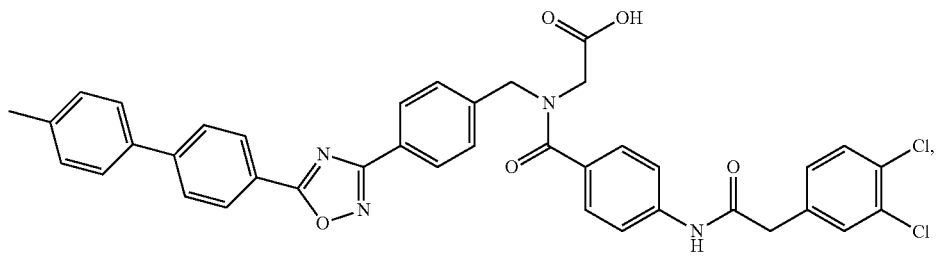
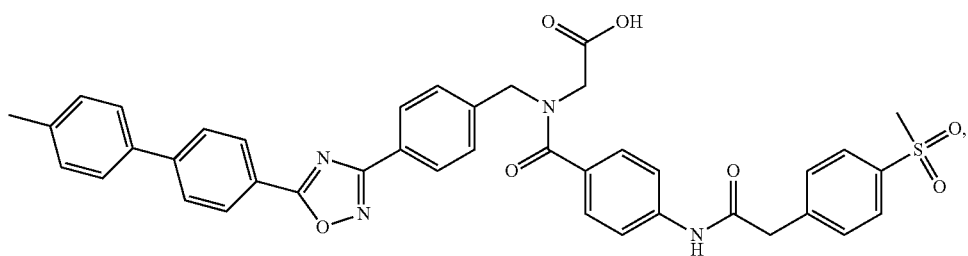
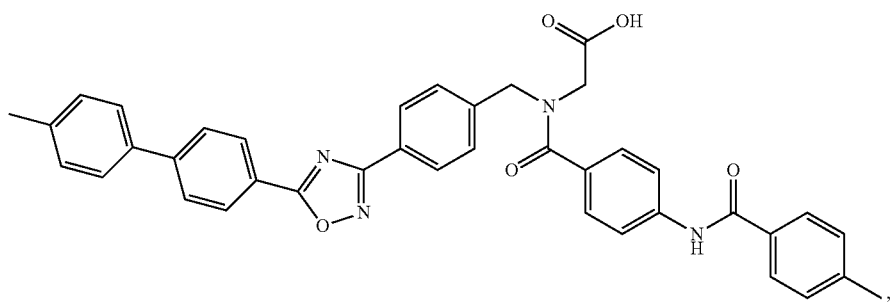
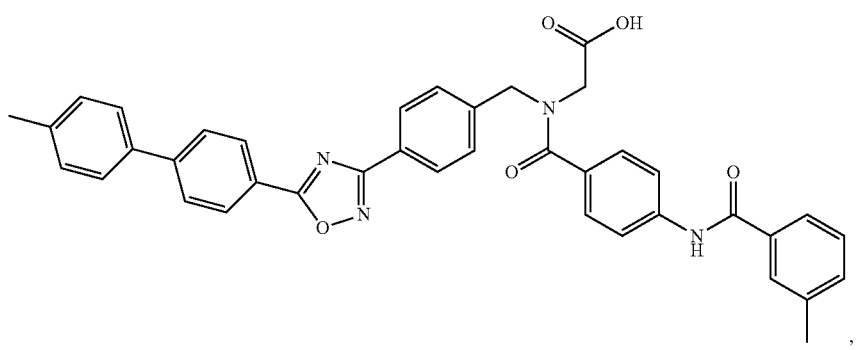

-continued
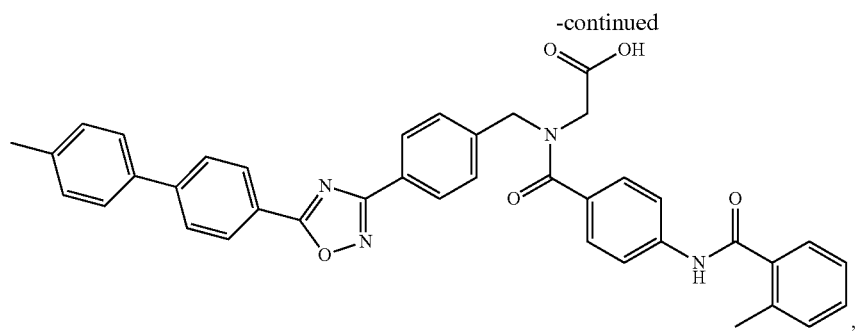
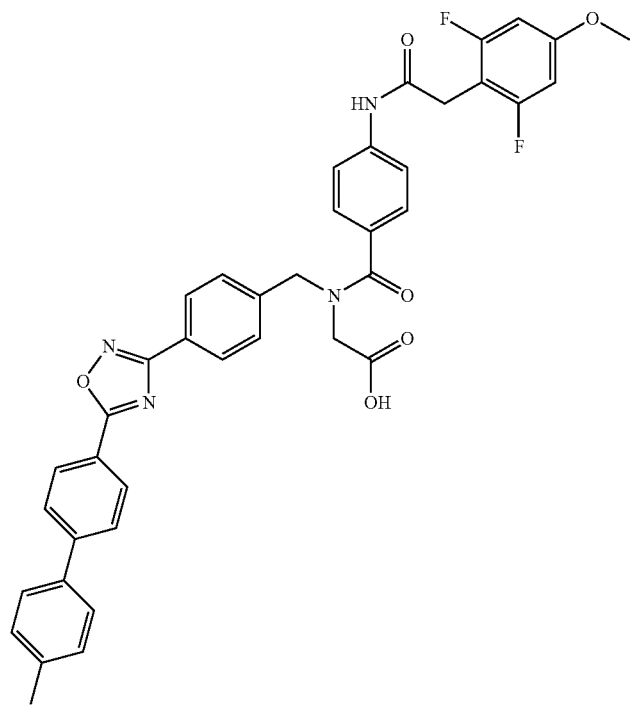
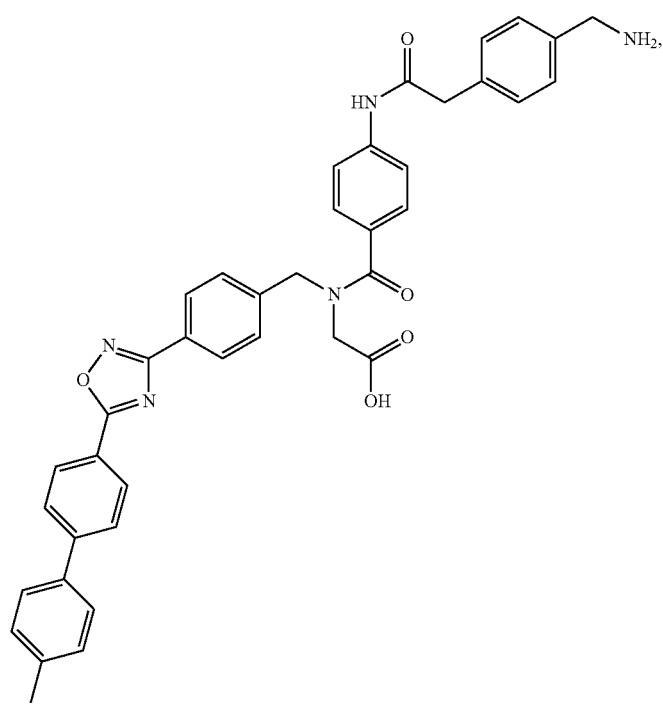

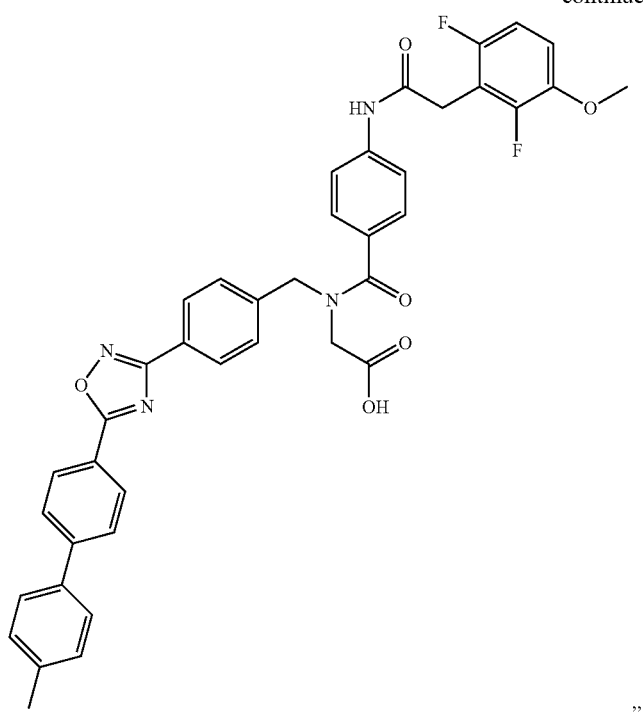
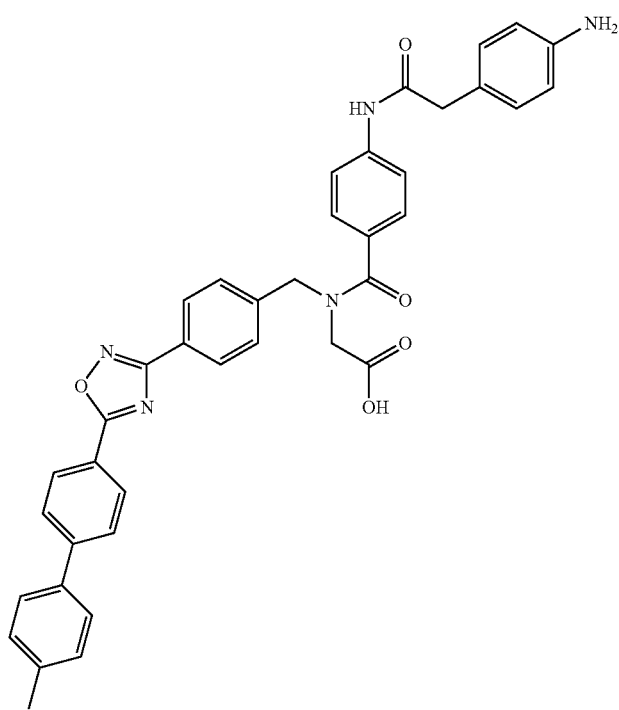

-continued
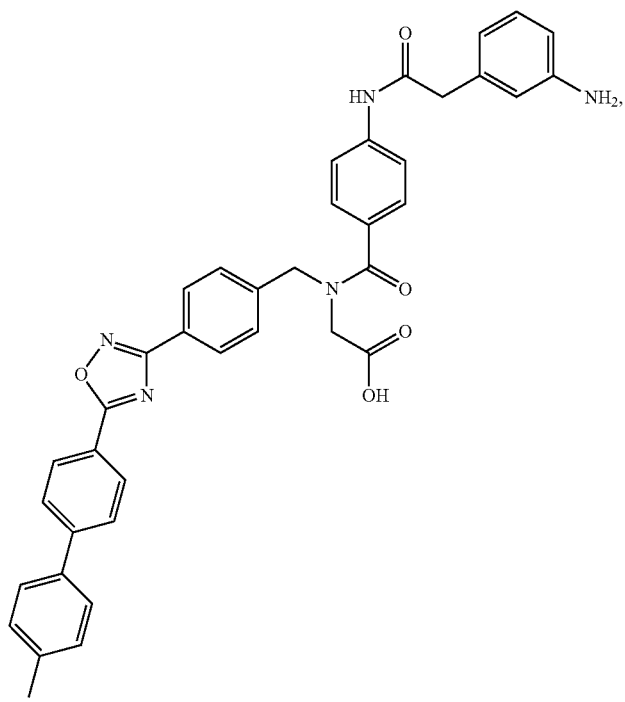
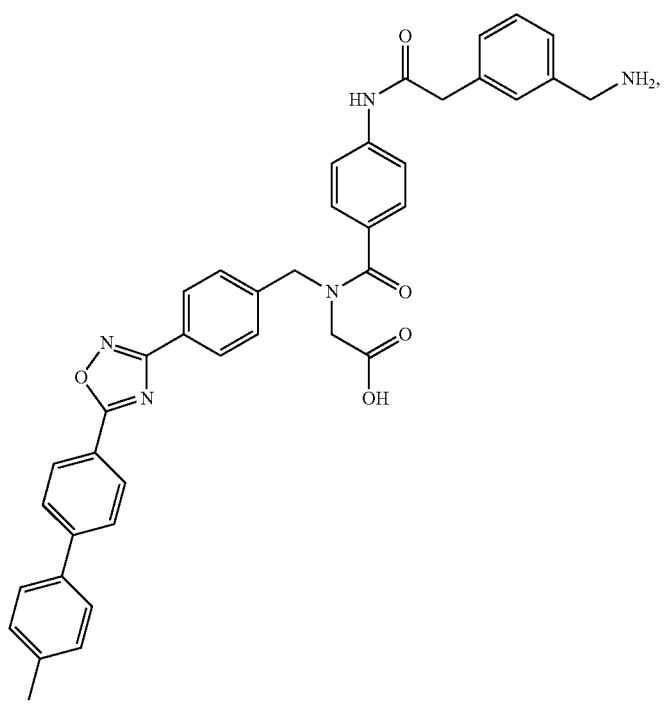

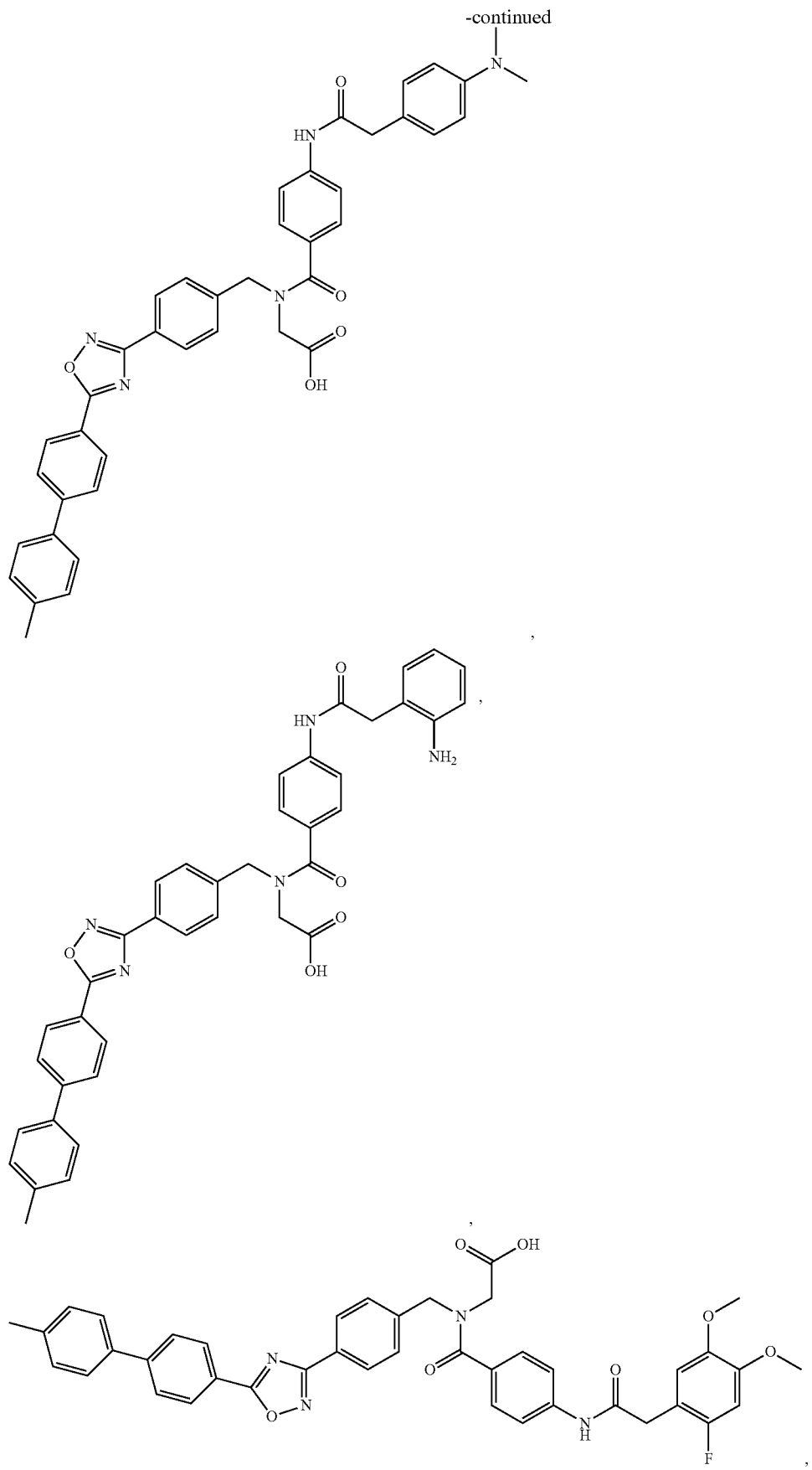

-continued
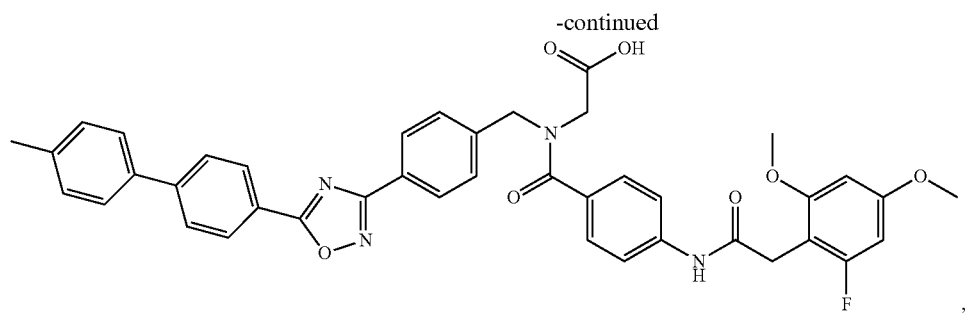
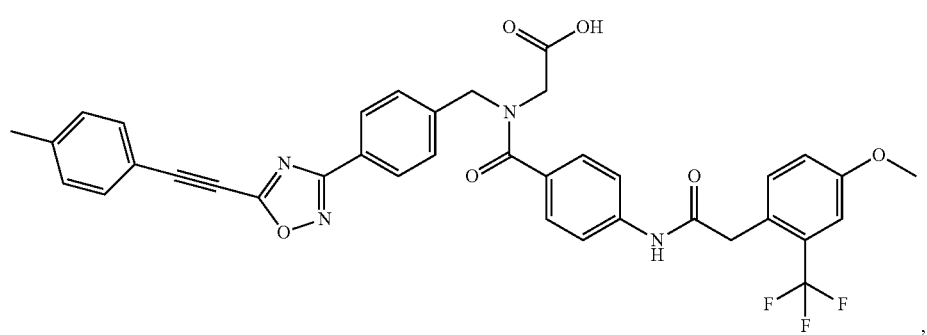
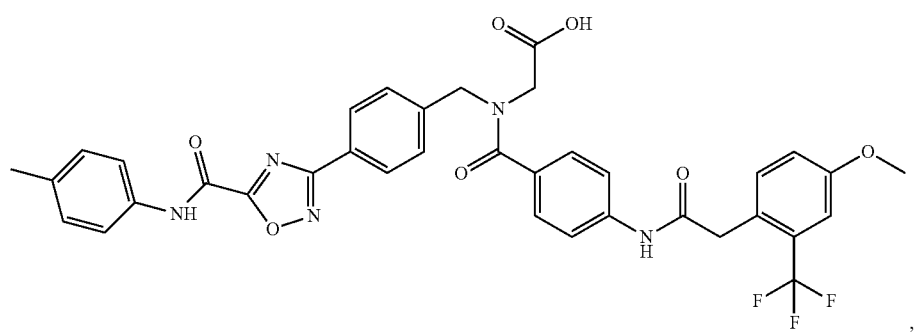
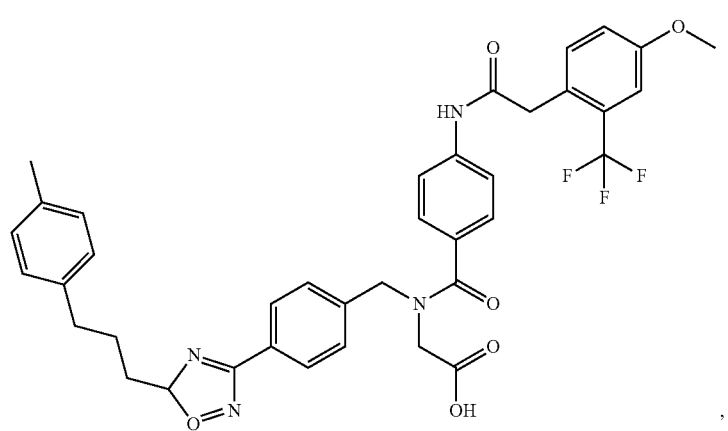

-continued
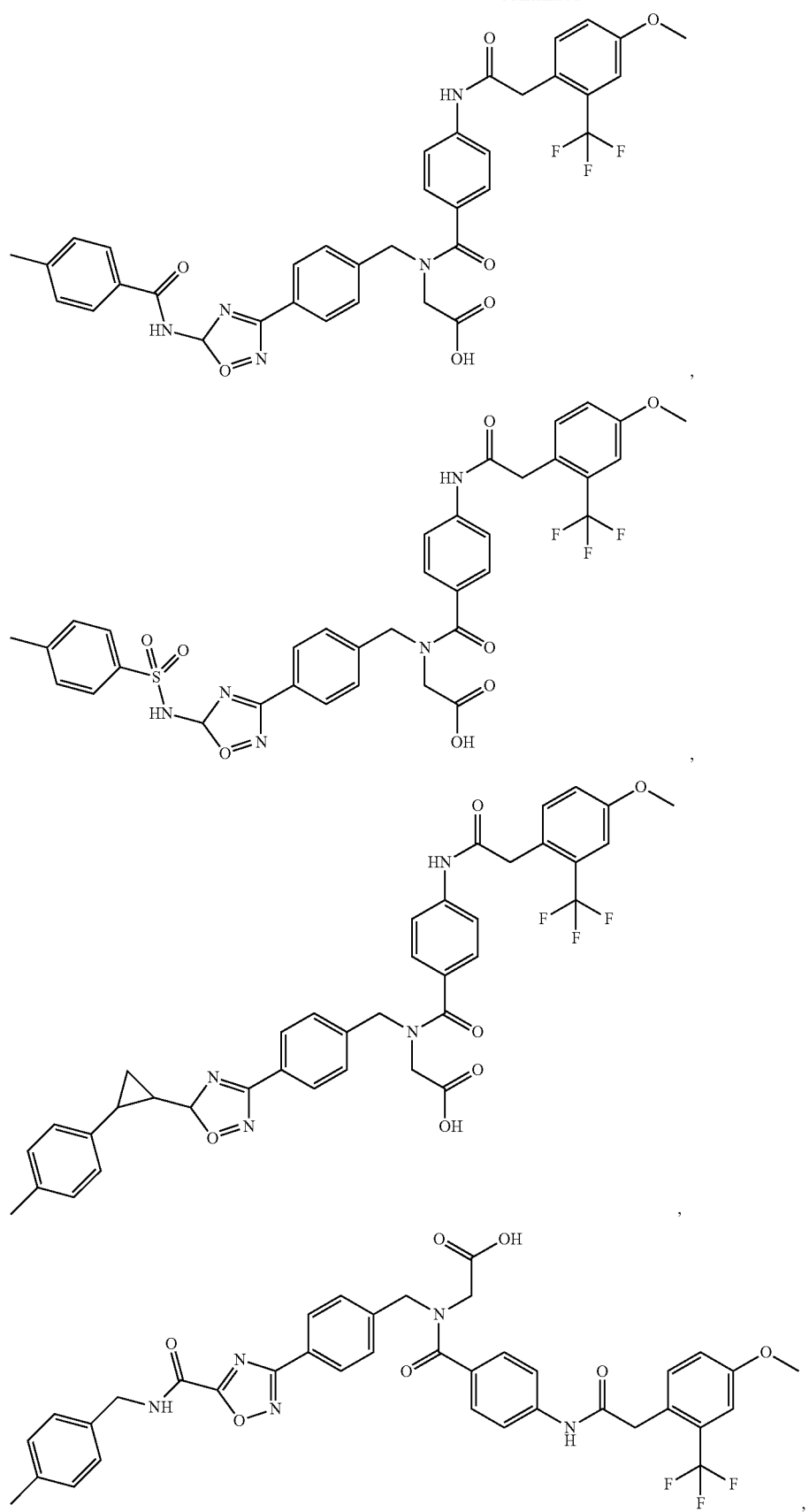

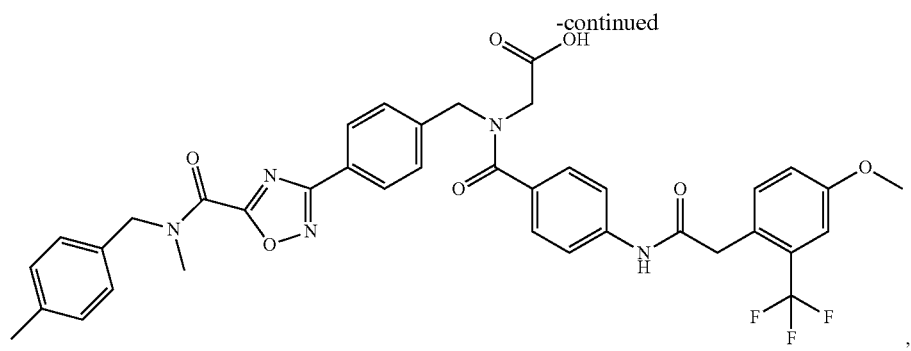
,
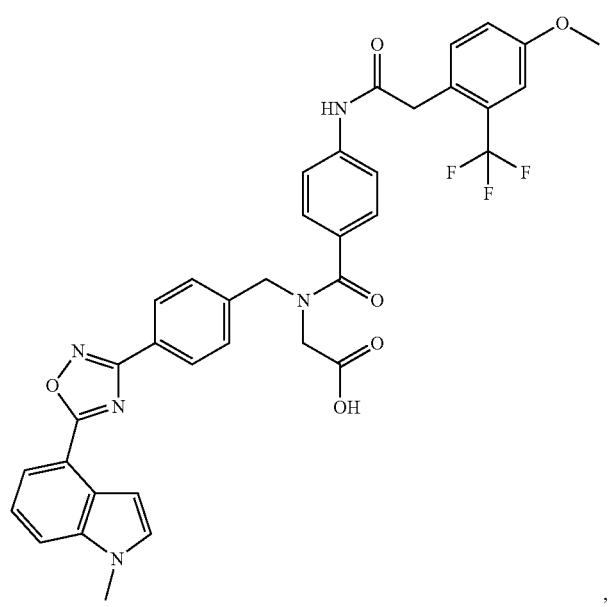
,
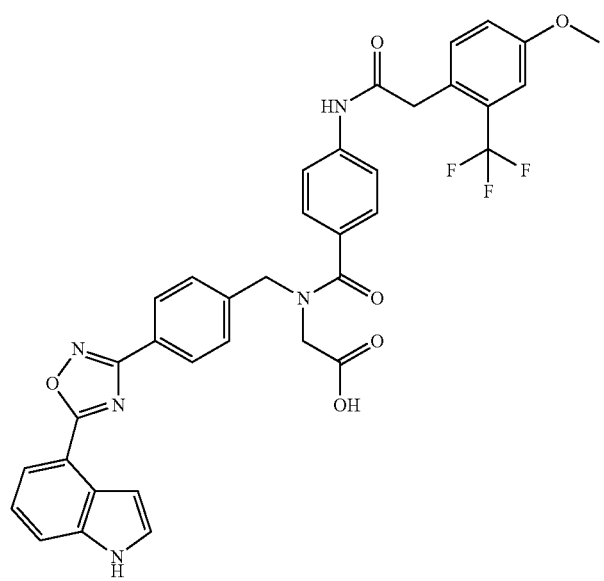
,

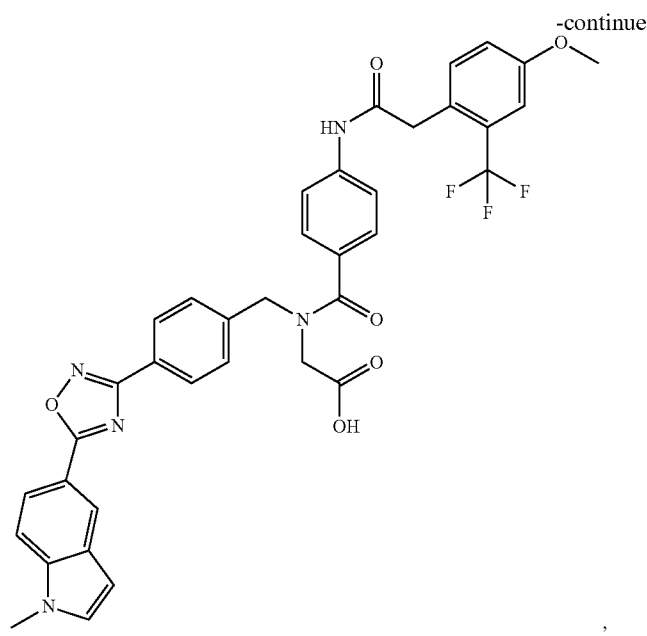
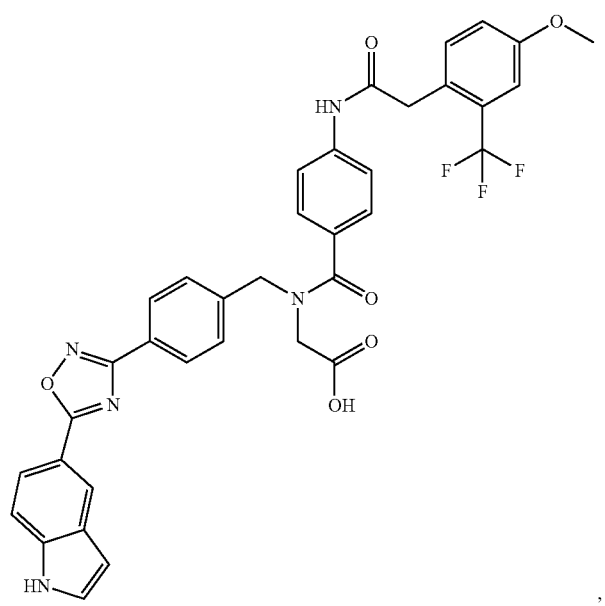

-continued
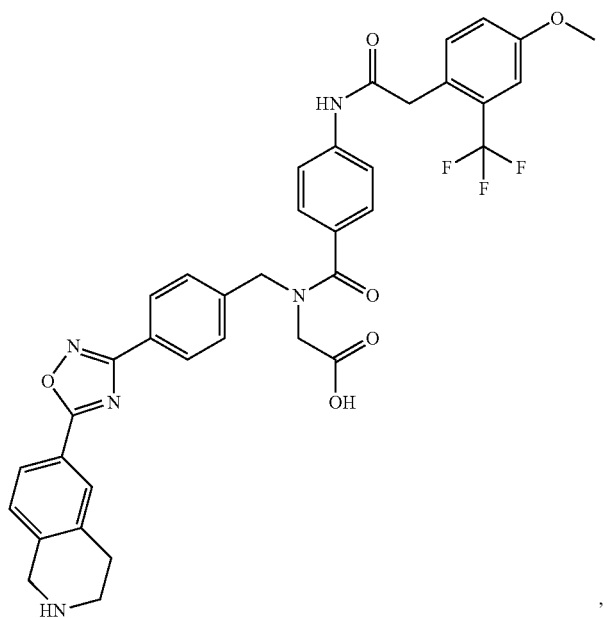
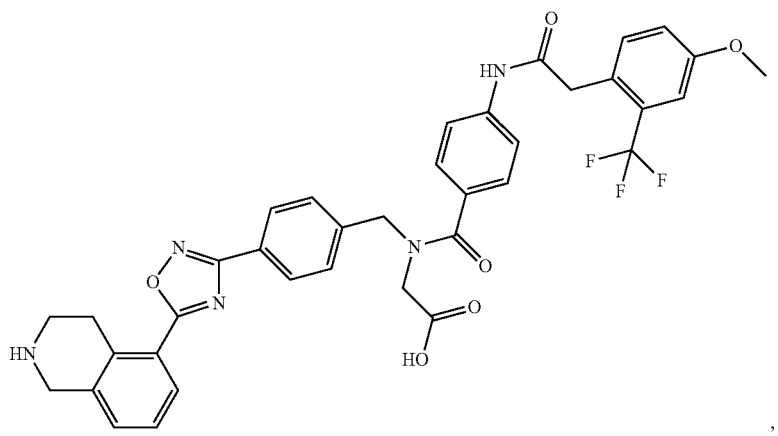

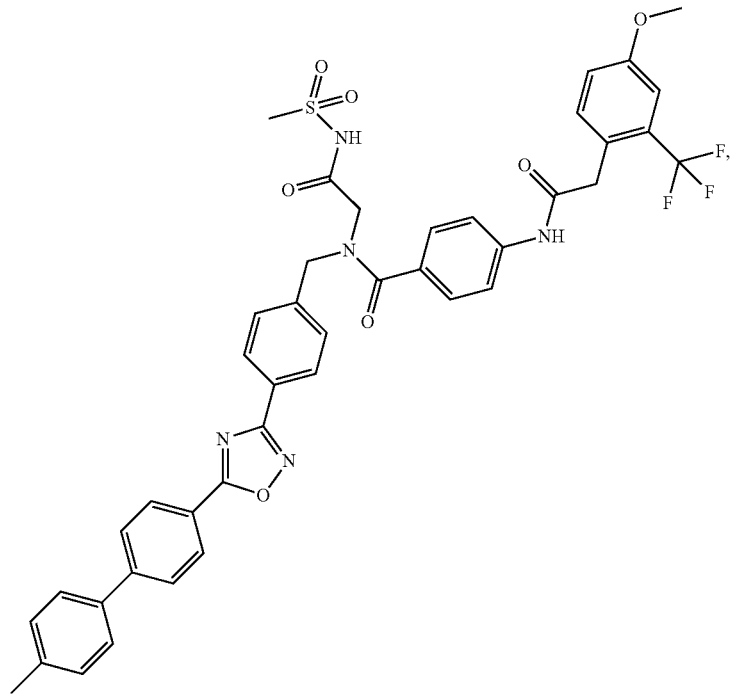
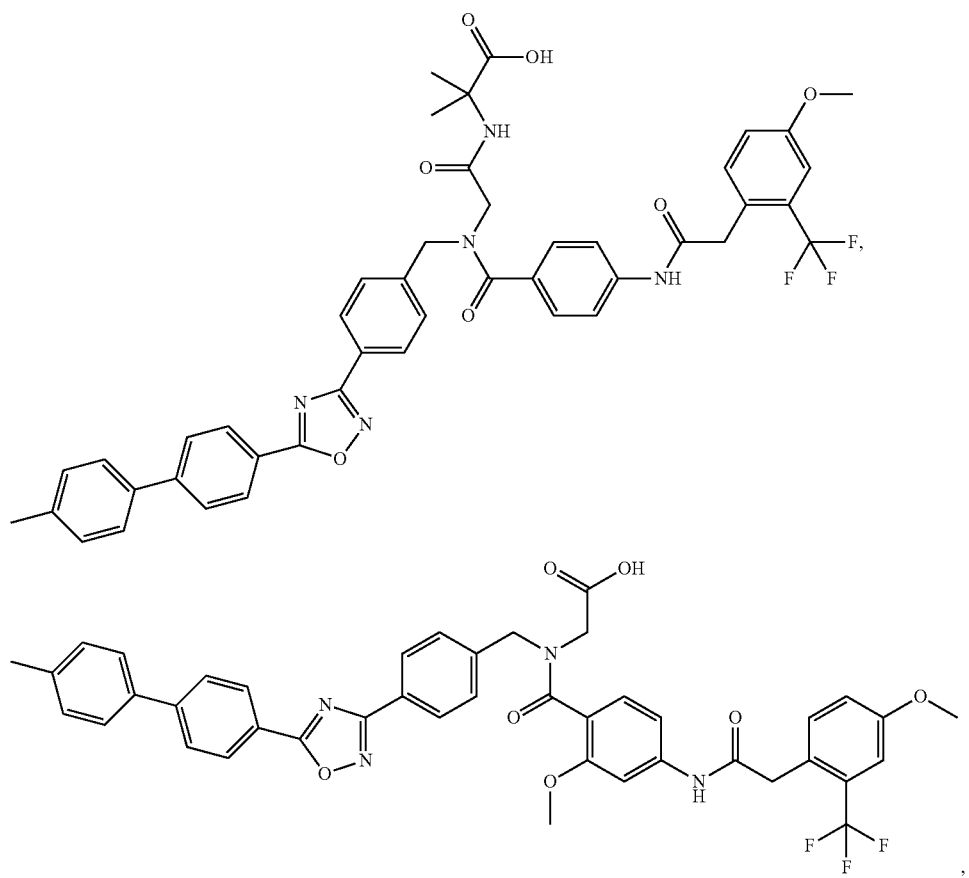

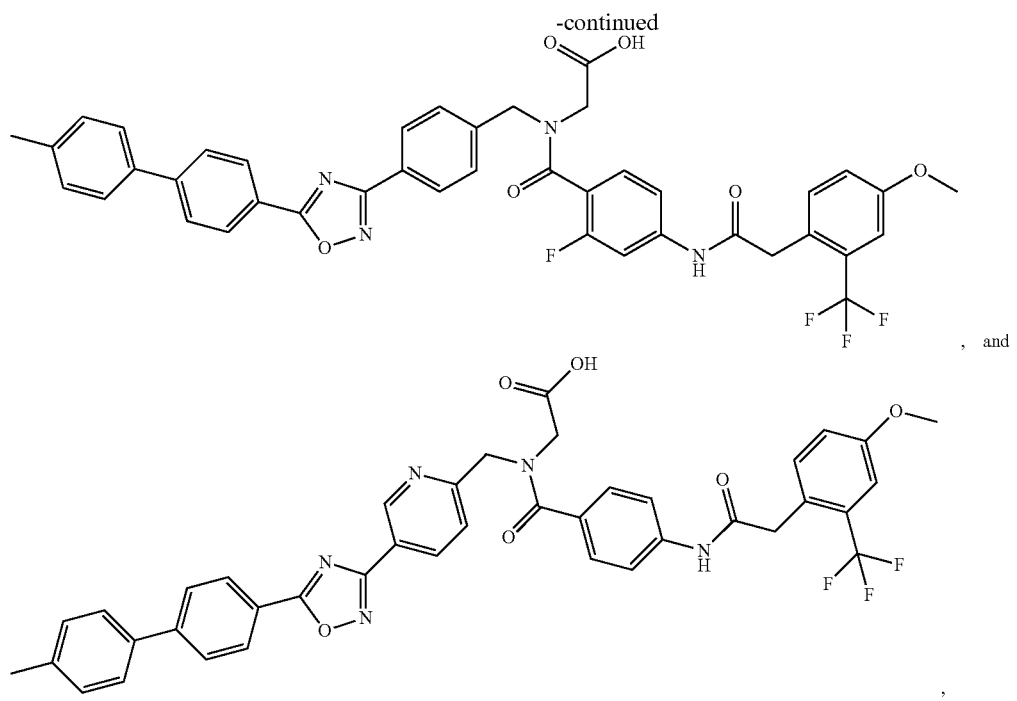
, and
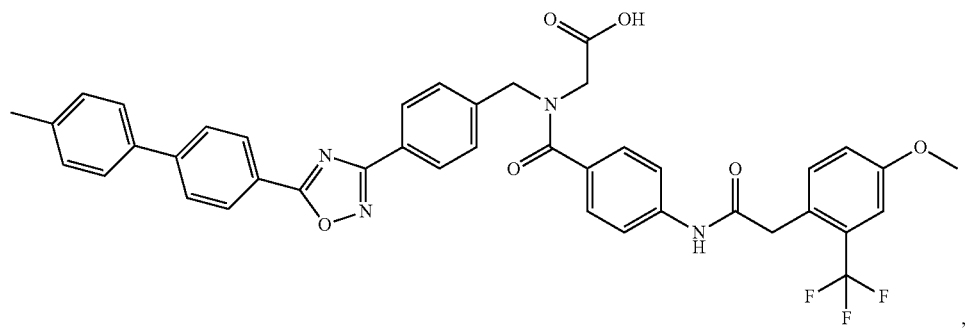
,
or any pharmaceutically acceptable salt thereof.
8. The method of claim 1 wherein the compound is selected from one of the following compounds:
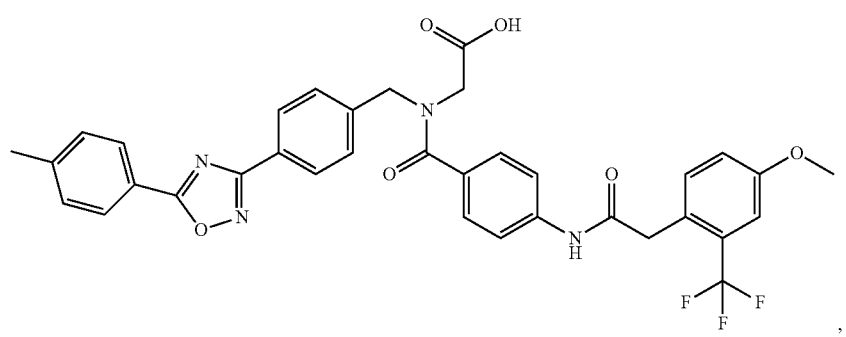
, -continued
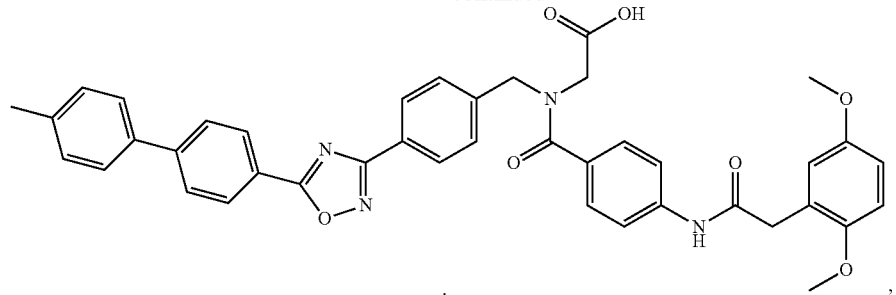
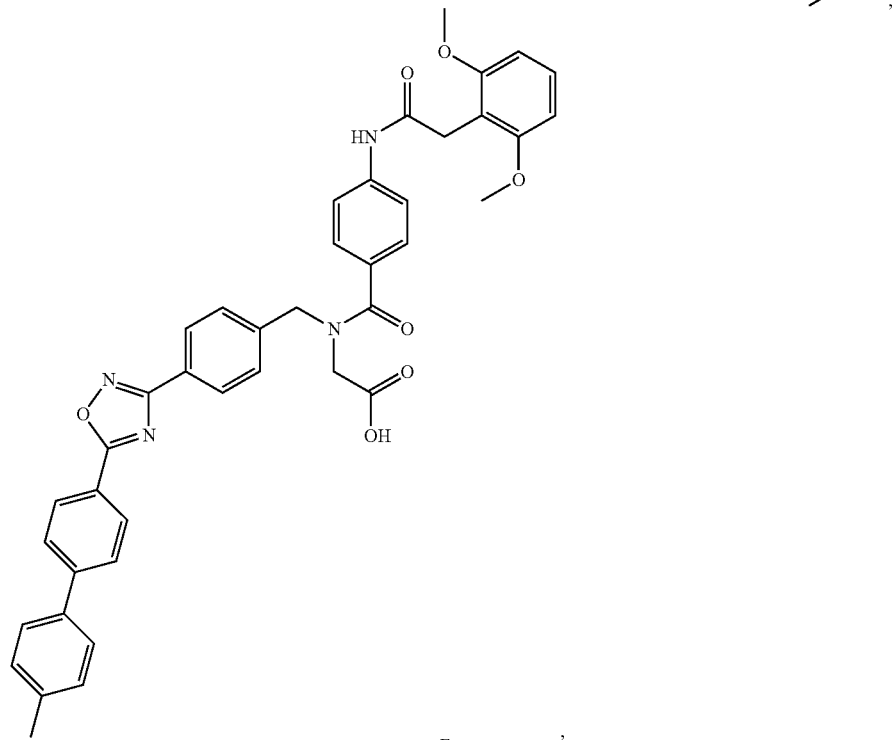
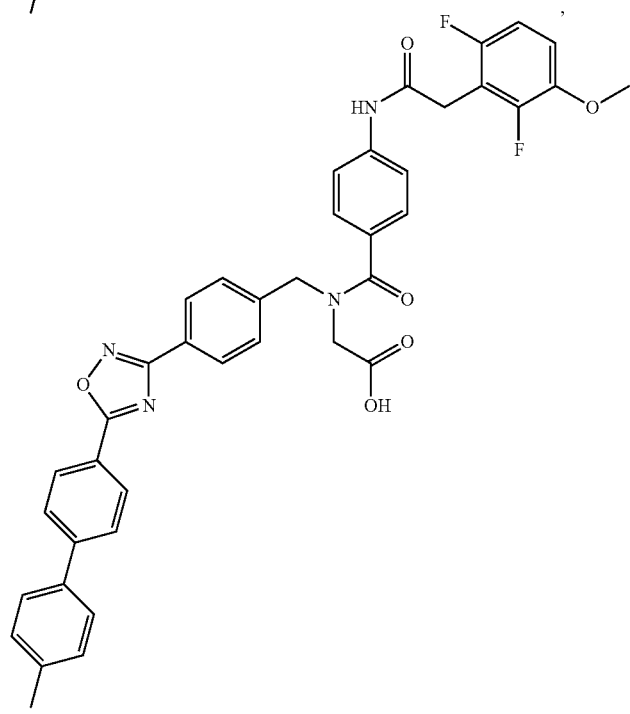
, and 603
-continued
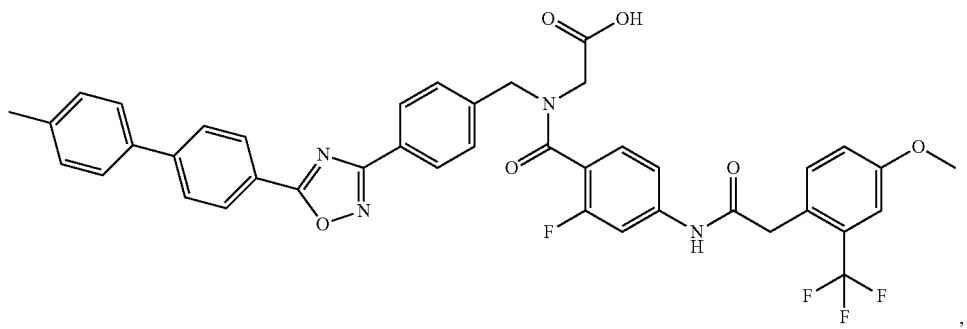
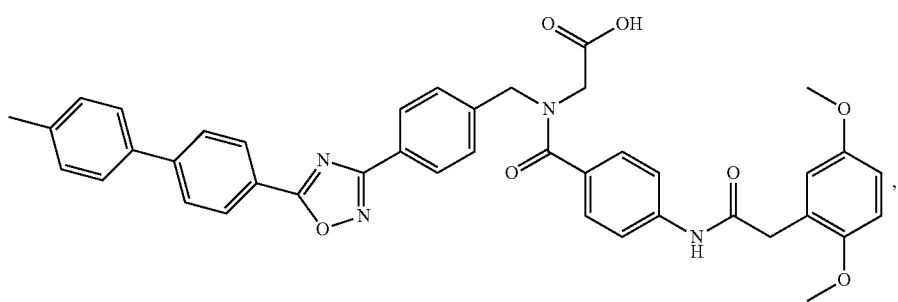
604
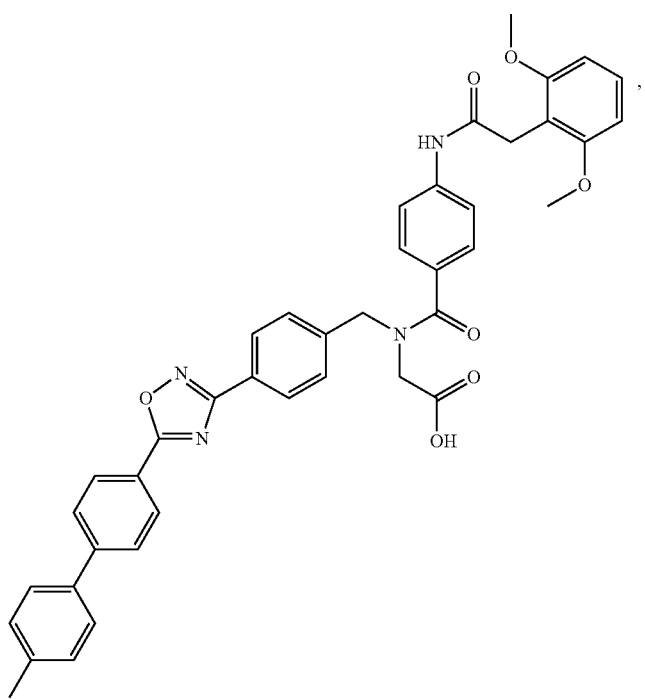

-continued
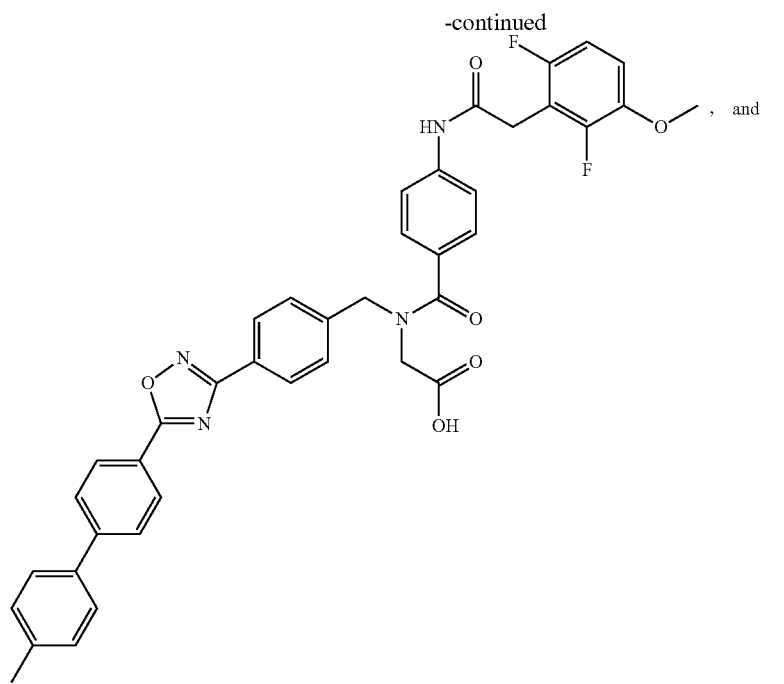, and
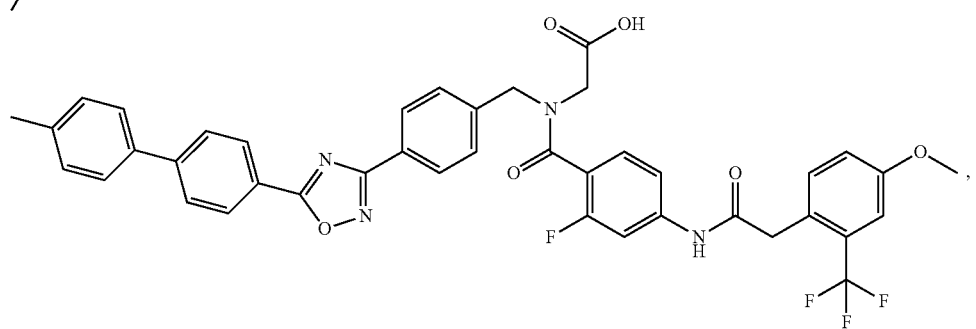
or any pharmaceutically acceptable salt thereof.

UNITED STATES PATENT AND TRADEMARK OFFICE
CERTIFICATE OF CORRECTION

PATENT NO. : 9,700,543 B2
APPLICATION NO. : 14/997364
DATED : July 11, 2017
INVENTOR(S) : Marcus F. Boehm et al.

Page 1 of 3

It is certified that error appears in the above-identified patent and that said Letters Patent is hereby corrected as shown below:

In the Claims

Column 561, Line 67:
"-$(CH_2)_b$-$NR_{20}$, -$(CH_2)_n$ -"
Should read:
-- -$(CH_2)_n$-$NR_{20}$, -$(CH_2)_n$- --.

Column 587:

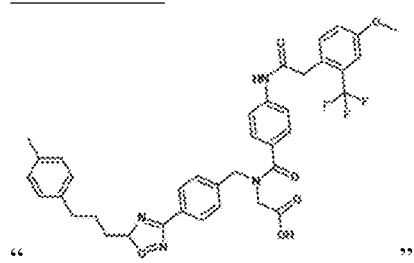

" "

Should read:

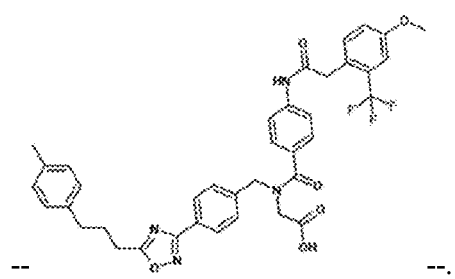

-- --.

Signed and Sealed this
Twenty-third Day of January, 2018

Joseph Matal
*Performing the Functions and Duties of the
Under Secretary of Commerce for Intellectual Property and
Director of the United States Patent and Trademark Office*

CERTIFICATE OF CORRECTION (continued)
U.S. Pat. No. 9,700,543 B2

Page 2 of 3

Column 589:

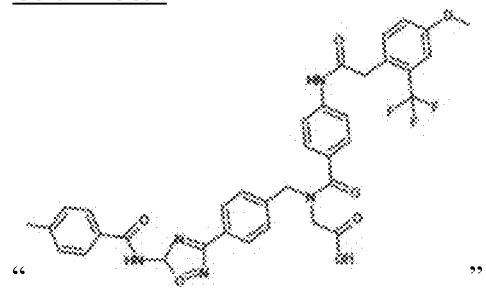

" "

Should read:

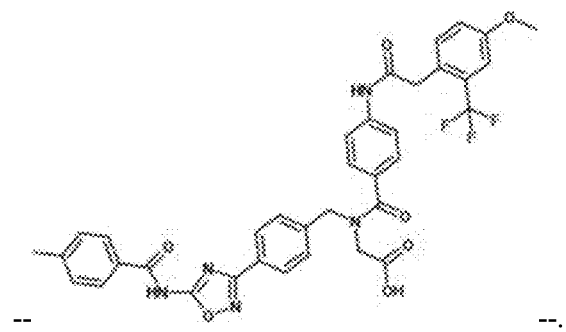

-- --.

Column 589:

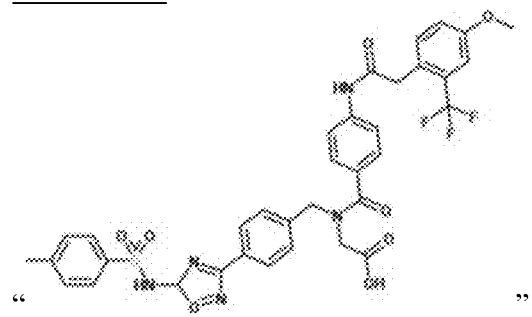

" "

Should read:

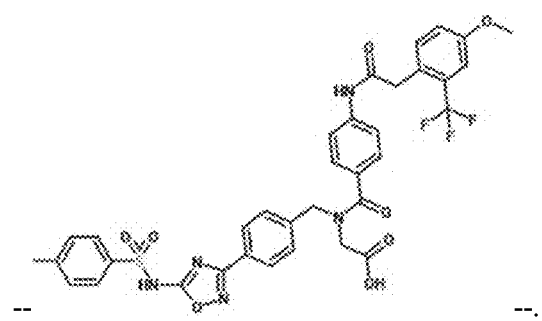

-- --.

CERTIFICATE OF CORRECTION (continued)
U.S. Pat. No. 9,700,543 B2

Page 3 of 3

Column 589:

"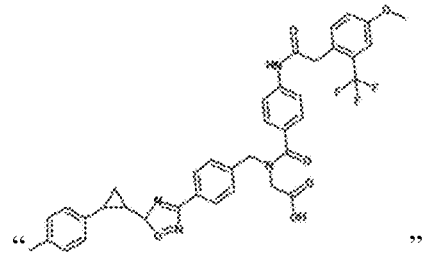",

Should read:

--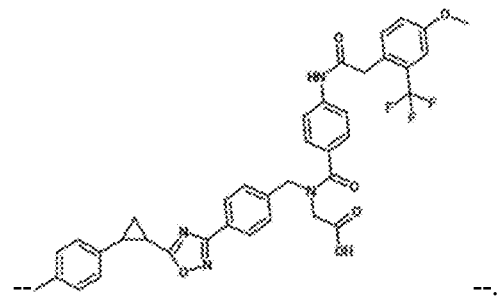--.